(12) United States Patent
Chen et al.

(10) Patent No.: US 11,183,641 B2
(45) Date of Patent: Nov. 23, 2021

(54) COMPOSITION FOR AN ORGANIC ELECTRONIC DEVICE AND ORGANIC ELECTRONIC DEVICE USING THE SAME

(71) Applicant: SHANGHAI NICHEM FINE CHEMICAL CO., LTD., Shanghai (CN)

(72) Inventors: Chi-Chung Chen, Hsinchu County (TW); Shwu-Ju Shieh, Hsinchu County (TW); Ming-Zer Lee, Hsinchu County (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 413 days.

(21) Appl. No.: 16/429,124

(22) Filed: Jun. 3, 2019

(65) Prior Publication Data
US 2019/0372014 A1 Dec. 5, 2019

Related U.S. Application Data

(60) Provisional application No. 62/680,625, filed on Jun. 5, 2018.

(51) Int. Cl.
*C07D 311/96* (2006.01)
*C07D 335/04* (2006.01)
(Continued)

(52) U.S. Cl.
CPC ........ *H01L 51/0067* (2013.01); *C07D 209/86* (2013.01); *C07D 213/22* (2013.01);
(Continued)

(58) Field of Classification Search
CPC ............ C07C 2603/97; C07C 2603/98; C07D 311/96; C07D 335/04; C07D 209/82;
(Continued)

(56) References Cited

U.S. PATENT DOCUMENTS

2018/0155312 A1* 6/2018 Wu ................. C07D 311/82

FOREIGN PATENT DOCUMENTS

CN 105679946 A 6/2016
CN 107011248 A 8/2017
(Continued)

*Primary Examiner* — Vu A Nguyen
(74) *Attorney, Agent, or Firm* — WPAT, PC

(57) ABSTRACT

Provided are a composition for an organic electronic device and an organic electronic device using the same. The composition includes a first host compound represented by the following Formula (I) and a second host compound represented by the following Formula (II), Formula (I)

(Continued)

-continued

Formula (II)

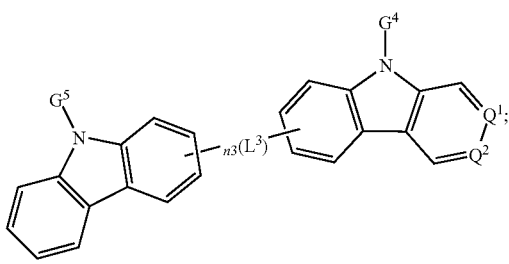

wherein Y is a single bond, O or S; $Z^1$ to $Z^3$ are each CH or adjacent two of $Z^1$ to $Z^3$ are joined together to form an aryl ring or a heteroaryl ring; two of $X^1$ to $X^3$ are each a nitrogen atom, the other of $X^1$ to $X^3$ is CH or a nitrogen atom; $Q^1$ and $Q^2$ are each CH or $Q^1$ and $Q^2$ are joined together to form an aryl ring.

19 Claims, 2 Drawing Sheets

(51) Int. Cl.
| | |
|---|---|
| *C07D 209/82* | (2006.01) |
| *C07D 209/86* | (2006.01) |
| *C09K 11/06* | (2006.01) |
| *H01L 51/00* | (2006.01) |
| *C07D 253/02* | (2006.01) |
| *C07D 239/26* | (2006.01) |
| *C07D 405/10* | (2006.01) |
| *C09K 11/02* | (2006.01) |
| *C07D 213/22* | (2006.01) |
| *C07D 251/24* | (2006.01) |
| *C07D 401/10* | (2006.01) |
| *C07D 405/04* | (2006.01) |
| *H01L 51/50* | (2006.01) |

(52) U.S. Cl.
CPC ......... *C07D 239/26* (2013.01); *C07D 251/24* (2013.01); *C07D 253/02* (2013.01); *C07D 401/10* (2013.01); *C07D 405/04* (2013.01); *C07D 405/10* (2013.01); *C09K 11/02* (2013.01); *C09K 11/06* (2013.01); *H01L 51/0058* (2013.01); *H01L 51/0072* (2013.01); *H01L 51/0073* (2013.01); *C09K 2211/1007* (2013.01); *C09K 2211/1029* (2013.01); *C09K 2211/1033* (2013.01); *C09K 2211/185* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC .. C07D 209/86; C07D 213/22; C07D 239/26; C07D 251/24; C07D 253/02; C07D 401/10; C07D 405/04; C07D 405/10; C09K 11/02; C09K 11/06; C09K 2211/1007; C09K 2211/1029; C09K 2211/1033; C09K 2211/185; H01L 51/0067; H01L 51/0058; H01L 51/0072; H01L 51/0073; H01L 51/5012; H01L 51/5056; H01L 51/5072; H01L 51/5088; H01L 51/5092; H01L 51/5096
See application file for complete search history.

(56) References Cited

FOREIGN PATENT DOCUMENTS

| | | | |
|---|---|---|---|
| TW | 201807855 A | 3/2018 | |
| WO | WO-2018021714 A1 * | 6/2018 | ........... C07D 311/82 |

* cited by examiner

COMPOSITION FOR AN ORGANIC ELECTRONIC DEVICE AND ORGANIC ELECTRONIC DEVICE USING THE SAME

CROSS-REFERENCE TO RELATED APPLICATION

Pursuant to 35 U.S.C. § 119(e), this application claims the benefits of the priority to U.S. Provisional Patent Application No. 62/680,625, filed Jun. 5, 2018. The contents of the prior application are incorporated herein by its entirety.

BACKGROUND OF THE INVENTION

1. Field of the Invention

The present invention relates to a composition for an organic electronic device and an organic electronic device using the same, more particularly to a composition that includes two host compounds for an emission layer and an organic electronic device using the same.

2. Description of the Prior Arts

With the advance of technology, various organic electronic devices that make use of organic materials have been energetically developed. Examples of the organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching W. Tang and Steven VanSlyke of Kodak Company deposited an electron transport material such as tris(8-hydroxyquinoline)aluminum(III) (abbreviated as $Alq_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 move to the EL via HIL and HTL and the electrons injected from the cathode 18 move to the EL via EIL and ETL. Recombination of the electrons and the holes occurs in the EL to generate excitons, thereby emitting a light when the excitons decay from excited state to ground state.

Another approach is to adopt 1,3,5-tris(1-phenyl-1H-benzimidazol-2-yl)benzene (TPBi) as a host material of the EL. However, even using the foresaid host material of the EL, the driving voltage and the current efficiency of OLEDs still need to be improved.

Therefore, the present invention provides a novel composition to mitigate or obviate the problems in the prior art.

SUMMARY OF THE INVENTION

An objective of the present invention is to provide a composition for an organic electronic device.

Another objective of the present invention is to provide an organic electronic device using the composition, so as to reduce the driving voltage and improve the current efficiency of the organic electronic device.

To achieve the foresaid objectives, the present invention provides a composition for an organic electronic device which comprises a first host compound and a second host compound.

The first host compound is represented by the following Formula (I):

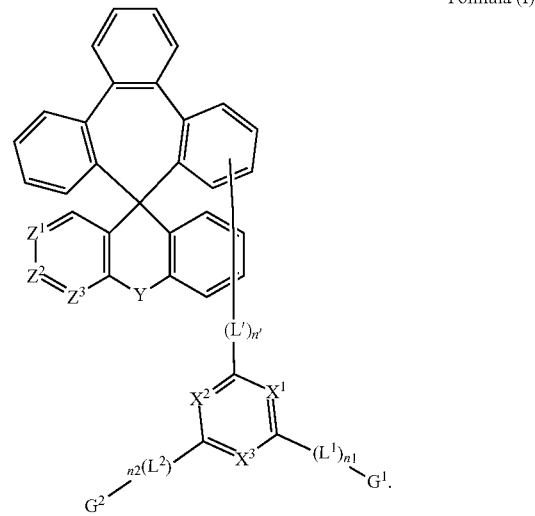

Formula (I)

In Formula (I), Y is a single bond, an oxygen atom or a sulfur atom.

In Formula (I), $Z^1$ to $Z^3$ are each independently CH, adjacent two of $Z^1$ to $Z^3$ in Formula (I) are joined together to form an aryl ring and a remaining one of $Z^1$ to $Z^3$ is CH, or adjacent two of $Z^1$ to $Z^3$ in Formula (I) are joined together to form a heteroaryl ring containing at least one furan group or at least one thiophene group and the remaining one of $Z^1$ to $Z^3$ is CH.

In Formula (I), two of $X^1$ to $X^3$ are each independently a nitrogen atom, and the other of $X^1$ to $X^3$ is CH or a nitrogen atom.

In Formula (I), L', $L^1$ and $L^2$ are each independently an arylene group having 6 to 18 ring carbon atoms. L', $L^1$ and $L^2$ are the same or different.

In Formula (I), n', n1 and n2 are each independently an integer from 0 to 2. n', n1 and n2 are the same or different.

In Formula (I), $G^1$ and $G^2$ are each independently an aryl group having 6 to 18 ring carbon atoms, an aryloxy group having 6 to 18 ring carbon atoms, an arylthioxy group having 6 to 18 ring carbon atoms, or a heteroaryl group containing a N, O, or S atom and having 3 to 30 ring carbon atoms. $G^1$ and $G^2$ are the same or different.

The second host compound is represented by the following Formula (II):

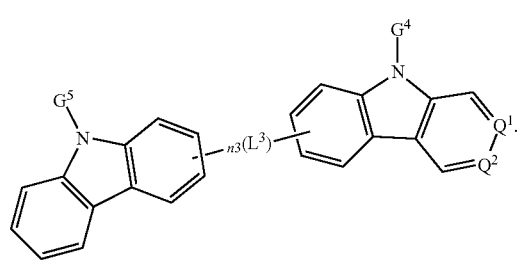

Formula (II)

In Formula (II), $L^3$ is an arylene group having 6 to 18 ring carbon atoms.

In Formula (II), n3 is an integer from 0 to 2.

In Formula (II), $Q^1$ and $Q^2$ are each independently CH, or $Q^1$ and $Q^2$ are joined together to form an aryl ring.

In Formula (II), $G^4$ and $G^5$ are each independently an aryl group having 6 to 18 ring carbon atoms, an aryloxy group having 6 to 18 ring carbon atoms, an arylthioxy group having 6 to 18 ring carbon atoms, or a heteroaryl group containing a N, O, or S atom and having 3 to 30 ring carbon atoms.

By means of containing the first host compound including a triazine moiety or, which is a pyrimidine moiety, and the second host compound whose main skeleton includes at least two carbazole moieties, the first and second host compounds of the composition can form an exciplex. That is, the first host compound is as an acceptor compound for the exciplex, and the second host compound is as a donor compound for the exciplex. Therefore, the composition for an organic electronic device can reduce the driving voltage and improve the current efficiency of the organic electronic device using the same.

In accordance with the present invention, the first host compound may be represented by the following Formula (I'):

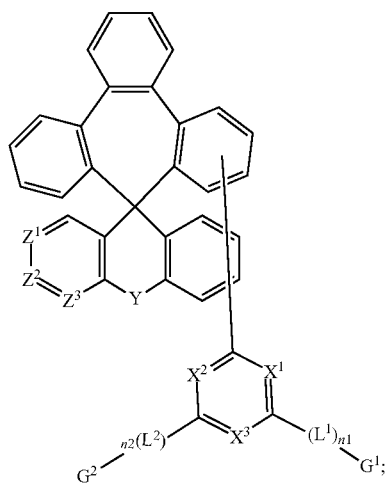

Formula (I')

wherein Y, $Z^1$ to $Z^3$, $X^1$ to $X^3$, $L^1$, $L^2$, n1, n2, $G^1$ and $G^2$ are as stated above.

In the case that Y is a single bond and all of $Z^1$ to $Z^3$ are each a (CH), and the first host compound may be, for example, represented by

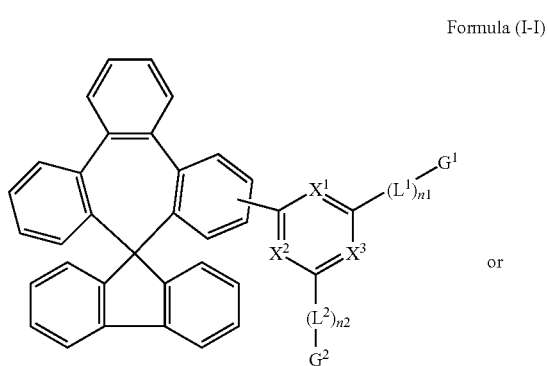

Formula (I-I)

or

Formula (I-XVI)

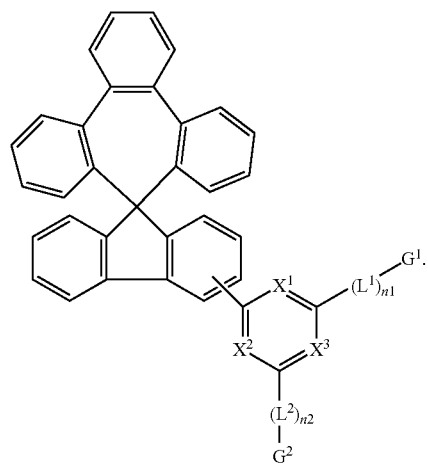

In the case that Y is a single bond, adjacent two of $Z^1$ to $Z^3$ are joined together to form a heteroaryl ring containing at least one furan group and the remaining one of $Z^1$ to $Z^3$ is CH, the first host compound may be, for example, represented by Formula (I-II)

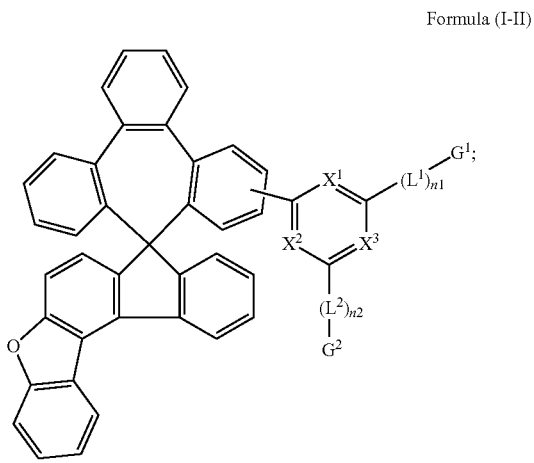

Formula (I-III)

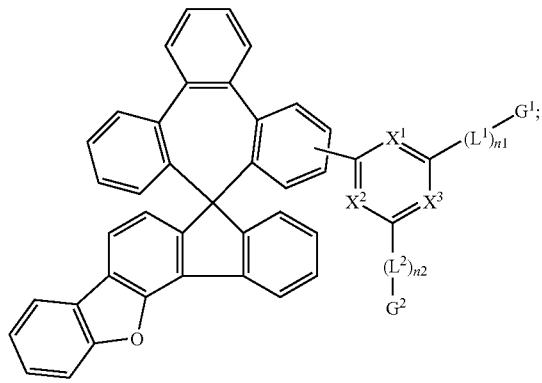

Formula (I-VI)

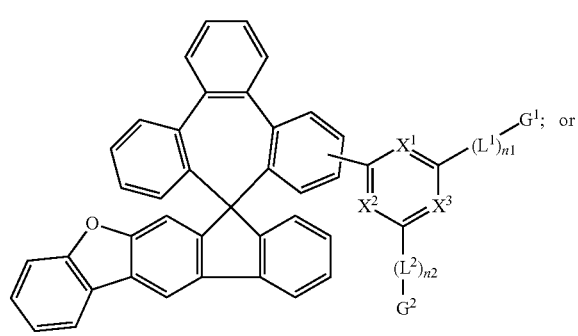

Formula (I-VII)

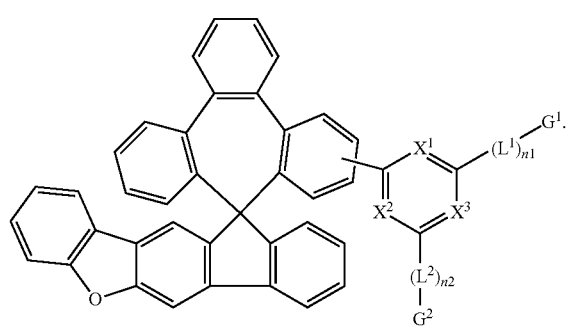

Formula (I-IV)

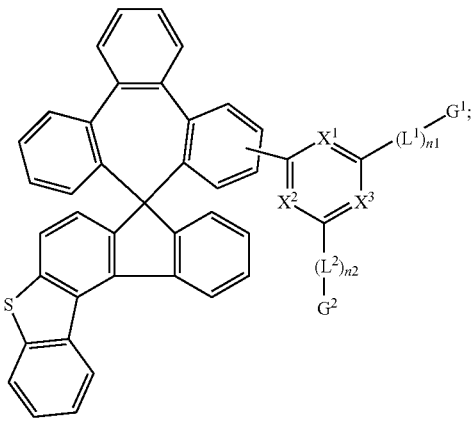

Formula (I-V)

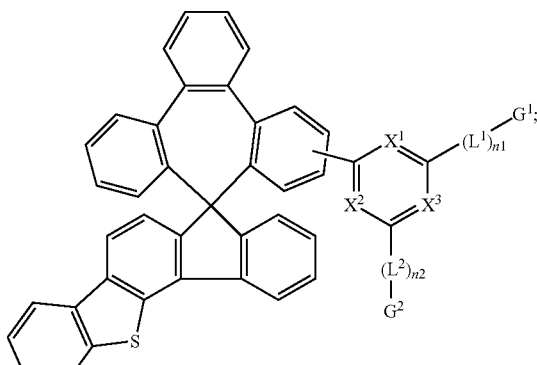

Formula (I-VIII)

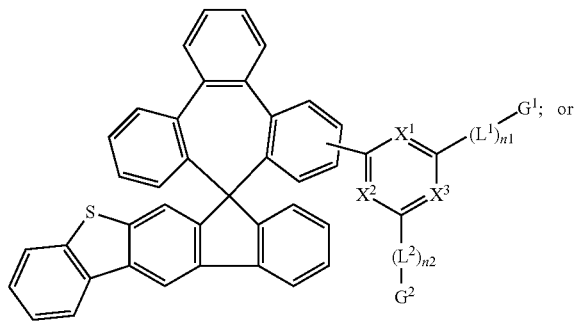

Formula (I-IX)

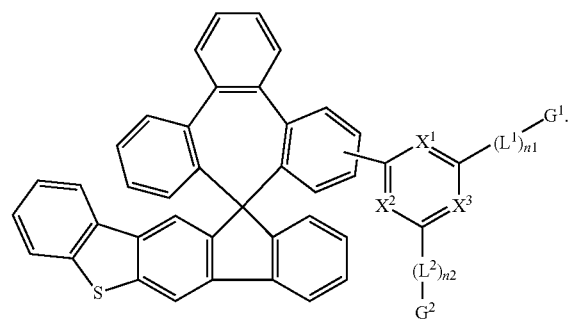

For Formulae (I-II) and (I-III), $Z^1$ is CH and $Z^2$ and $Z^3$ are joined together to form one furan group.

For Formulae (I-VI) and (I-VII), $Z^1$ and $Z^2$ are joined together to form one furan group and $Z^3$ is CH.

In the case that Y is a single bond, adjacent two of $Z^1$ to $Z^3$ are joined together to form a heteroaryl ring containing at least one thiophene group and the remaining one of $Z^1$ to $Z^3$ is CH, the first host compound may be, for example, represented by For Formulae (I-IV) and (I-V), $Z^1$ is CH and $Z^2$ and $Z^3$ are joined together to form one thiophene group.

For Formulae (I-VIII) and (I-IX), $Z^1$ and $Z^2$ are joined together to form one thiophene group and $Z^3$ is CH.

In the case that Y is an oxygen atom and $Z^1$ to $Z^3$ are each independently CH, or in the case that Y is an oxygen atom and adjacent two of $Z^1$ to $Z^3$ are joined together to form an aryl ring and the remaining one of $Z^1$ to $Z^3$ is CH, and the first host compound may be, for example, represented by Formula (I-X)

Formula (I-XI)

Formula (I-XII)

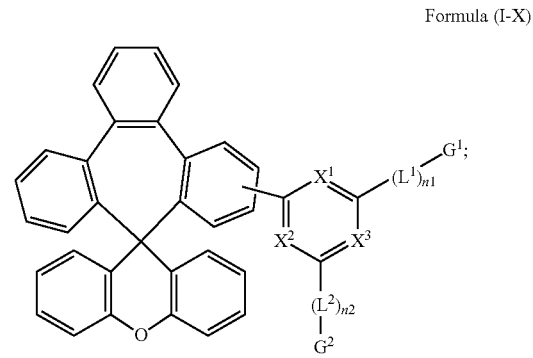

For Formula (I-X), all of $Z^1$ to $Z^3$ are each a (CH).

For Formula (I-XI), $Z^1$ is CH and $Z^2$ and $Z^3$ are joined together to form one naphthyl group.

For Formula (I-XII), $Z^1$ and $Z^2$ are joined together to form one naphthyl group and $Z^3$ is CH.

In the case that Y is a sulfur atom and $Z^1$ to $Z^3$ are each independently CH, or in the case that Y is a sulfur atom and adjacent two of $Z^1$ to $Z^3$ are joined together to form an aryl ring and the remaining one of $Z^1$ to $Z^3$ is CH, the first host compound may be, for example, represented by Formula (I-XIII)

Formula (I-XIV)

Formula (I-XV)

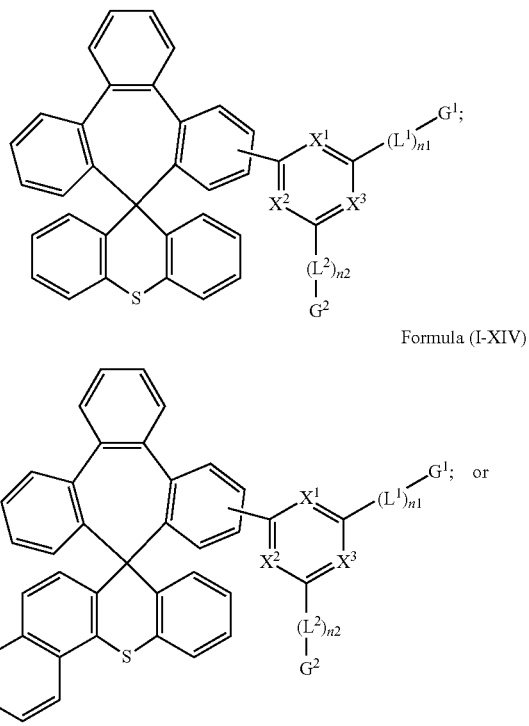

For Formula (I-XIII), all of $Z^1$ to $Z^3$ are each a (CH).

For Formula (I-XIV), $Z^1$ is CH and $Z^2$ and $Z^3$ are joined together to form one naphthyl group.

For Formula (I-XV), $Z^1$ and $Z^2$ are joined together to form one naphthyl group and $Z^3$ is CH.

Preferably, L', $L^1$ and $L^2$ are each independently a phenylene group.

Preferably, n' is the integer 0 or 1.

Preferably, n1 and n2 are each independently the integer 0 or 1. In some cases, both n1 and n2 are the integer 0. In some other cases, both n1 and n2 are the integer 1. In some other cases, n1 is the integer 1 and n2 is the integer 0. In some other cases, n1 is 0 and n2 is the integer 1.

Specifically, $G^1$ and $G^2$ may be a specific aromatic substitution. The specific aromatic substitution may be selected from the group consisting of:

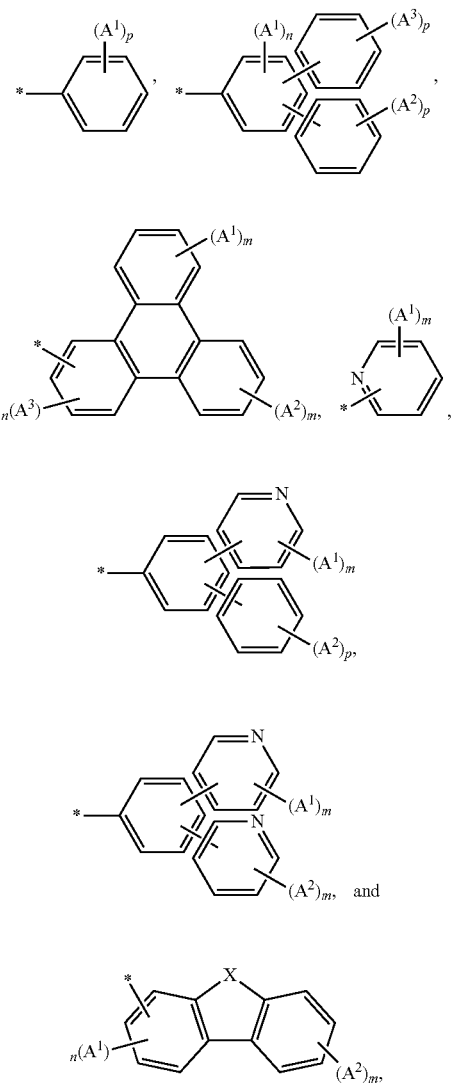

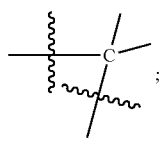

where X is O, S, or wherein * is the bonding site;

p is an integer from 1 to 5, m is an integer from 1 to 4, n is an integer from 1 to 3; and $A^1$ to $A^3$ are each independently selected from the group consisting of: a hydrogen atom, a deuterium atom, a halo group, a cyano group, a nitro group, an alkyl group having 1 to 6 carbon atoms, an alkenyl group having 2 to 6 carbon atoms, and an alkynyl group having 2 to 6 carbon atoms.

Specifically, the group of $(L^1)_{n1}$-$G^1$ and $(L^2)_{n2}$-$G^2$ of the first host compound represented by Formula (I) or Formula (I') may be each independently selected from the group consisting of:

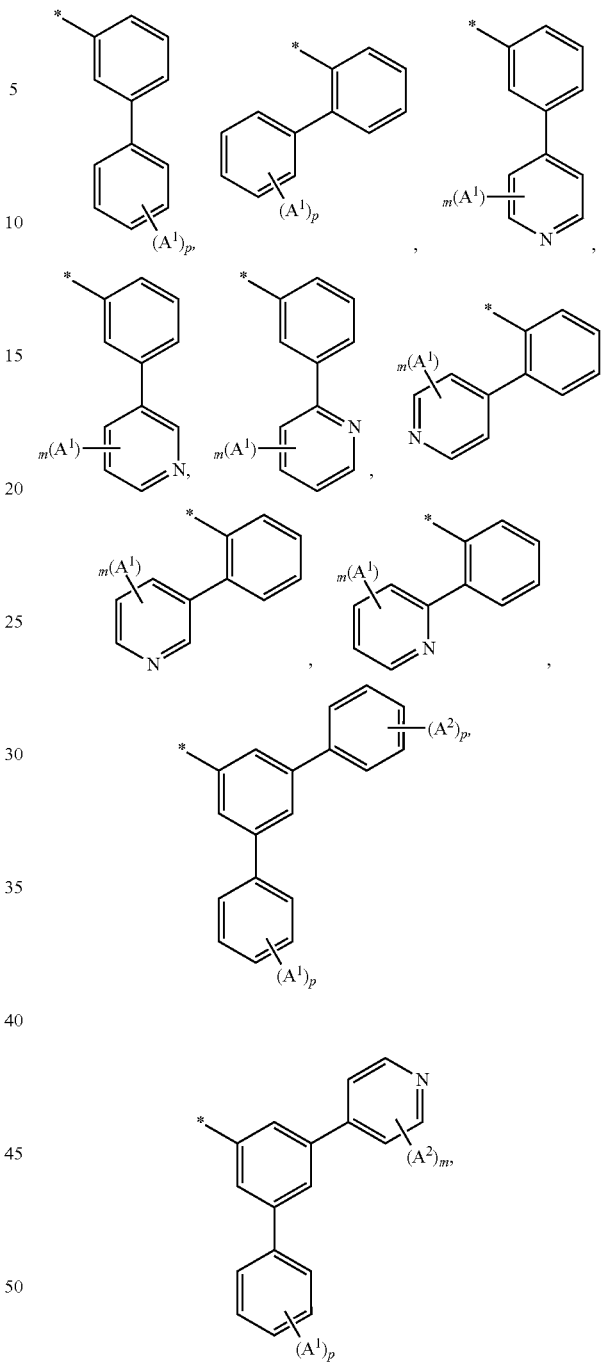

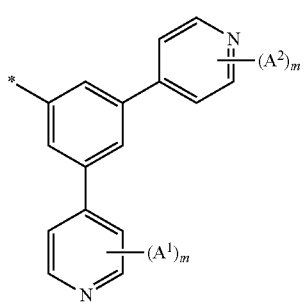

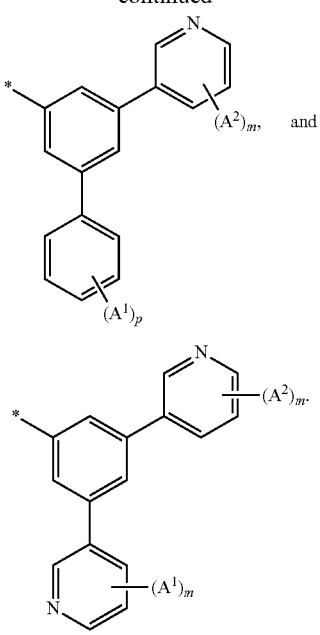

Preferably, the aryl group having 6 to 18 ring carbon atoms represented by $G^1$ or $G^2$ may be selected from the group consisting of:

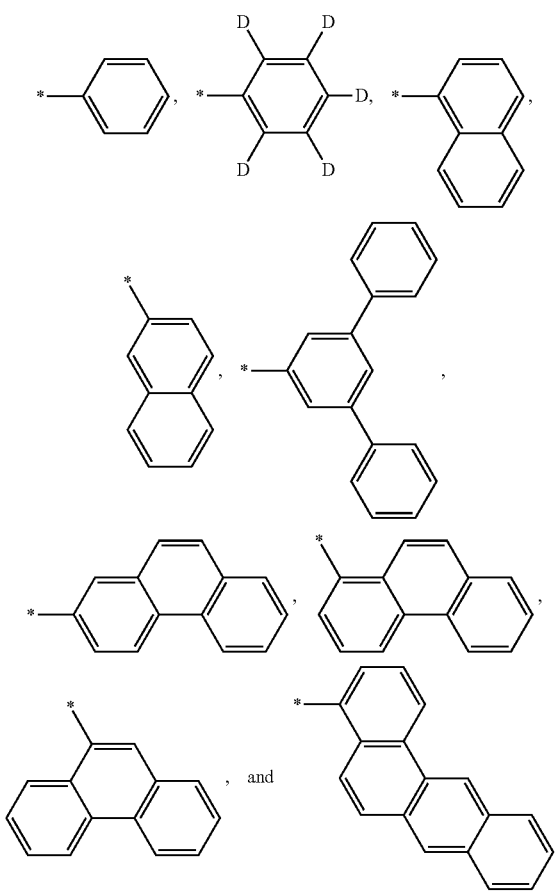

More preferably, the aryl group having 6 to 18 ring carbon atoms represented by $G^1$ or $G^2$ may be selected from the group consisting of: a phenyl group, a naphthyl group and a 3, 5-diphenylphenyl group.

Preferably, the heteroaryl group containing a N, O, or S atom and having 3 to 30 ring carbon atoms represented by $G^1$ or $G^2$ may be selected from the group consisting of:

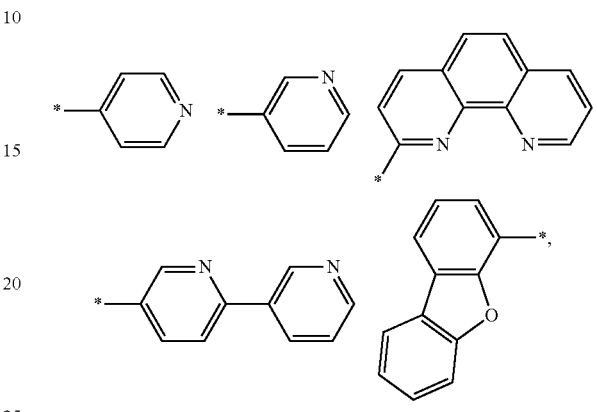

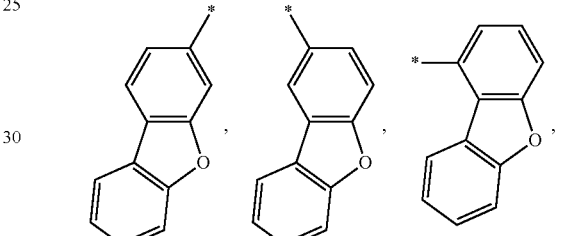

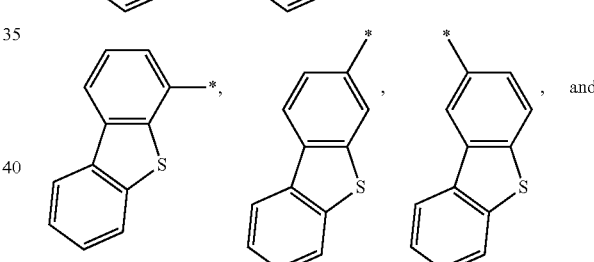

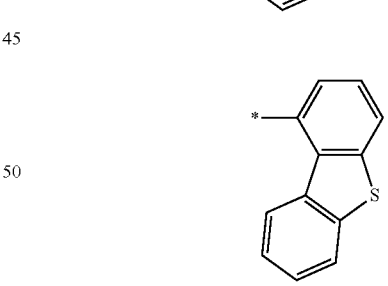

Preferably, the group of

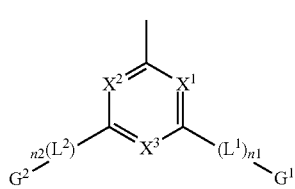

of the first host compound represented by Formula (I) or Formula (I') may be selected from the group consisting of:
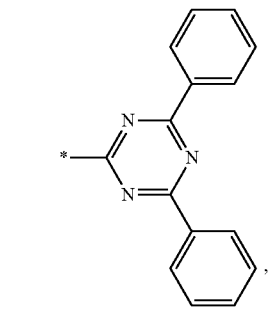
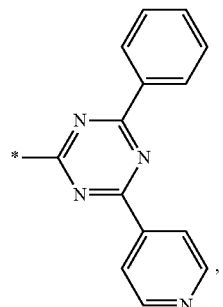
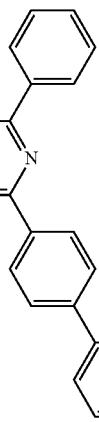
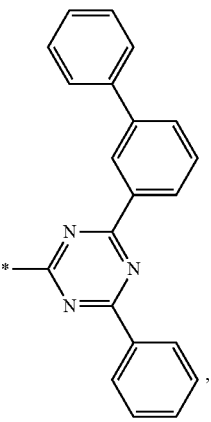
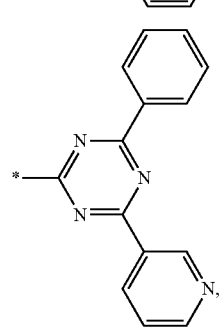
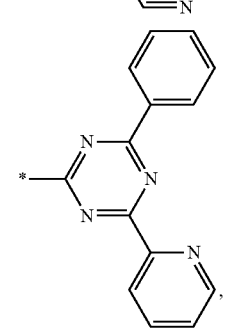
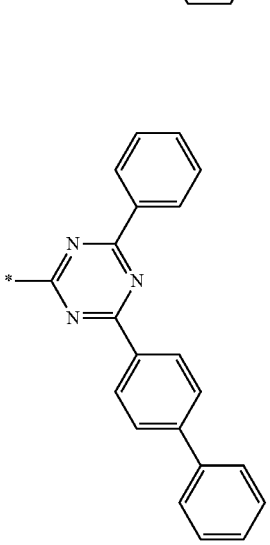
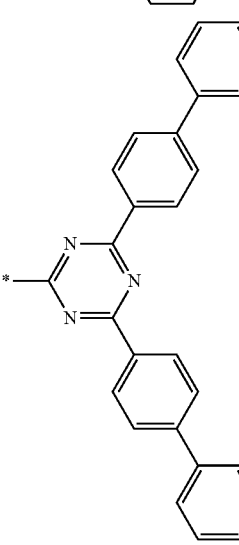
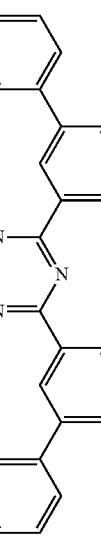
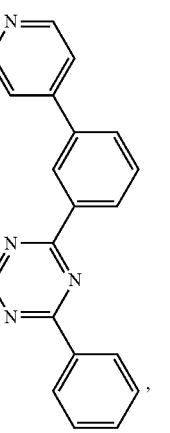
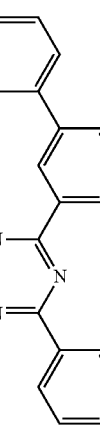
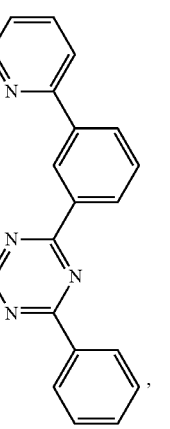

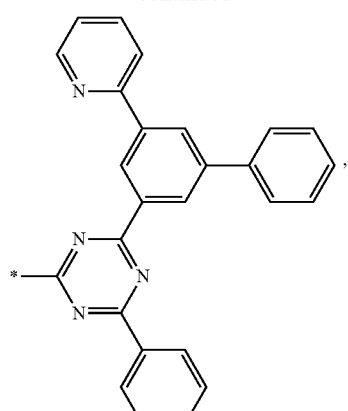
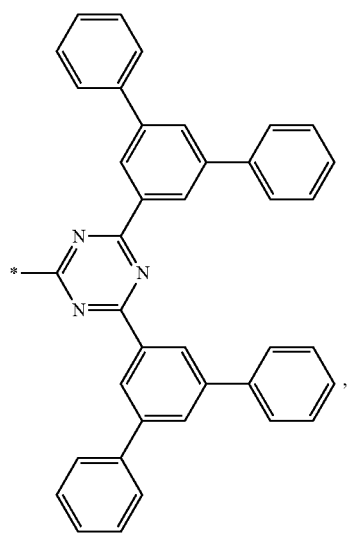
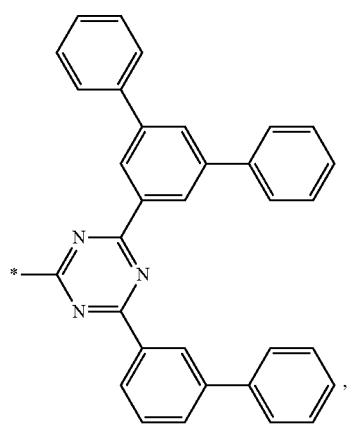
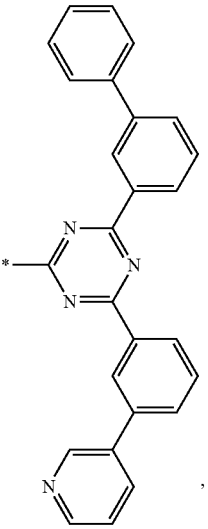
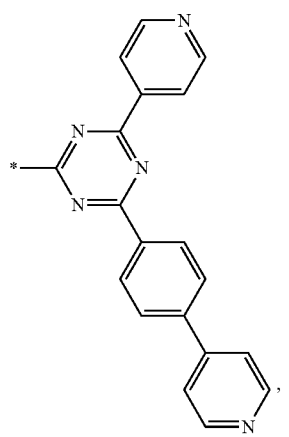
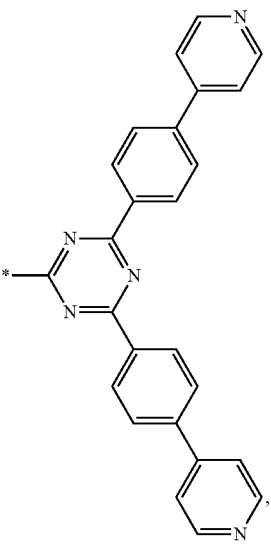

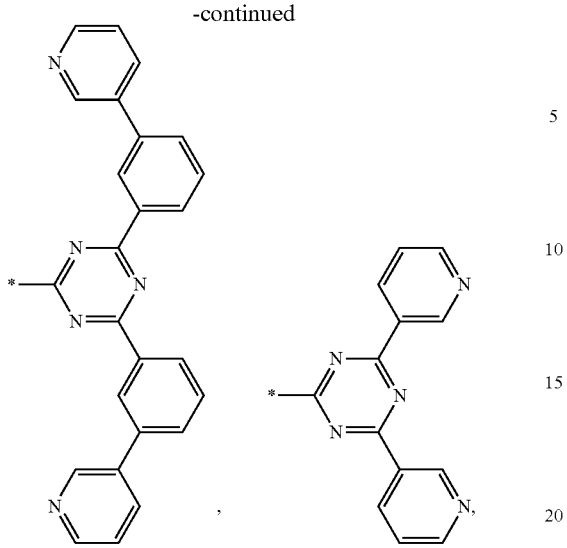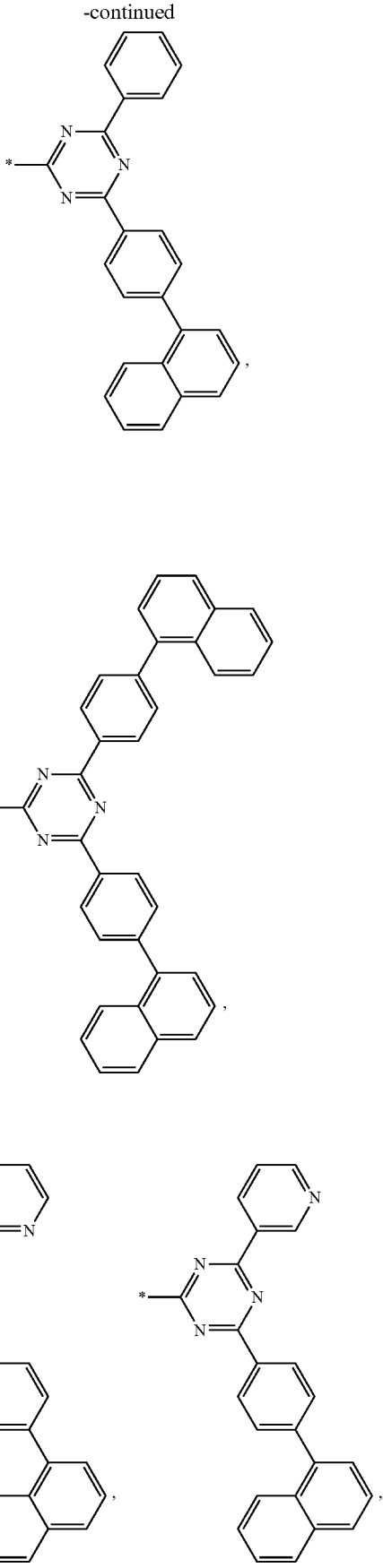

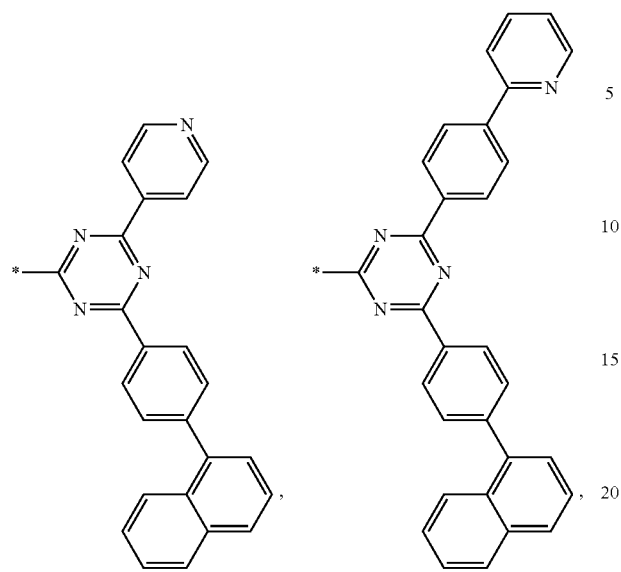
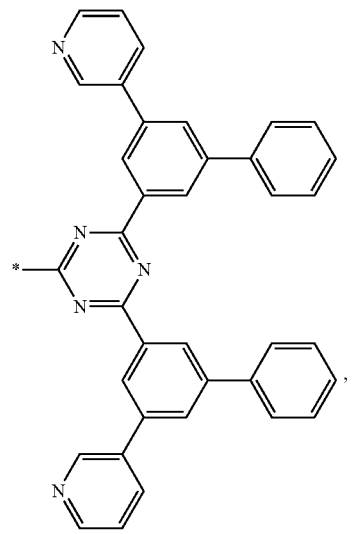
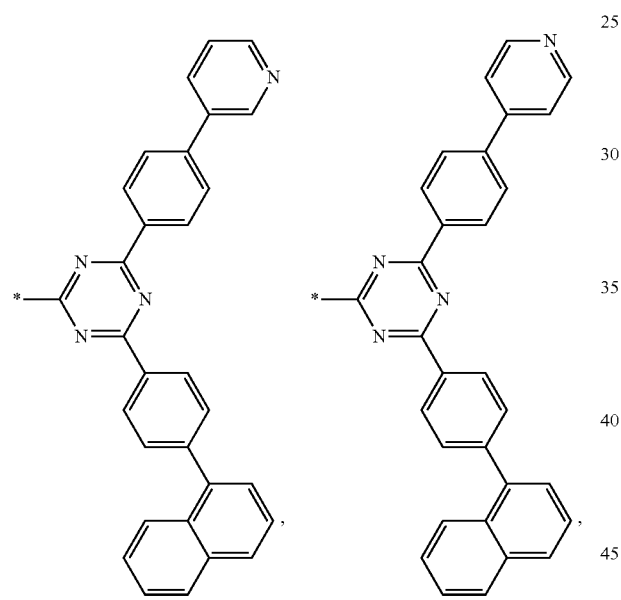
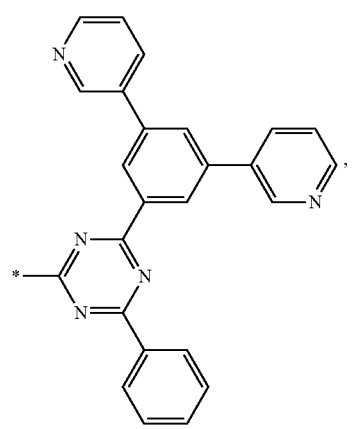
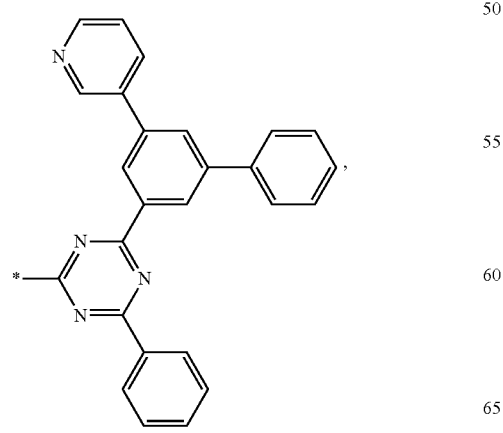
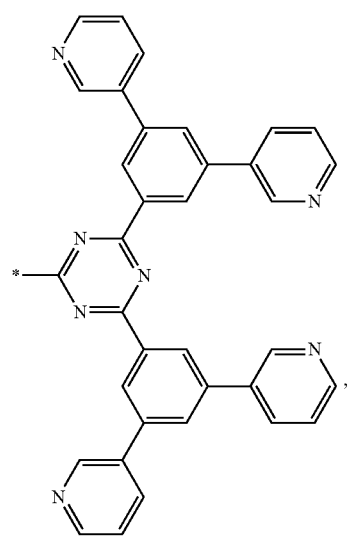

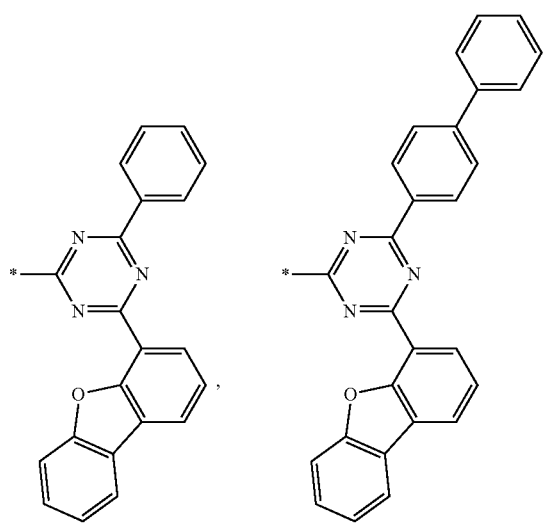
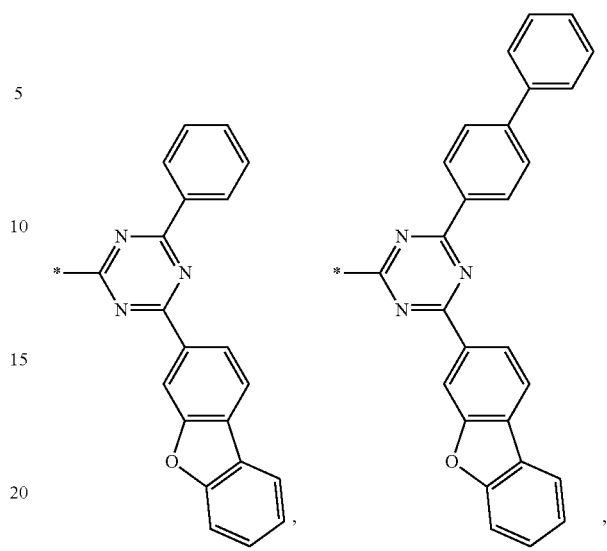
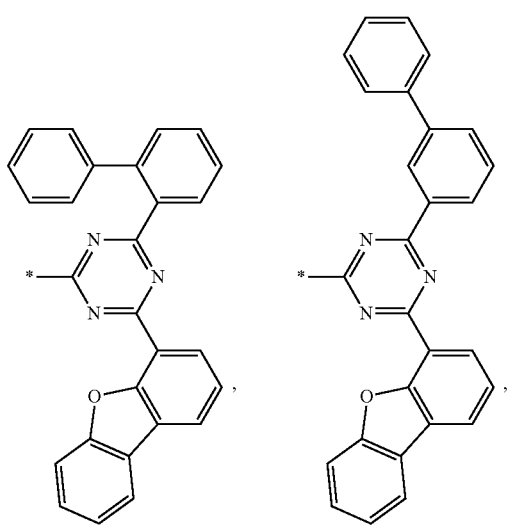
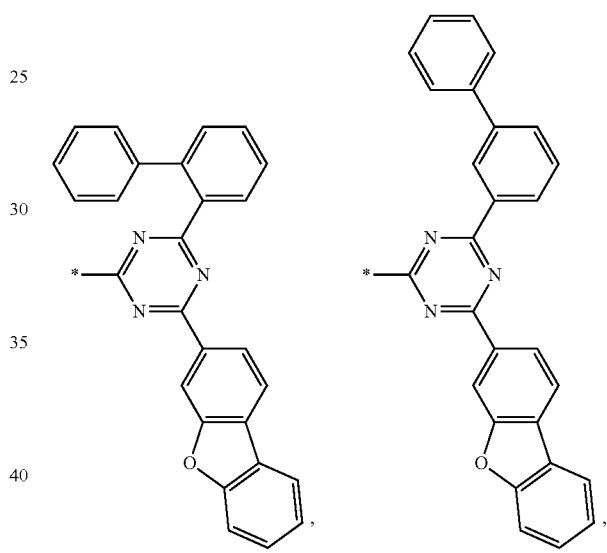
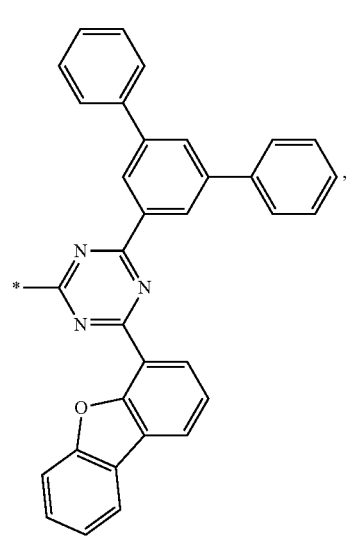
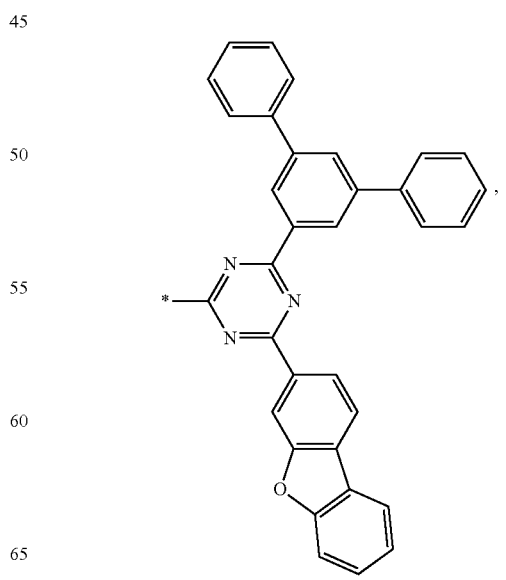

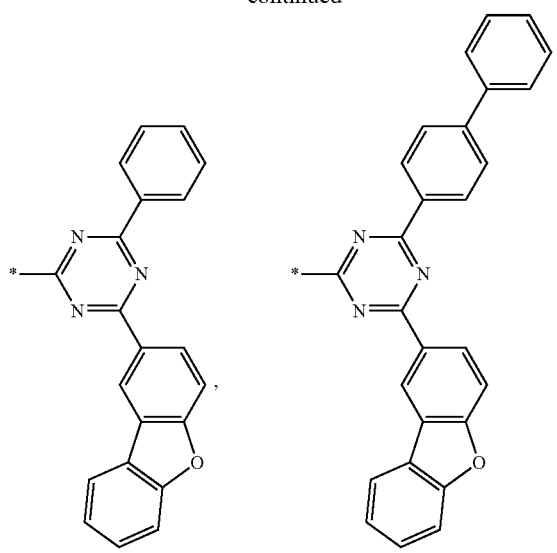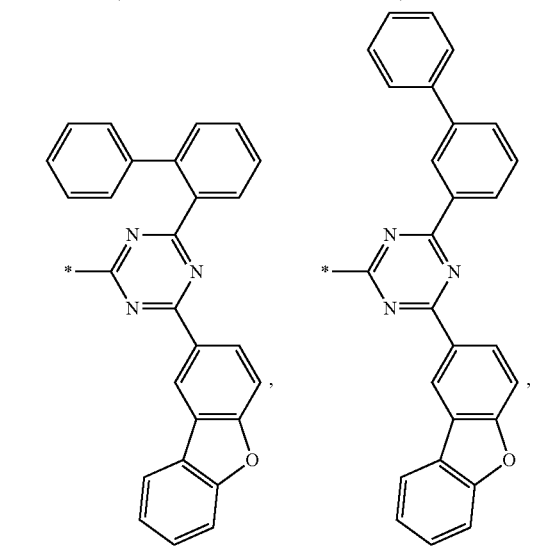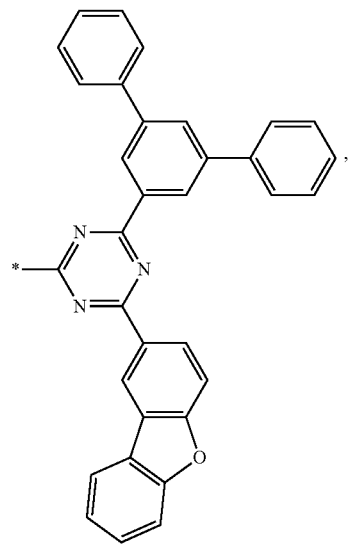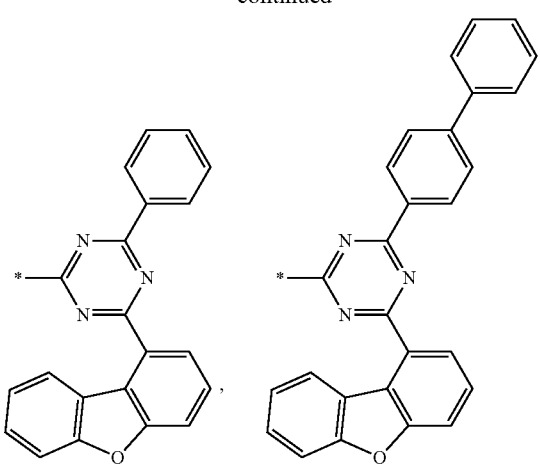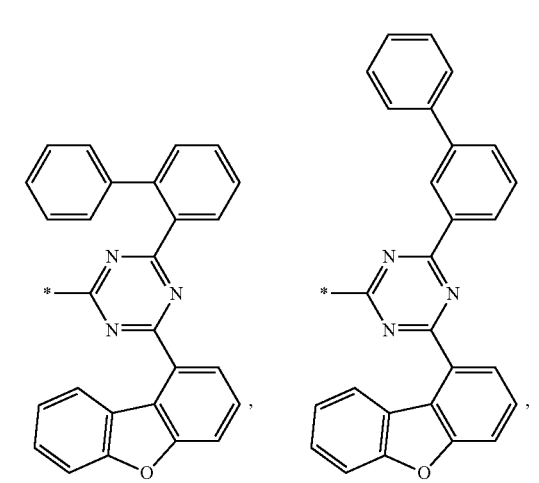

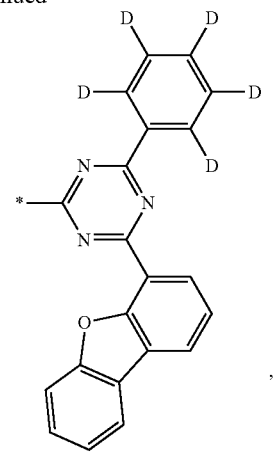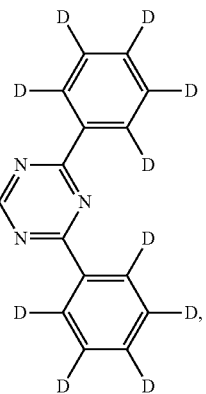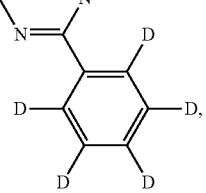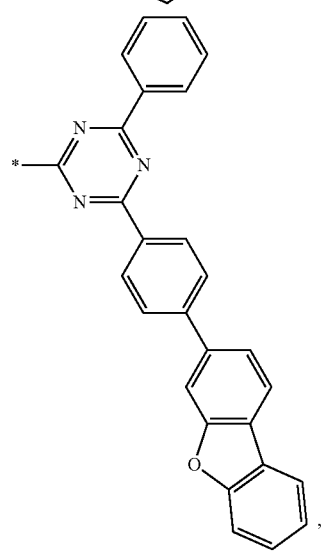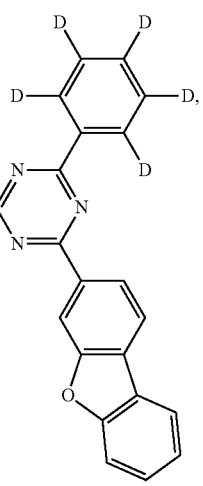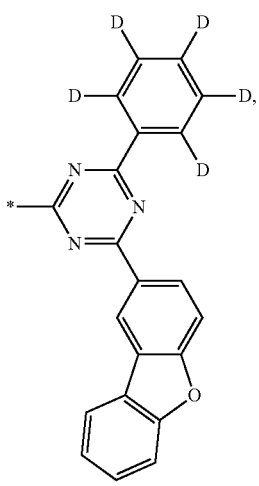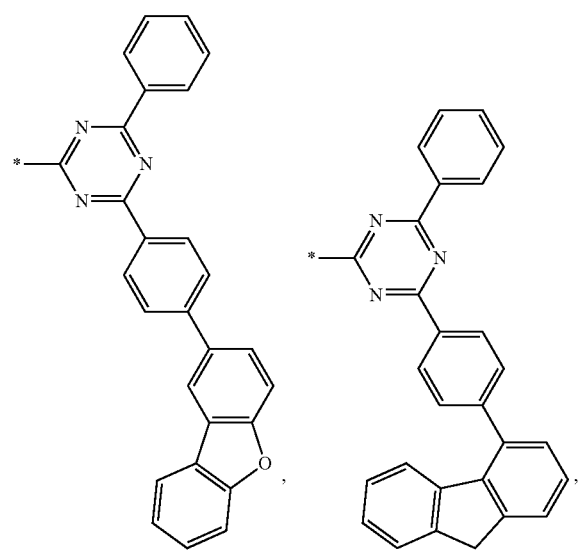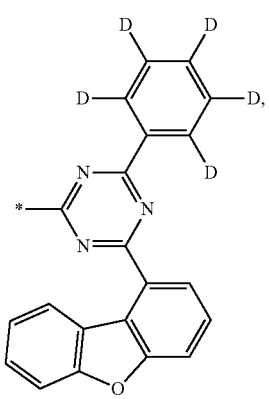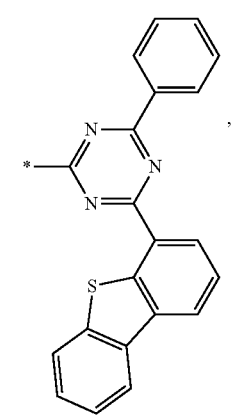

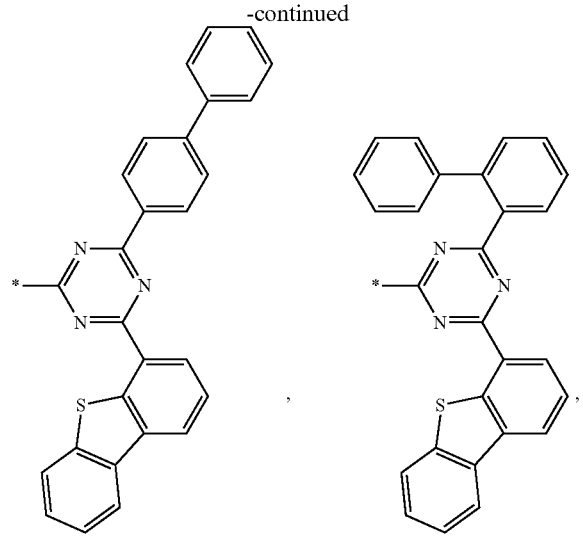
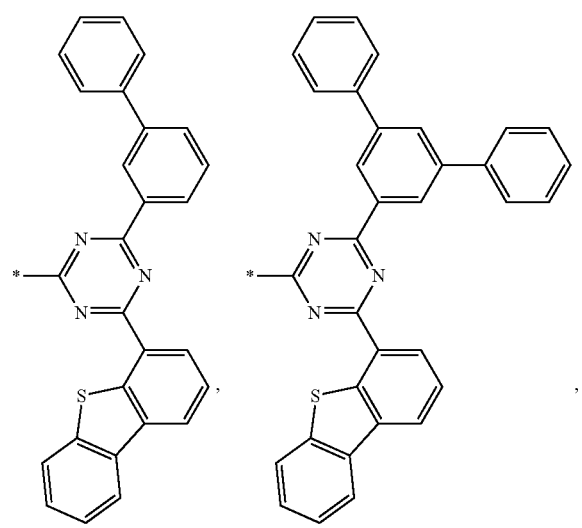
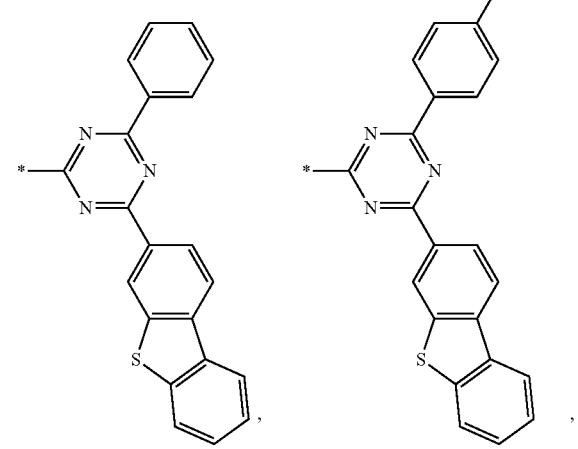
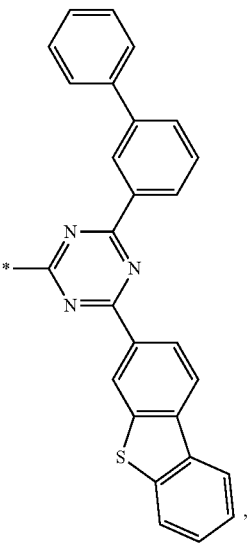
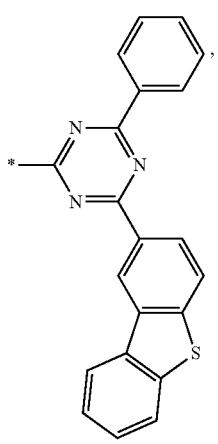
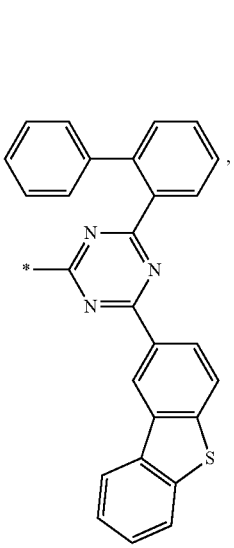

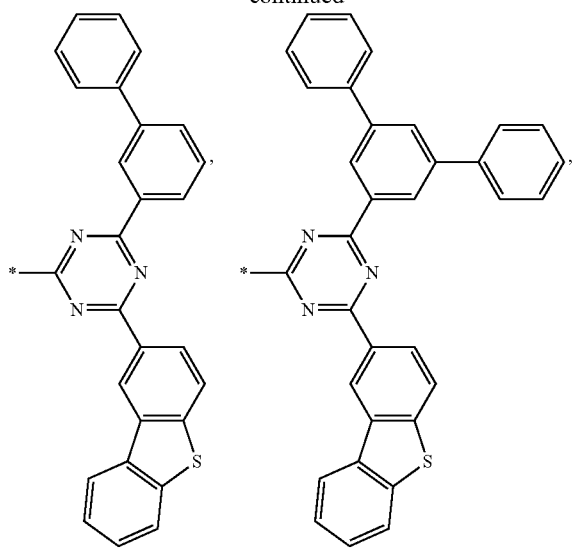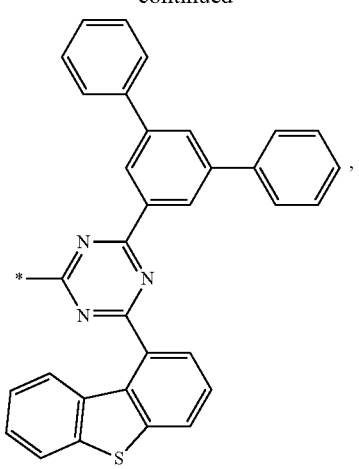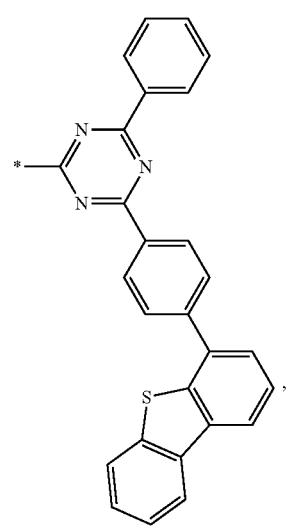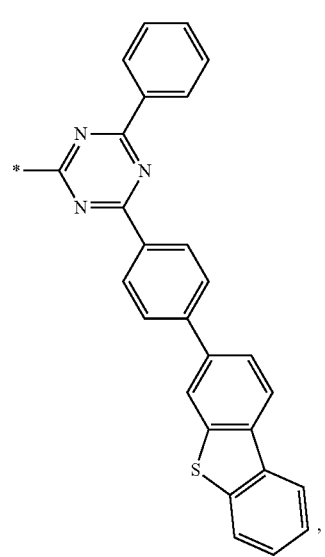

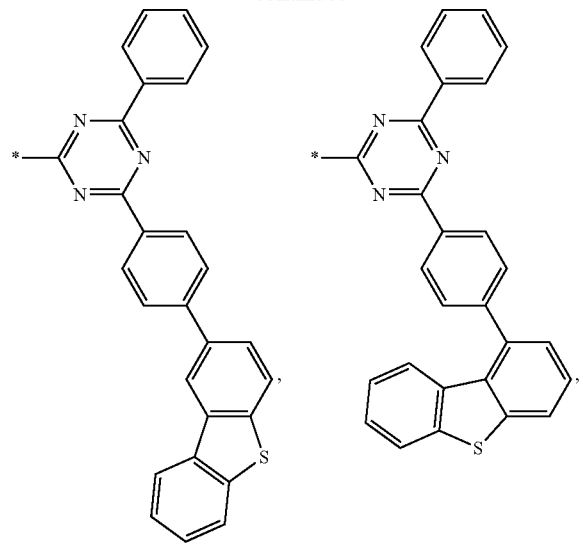

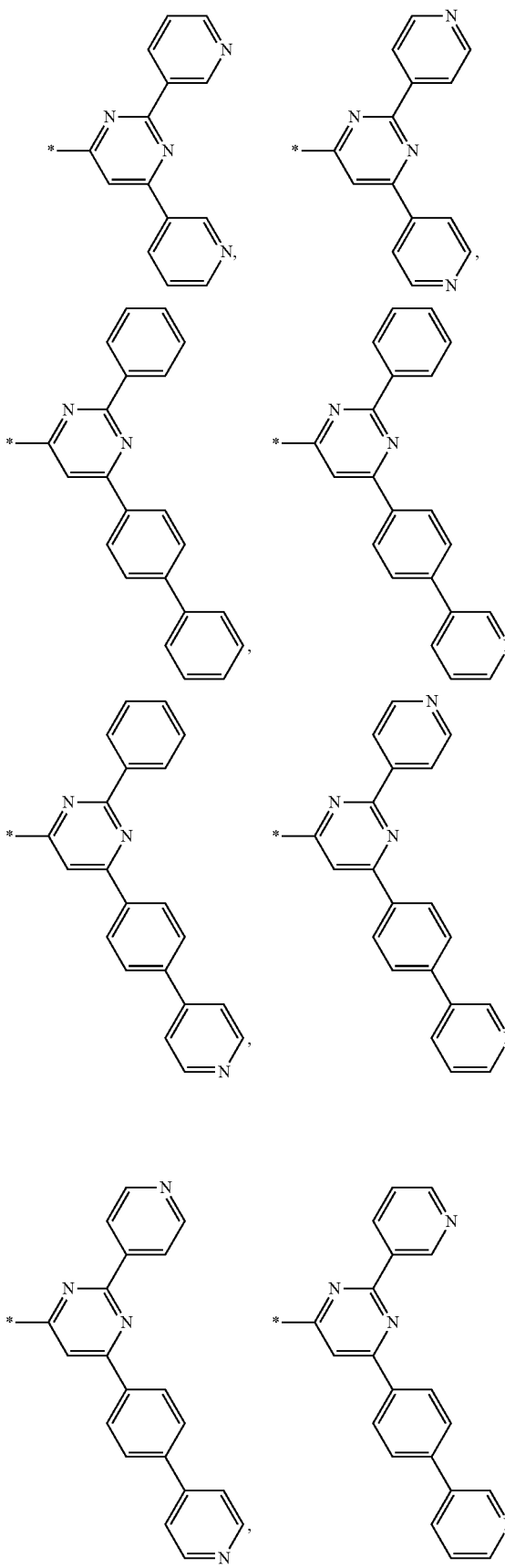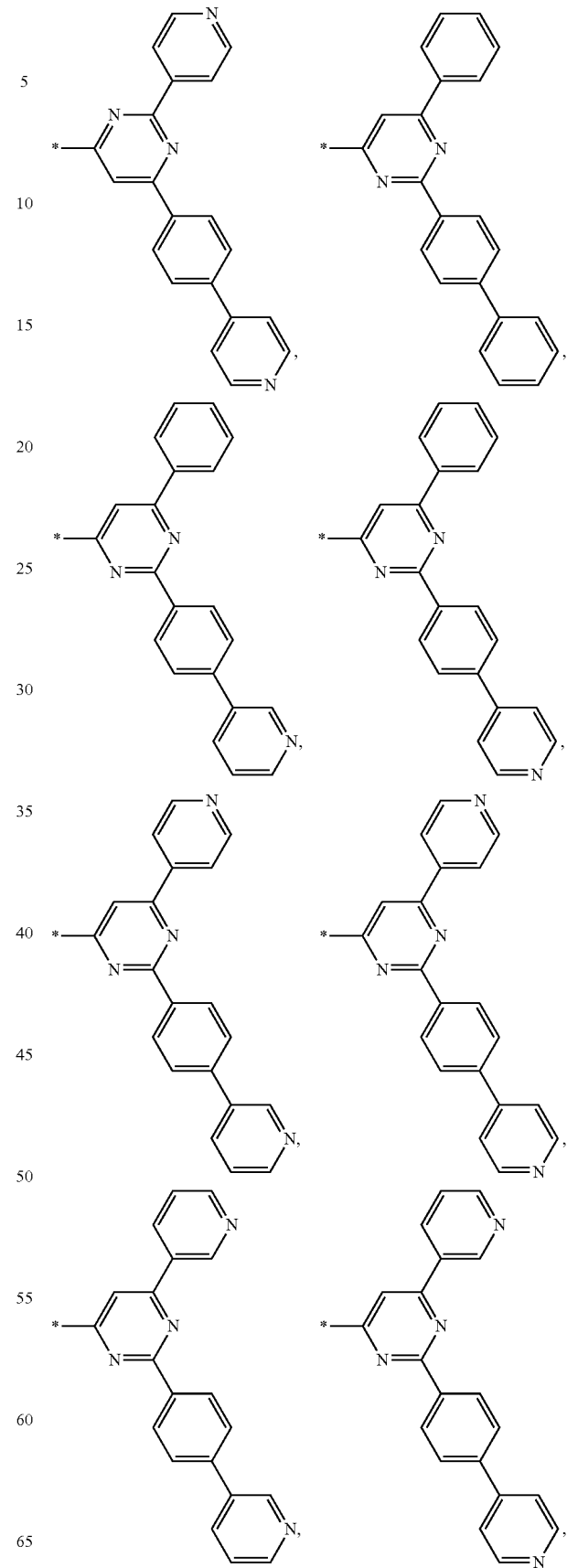

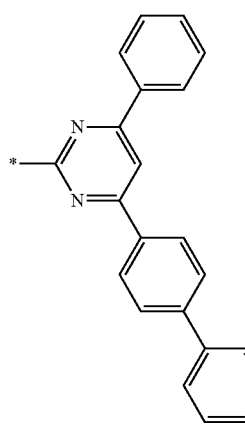
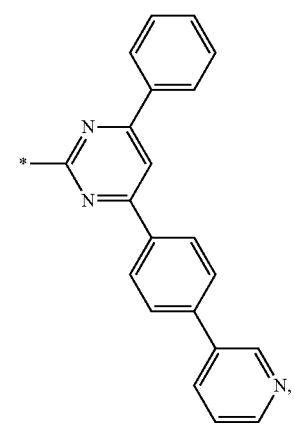
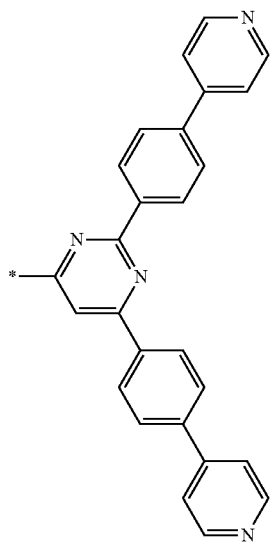
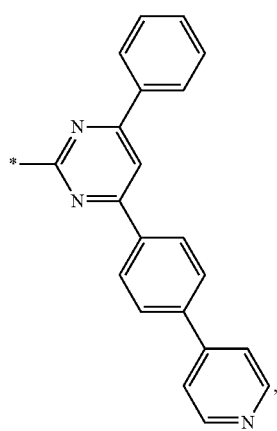
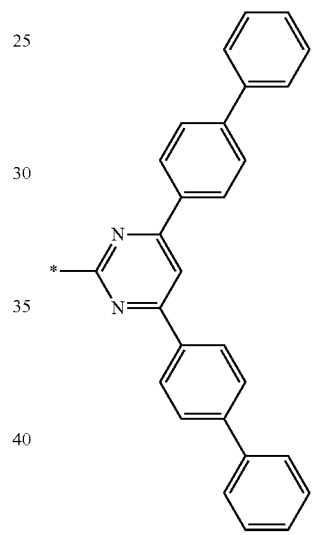
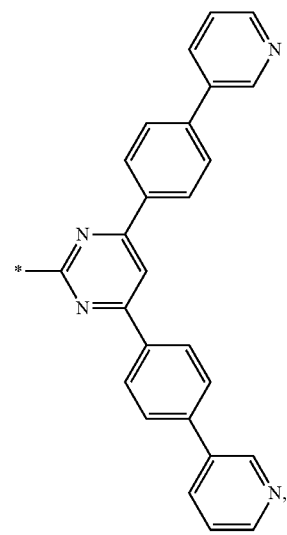
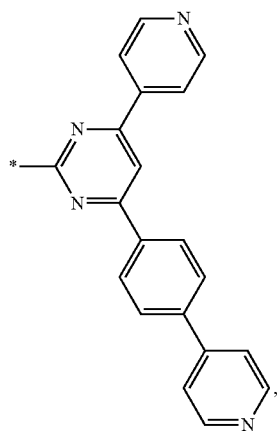
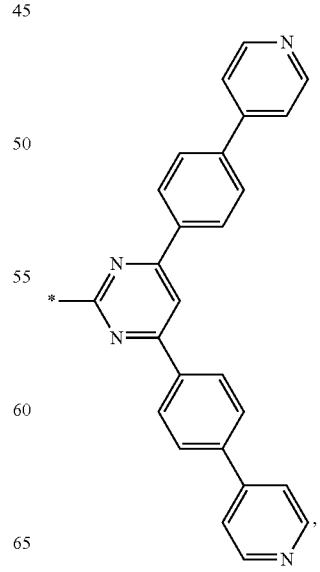
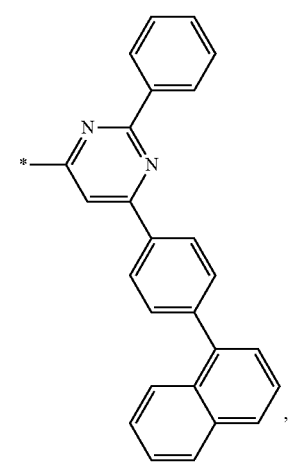

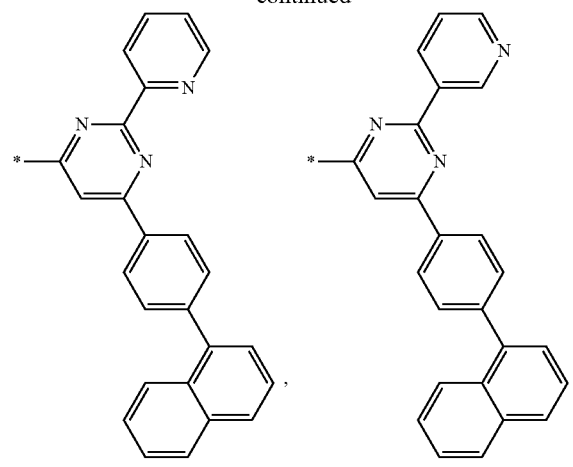
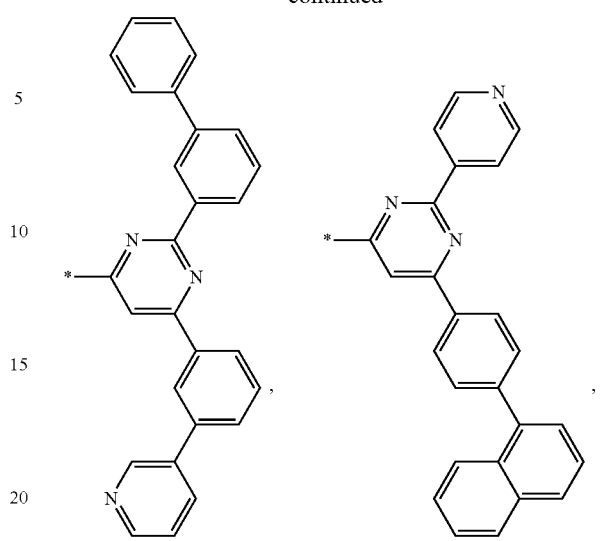
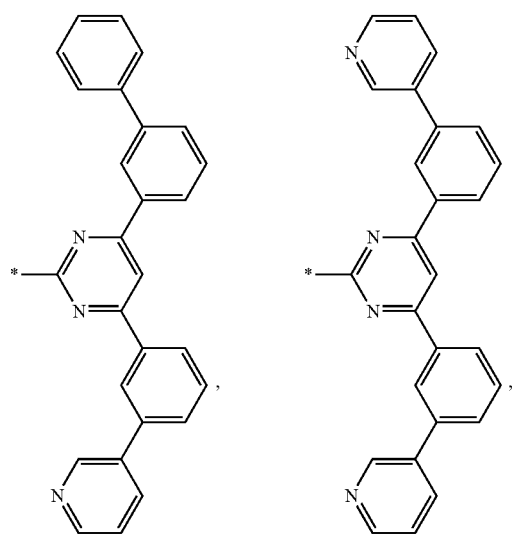
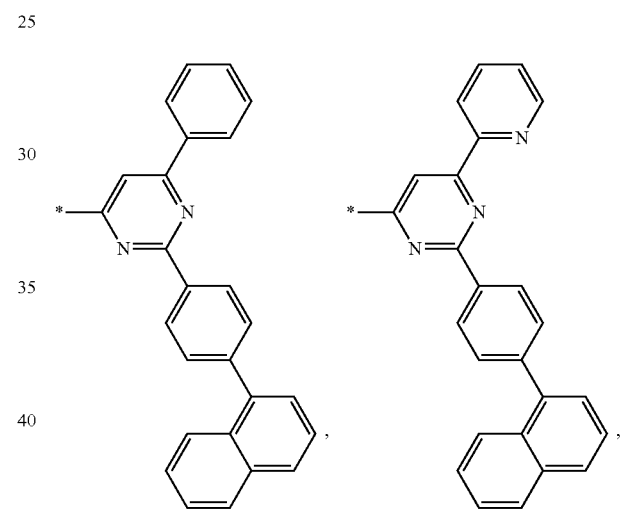
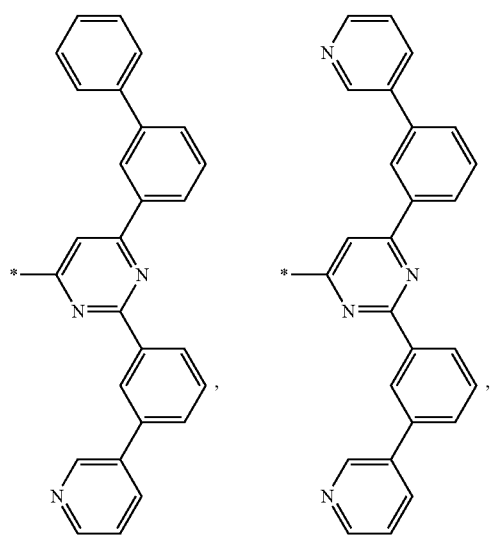
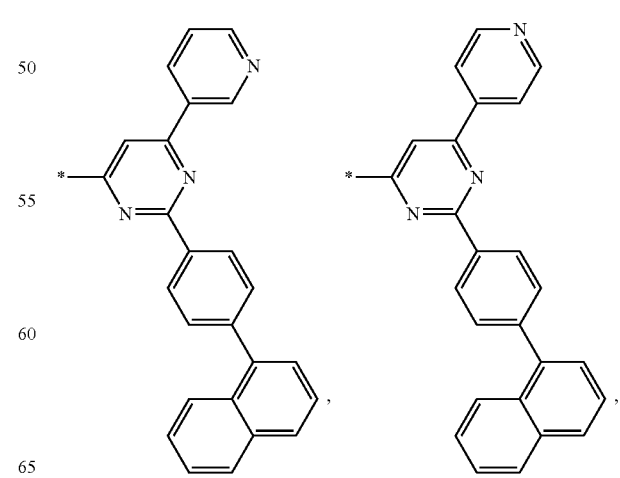

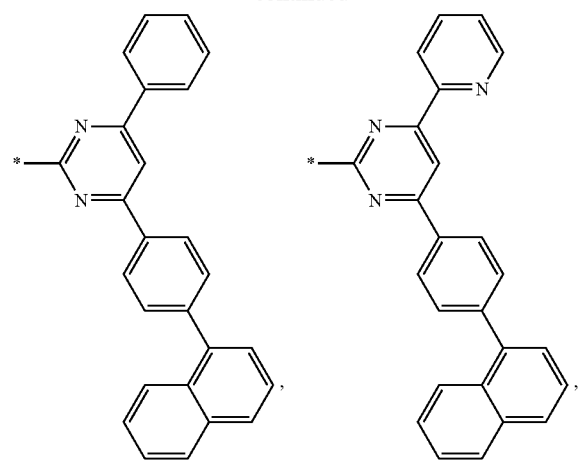
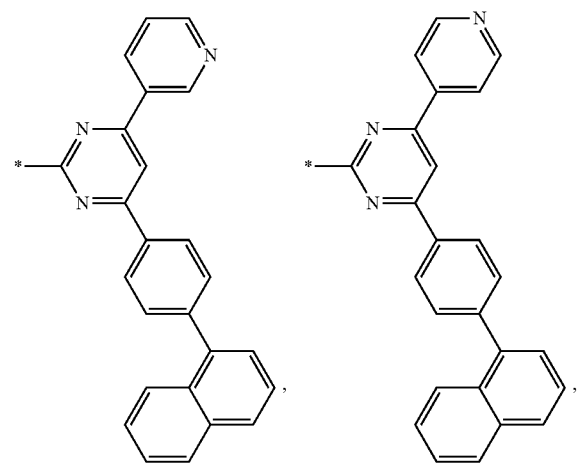
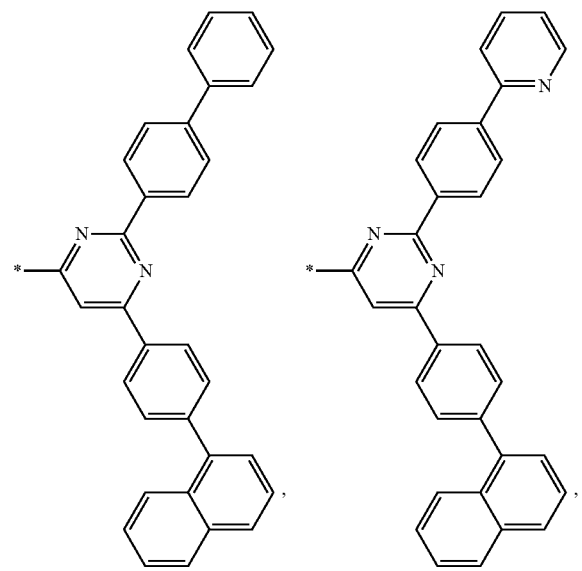 [SMILES: *c1nc(-c2ccncc2)nc(-c2ccc(-c3cccc4ccccc34)cc2)n1 ; *c1nc(-c2ccc(-c3ccccn3)cc2)nc(-c2ccc(-c3cccc4ccccc34)cc2)n1]
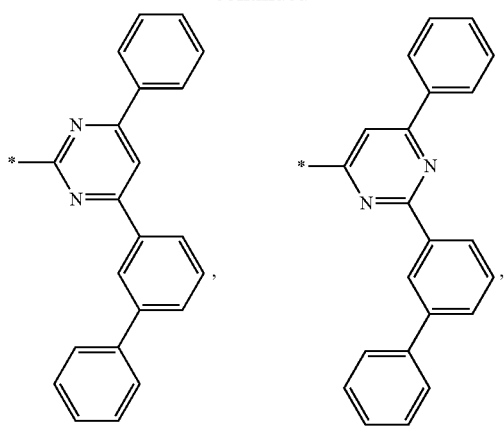
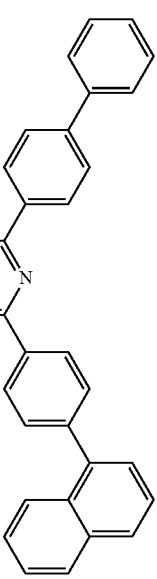
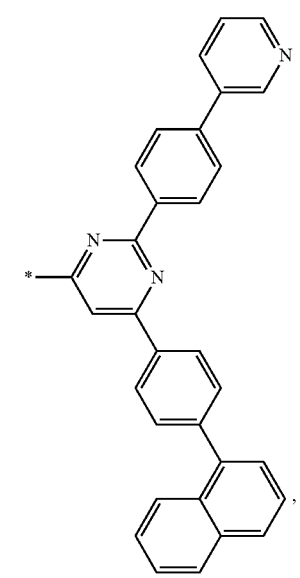

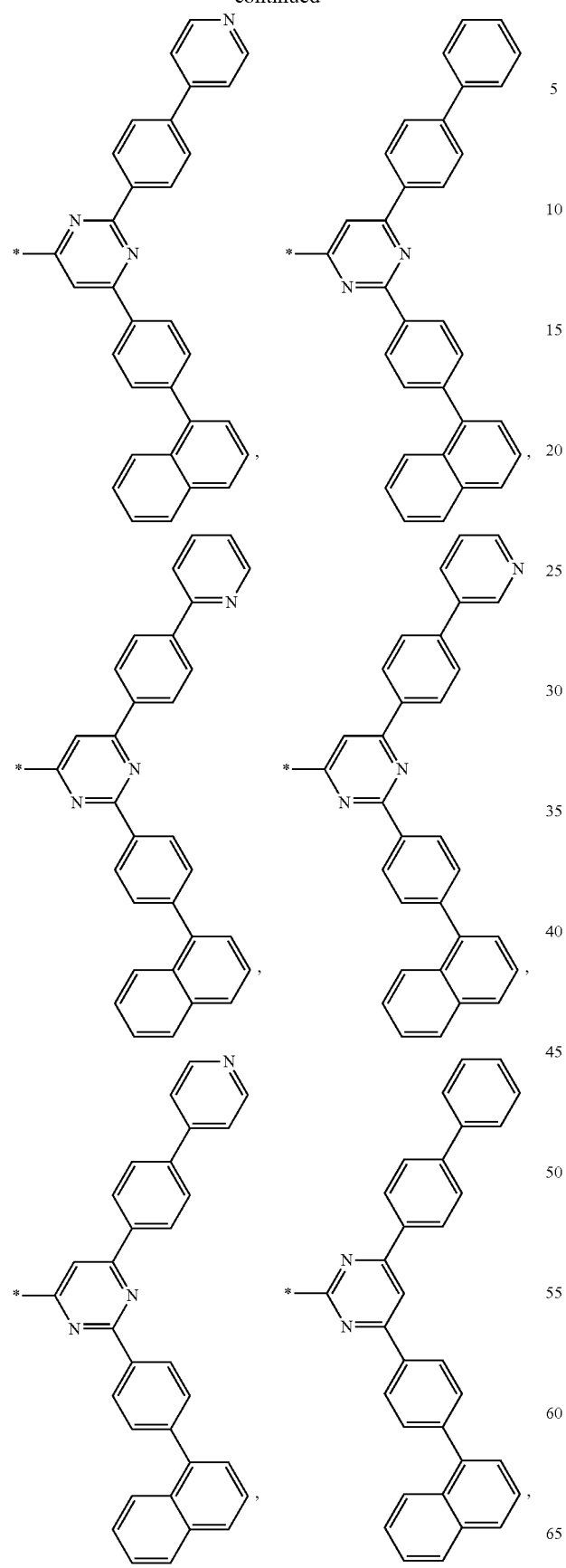
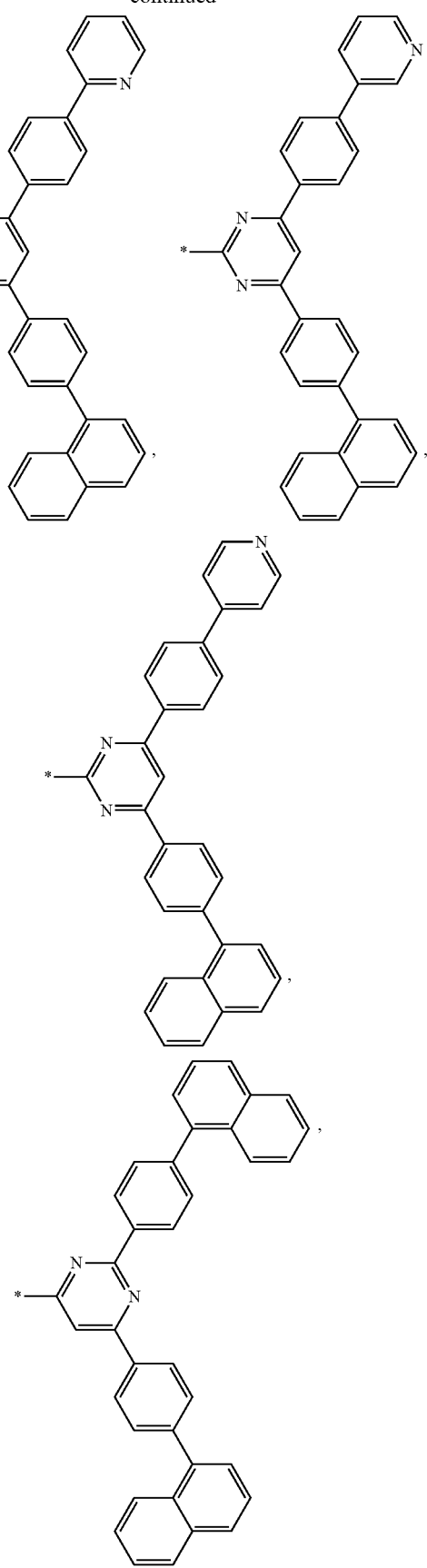

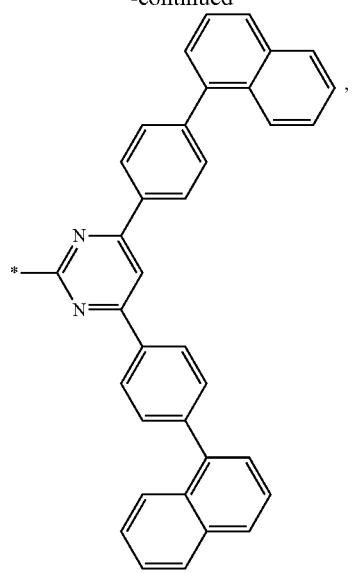
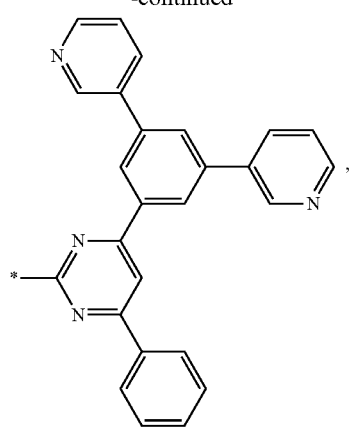
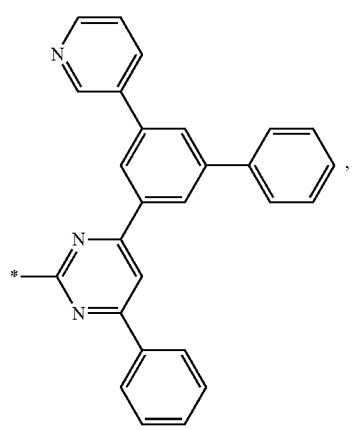
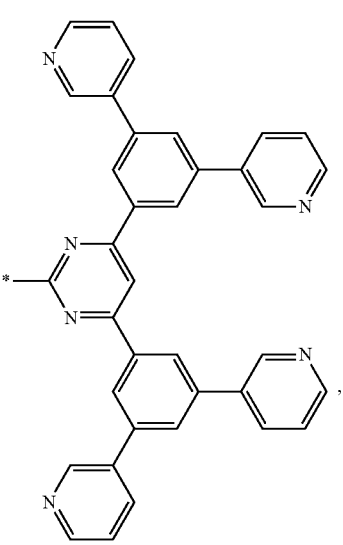
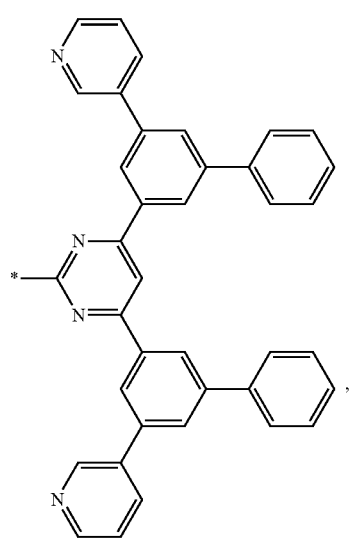
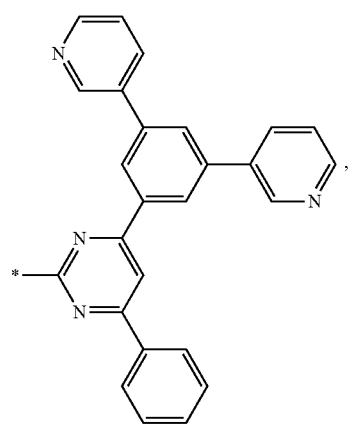

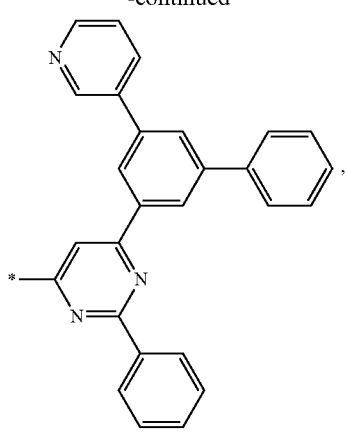
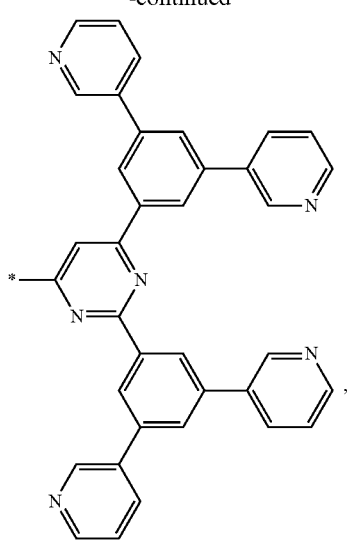
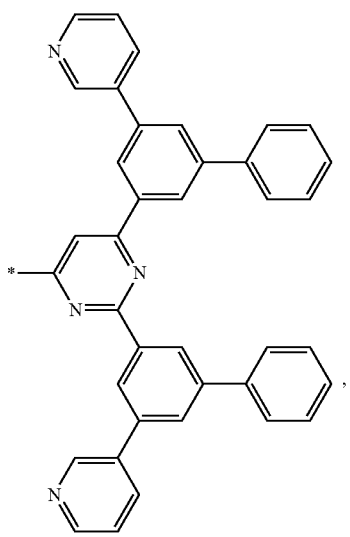
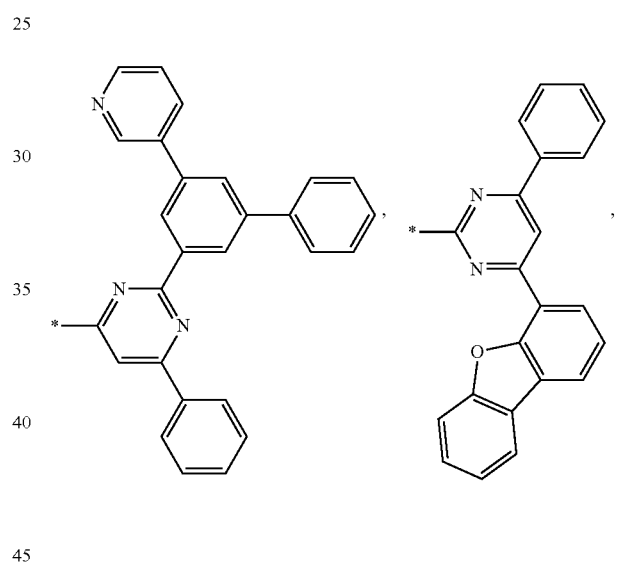
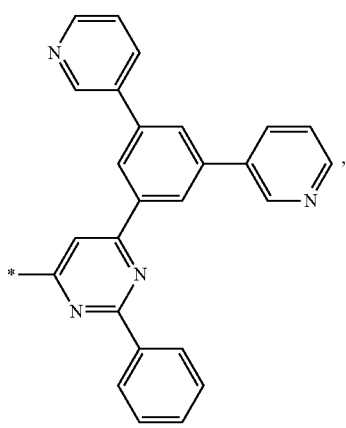
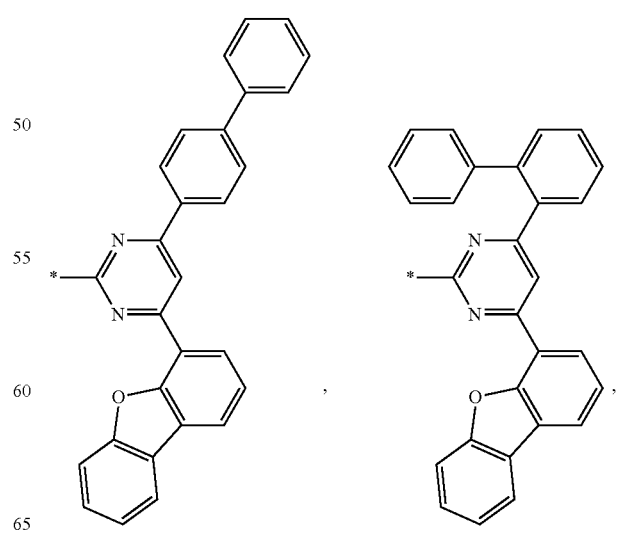

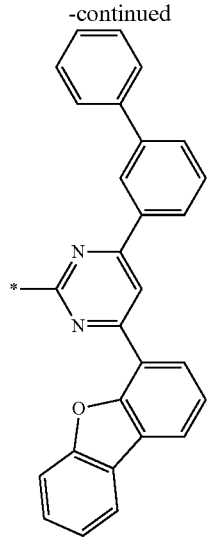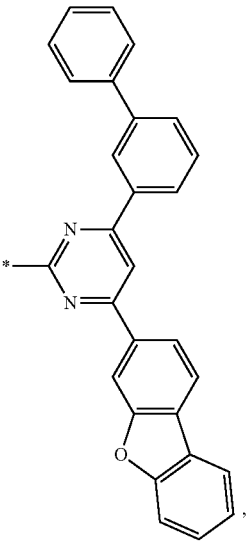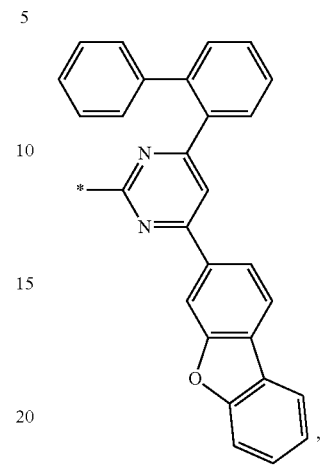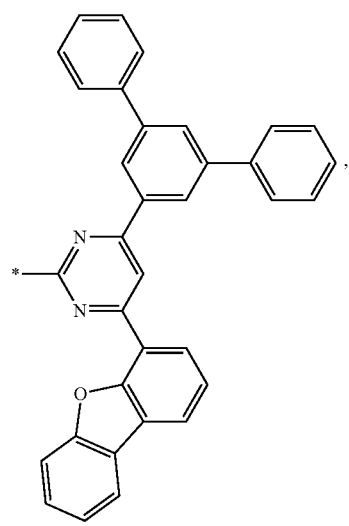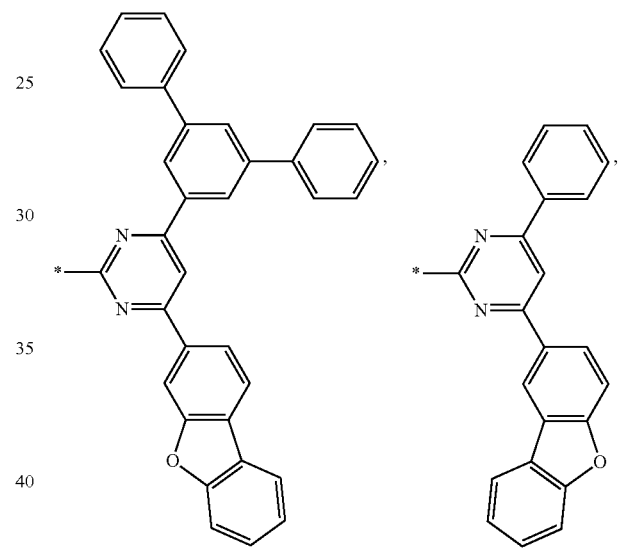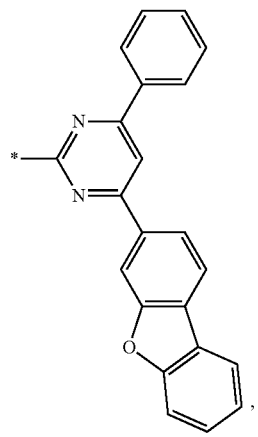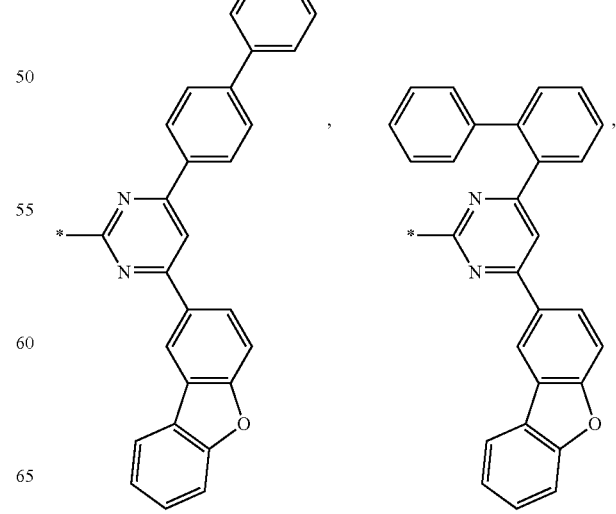

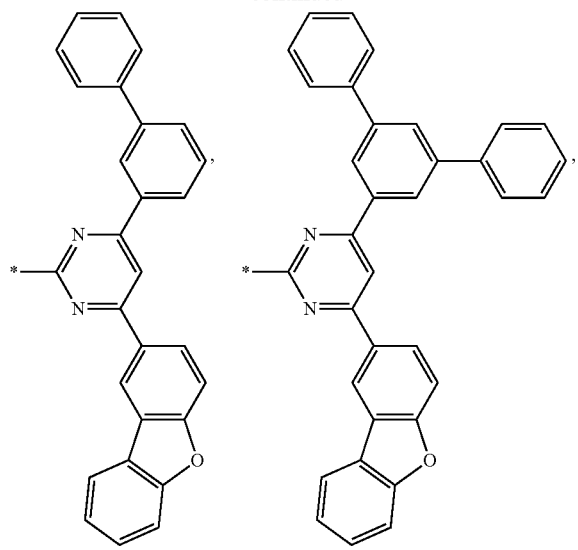
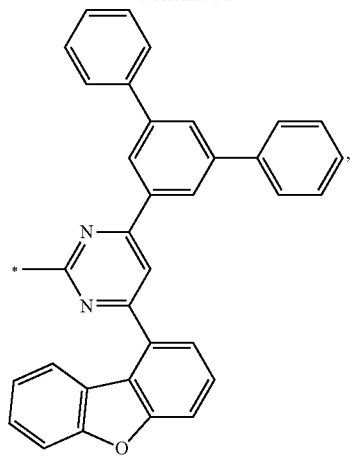
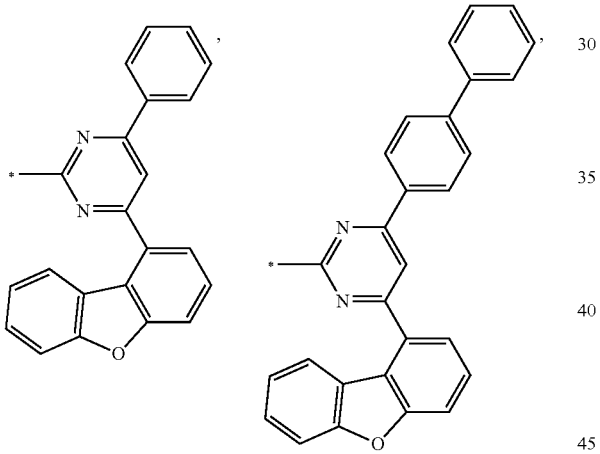
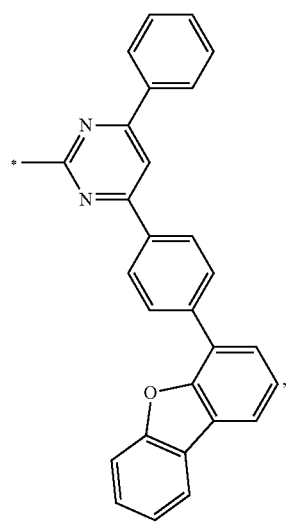
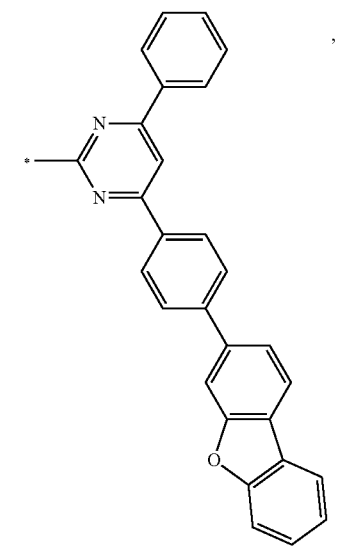

-continued
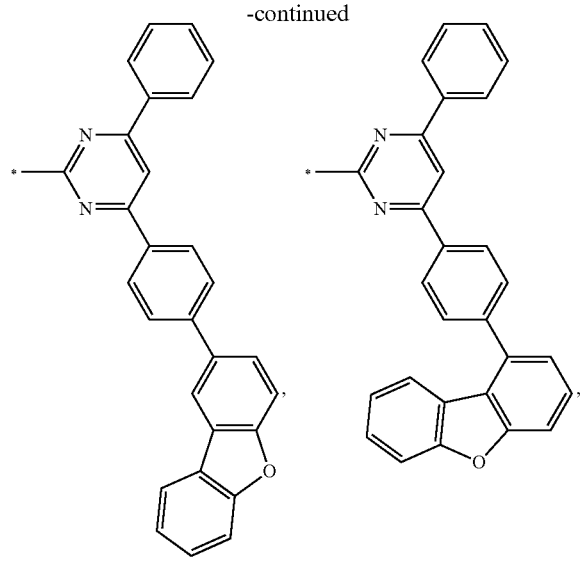
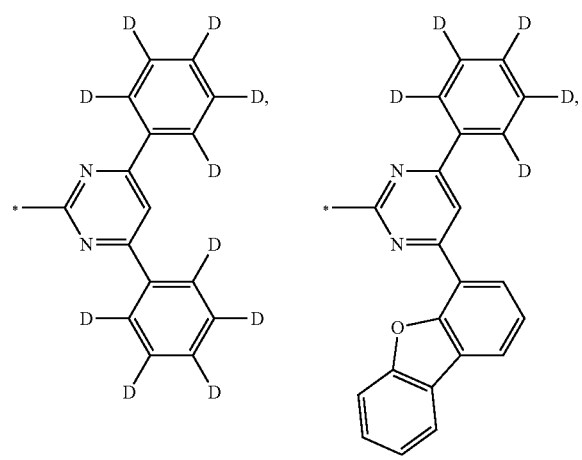
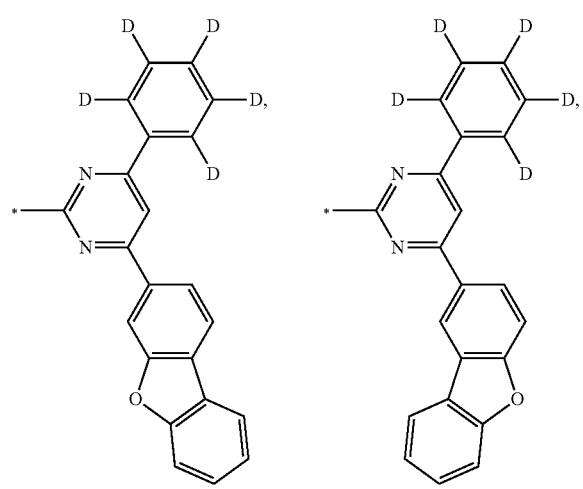
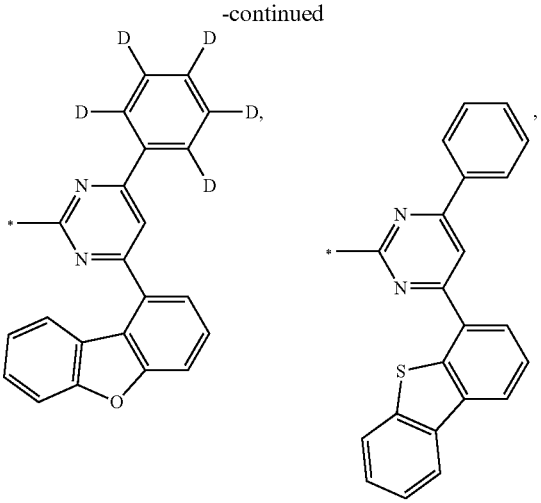
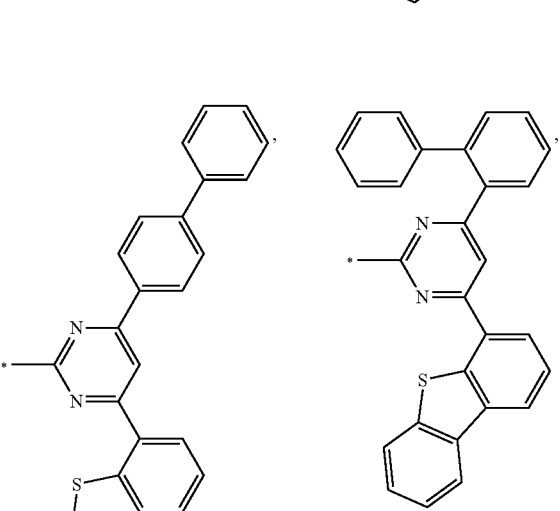
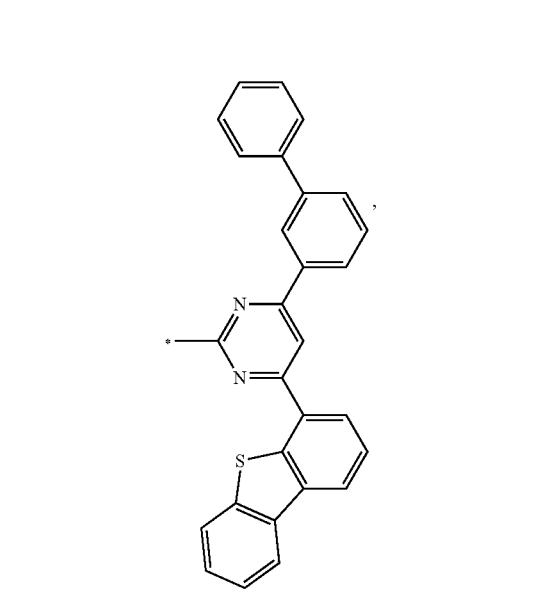

53
-continued
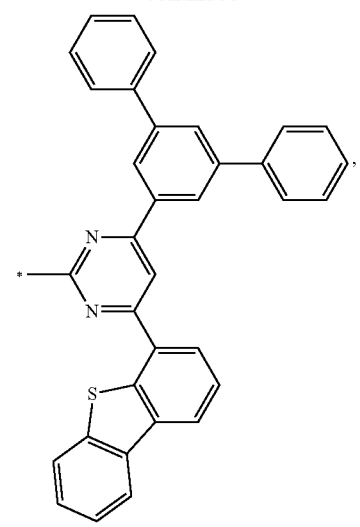
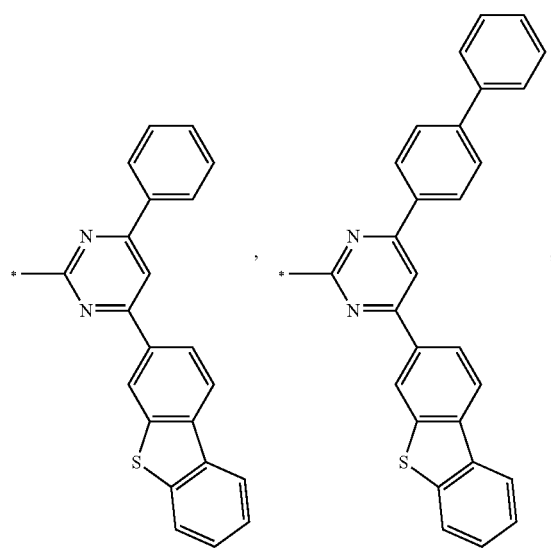
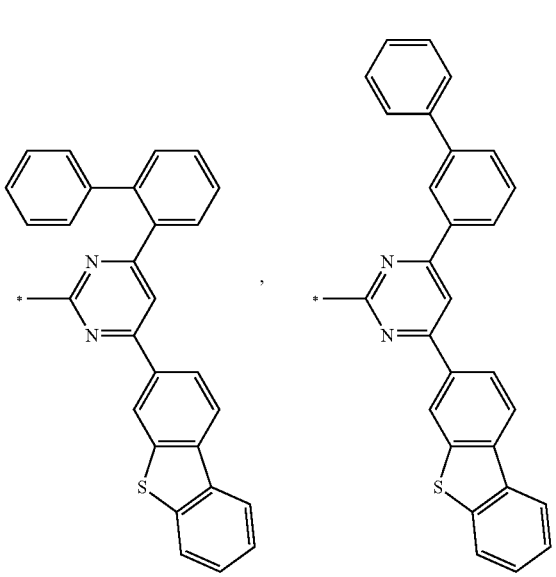
54
-continued
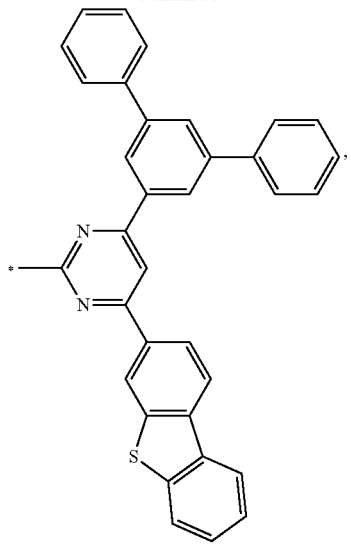
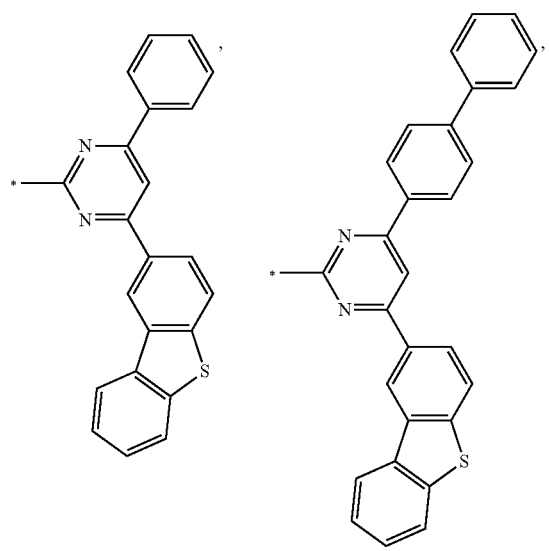
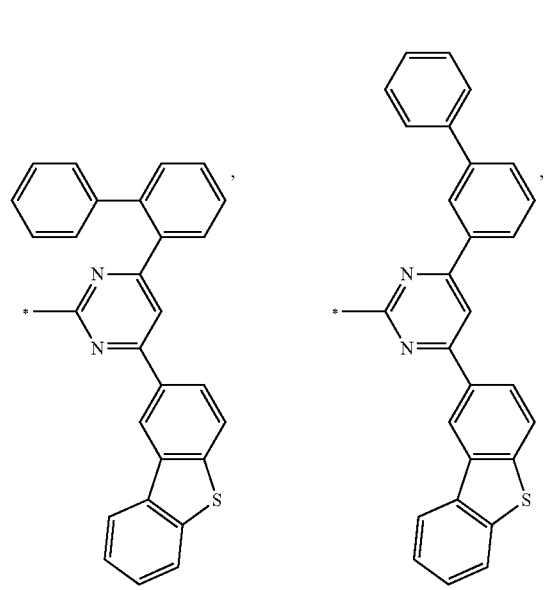

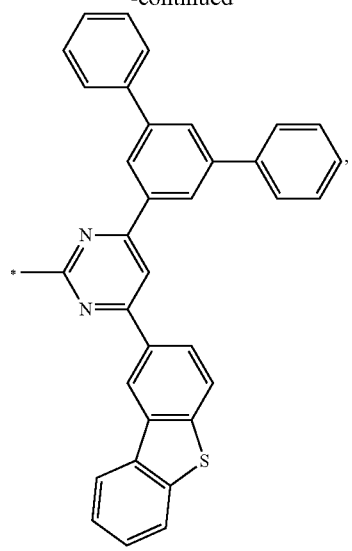
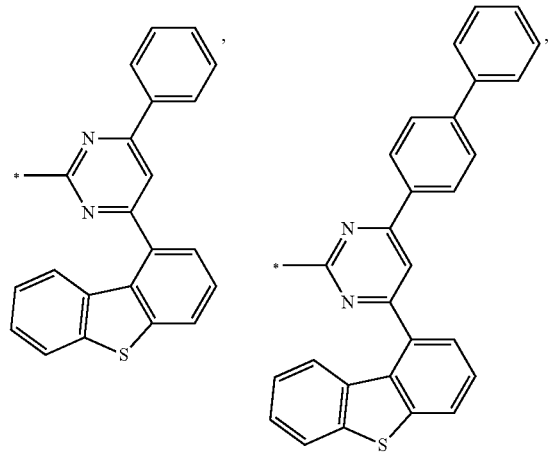
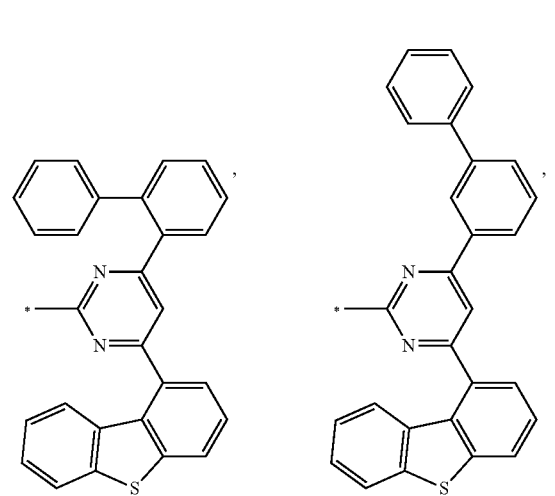
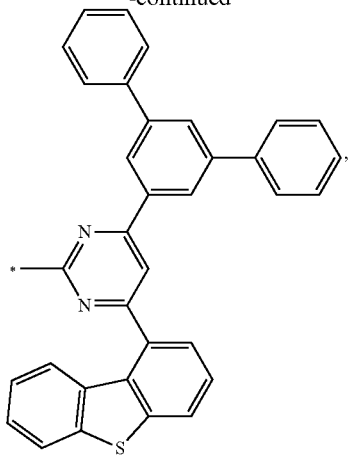
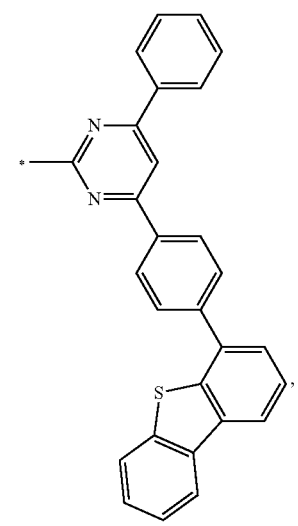
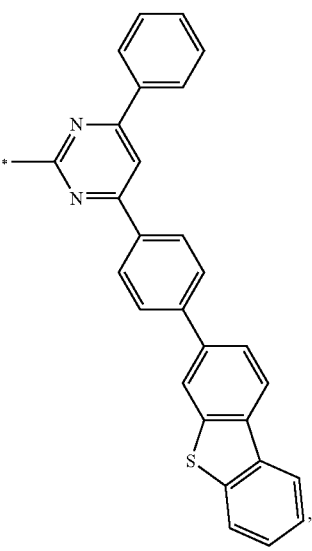

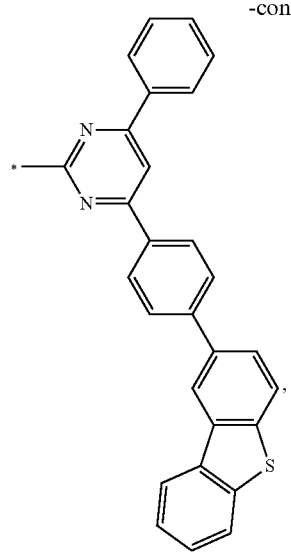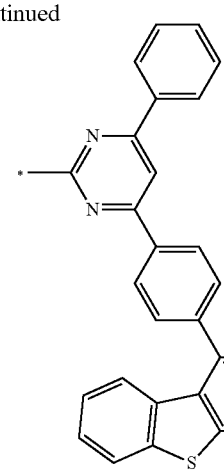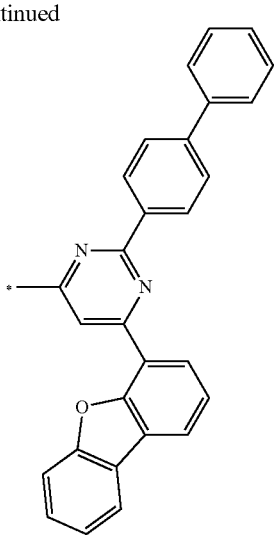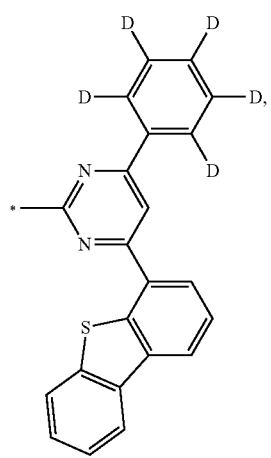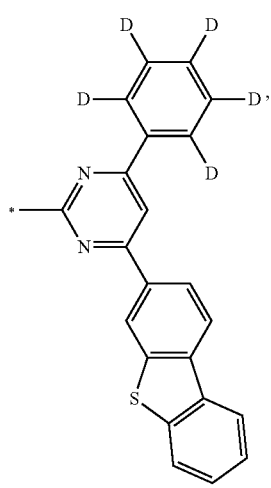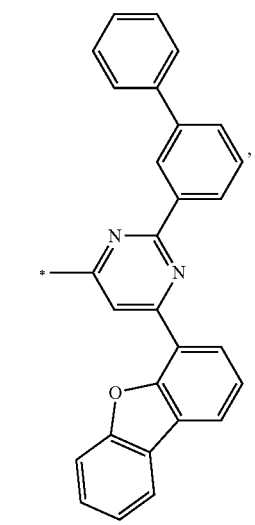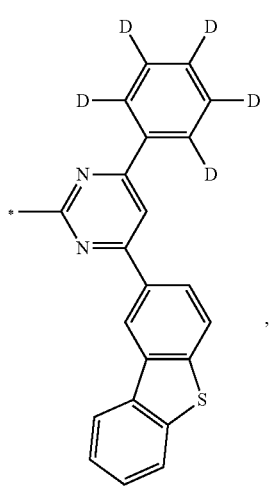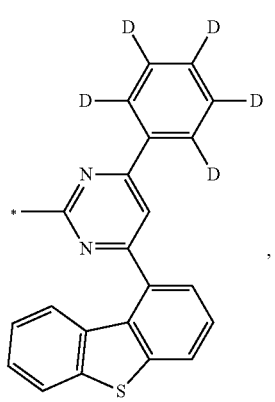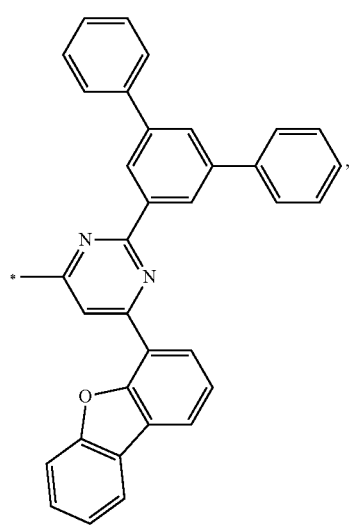

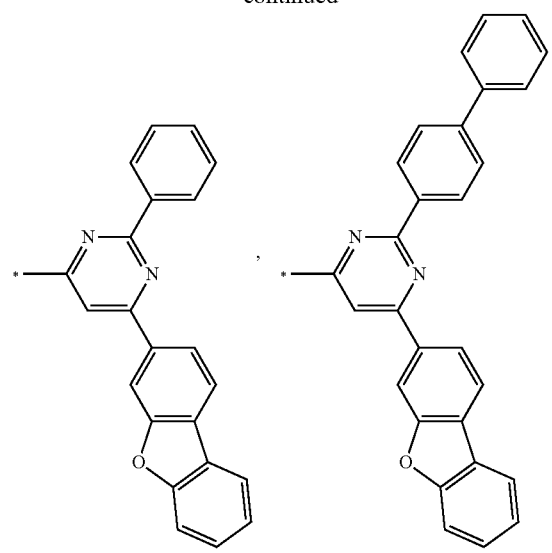
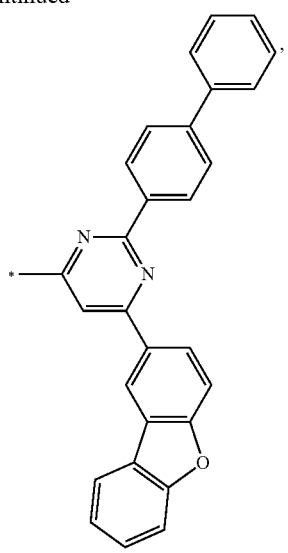
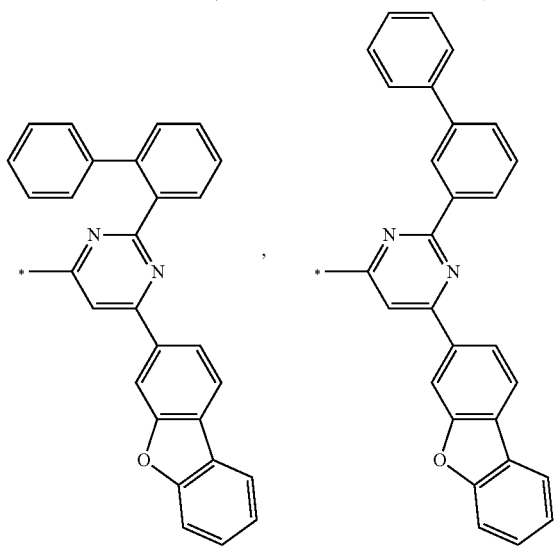
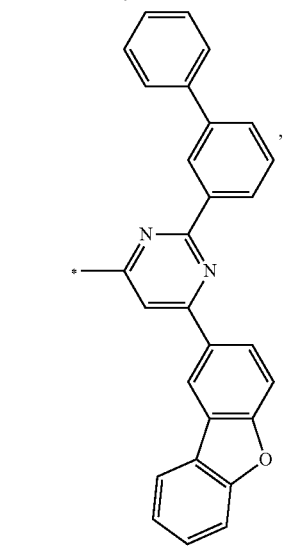
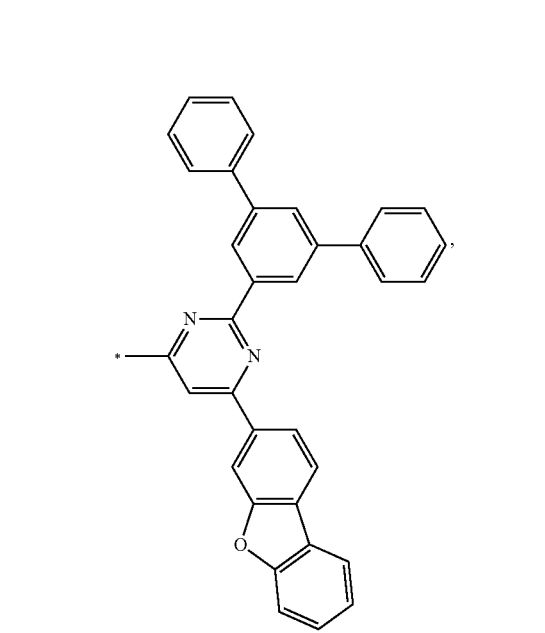
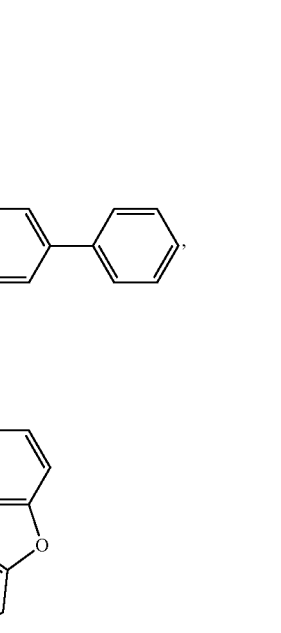

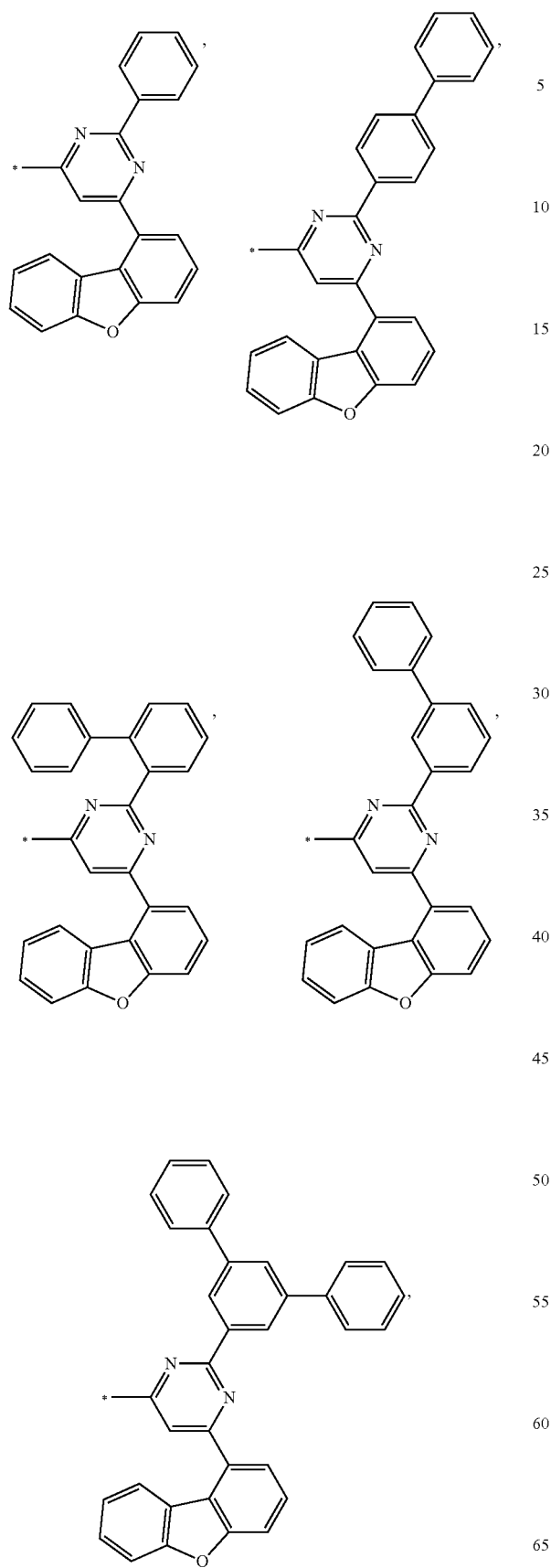
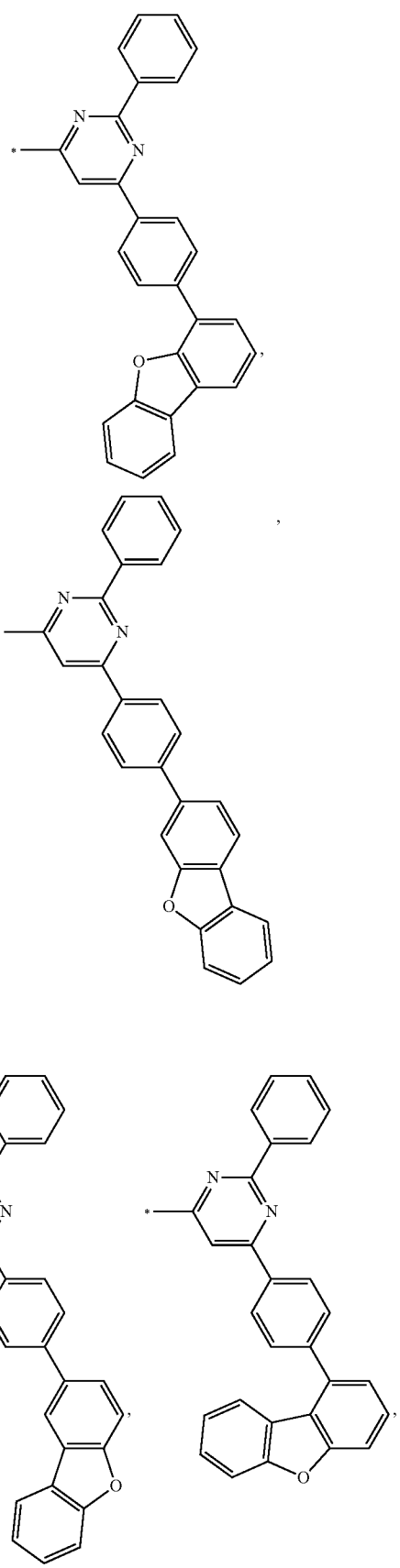

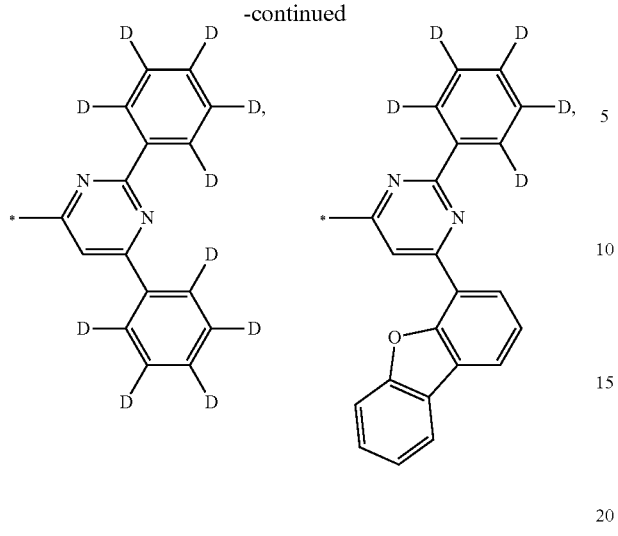
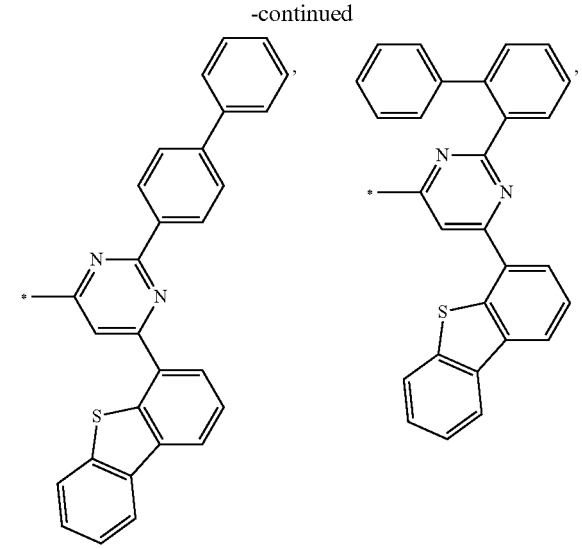
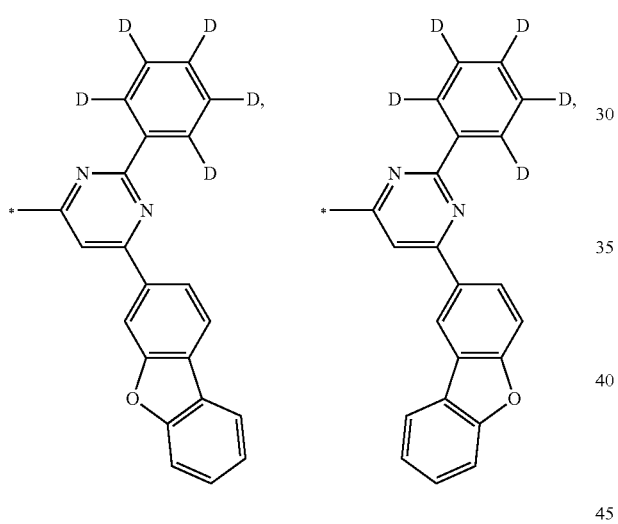
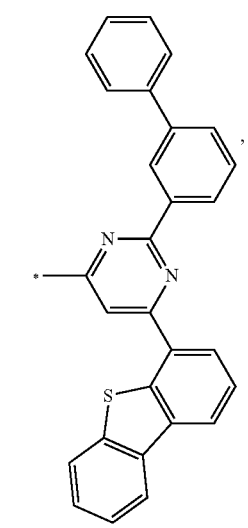
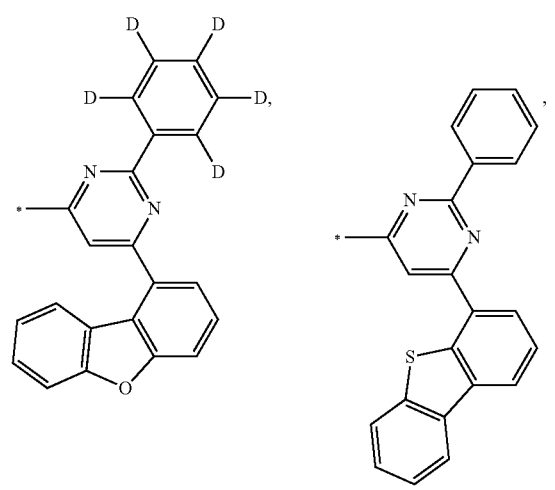
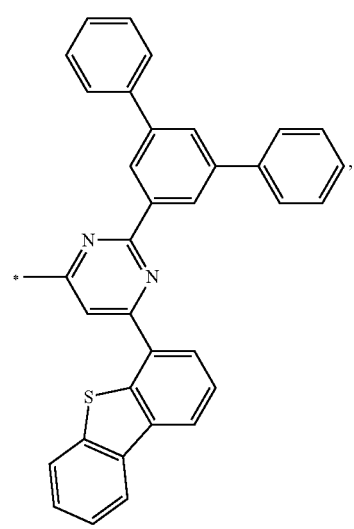

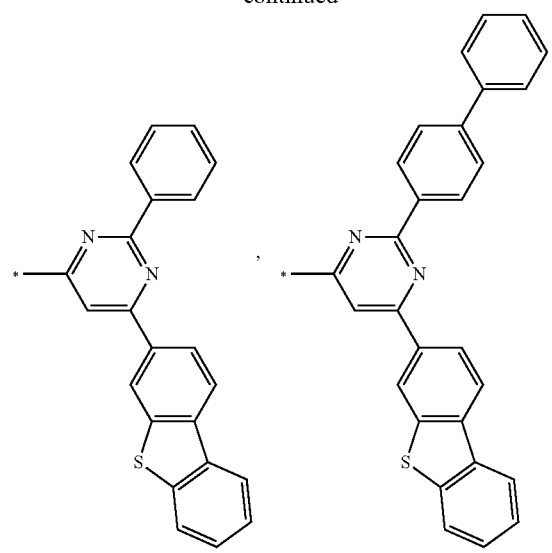
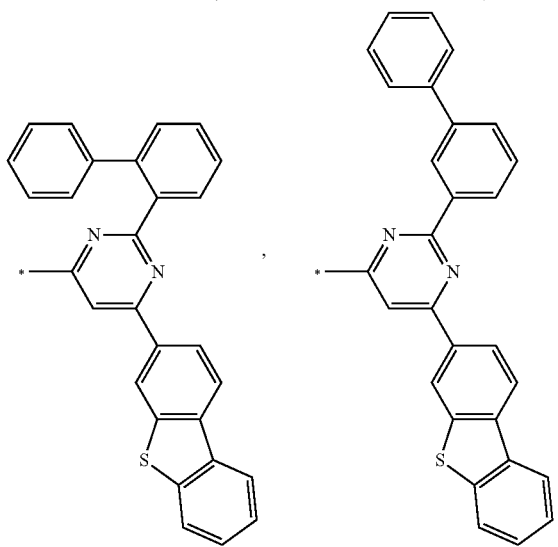
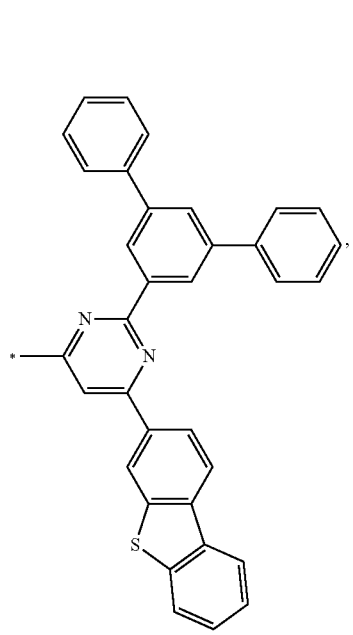
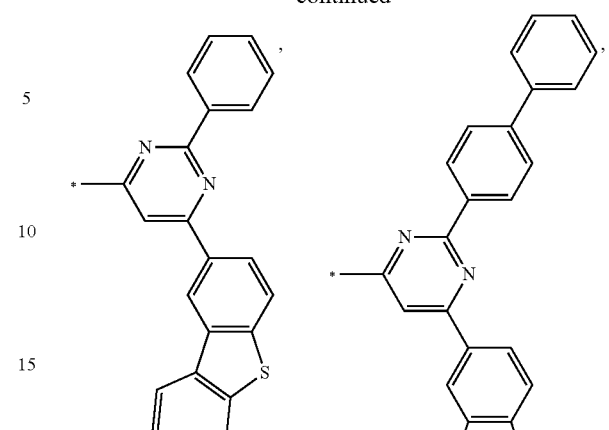
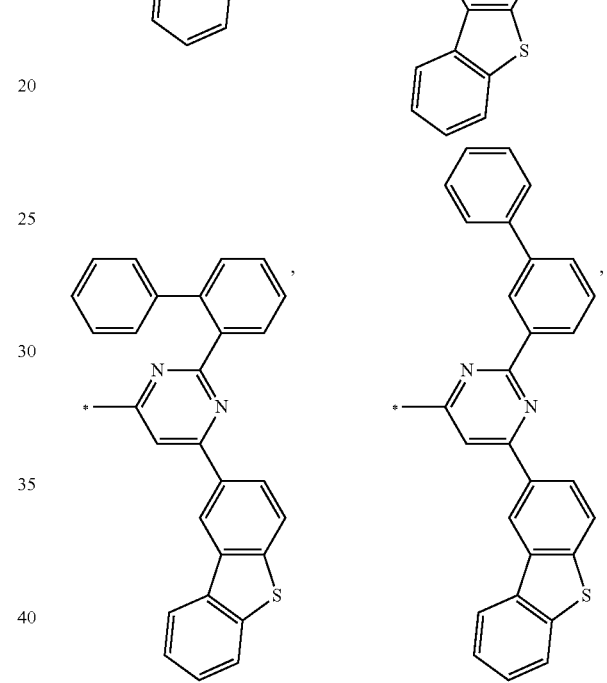
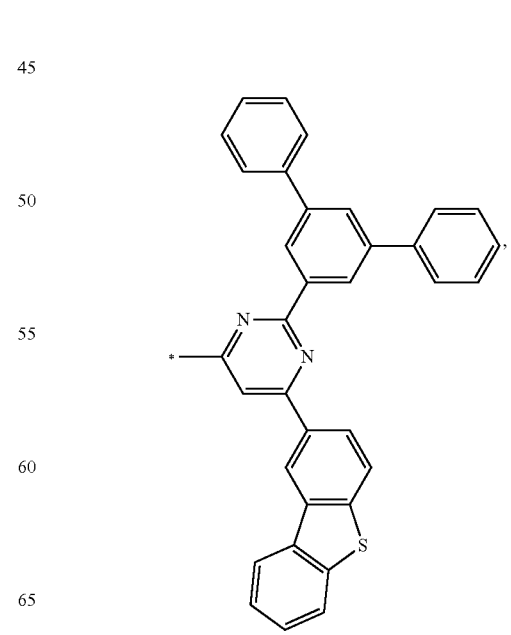

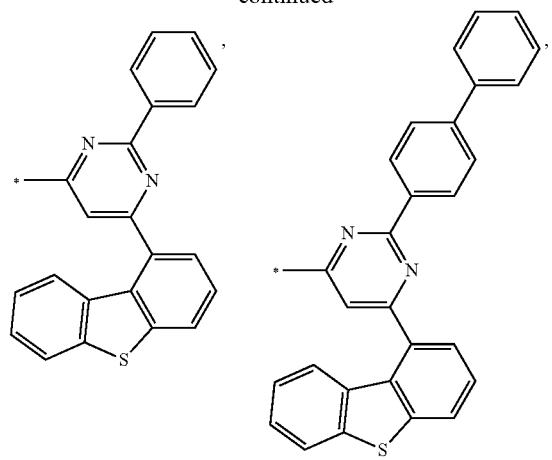
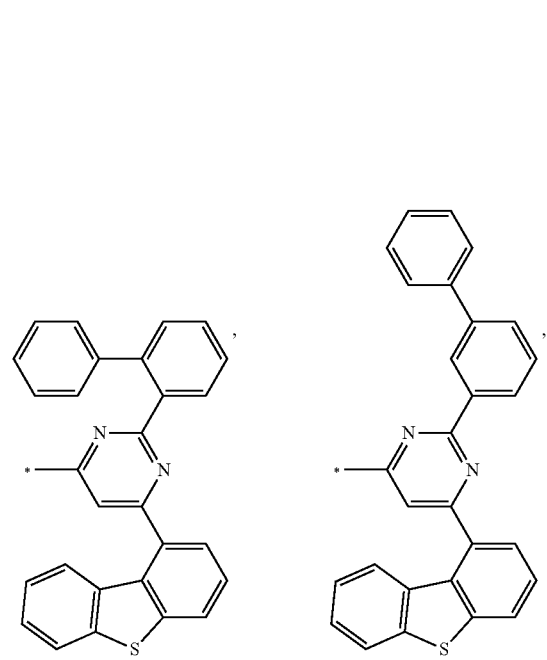
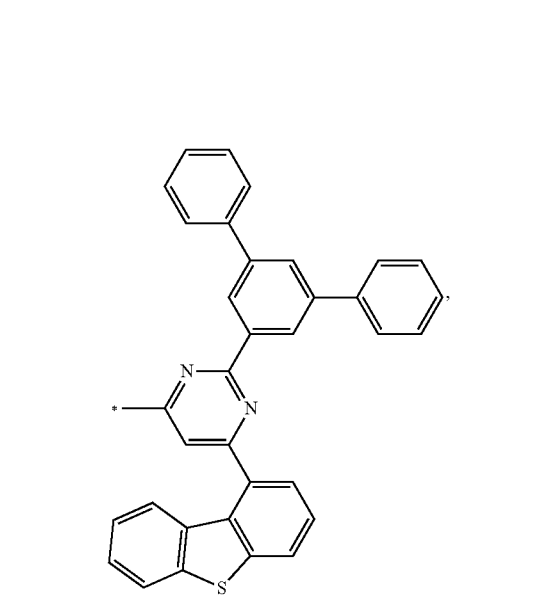
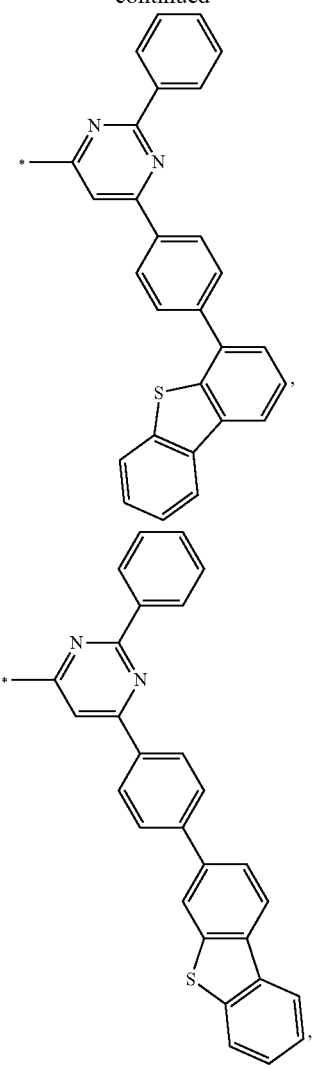
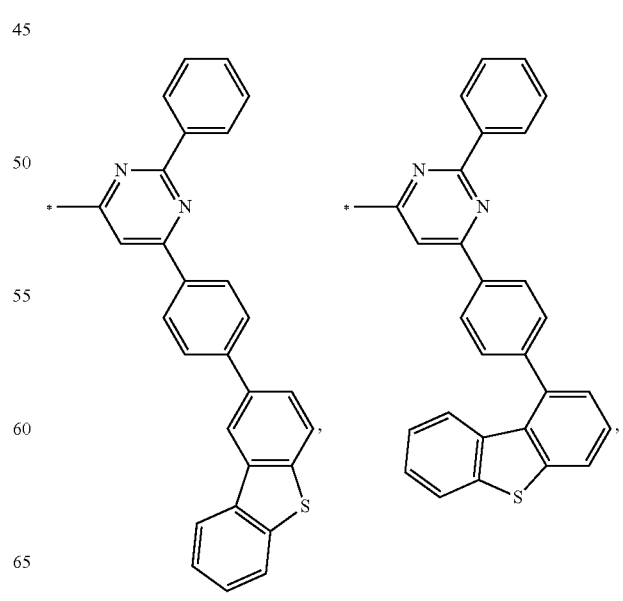

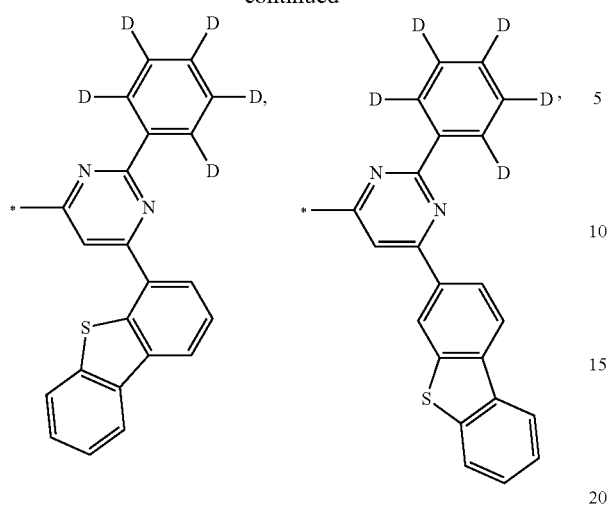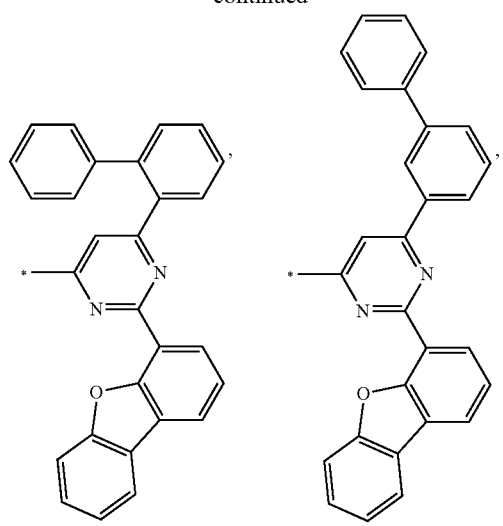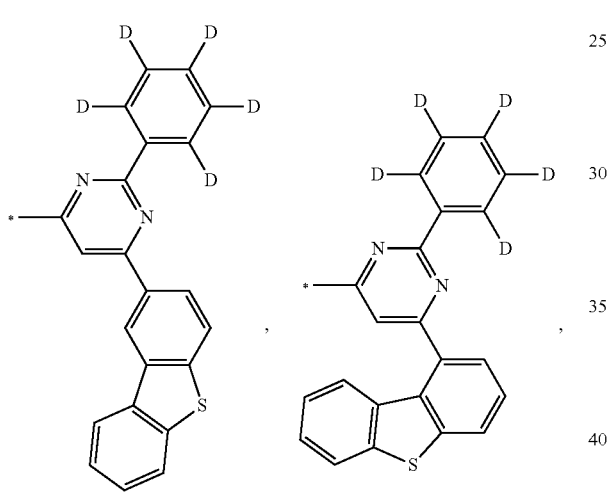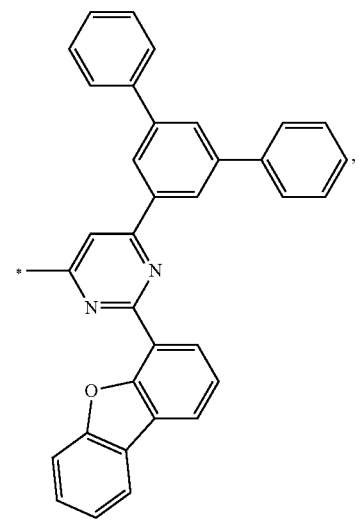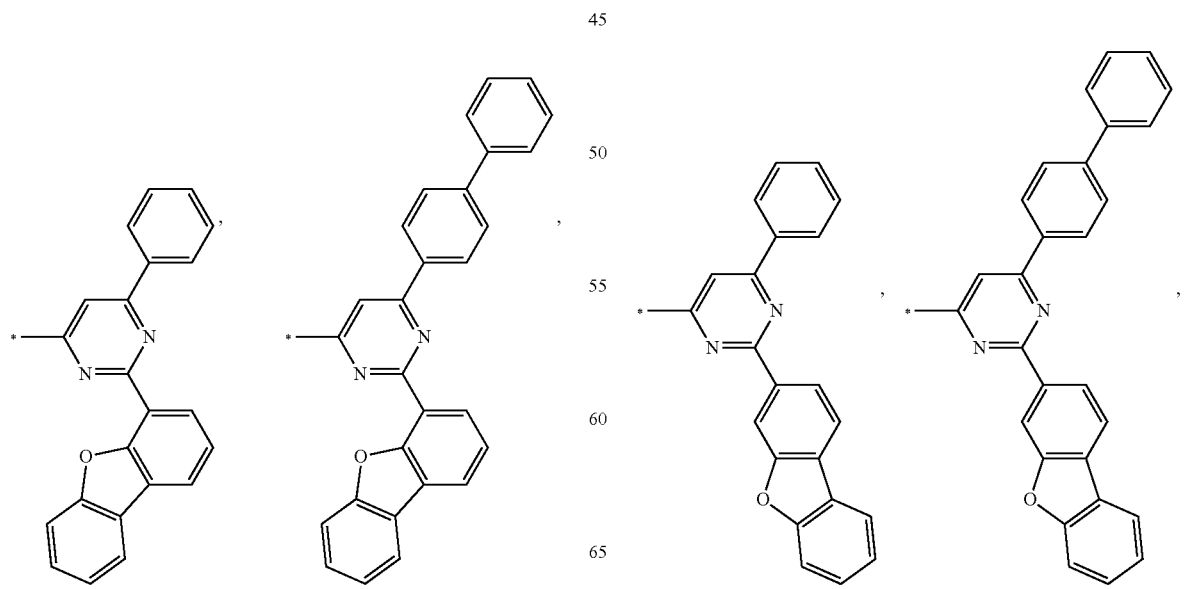

71
-continued
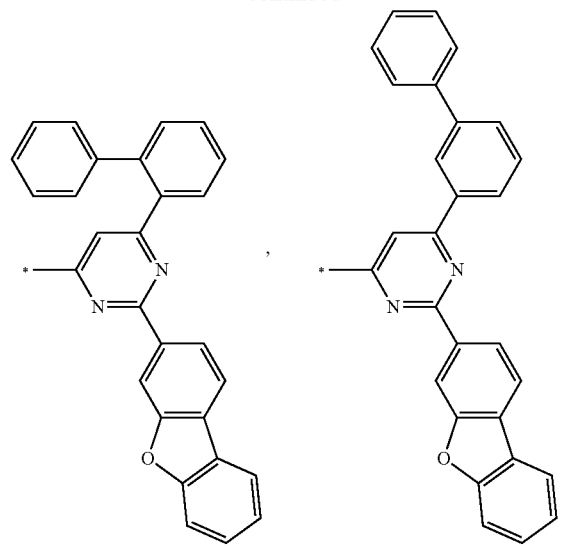
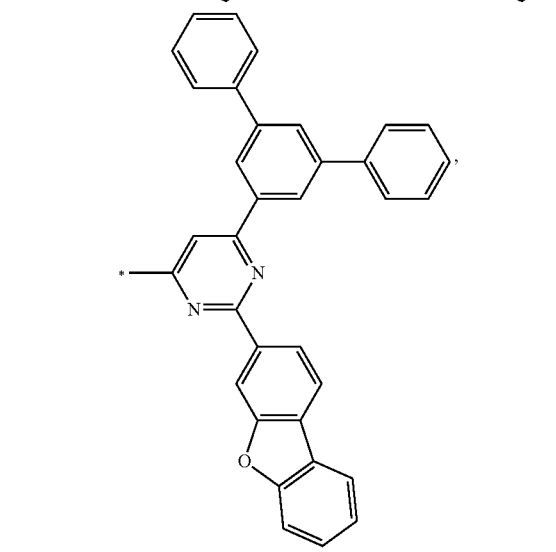
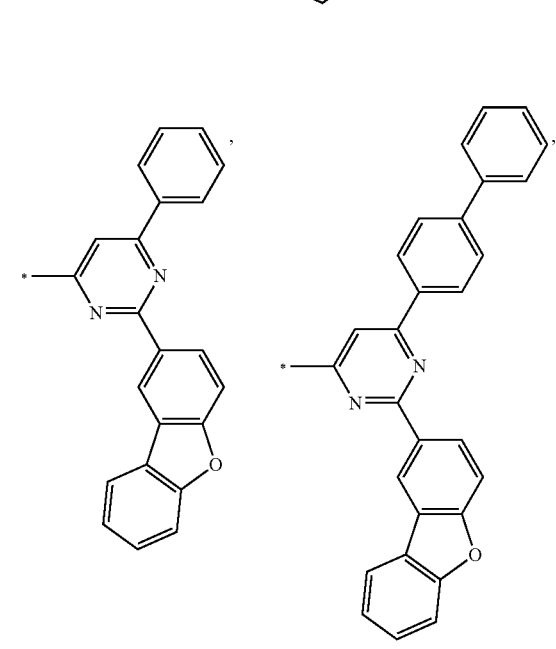
72
-continued
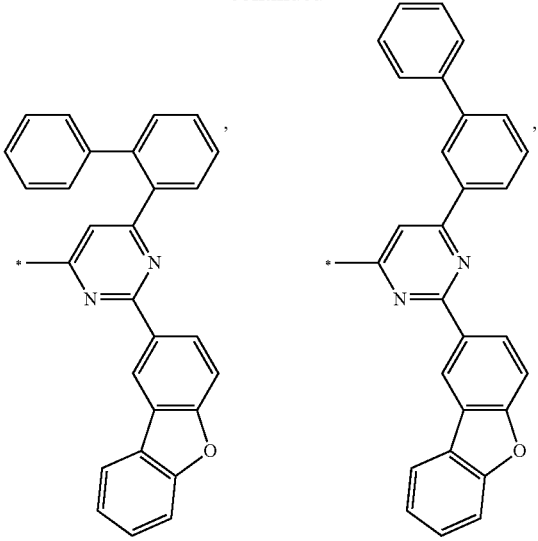
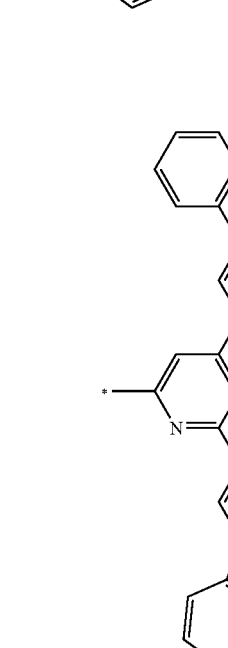
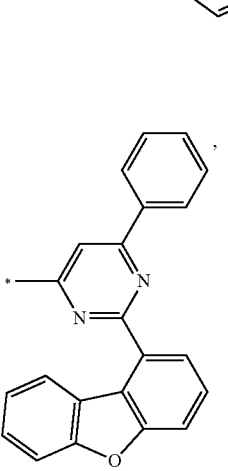

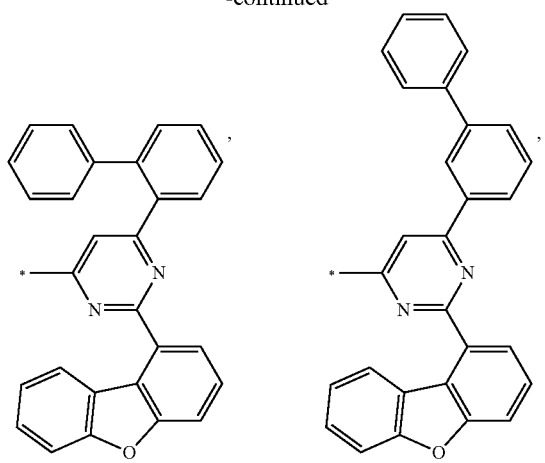
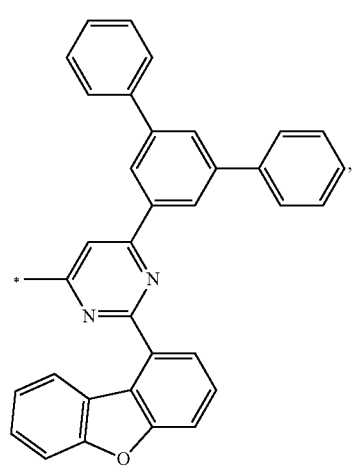
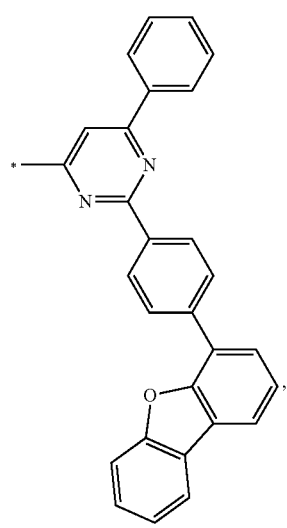
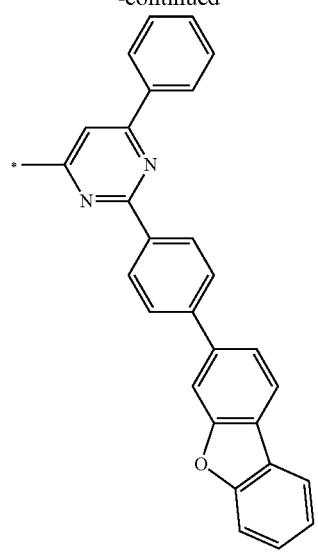
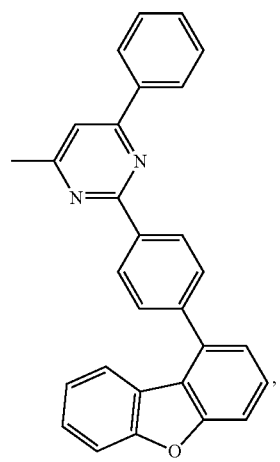
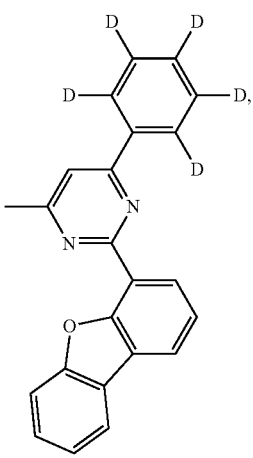
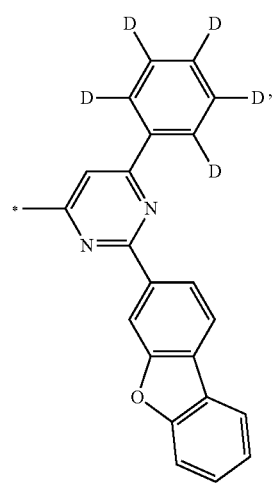

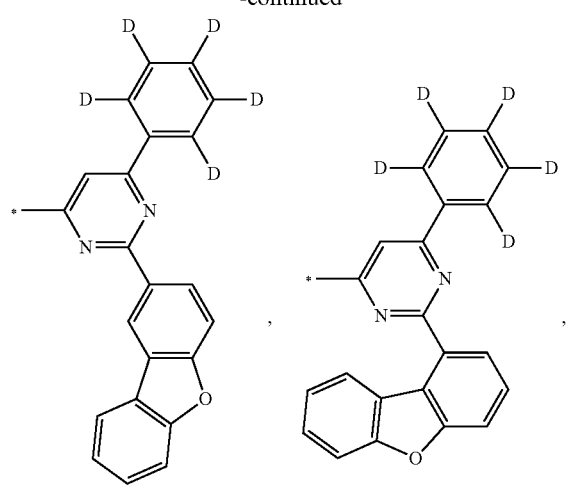
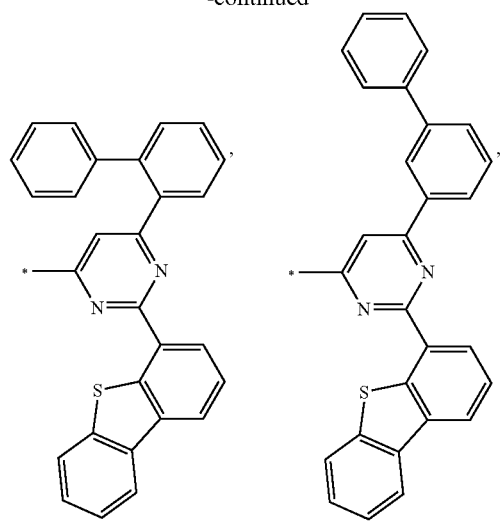
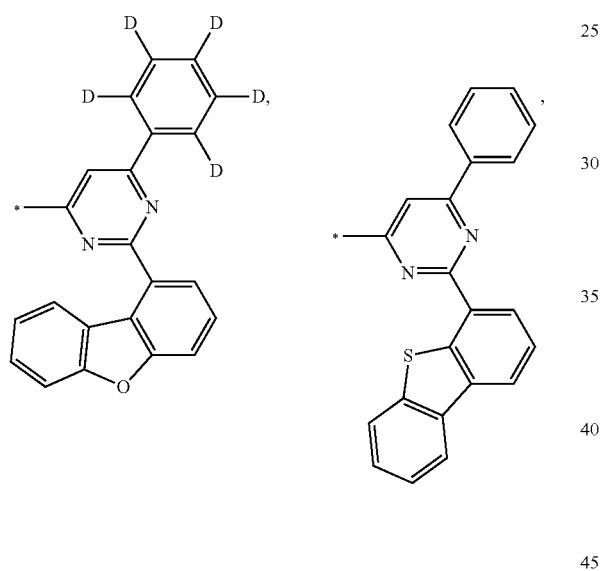
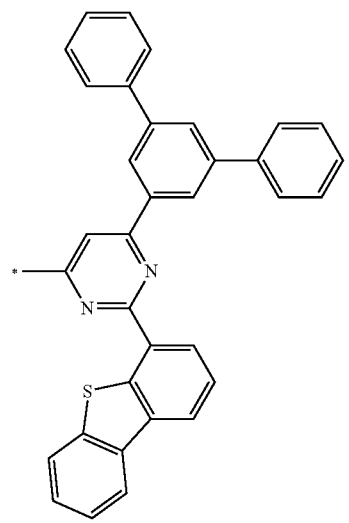
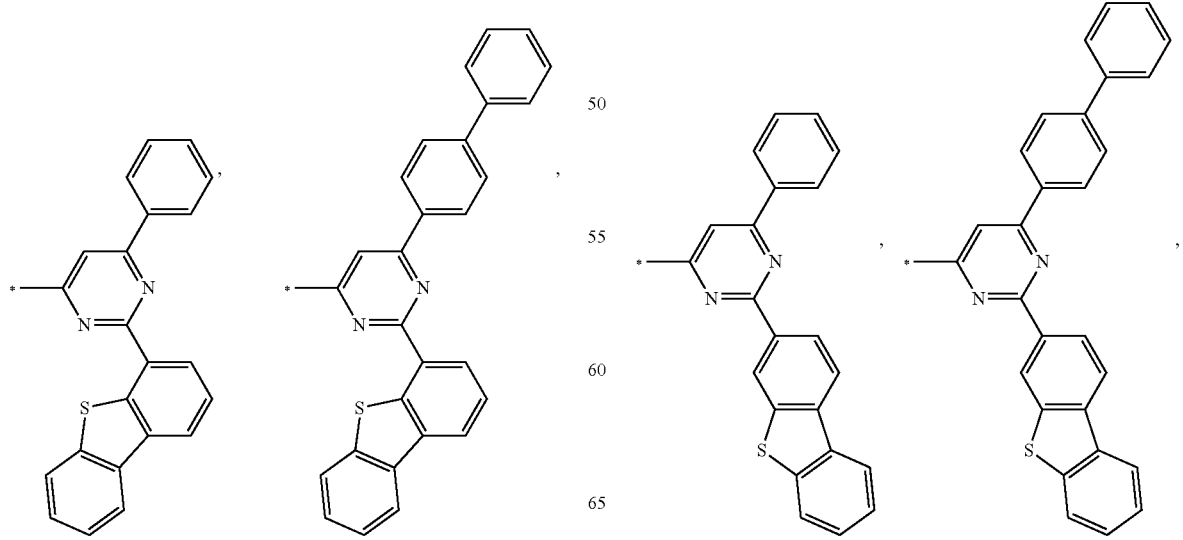

77
-continued
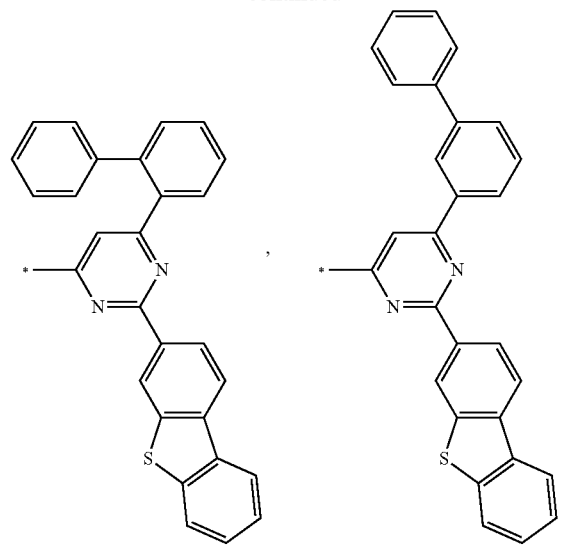
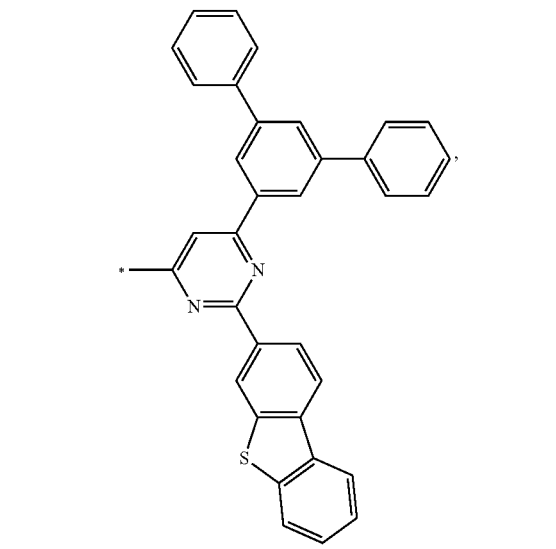
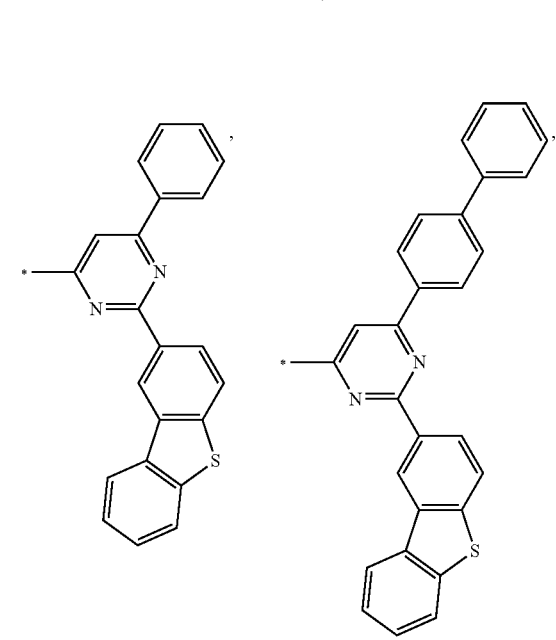
78
-continued
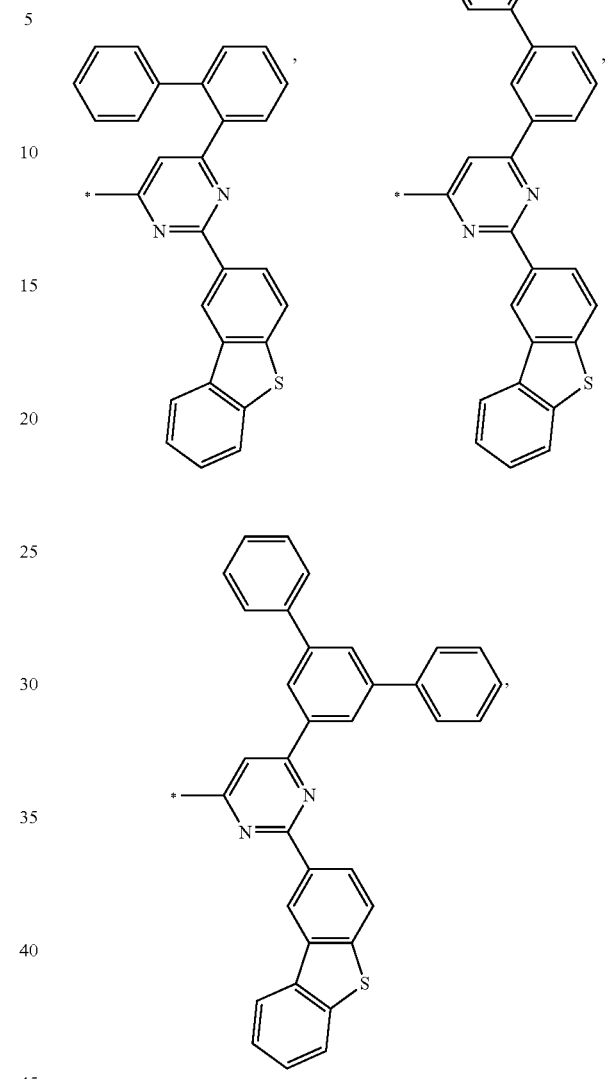
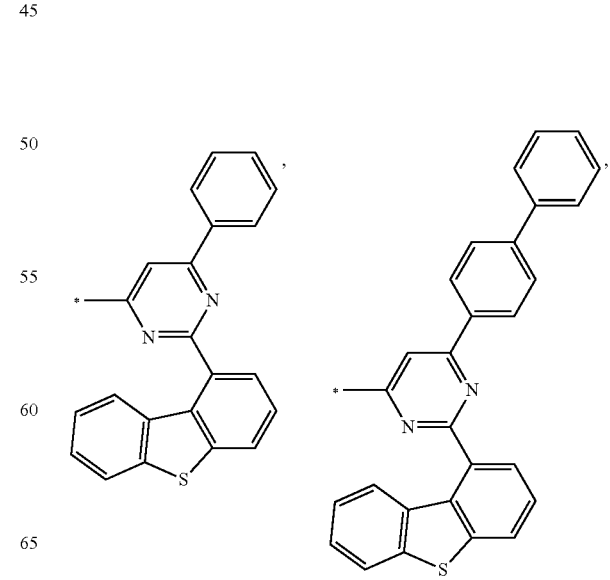

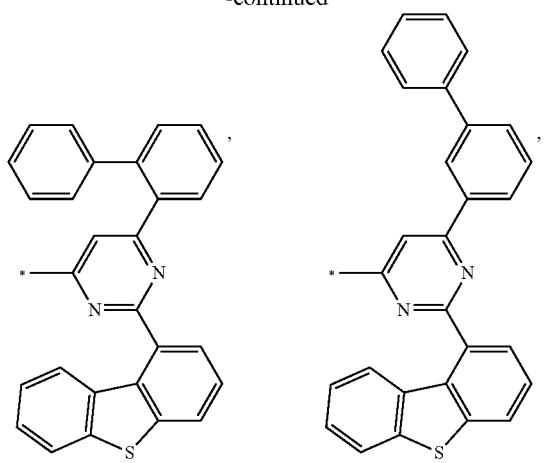
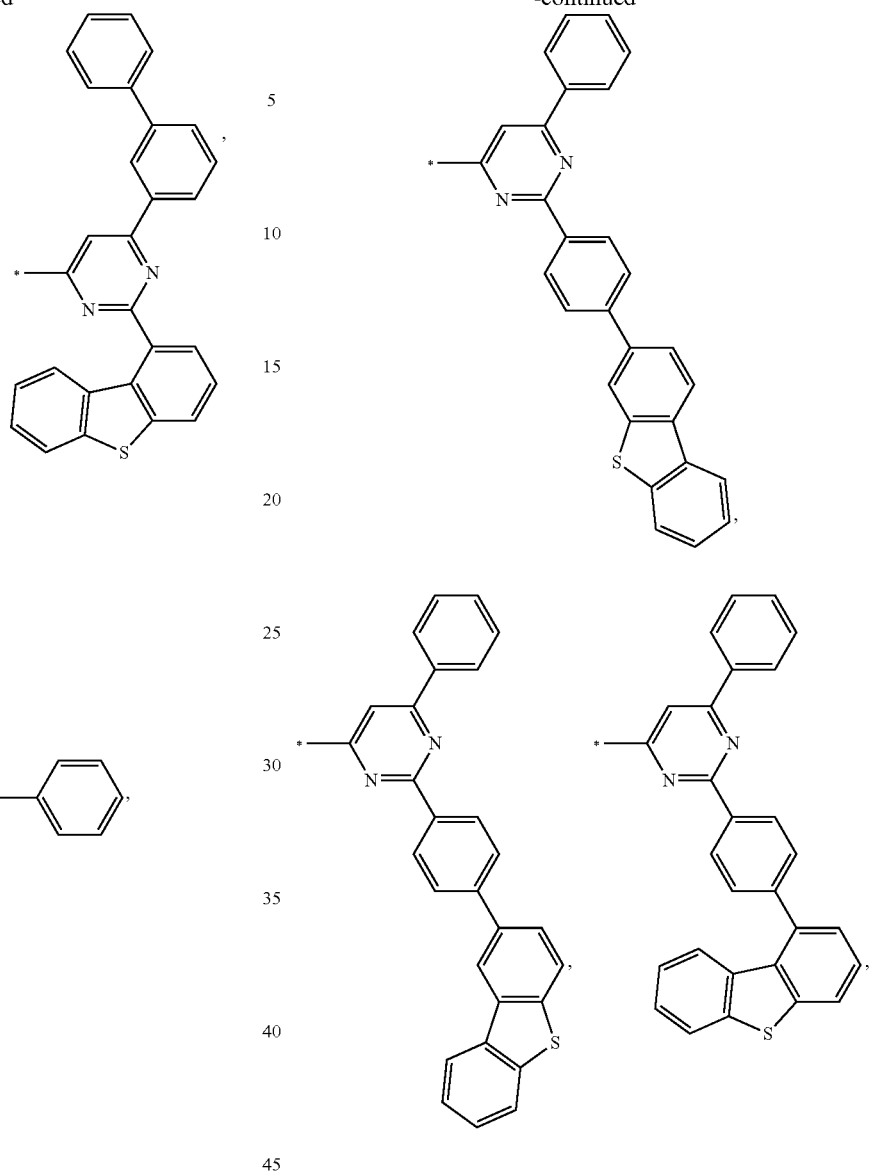
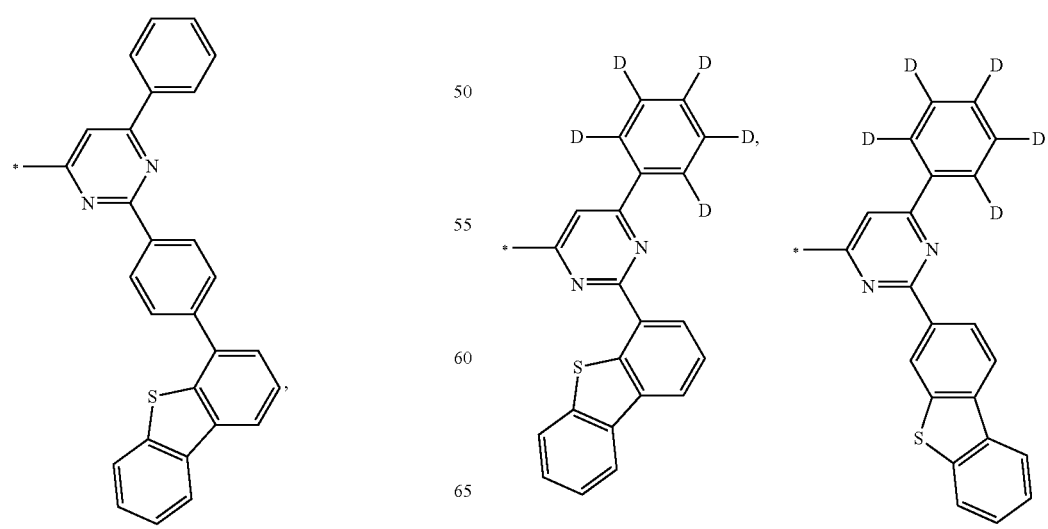

-continued
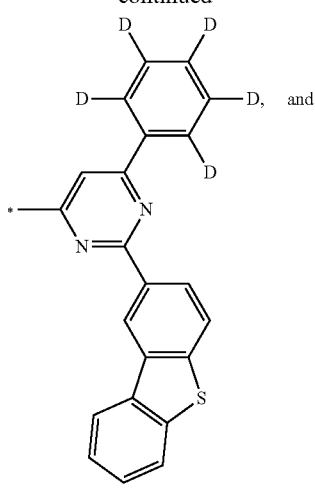
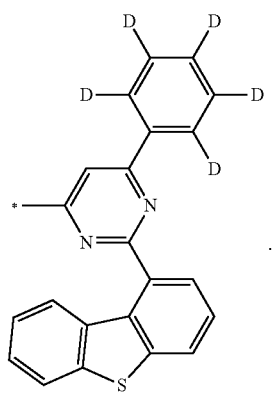
For example, the first host compound may be selected from the group consisting of:
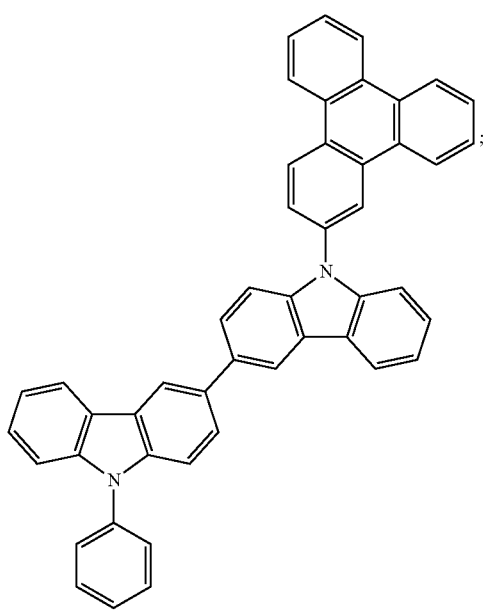
-continued
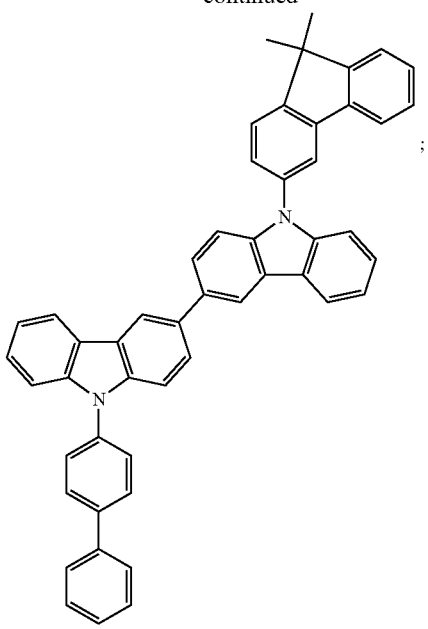
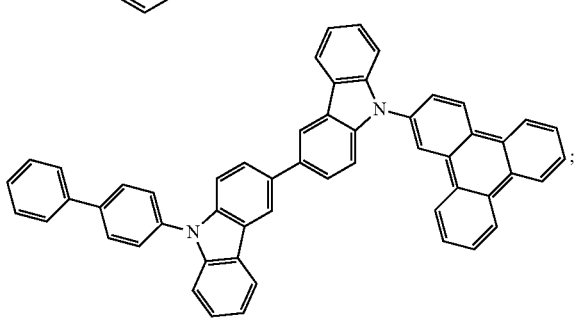
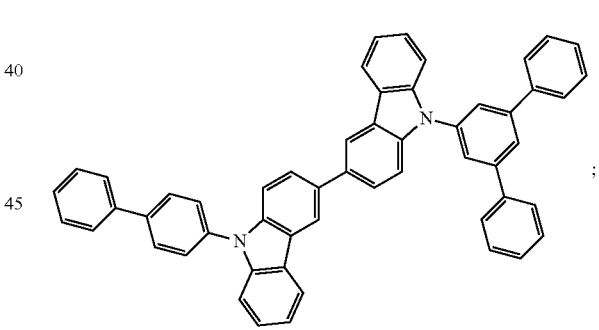

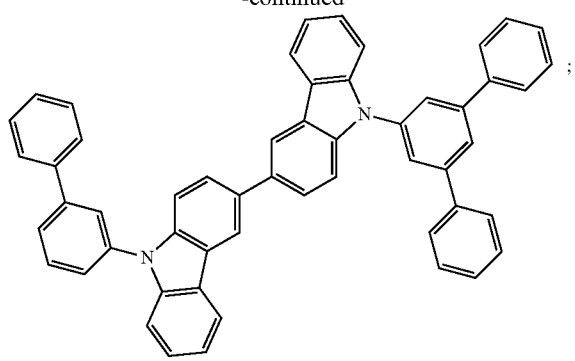
Compound I-5
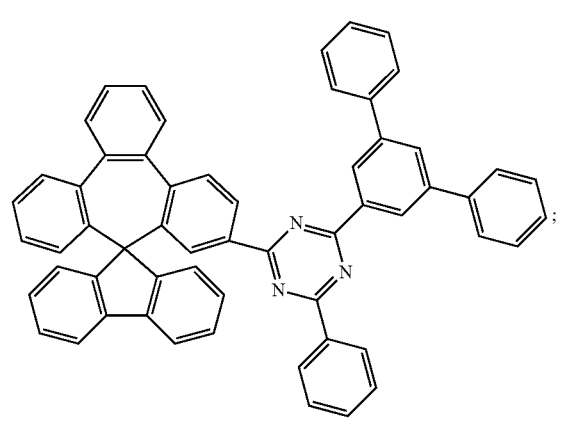
Compound I-6
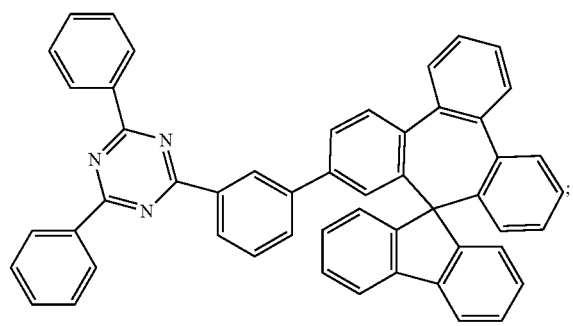
Compound I-7
Compound I-8
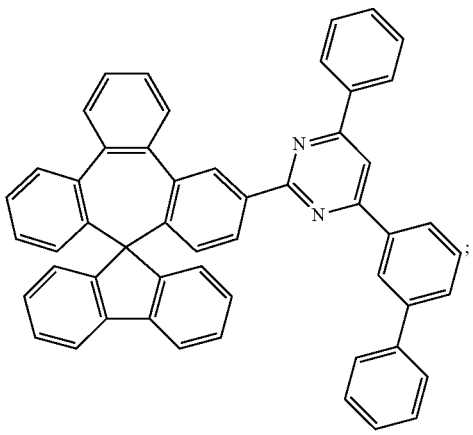
Compound I-9
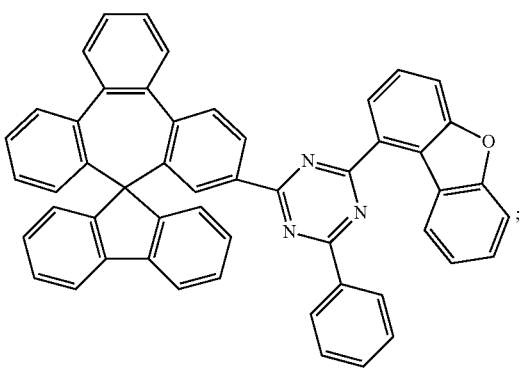
Compound I-10
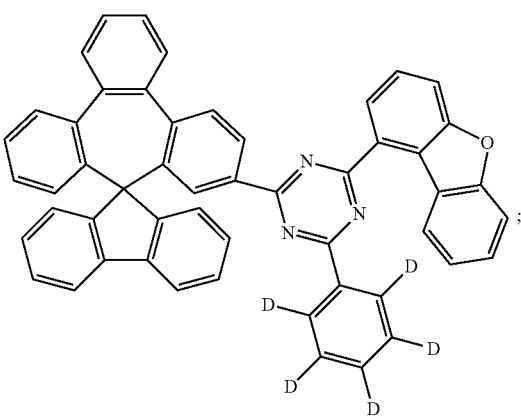

Compound I-11
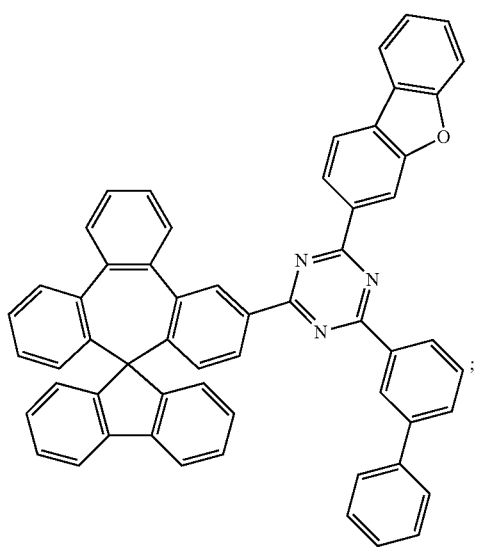
Compound I-14
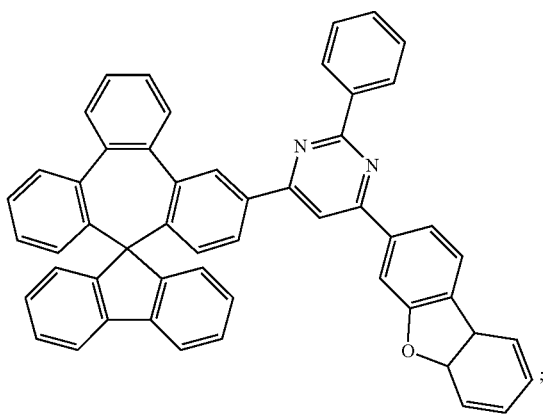
Compound I-12
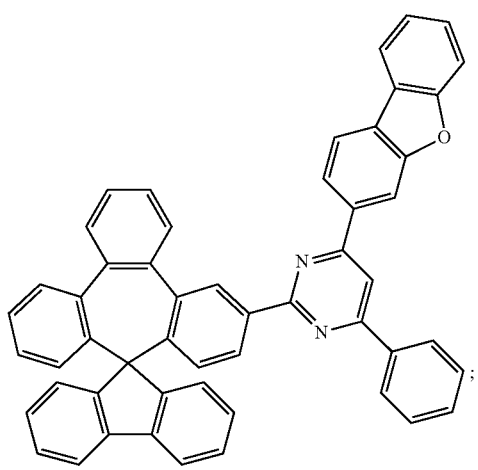
Compound I-15
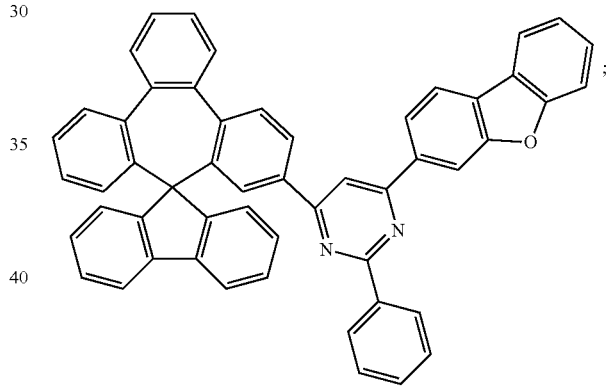
Compound I-13
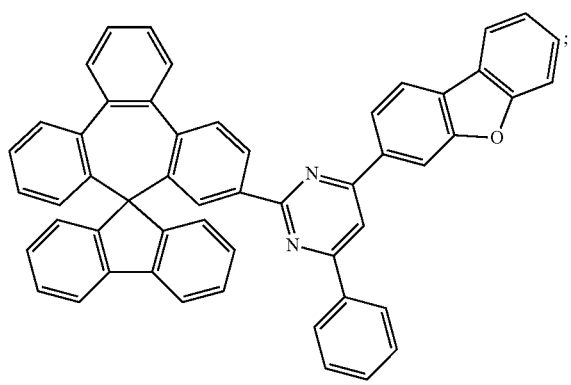
Compound I-16
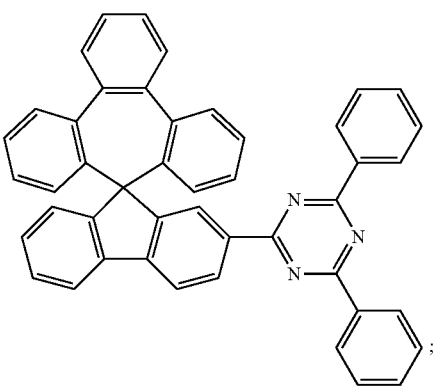

Compound I-17
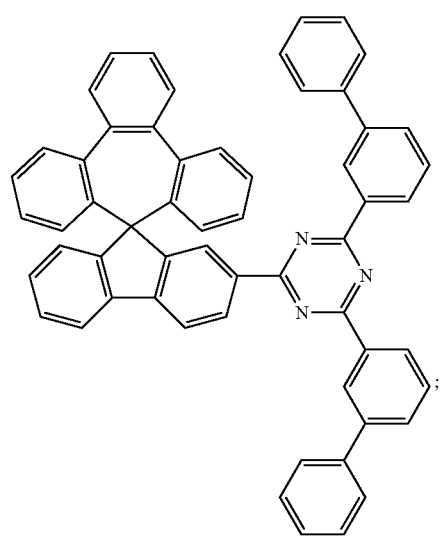
Compound I-18
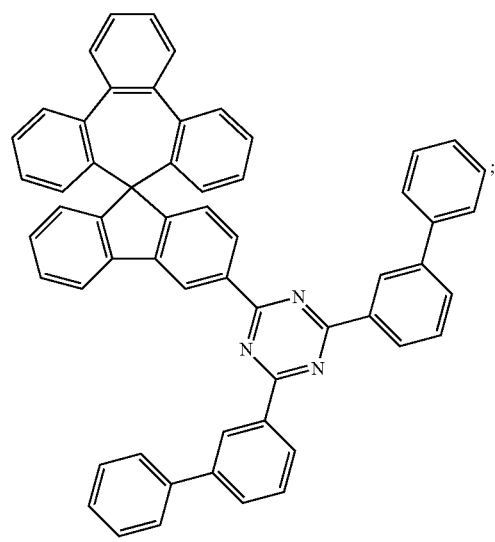
Compound I-19
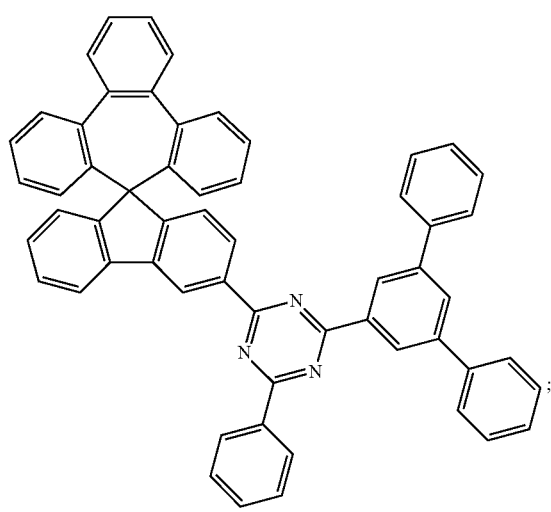
Compound I-20
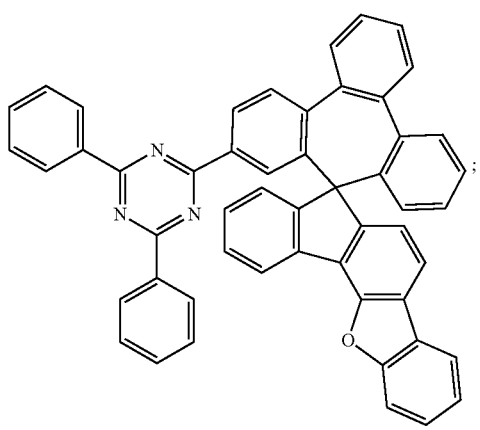
Compound I-21
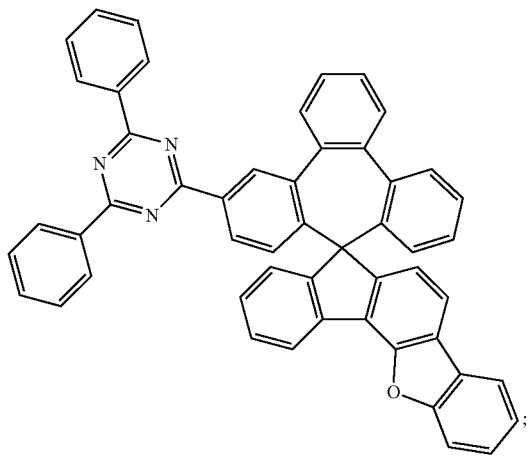
Compound I-22
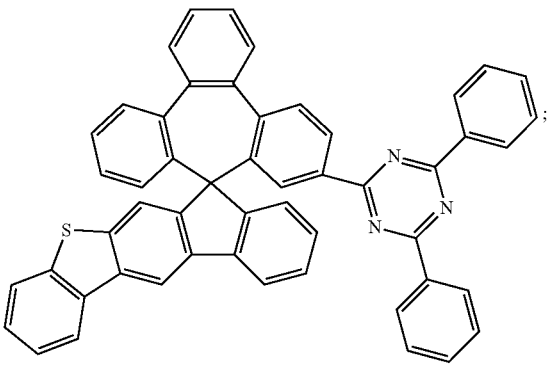

Compound I-23
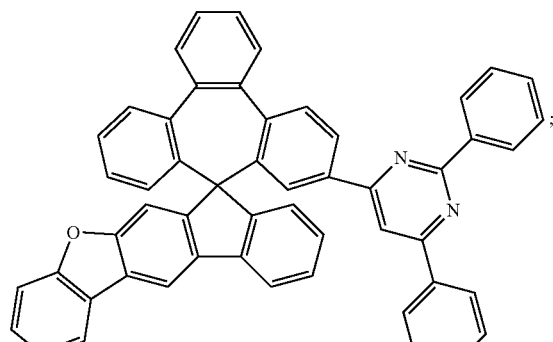
Compound I-24
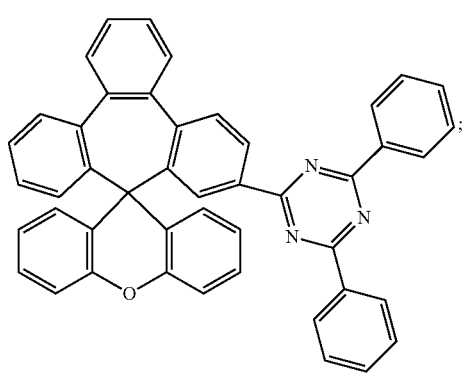
Compound I-25
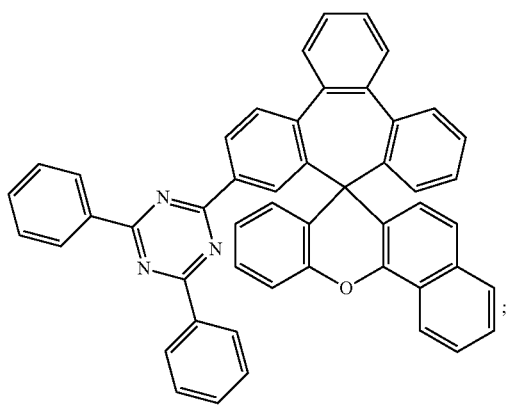
Compound I-26
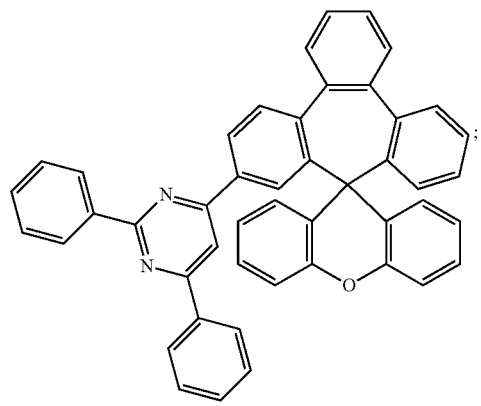
Compound I-27
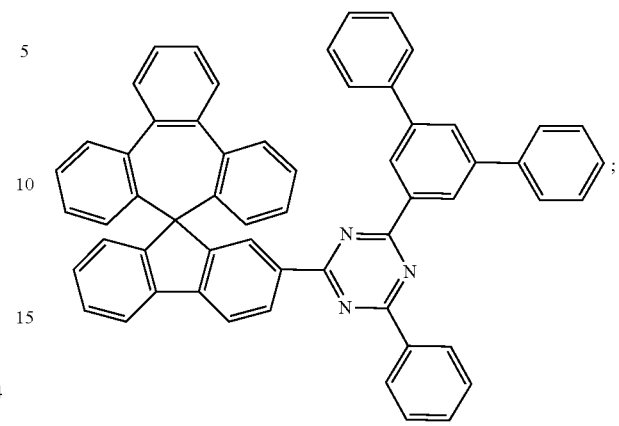
Compound I-28
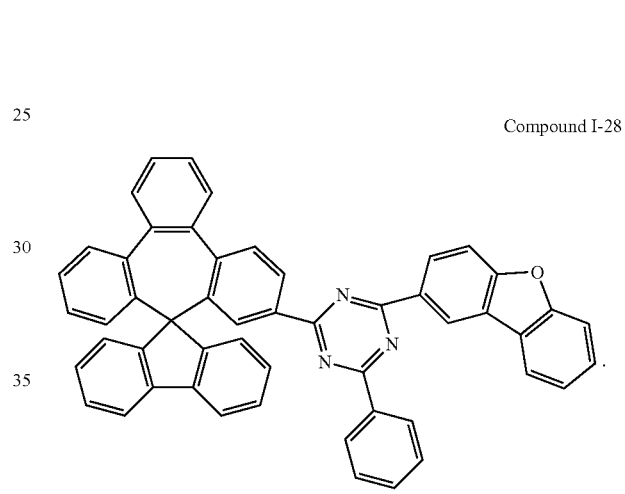
Compound I-29
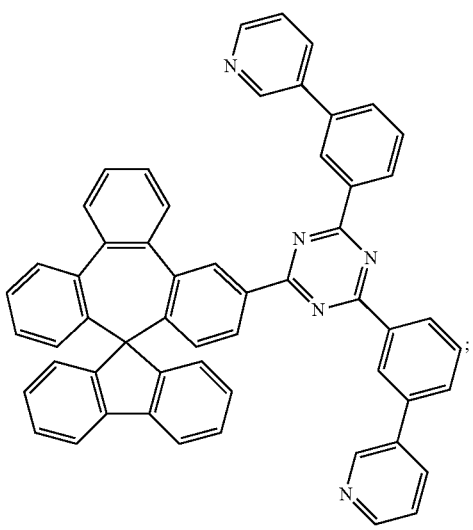

Compound I-30
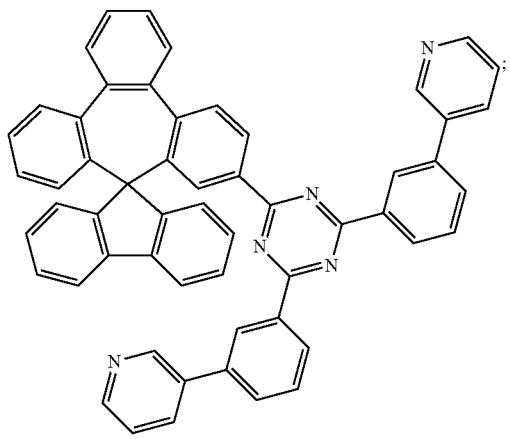
Compound I-33
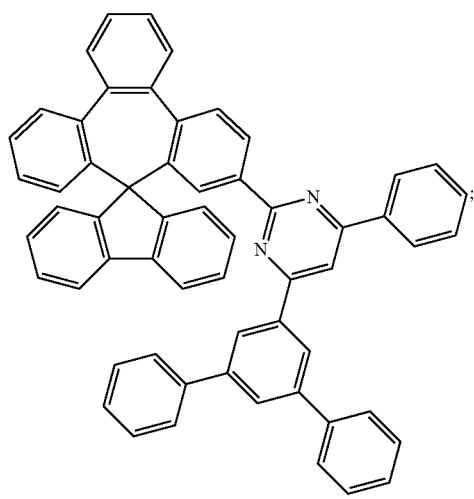
Compound I-31
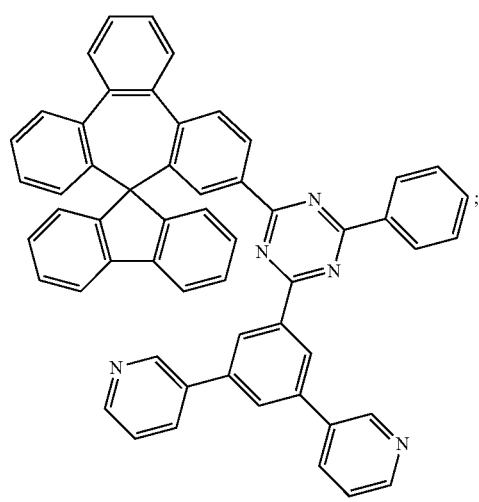
Compound I-34
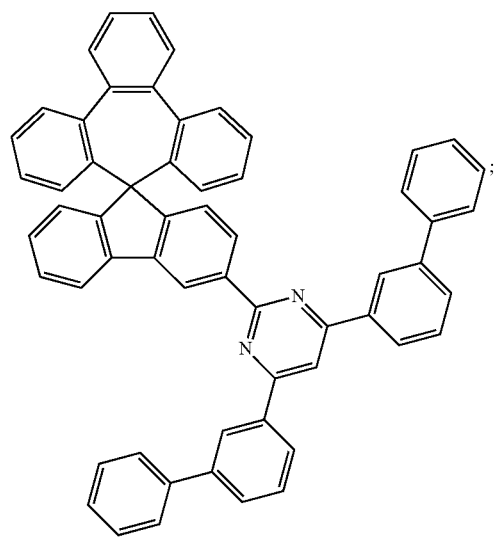
Compound I-32
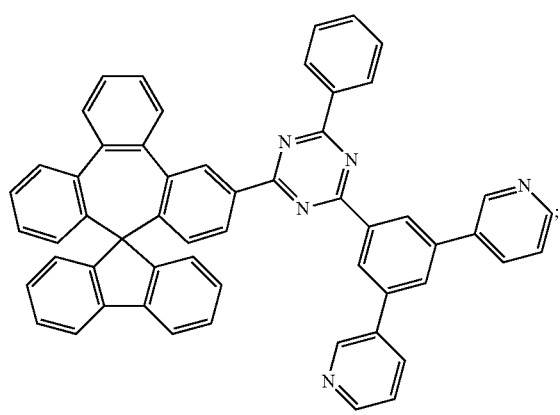
Compound I-35
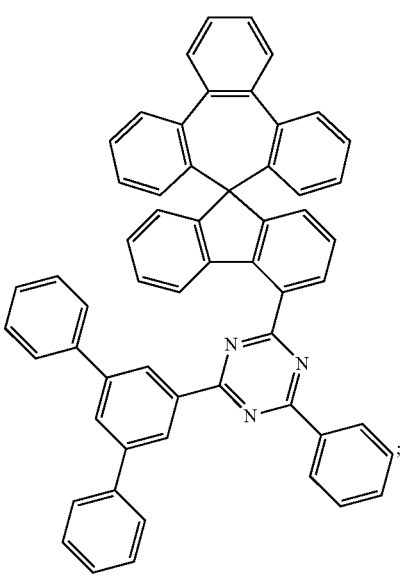

Compound I-36
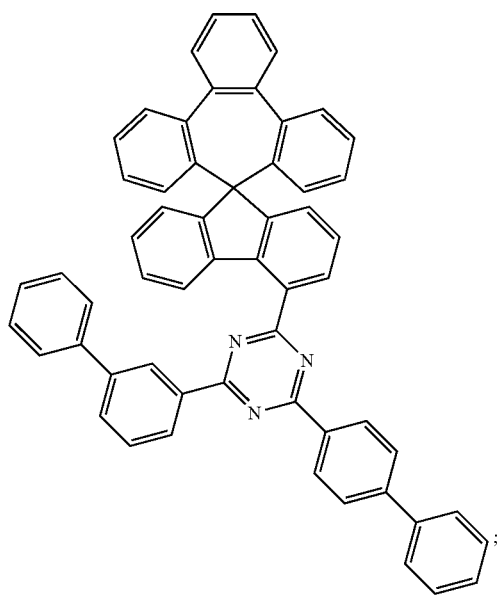
Compound I-37
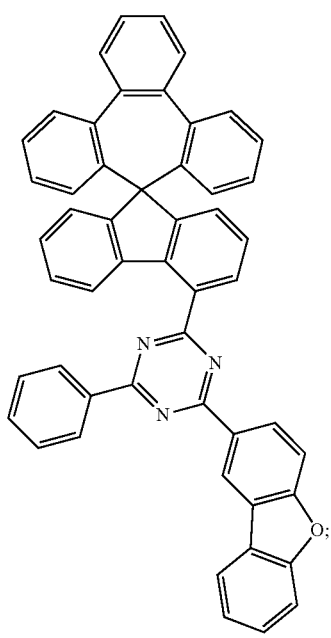
Compound I-38
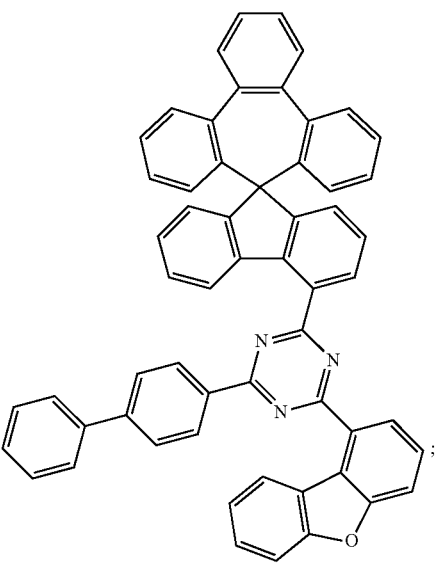
Compound I-39
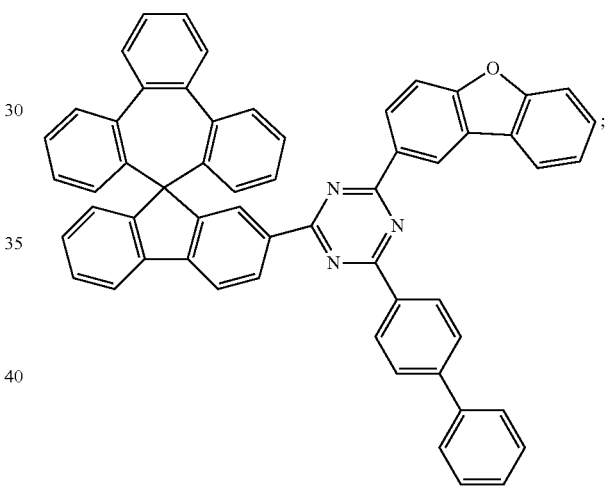
Compound I-40
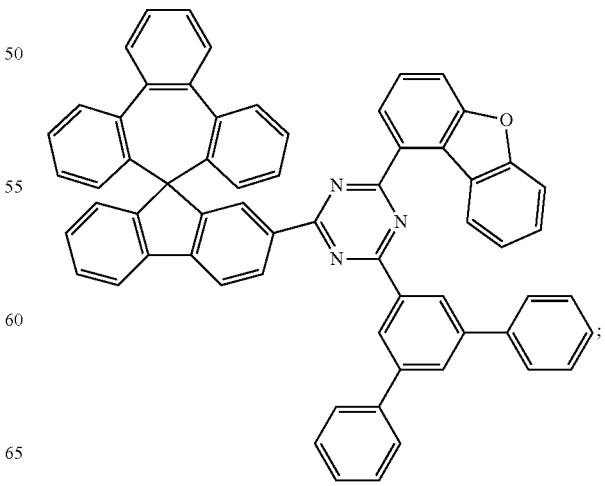

-continued
Compound I-41
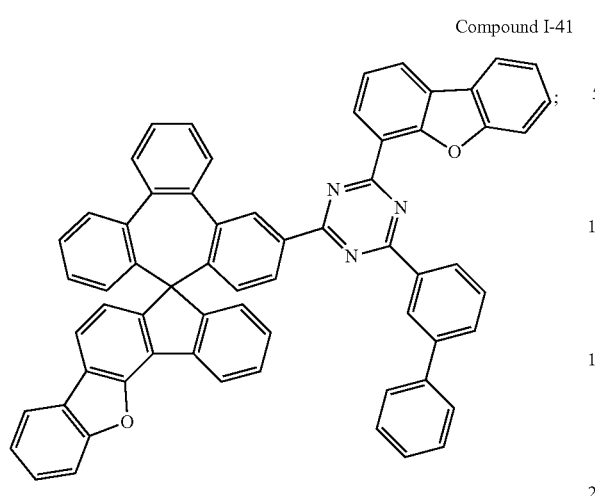
Compound I-42
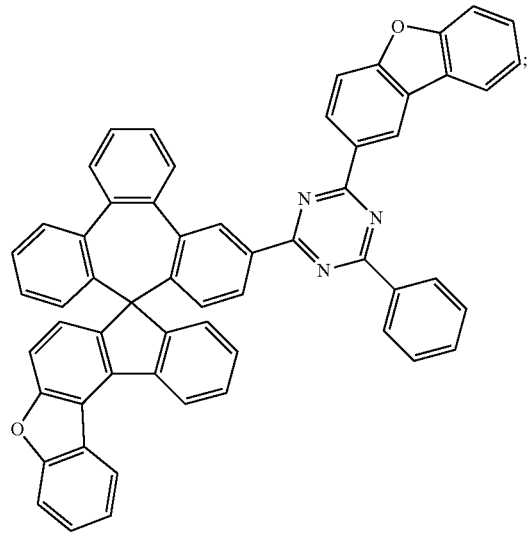
Compound I-43
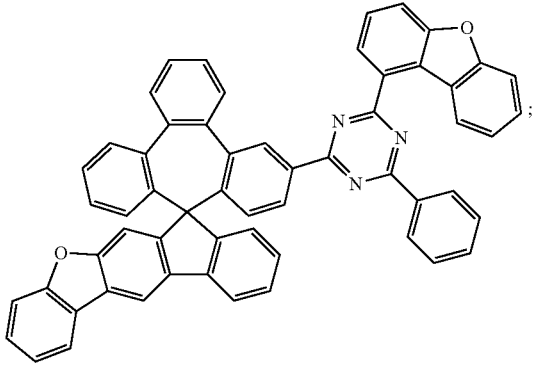
-continued
Compound I-44
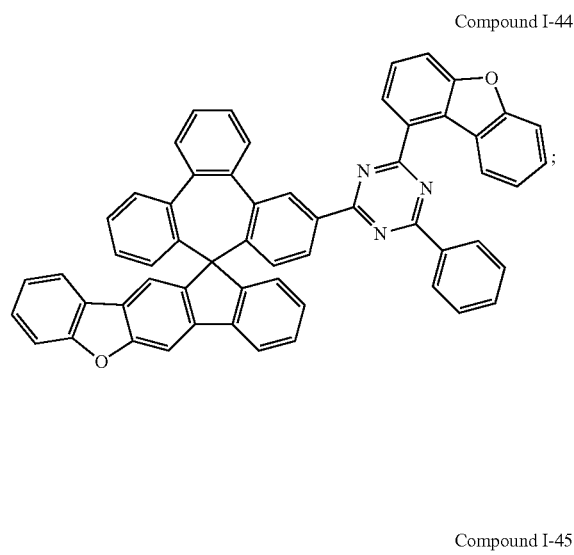
Compound I-45
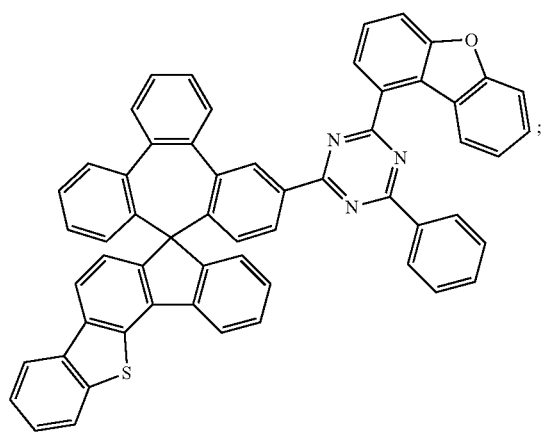
Compound I-46
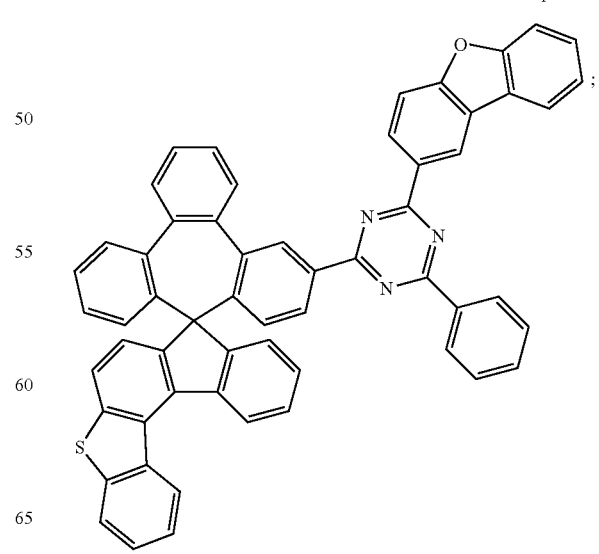

Compound I-47
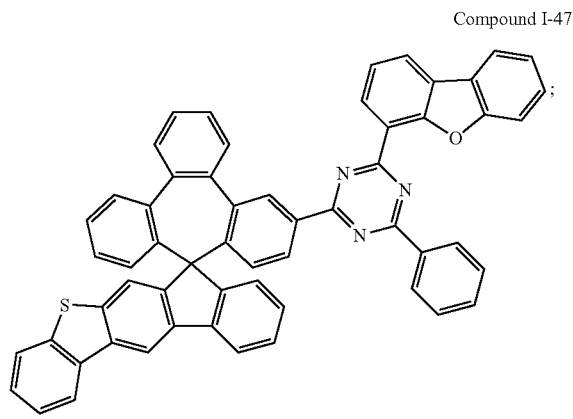
Compound I-48
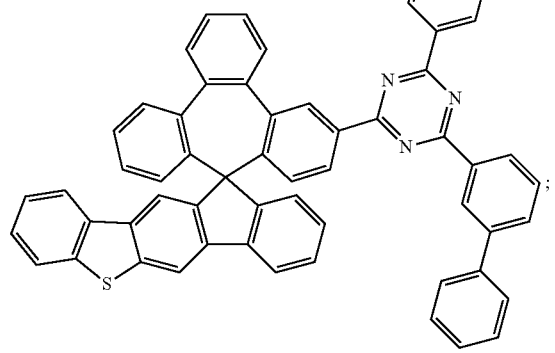
Compound I-49
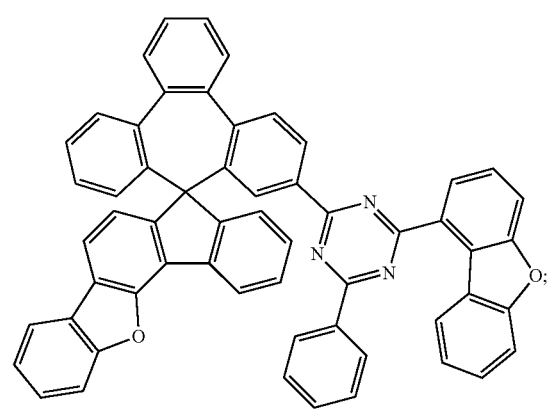
Compound I-50
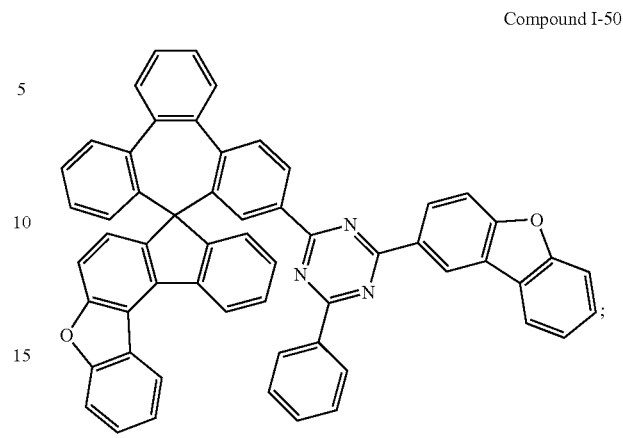
Compound I-51
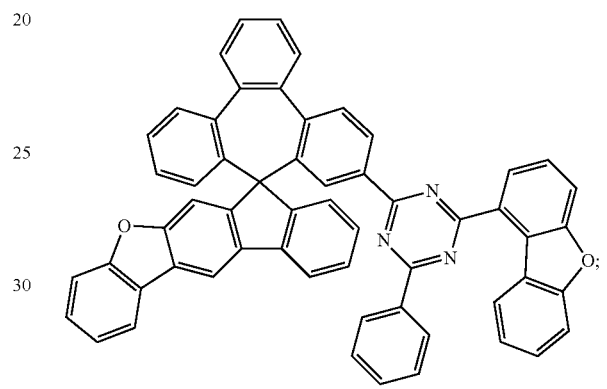
Compound I-52
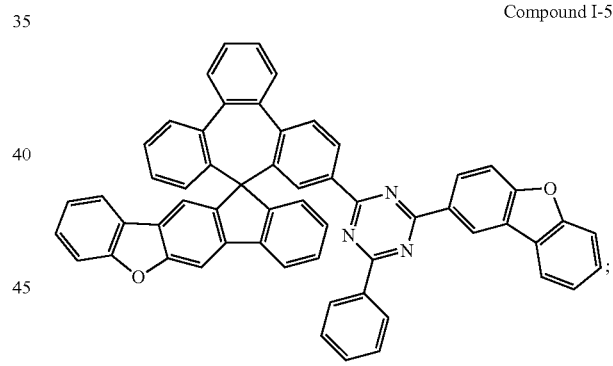
Compound I-53
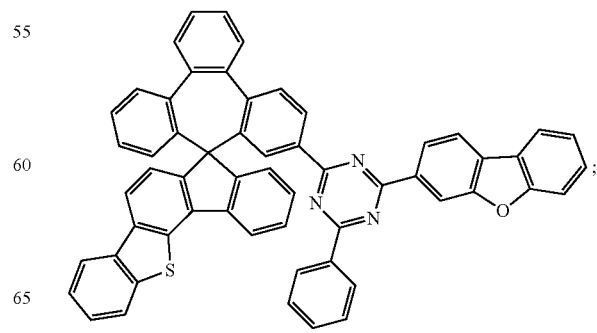

Compound I-54
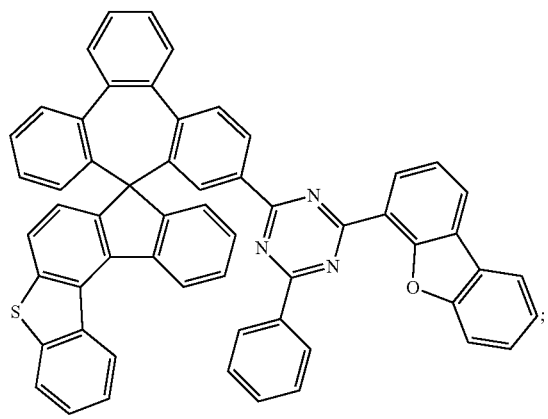
Compound I-55
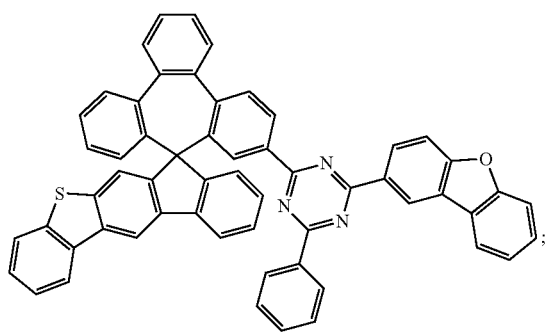
Compound I-56
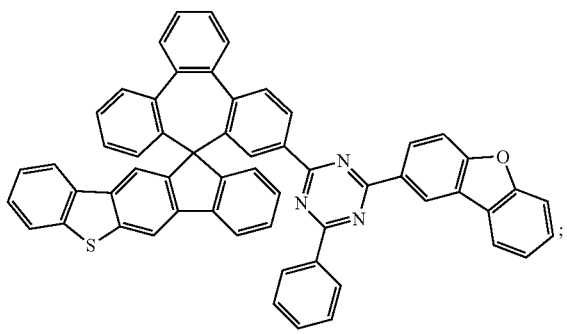
Compound I-57
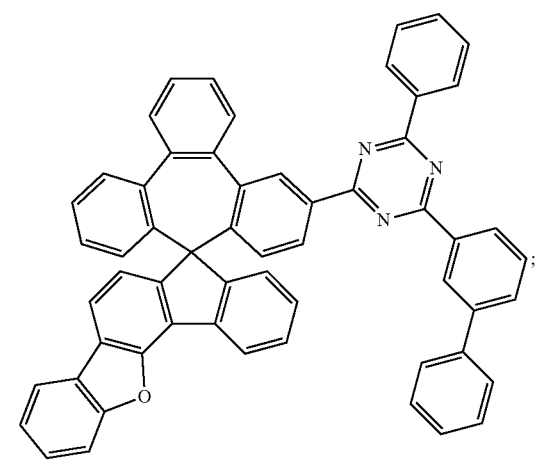
Compound I-58
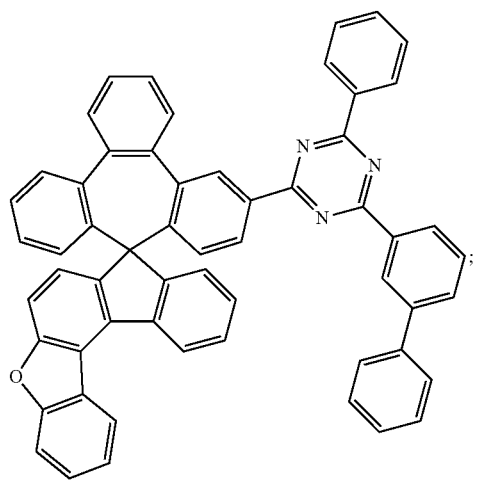
Compound I-59
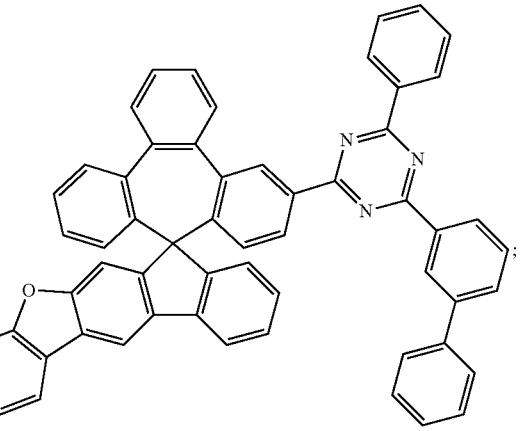
Compound I-60
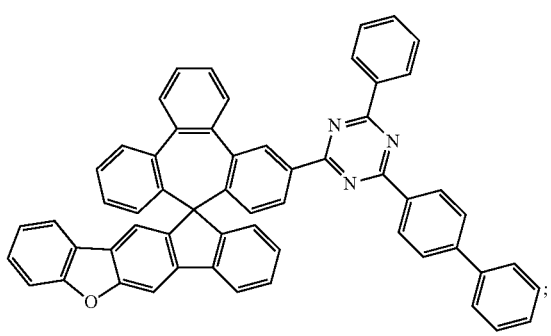

Compound i-61
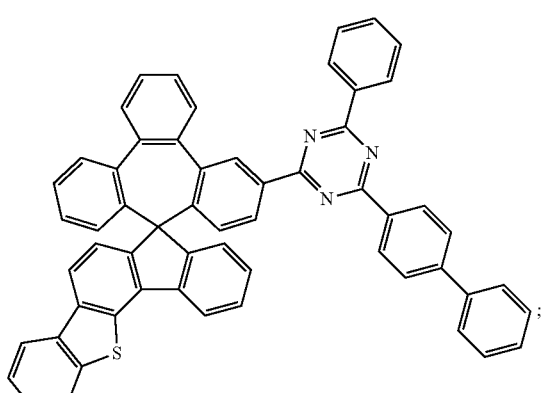
Compound I-62
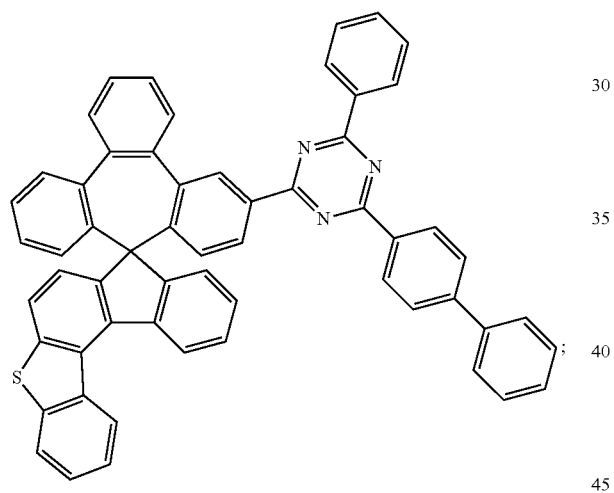
Compound i-63
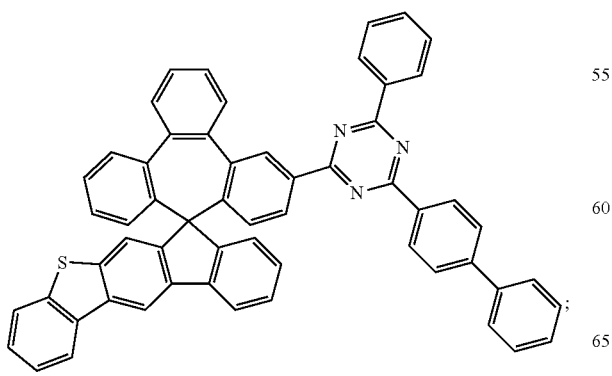
Compound I-64
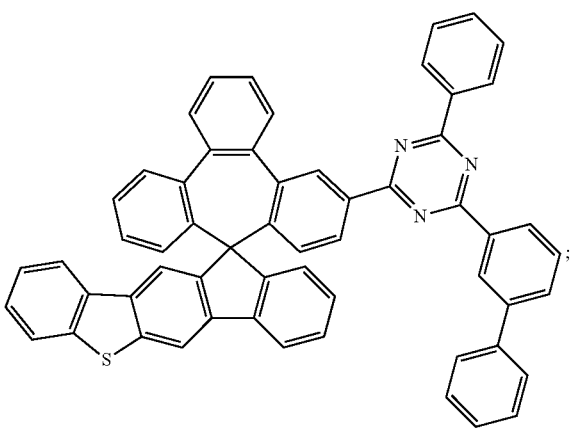
Compound I-65
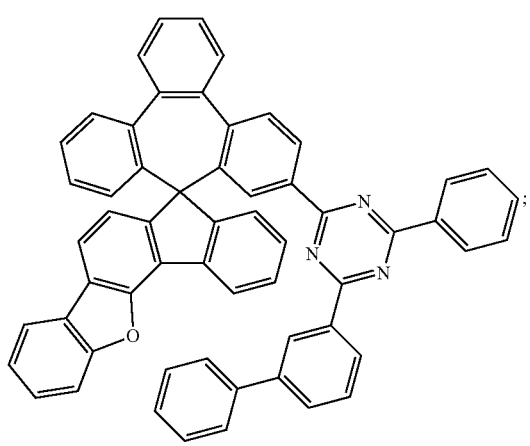
Compound I-66
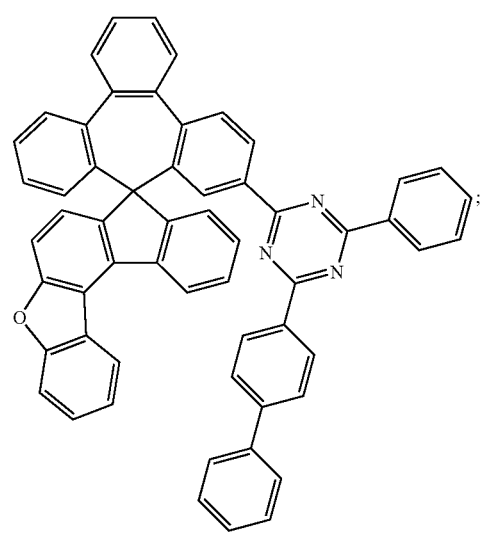

Compound I-67
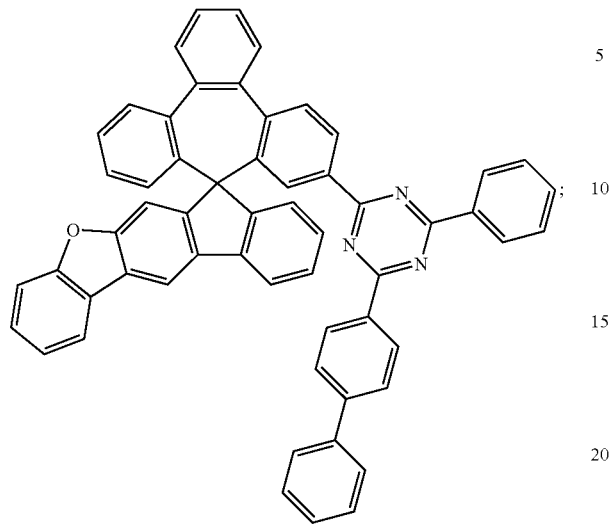
Compound I-68
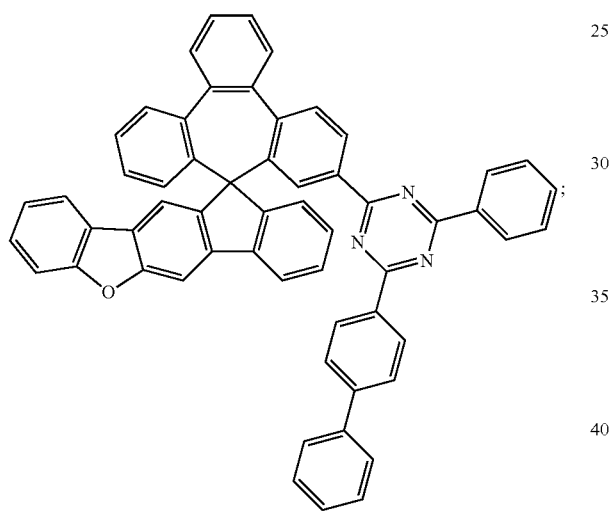
Compound I-69
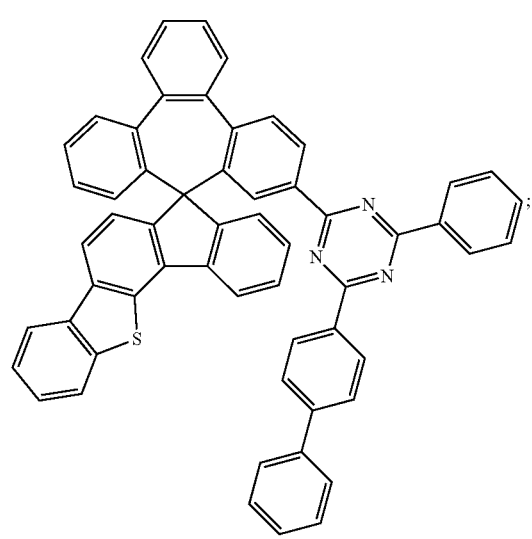
Compound i-70
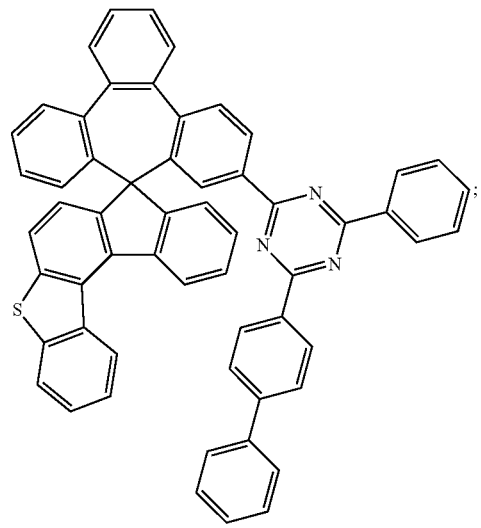
Compound I-71
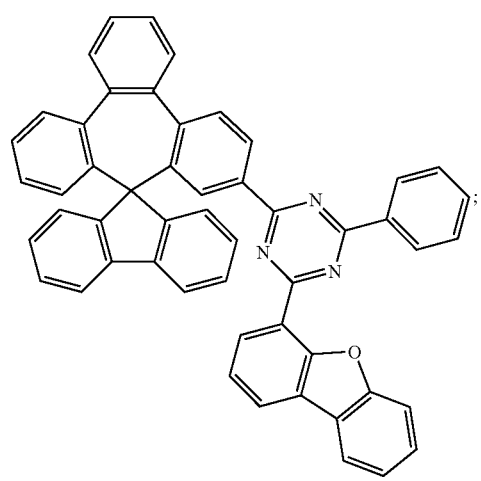
Compound I-72
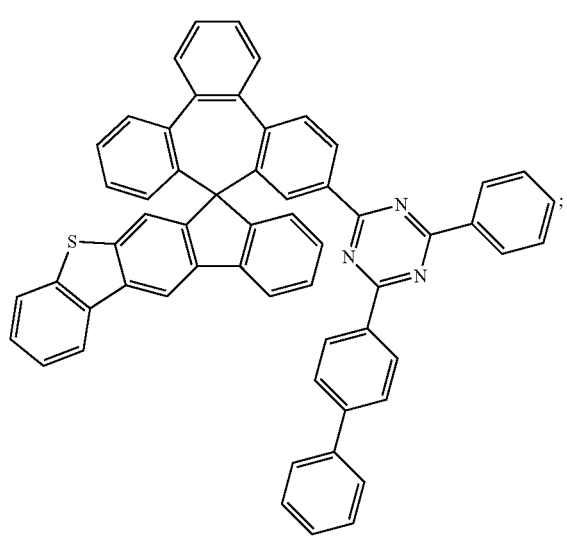

-continued
Compound I-73
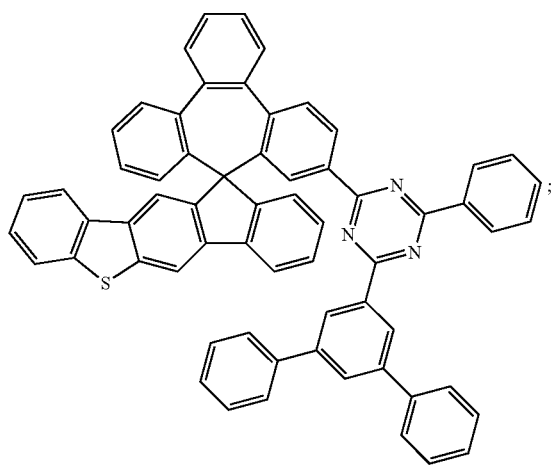
Compound I-74
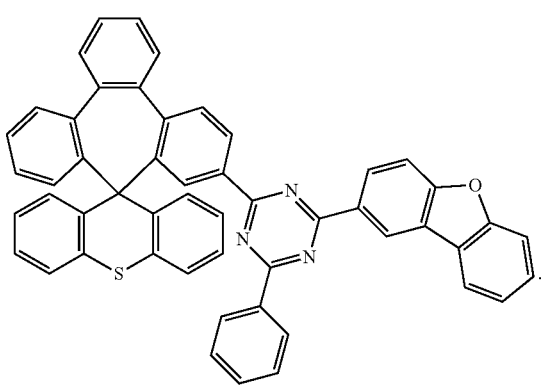
Compound I-75
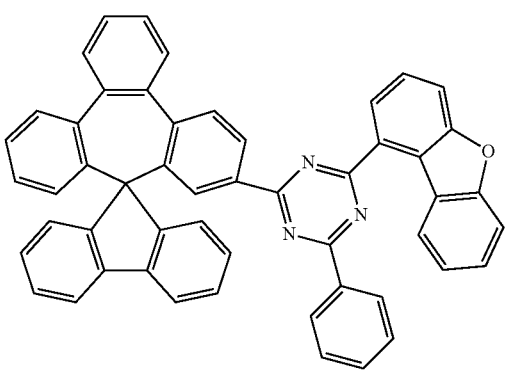
For example, the first host compound may be any one of the following compound:
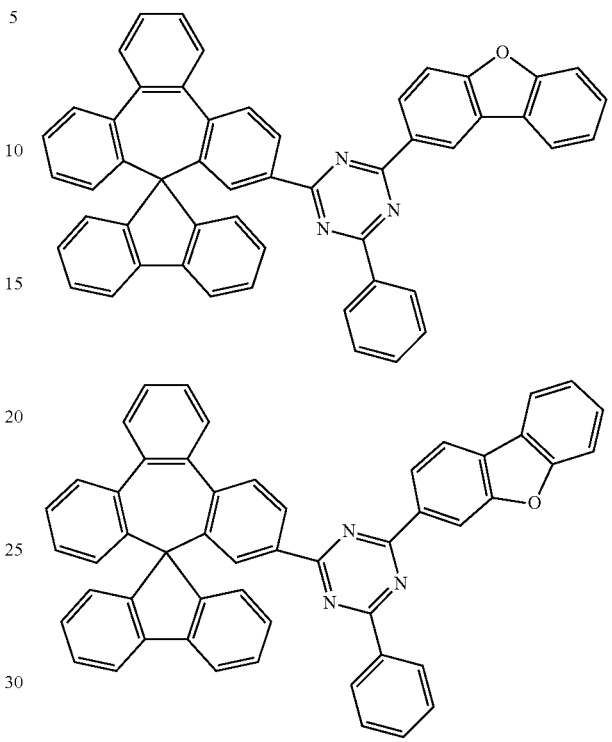
and
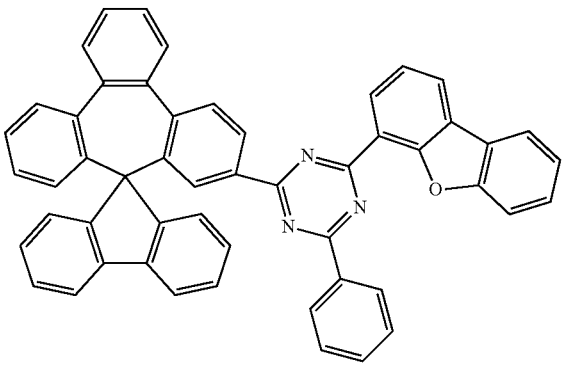

107
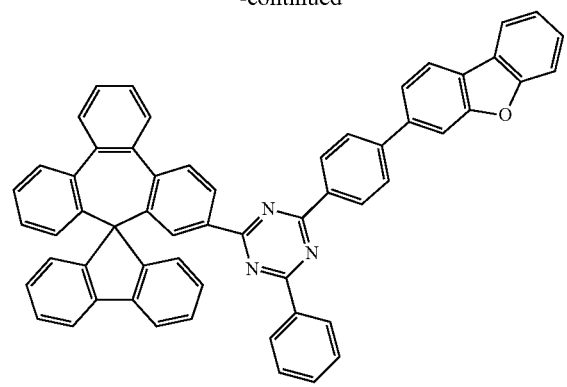
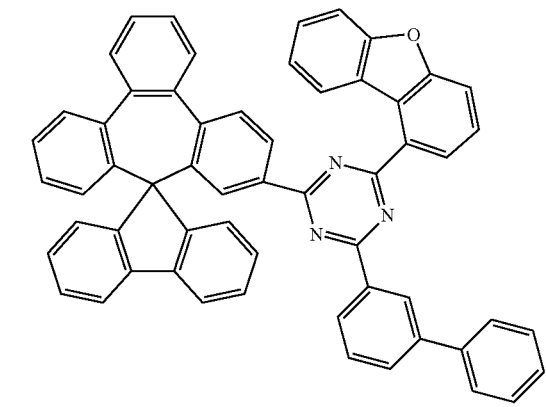
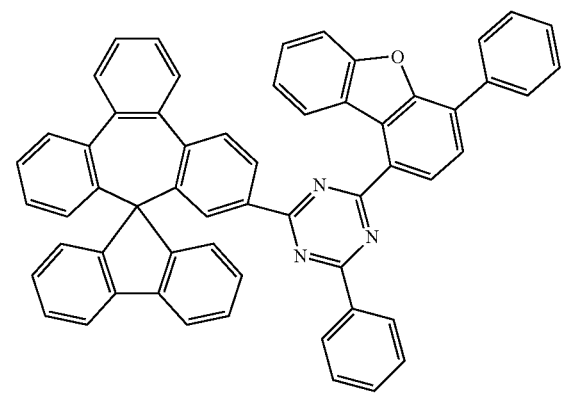
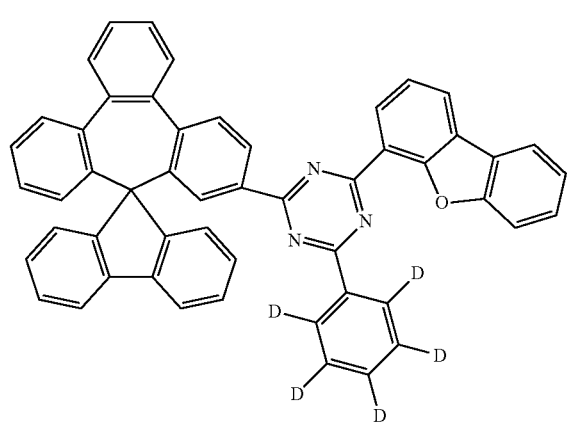
108
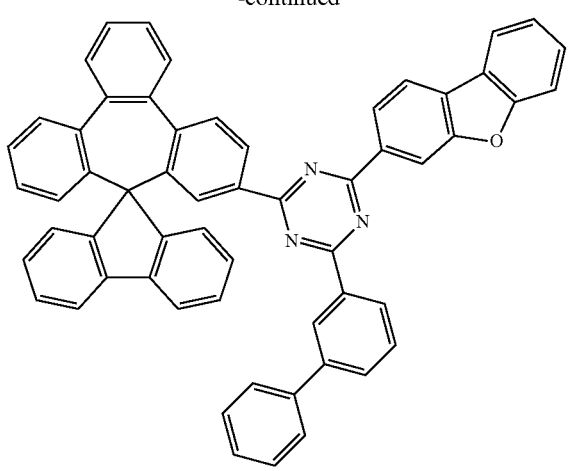
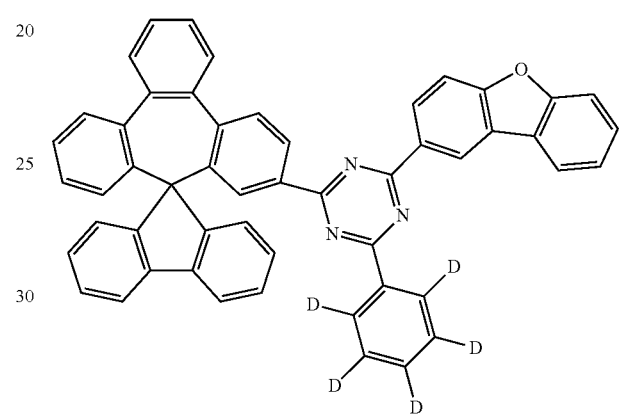
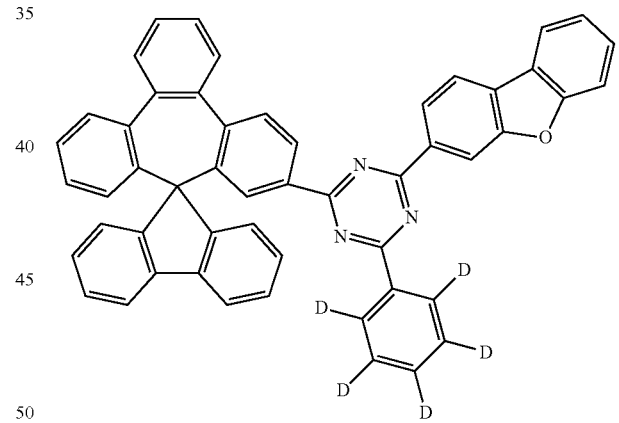
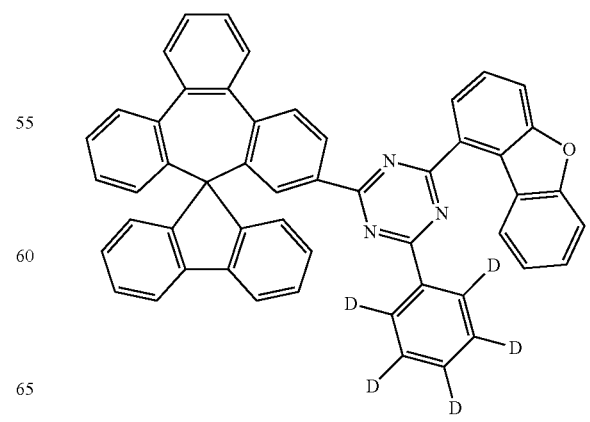

109
-continued
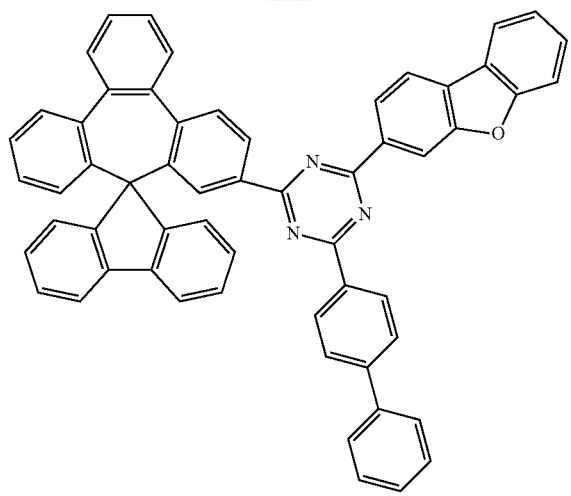
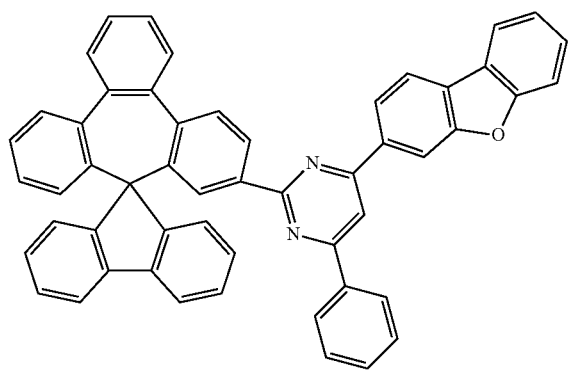
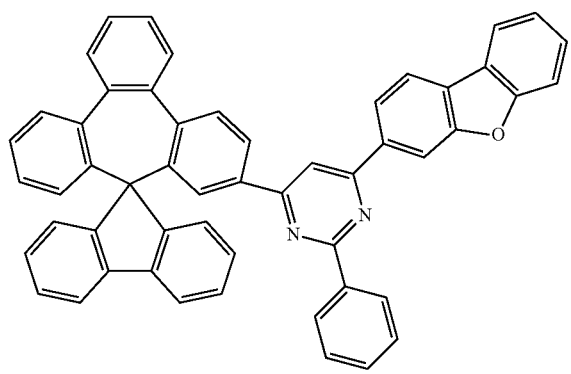
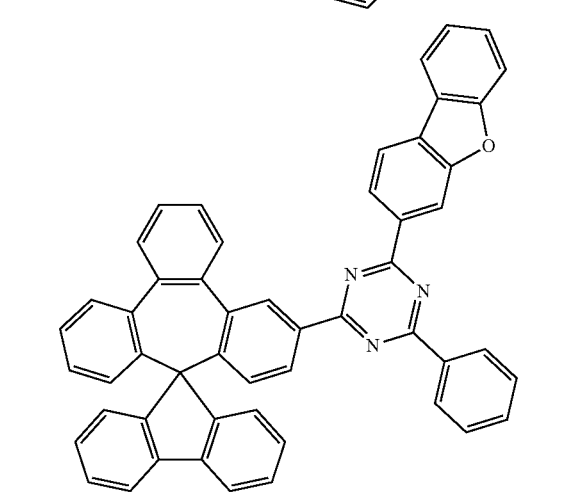
110
-continued
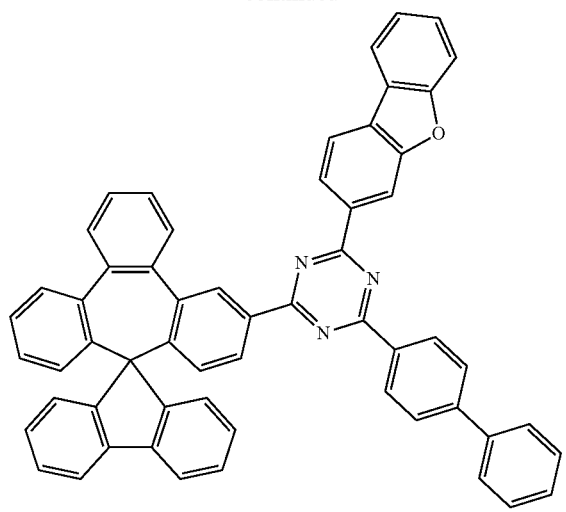

111
-continued
112
-continued
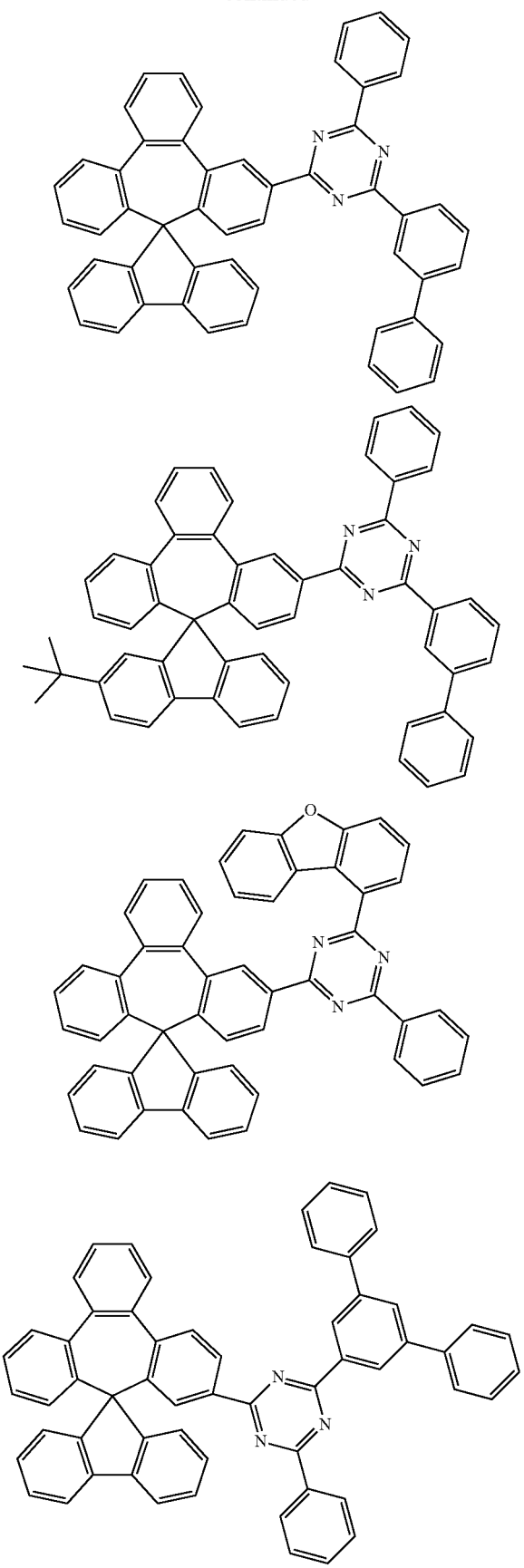
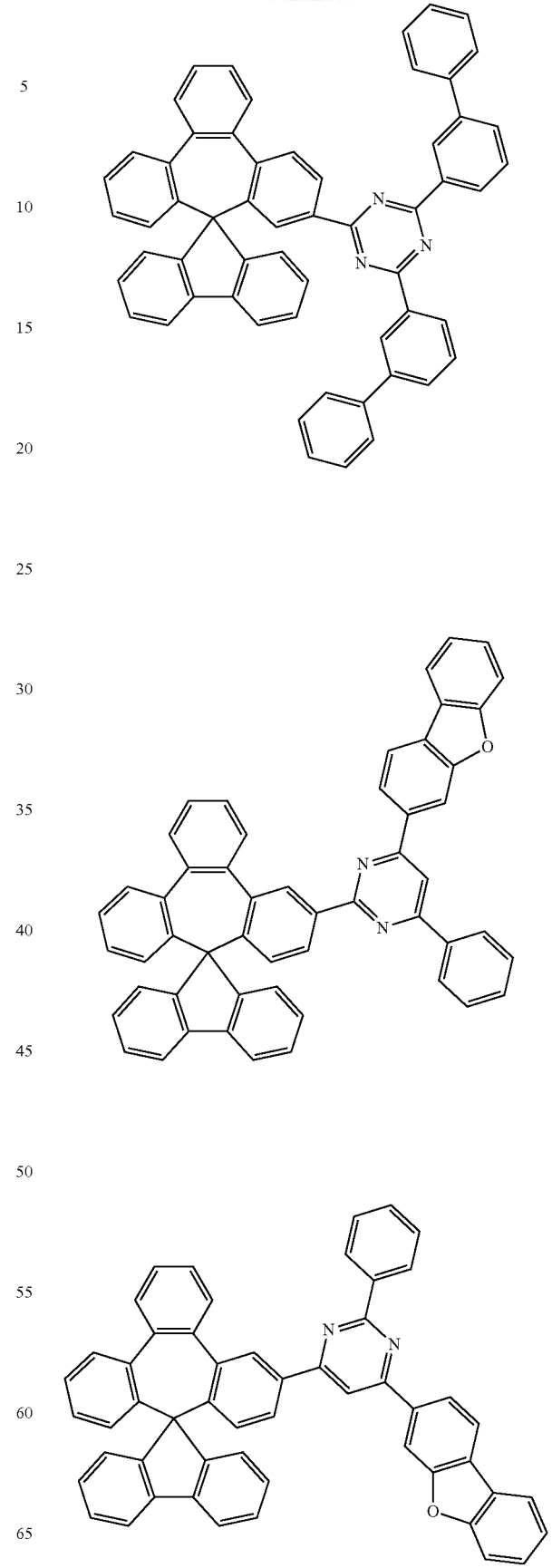

113
-continued
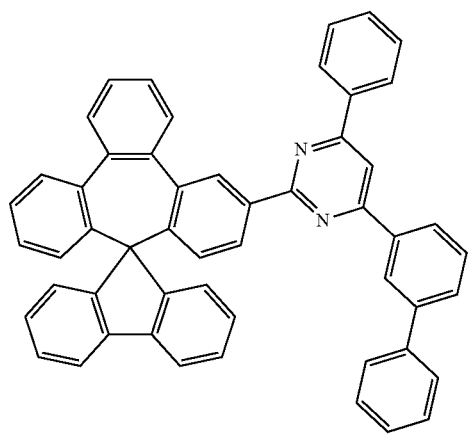
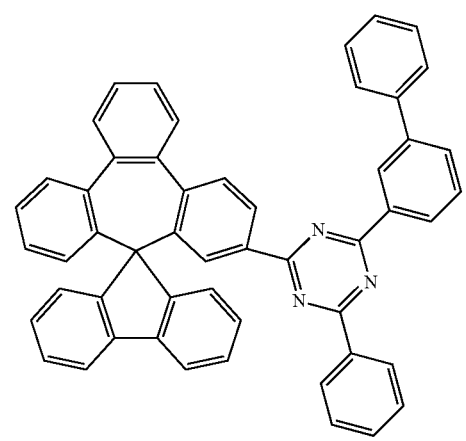
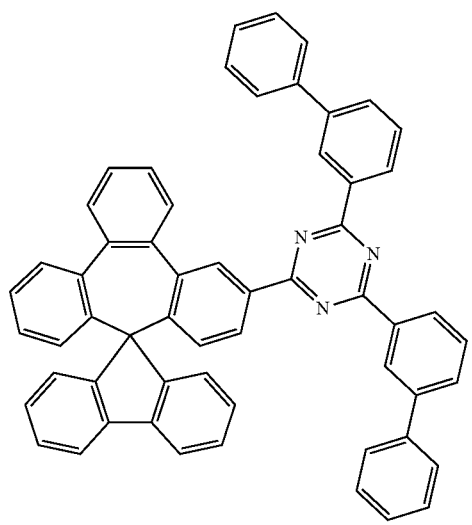
114
-continued
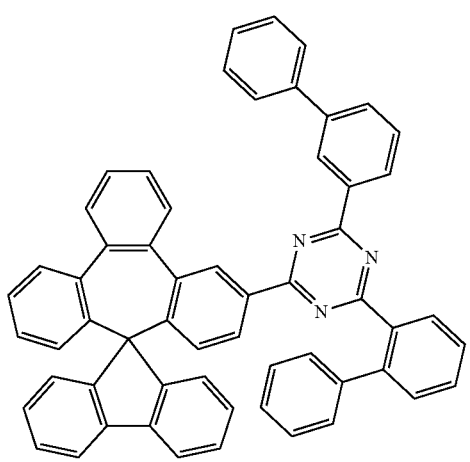
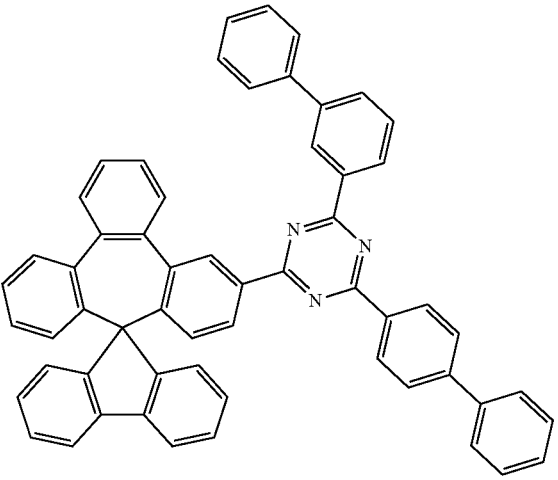
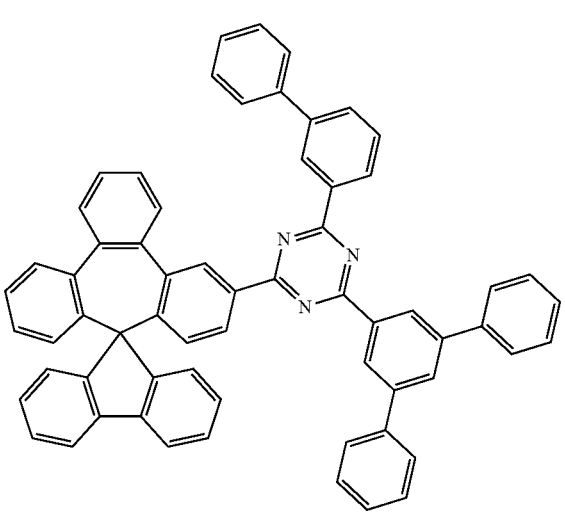

115
-continued
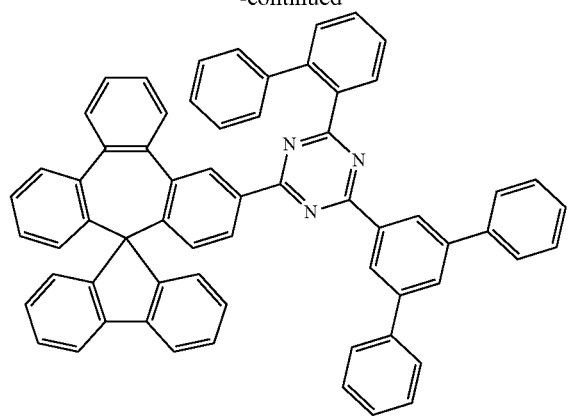
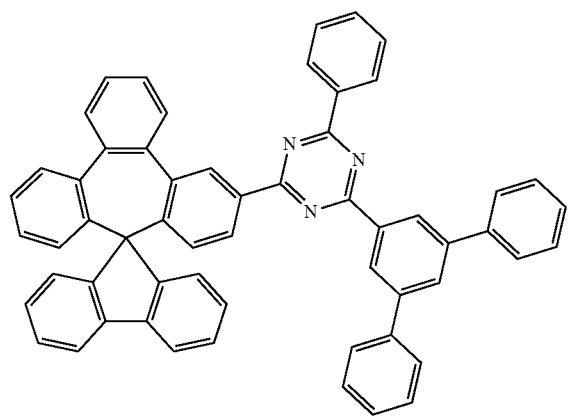
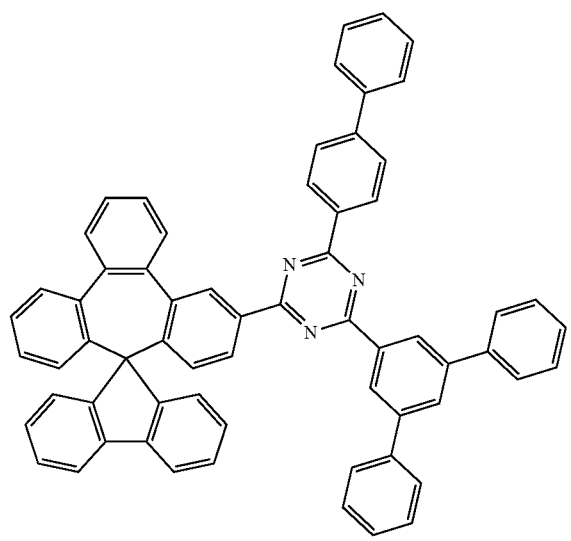
116
-continued
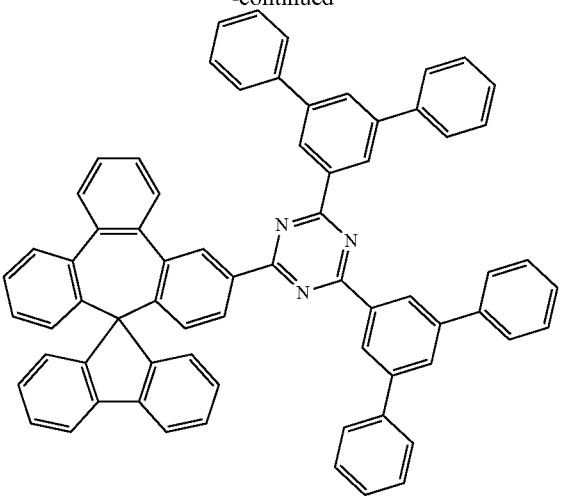
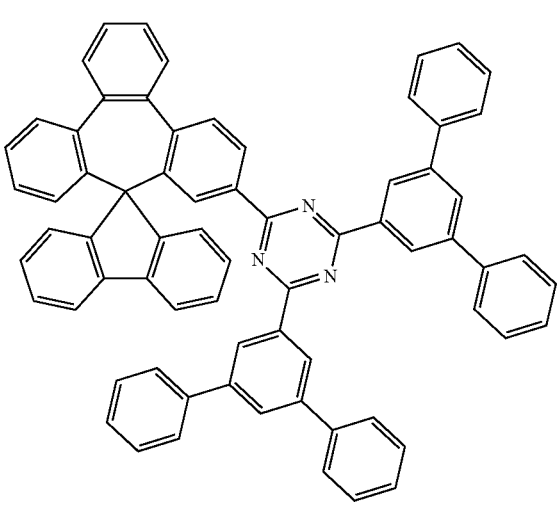
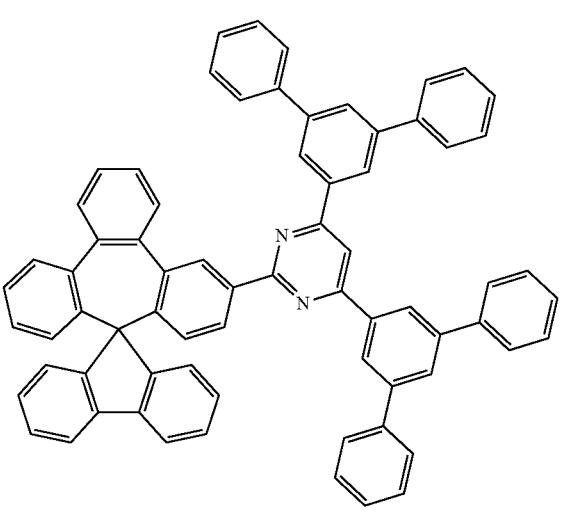

117
-continued
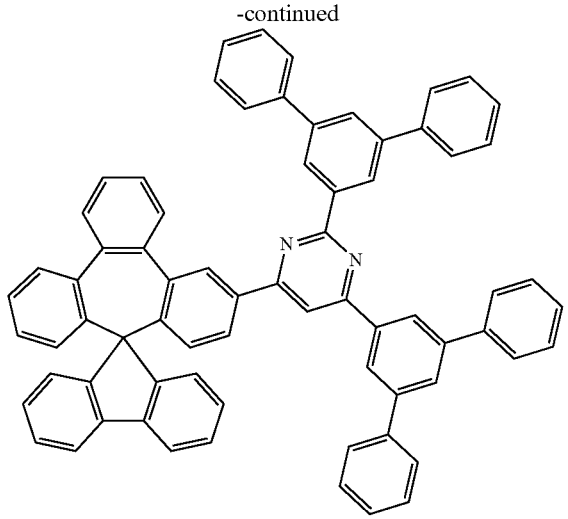
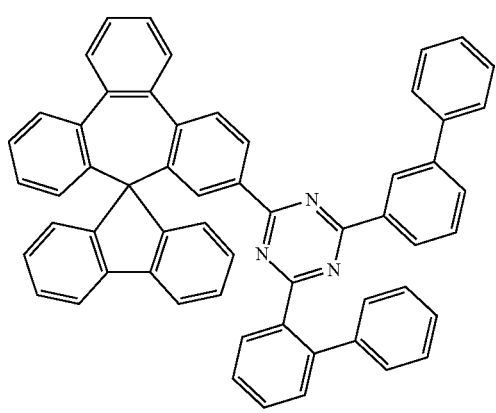
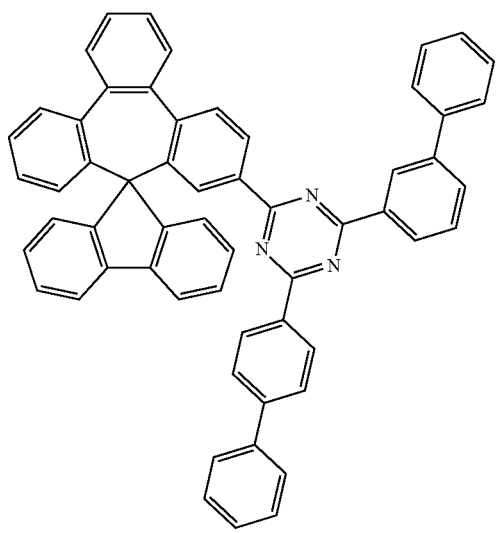
118
-continued
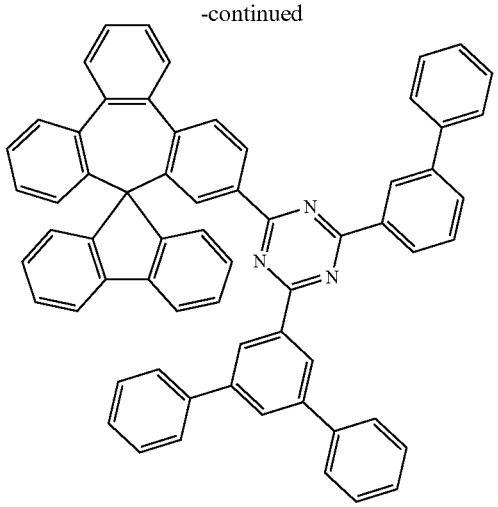
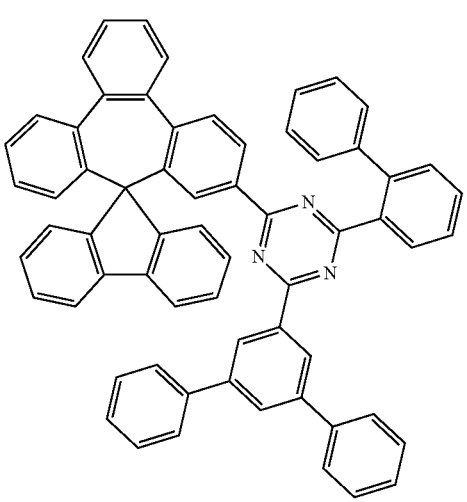
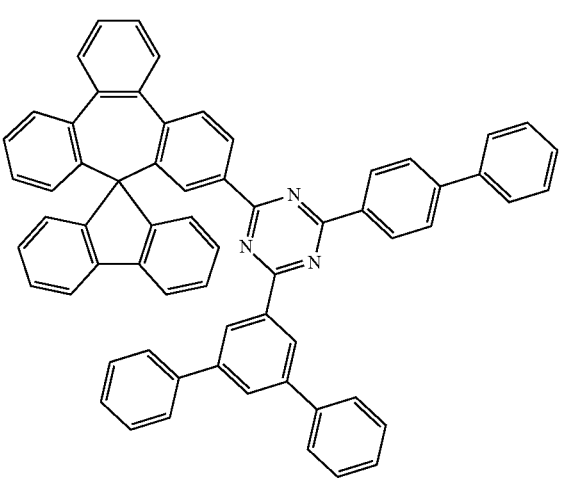

119
-continued
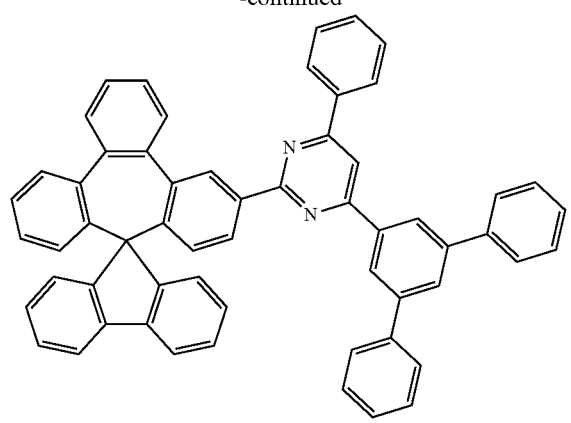
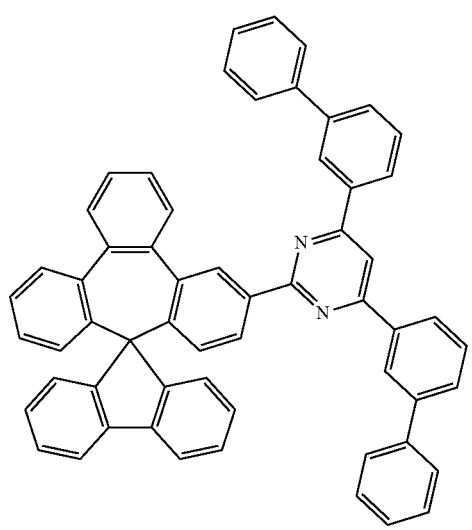
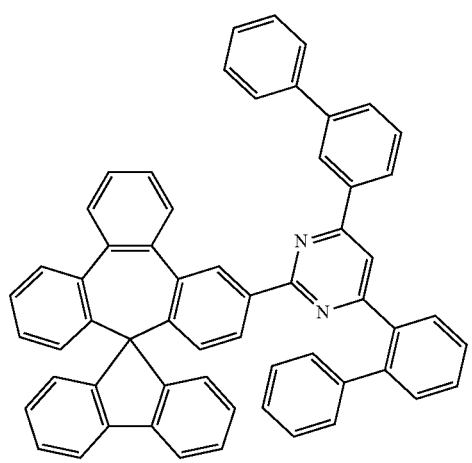
120
-continued
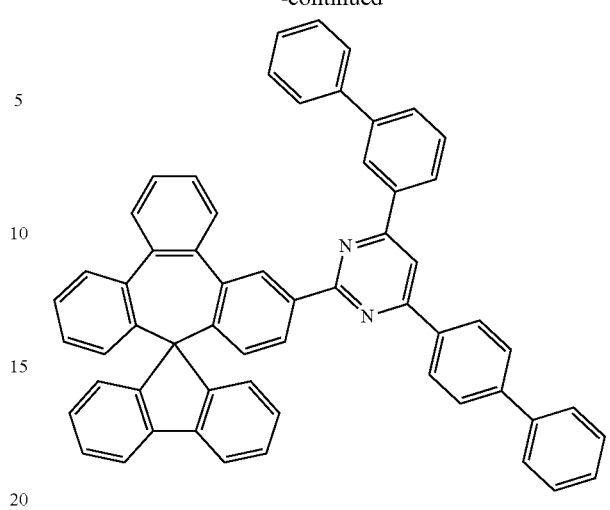
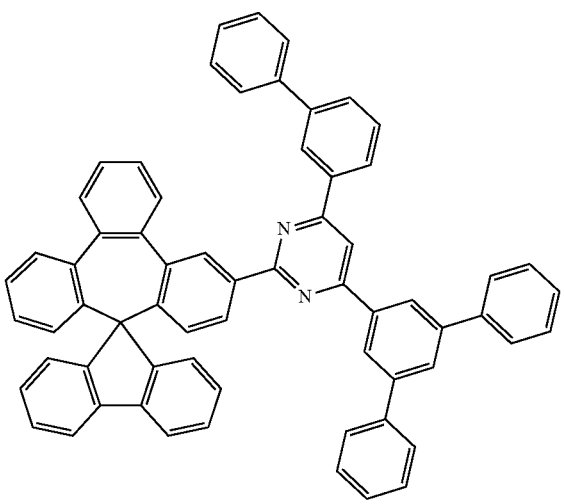
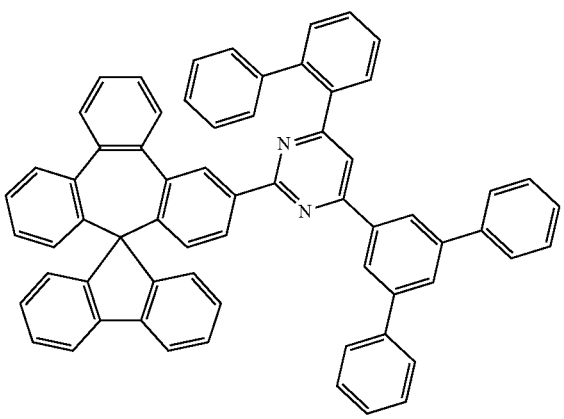

121
-continued
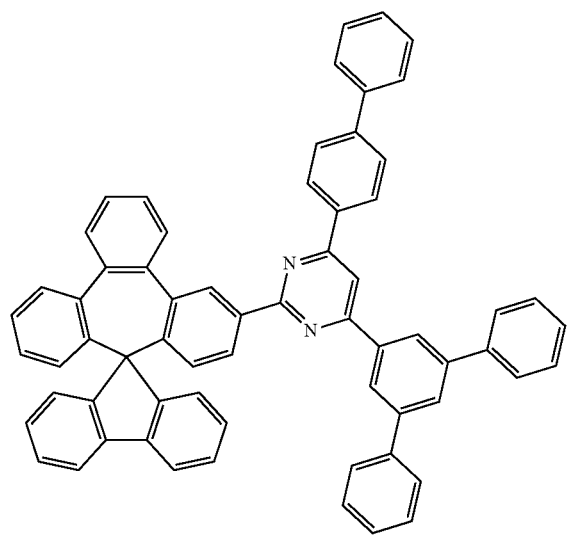
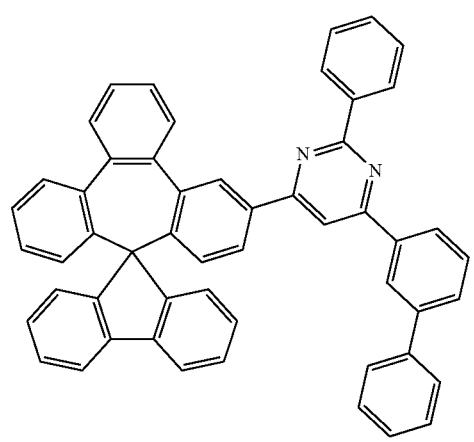
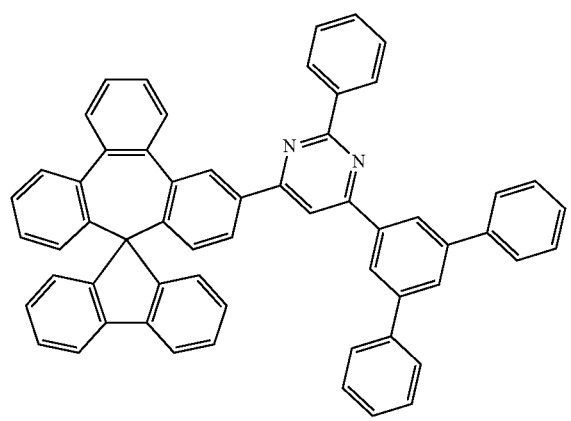
122
-continued
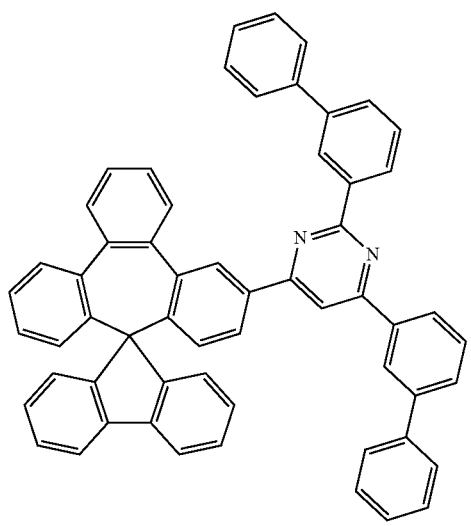
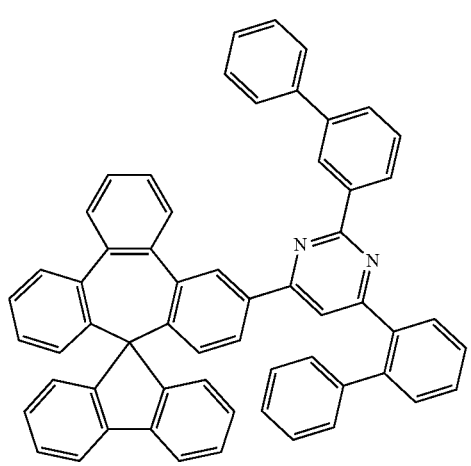
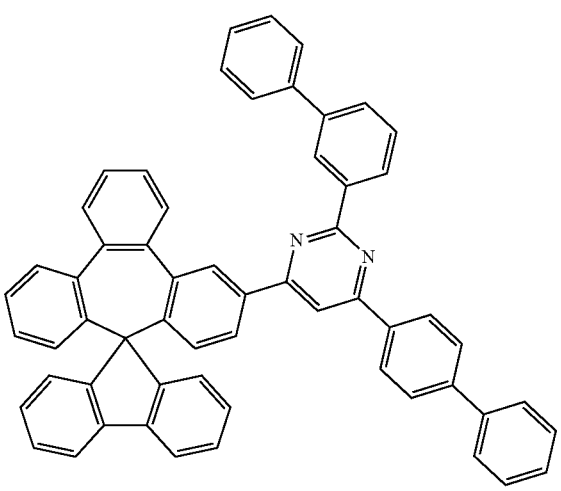

123
-continued
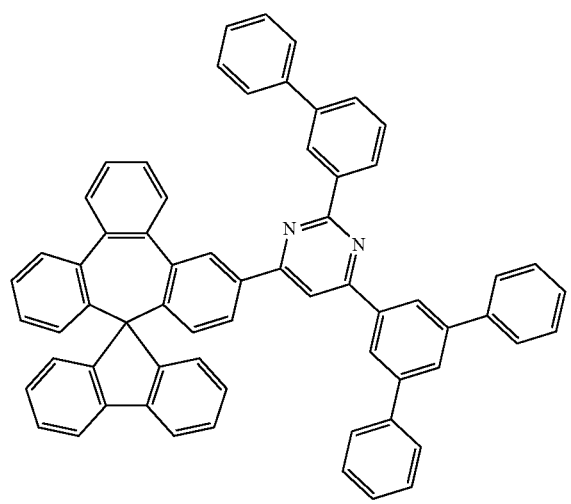
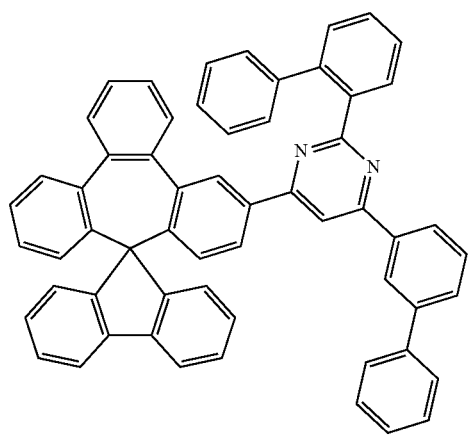
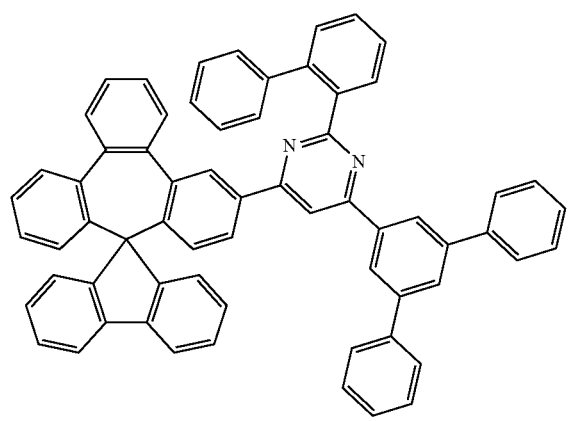
124
-continued
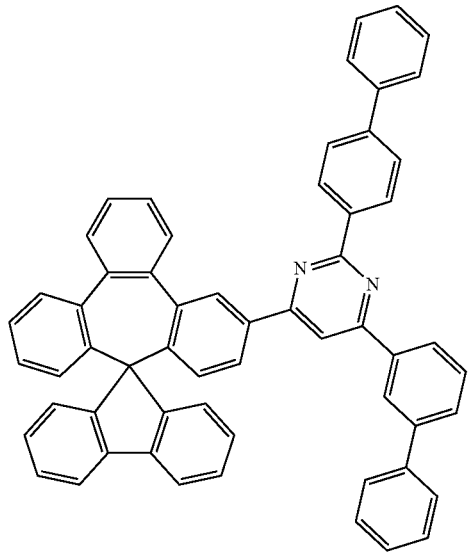
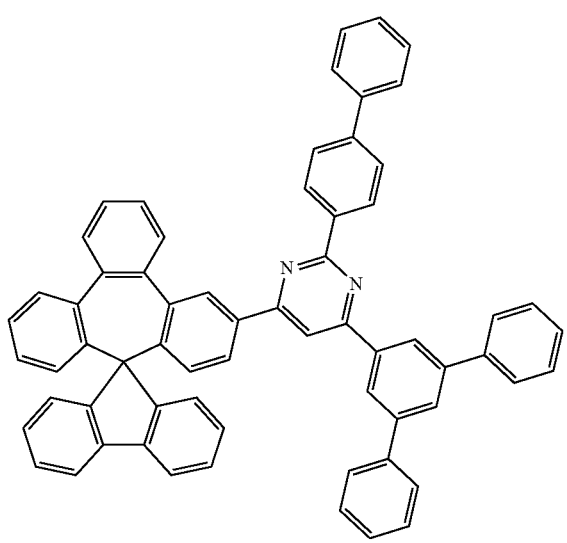
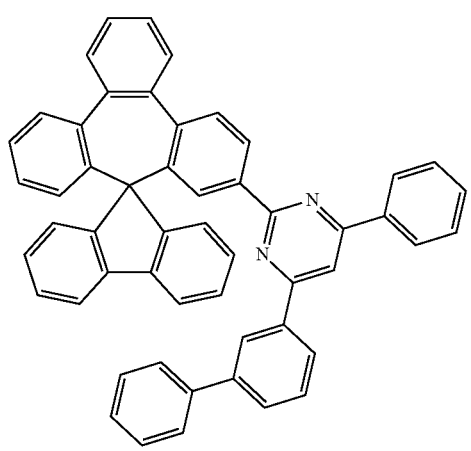

125
-continued
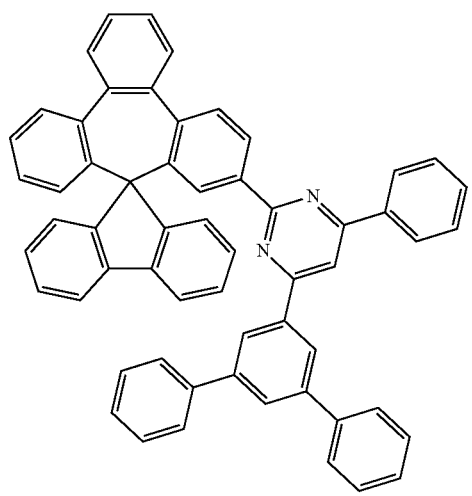
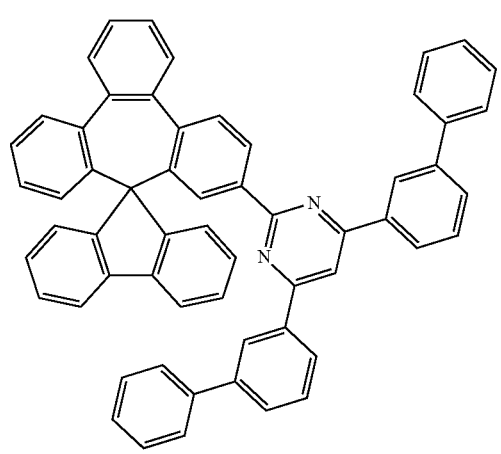
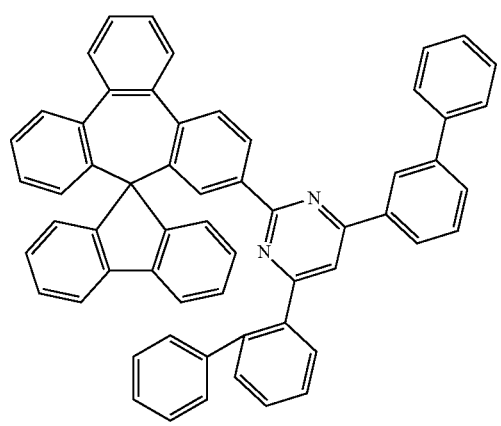
126
-continued
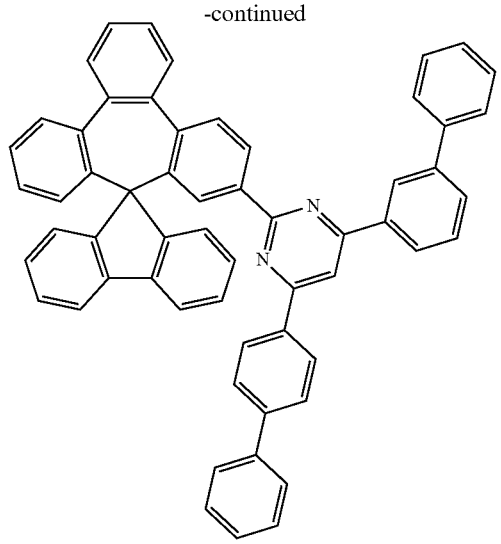
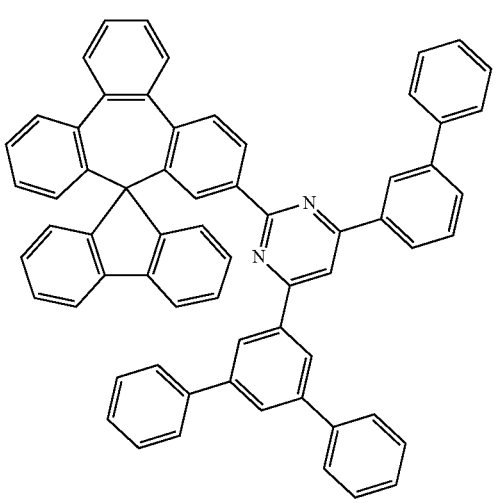

127
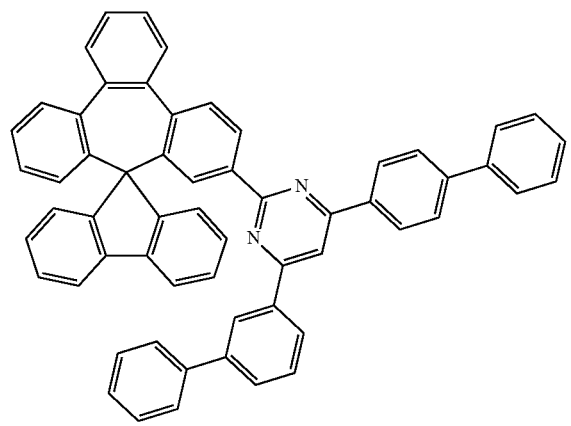
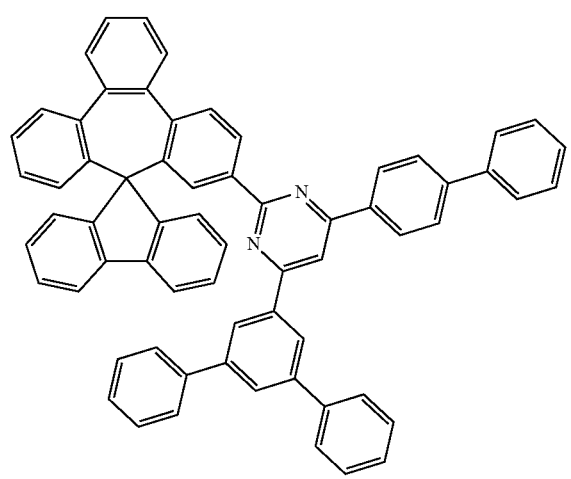
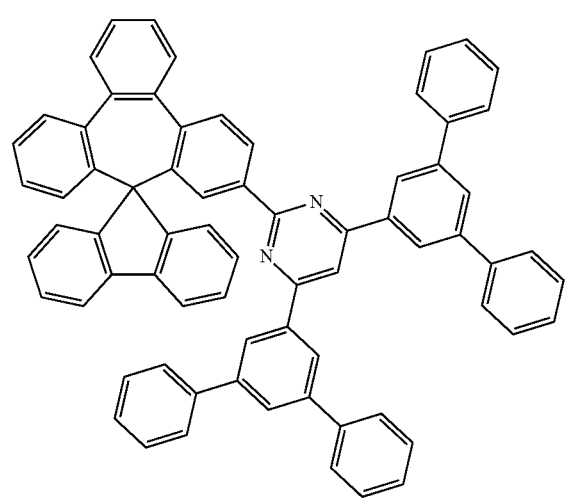
128
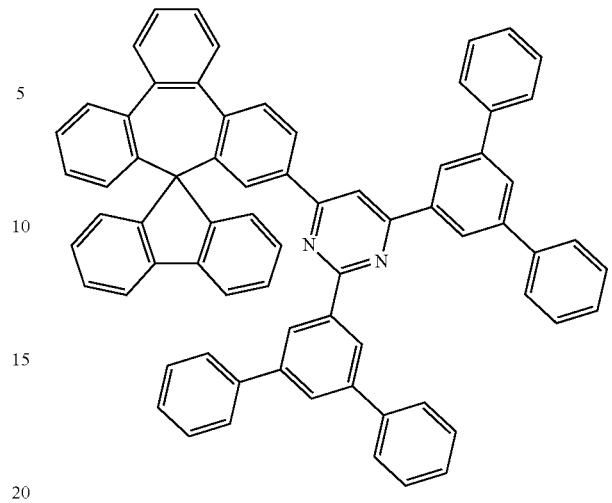
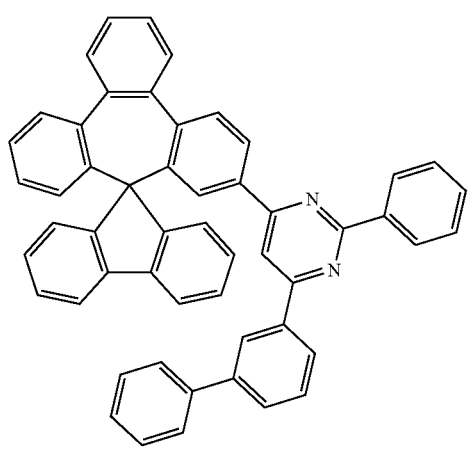
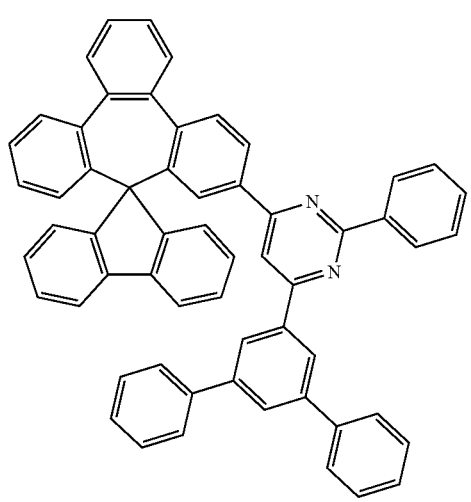

129
-continued
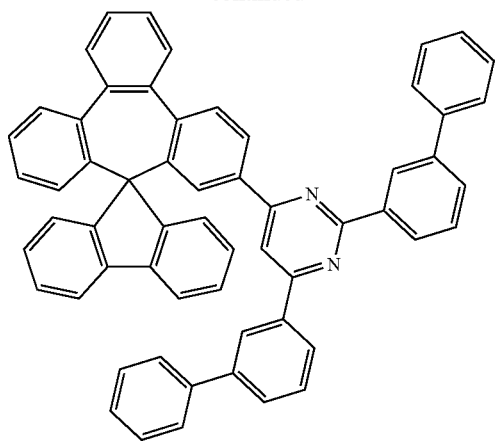
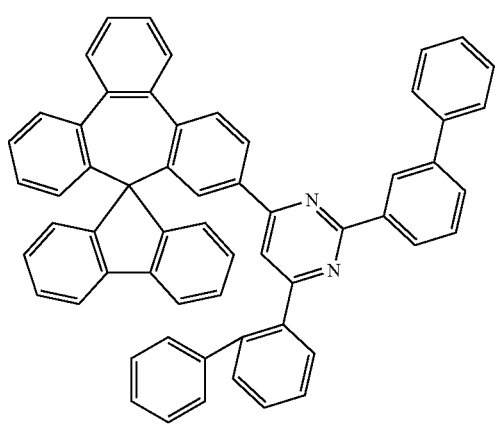
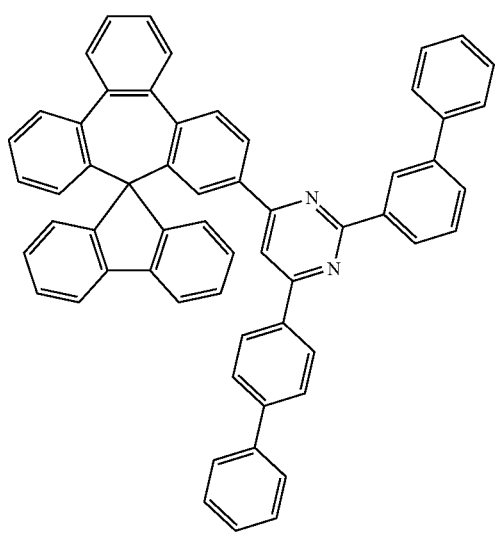
130
-continued
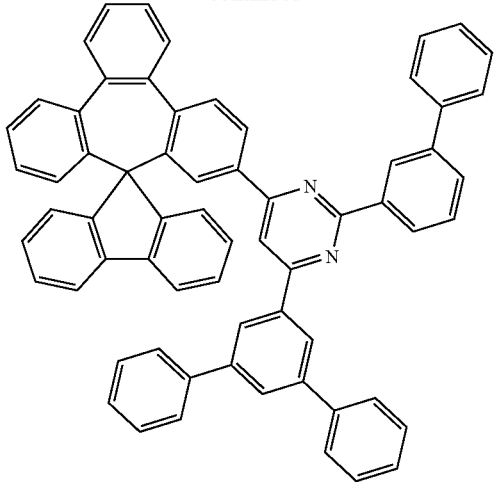
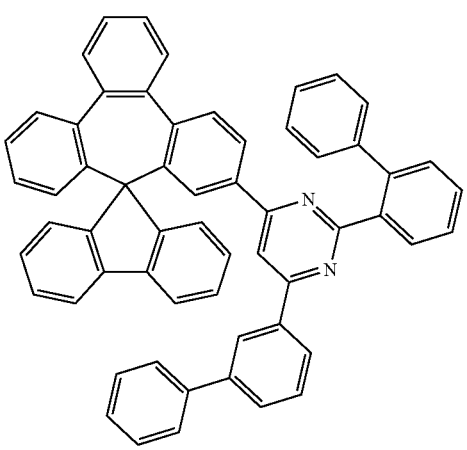
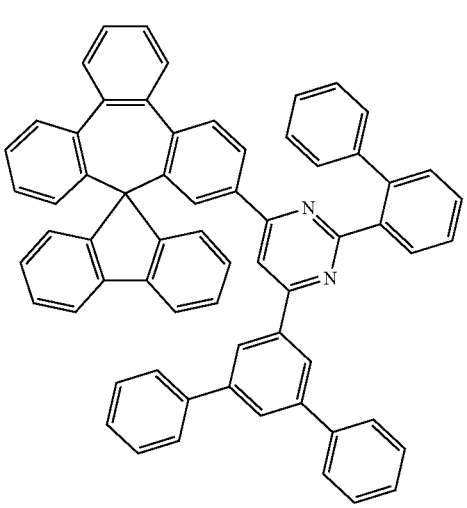

131
-continued
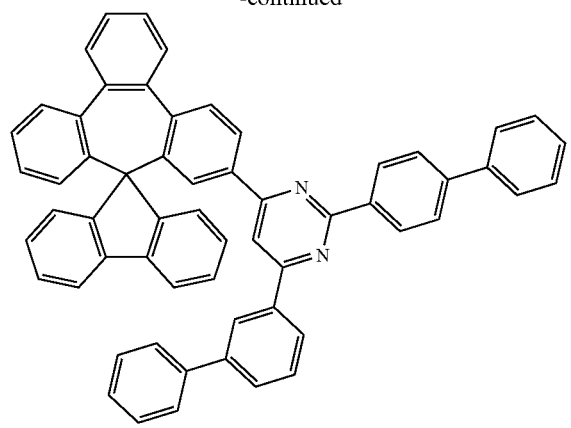
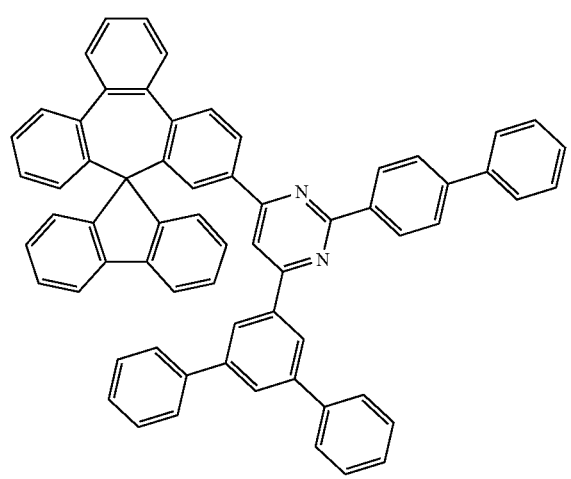
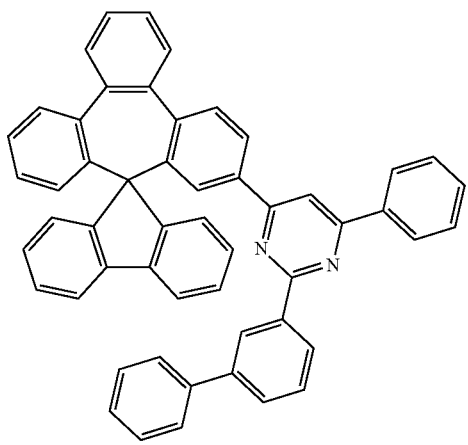
132
-continued
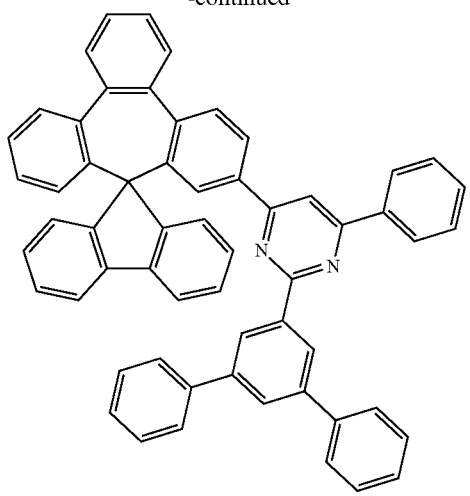
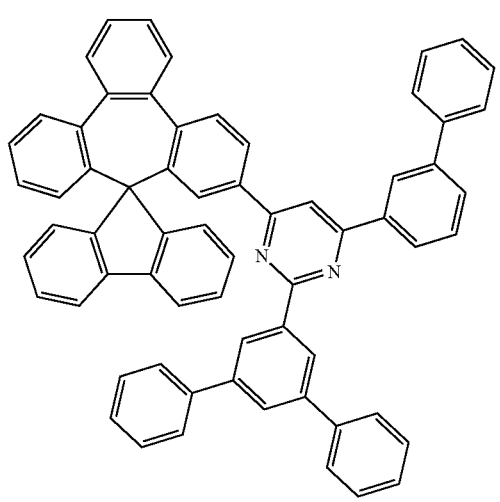
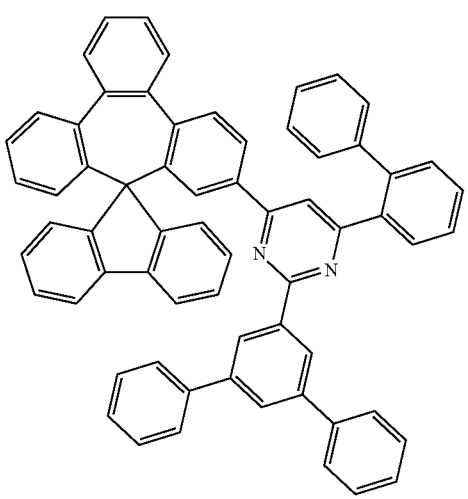

133
-continued
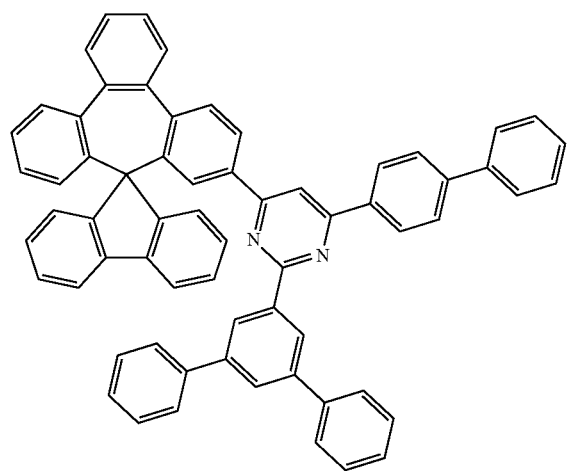
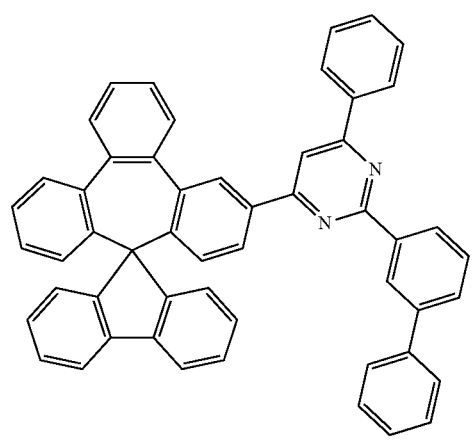
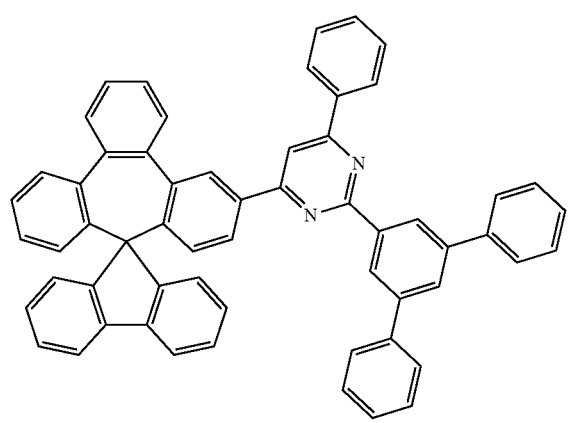
134
-continued
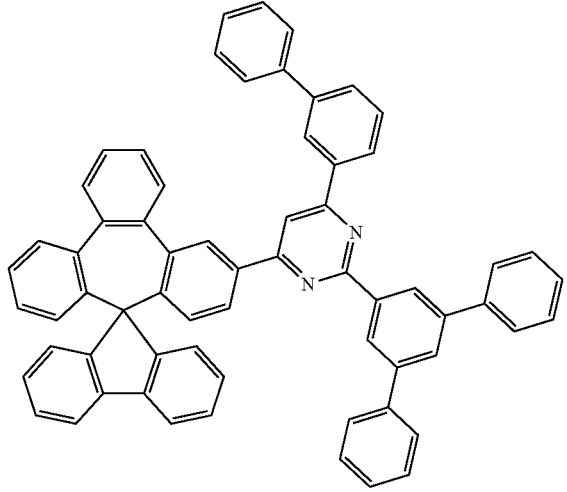
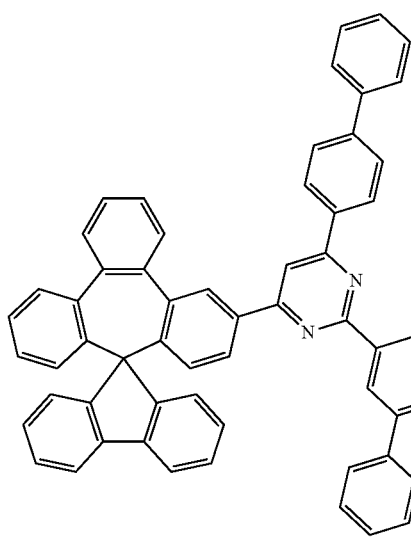

135
-continued
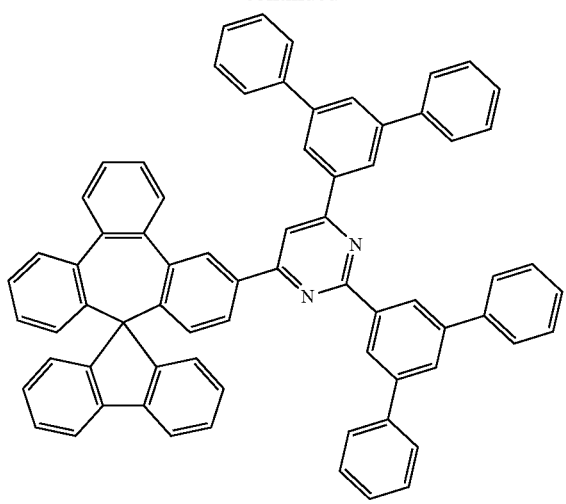
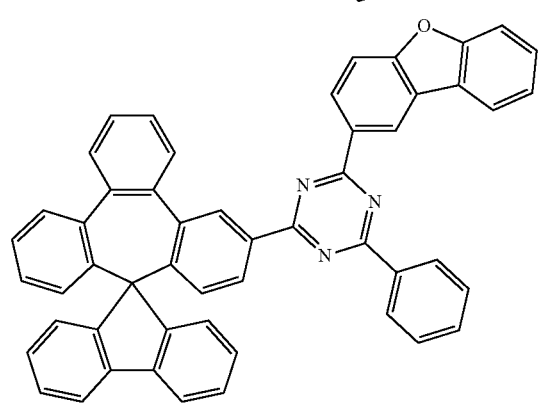
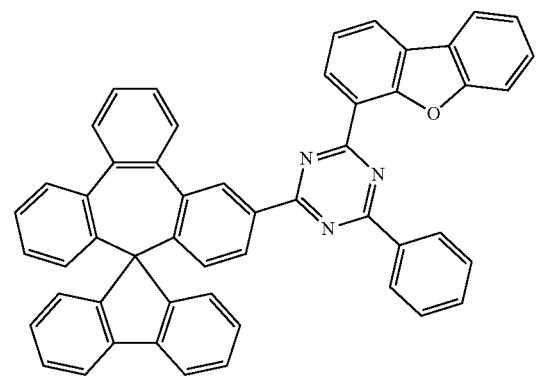
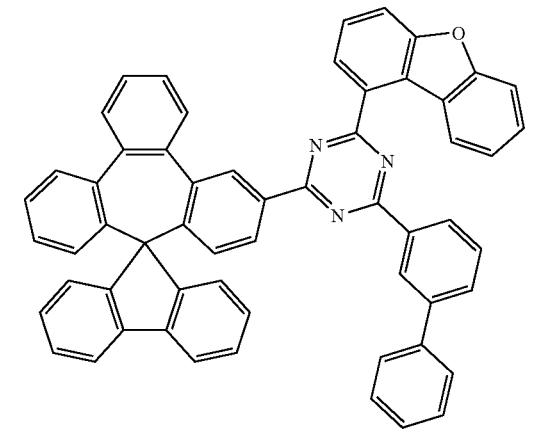
136
-continued
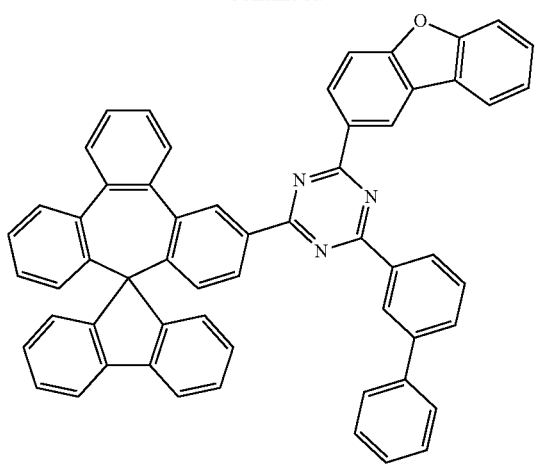
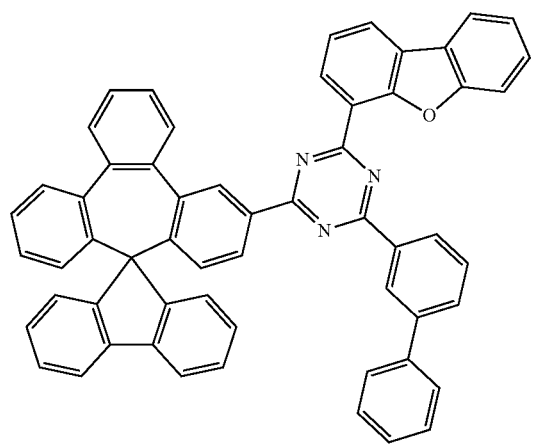
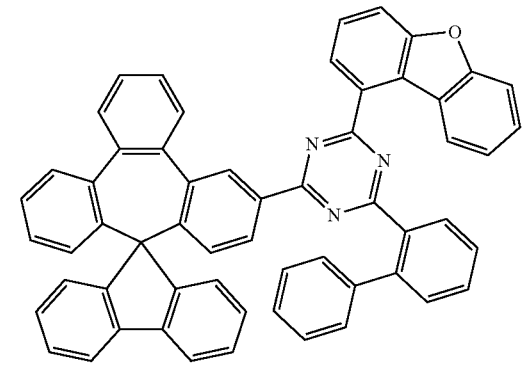
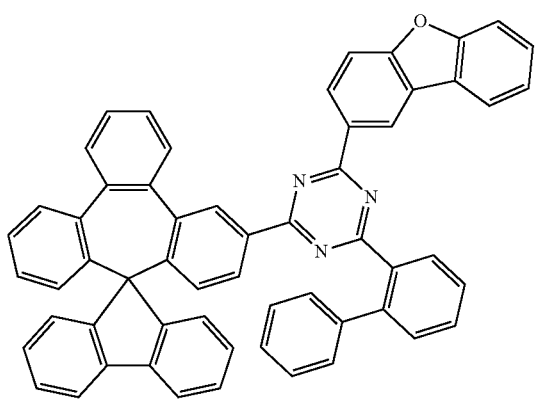

137
-continued
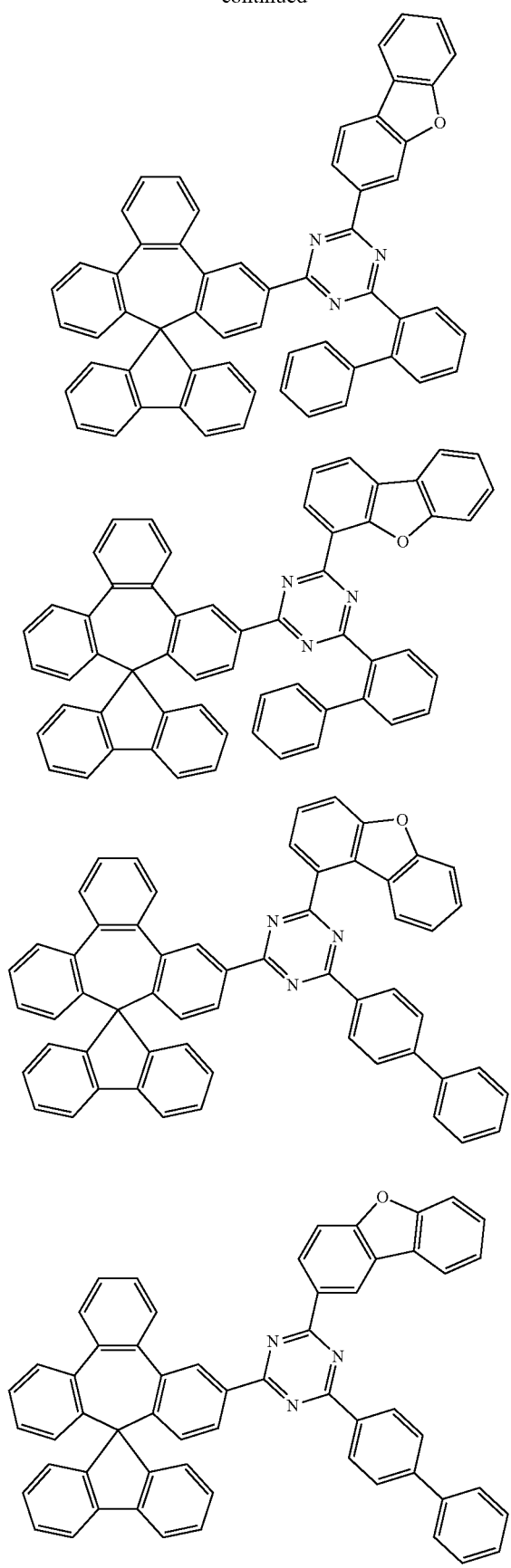
138
-continued
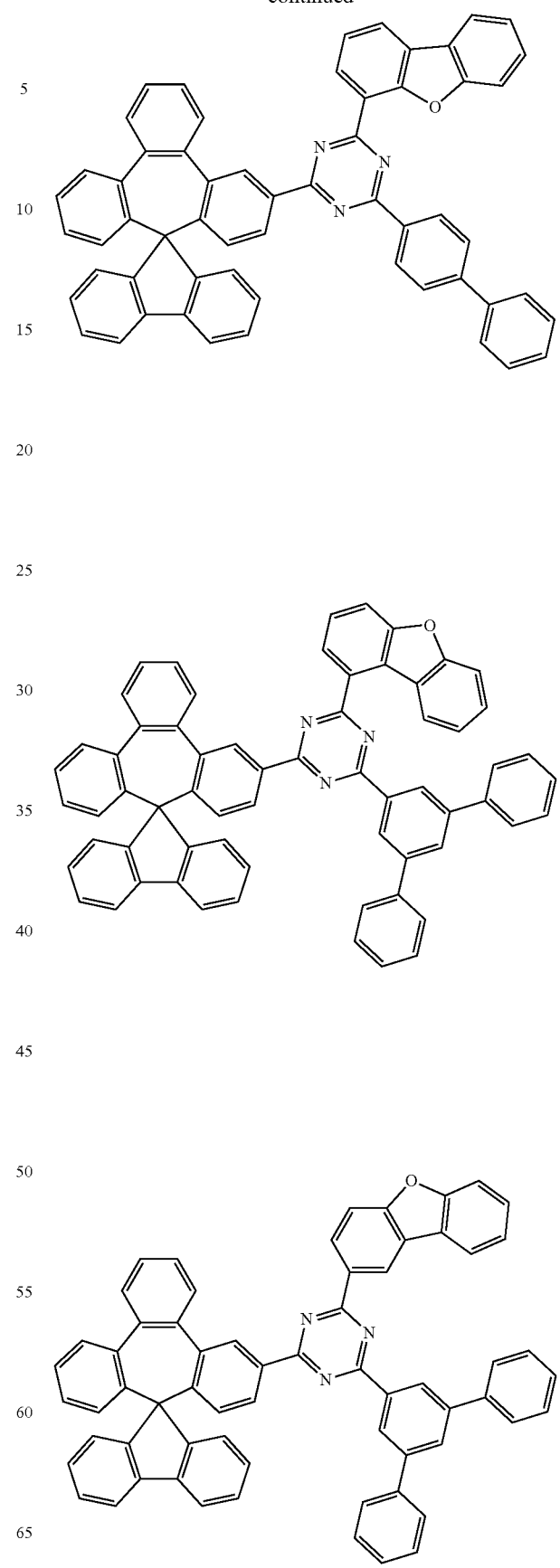

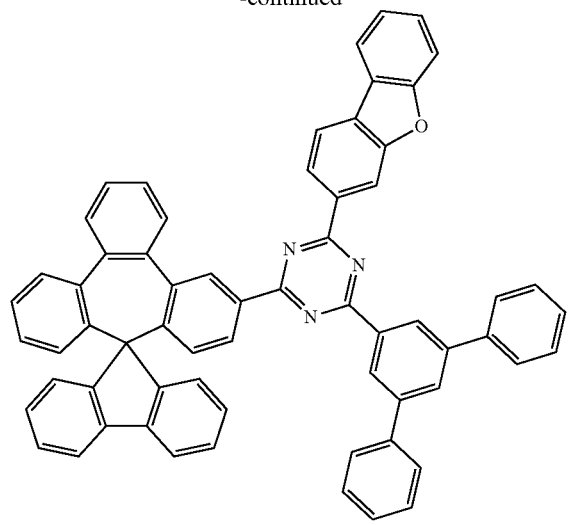
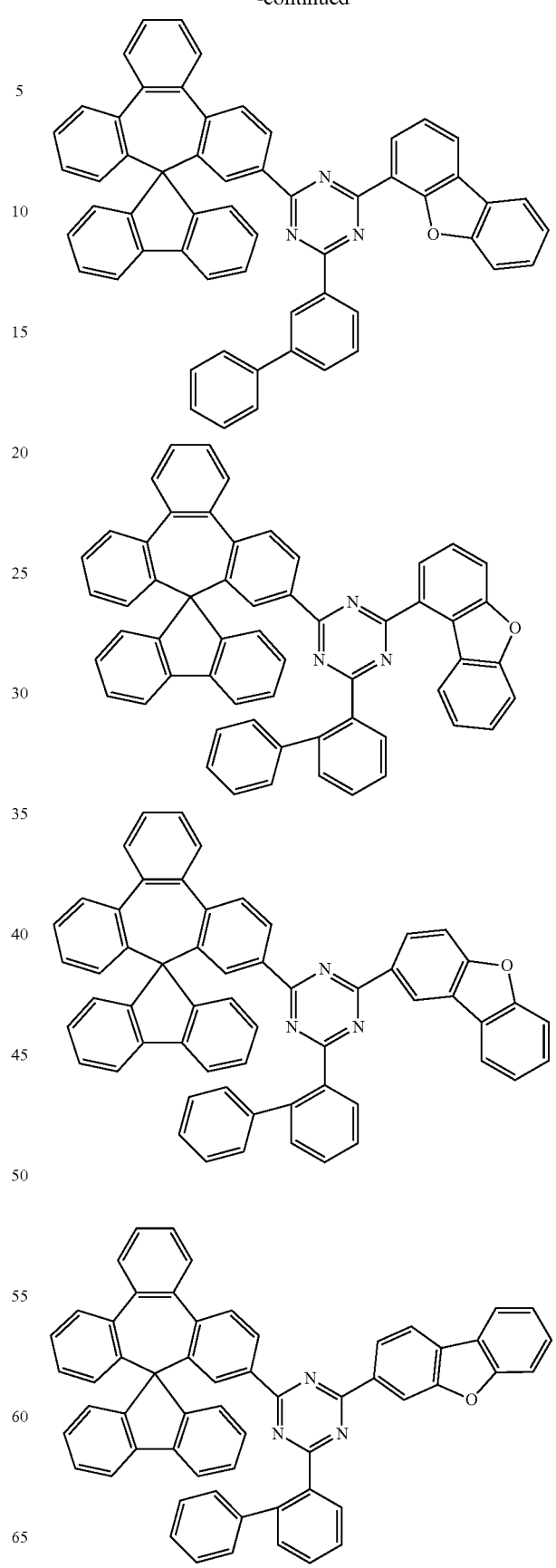

141
-continued
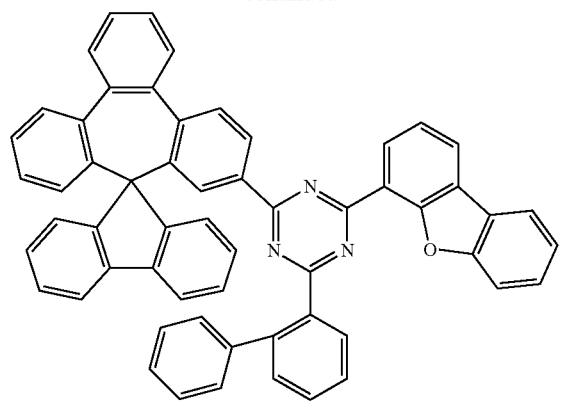
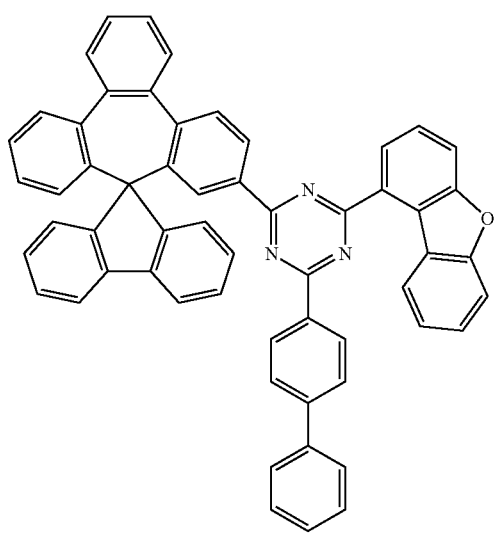
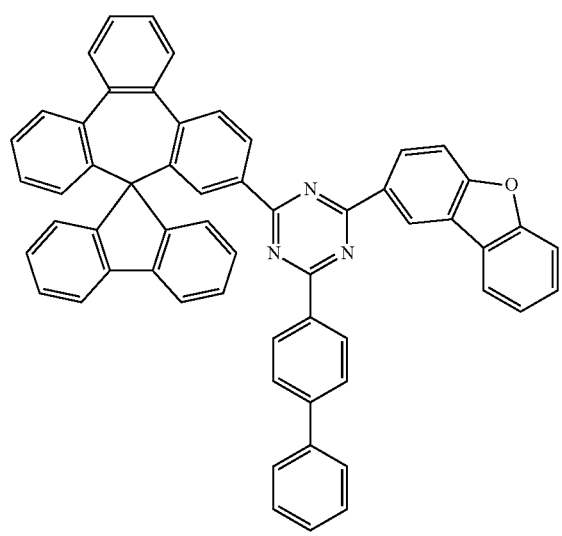
142
-continued
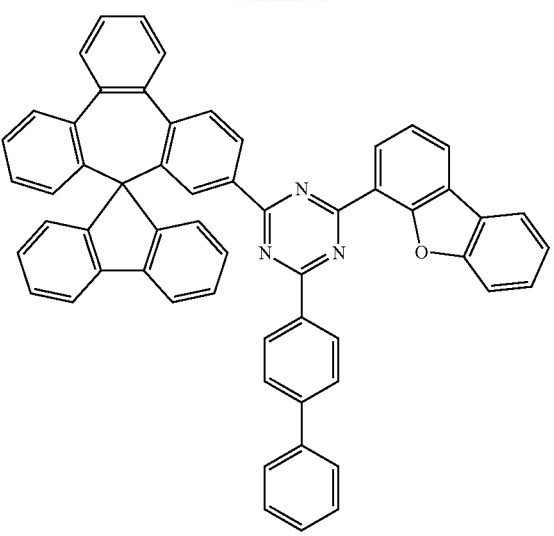
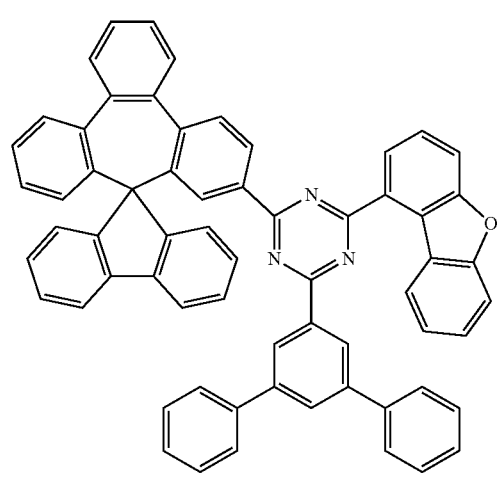
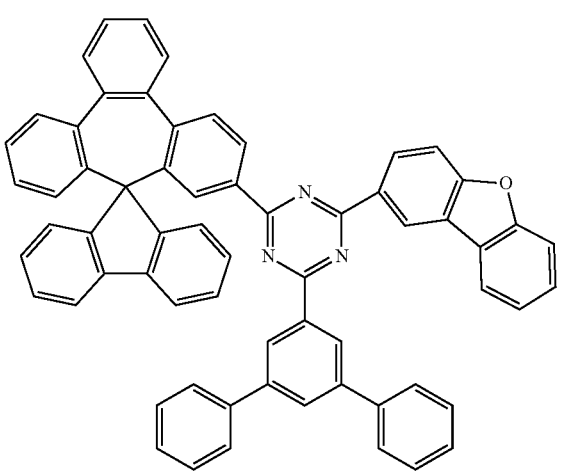

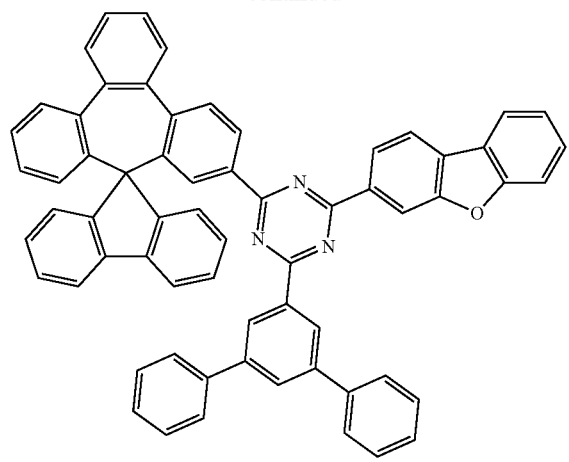
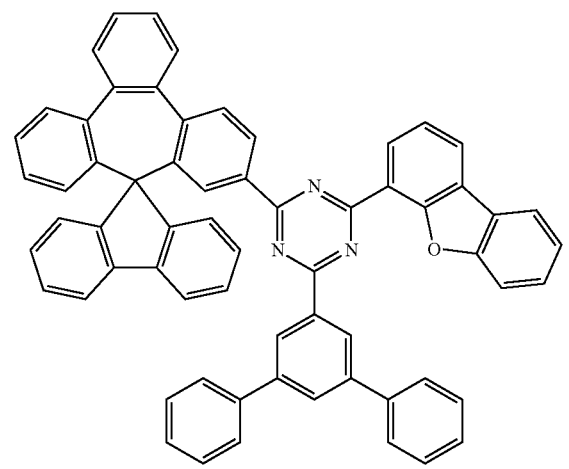
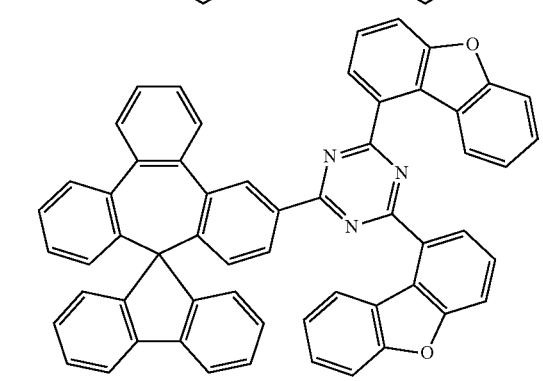
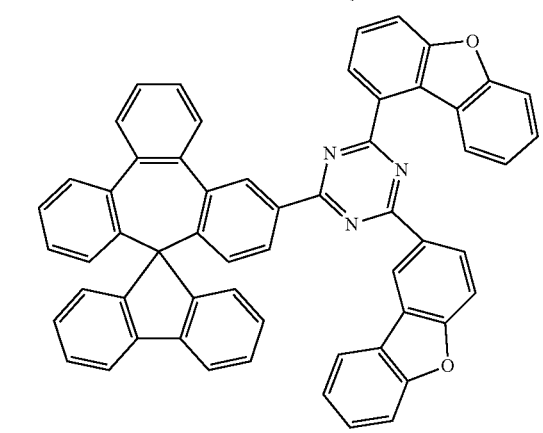
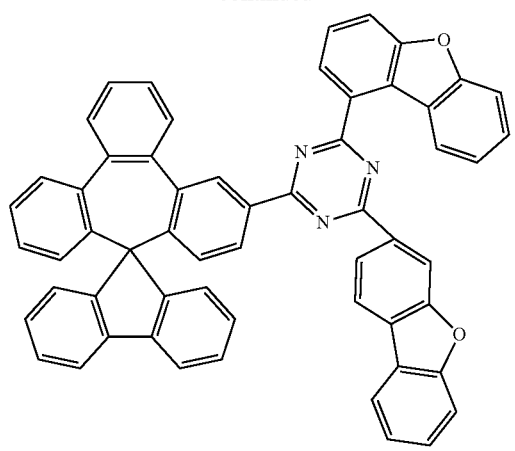
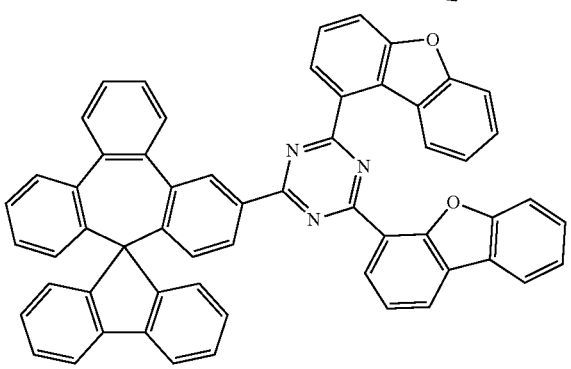
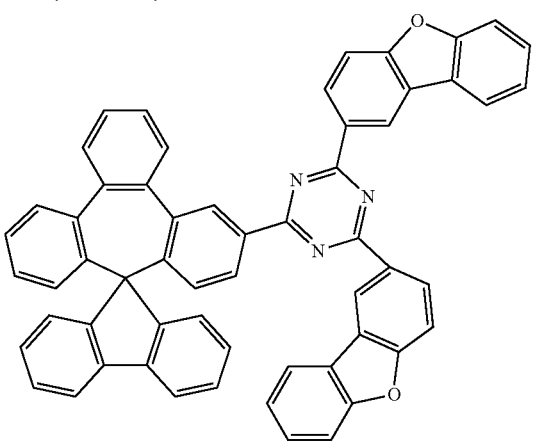
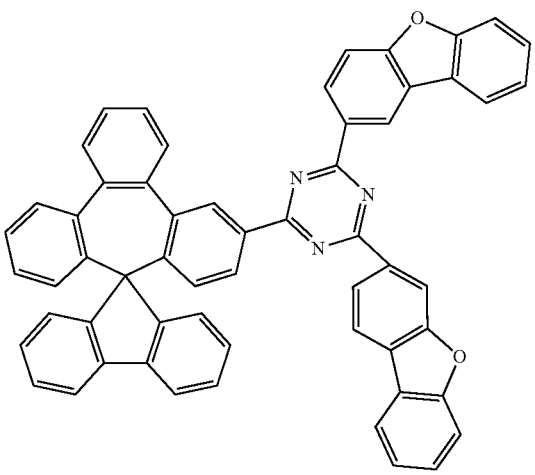

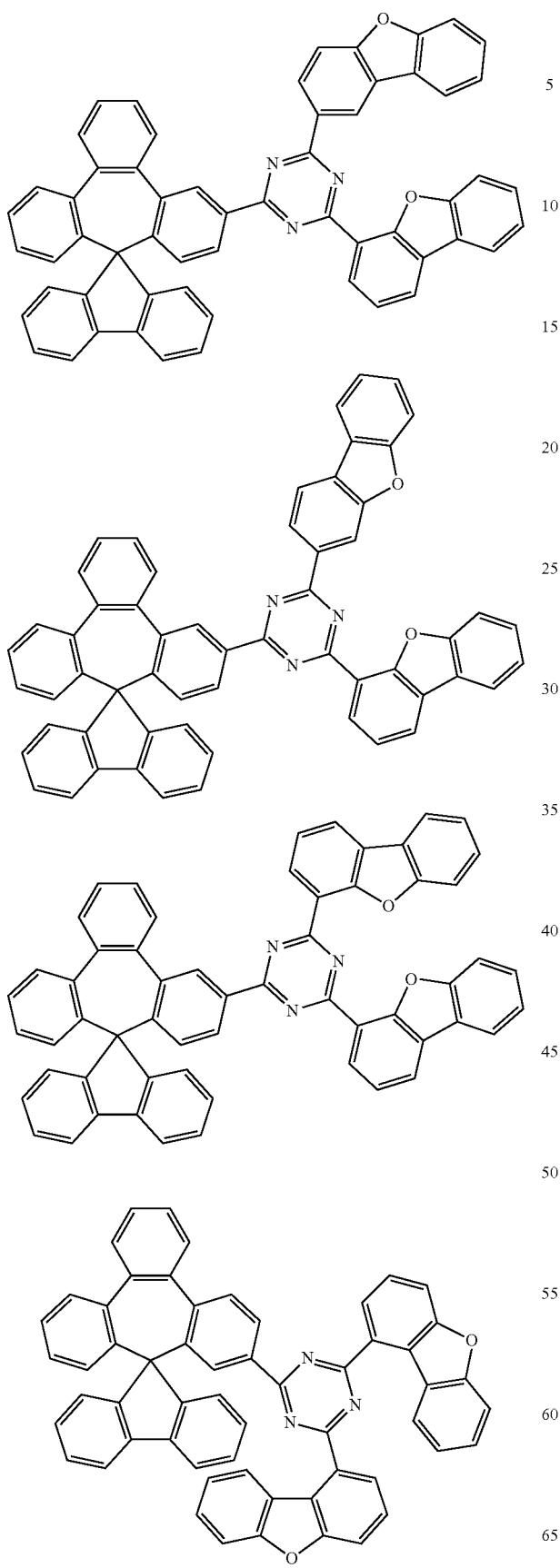
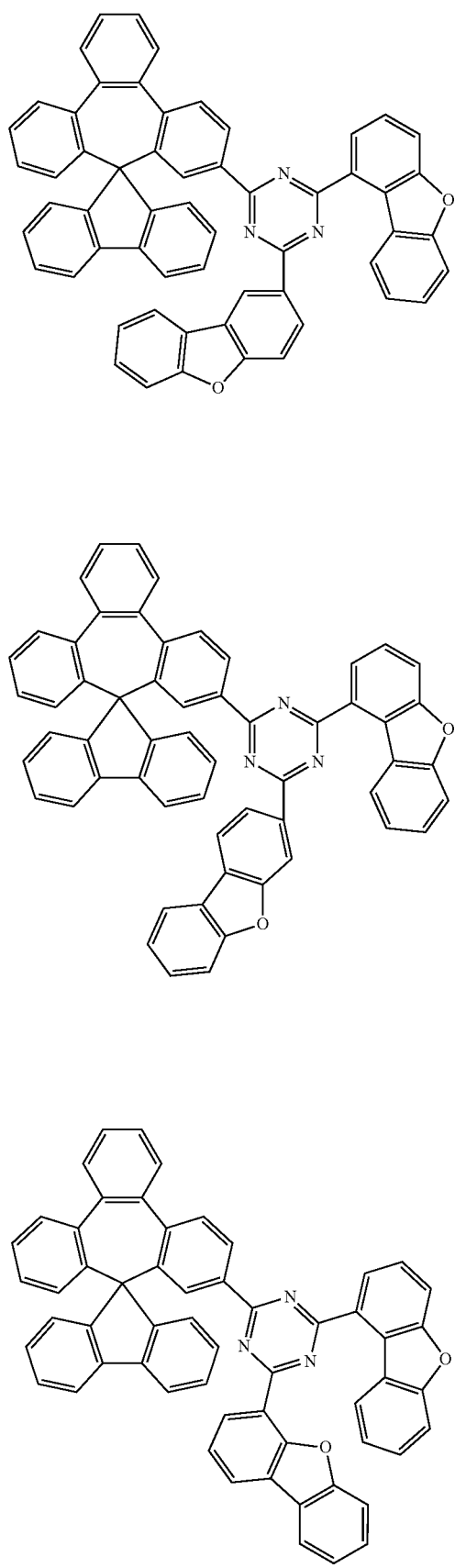

147
-continued
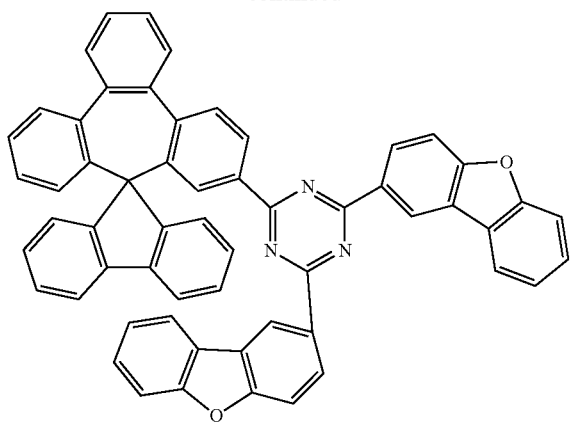
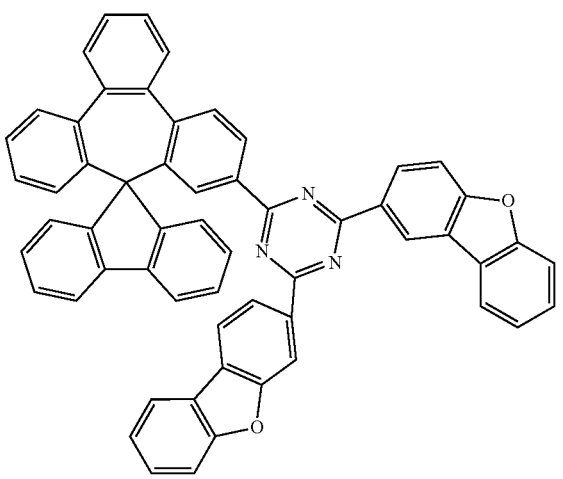
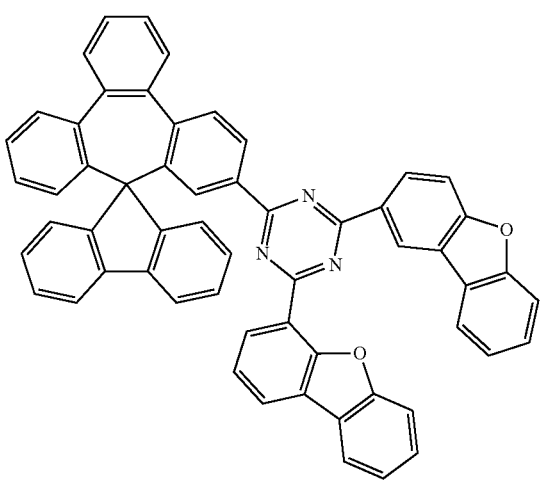
148
-continued
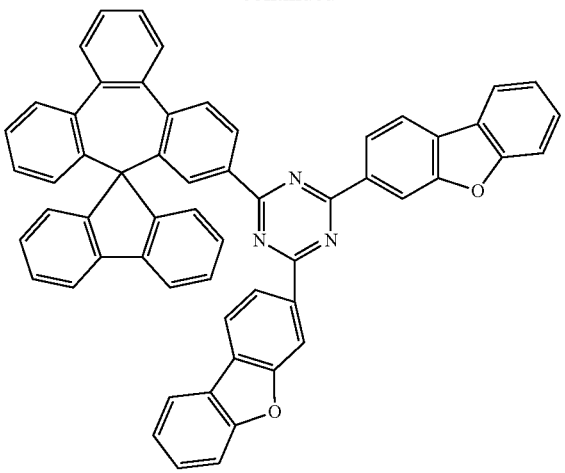
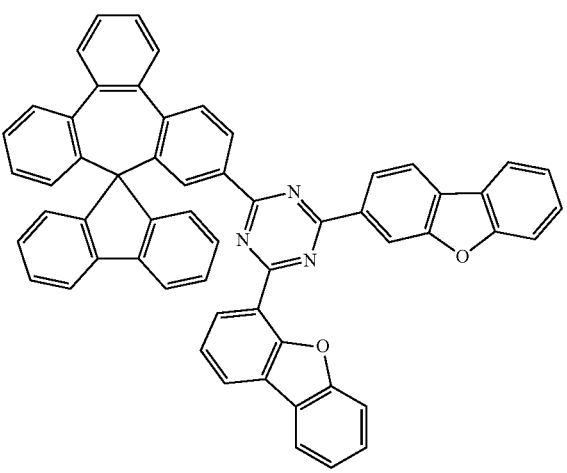
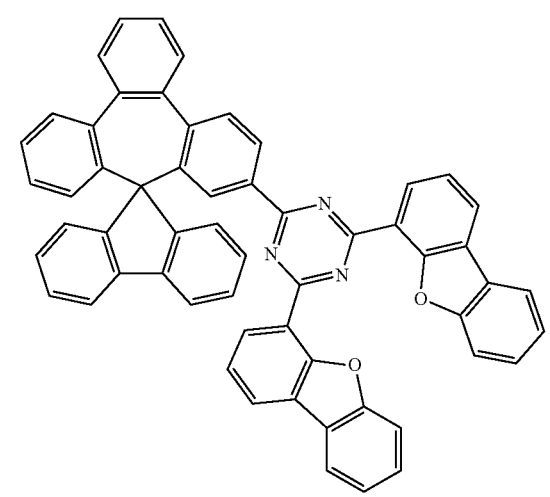

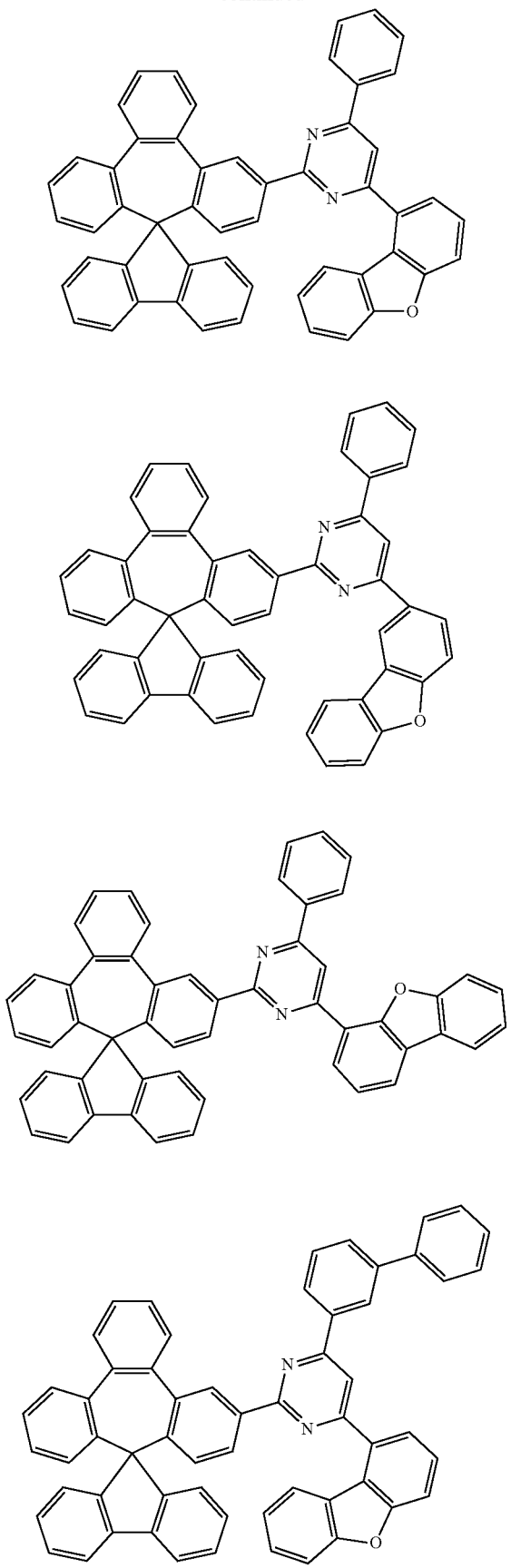

151
-continued
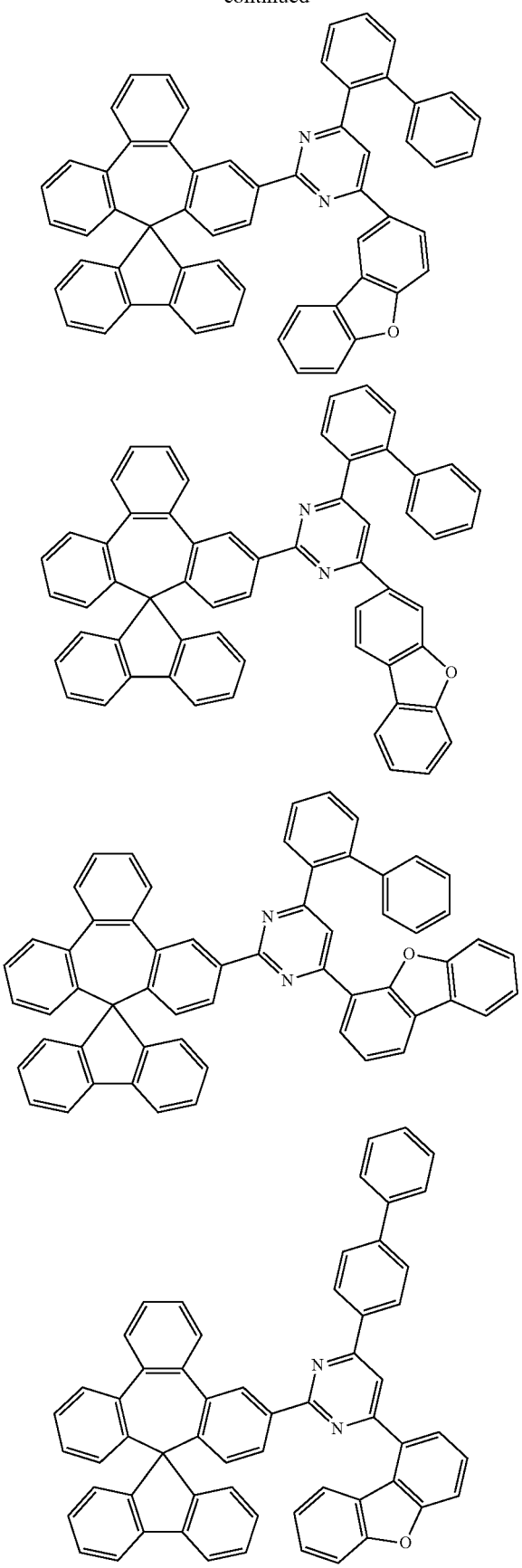
152
-continued
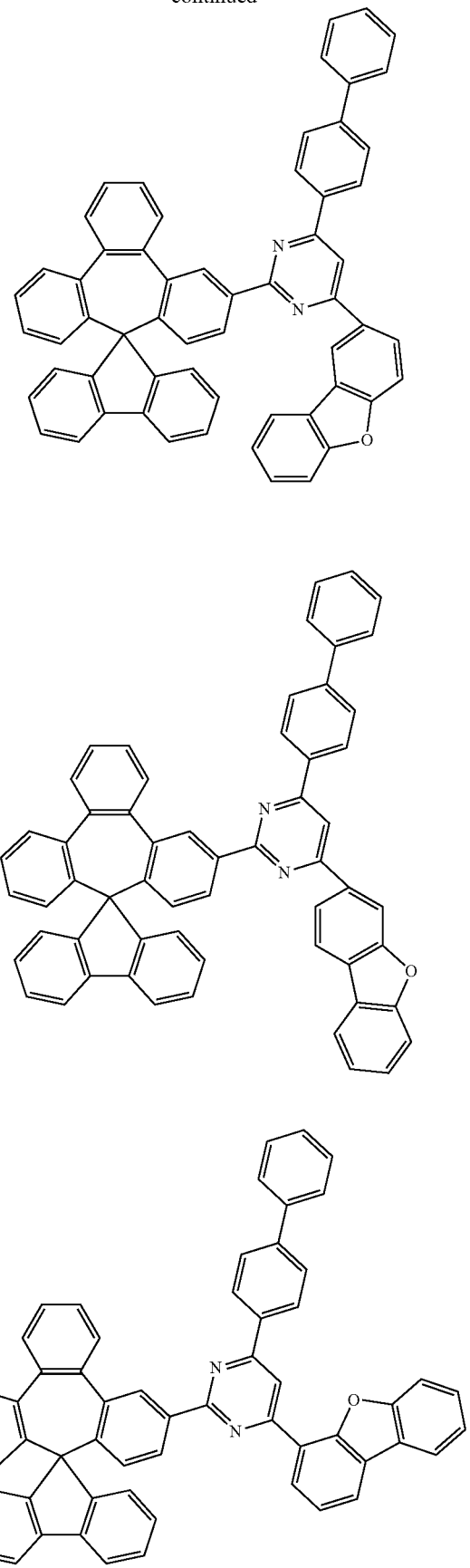

153
-continued
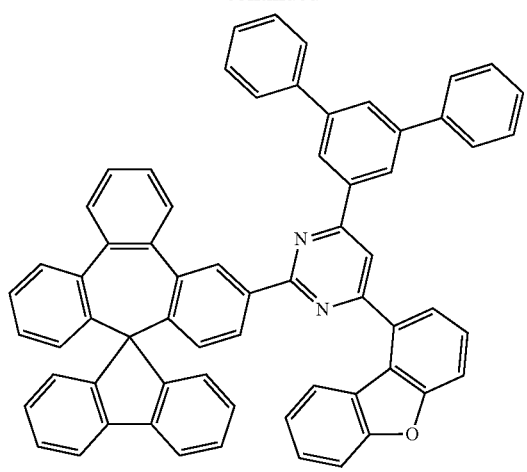
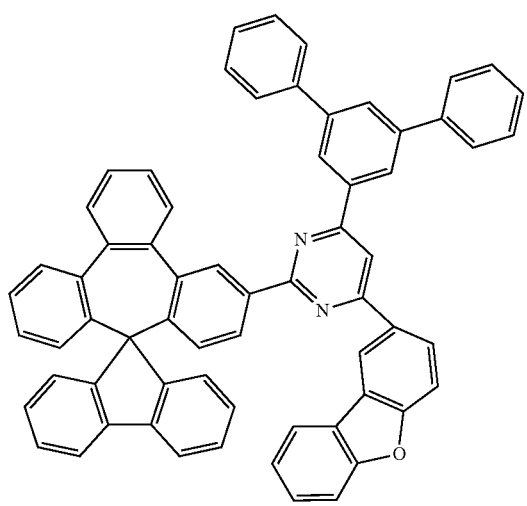
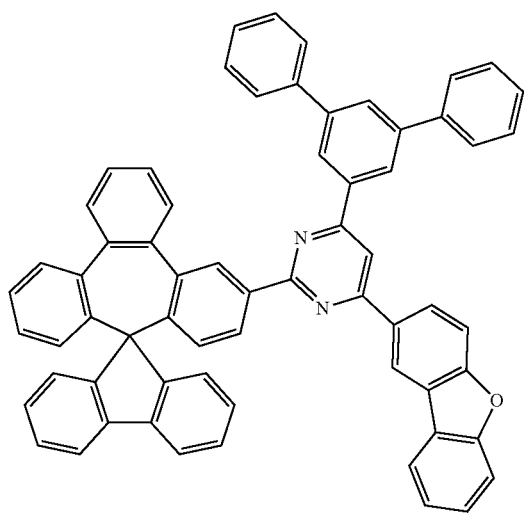
154
-continued
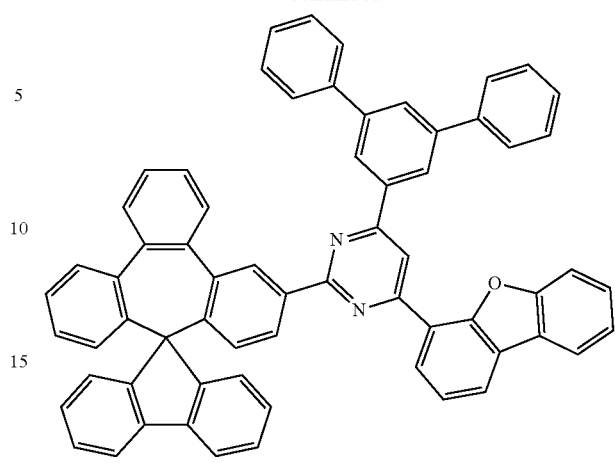
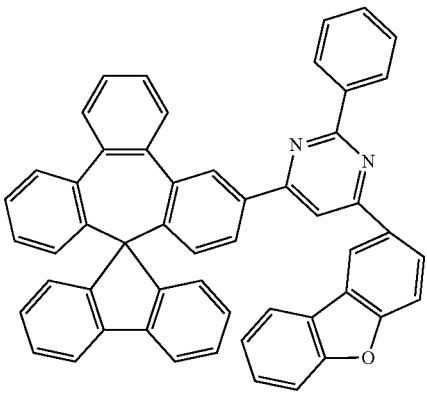
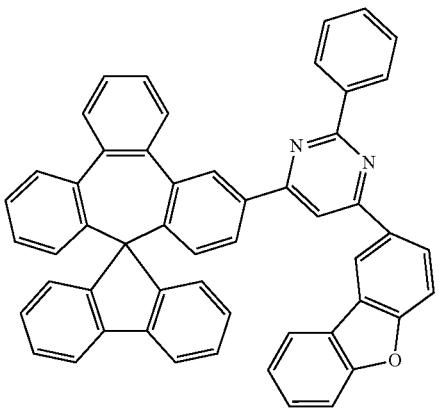
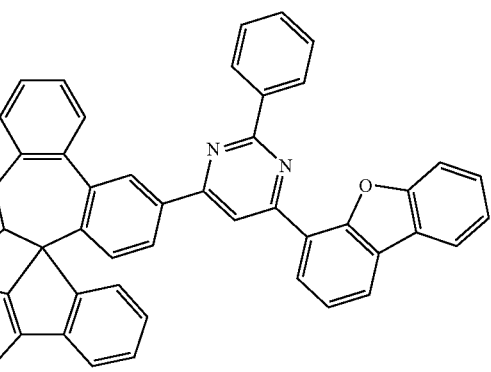

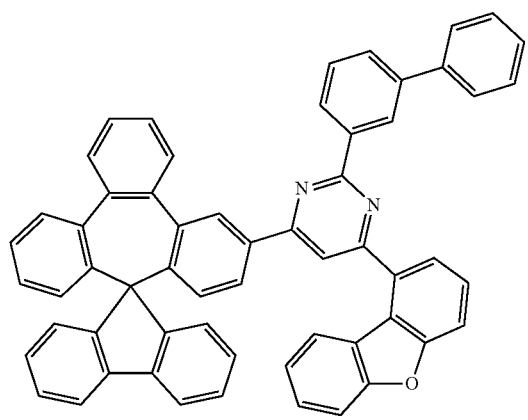
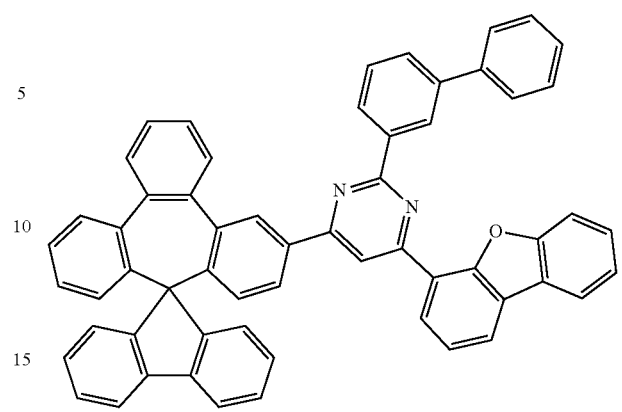
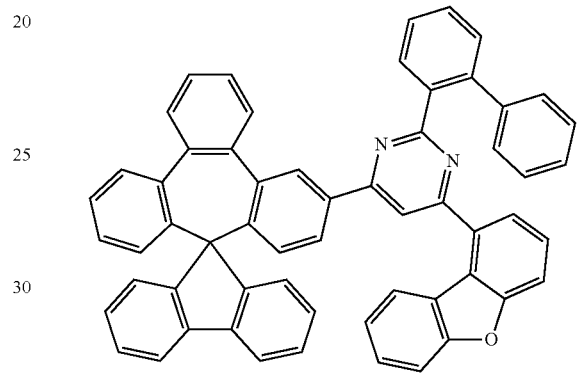
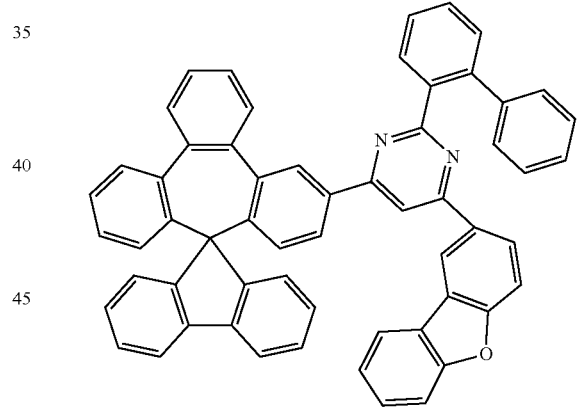
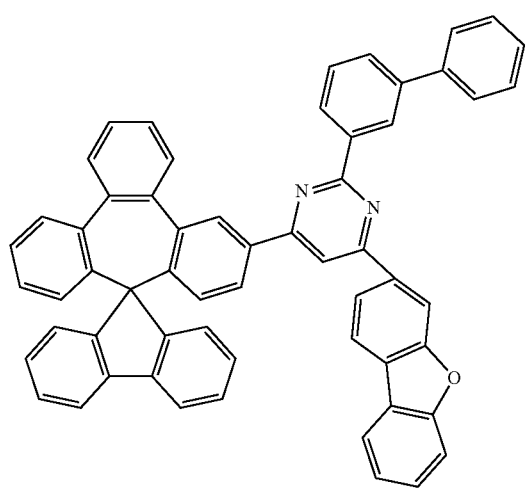
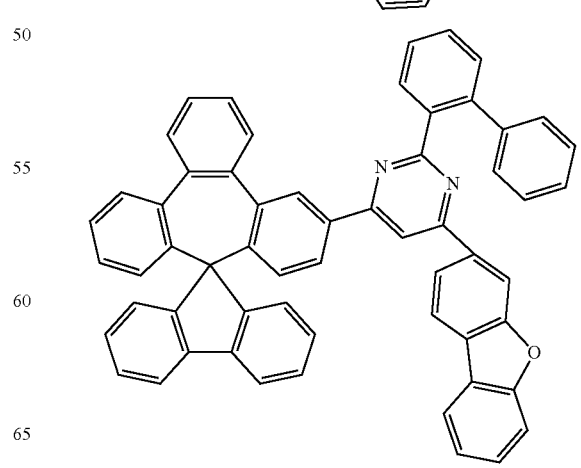

157
-continued
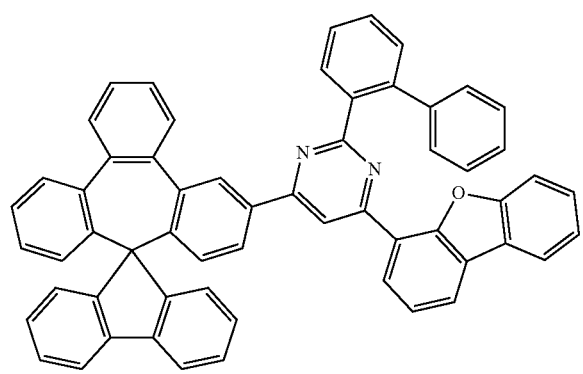
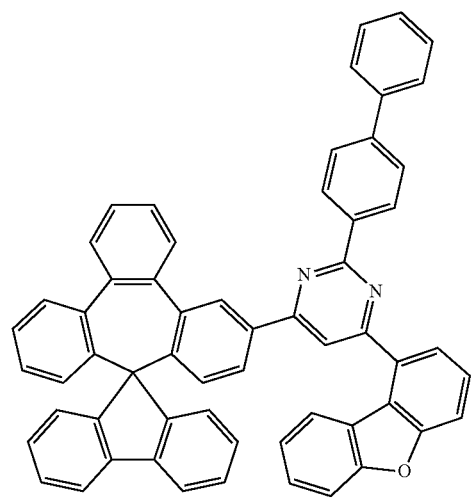
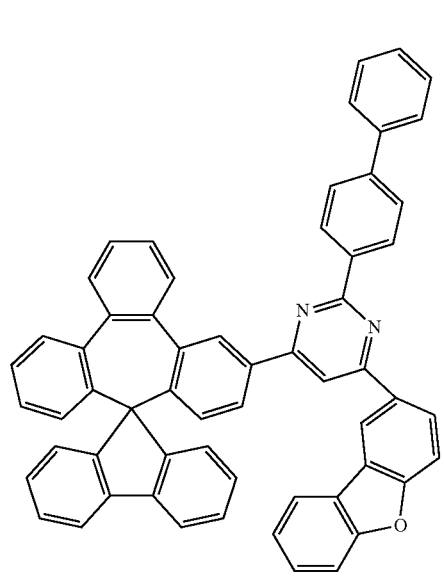
158
-continued
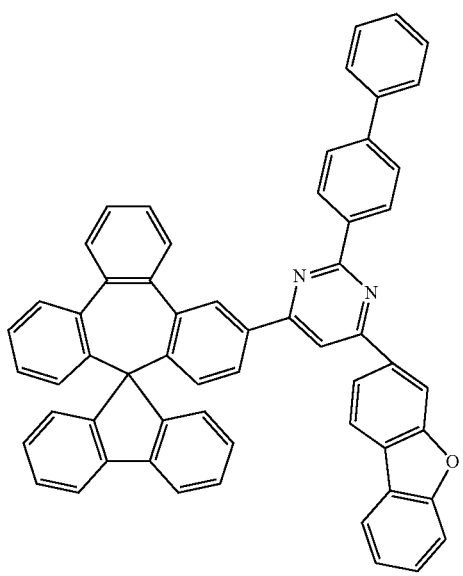
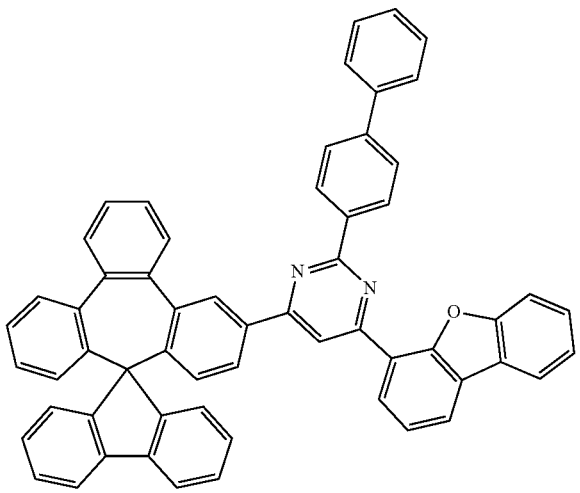

159
-continued
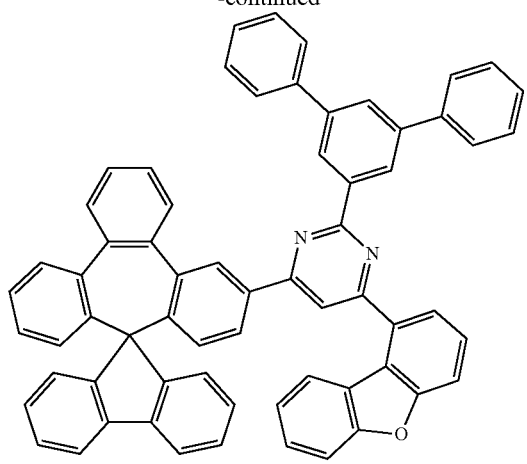
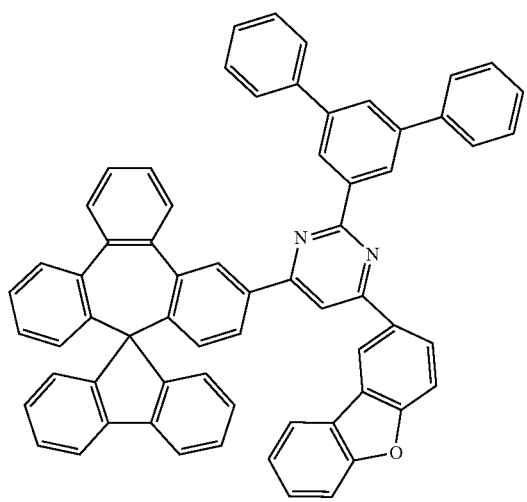
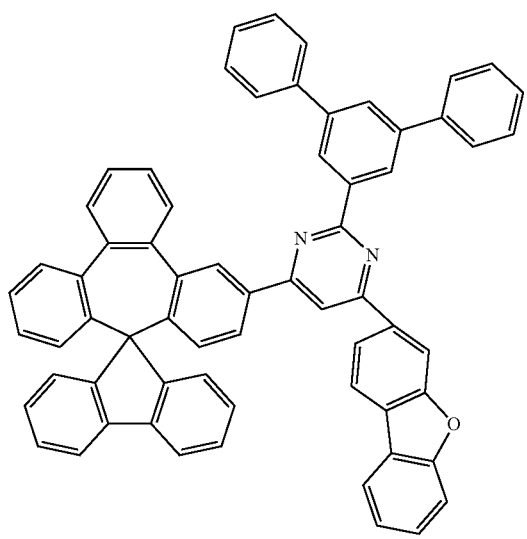
160
-continued
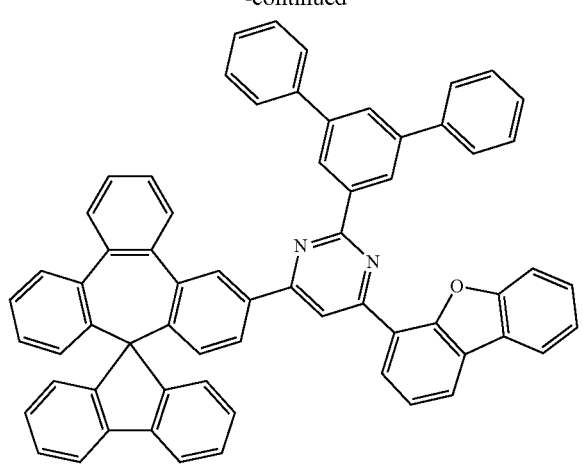
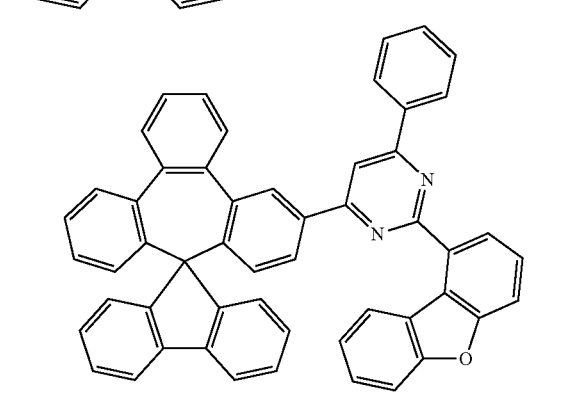
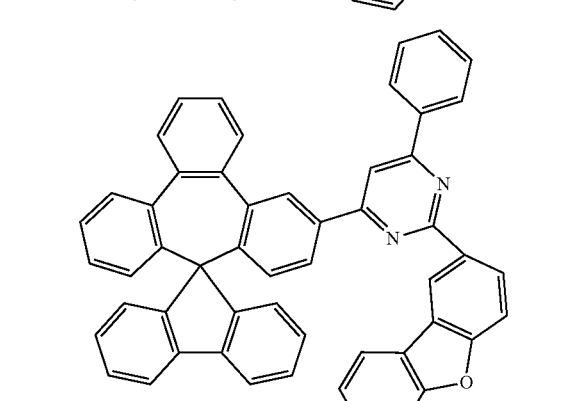
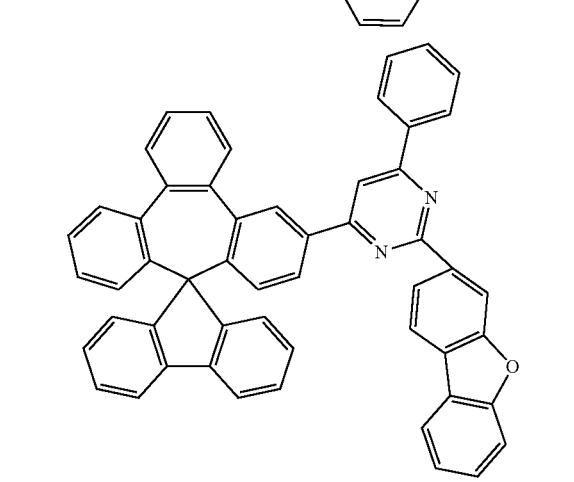

161
-continued
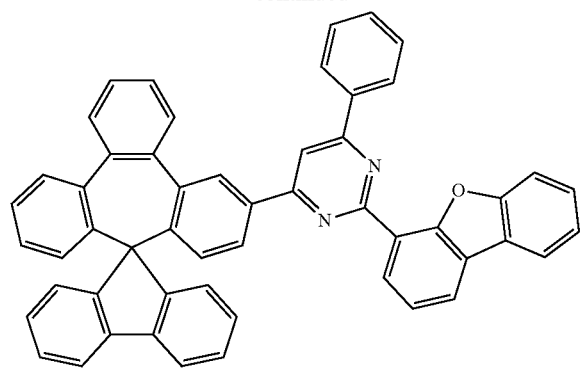
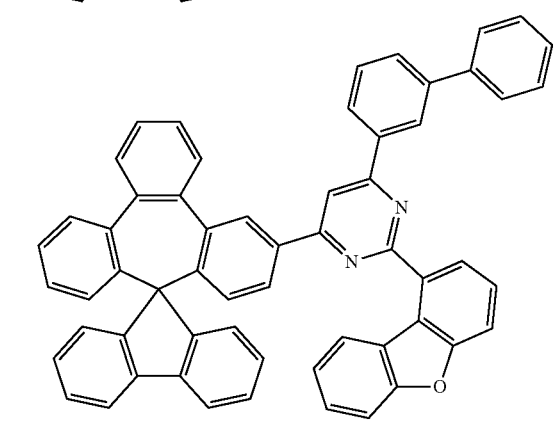
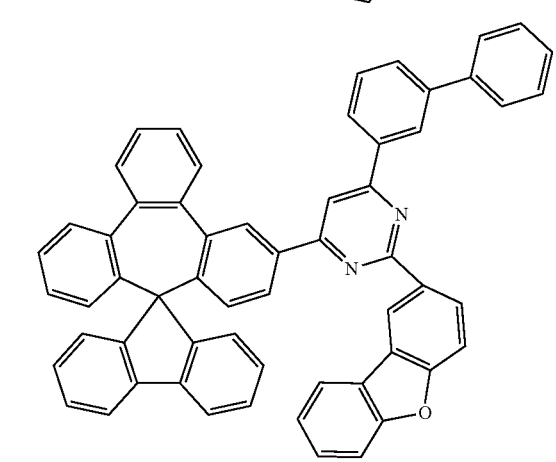
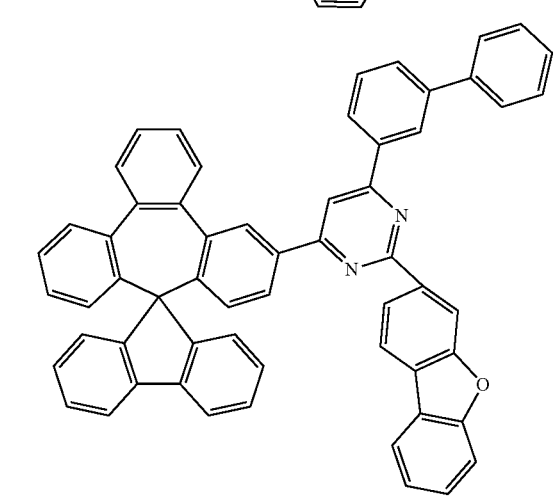
162
-continued
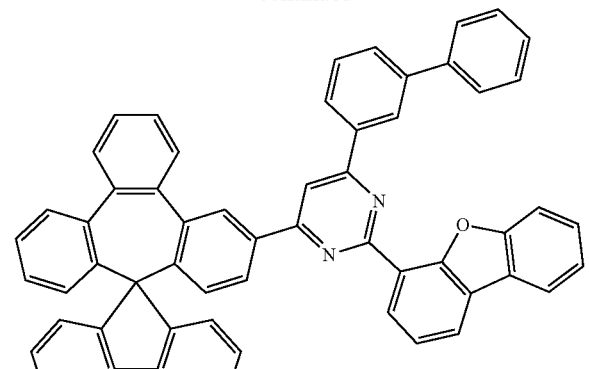
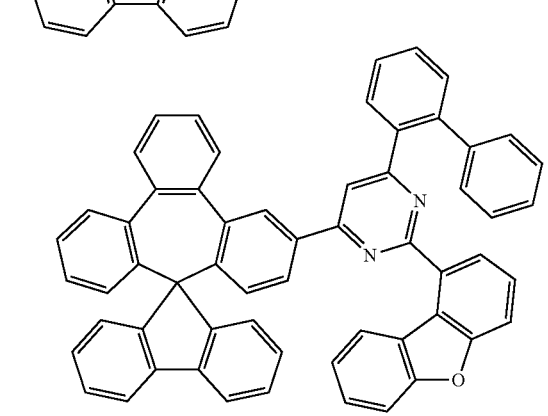
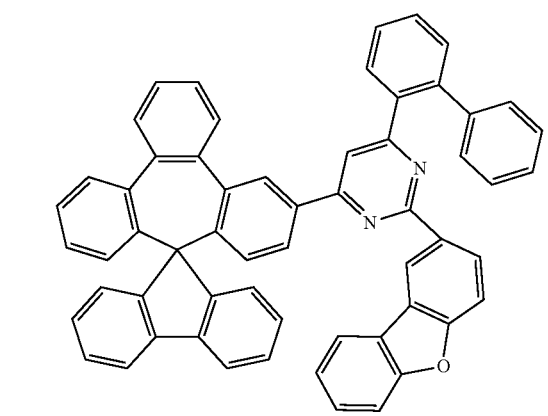
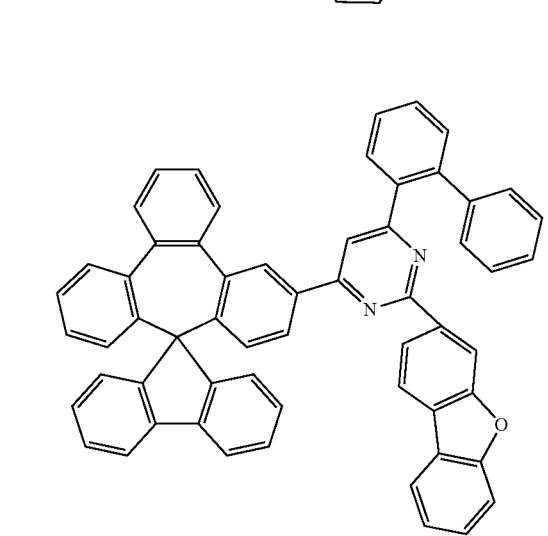

163
-continued
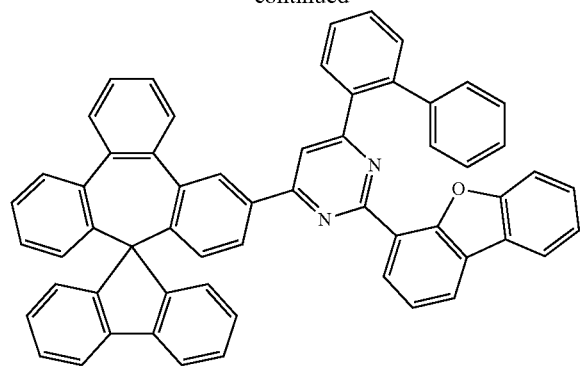
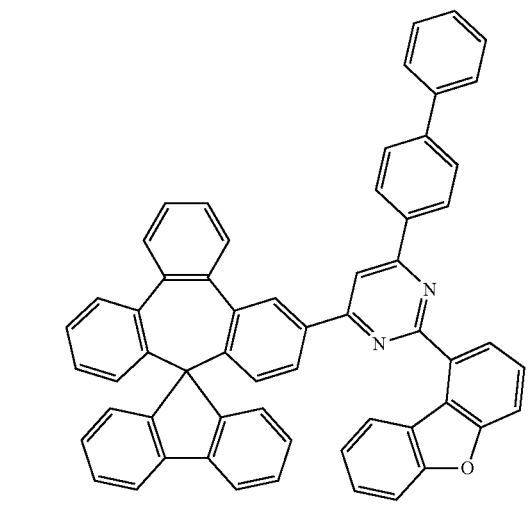
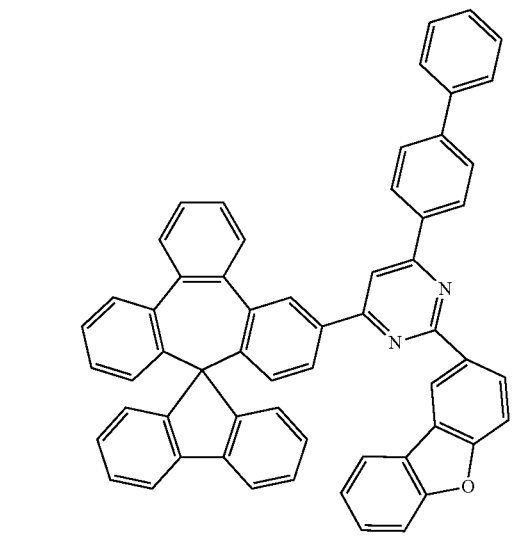
164
-continued
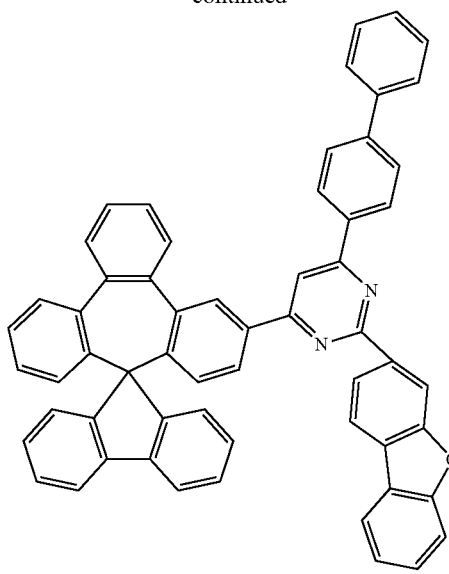
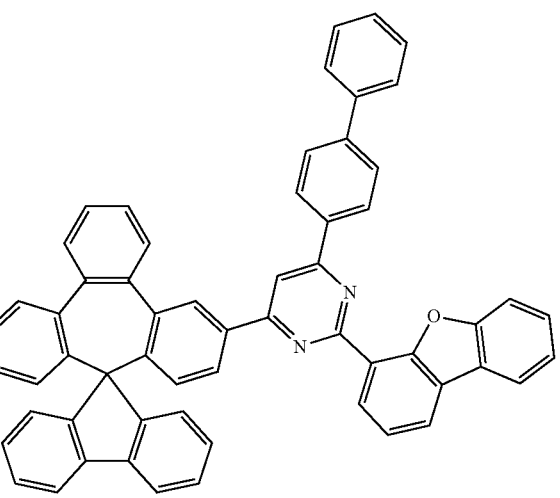
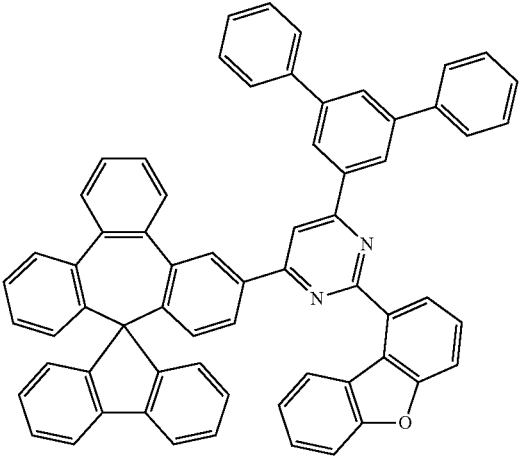

-continued
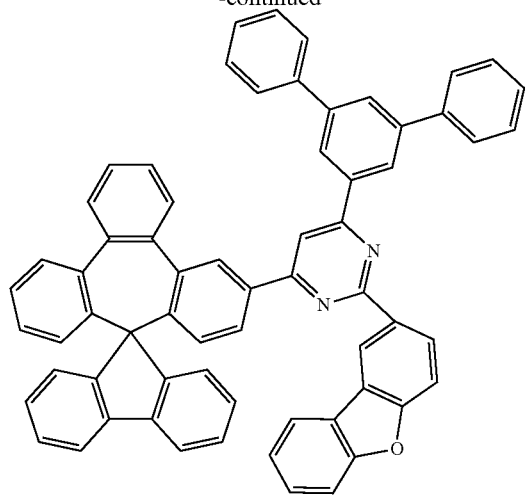
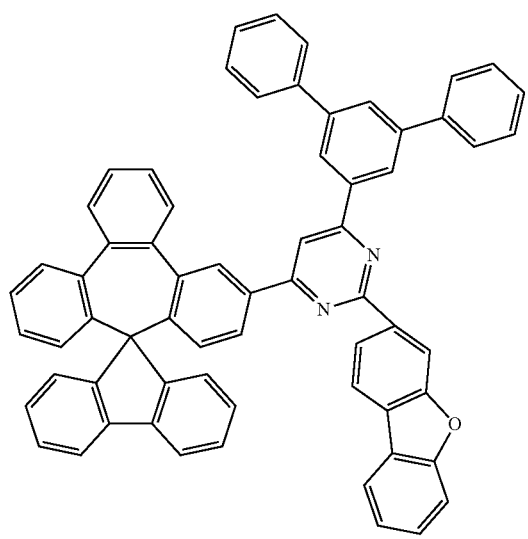
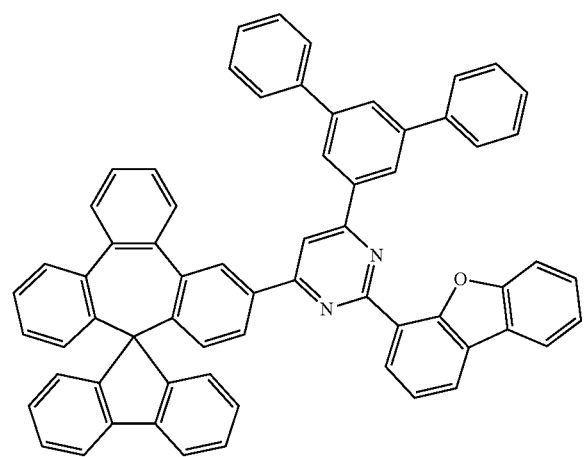
-continued
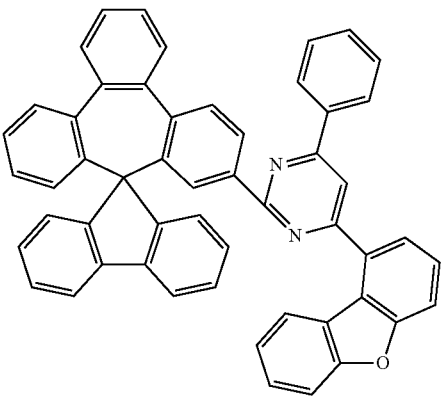
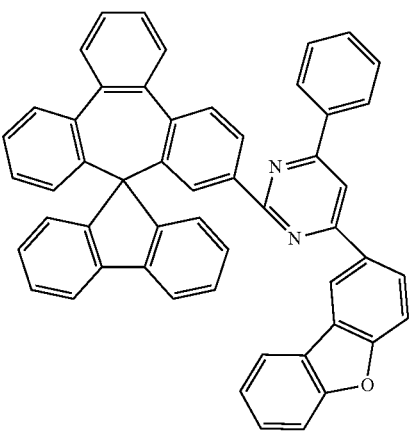
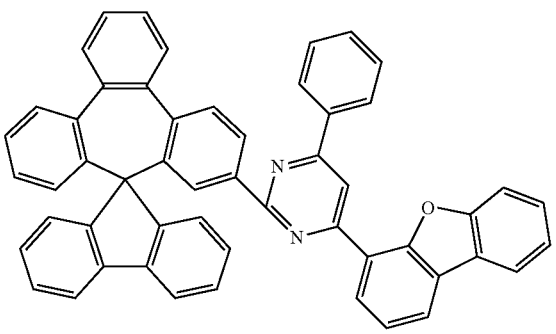
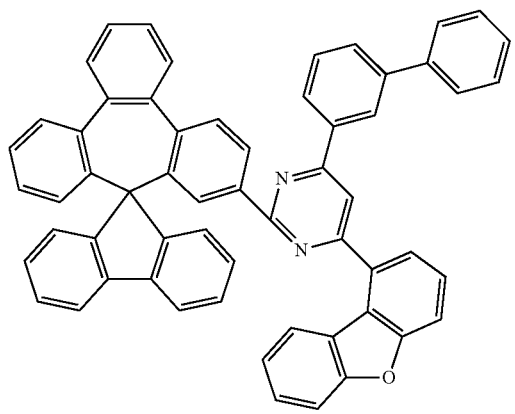

167
-continued
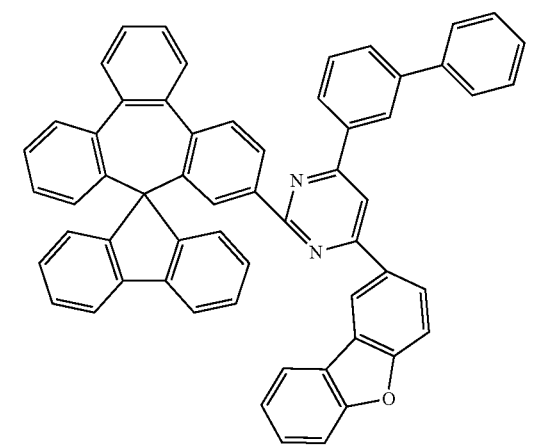
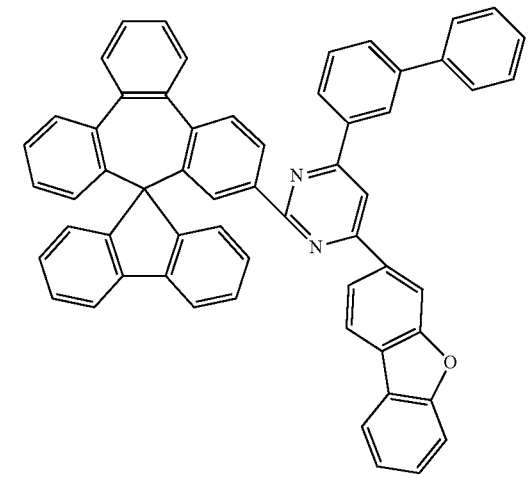
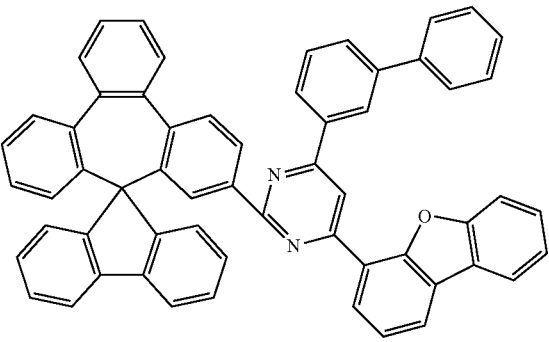
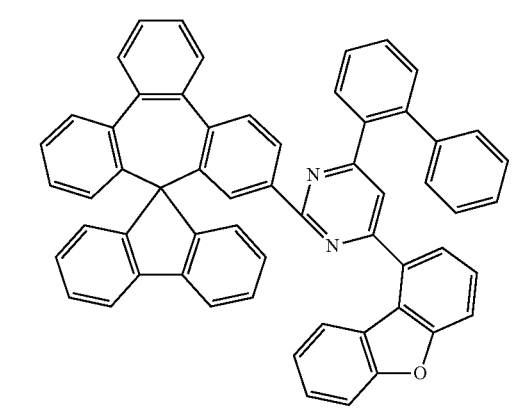
168
-continued
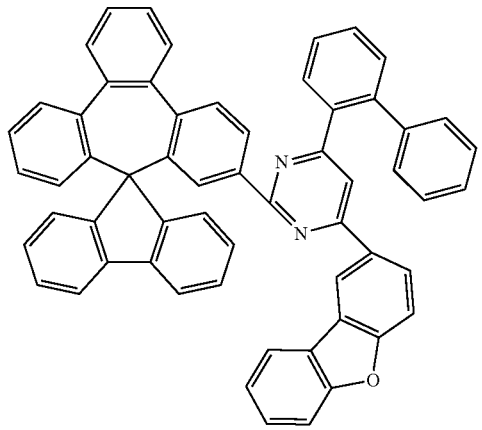
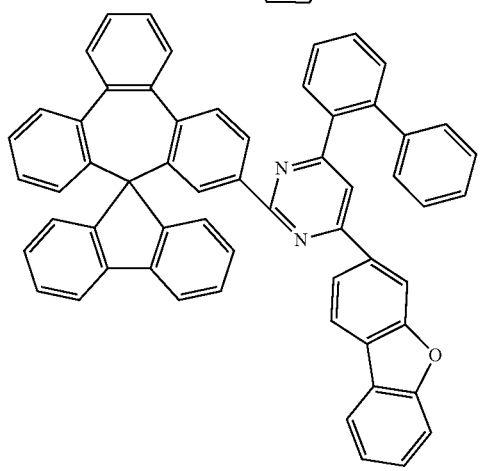
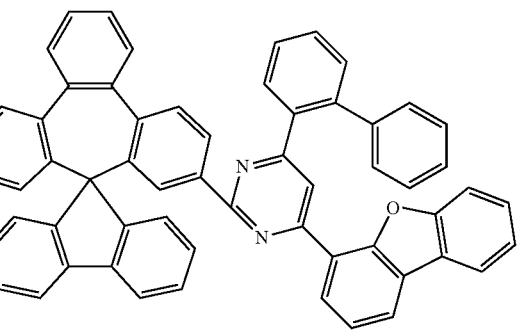
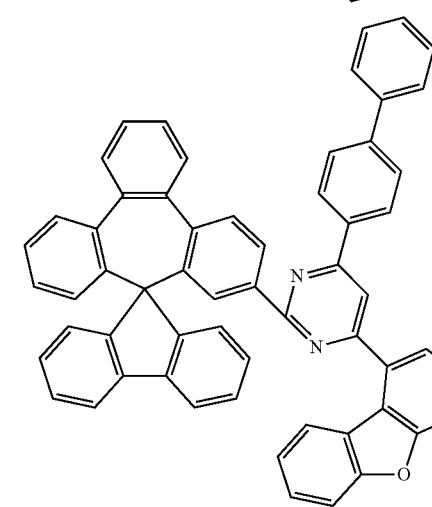

169
-continued
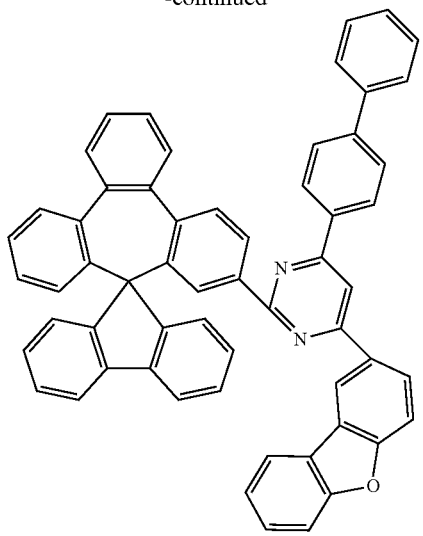
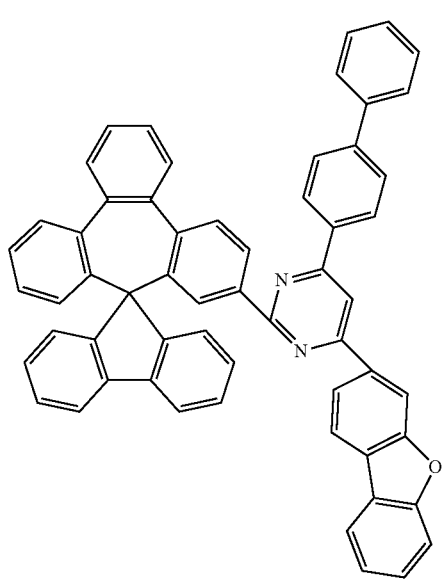
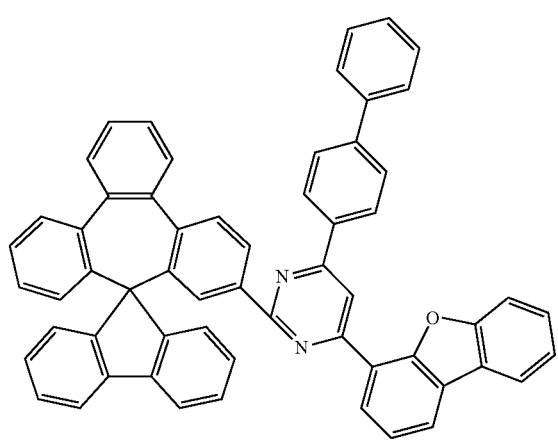
170
-continued
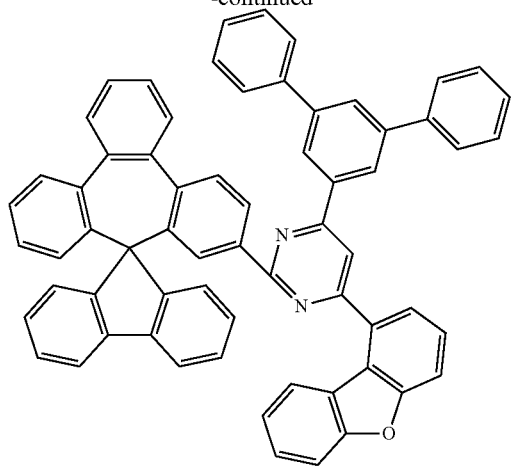
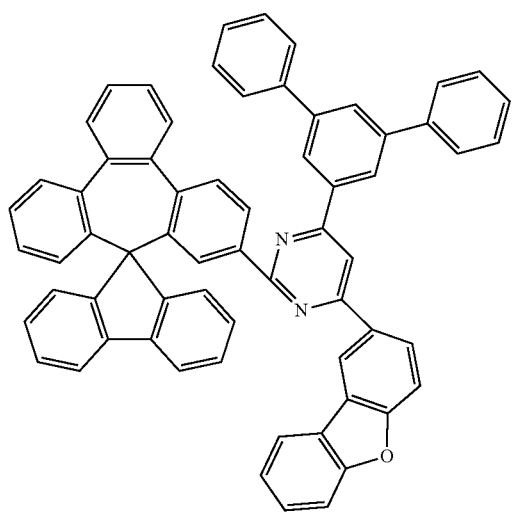

171
-continued
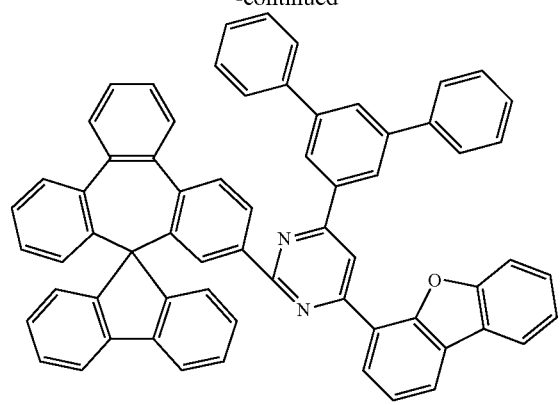
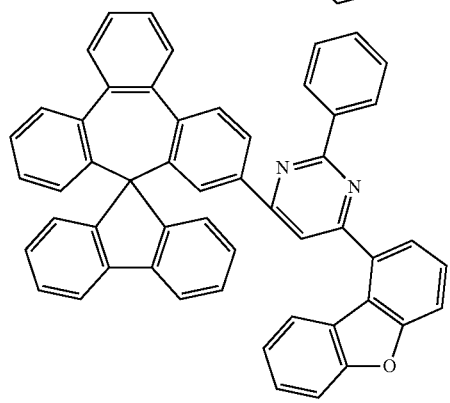
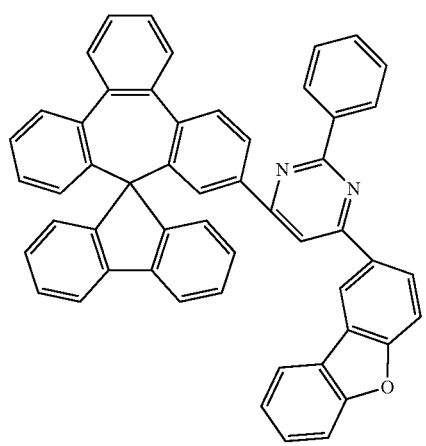
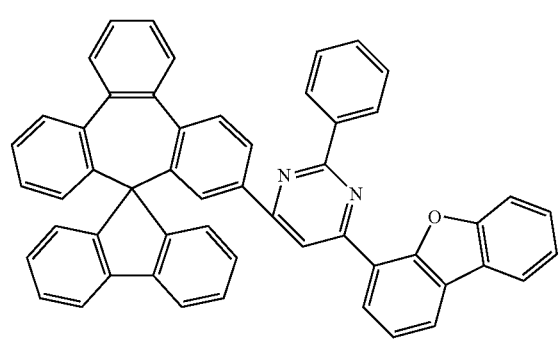
172
-continued
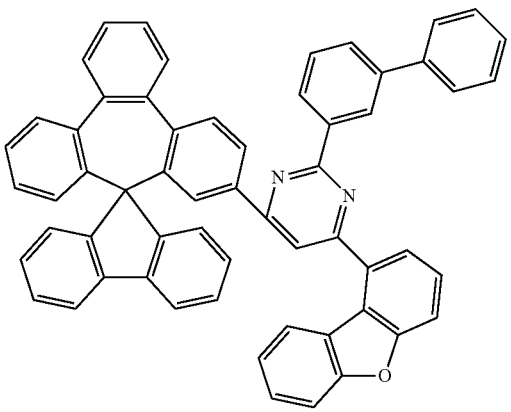
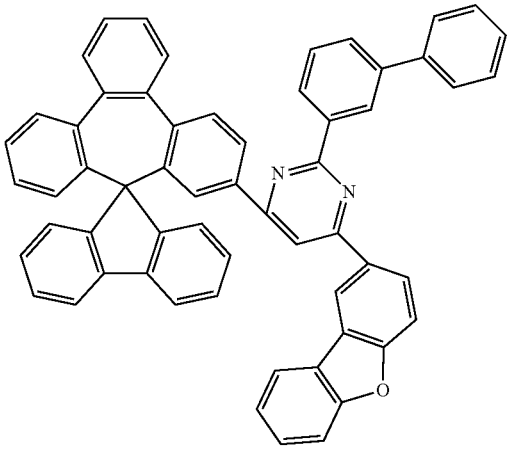
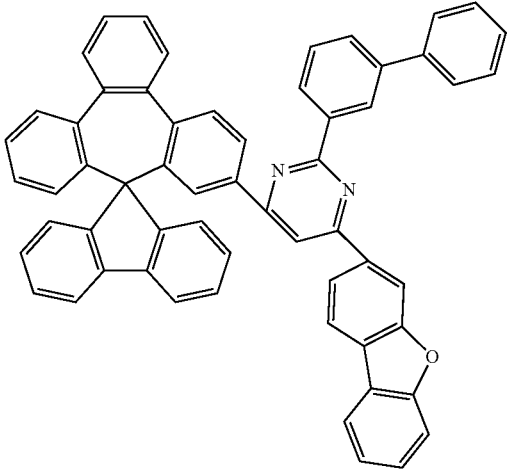
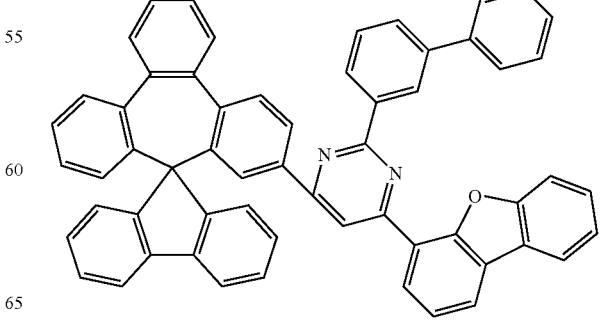

173
-continued
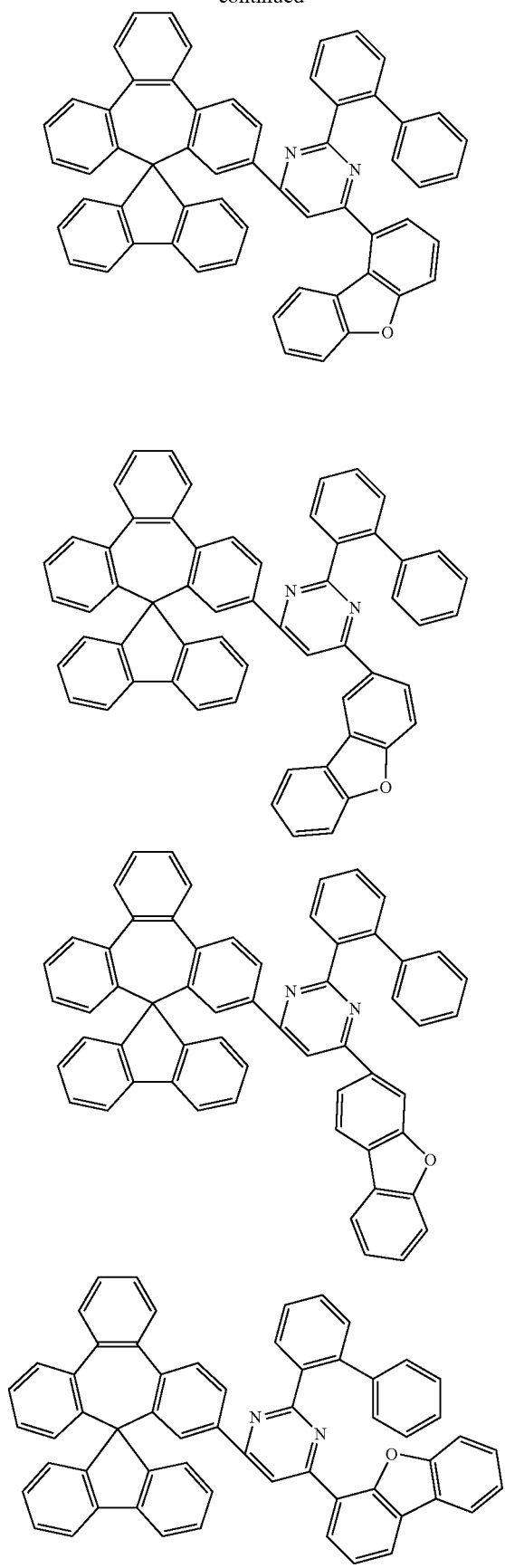
174
-continued
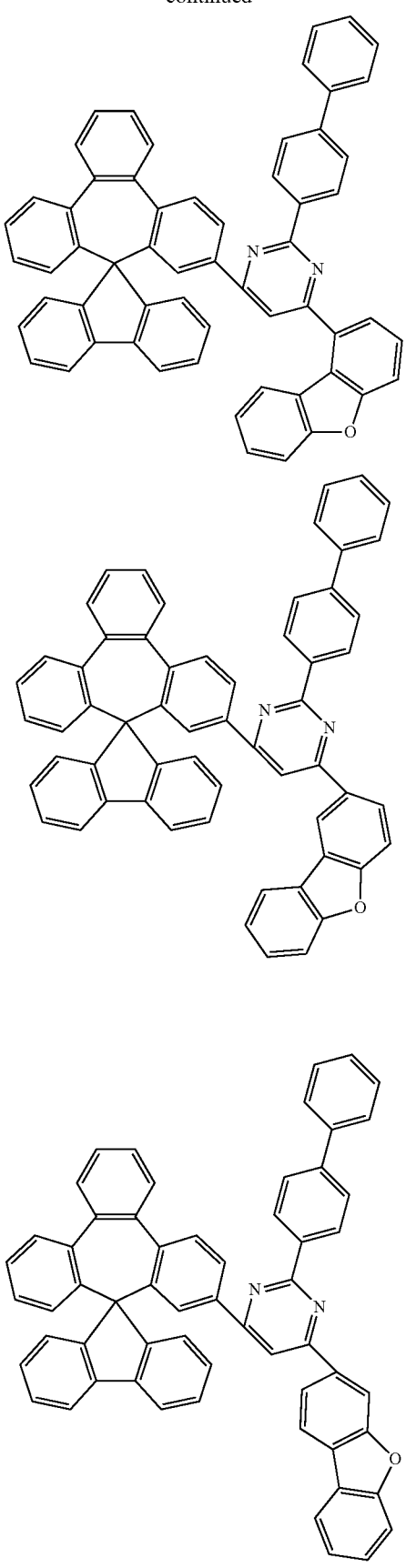

175
-continued
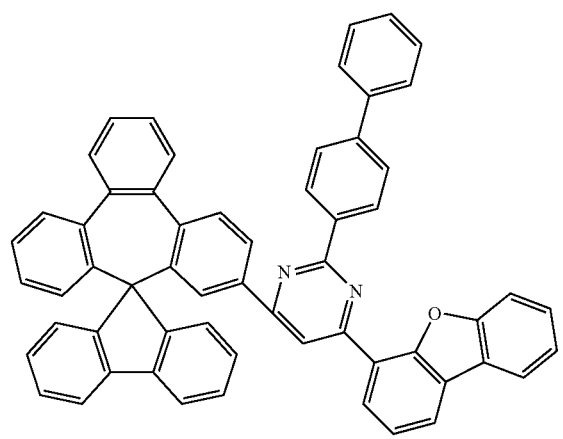
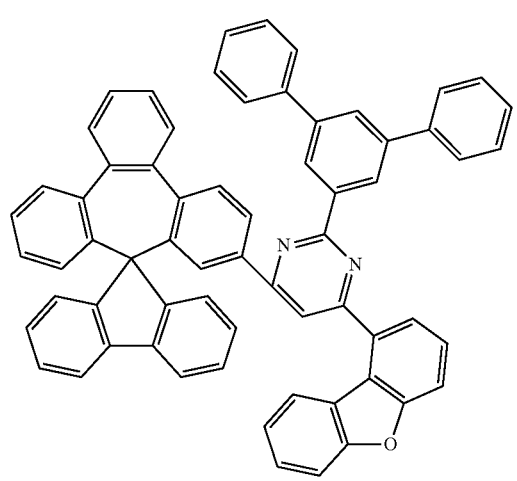
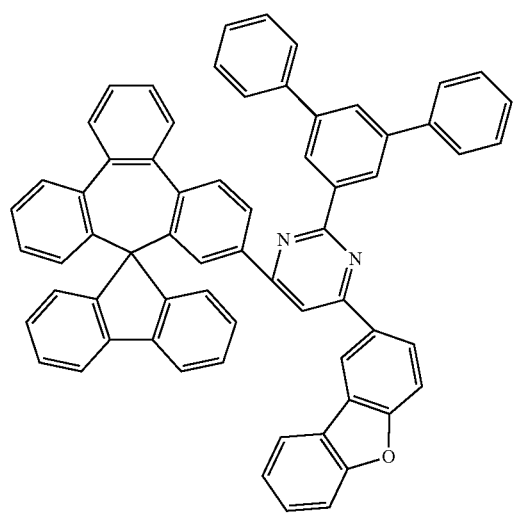
176
-continued
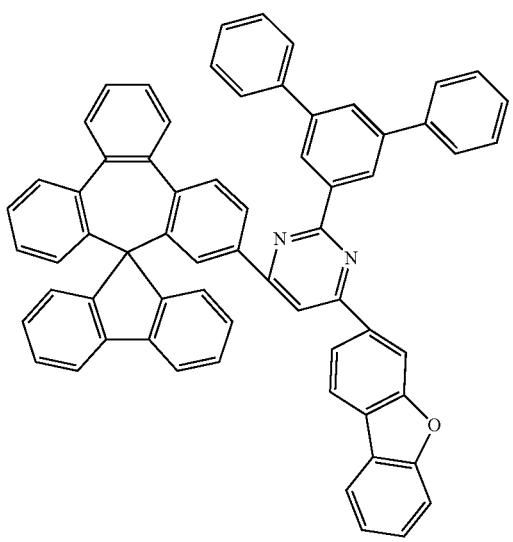
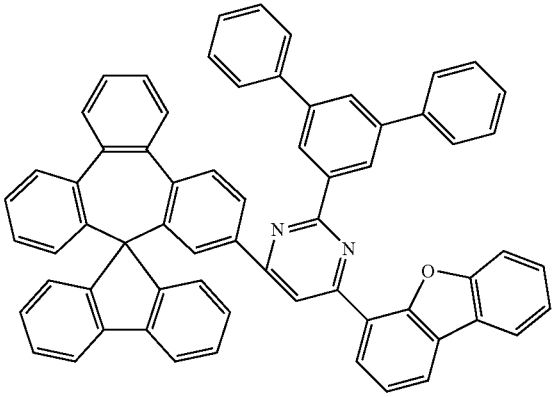
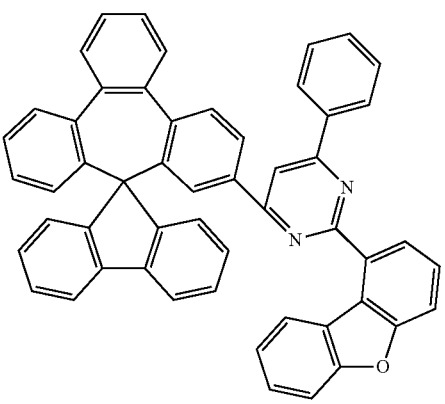

177
-continued
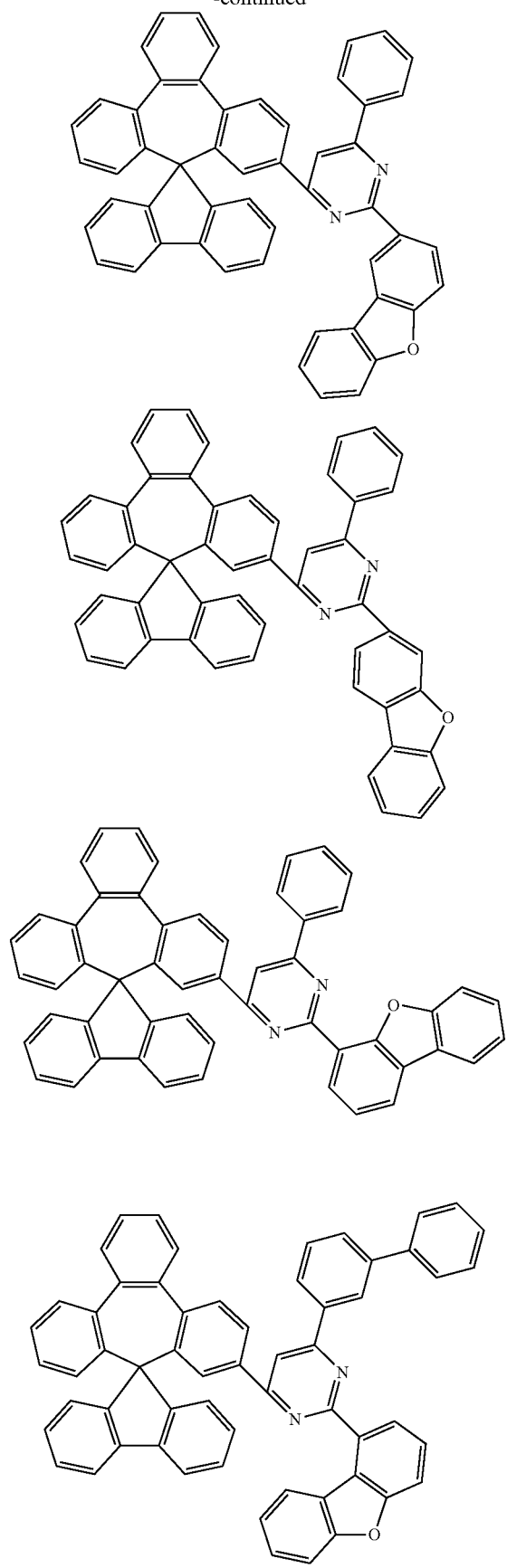
178
-continued
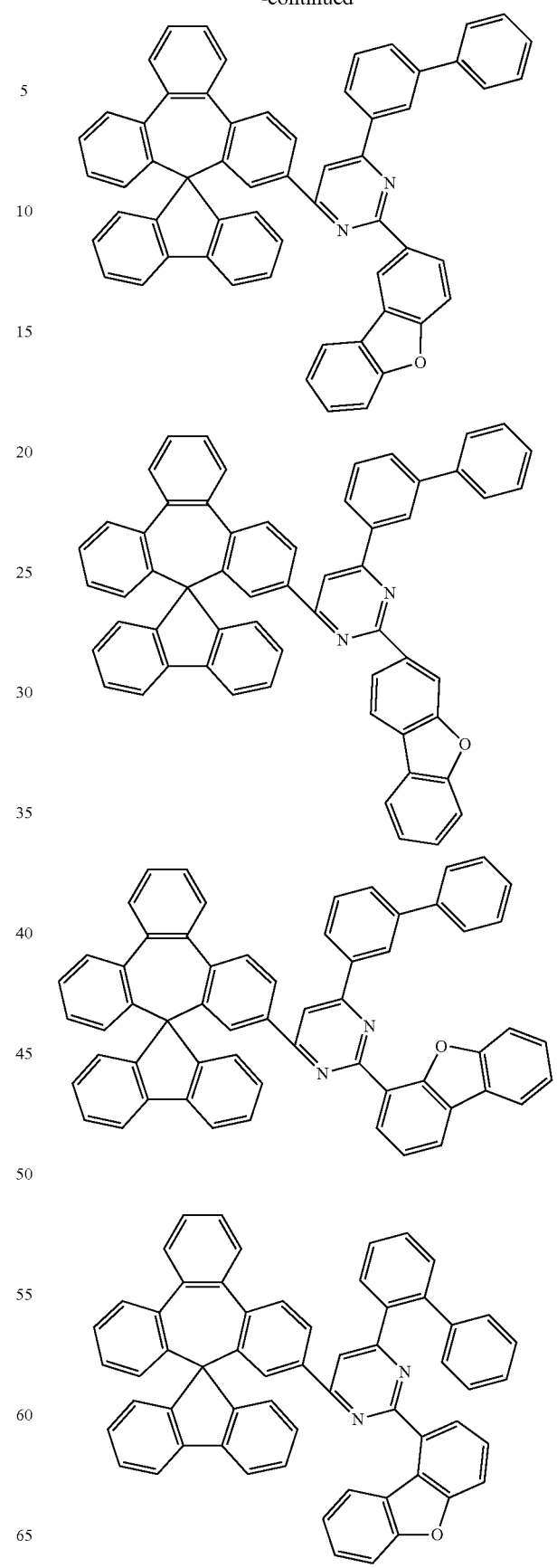

179
-continued
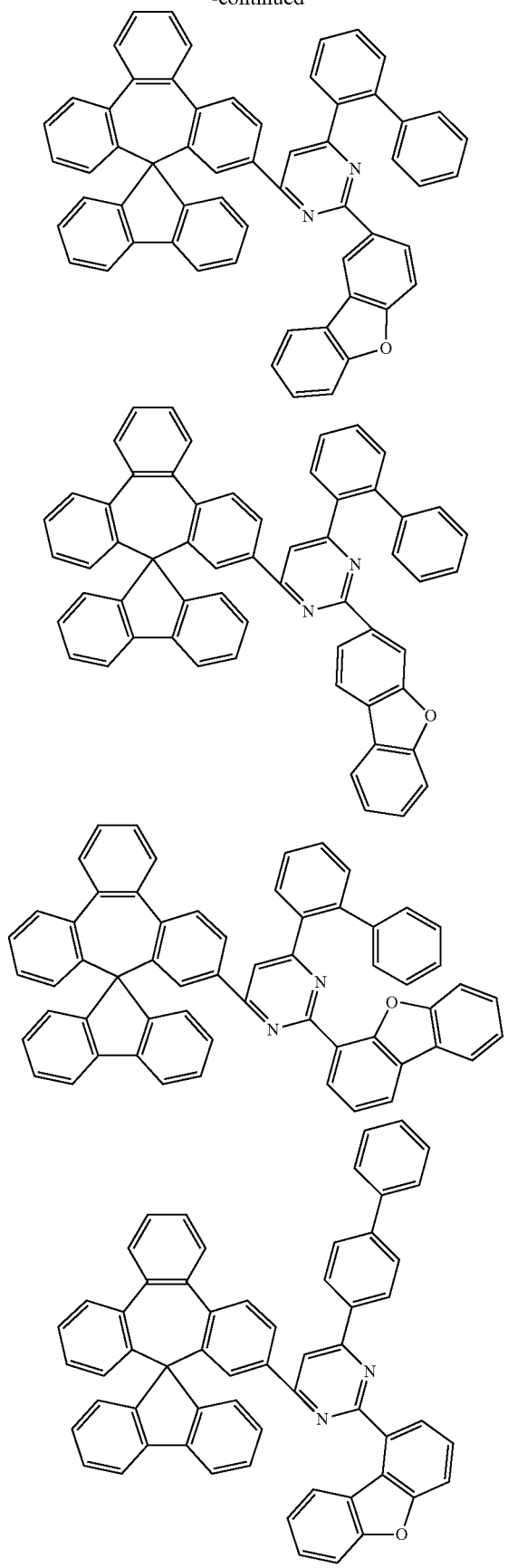
180
-continued
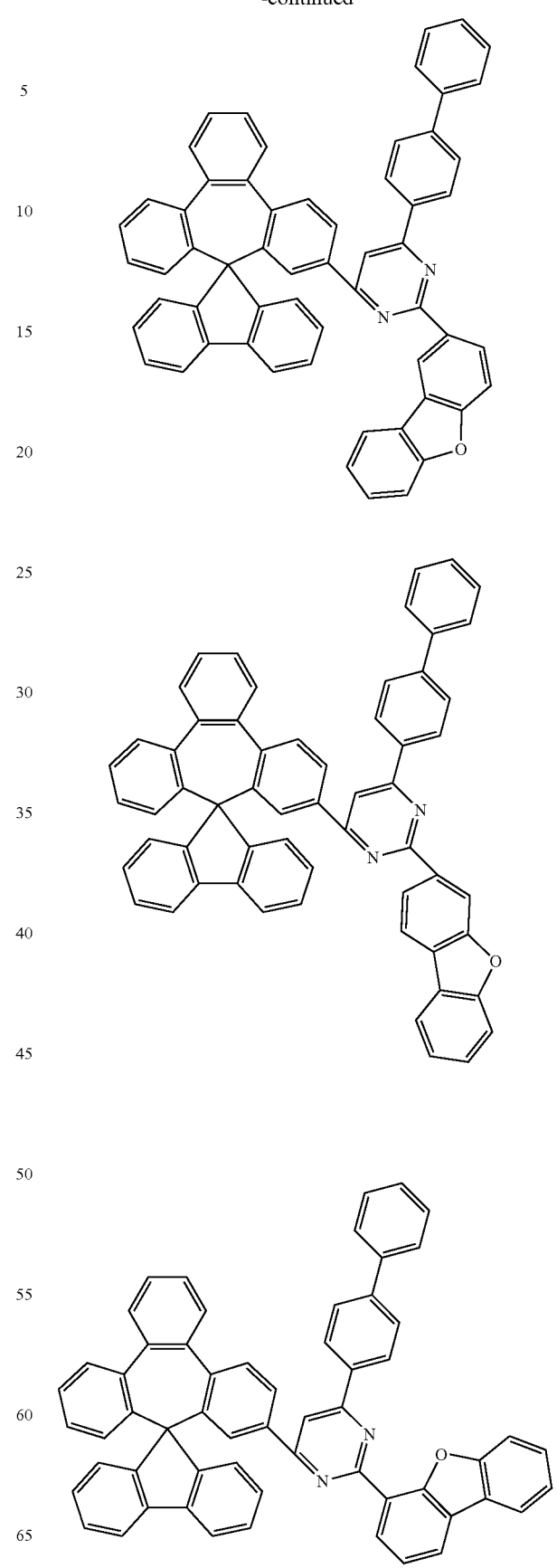

181
-continued
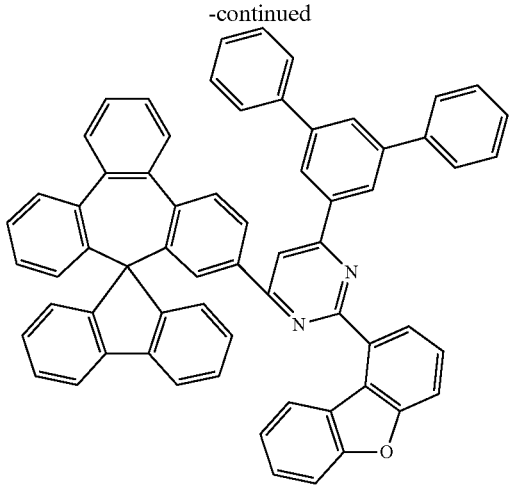
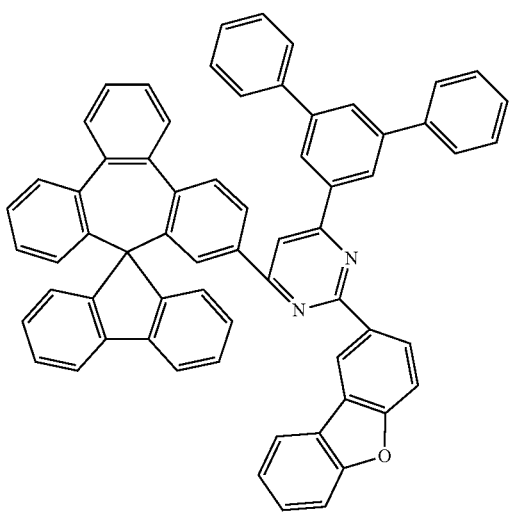
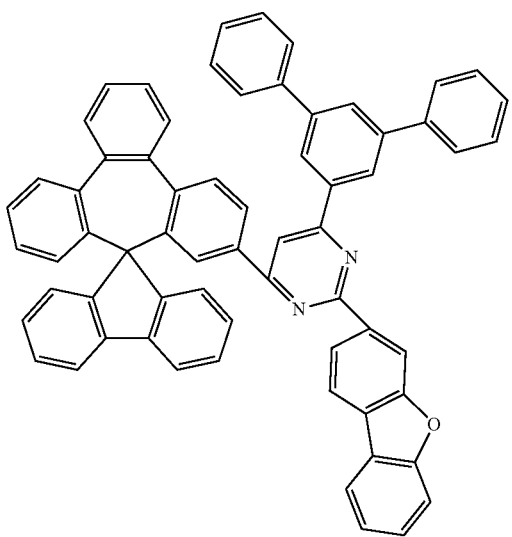
182
-continued
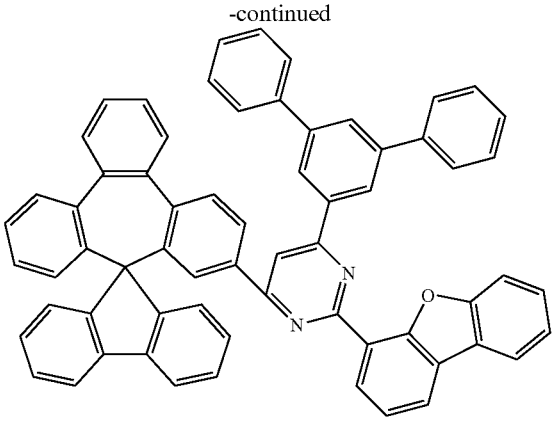
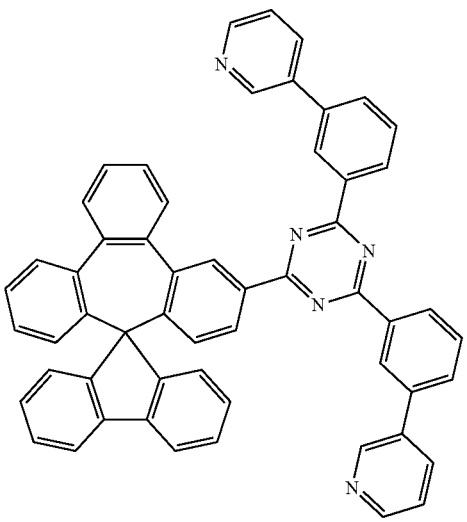
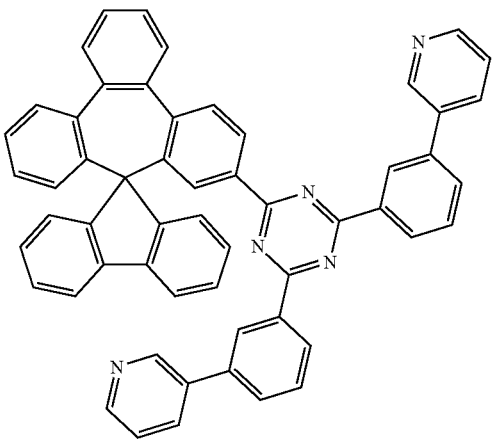

183
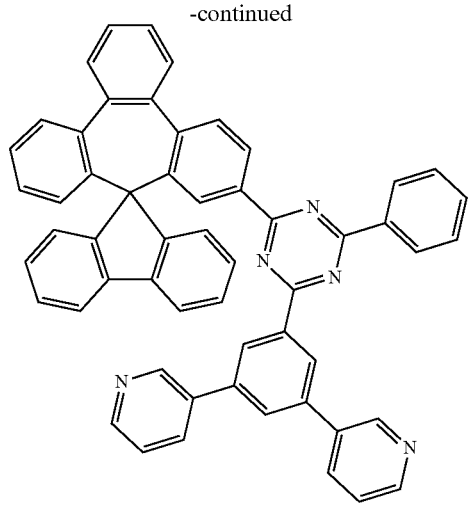
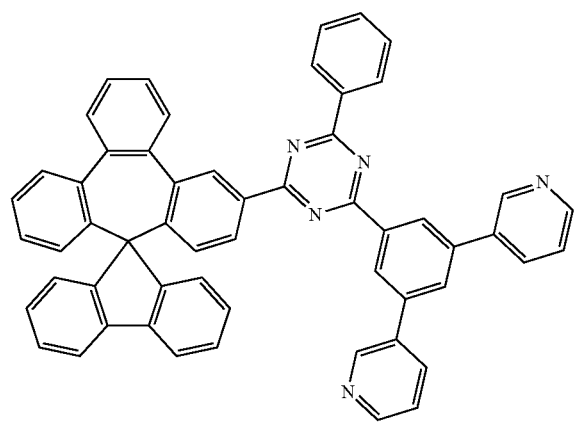
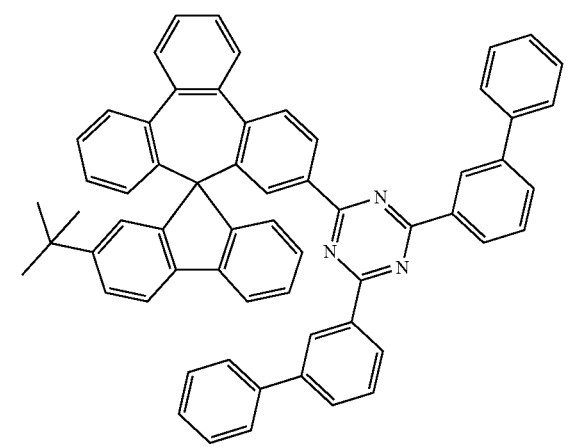
184
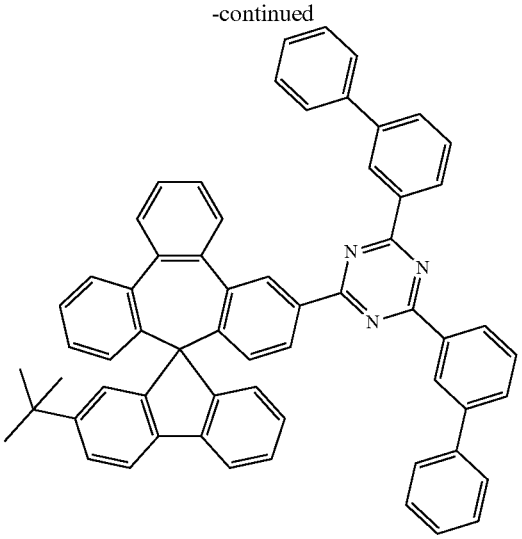
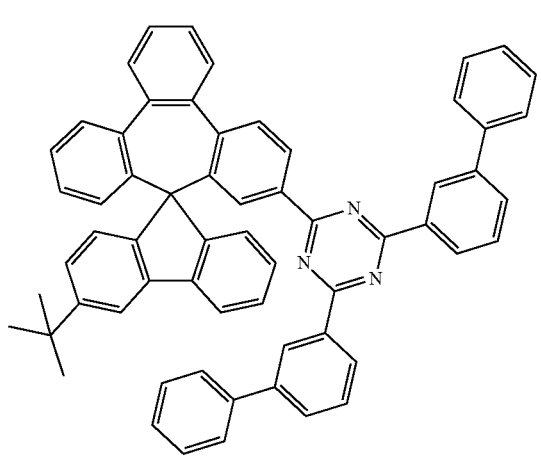
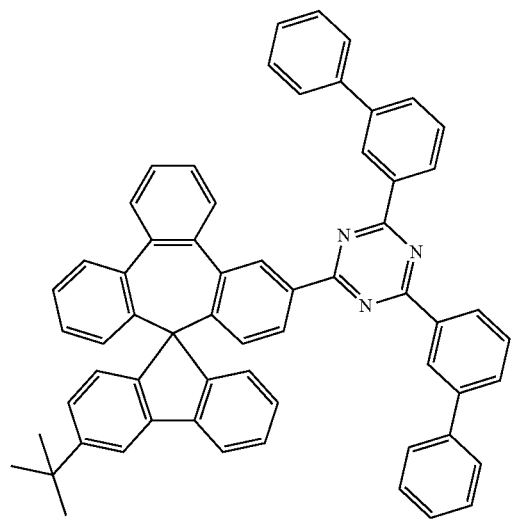

185
-continued
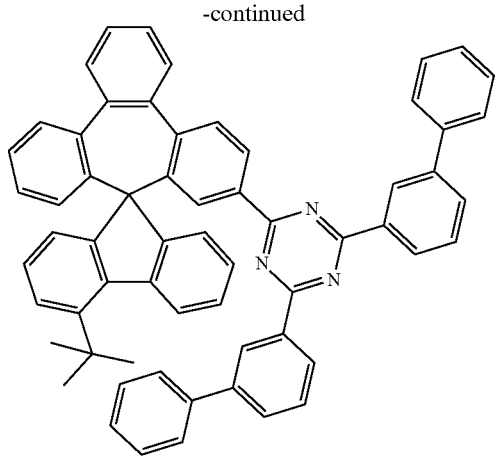
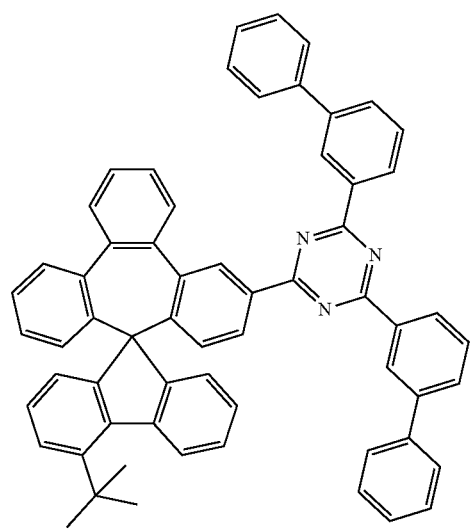
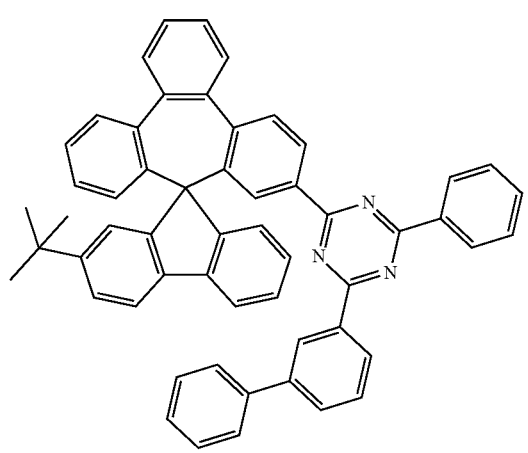
186
-continued
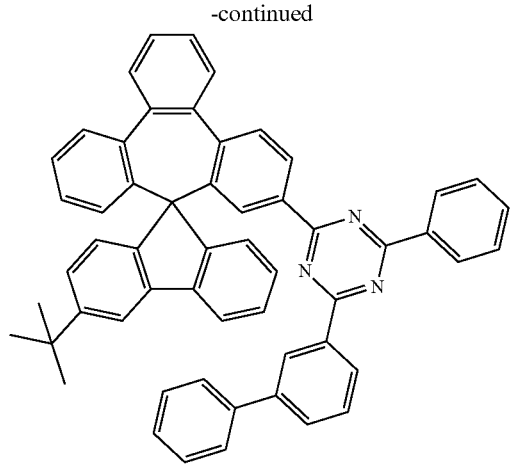
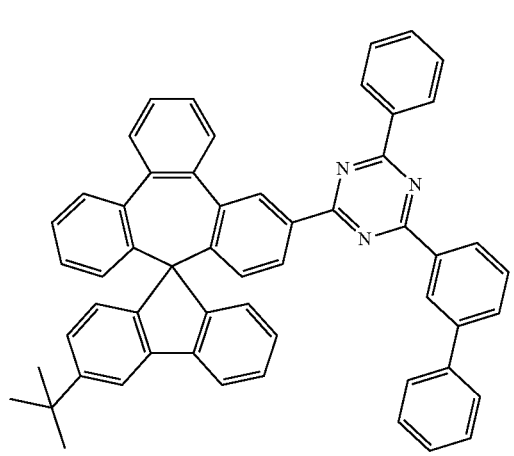
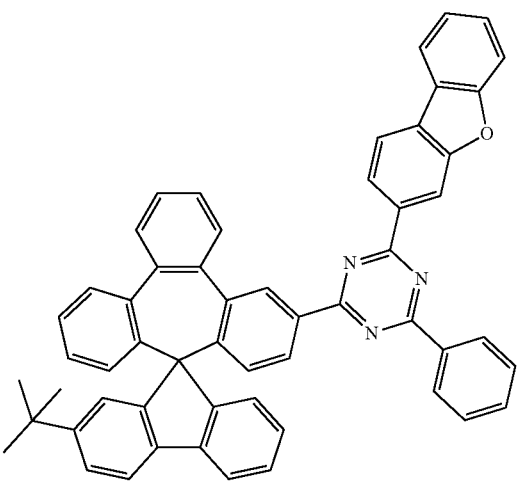

187
-continued
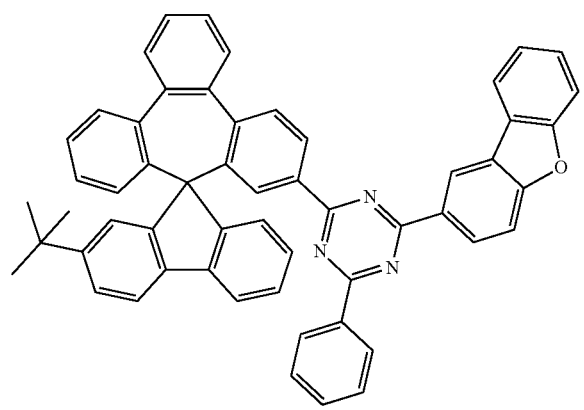
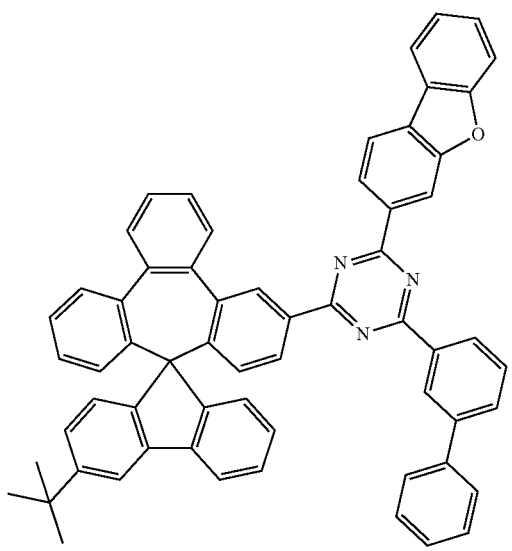
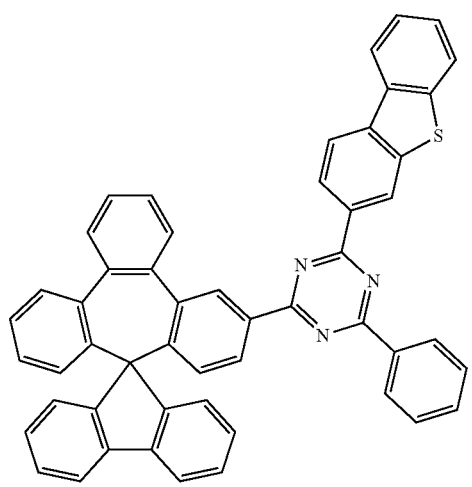
188
-continued
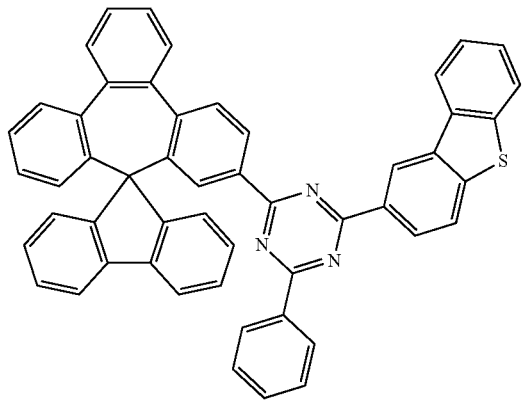
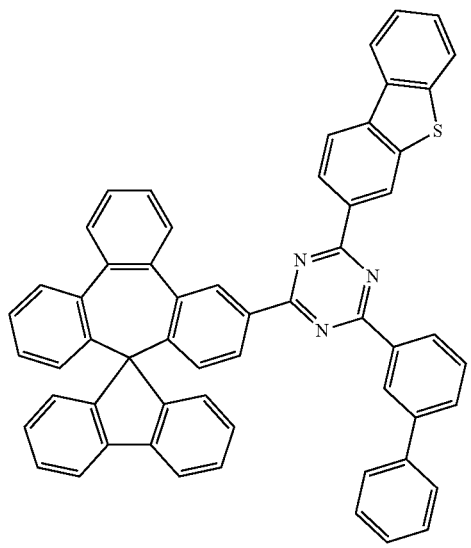
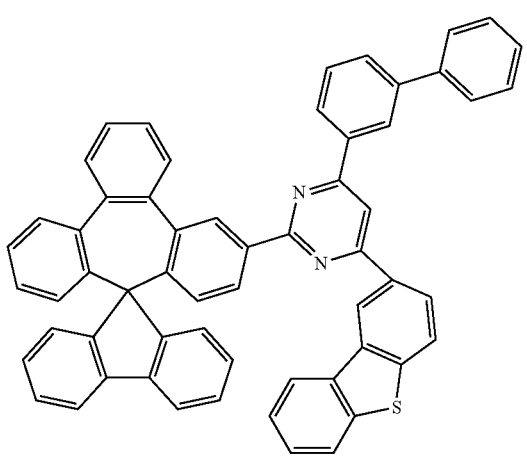

189
-continued
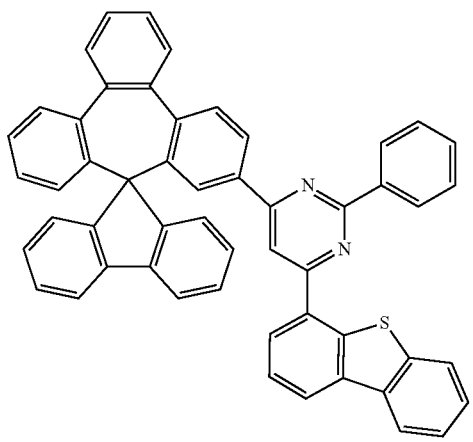
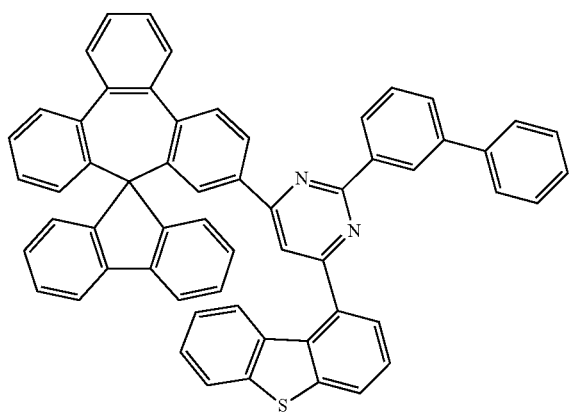
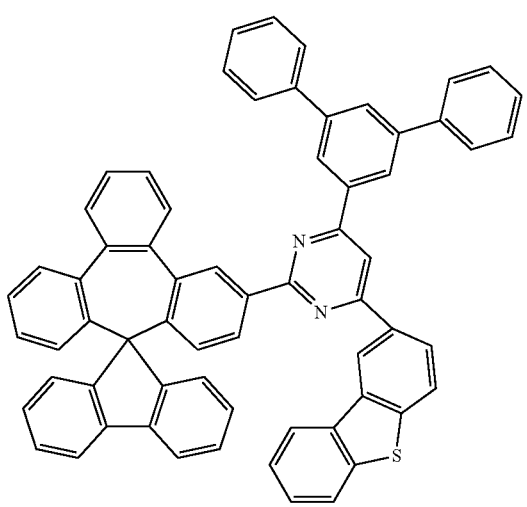
190
-continued
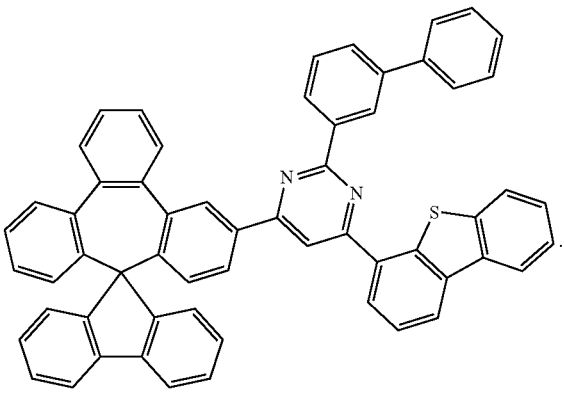
Or, for example, the first host compound may be any one of the following compound:
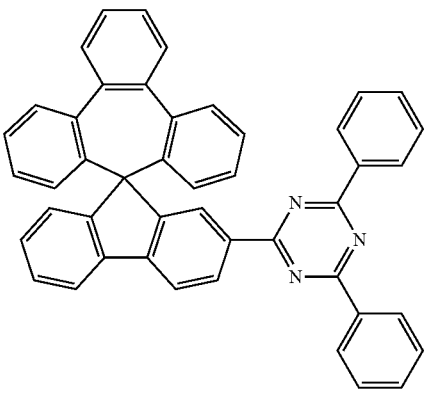
or
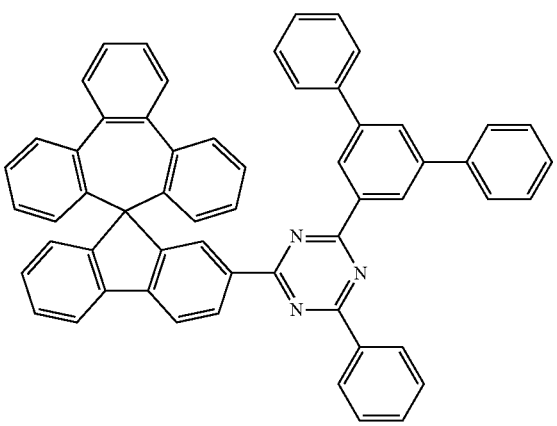

191
-continued
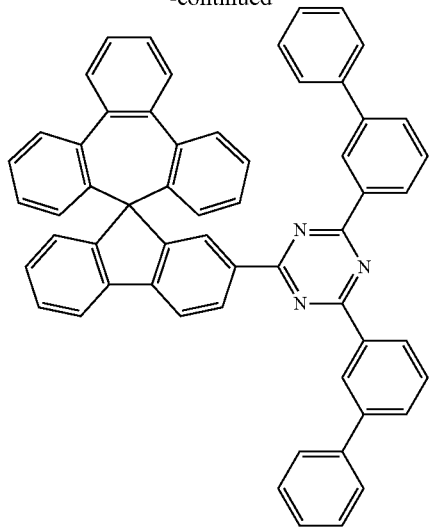
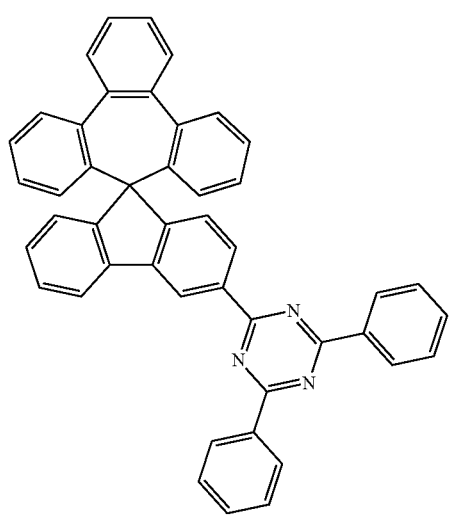
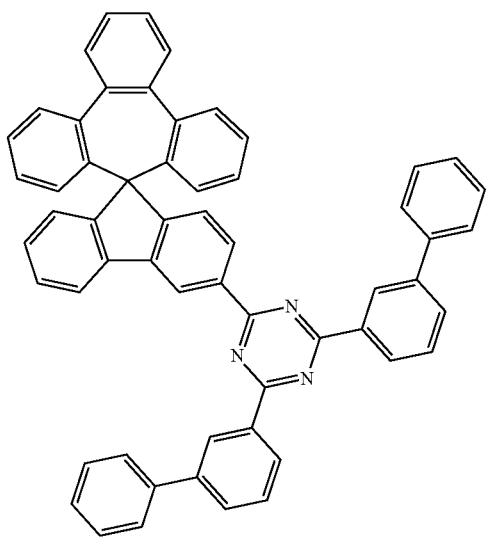
192
-continued
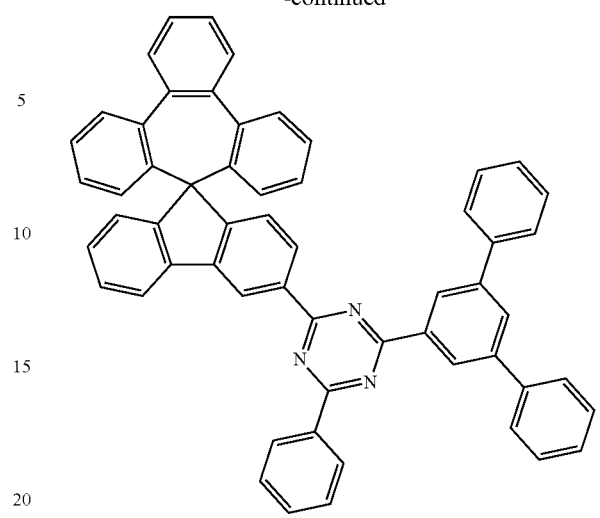
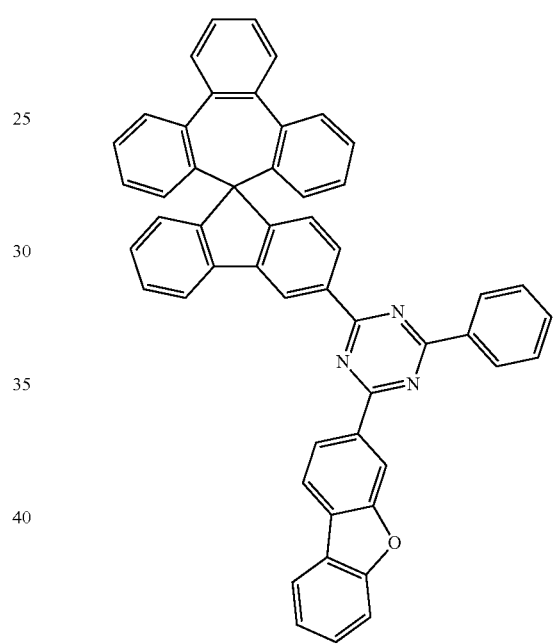
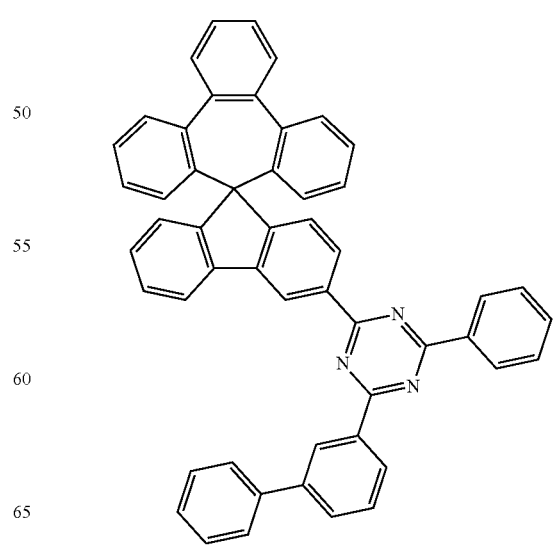

-continued
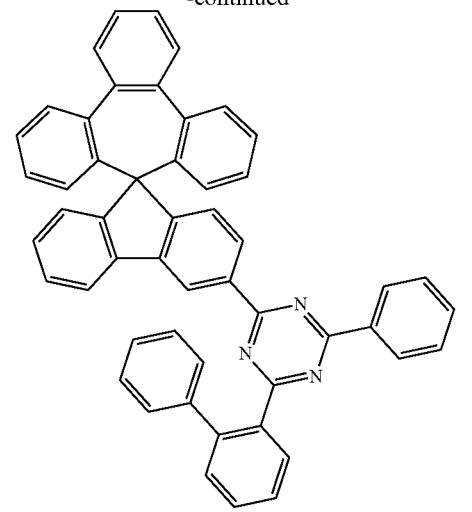
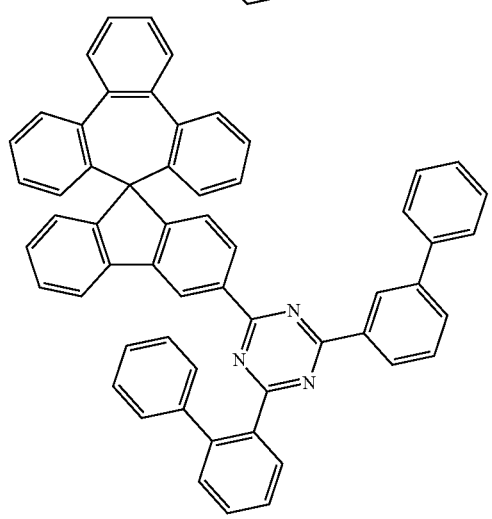
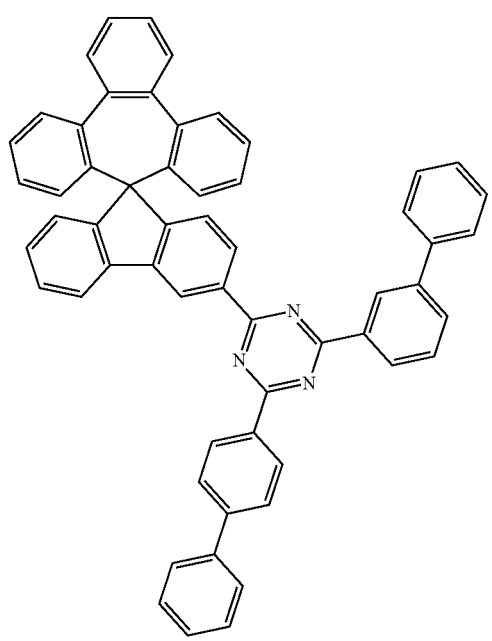
-continued
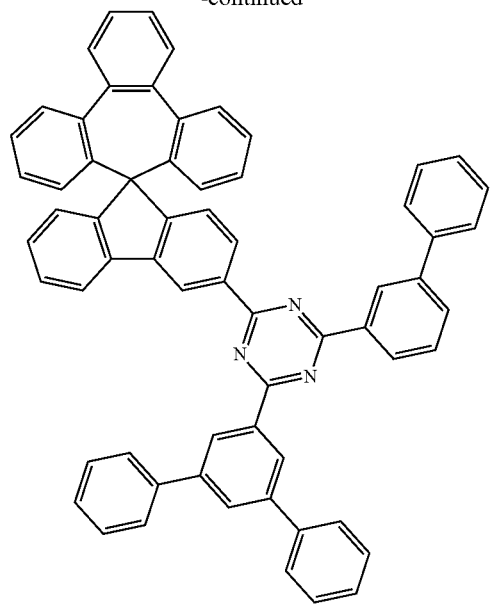
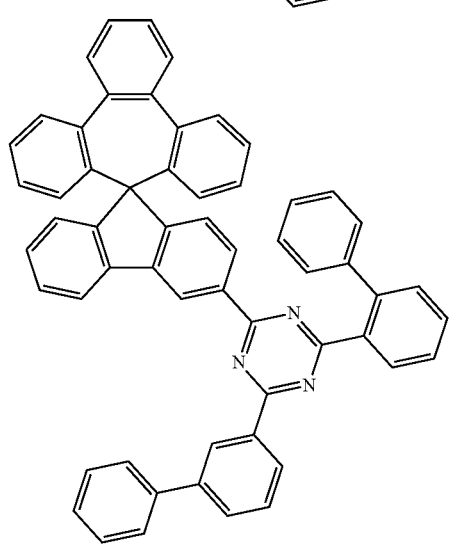
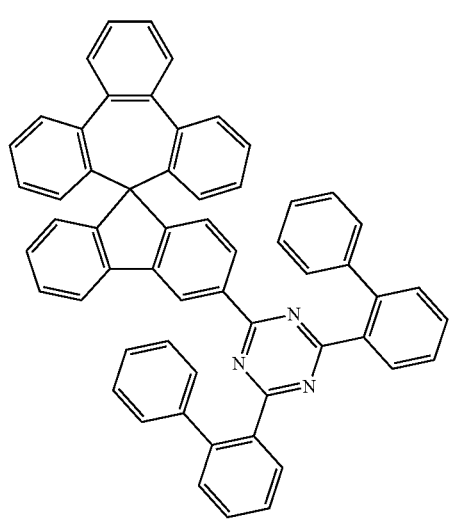

195
-continued
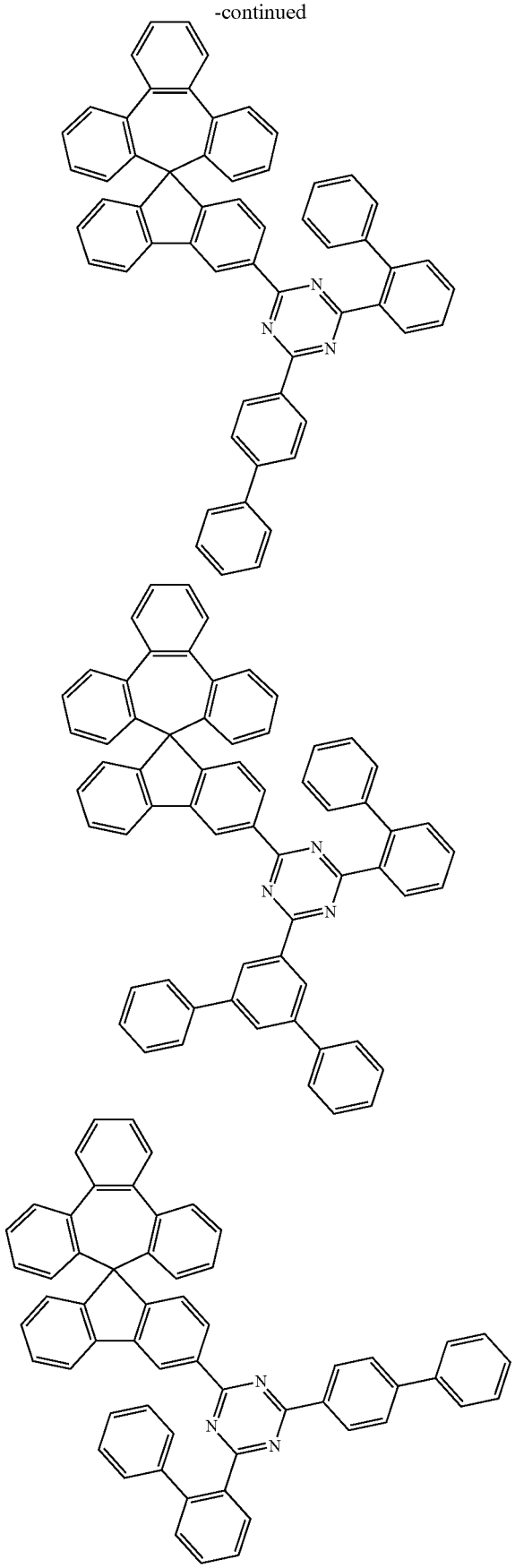
196
-continued
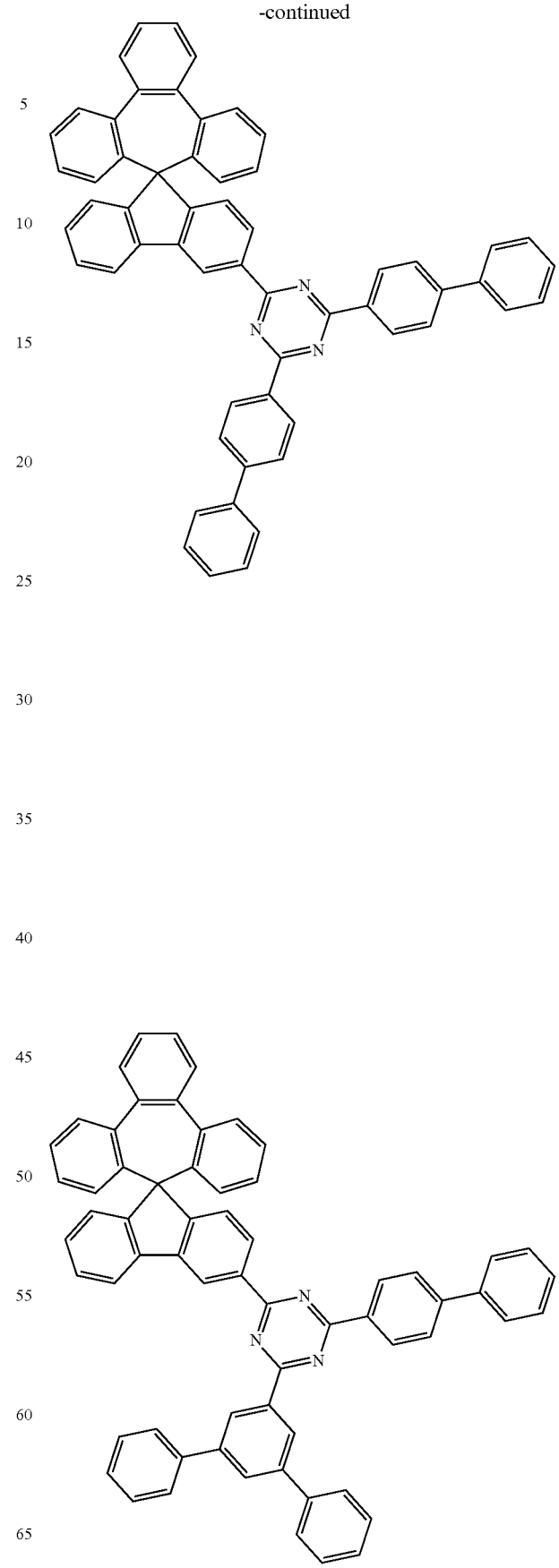

197
-continued
198
-continued
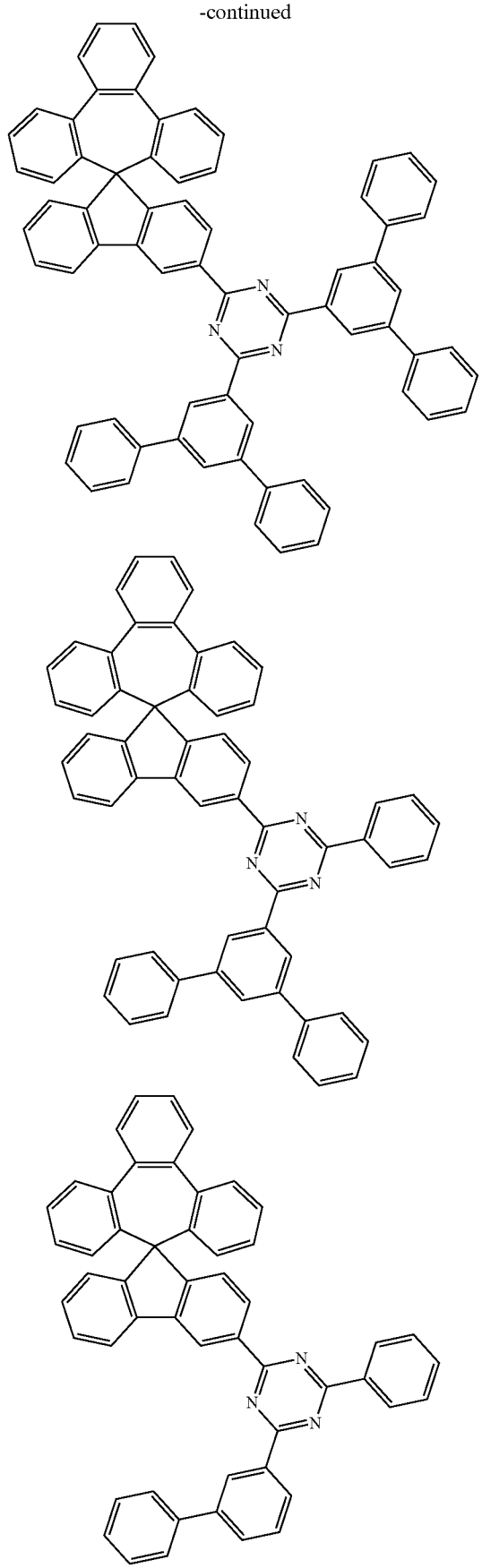
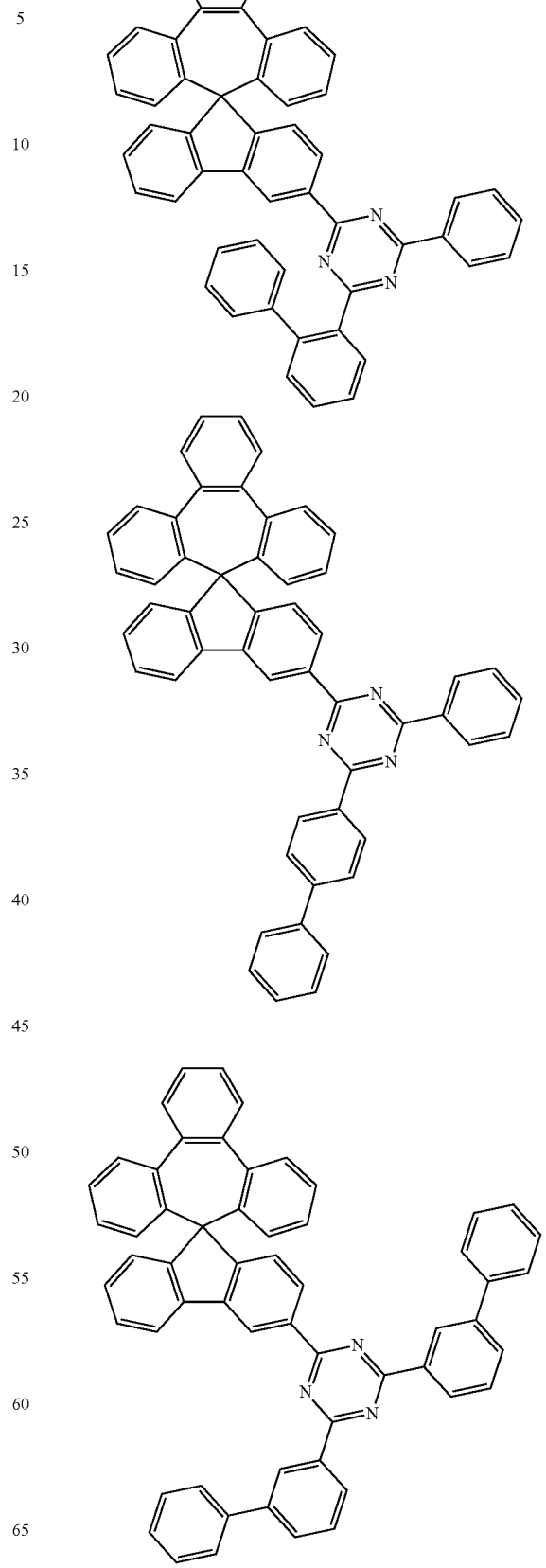

199
-continued
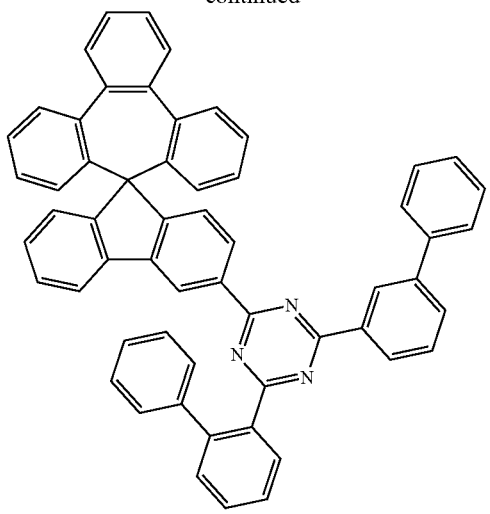
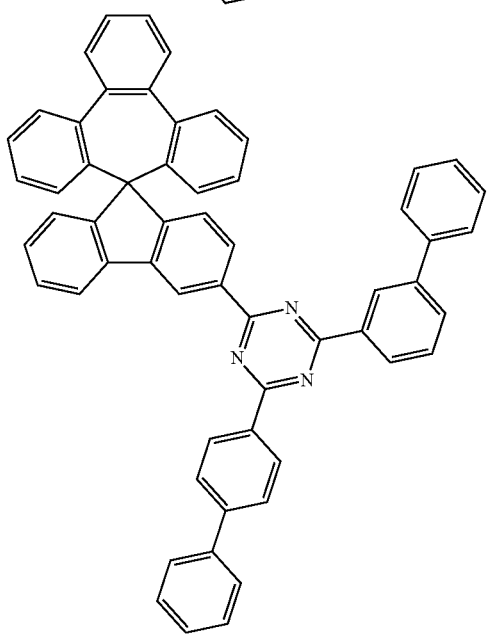
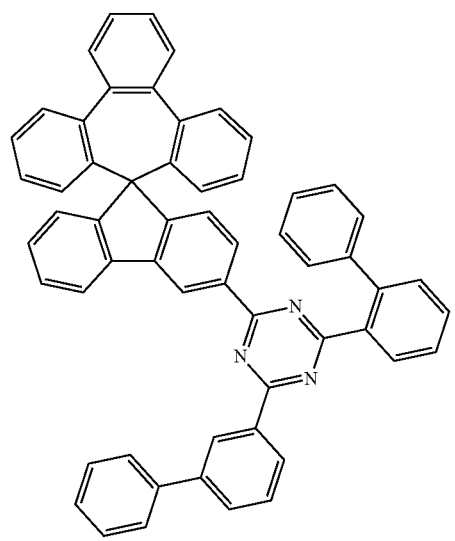
200
-continued
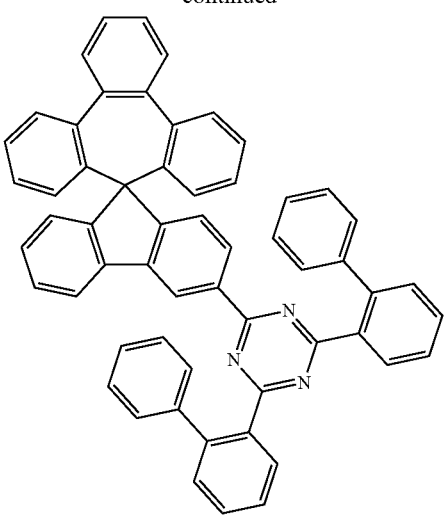
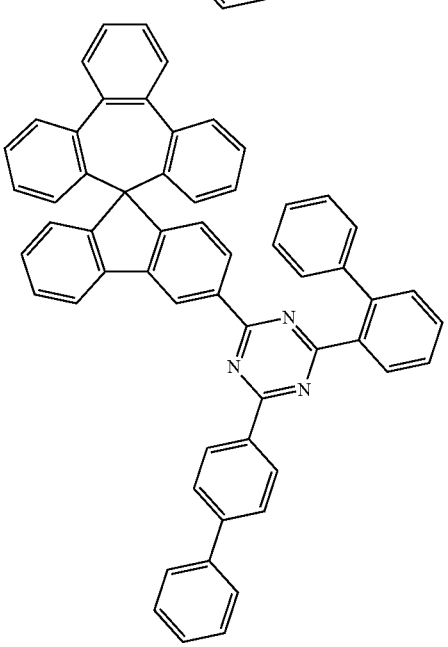
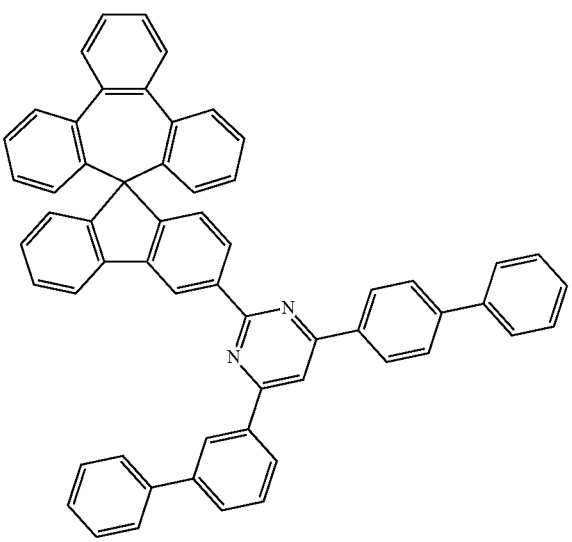

201
-continued
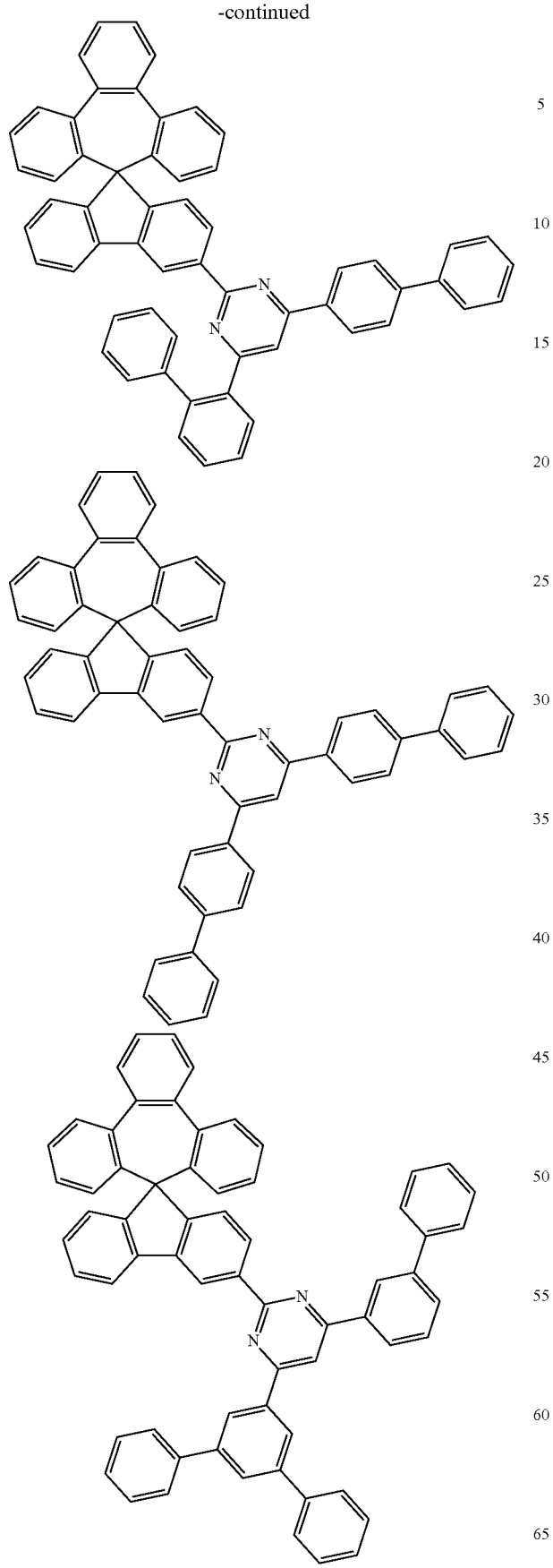
202
-continued
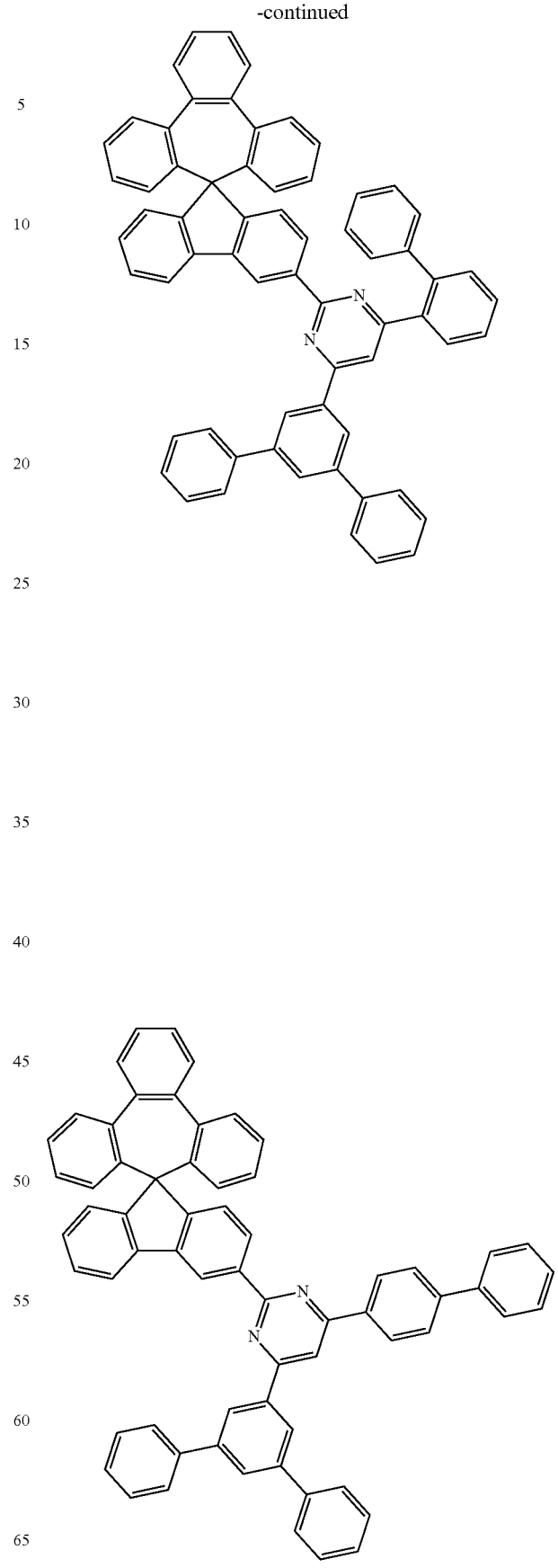

203
-continued
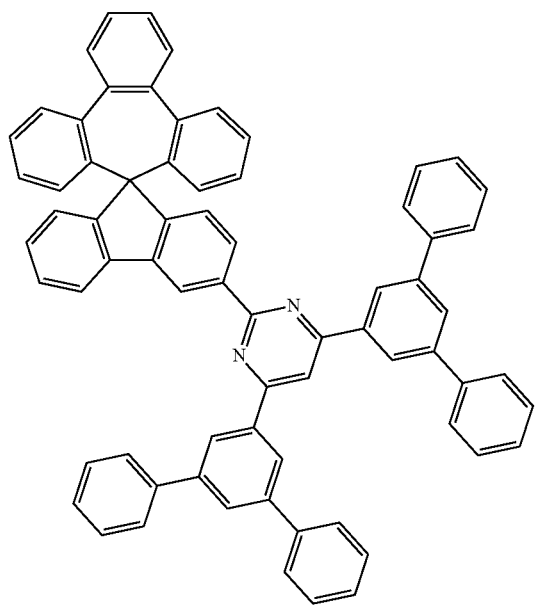
204
-continued
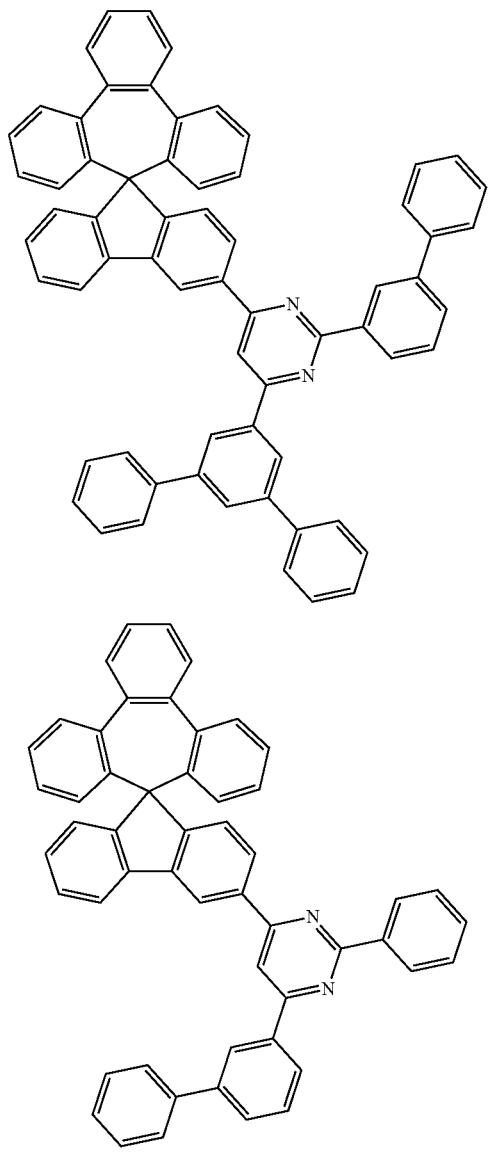
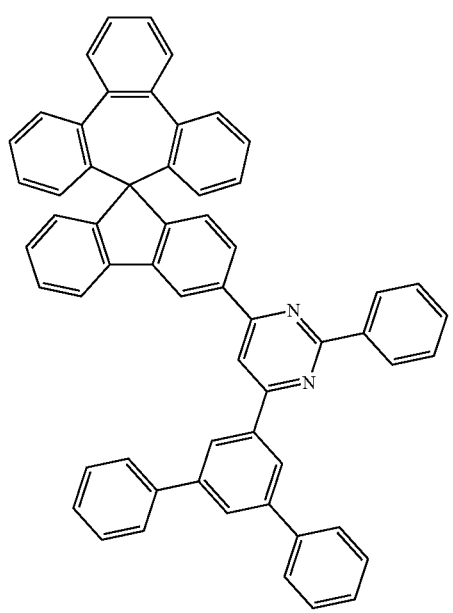

205
-continued
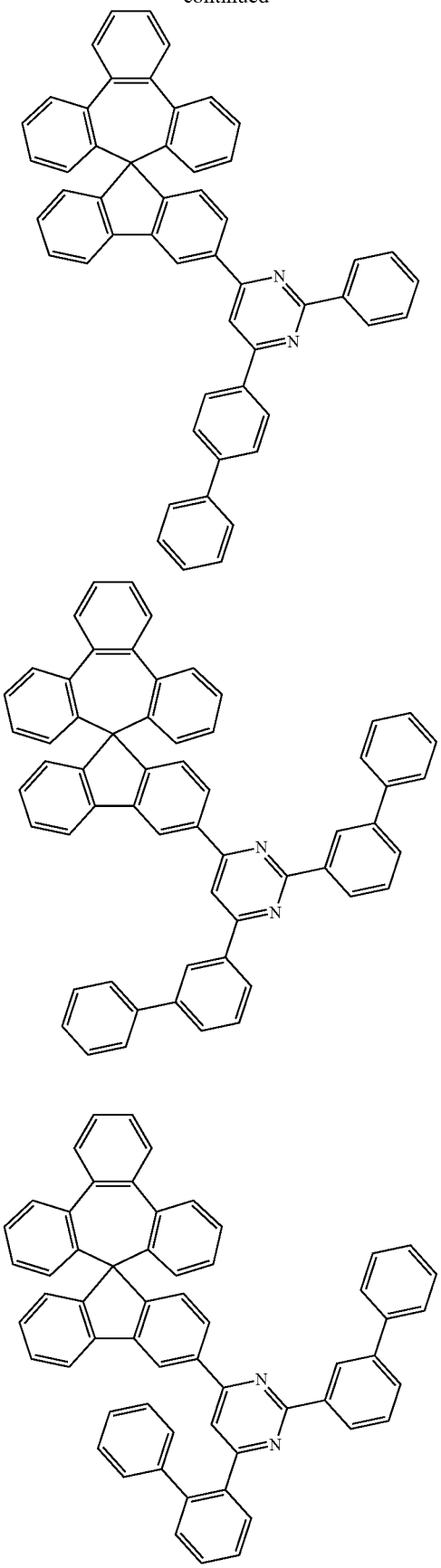
206
-continued
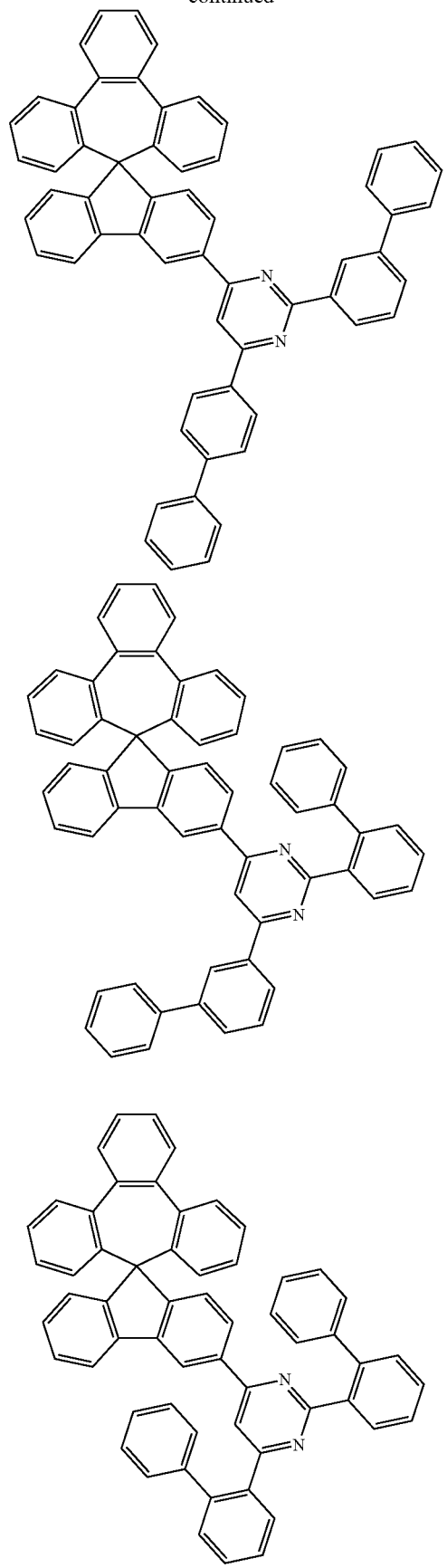

207
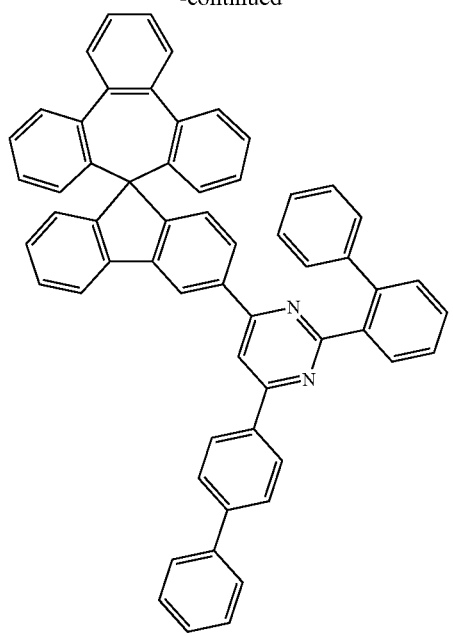
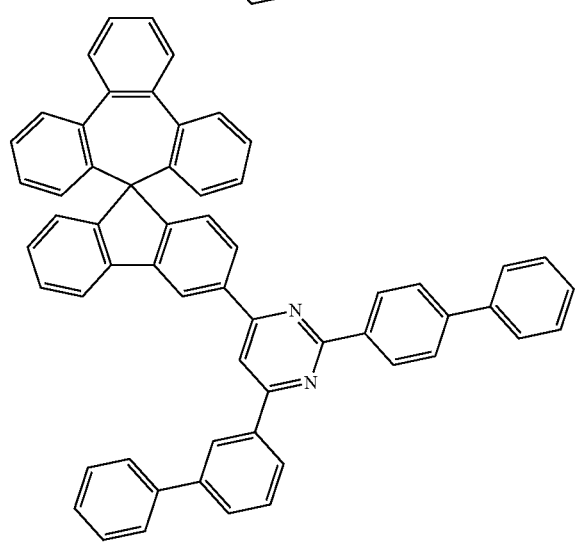
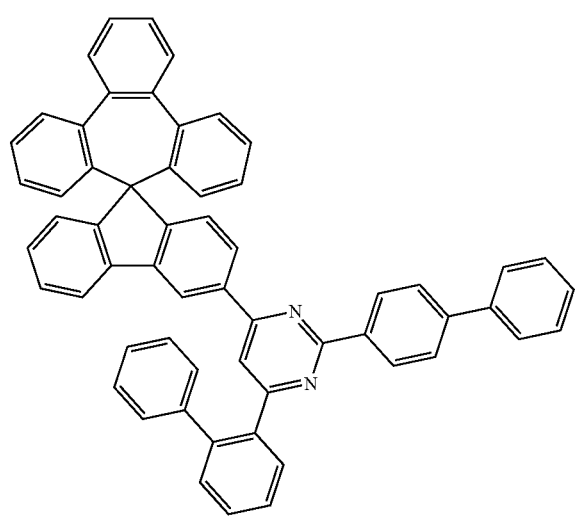
208
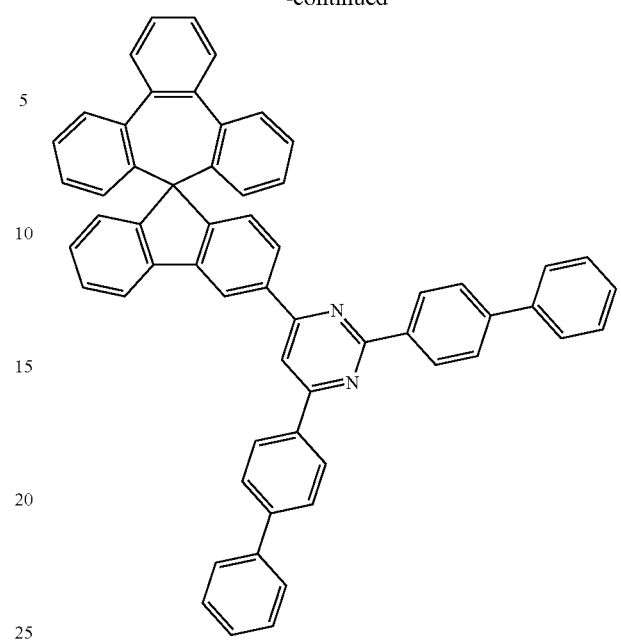
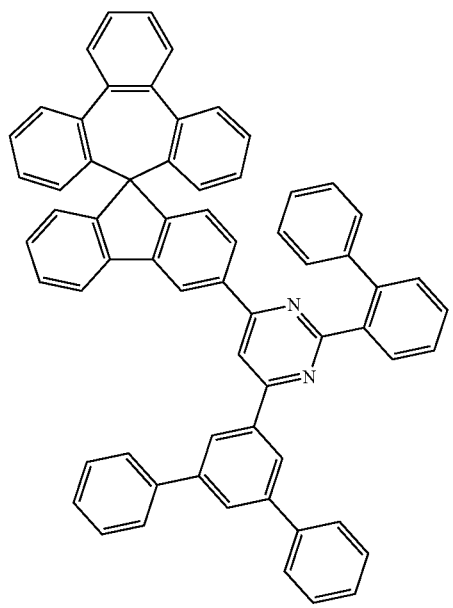

209
-continued
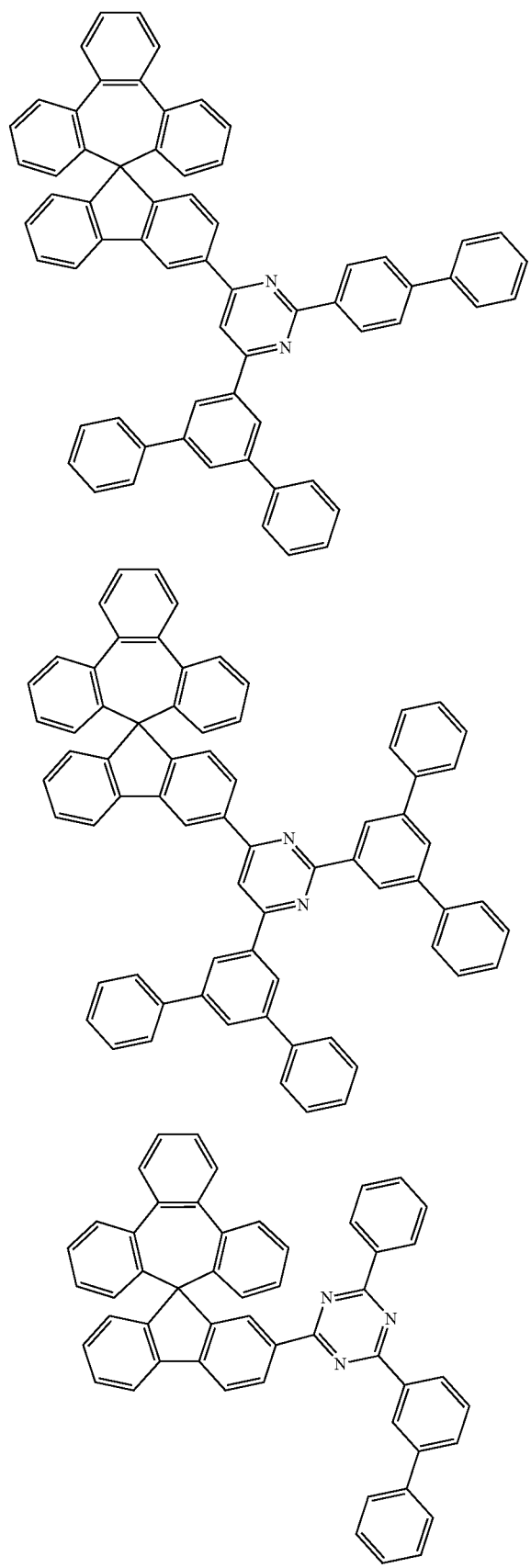
210
-continued
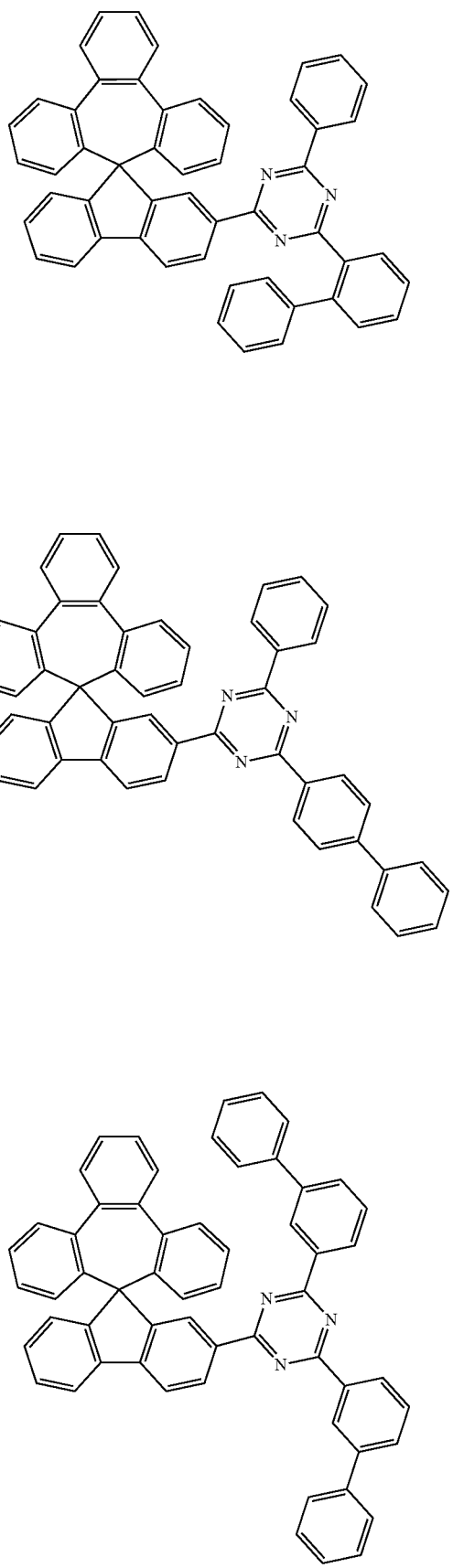

211
-continued
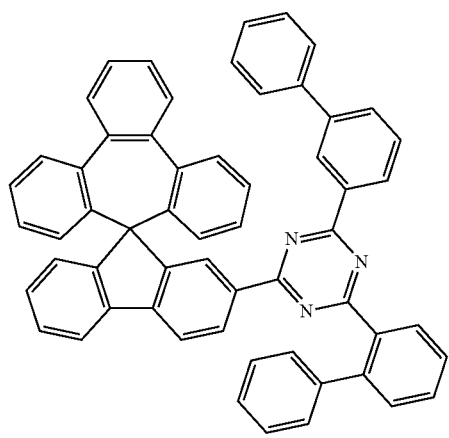
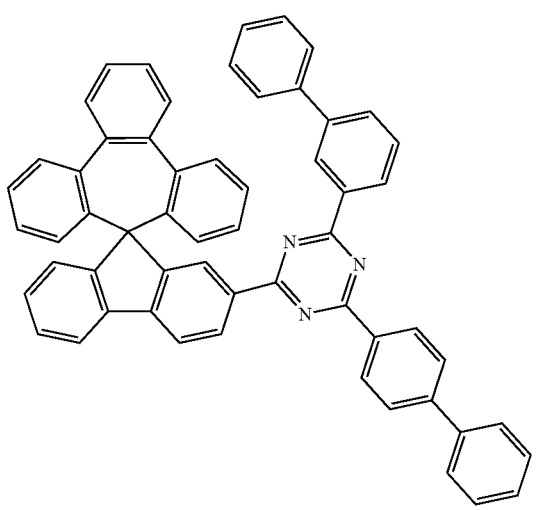
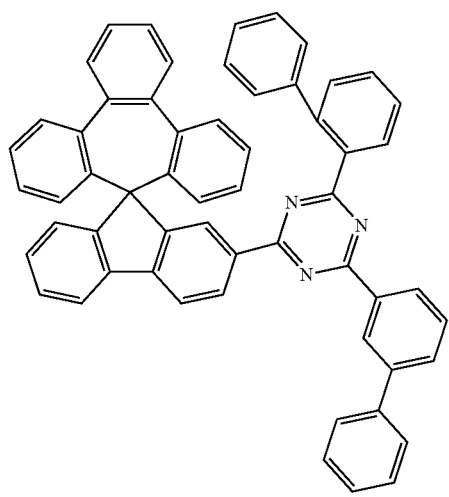
212
-continued
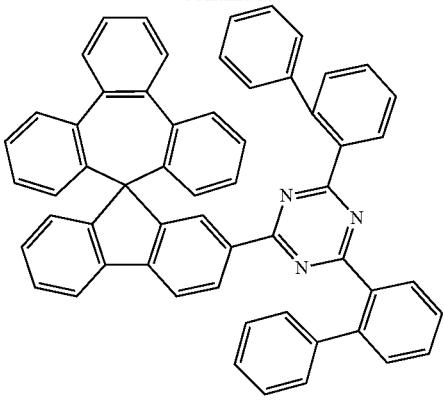
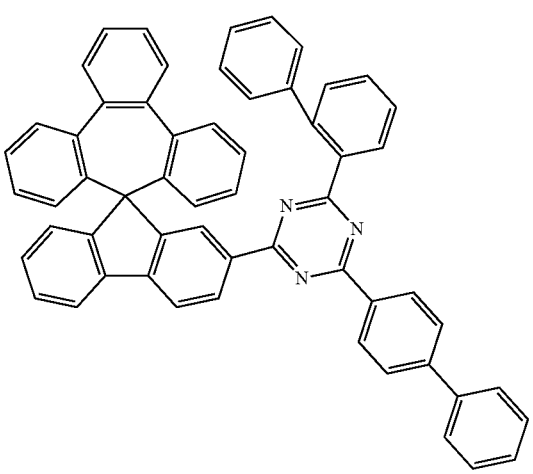
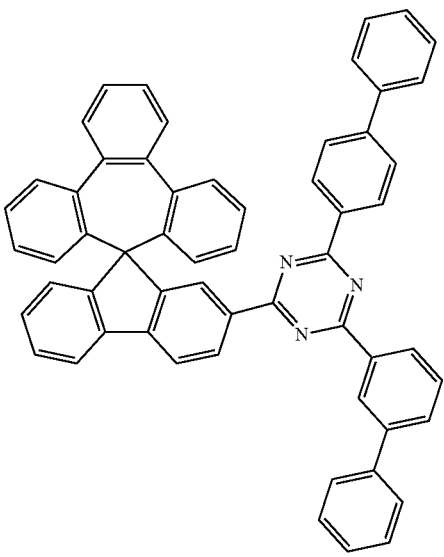

213
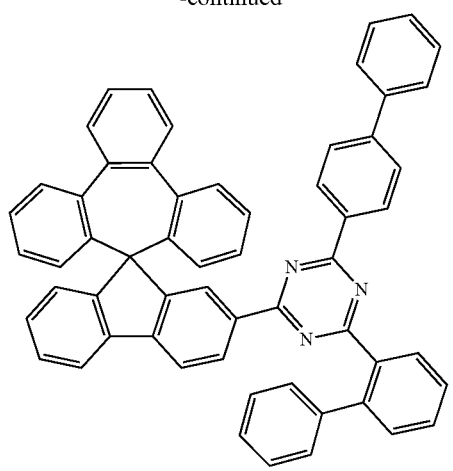
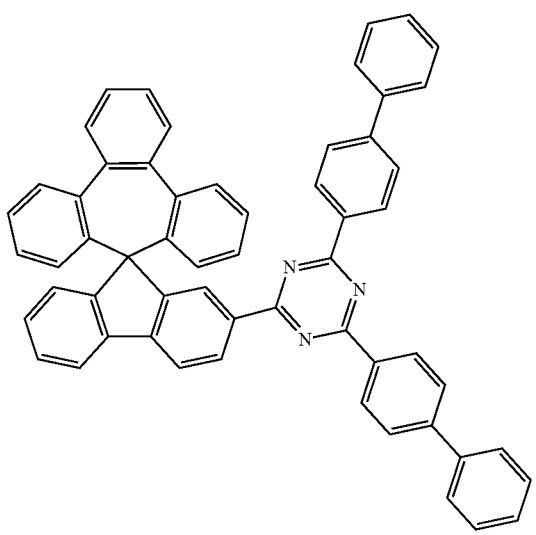
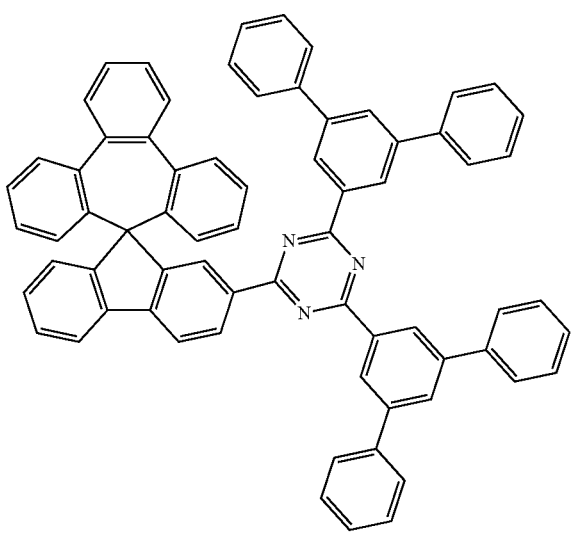
214
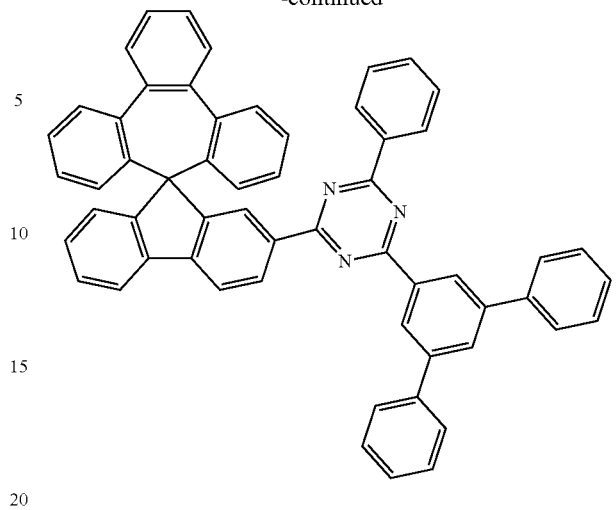
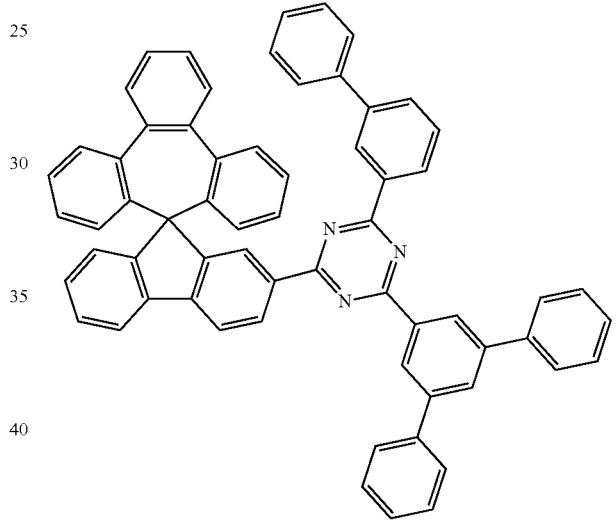
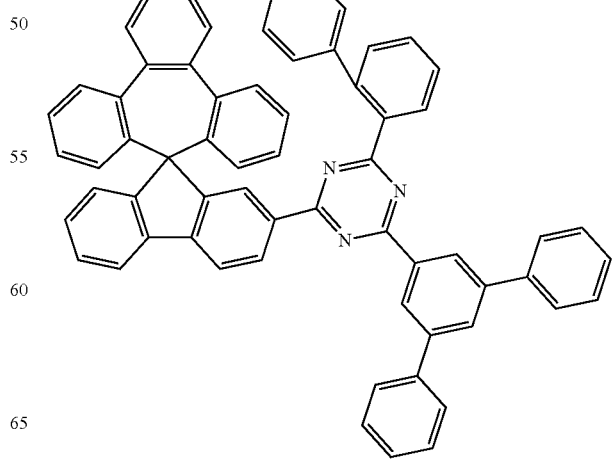

215
-continued
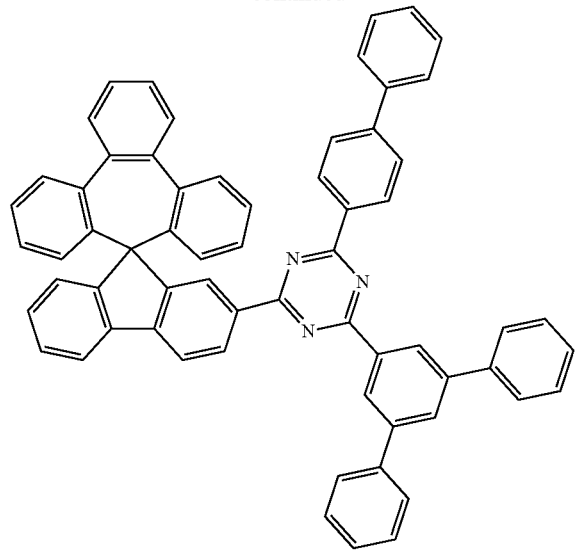
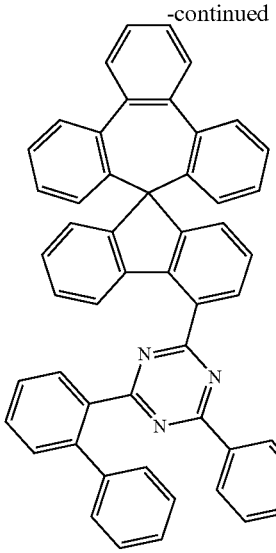
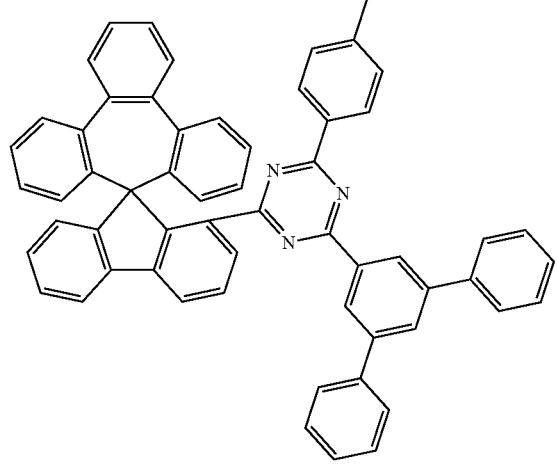
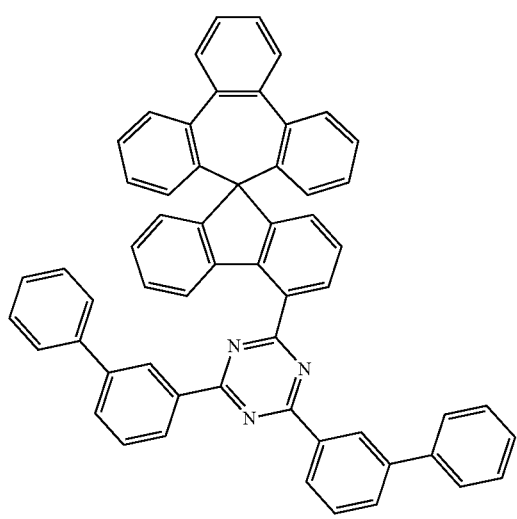
216
-continued
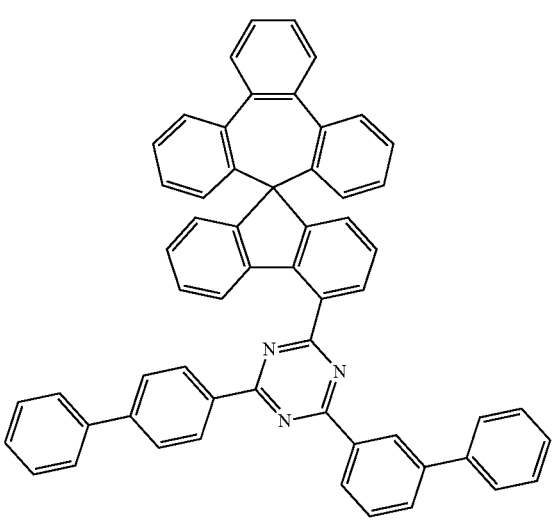
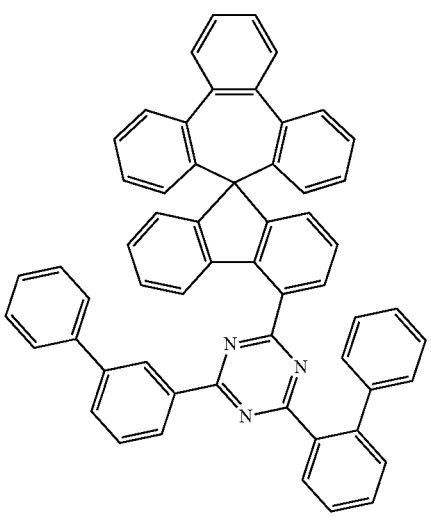

217
-continued
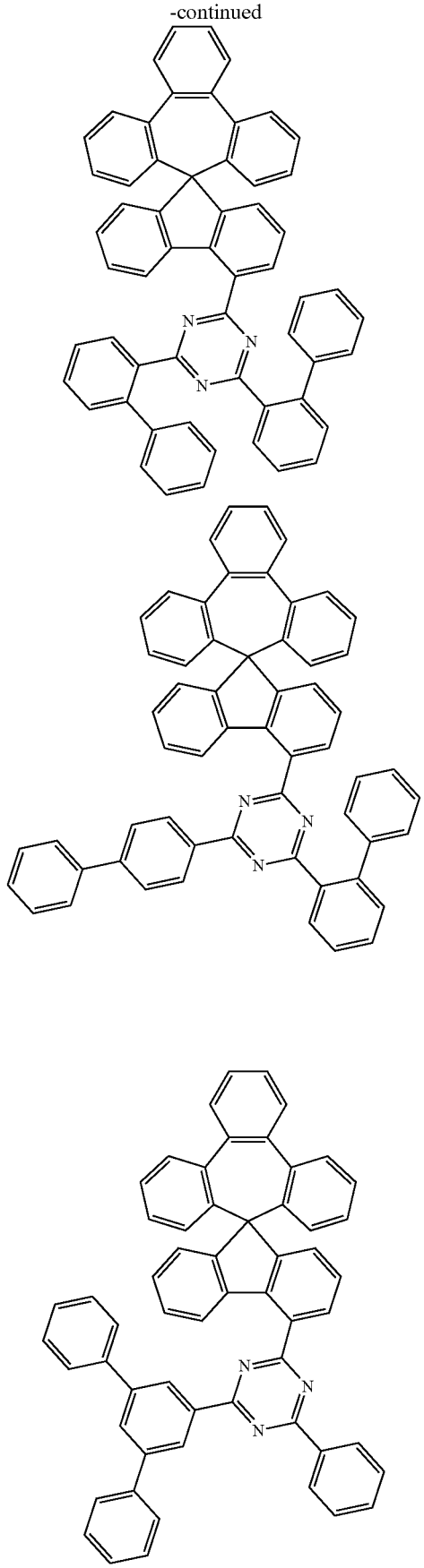
218
-continued
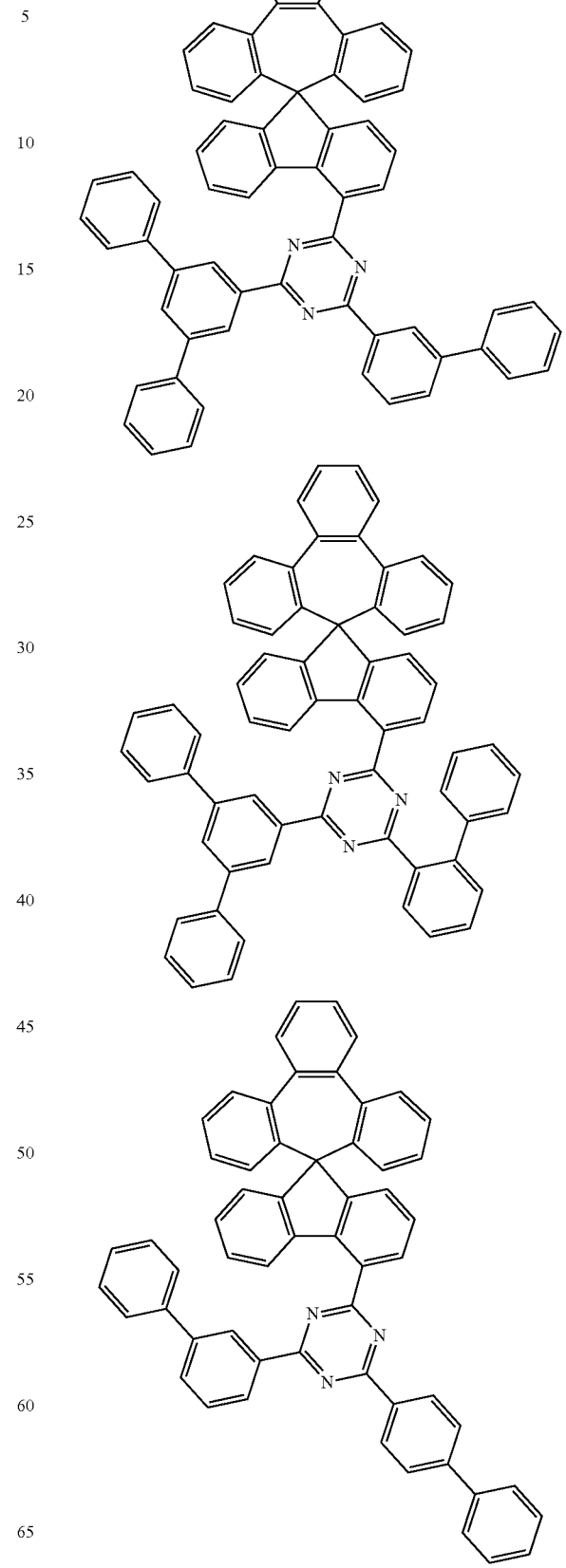

219
-continued
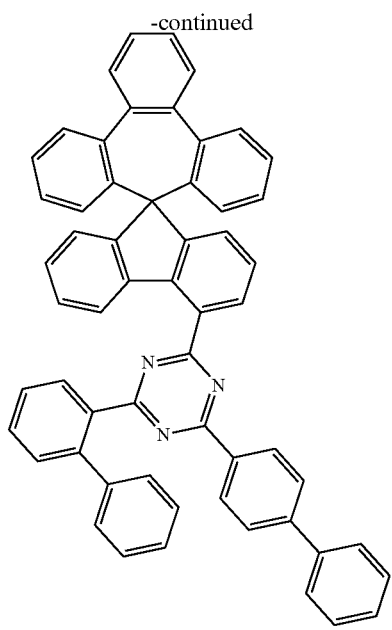
220
-continued
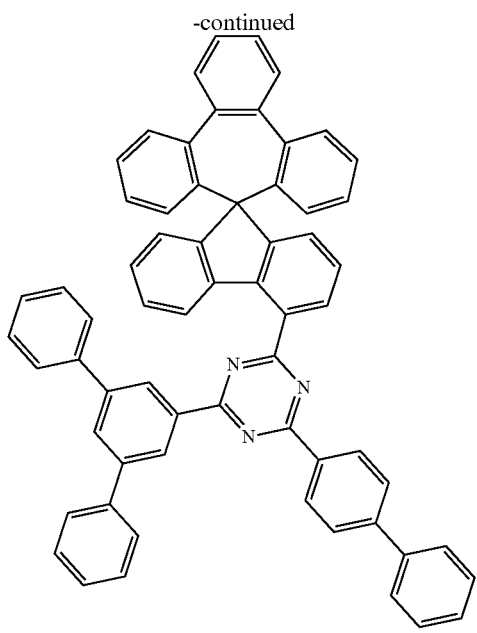
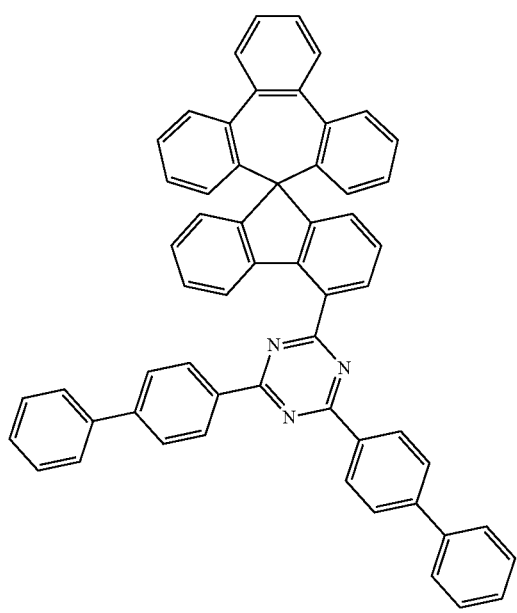
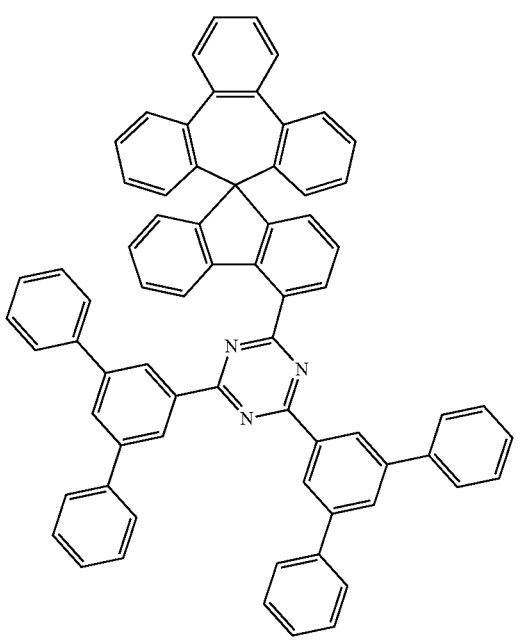

221
-continued
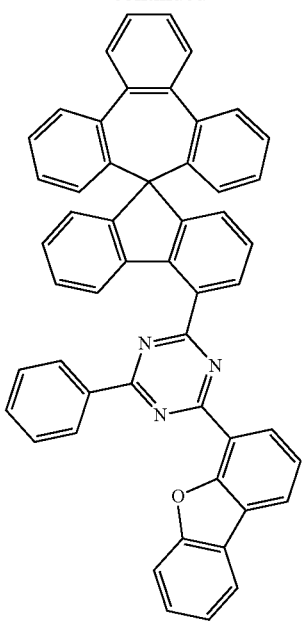
222
-continued
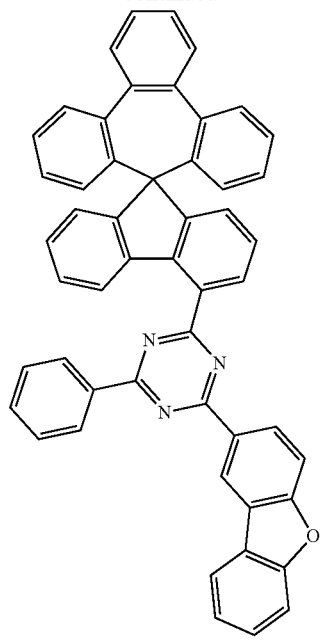
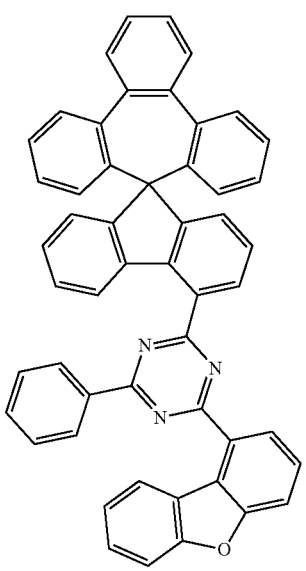
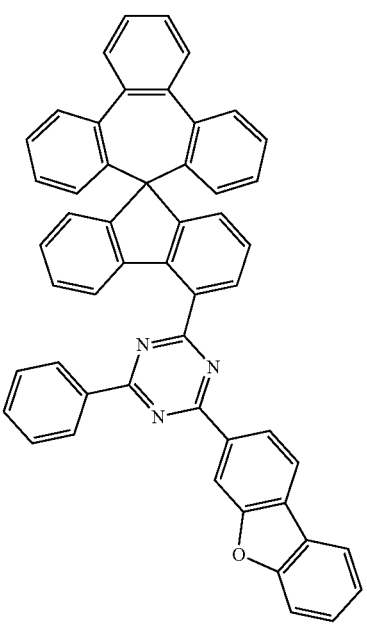

223
-continued
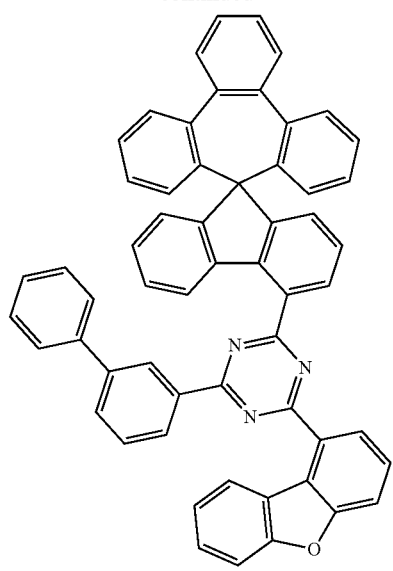
224
-continued
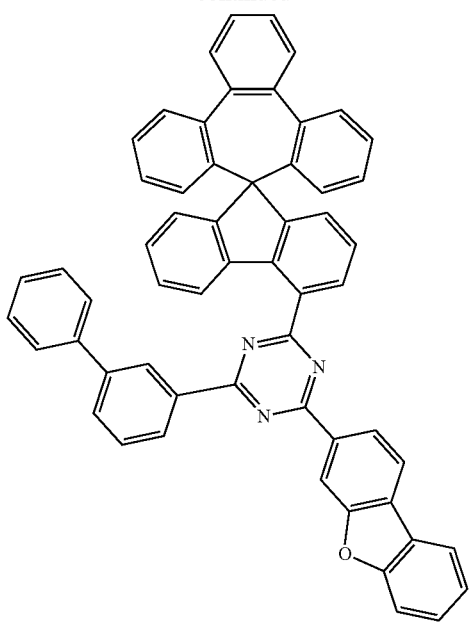
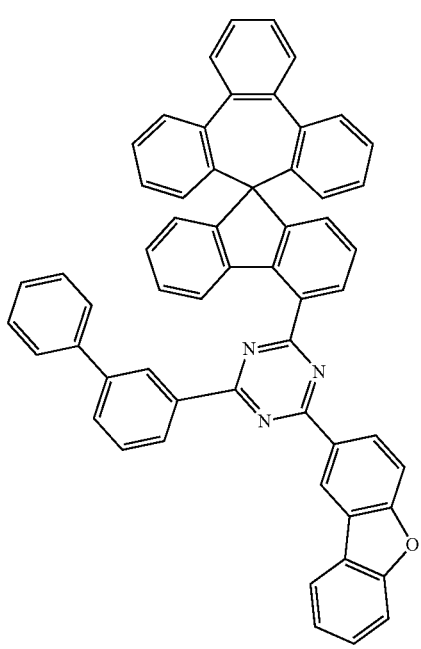
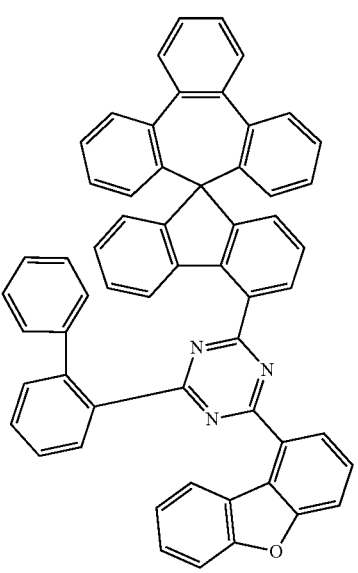

225
-continued
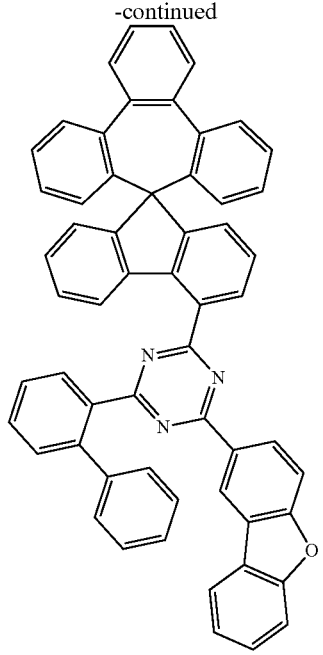
226
-continued
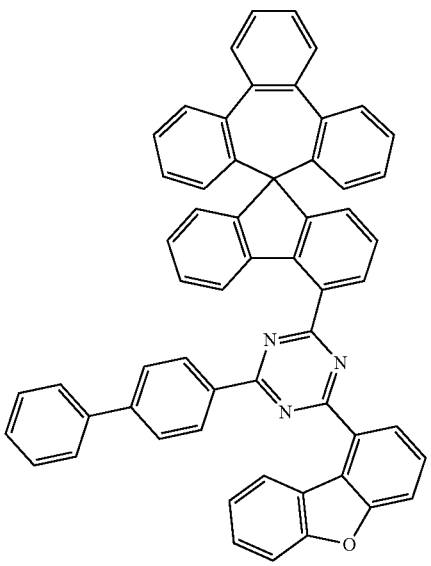
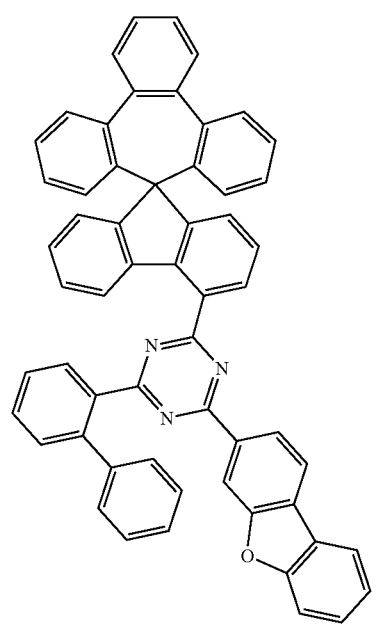
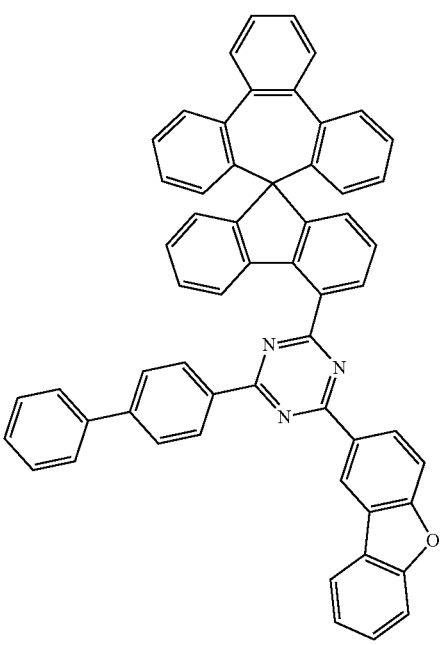

227
-continued
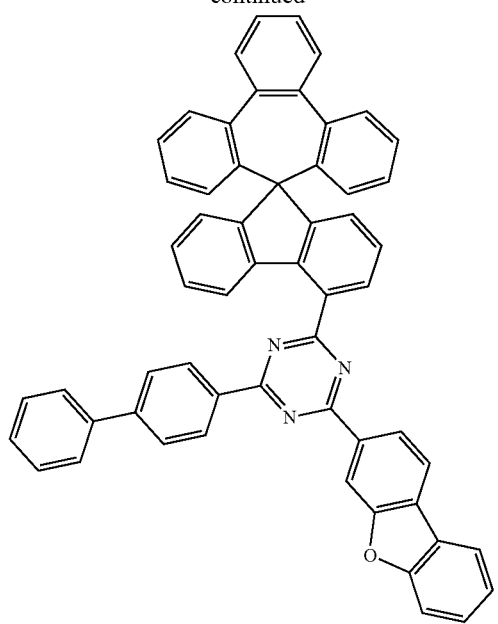
228
-continued
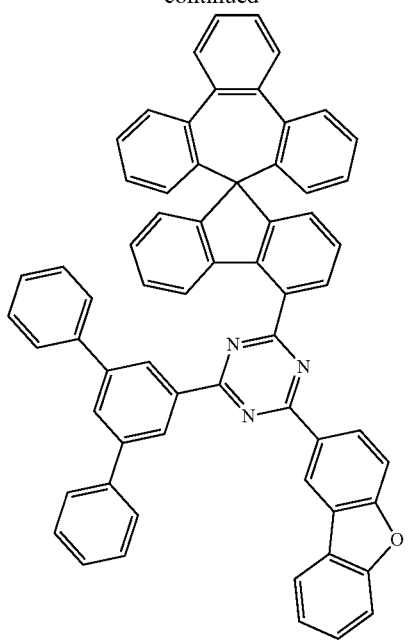
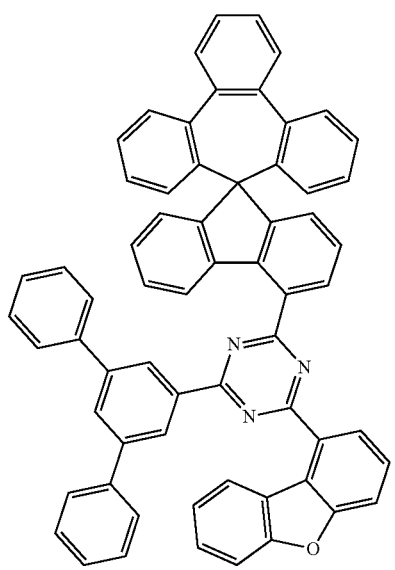
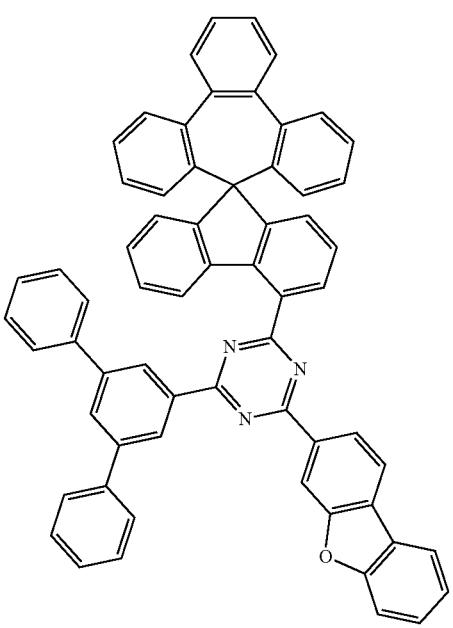

229
-continued
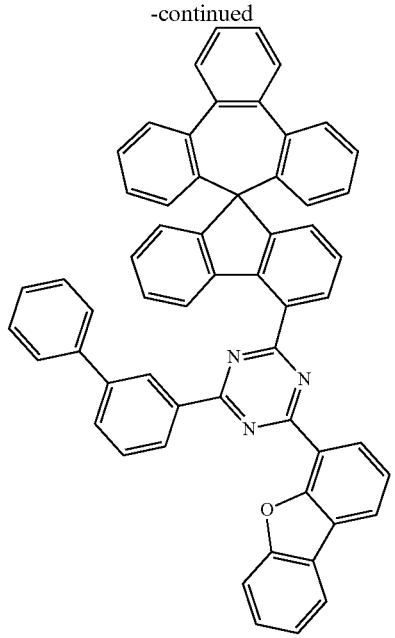
230
-continued
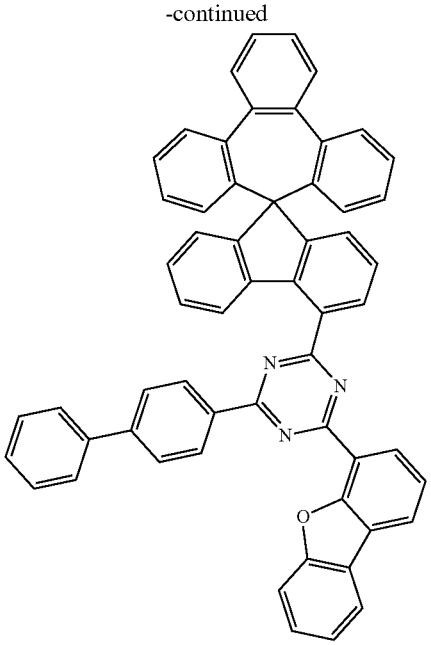
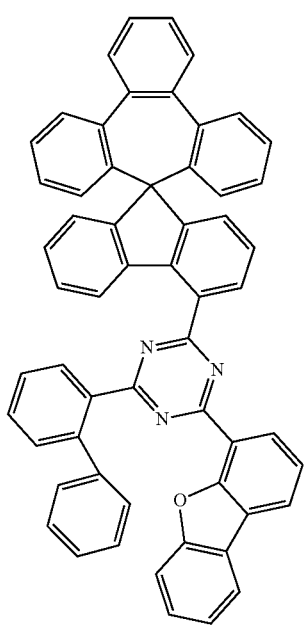
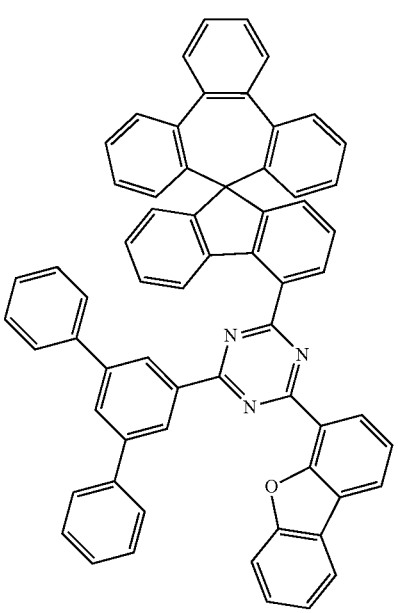

231
-continued
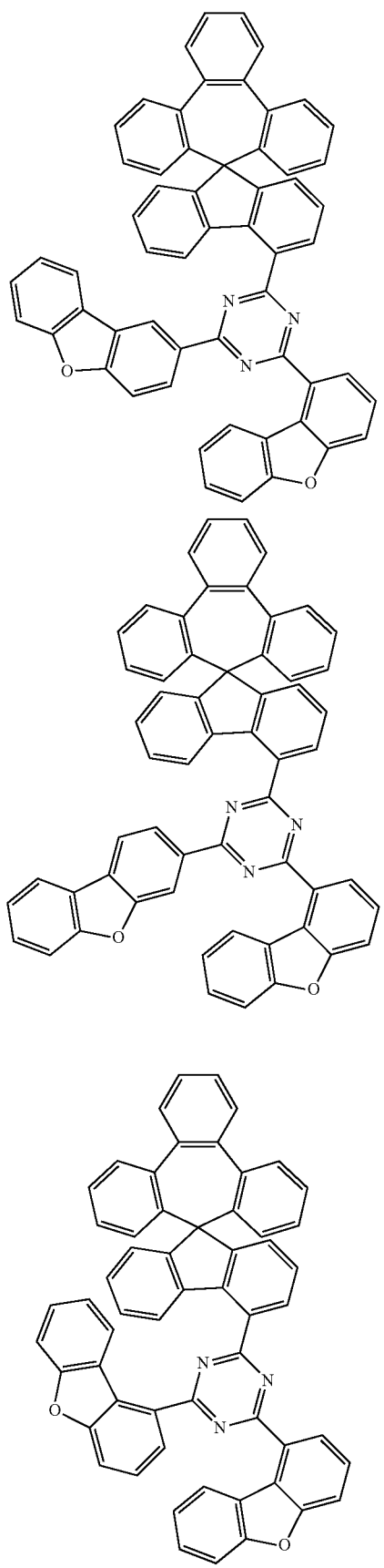
232
-continued

233
-continued
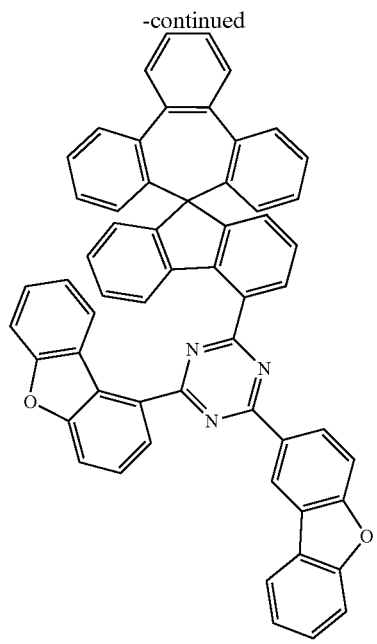
234
-continued
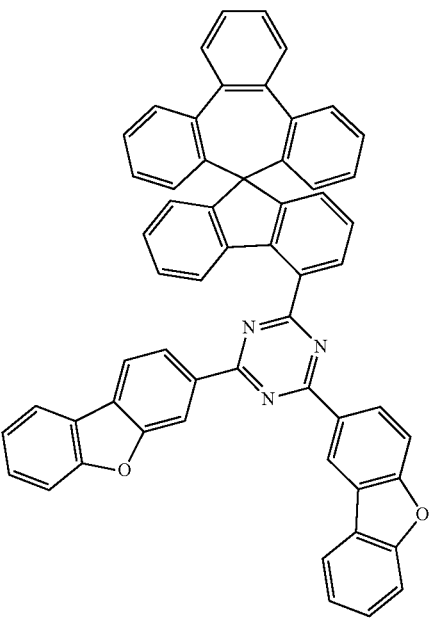
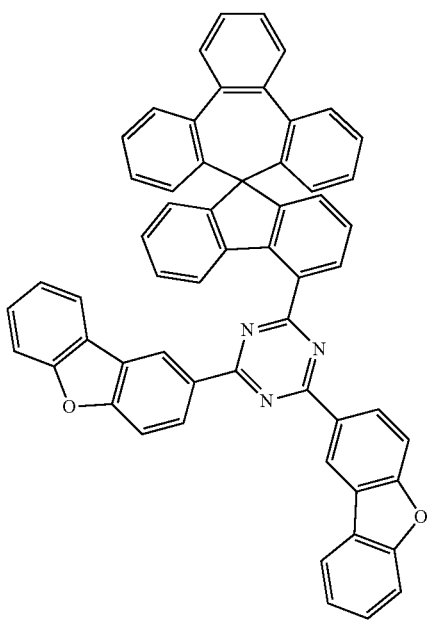
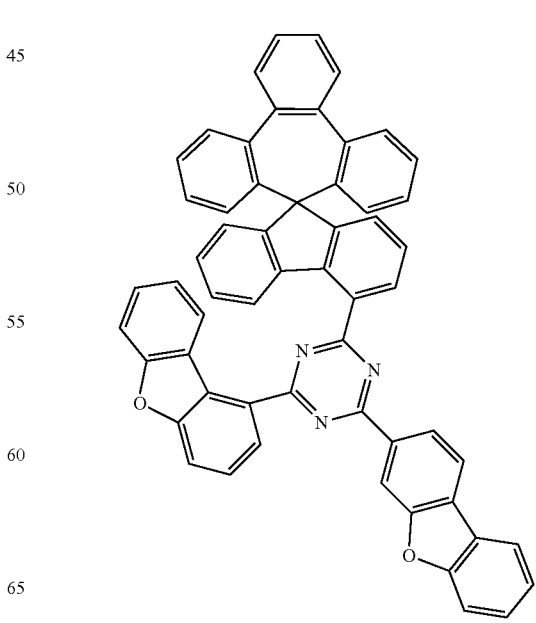

235
-continued
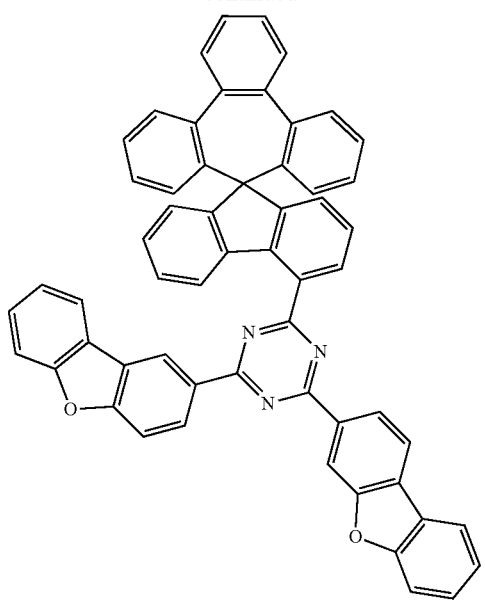
236
-continued
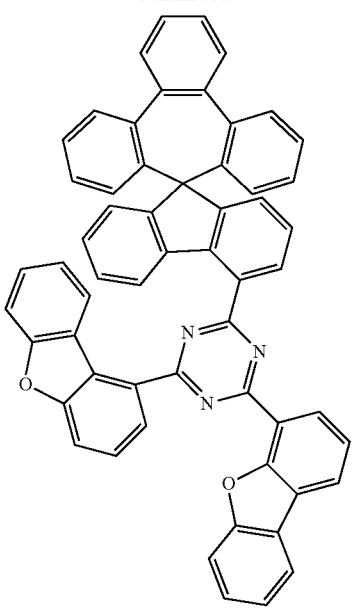
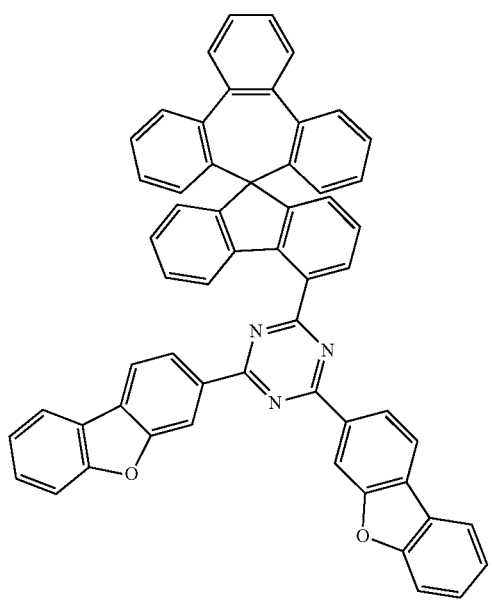
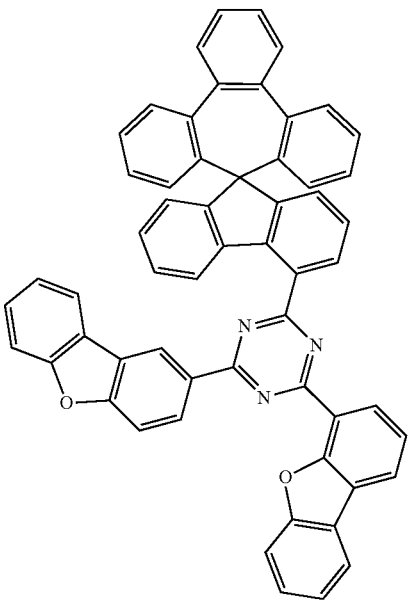

237
-continued
238
-continued
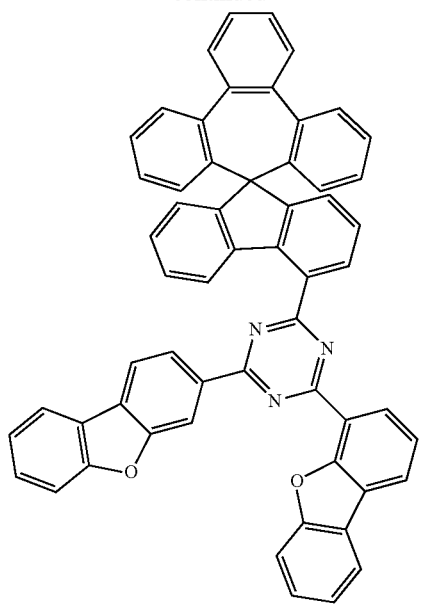
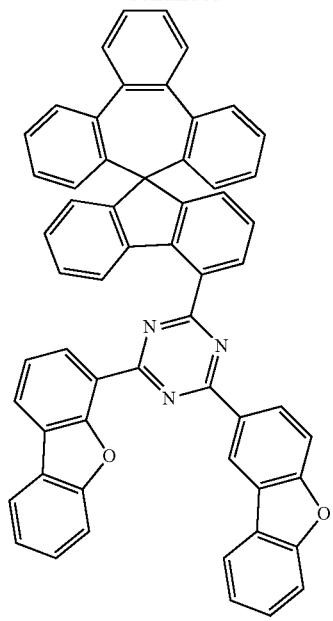
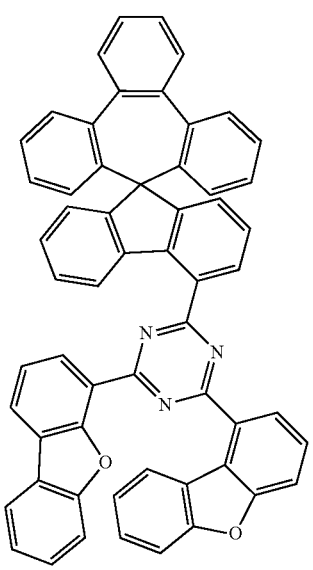

239
-continued
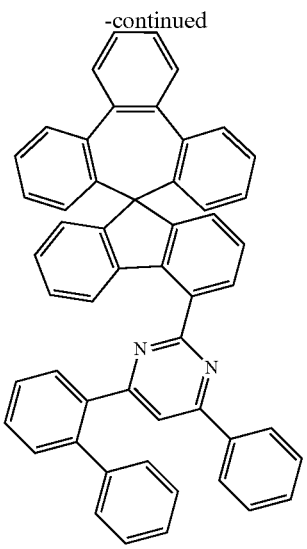
240
-continued
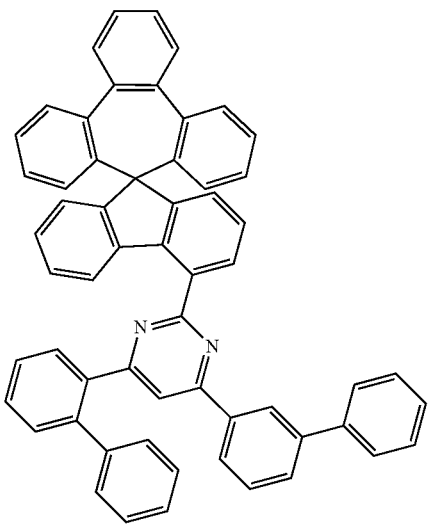
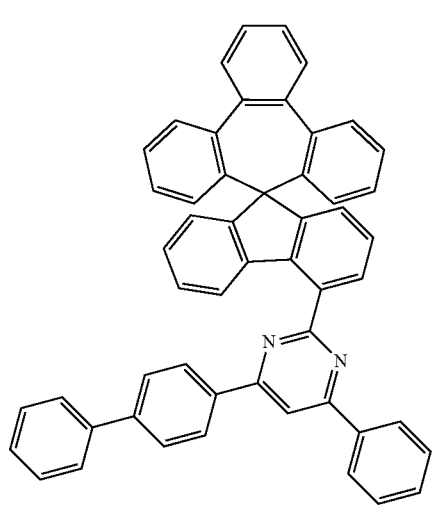
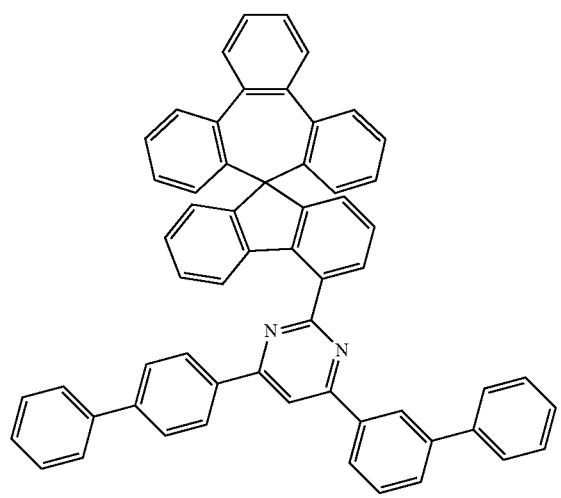
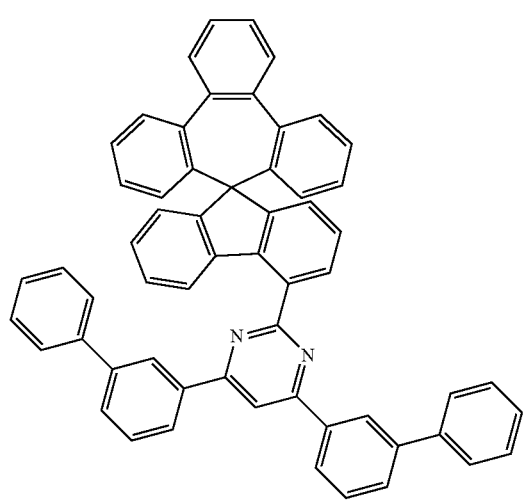
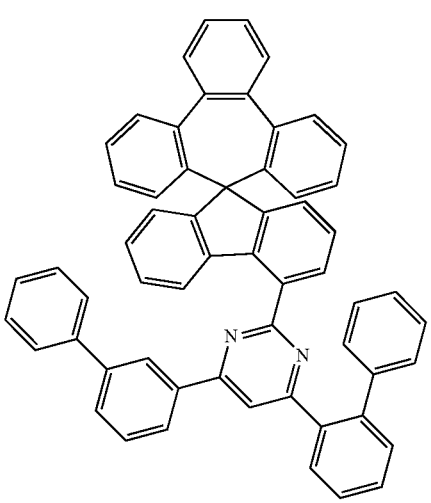

241
-continued
242
-continued
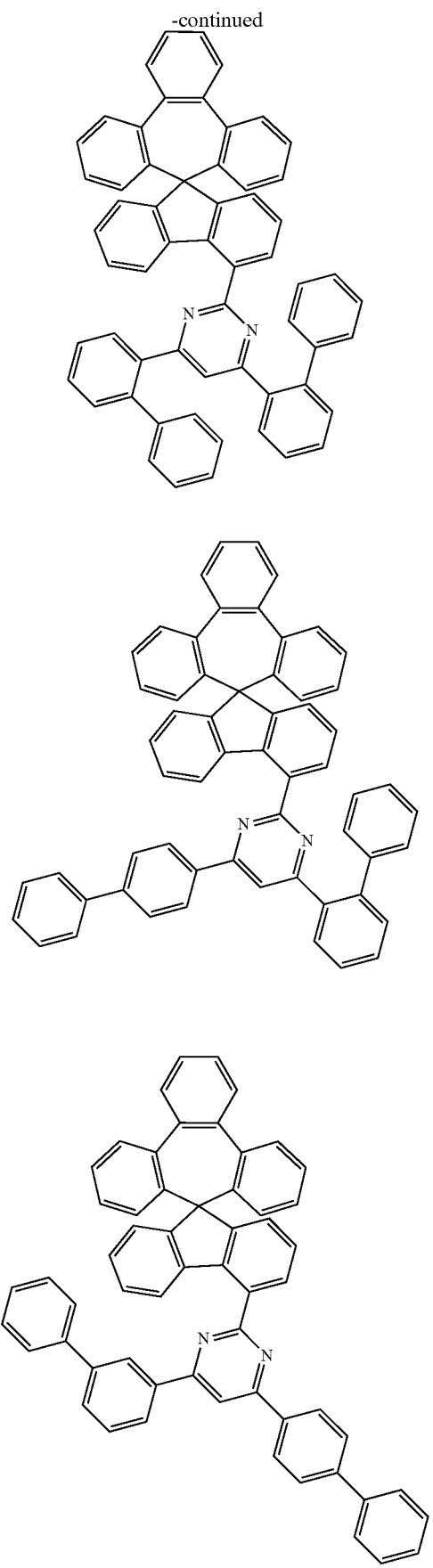
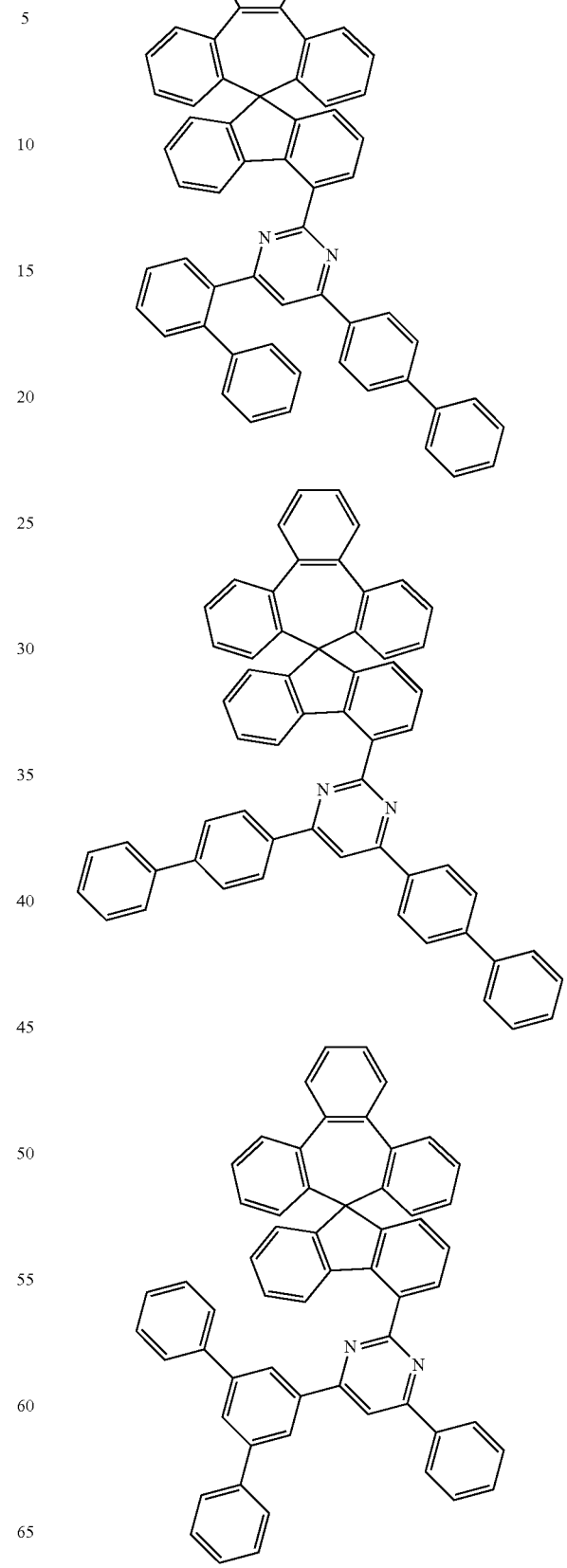

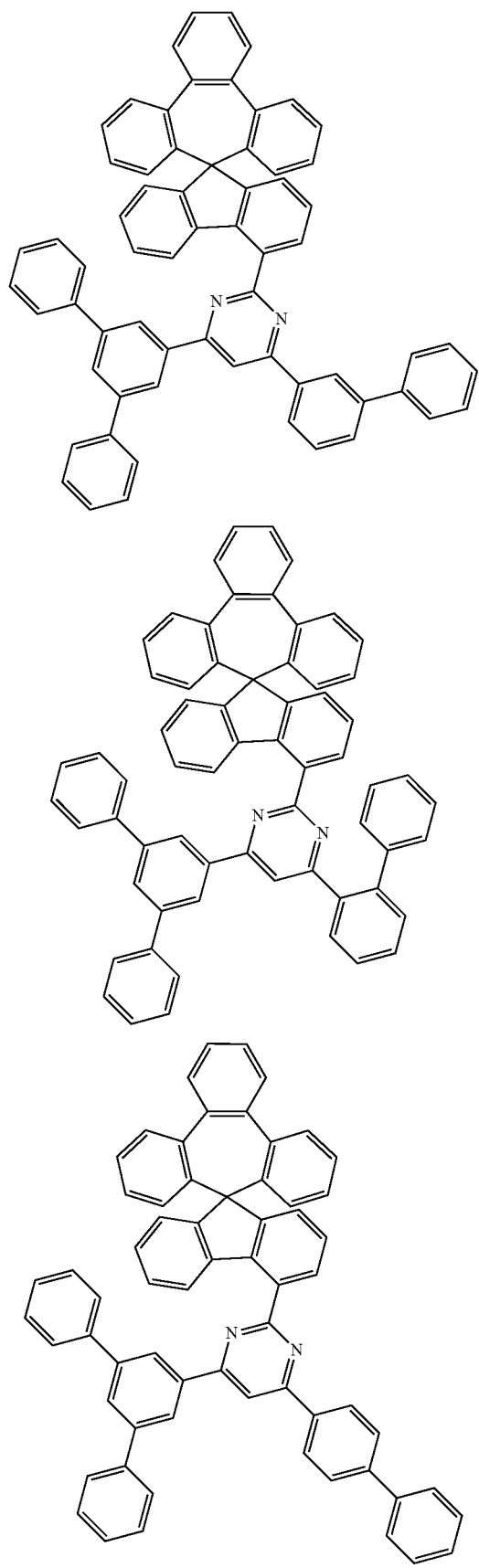
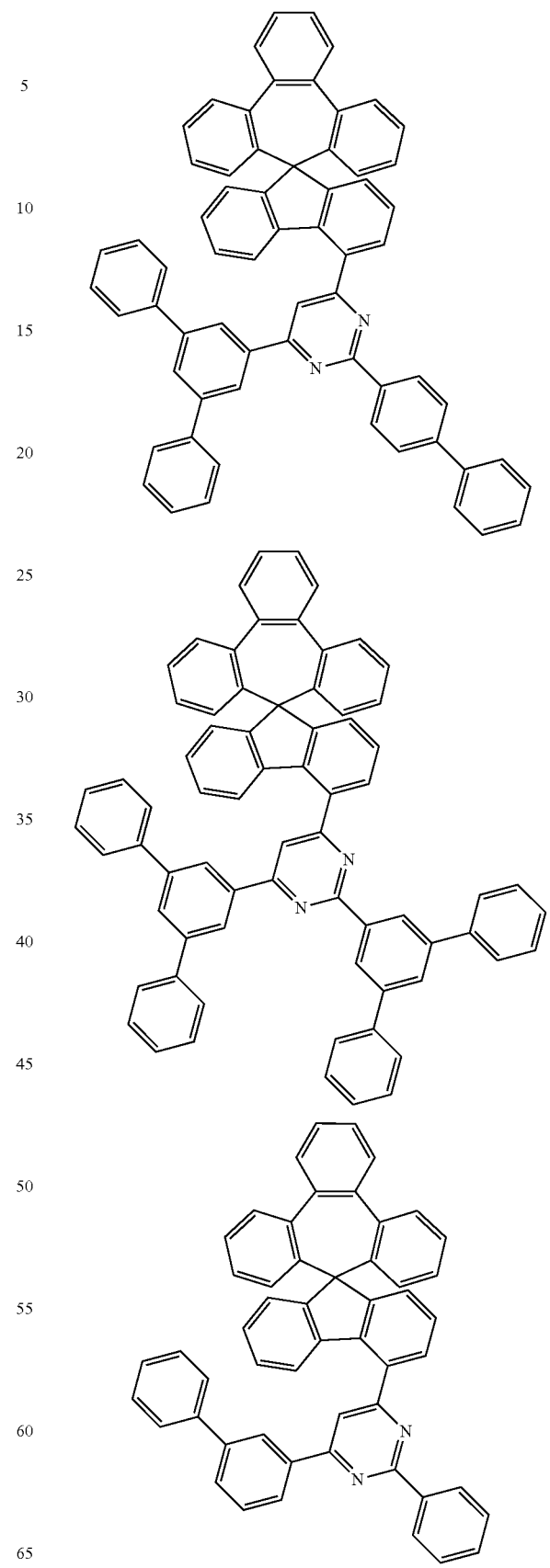

245
-continued
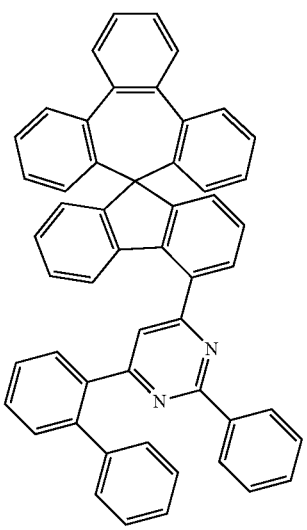
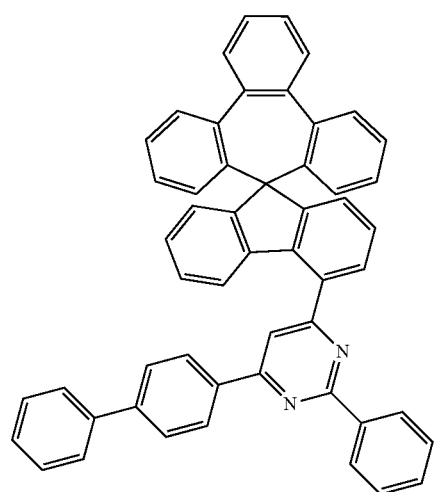
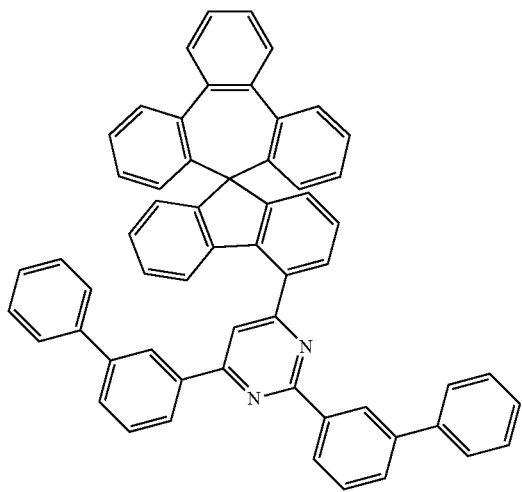
246
-continued
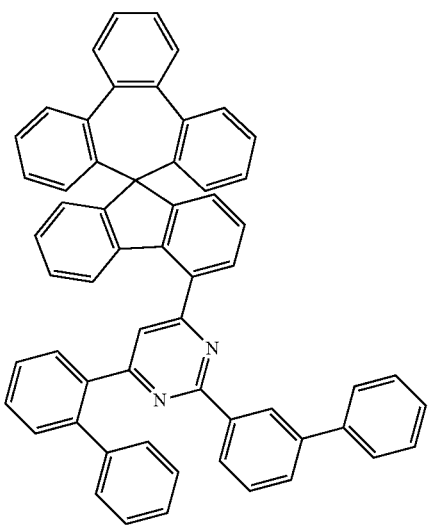
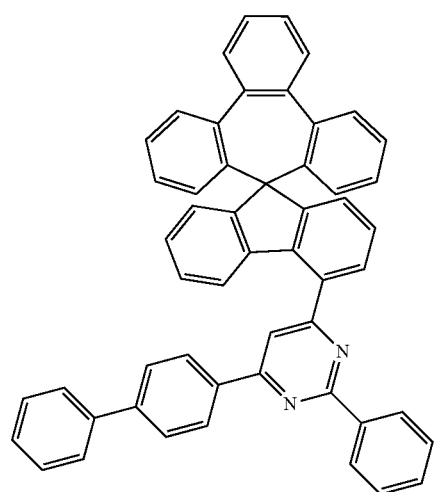
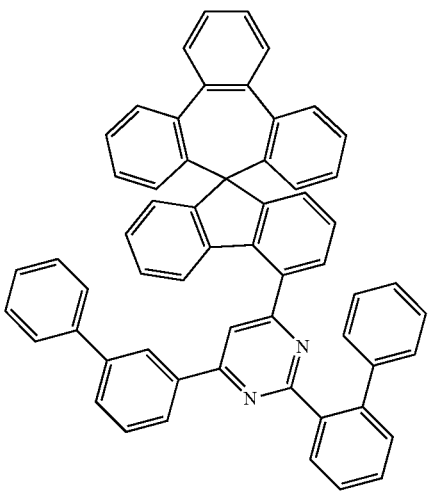

247
-continued
248
-continued
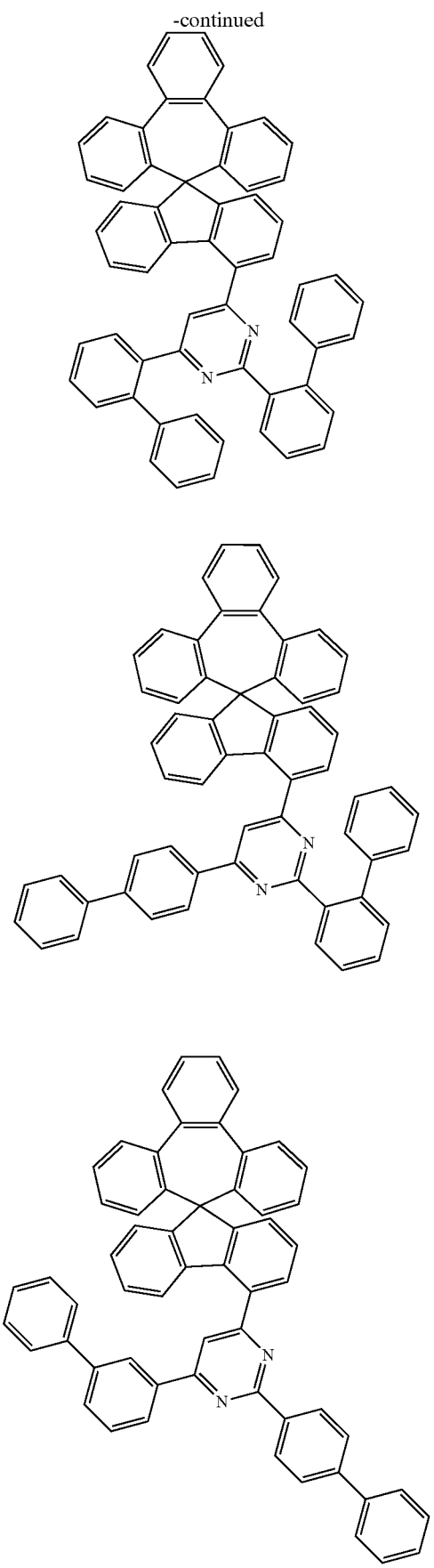
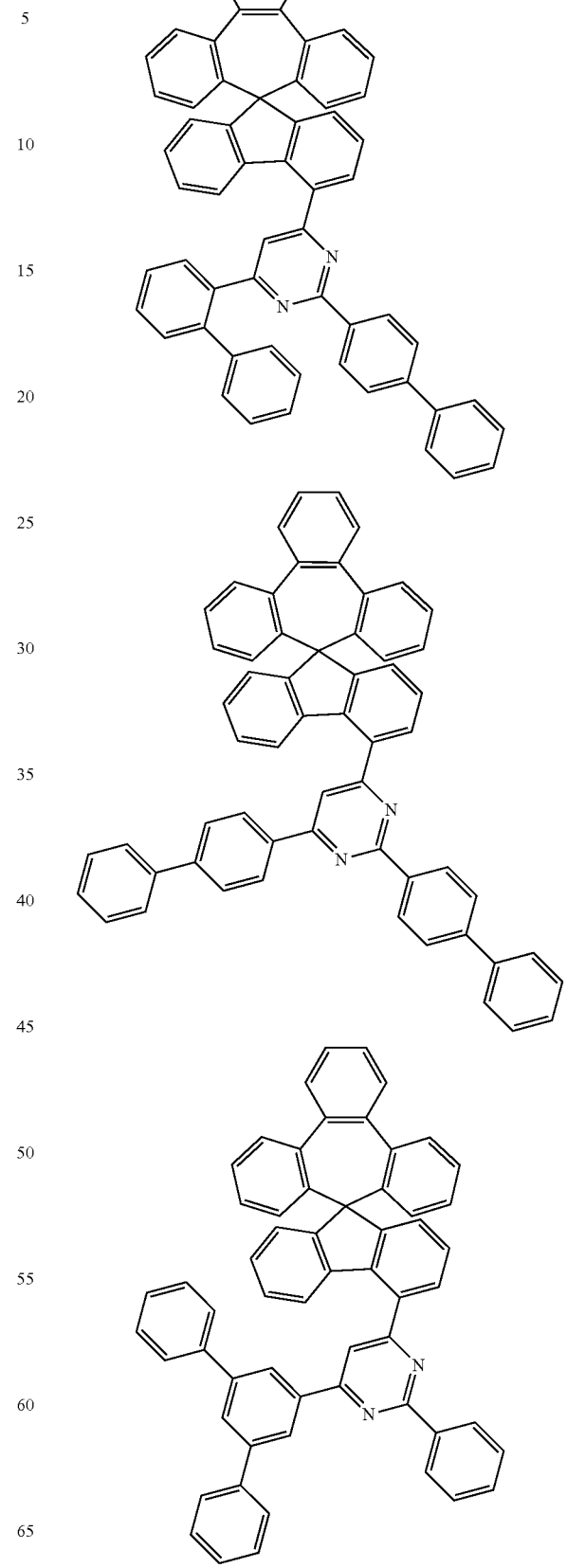

249
-continued
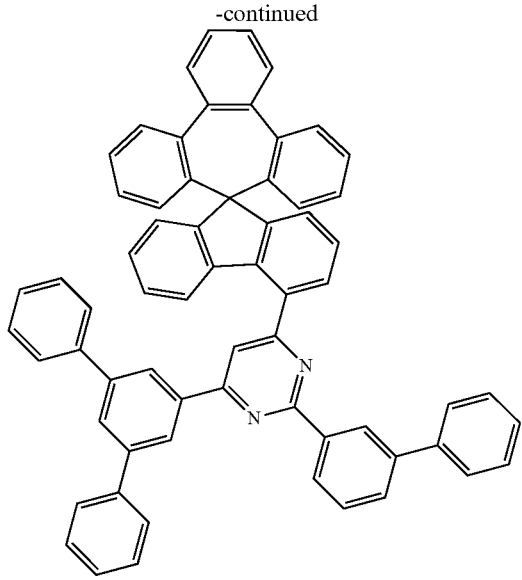
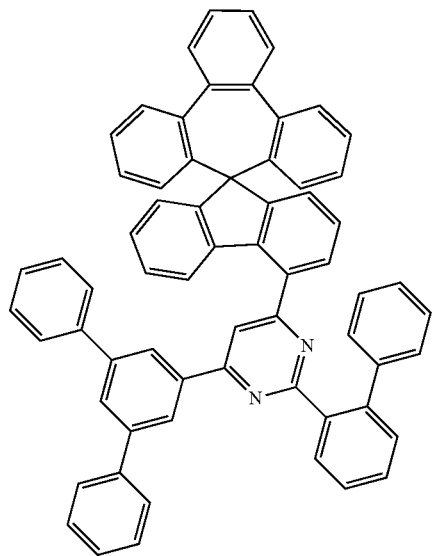
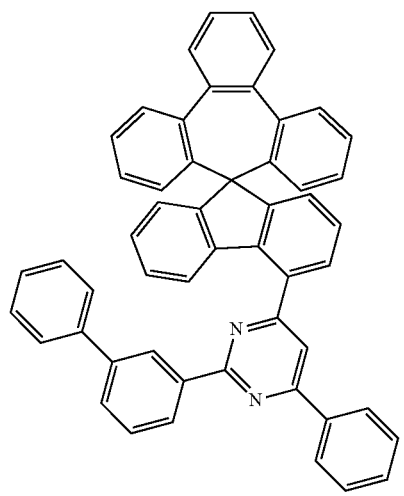
250
-continued
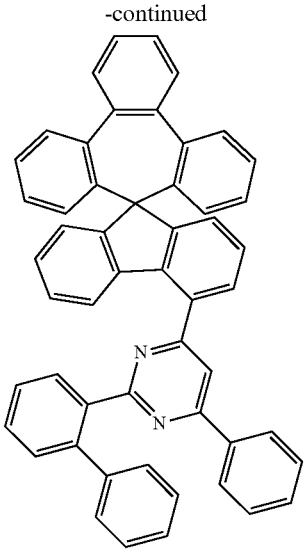
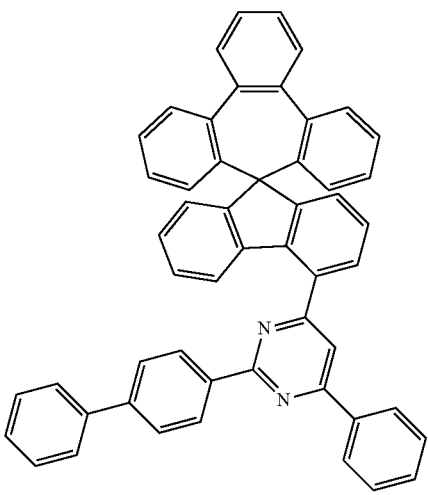
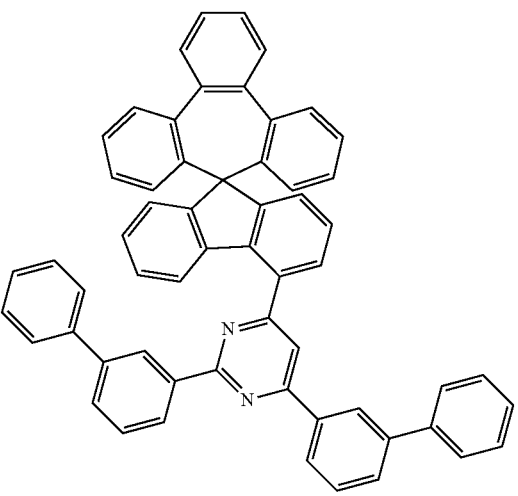

251
-continued
252
-continued
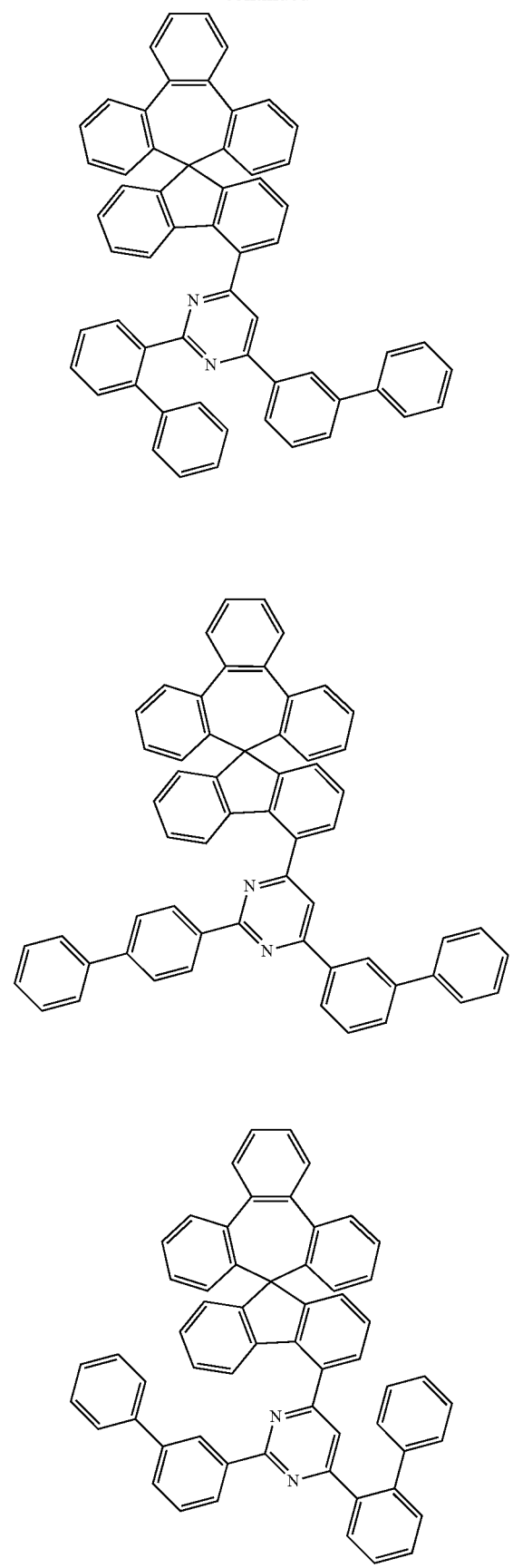
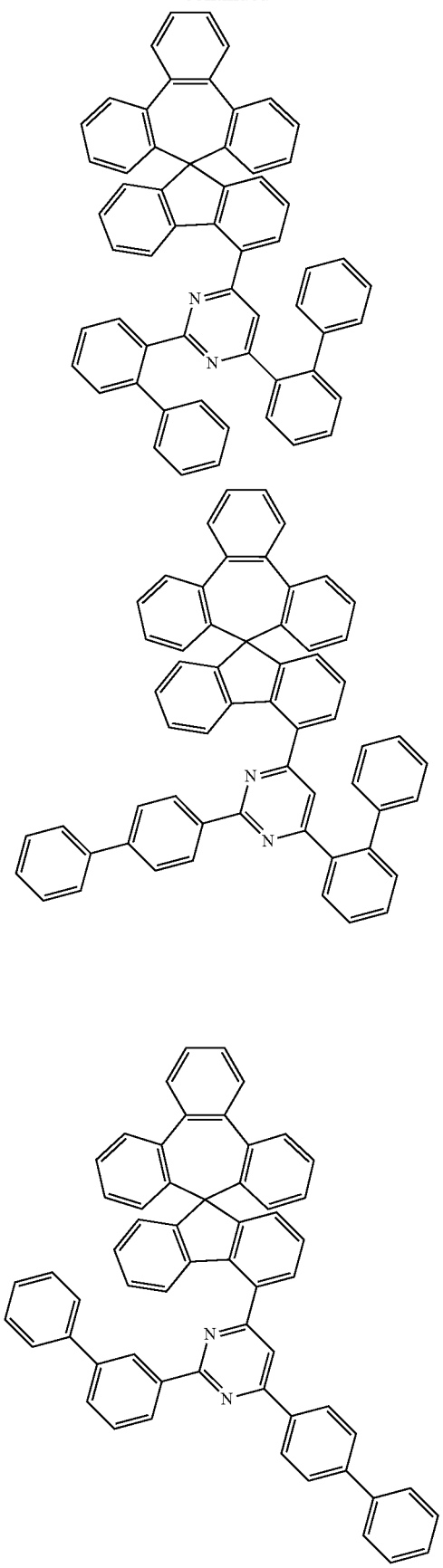

253
-continued
254
-continued
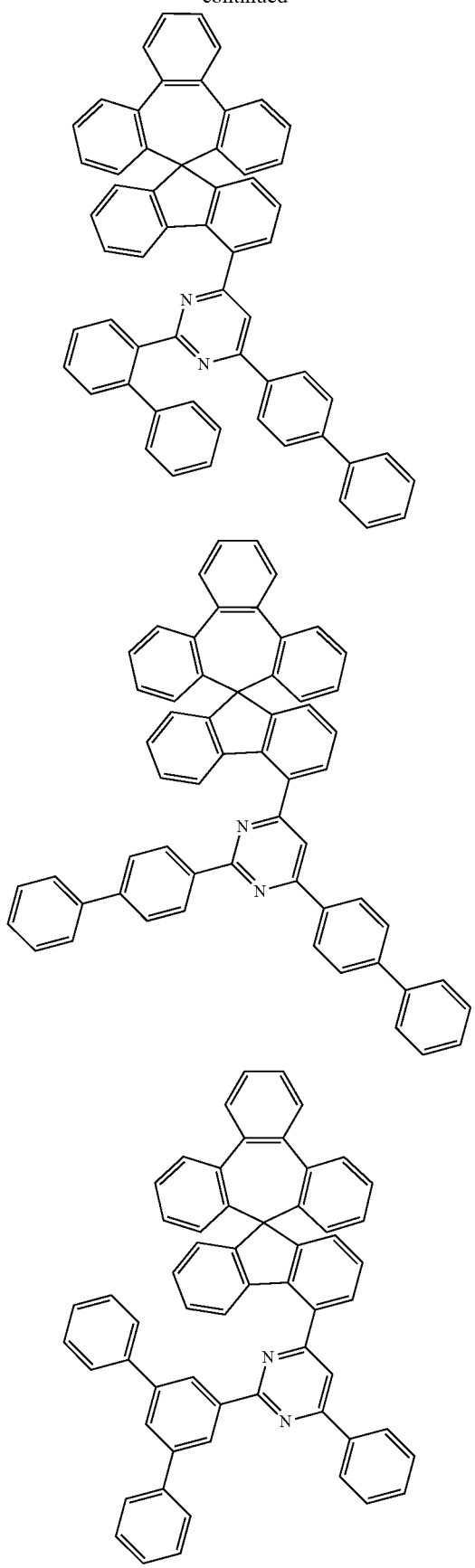
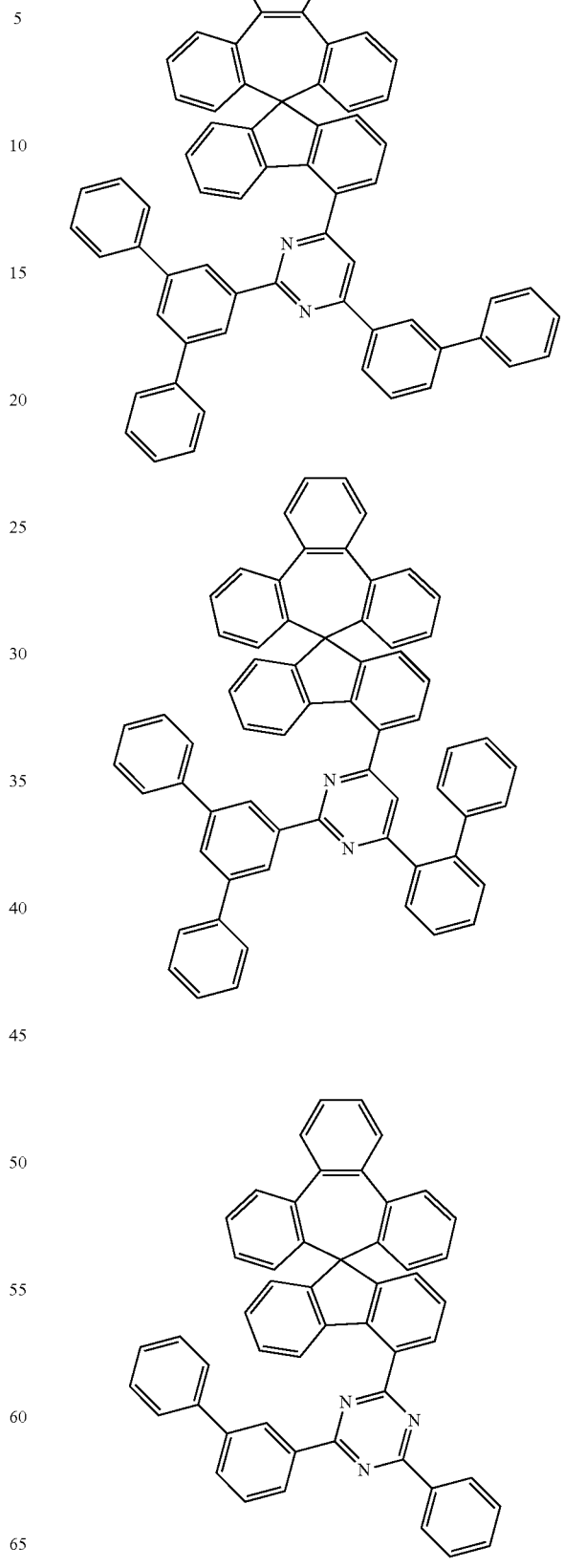

-continued
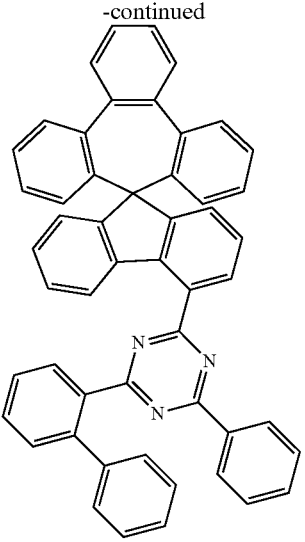
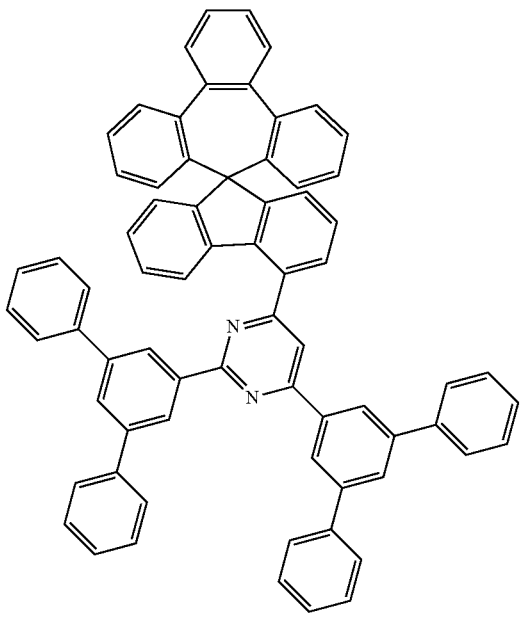
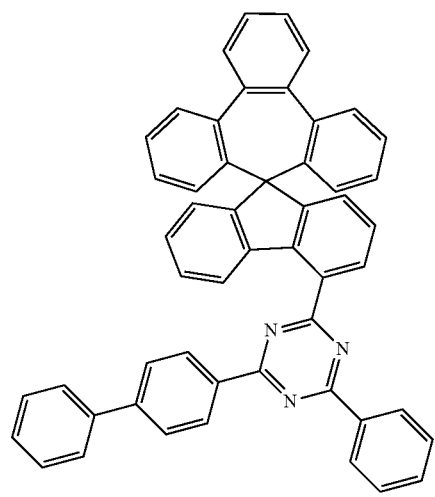
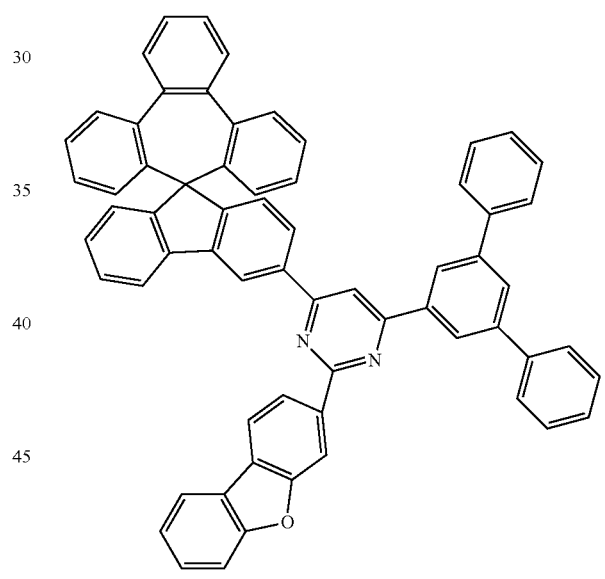
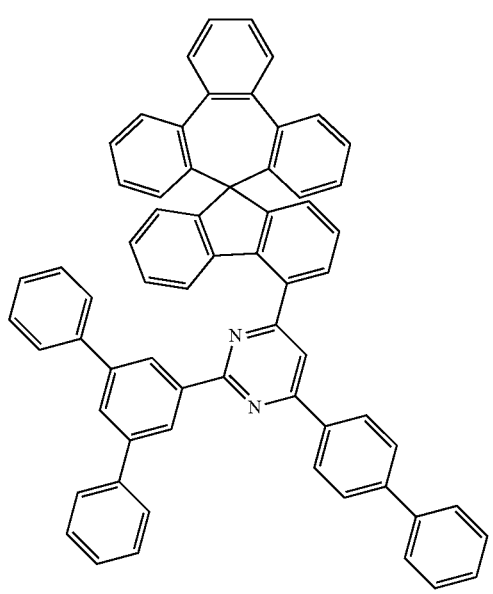
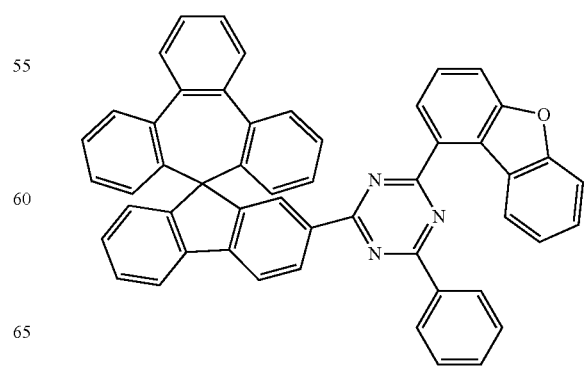

257
-continued
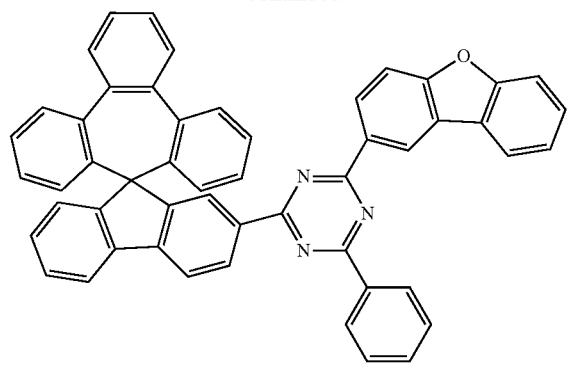
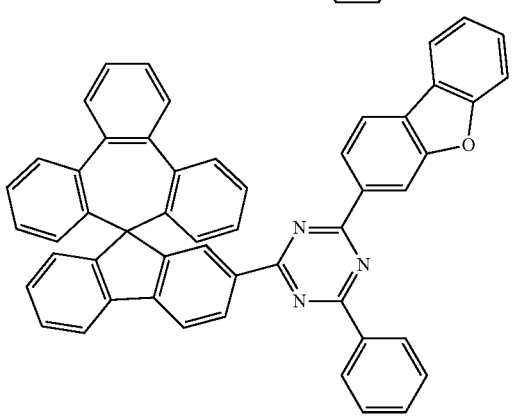
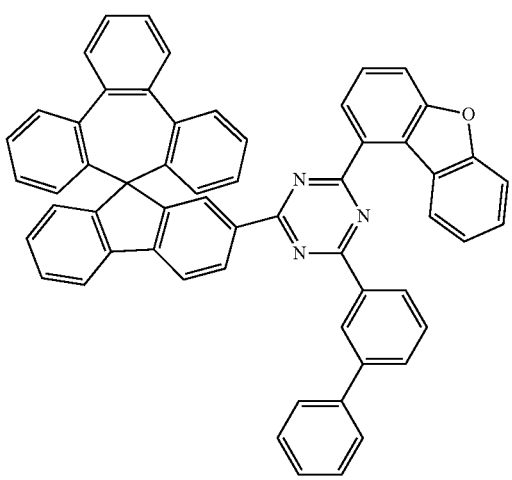
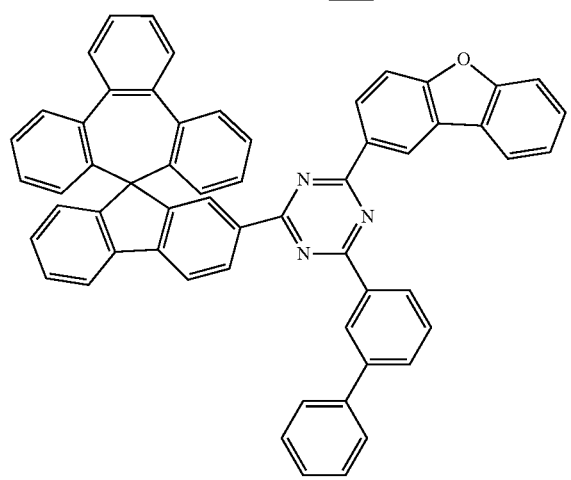
258
-continued
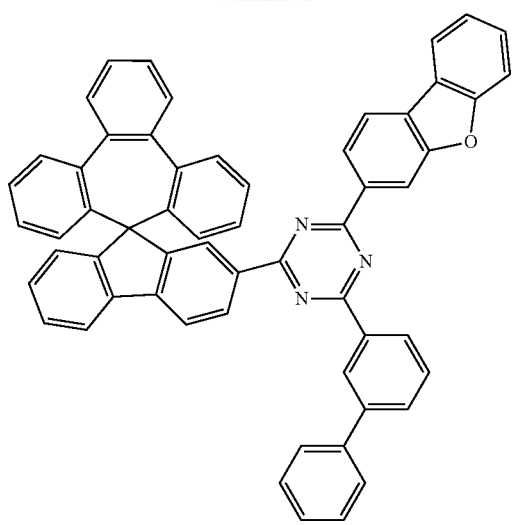
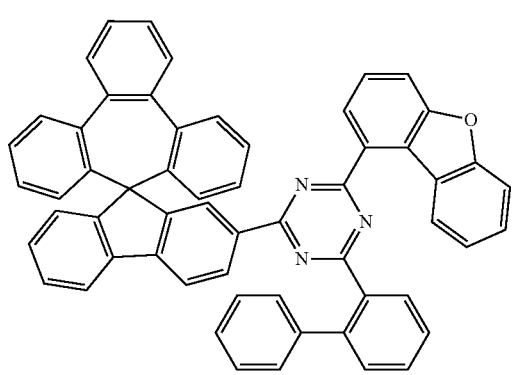
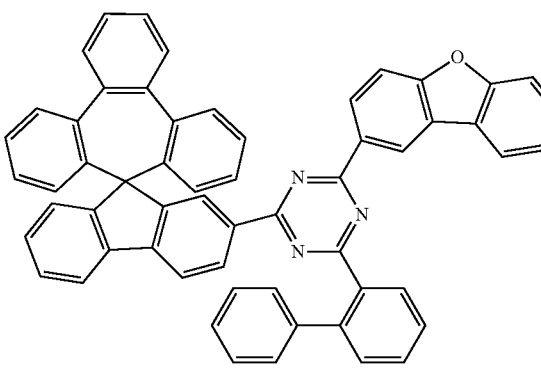
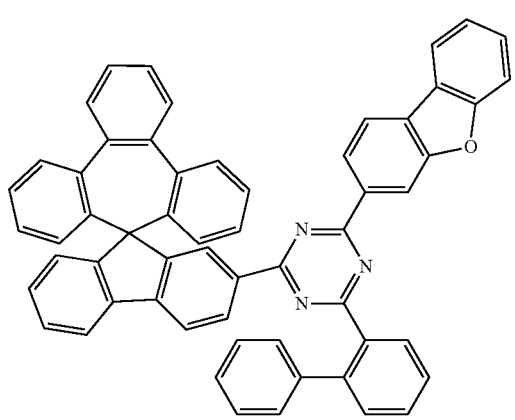

259
-continued
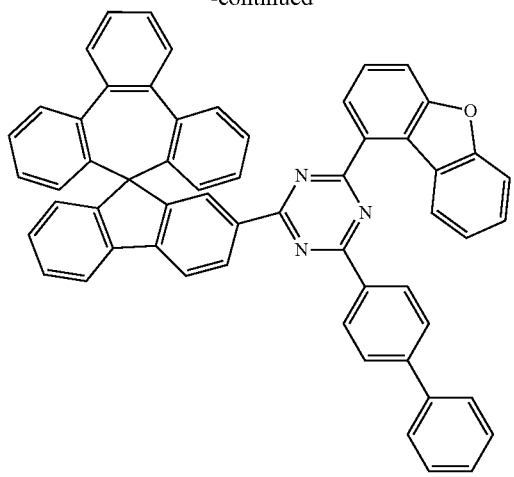
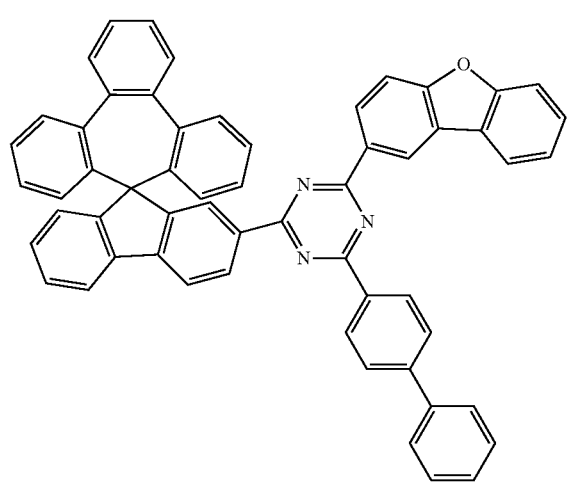
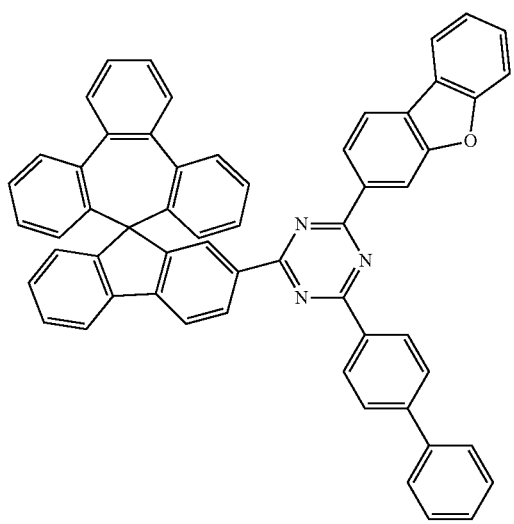
260
-continued
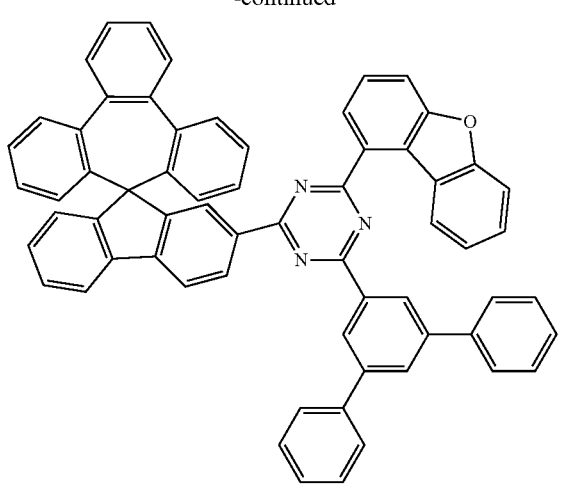
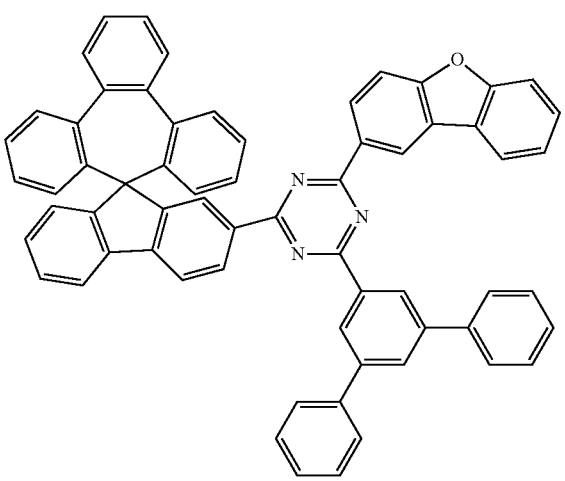
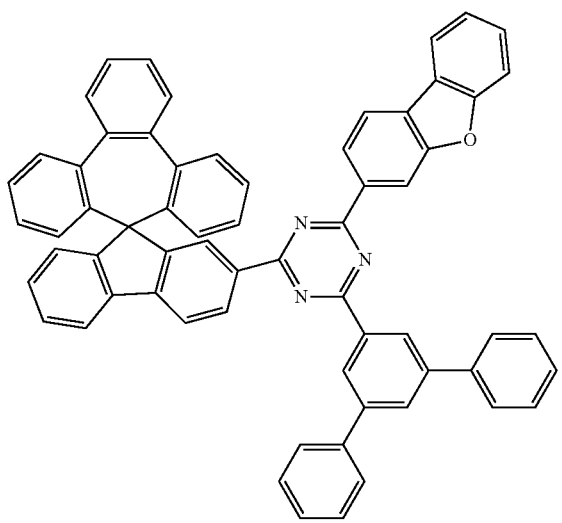

261
-continued
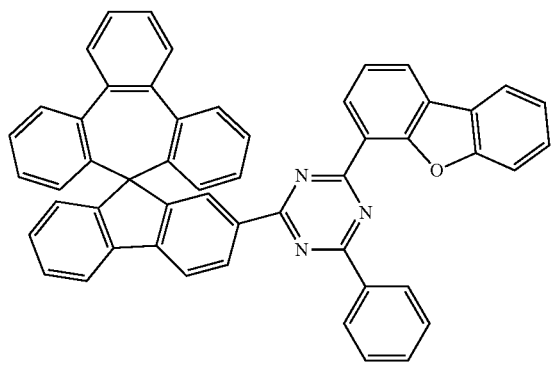
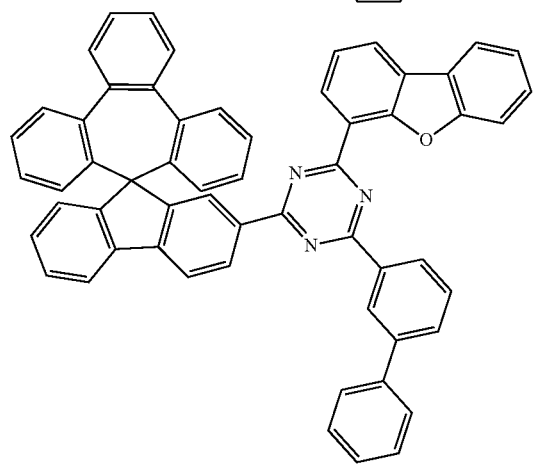
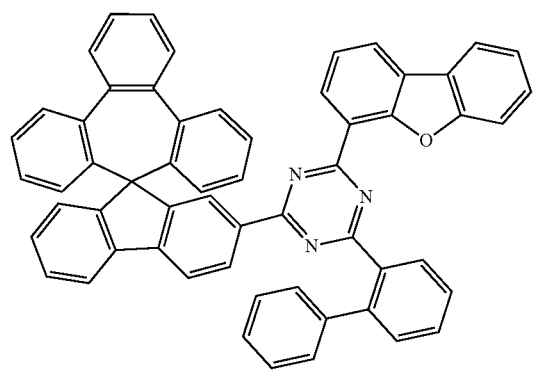
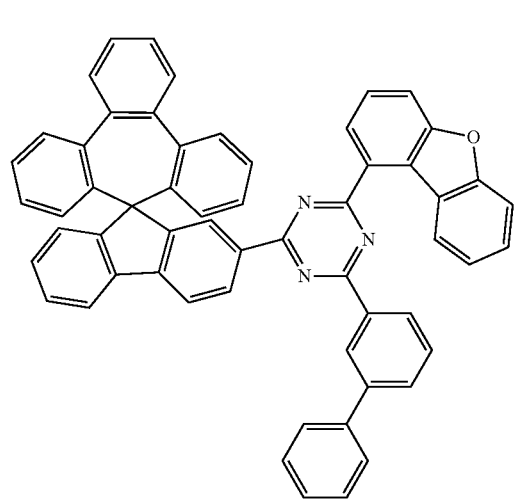
262
-continued
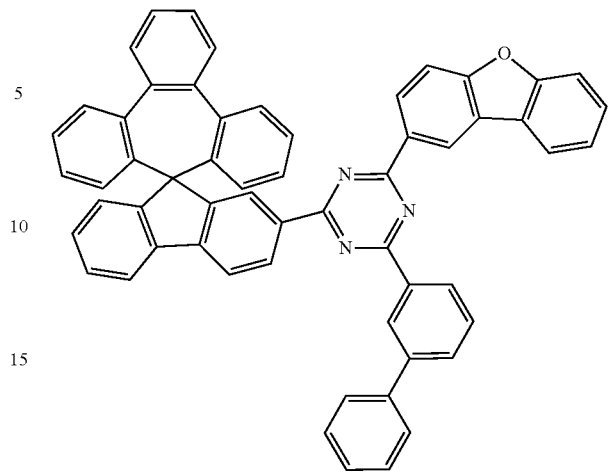
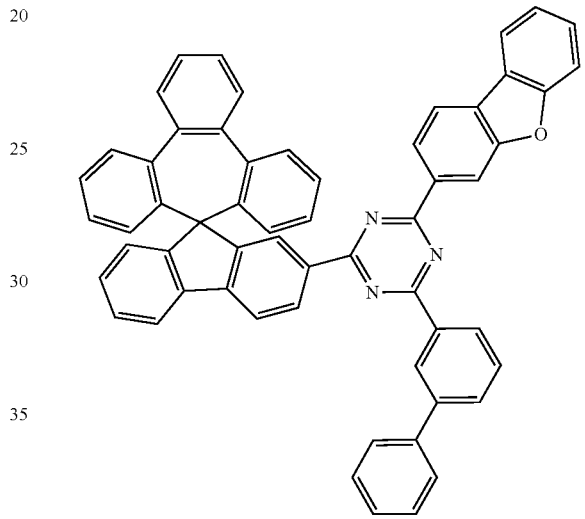
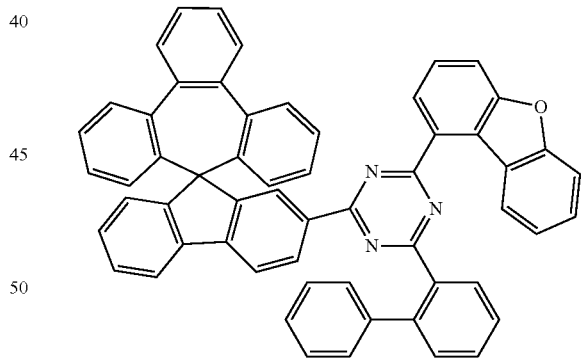
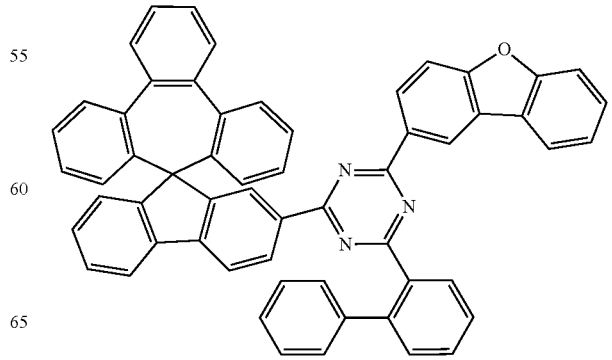

263
-continued
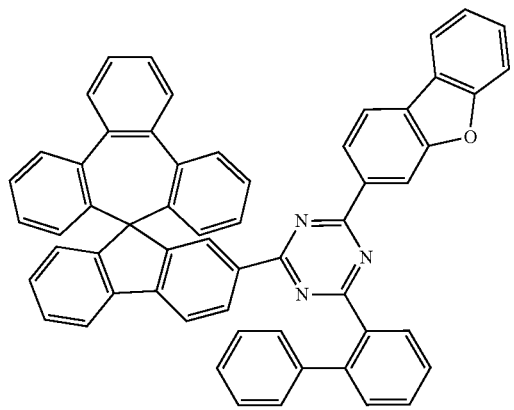
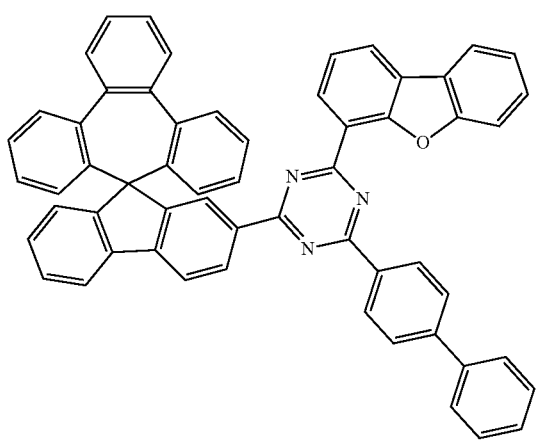
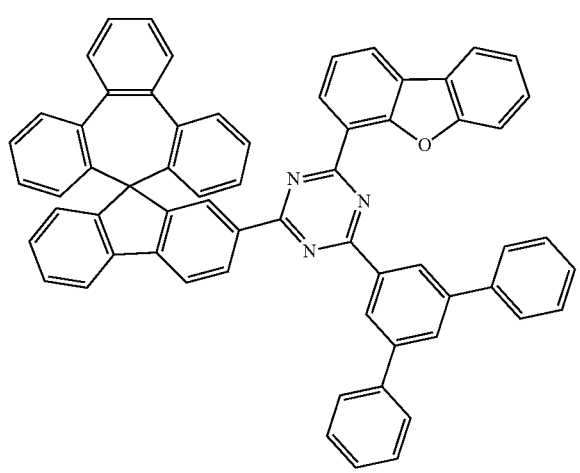
264
-continued
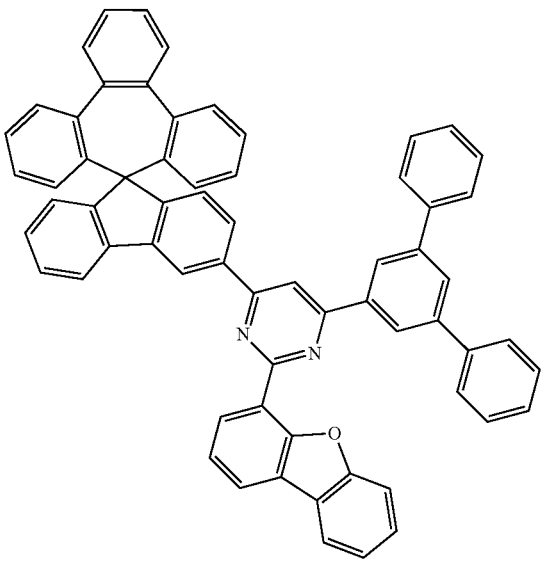
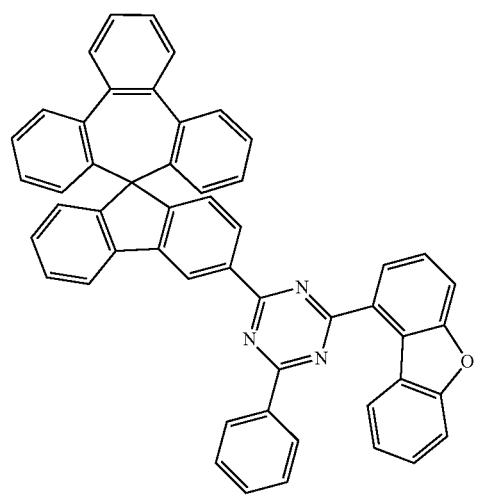
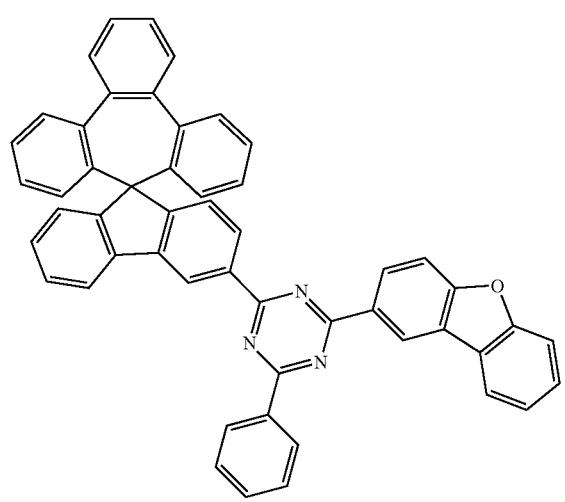

265
-continued
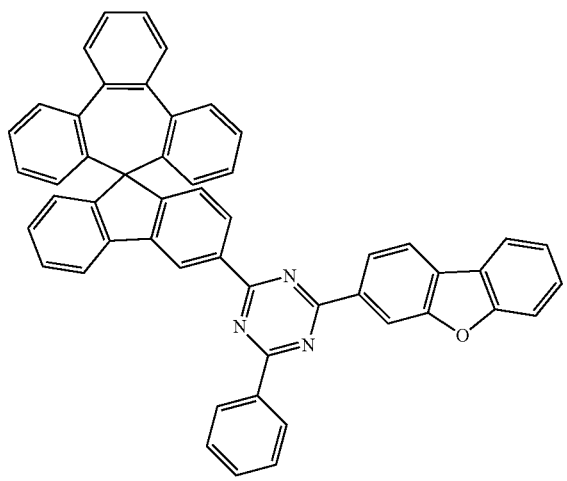
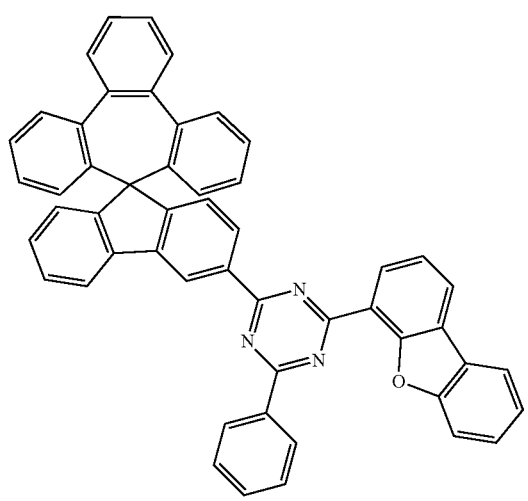
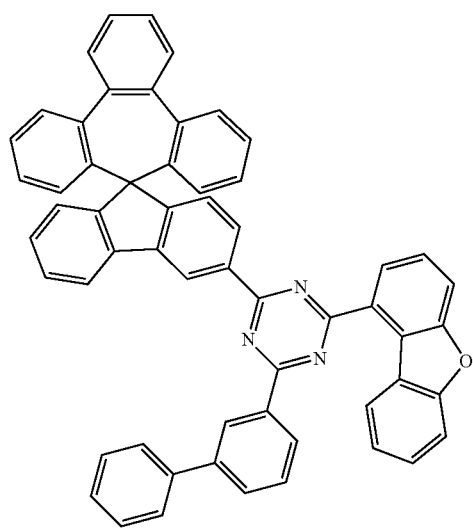
266
-continued
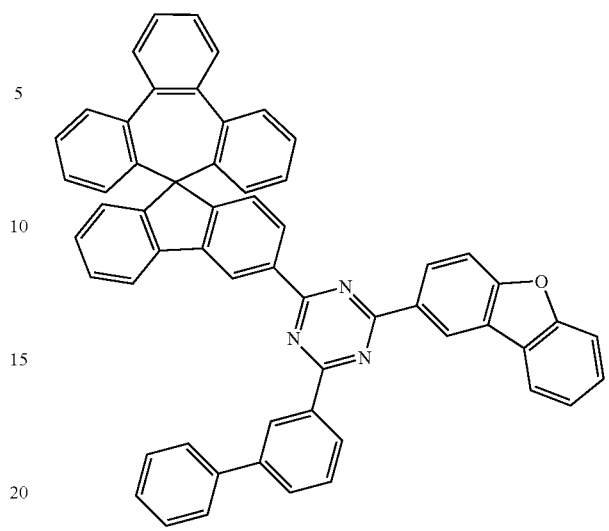
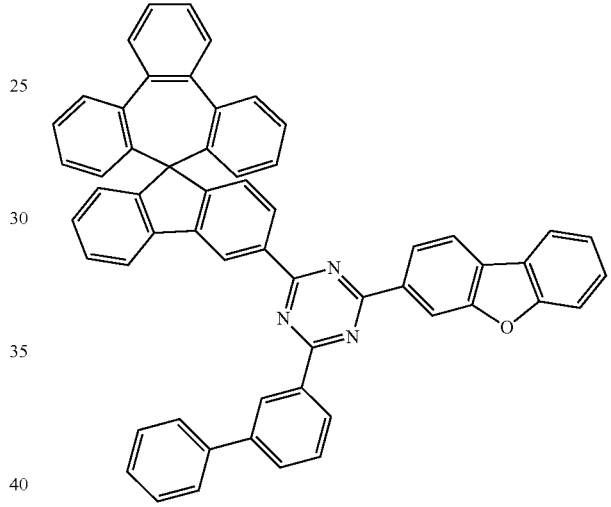
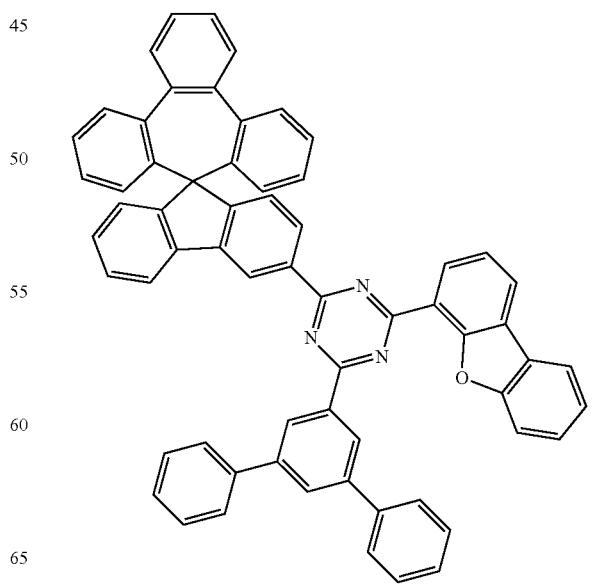

267
-continued
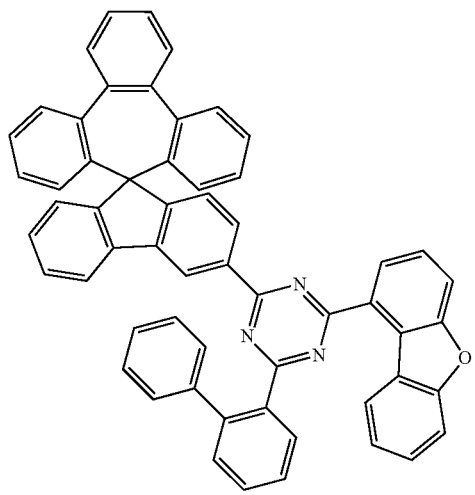
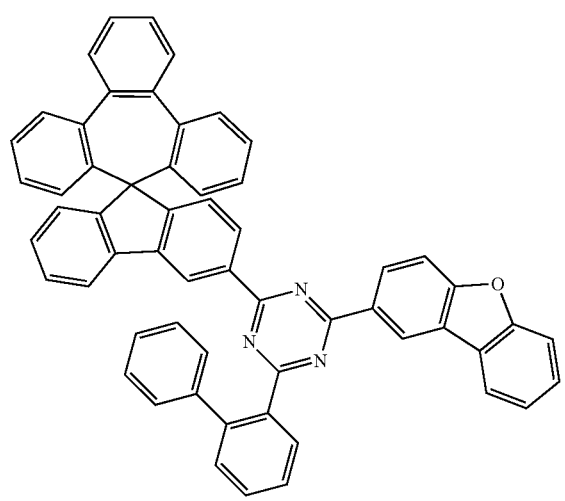
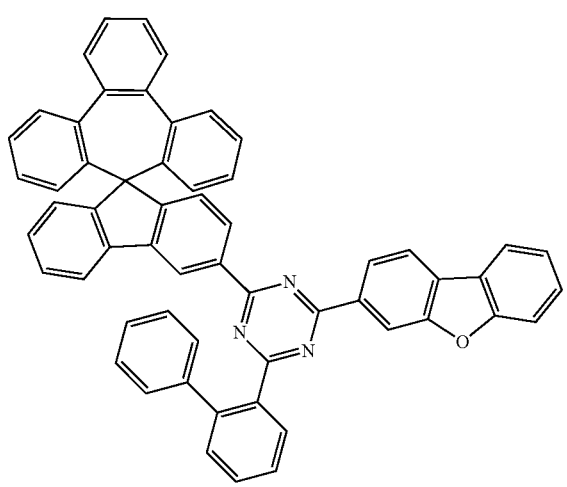
268
-continued
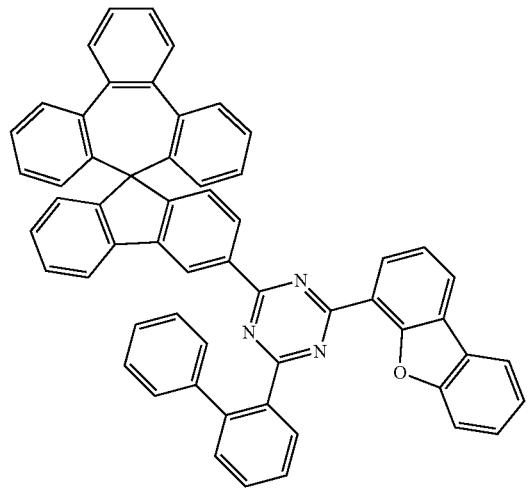
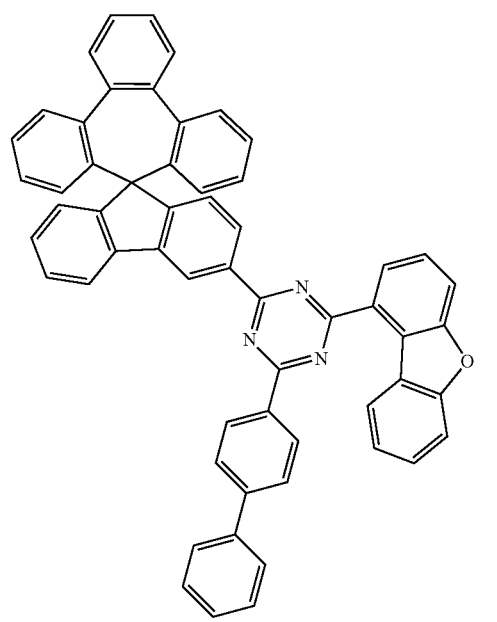
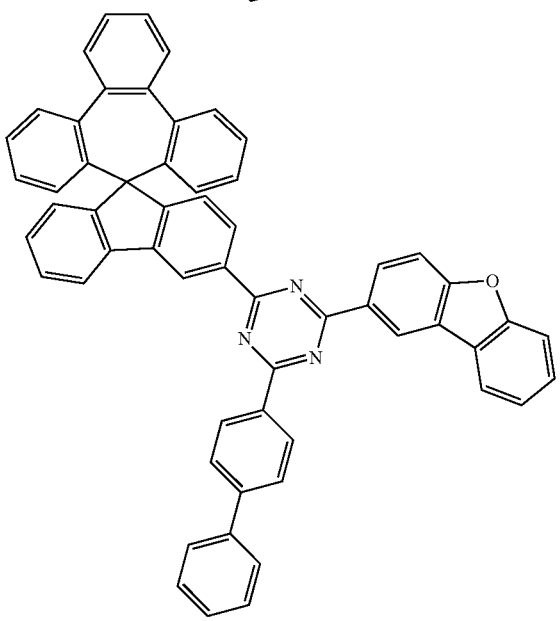

269
-continued
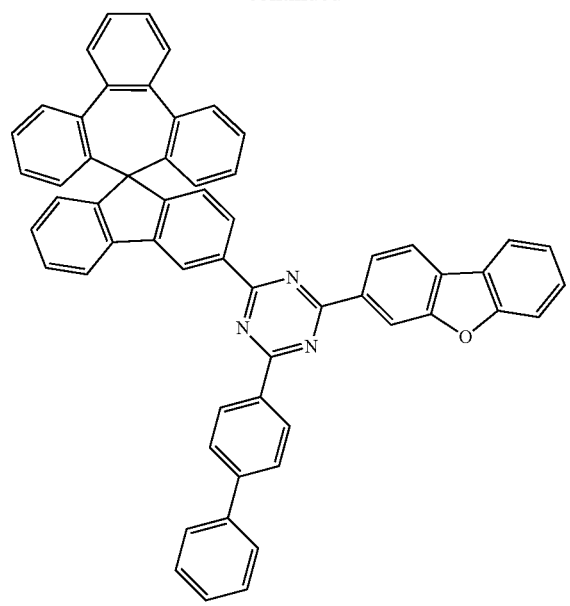
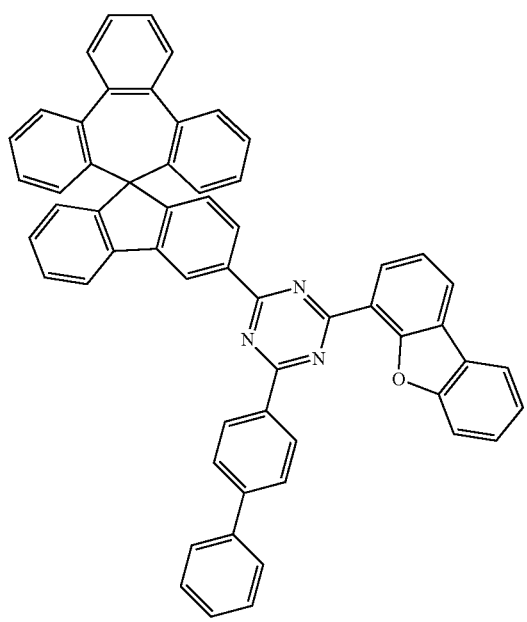
270
-continued
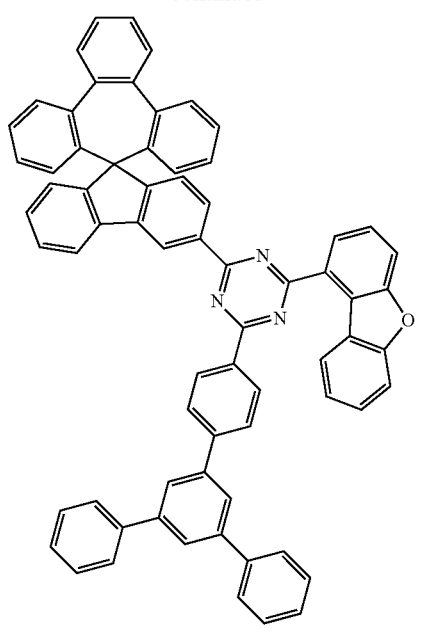
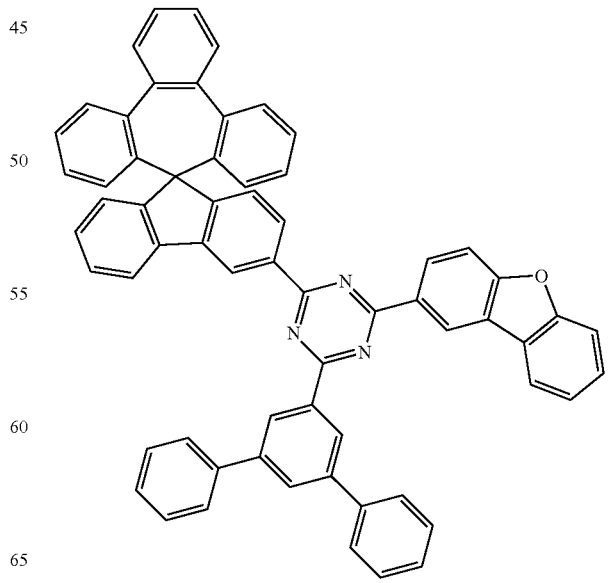

271
-continued
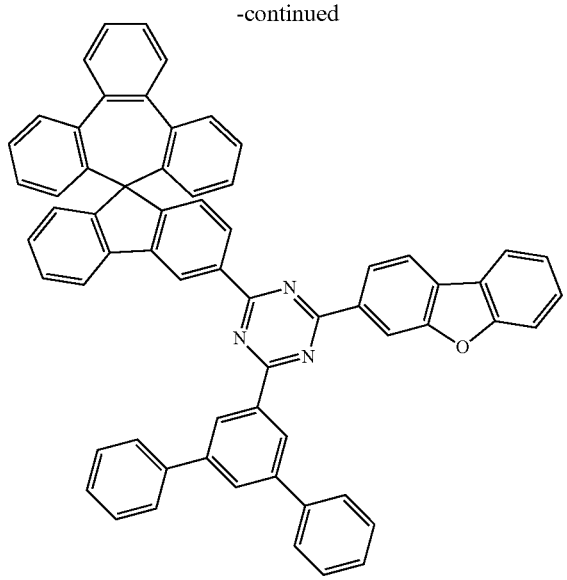
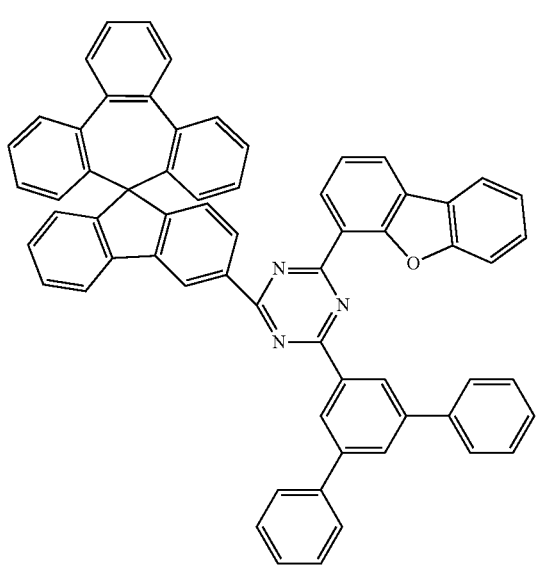
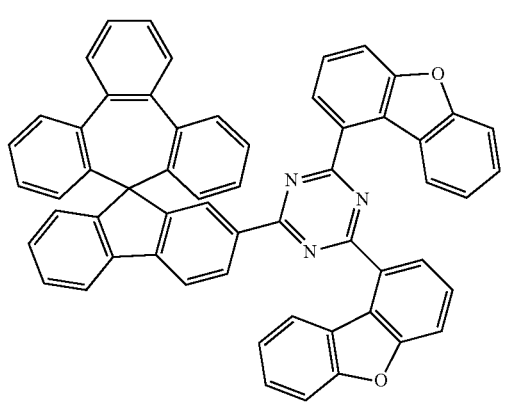
272
-continued
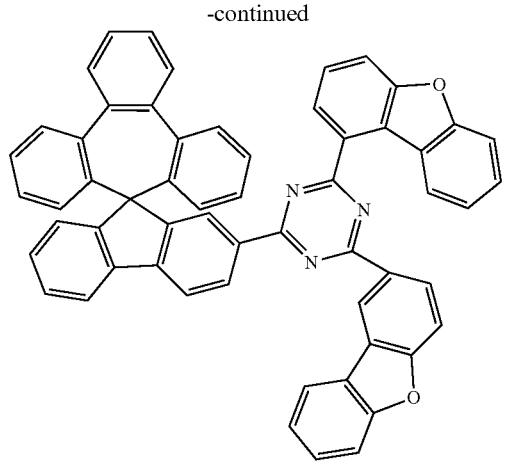
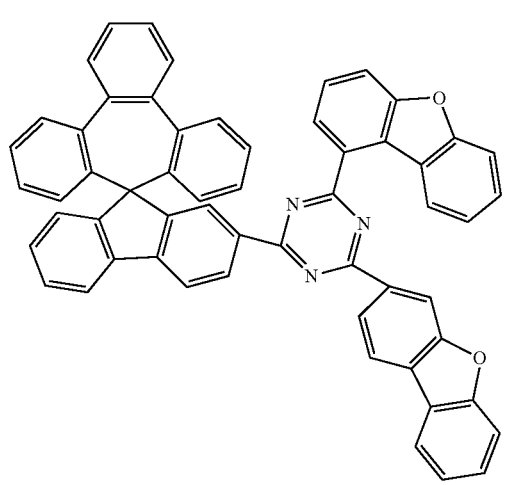
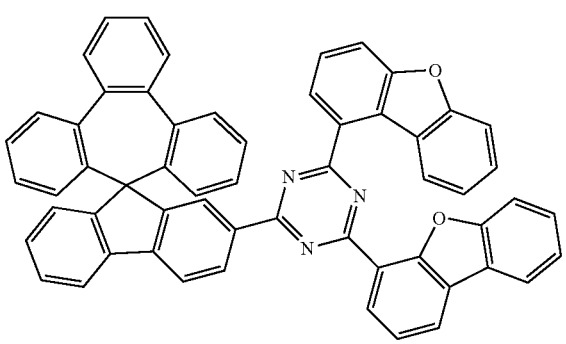

273
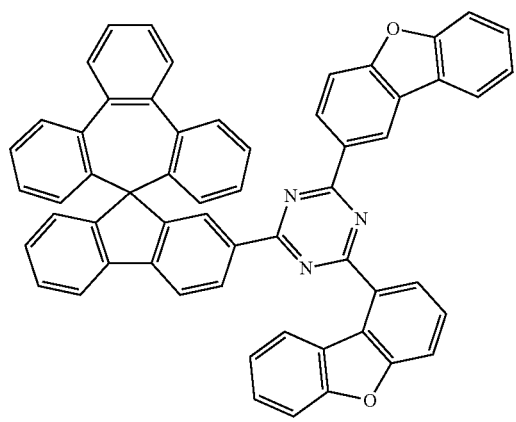
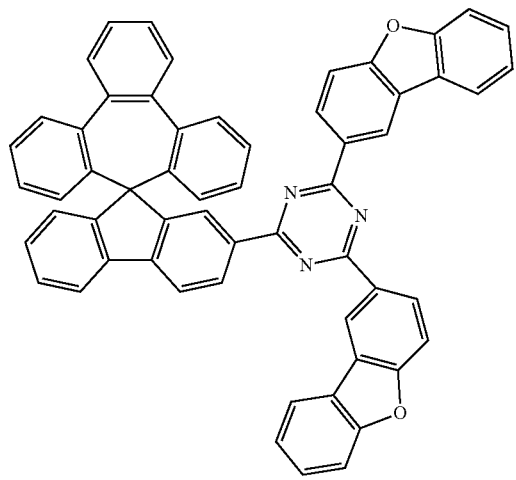
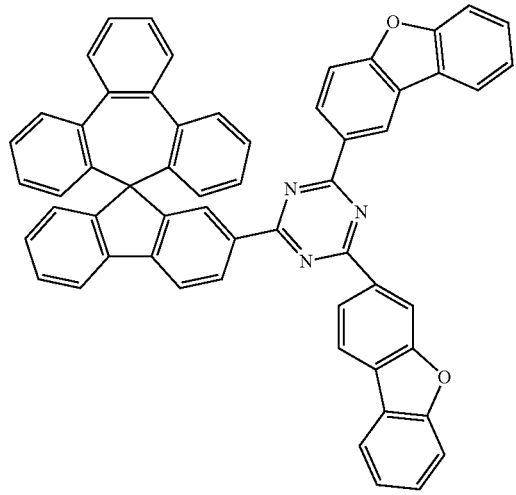
274
-continued
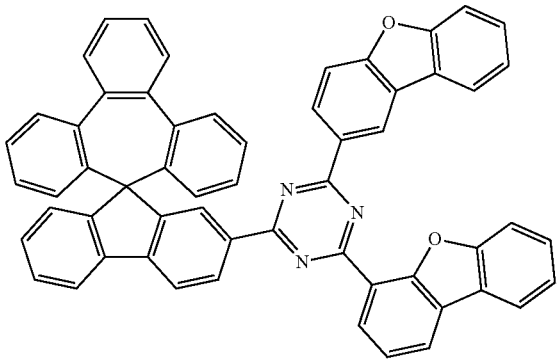 [SMILES: c1ccc2c(c1)-c1ccccc1C1(c3ccccc3-2)c2ccccc2-c2ccc(-c3nc(-c4ccc5oc6ccccc6c5c4)nc(-c4cccc5c4oc4ccccc45)n3)cc21]
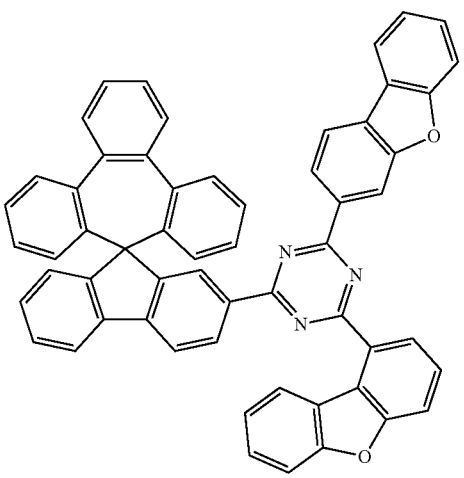
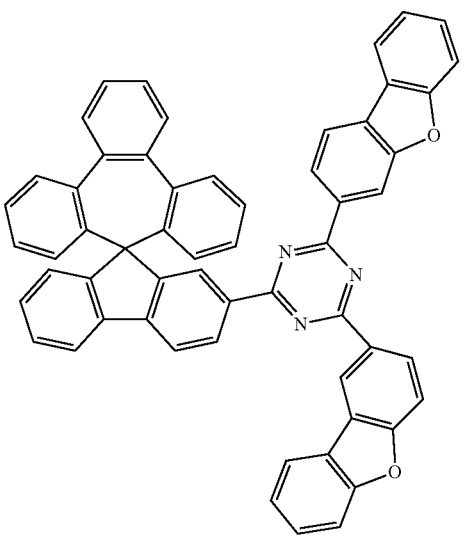

275
-continued
276
-continued
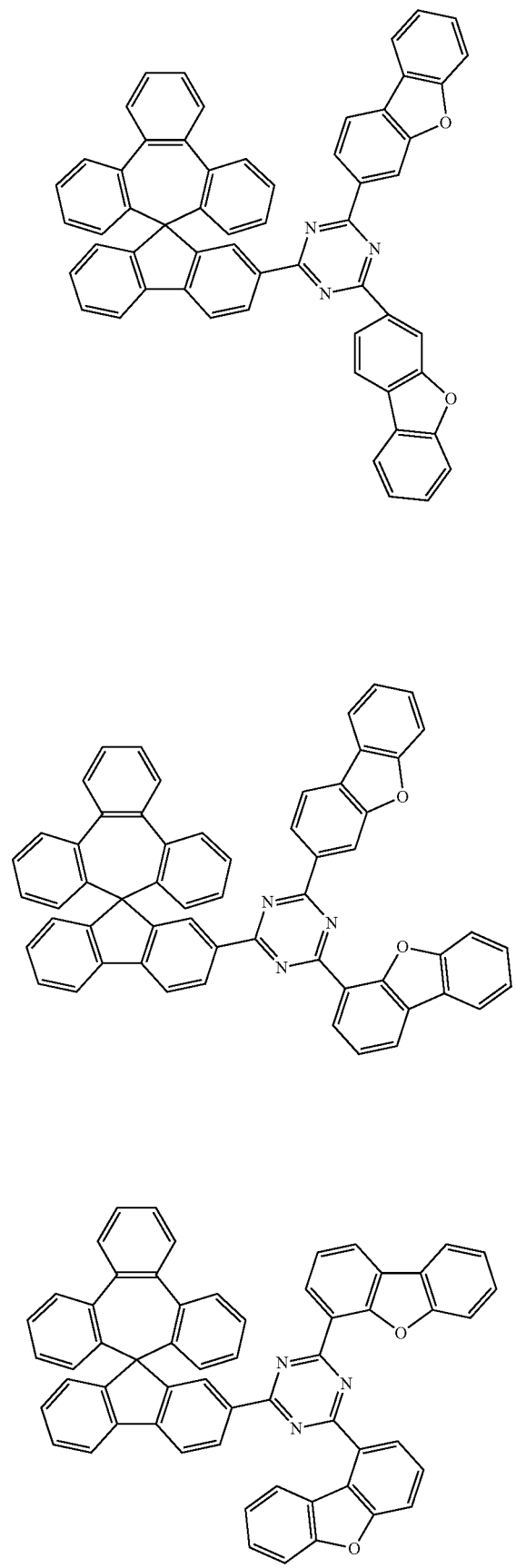
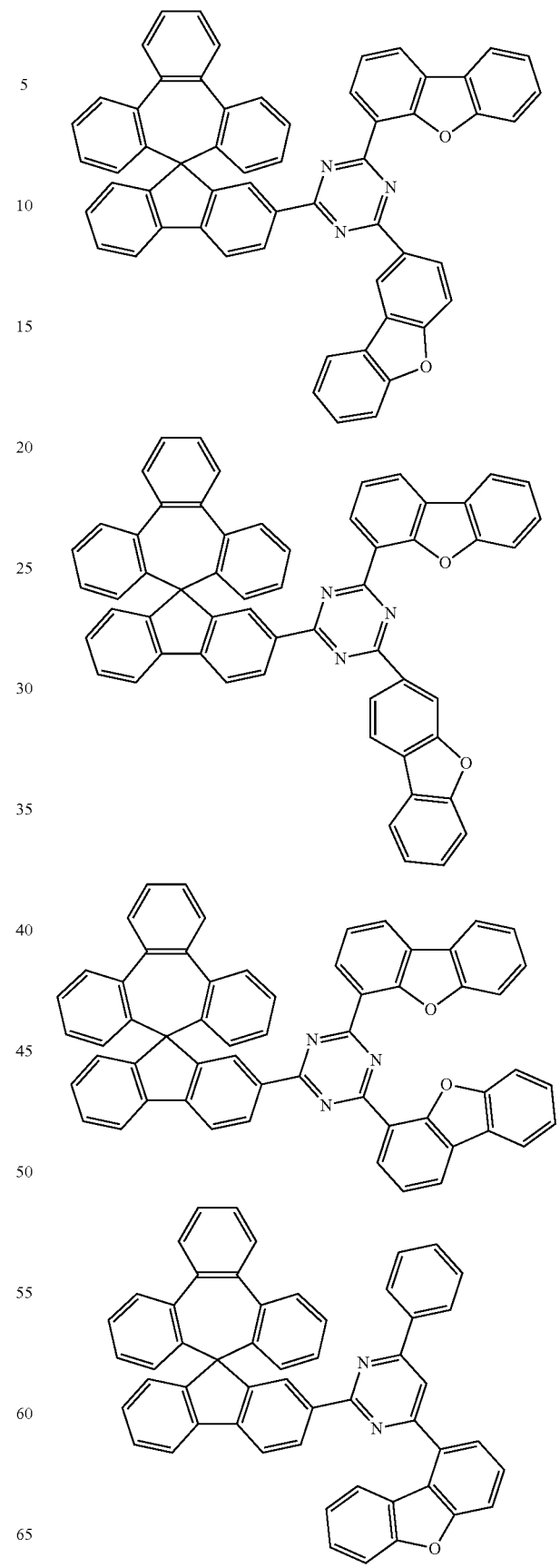

277
-continued
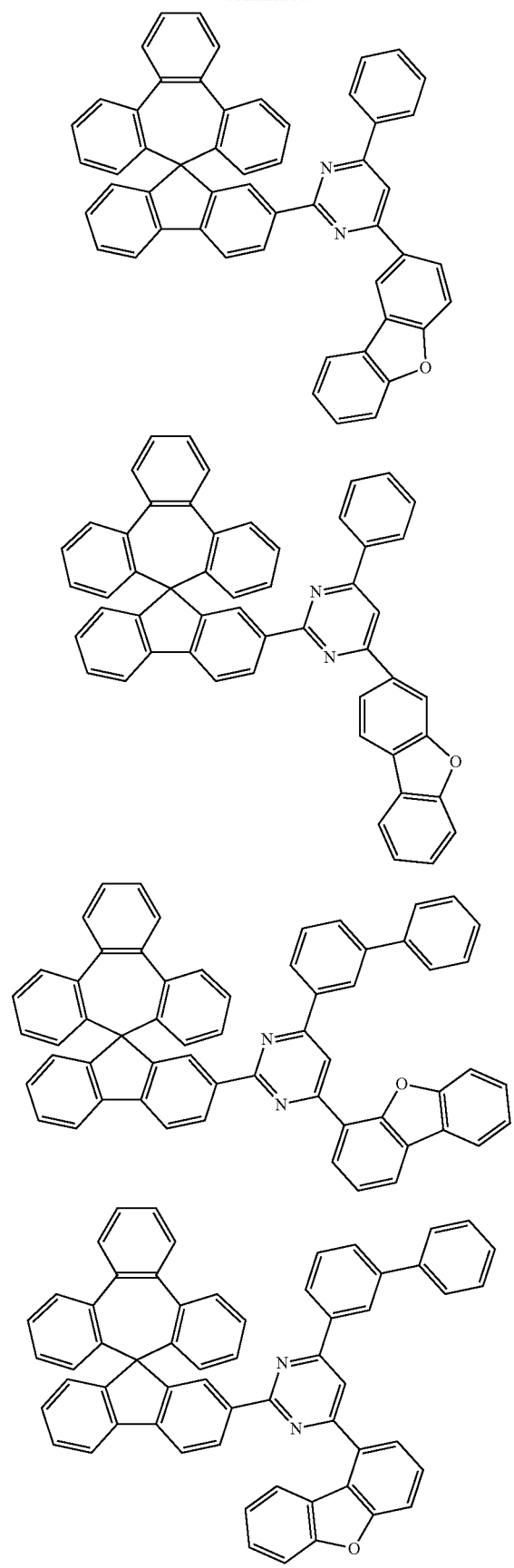
278
-continued
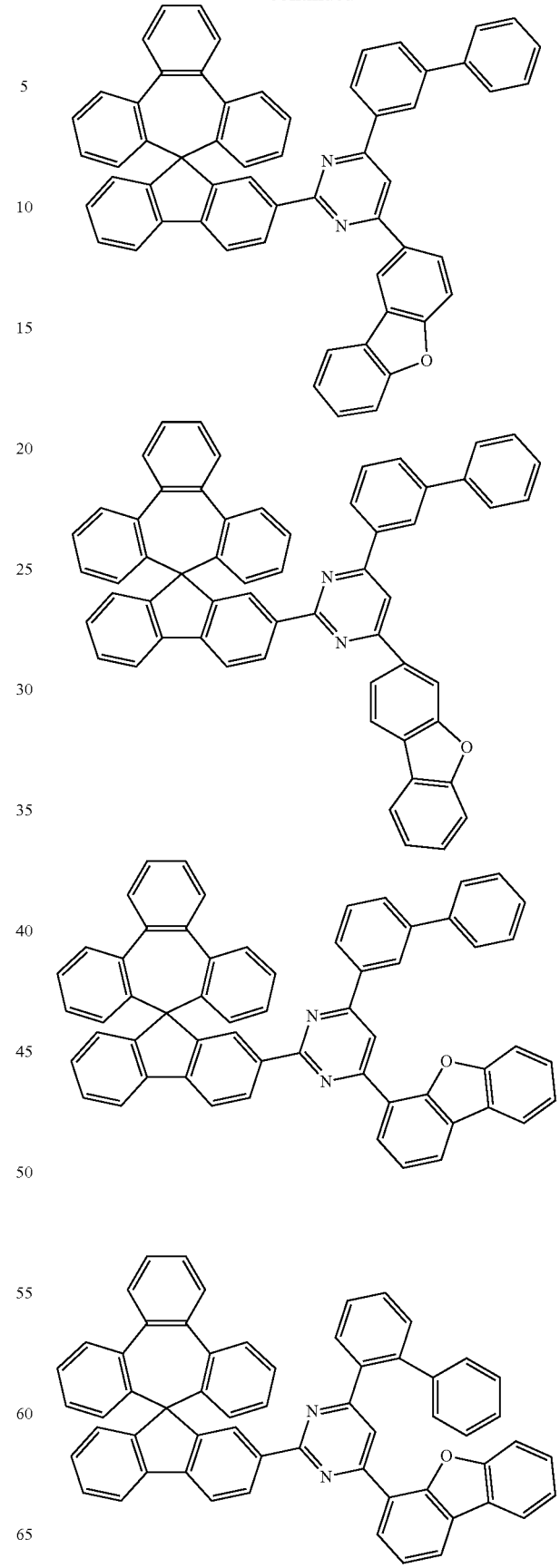

279
-continued
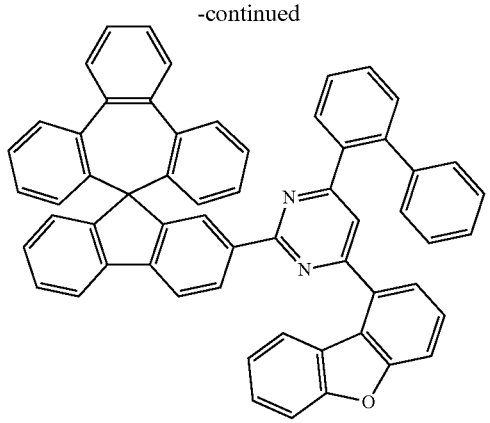
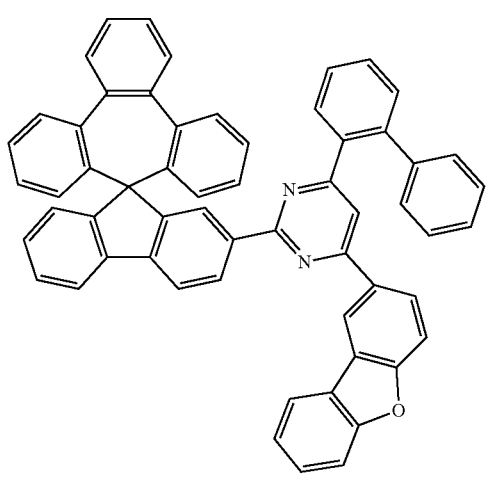
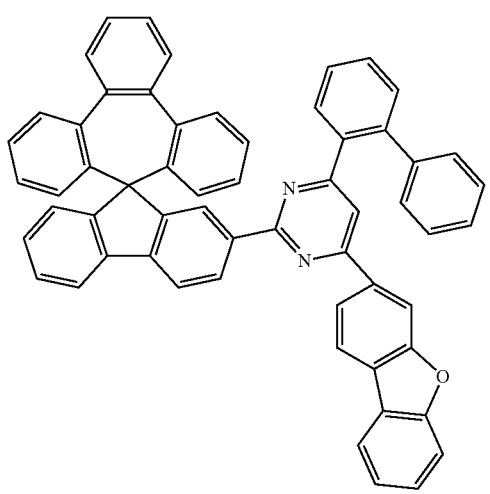
280
-continued
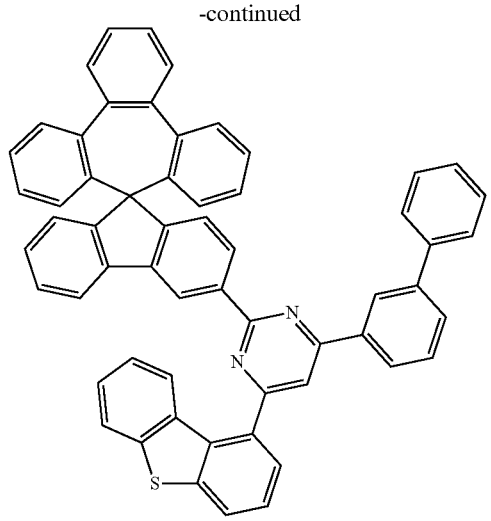
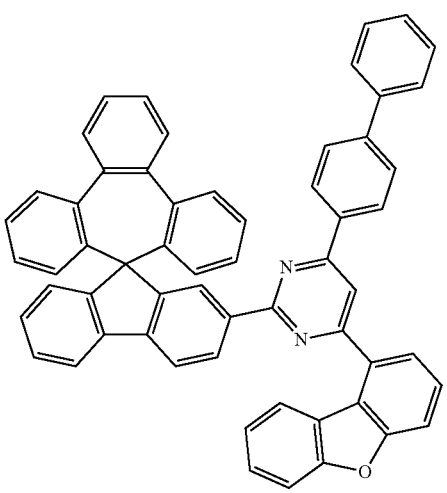
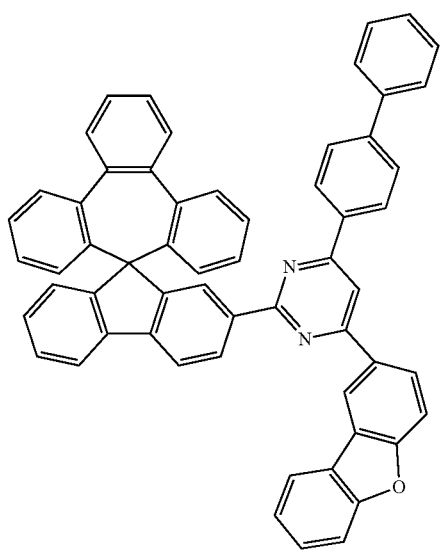

281
-continued
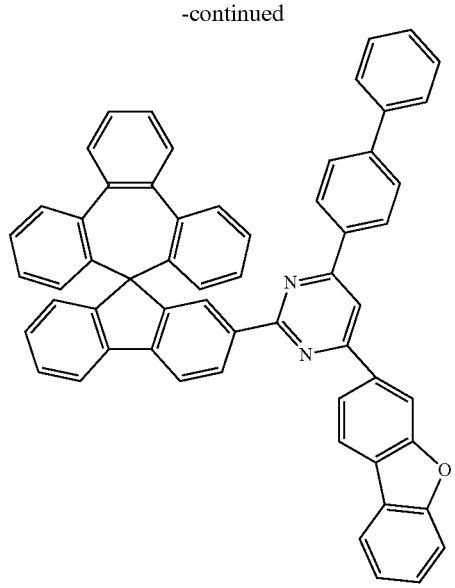
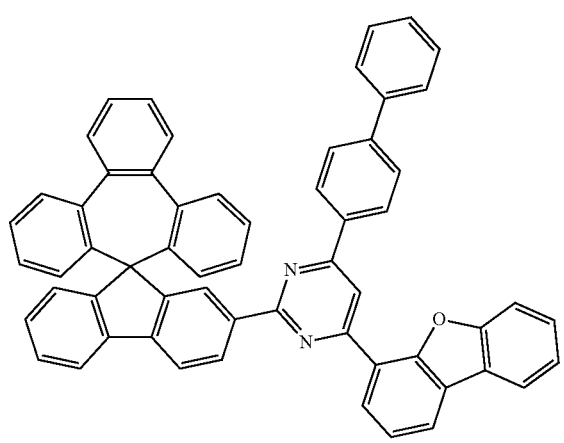 [SMILES: c1ccc(-c2ccc(-c3cc(-c4cccc5c4oc4ccccc45)nc(-c4ccc5c(c4)C4(c6ccccc6-c6ccccc6-c6ccccc64)c4ccccc4-5)n3)cc2)cc1]
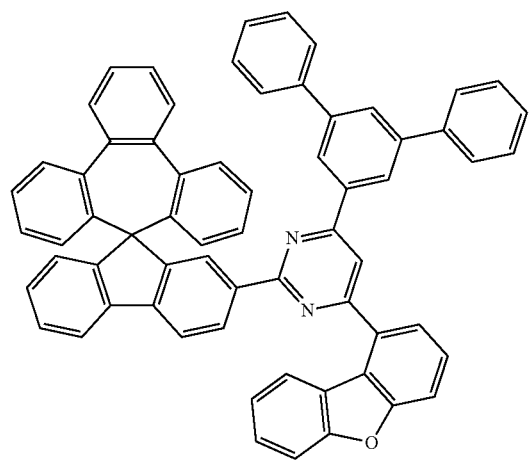
282
-continued
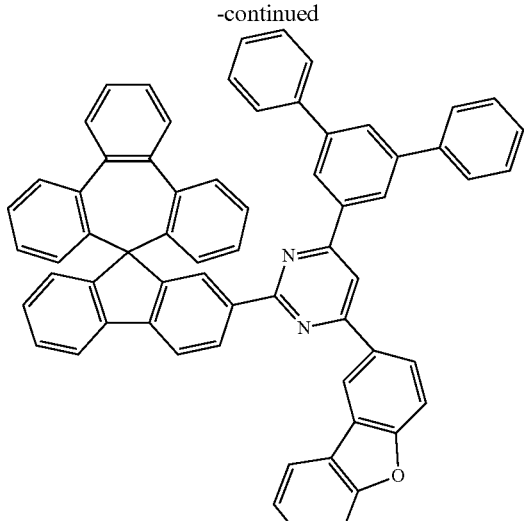
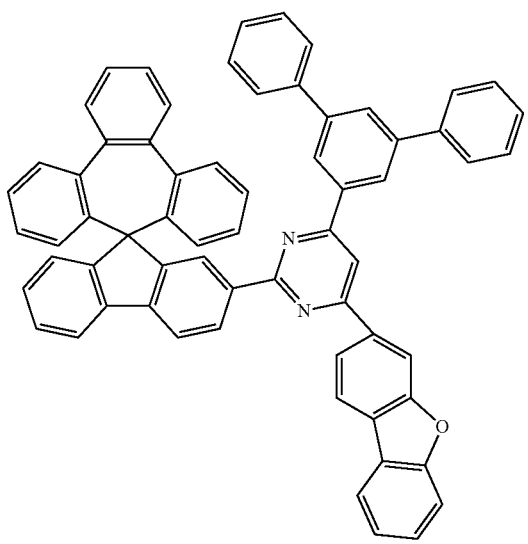
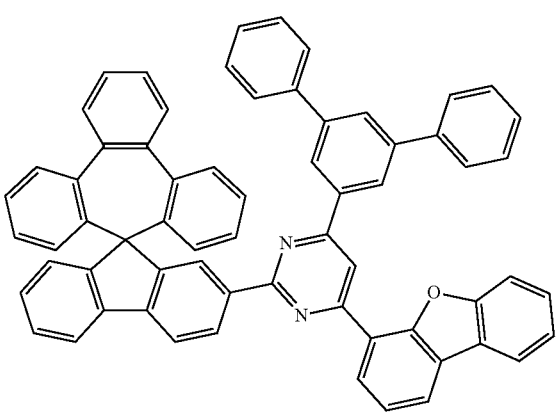 [SMILES: c1ccc(-c2cc(-c3ccccc3)cc(-c3cc(-c4cccc5c4oc4ccccc45)nc(-c4ccc5c(c4)C4(c6ccccc6-c6ccccc6-c6ccccc64)c4ccccc4-5)n3)c2)cc1]

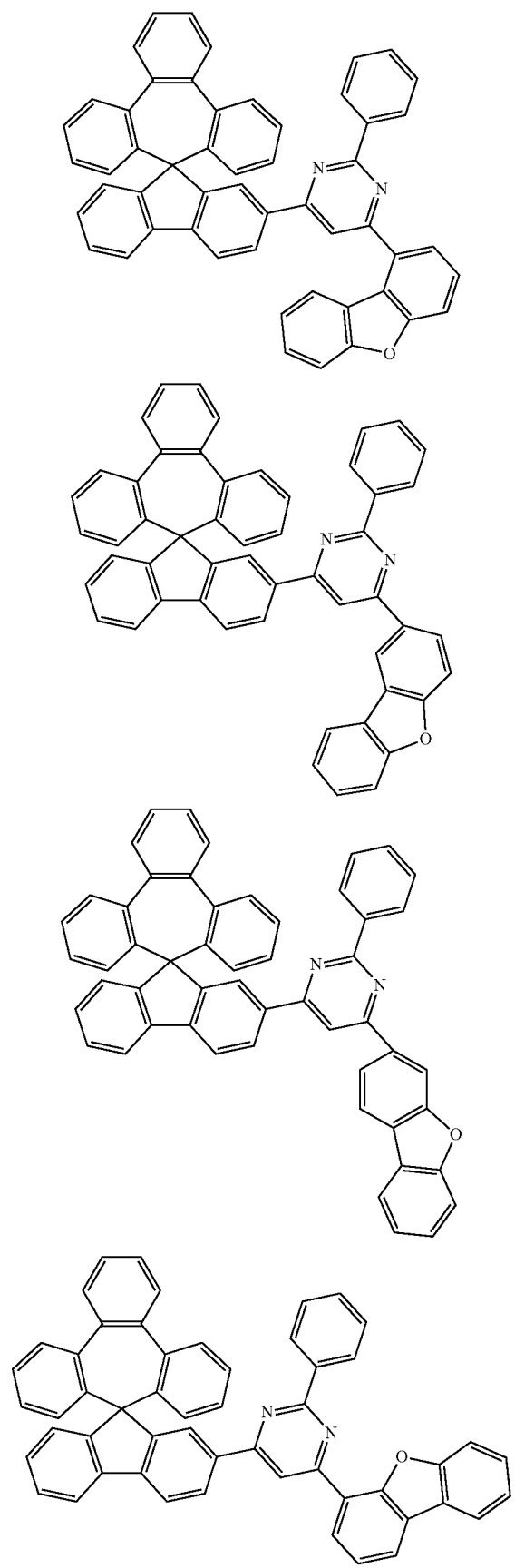
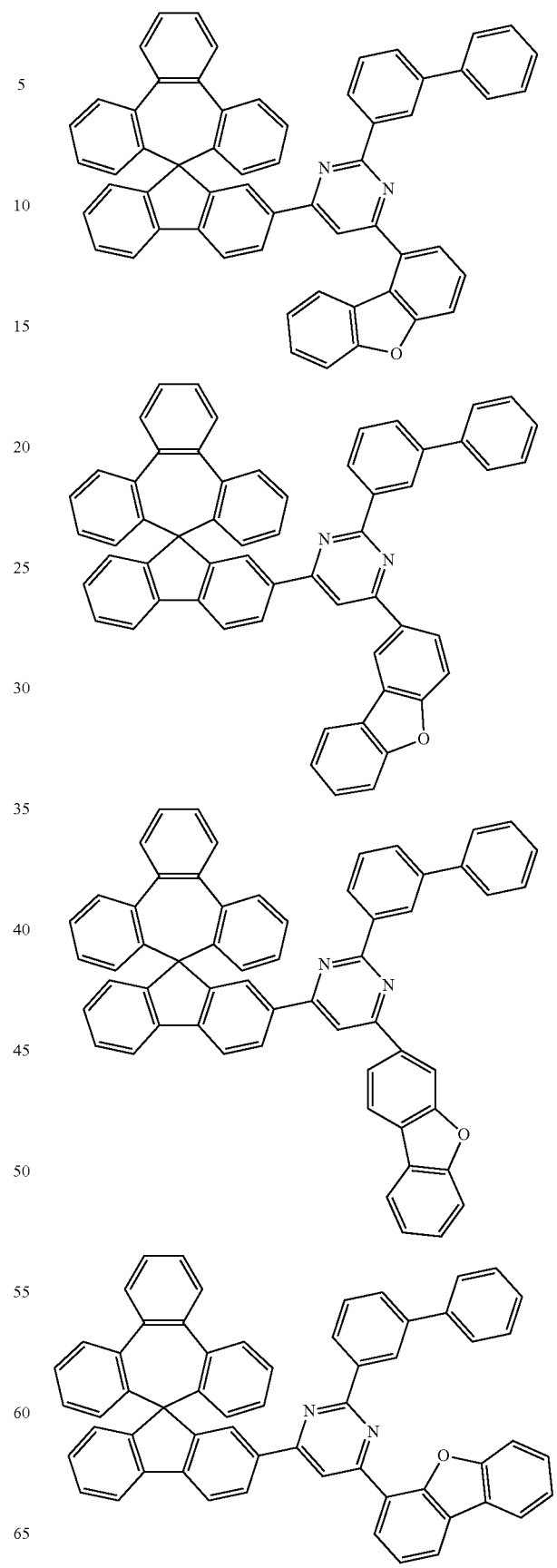

285
-continued
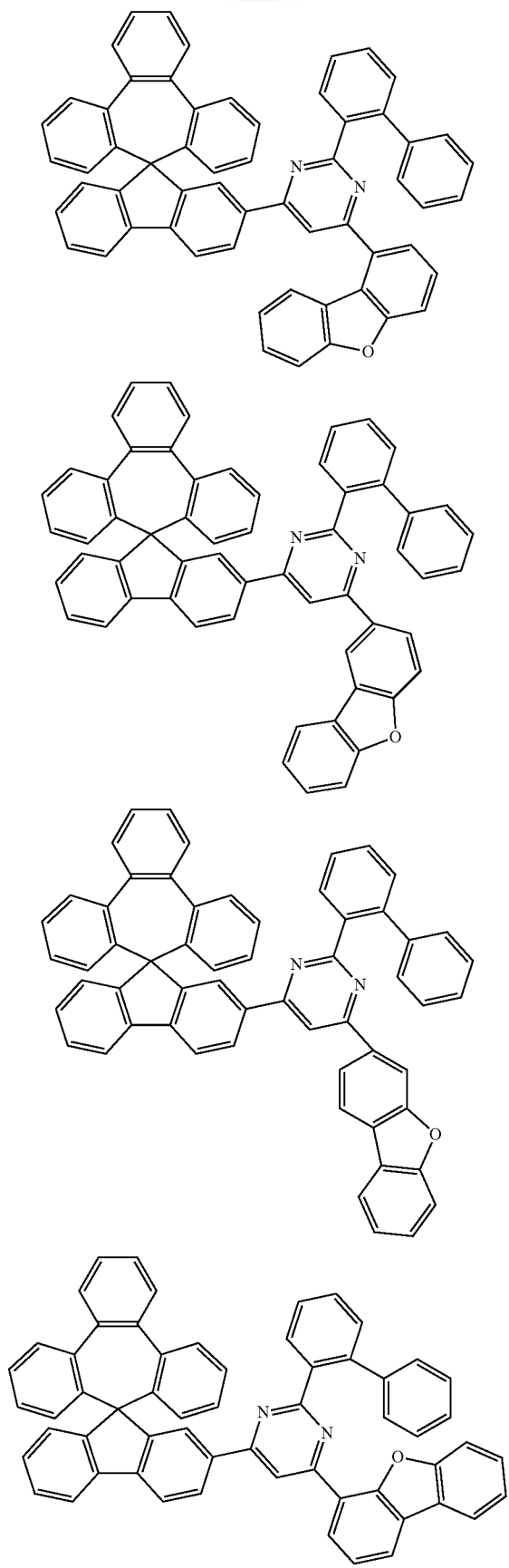
286
-continued
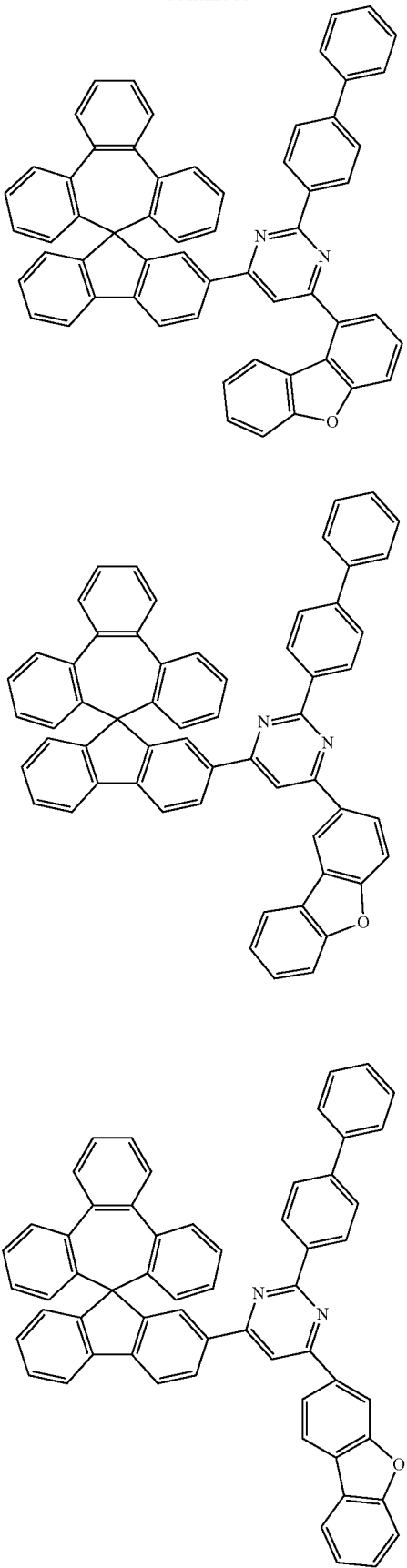

287
-continued
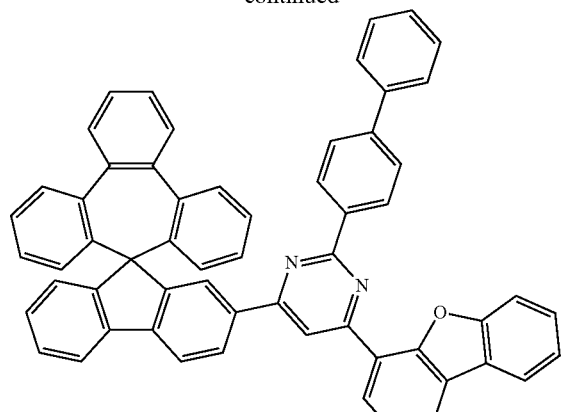
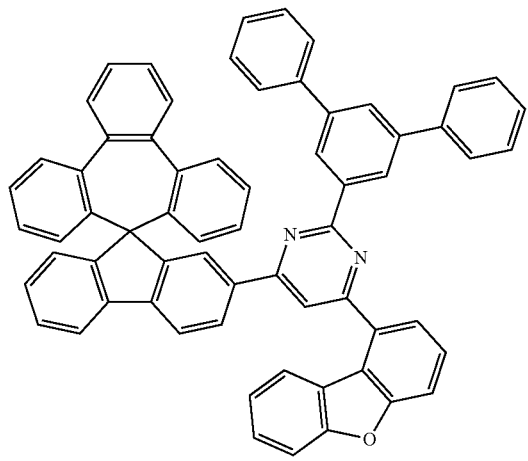
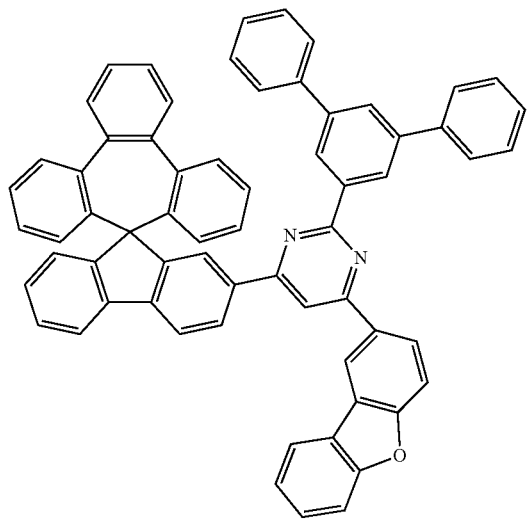
288
-continued
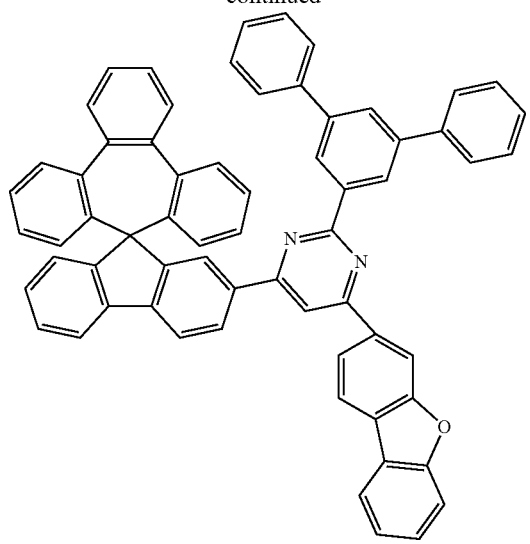
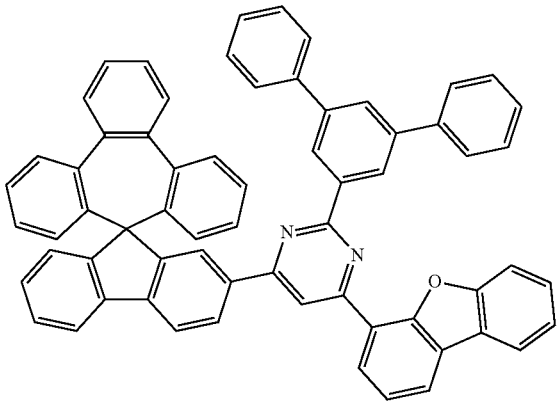 [SMILES: c1ccc(-c2cc(-c3ccccc3)cc(-c3nc(-c4ccc5c(c4)C4(c6ccccc6-c6ccccc6-c6ccccc64)c4ccccc4-5)cc(-c4cccc5c4oc4ccccc45)n3)c2)cc1]
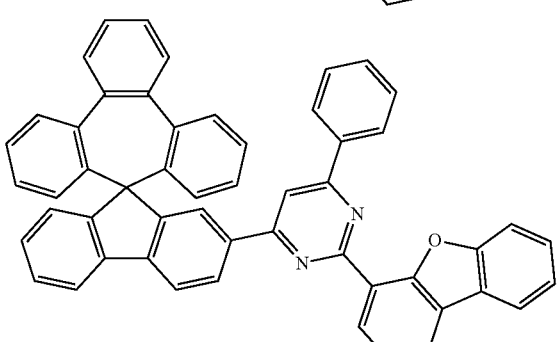
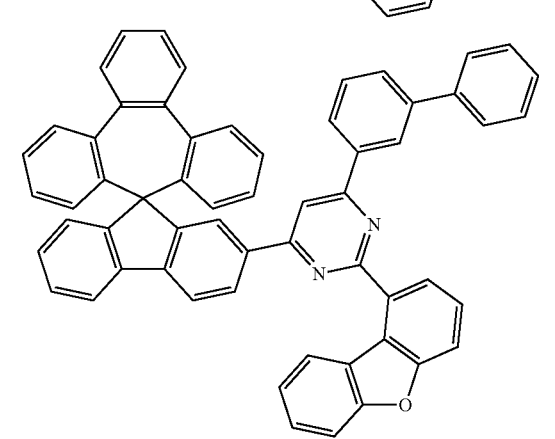

289
-continued
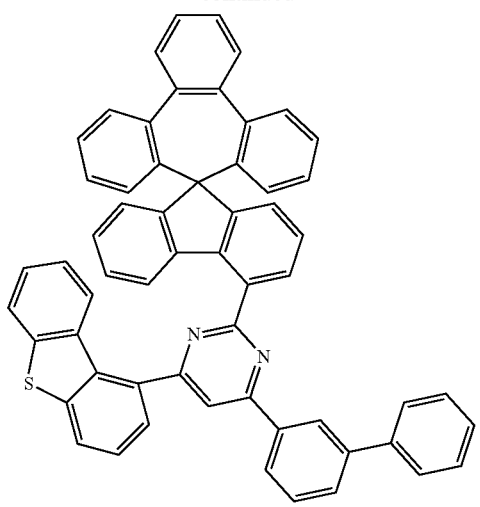
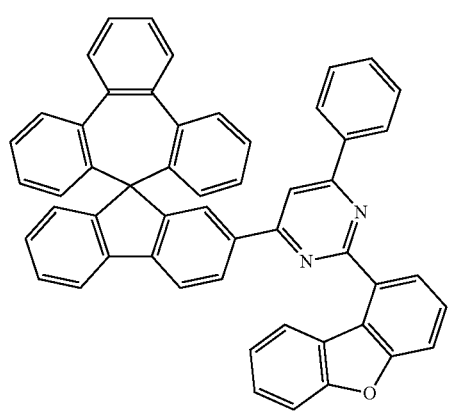
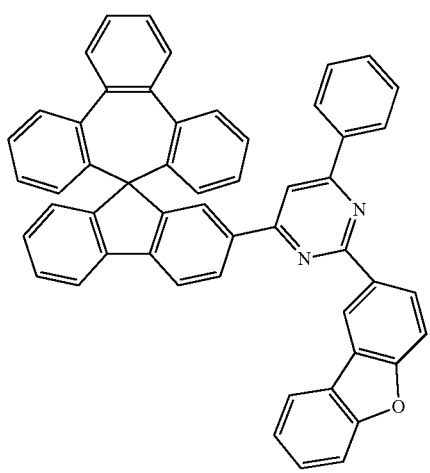
290
-continued
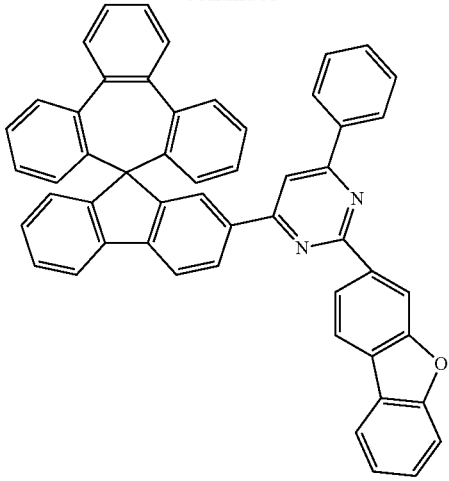
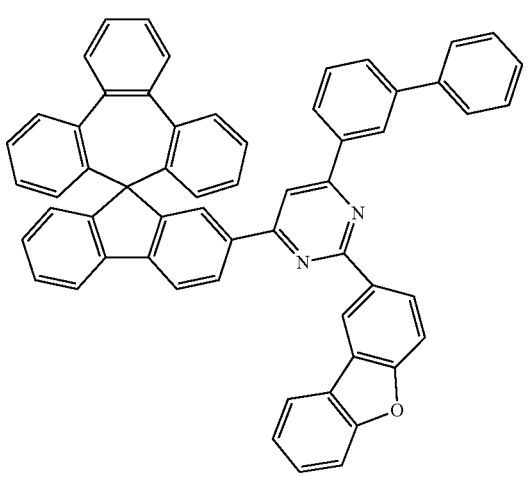
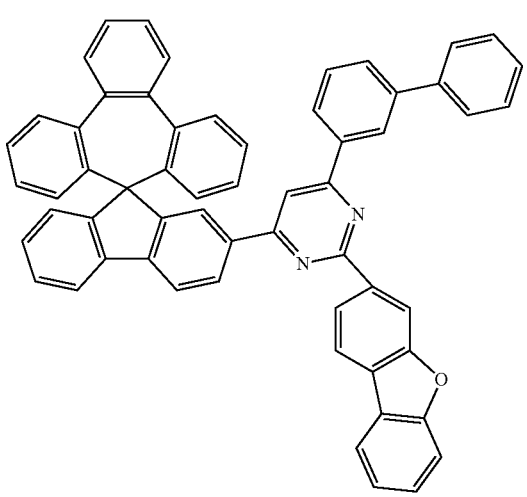

291
-continued
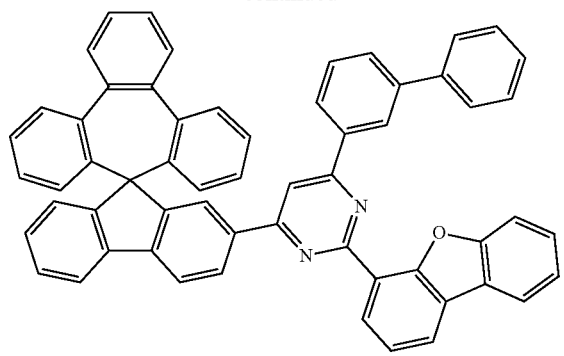
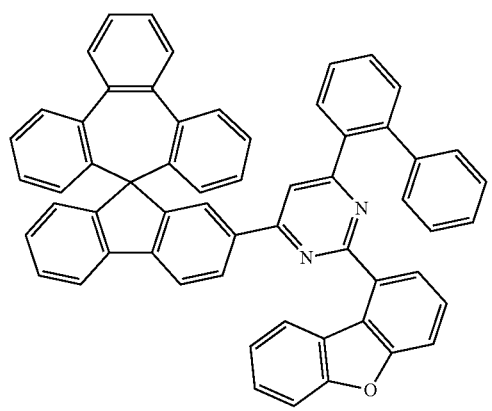
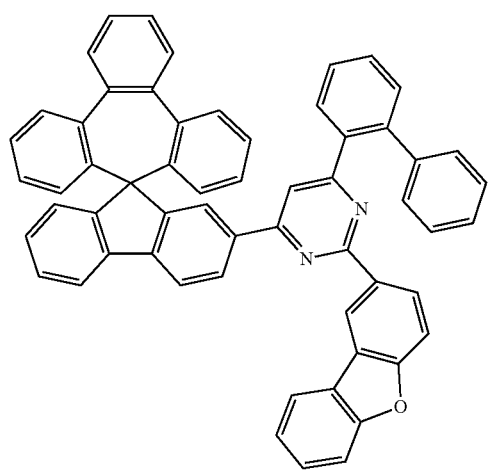
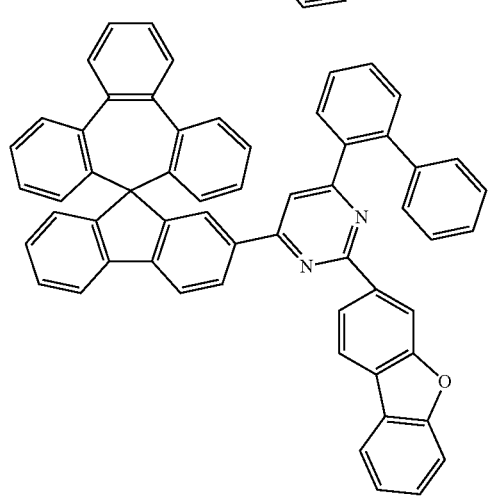
292
-continued
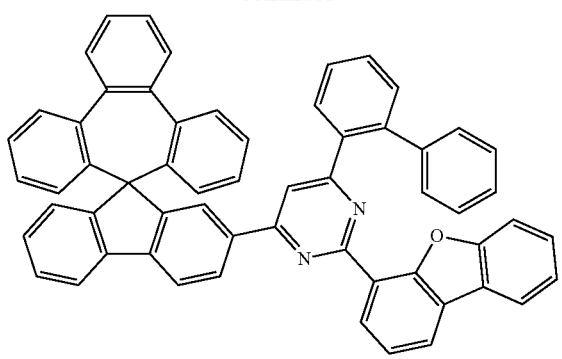 [SMILES: c1ccc(-c2ccccc2-c2cc(-c3ccc4c(c3)C3(c5ccccc5-c5ccccc5-c5ccccc53)c3ccccc3-4)nc(-c3cccc4c3oc3ccccc34)n2)cc1]
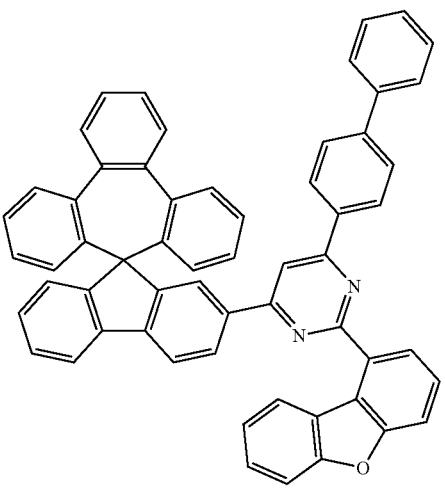
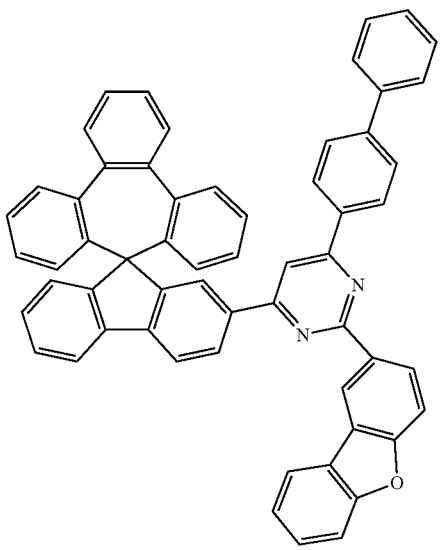

293
-continued
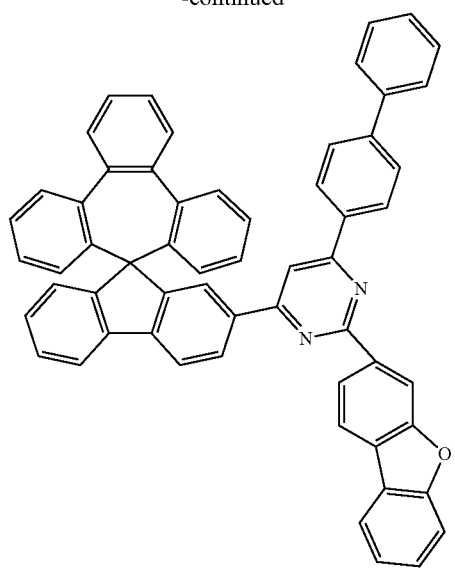
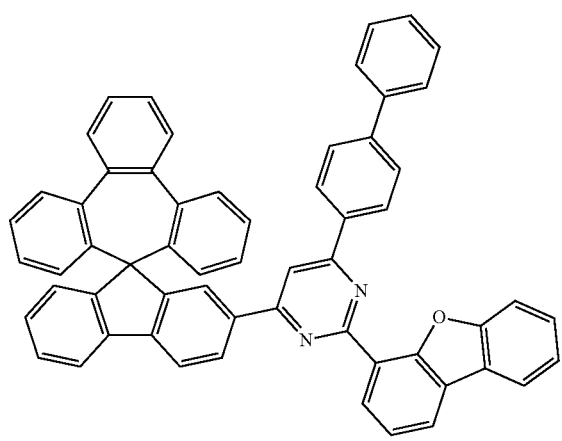 [SMILES: c1ccc(-c2ccc(-c3cc(-c4ccc5c(c4)C4(c6ccccc6-c6ccccc6-c6ccccc64)c4ccccc4-5)nc(-c4cccc5c4oc4ccccc45)n3)cc2)cc1]
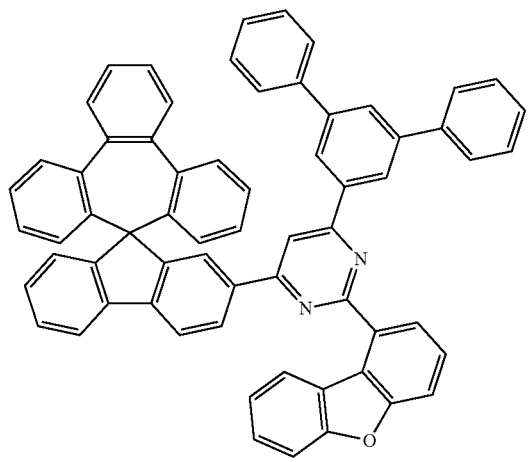
294
-continued
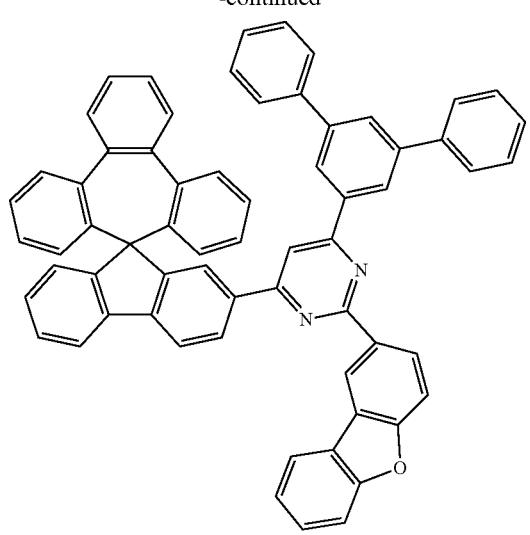
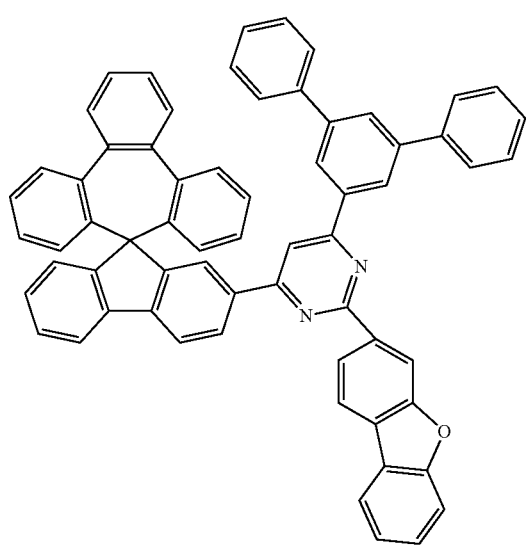
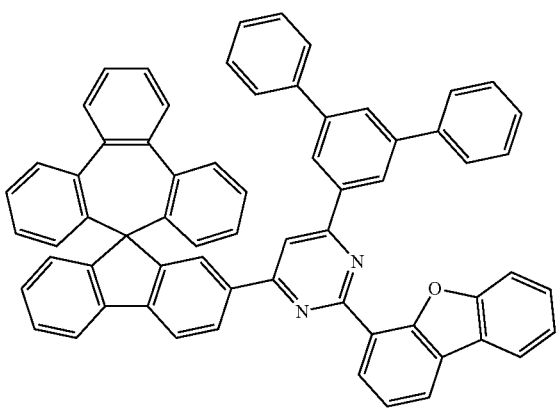 [SMILES: c1ccc(-c2cc(-c3ccccc3)cc(-c3cc(-c4ccc5c(c4)C4(c6ccccc6-c6ccccc6-c6ccccc64)c4ccccc4-5)nc(-c4cccc5c4oc4ccccc45)n3)c2)cc1]

295
-continued
296
-continued
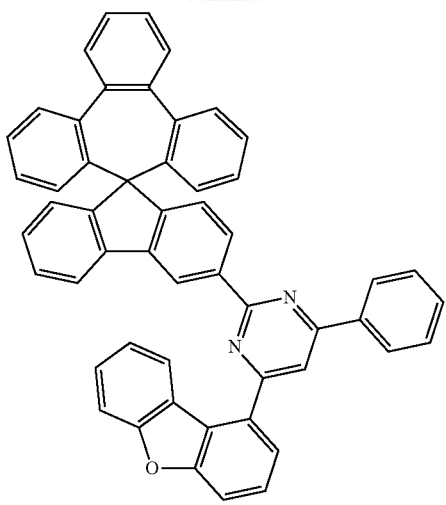
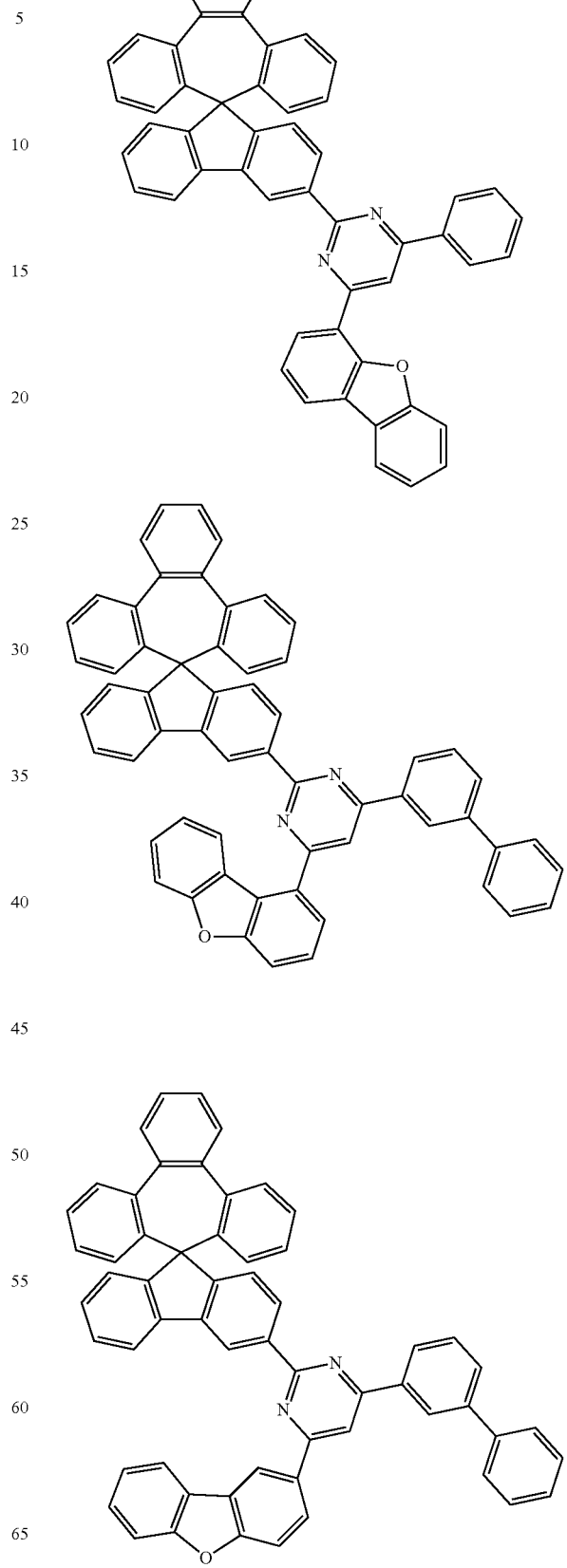

297
-continued
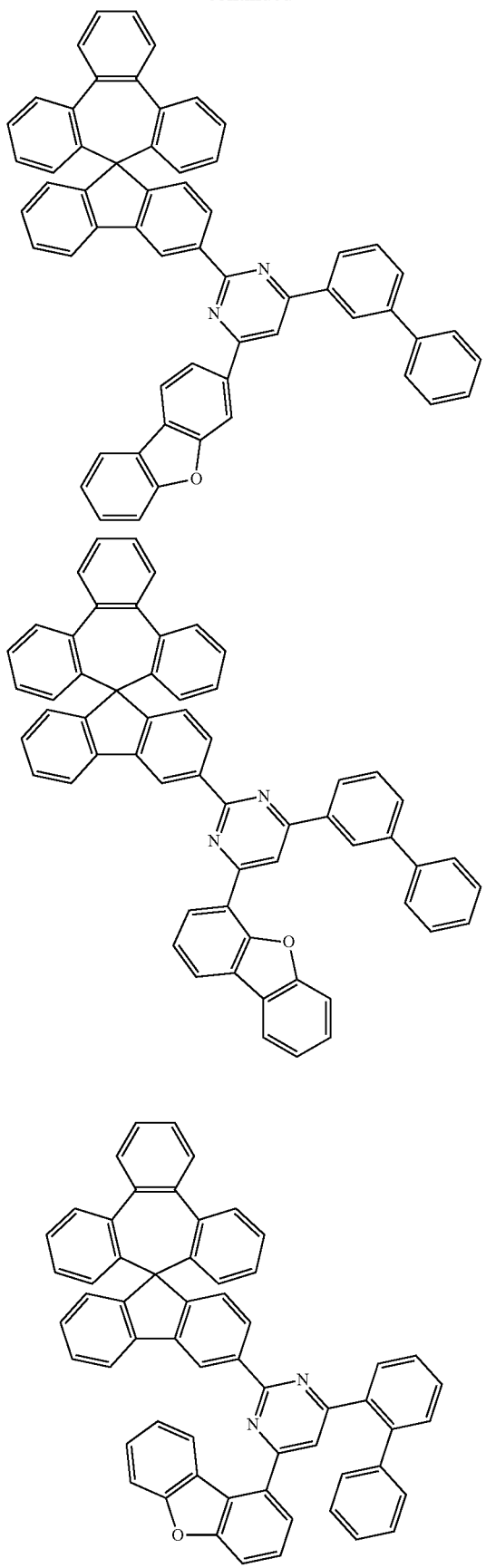
298
-continued
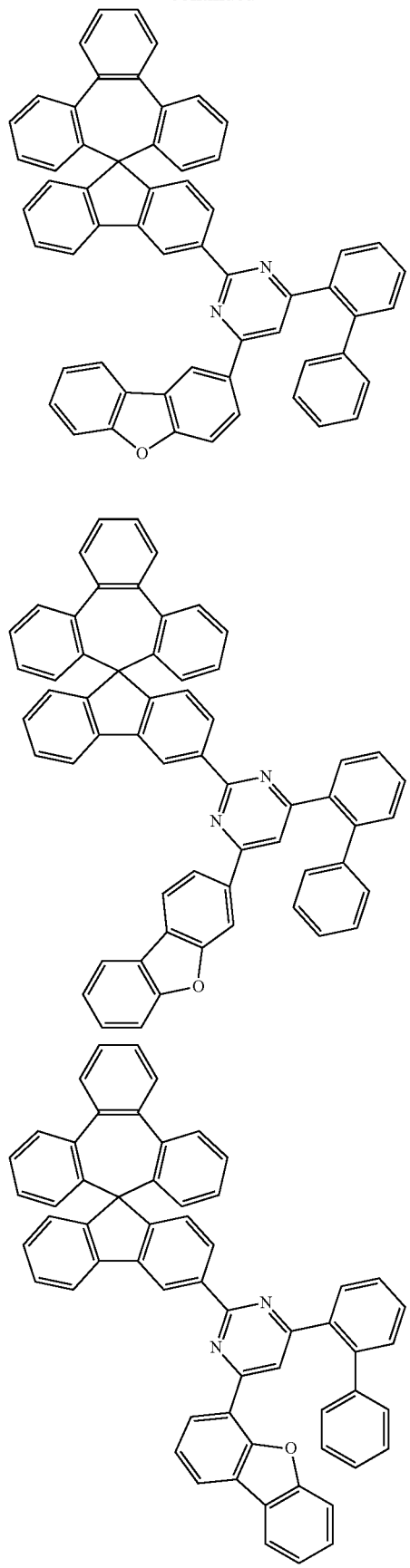

299
-continued
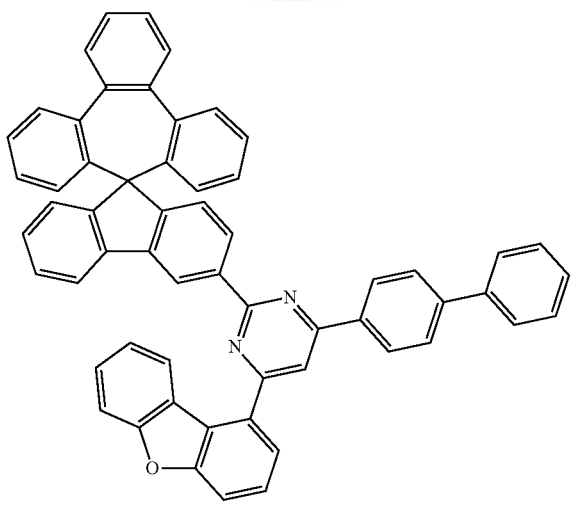
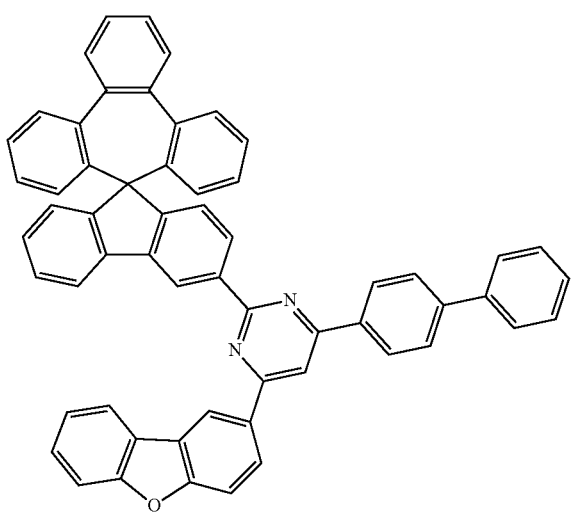
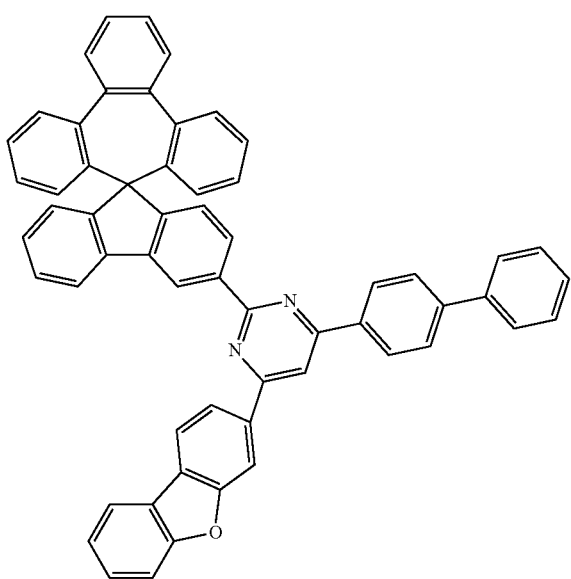
300
-continued
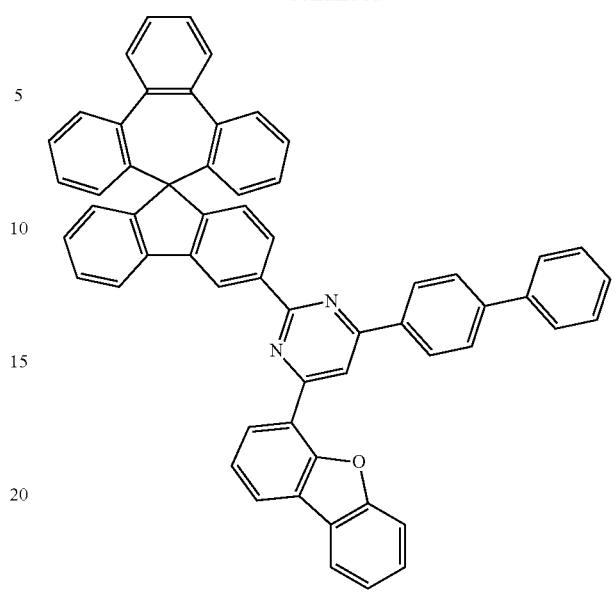
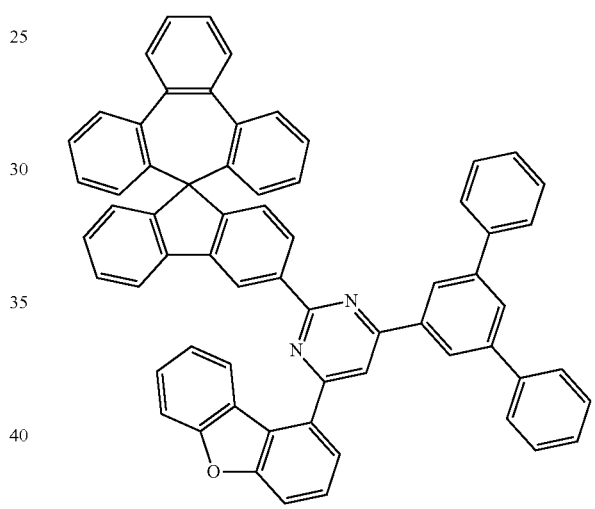
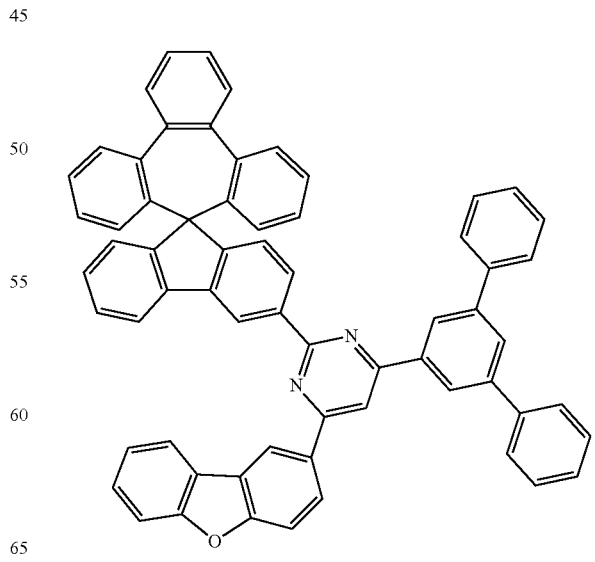

301
-continued
302
-continued
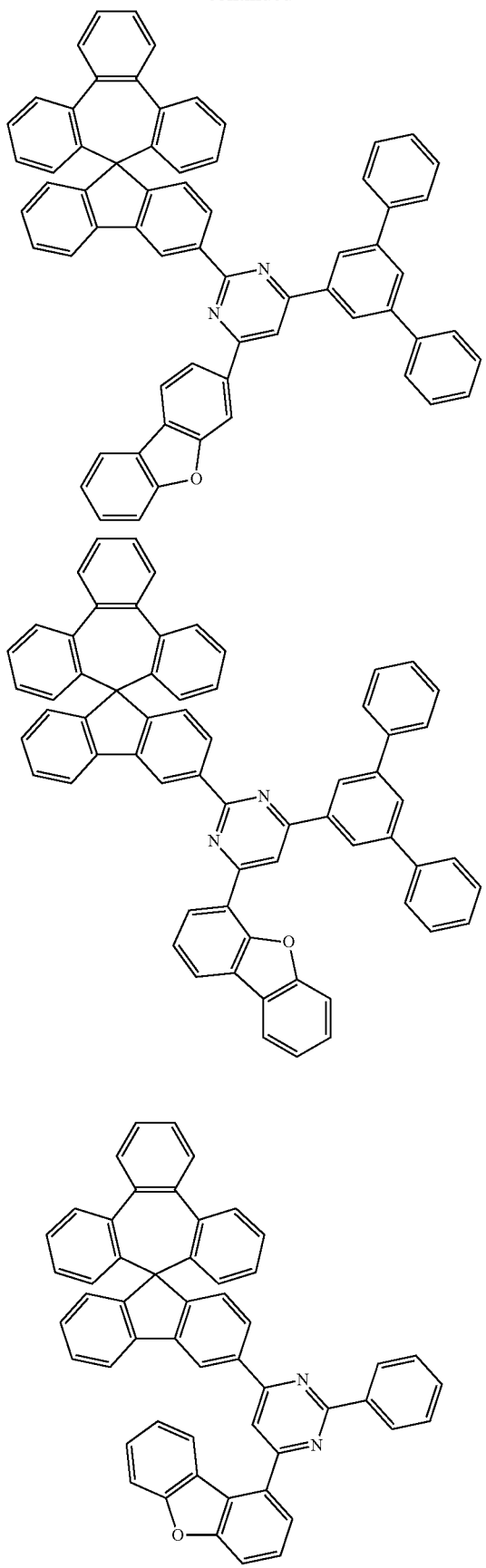
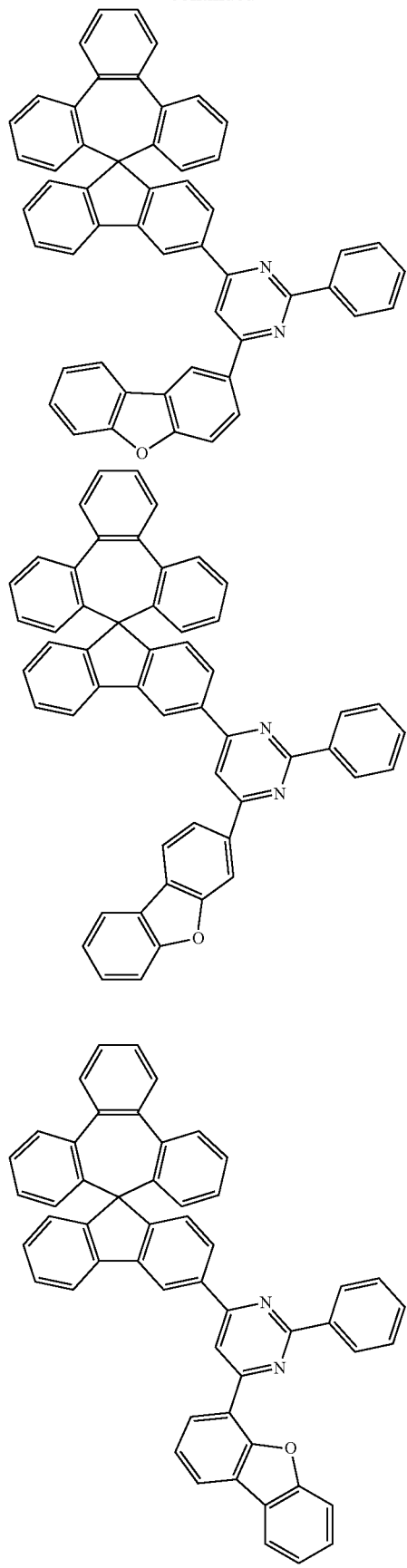

303
-continued
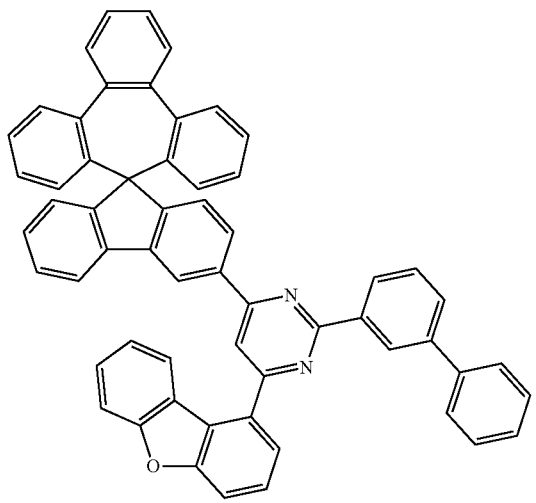
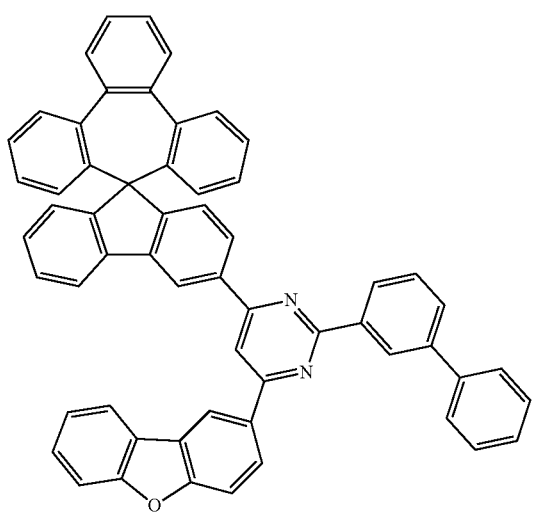
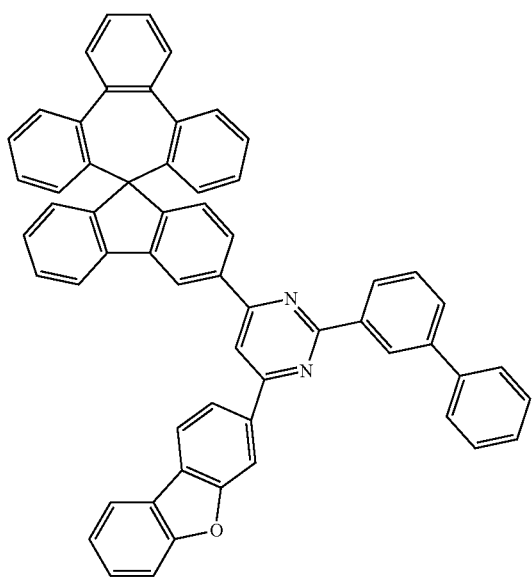
304
-continued
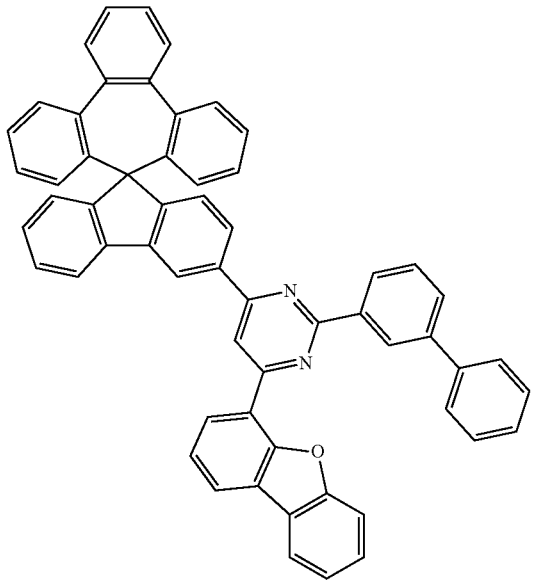 [SMILES: c1ccc(-c2cccc(-c3nc(-c4ccc5c(c4)-c4ccccc4C54c5ccccc5-c5ccccc5-c5ccccc54)cc(-c4cccc5c4oc4ccccc45)n3)c2)cc1]
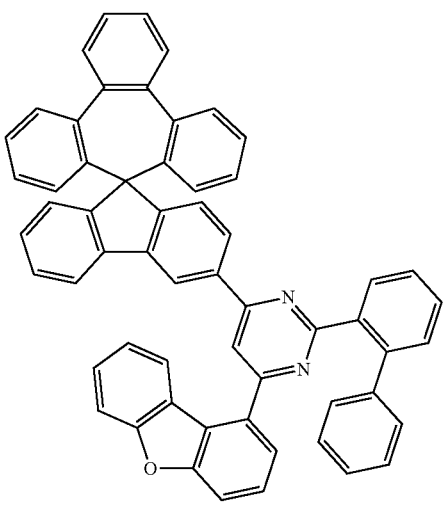
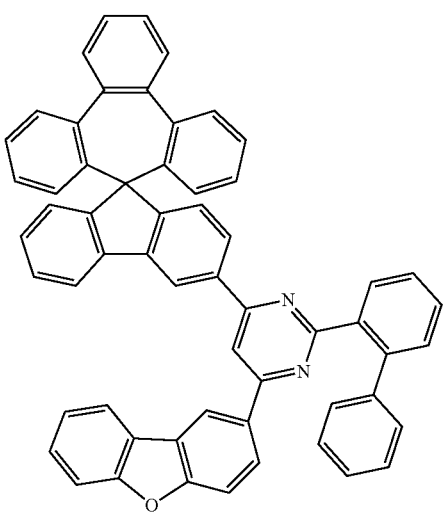

305
-continued
306
-continued
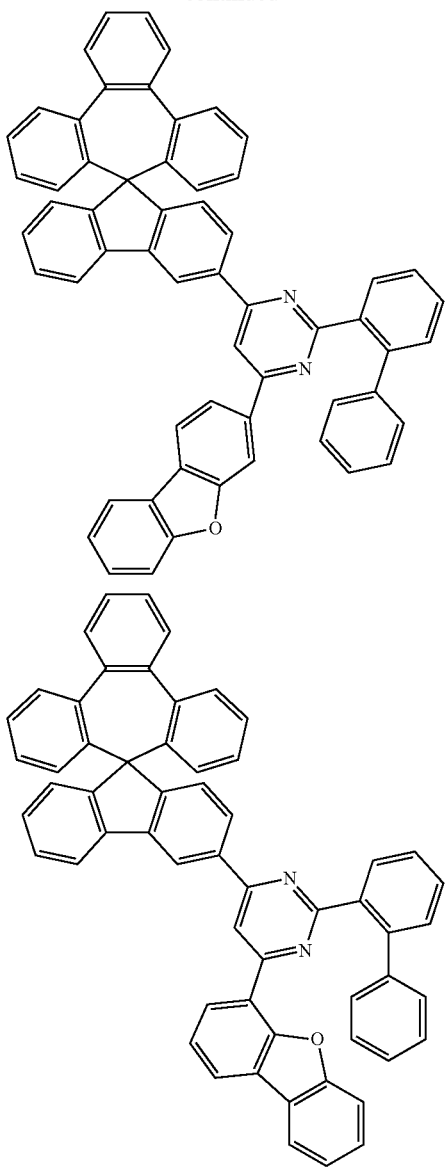
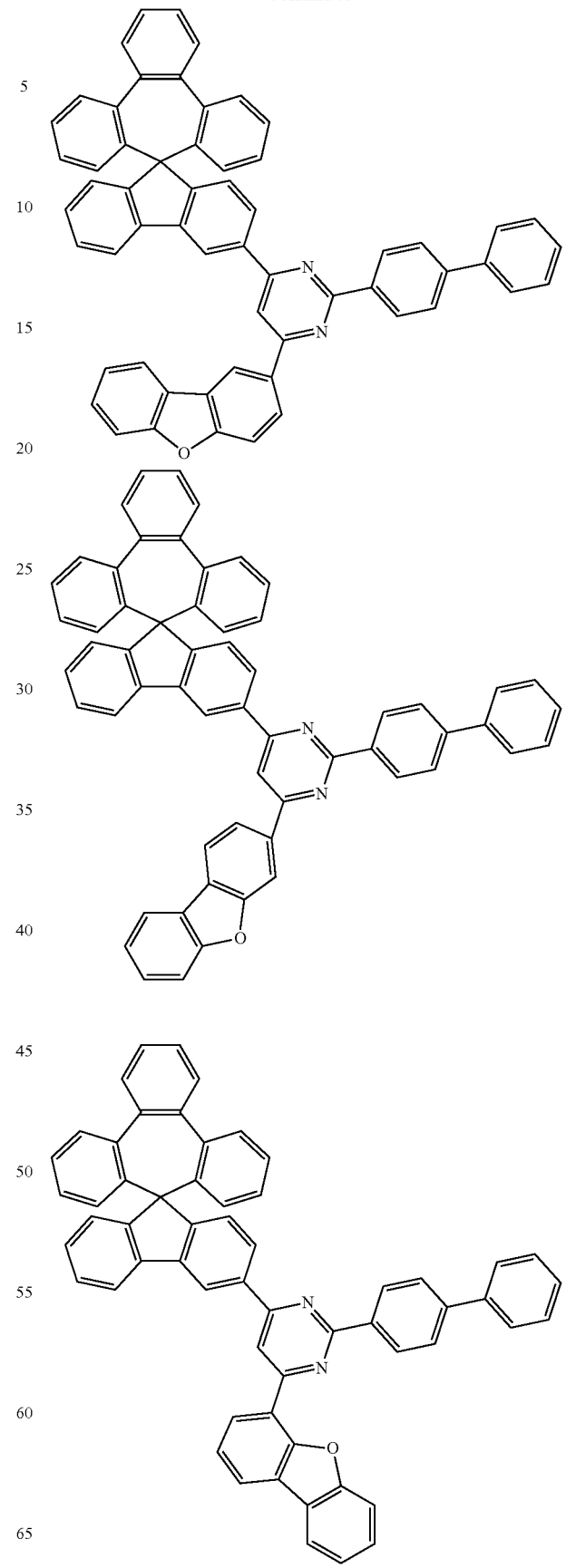

307
-continued
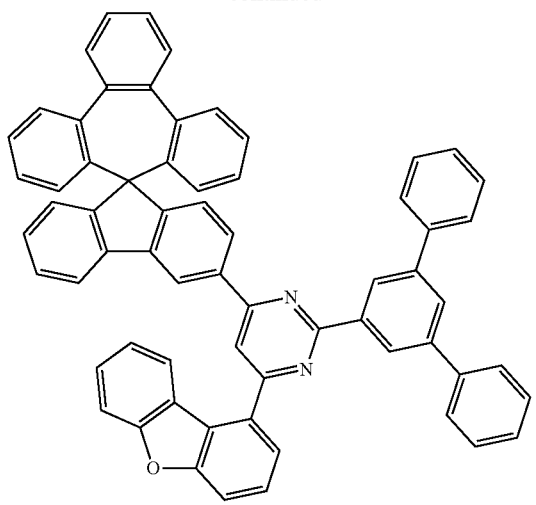
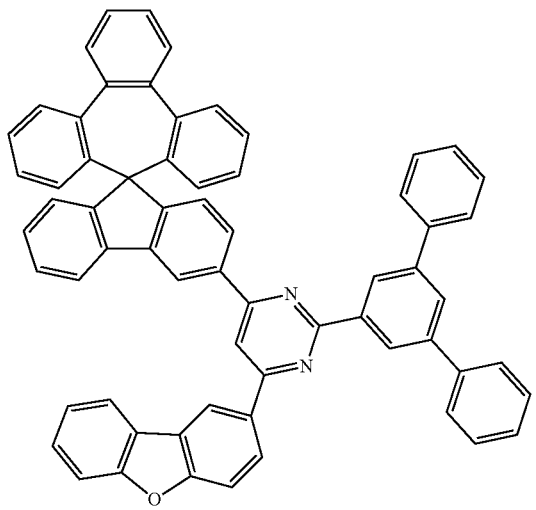
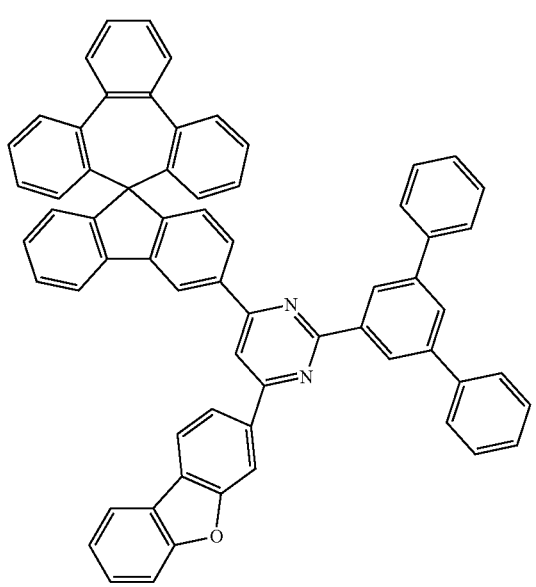
308
-continued
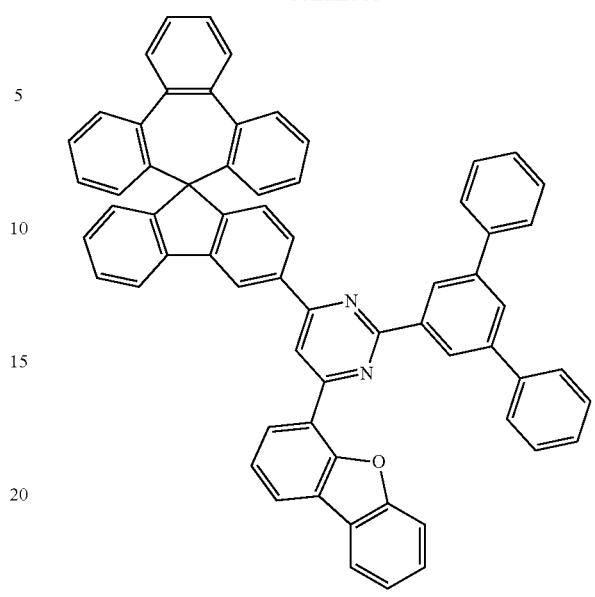
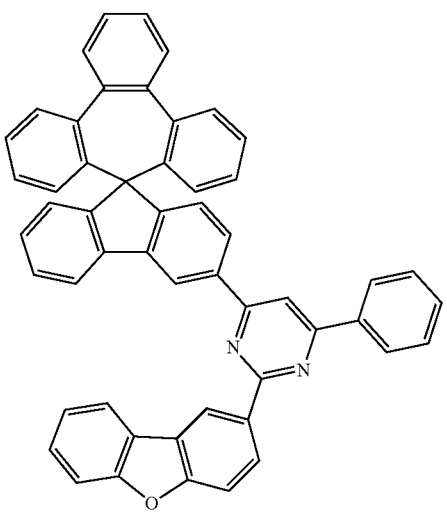

309
-continued
310
-continued
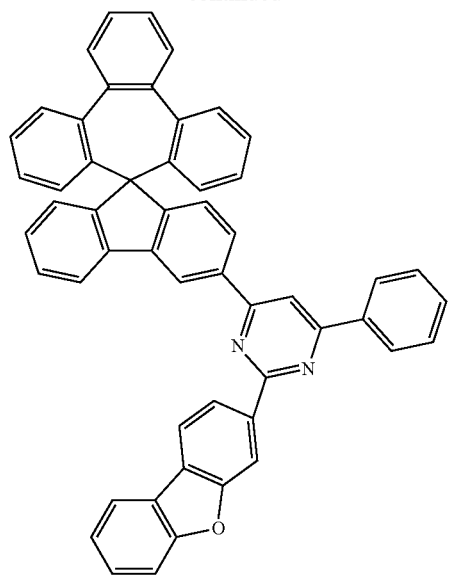
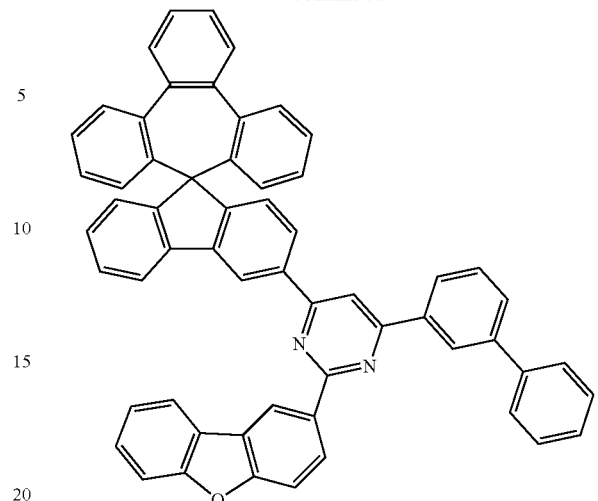
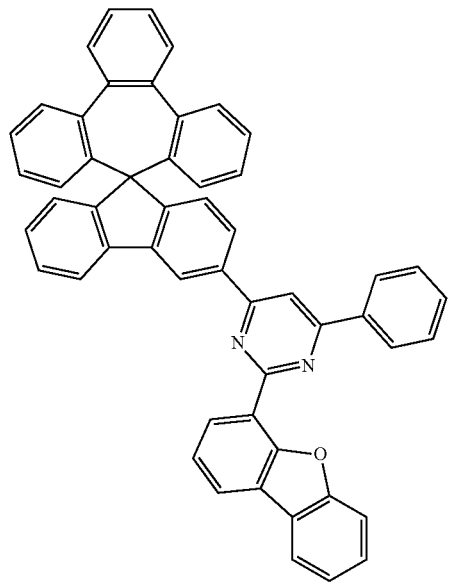 [SMILES: c1ccc(-c2cc(-c3ccc4c(c3)-c3ccccc3C43c4ccccc4-c4ccccc4-c4ccccc43)nc(-c3cccc4c3oc3ccccc34)n2)cc1]
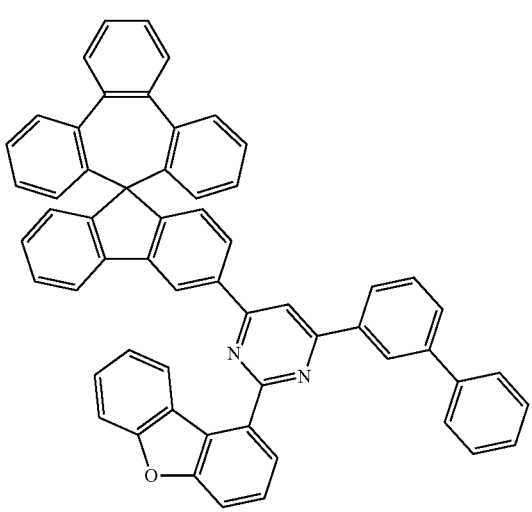

311
-continued
312
-continued
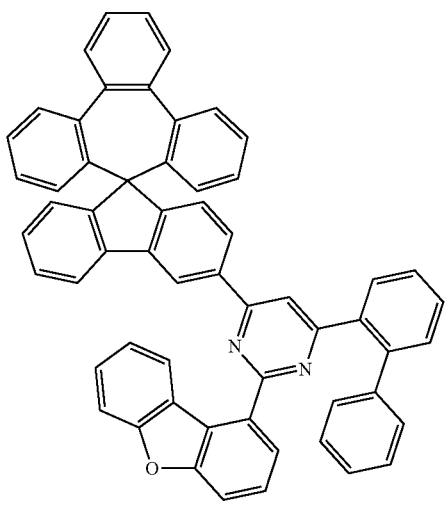
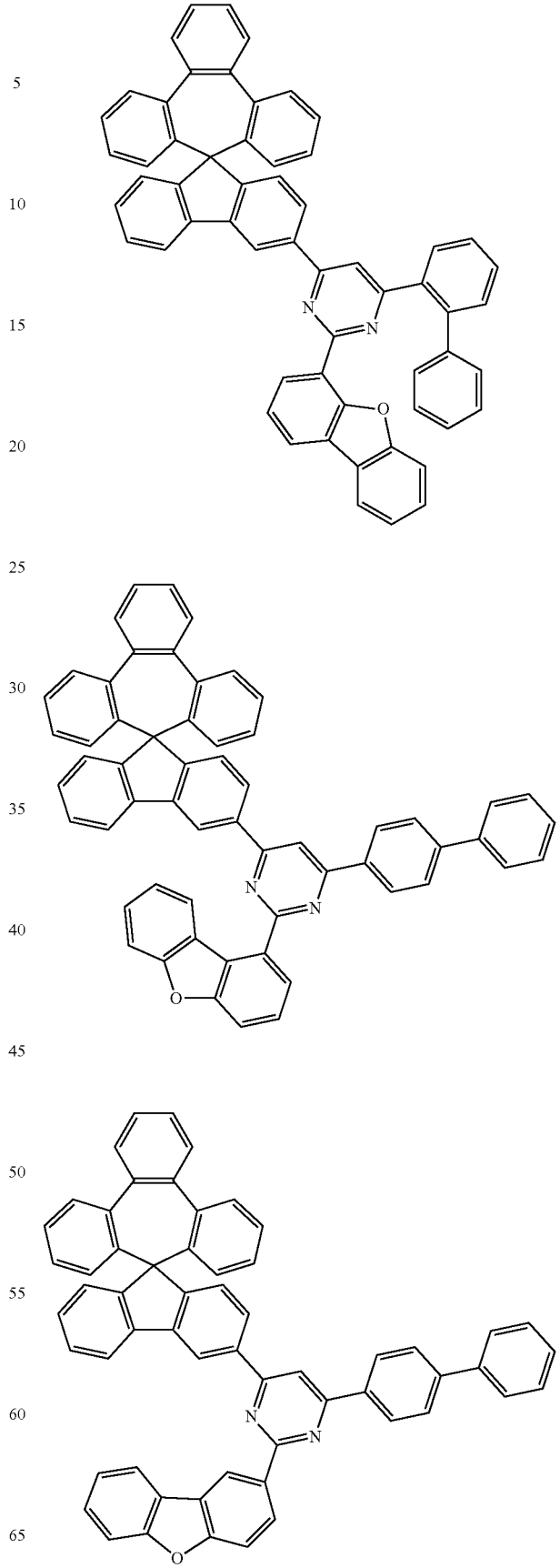

313
-continued
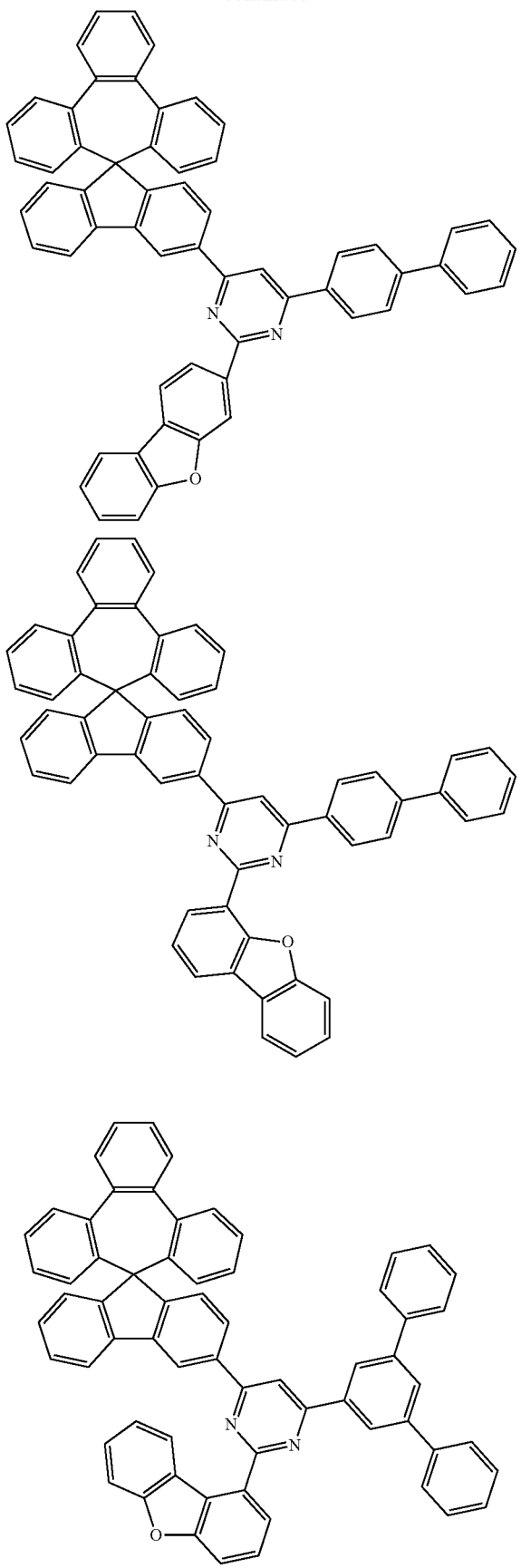
314
-continued
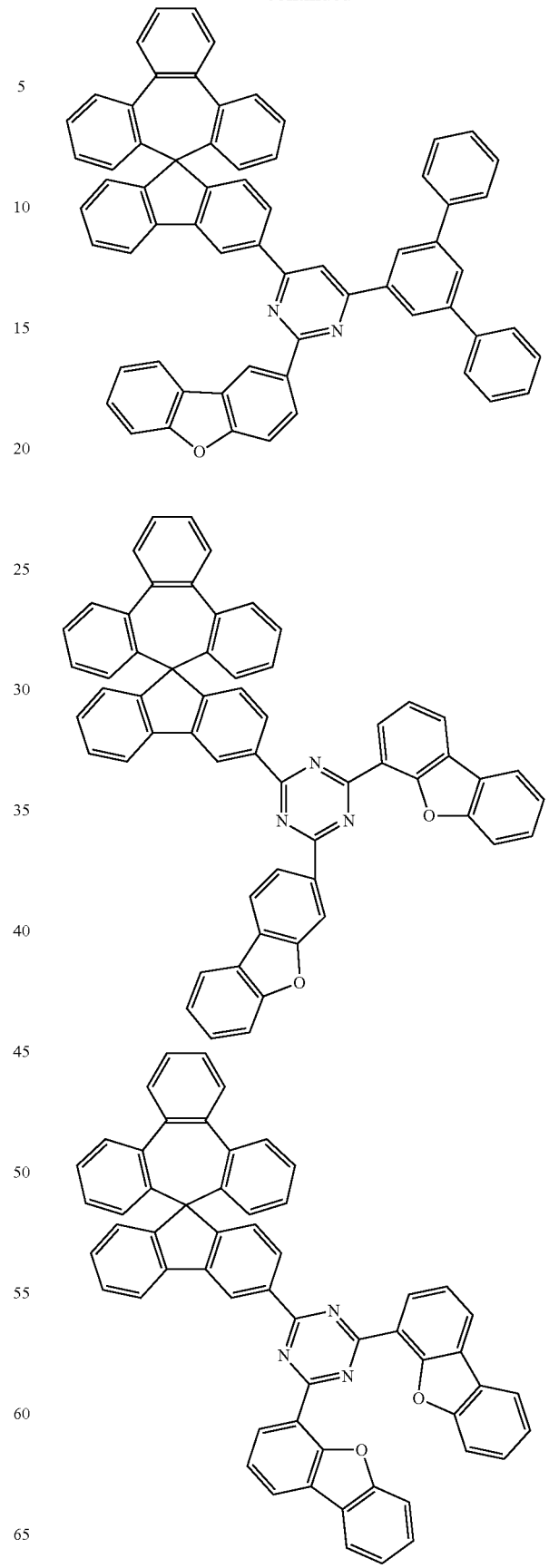

315
-continued
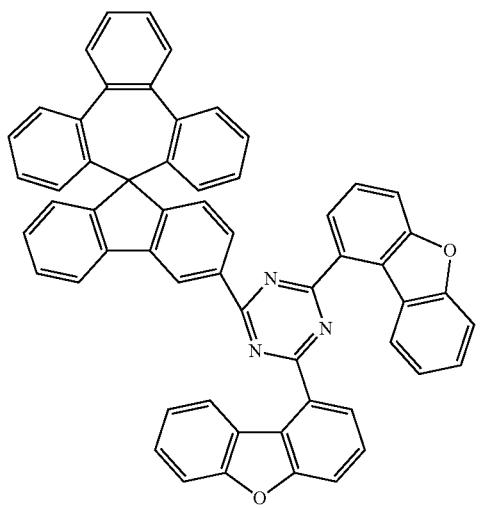
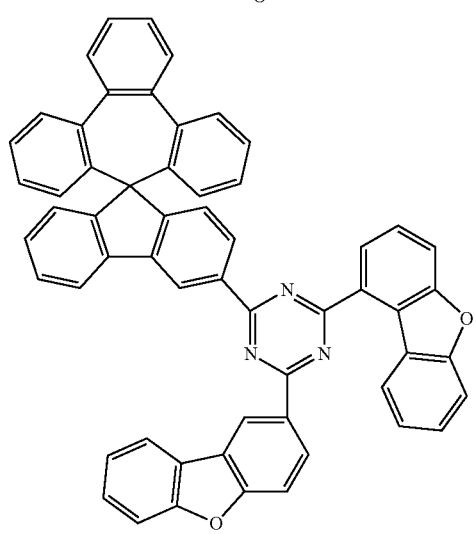
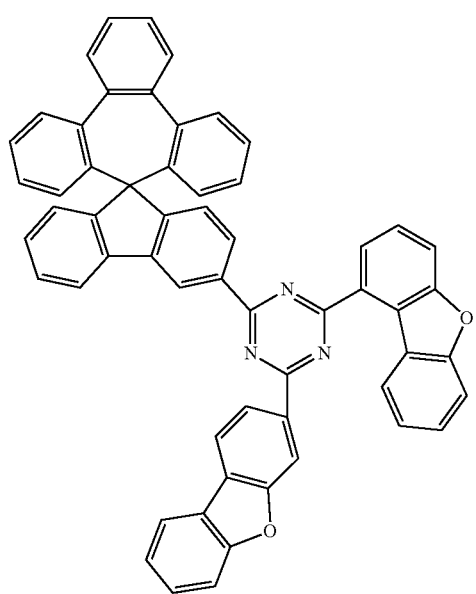
316
-continued
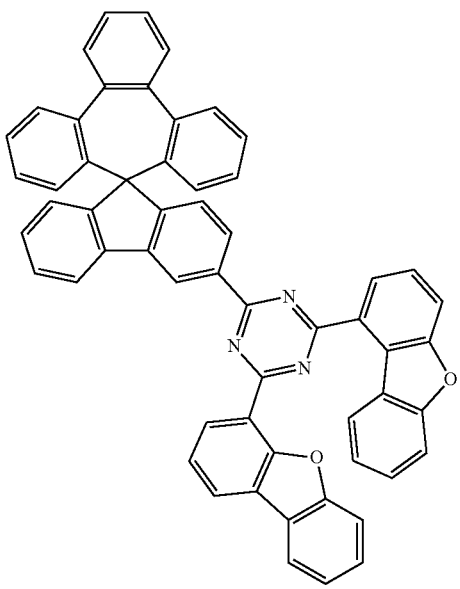
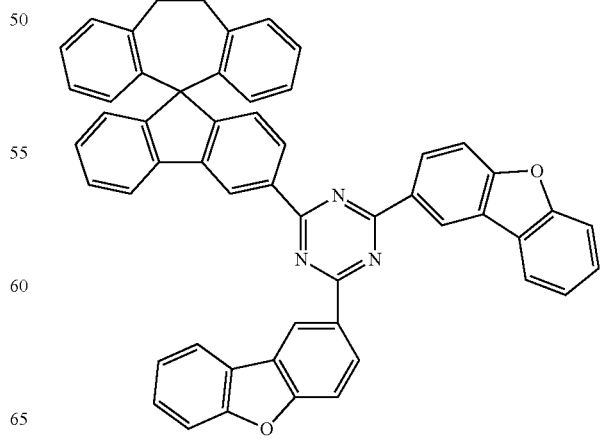

317
-continued
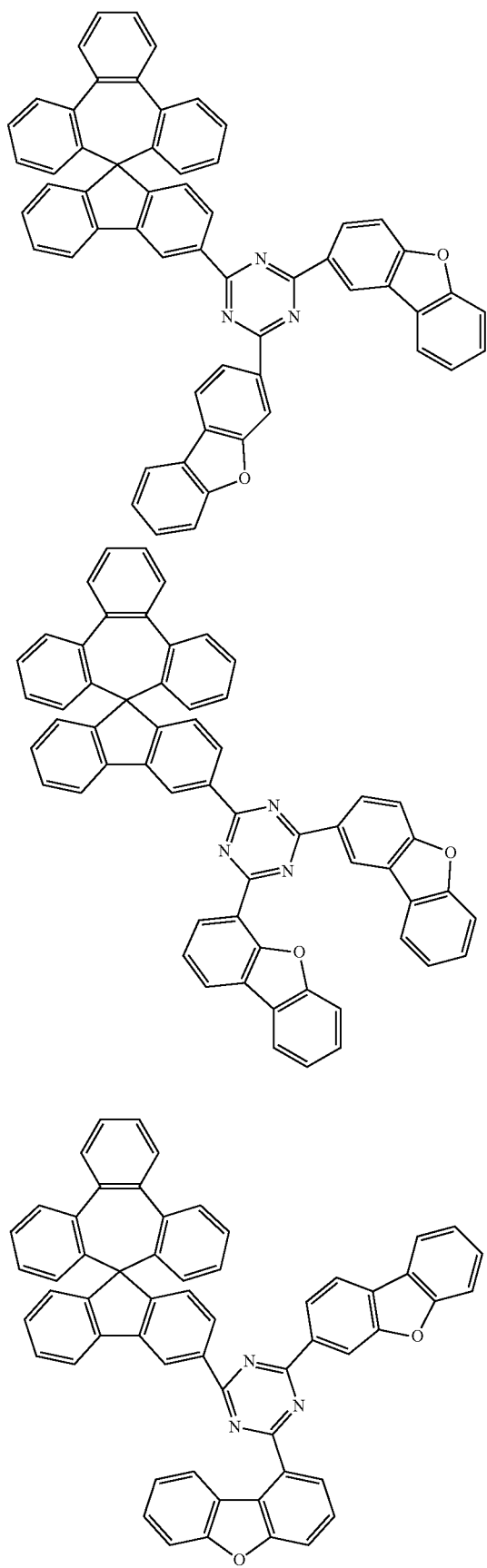
318
-continued
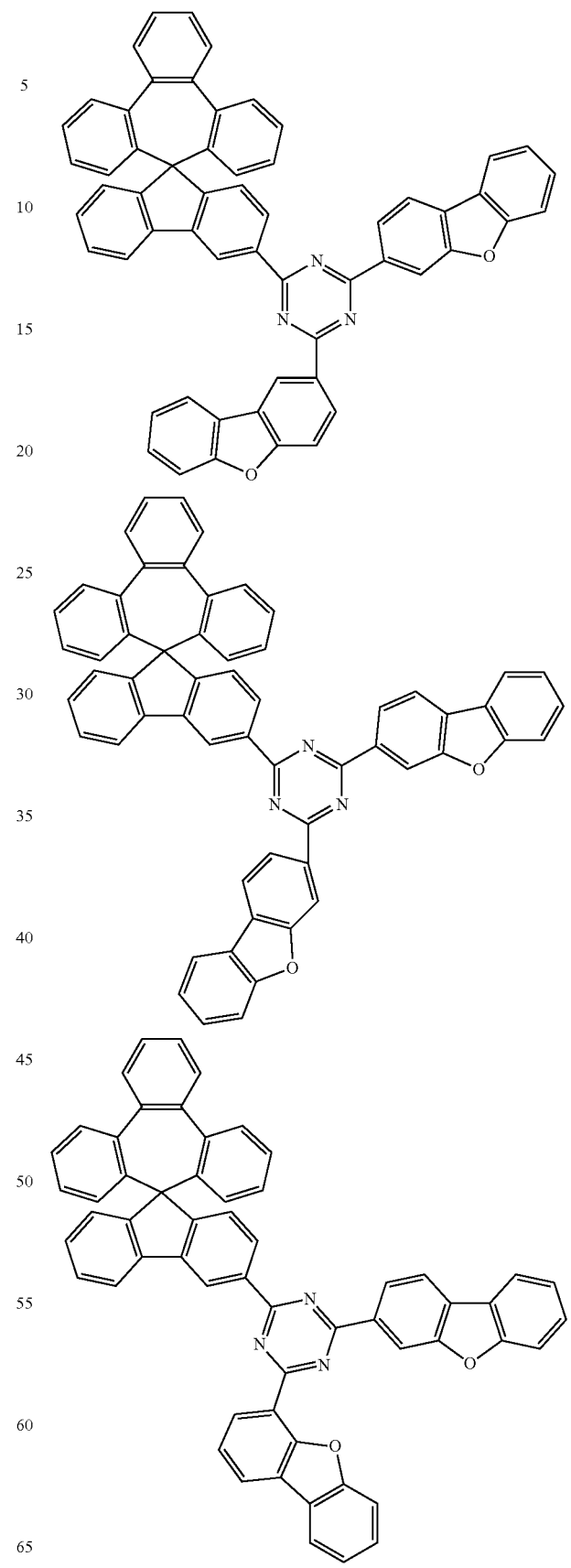

319
-continued
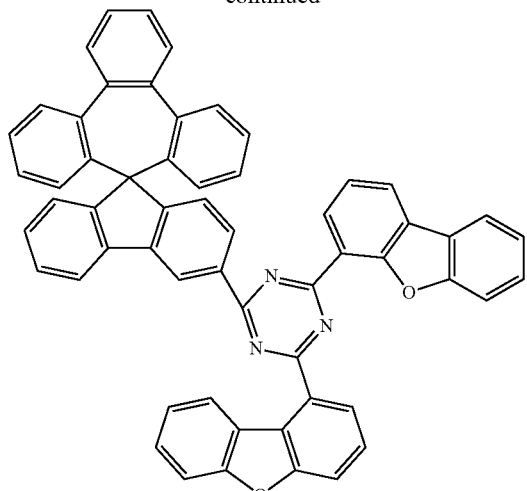
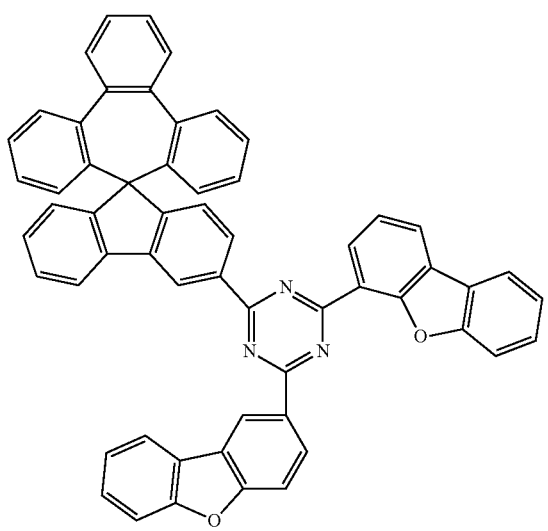
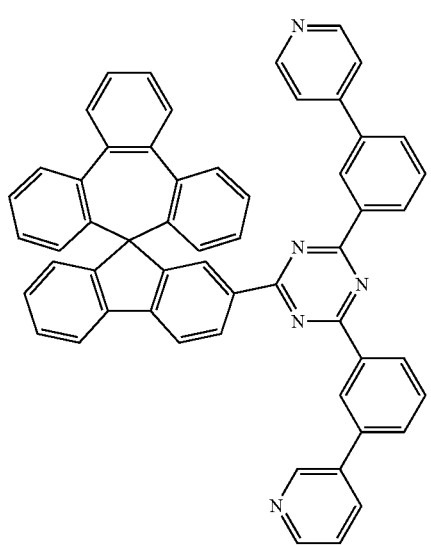
320
-continued
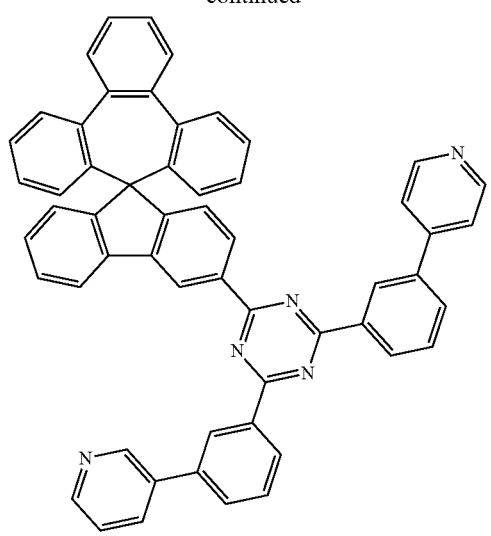
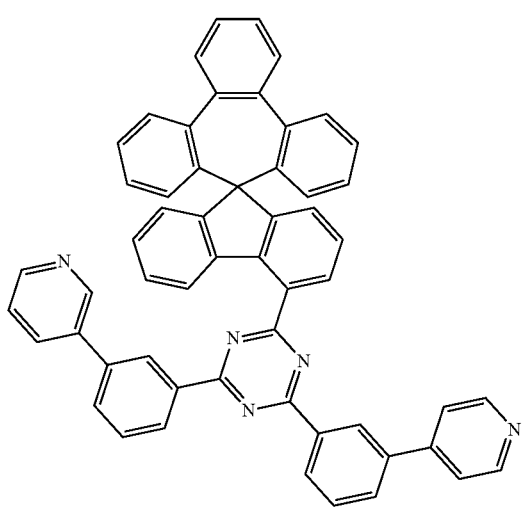
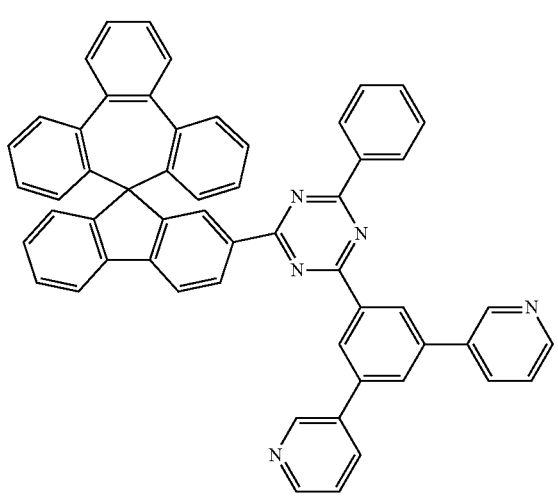

321
-continued
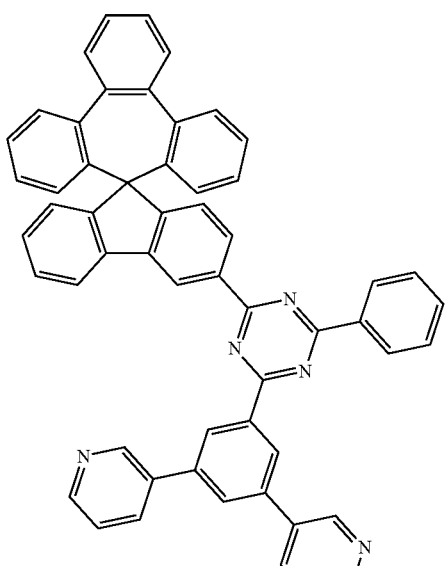
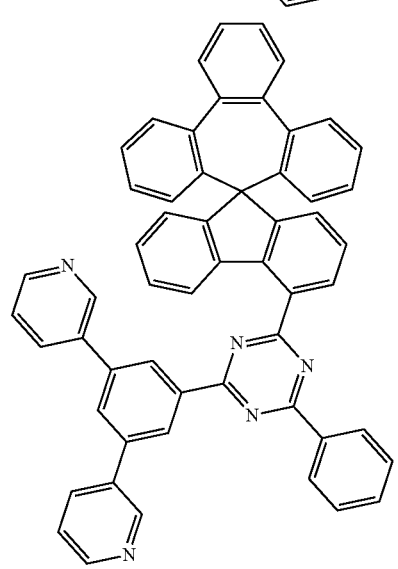
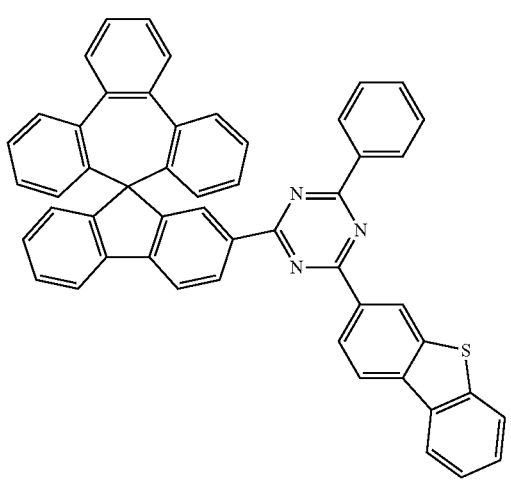
322
-continued
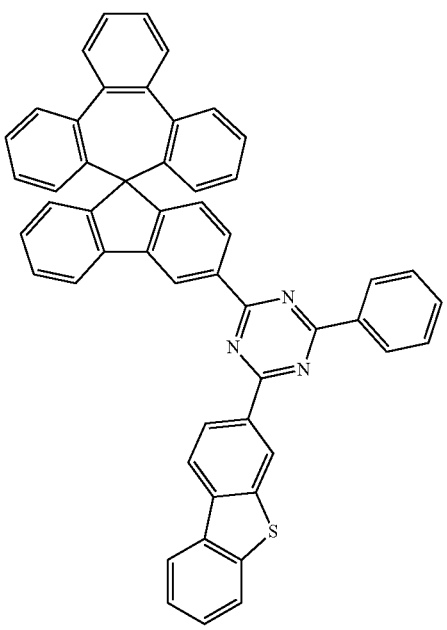
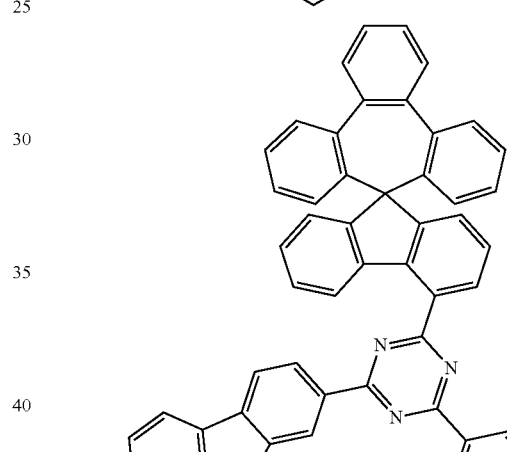
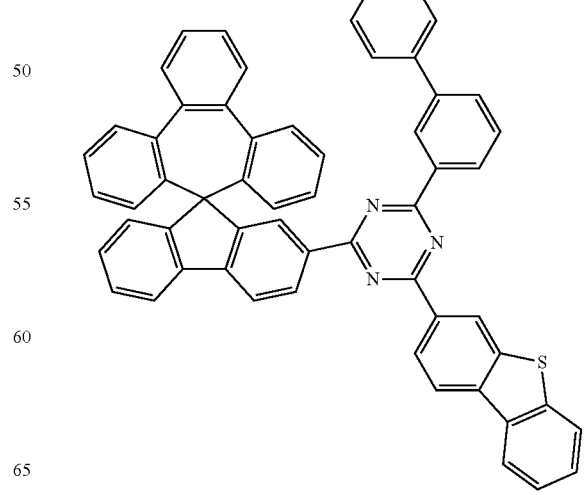

323
-continued
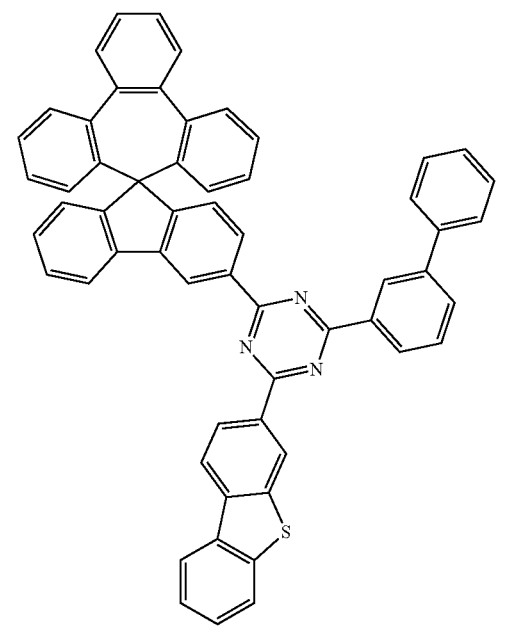
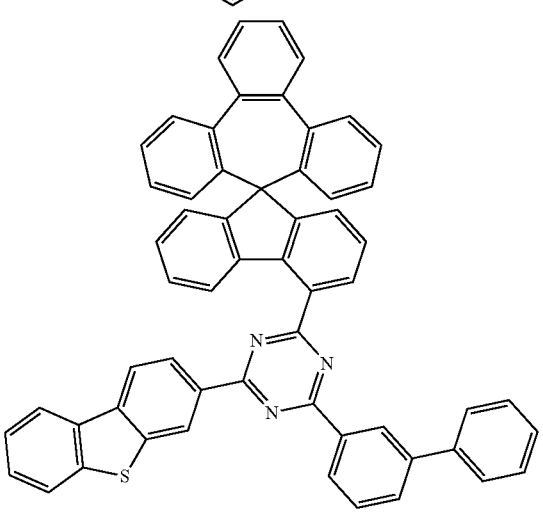
324
-continued
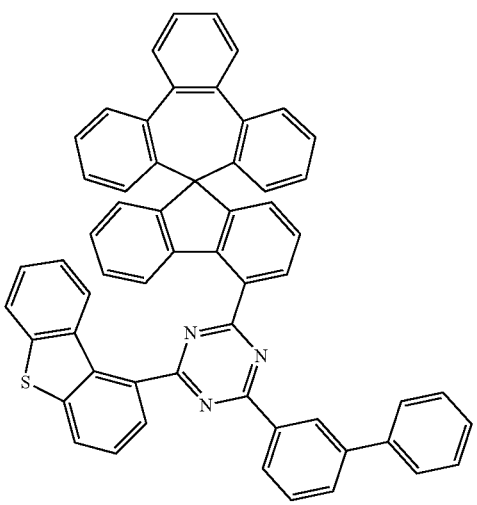
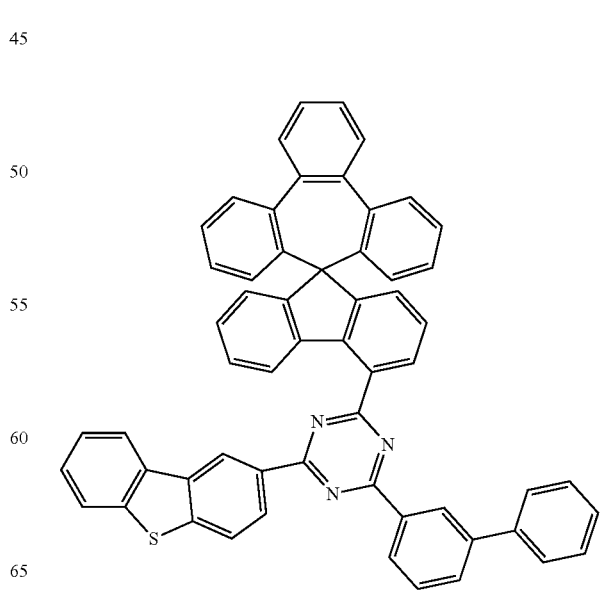

325
-continued
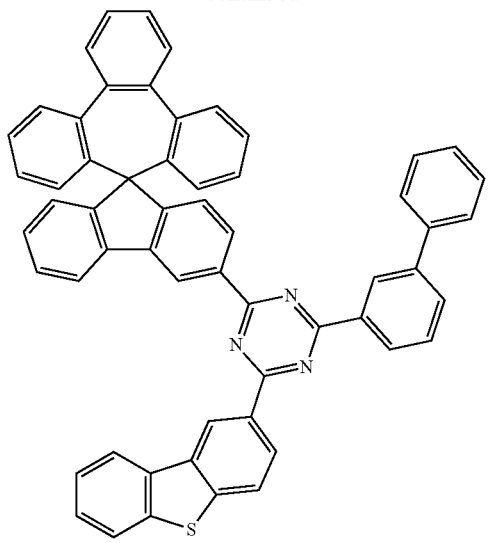
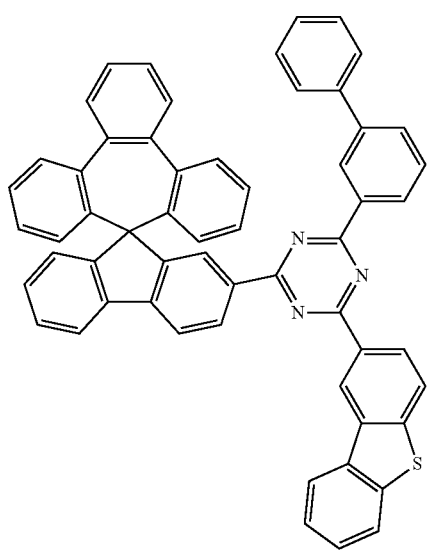
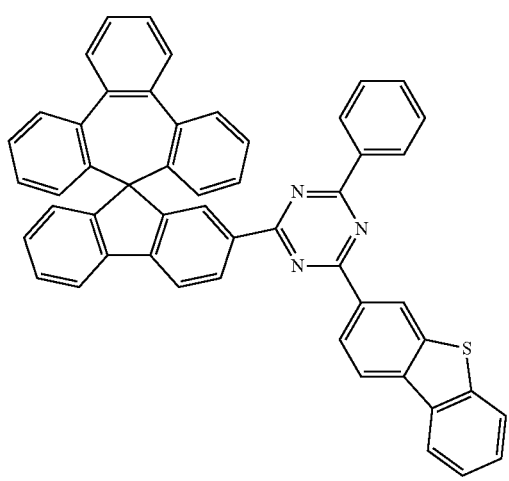
326
-continued
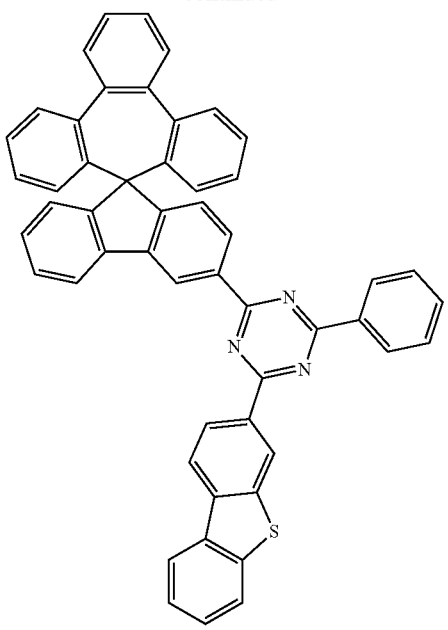
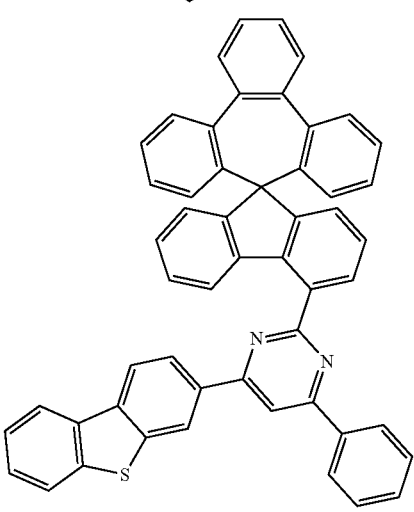
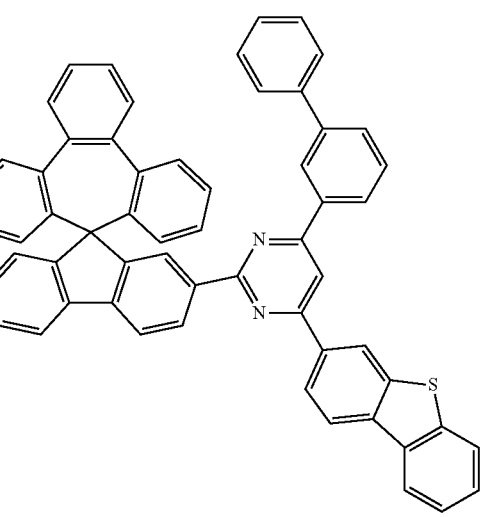

327
-continued
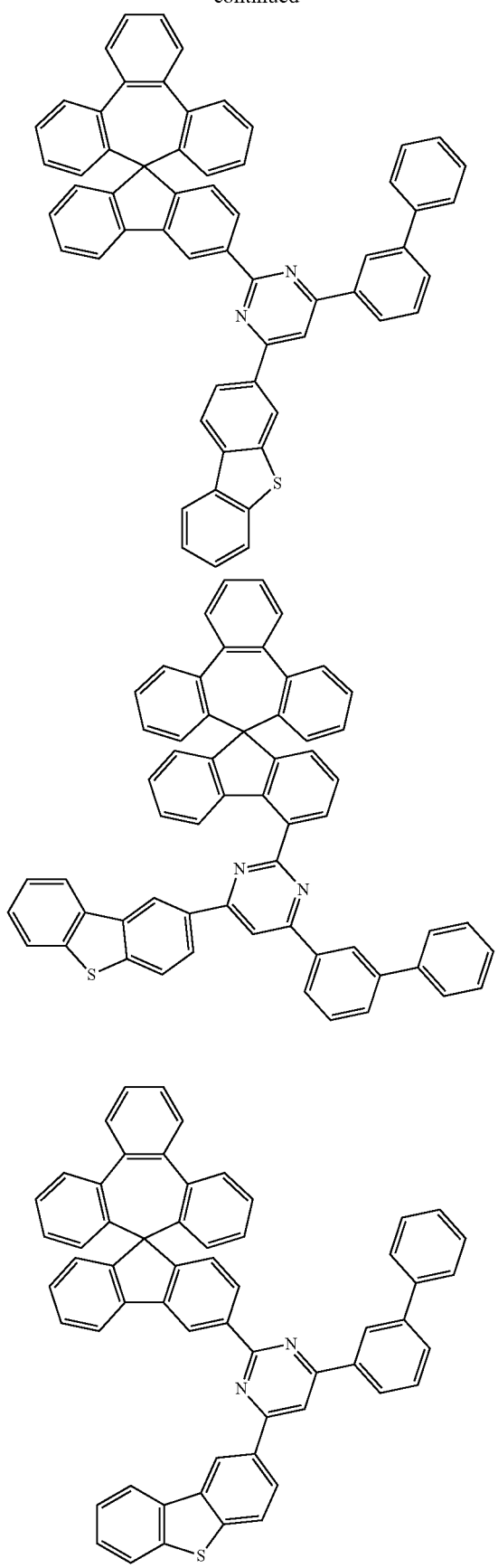
328
-continued
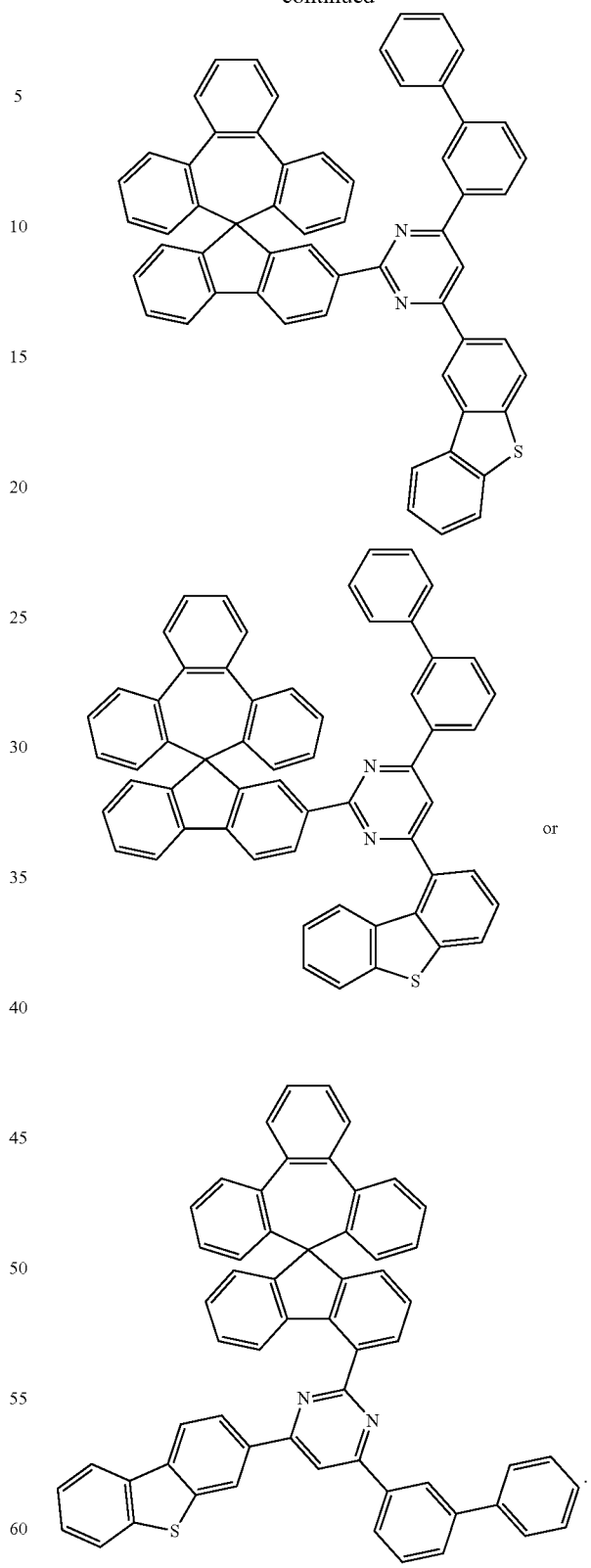
The first host material also may be any one of the compounds disclosed in U.S. Patent Application Publications No. 2017/0213978 A1, No. 2017/0213970 A1, No. 2018/0159044 A1, and No. 2018/0155312 A1.

Preferably, the second host compound may be represented by any one of the following Formulae (II-I) to (II-III):

Formula (II-I)

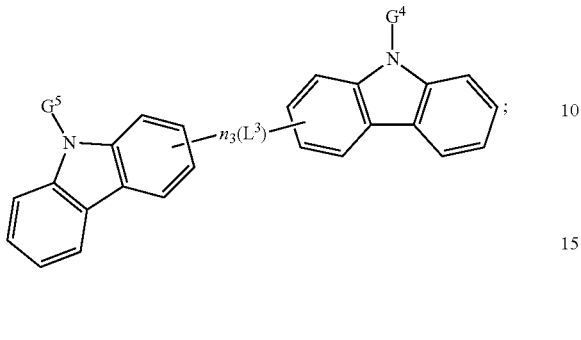

Formula (II-II)

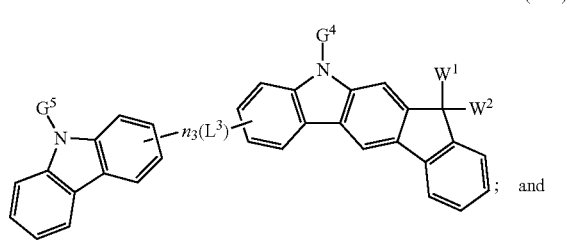
; and

Formula (II-III)

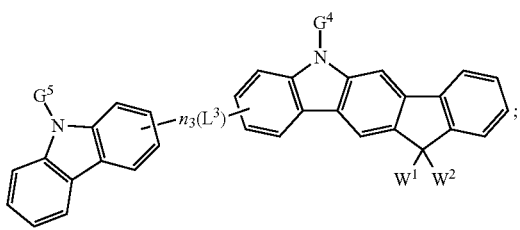

wherein $W^1$ and $W^2$ are each independently a methyl group, an ethyl group, a propyl group, a butyl group or a phenyl group.

For Formula (II-I), both $Q^1$ and $Q^2$ are each a (CH).

For Formulae (II-II) and (II-III), $Q^1$ and $Q^2$ are joined together to form an aryl ring.

Preferably, $L^3$ is a phenylene group.

Preferably, n3 is an integer 0 or 1.

Specifically, $G^4$ and $G^5$ may be a specific aromatic substitution. The specific aromatic substitution may be selected from the group consisting of:

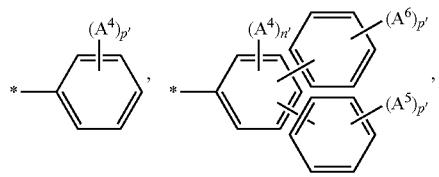

-continued

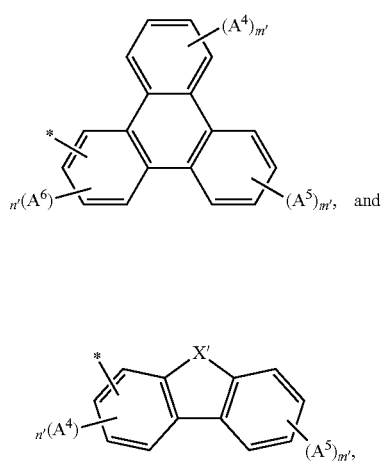
and

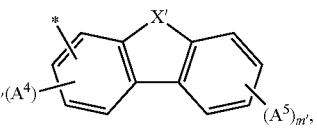

where X' is O, S, or

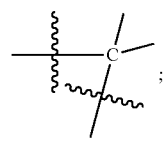 [SMILES: *C(*)(C)C]

wherein * is the bonding site;

p' is an integer from 1 to 5, m' is an integer from 1 to 4, and n' is an integer from 1 to 3; and $A^4$ to $A^6$ are each independently selected from the group consisting of: a hydrogen atom, a deuterium atom, a halo group, a cyano group, a nitro group, an alkyl group having 1 to 6 carbon atoms, an alkenyl group having 2 to 6 carbon atoms, and an alkynyl group having 2 to 6 carbon atoms.

Preferably, the aryl group having 6 to 18 ring carbon atoms represented by $G^4$ or $G^5$ may be selected from the group consisting of: a phenyl group, a biphenylyl group, and a naphthyl group.

More preferably, $G^4$ and $G^5$ are each independently selected from the group consisting of:

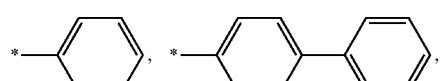

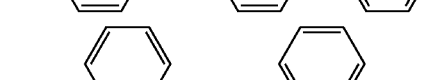

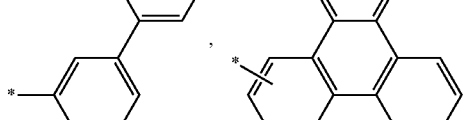
and

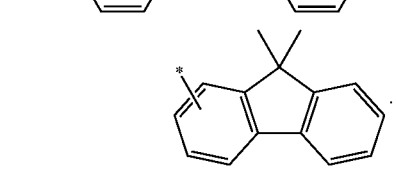

For example, the second host compound may be selected from the group consisting of:
Compound II-1
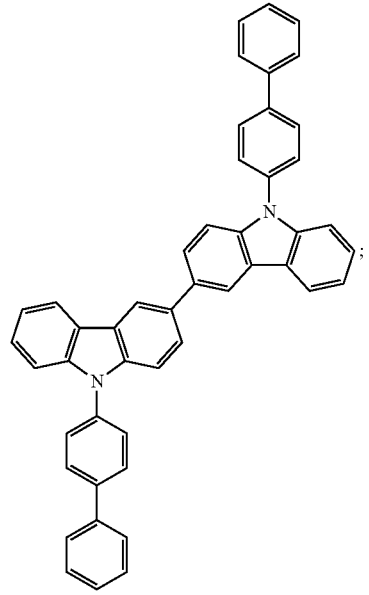
Compound II-2
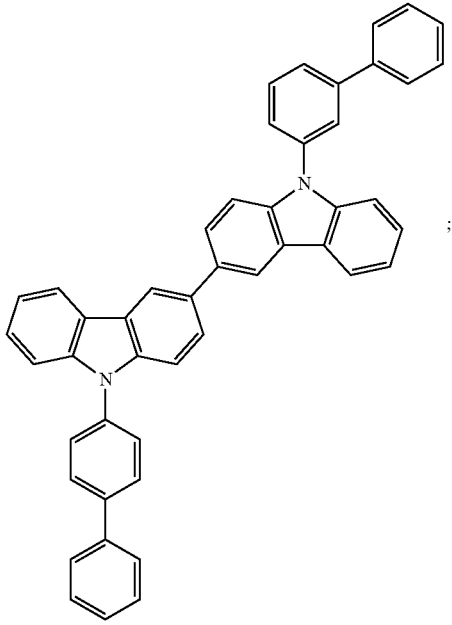
Compound II-3
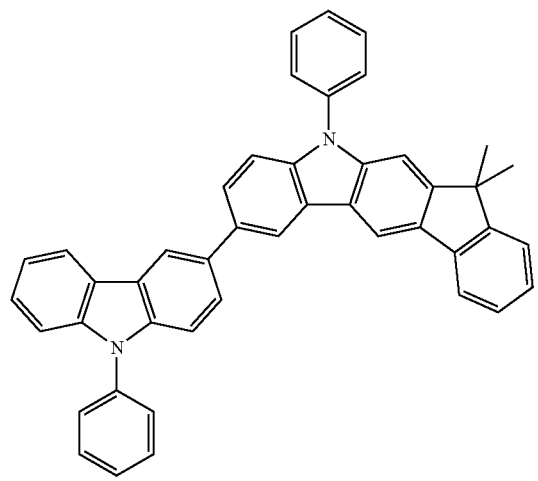
Compound II-4
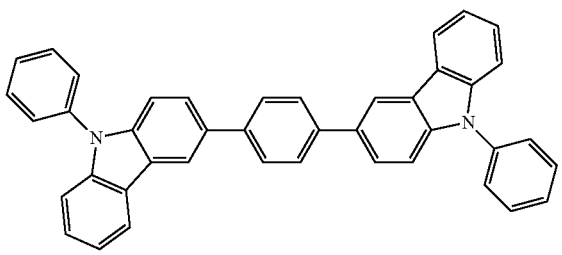

-continued
Compound II-5
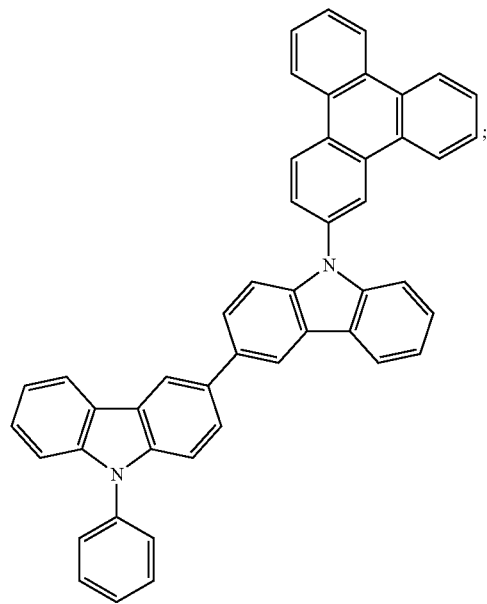
Compound II-6
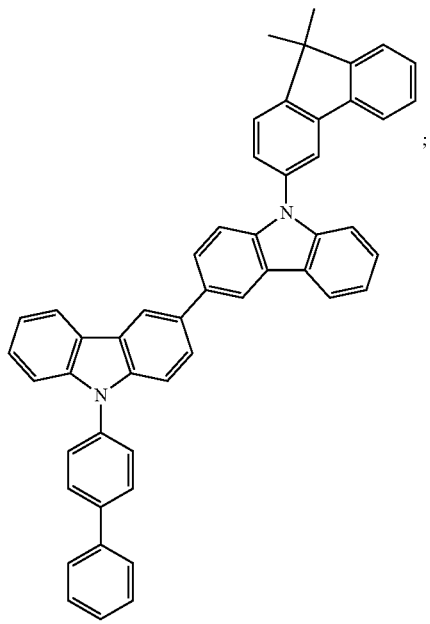
Compound II-7
Compound II-8
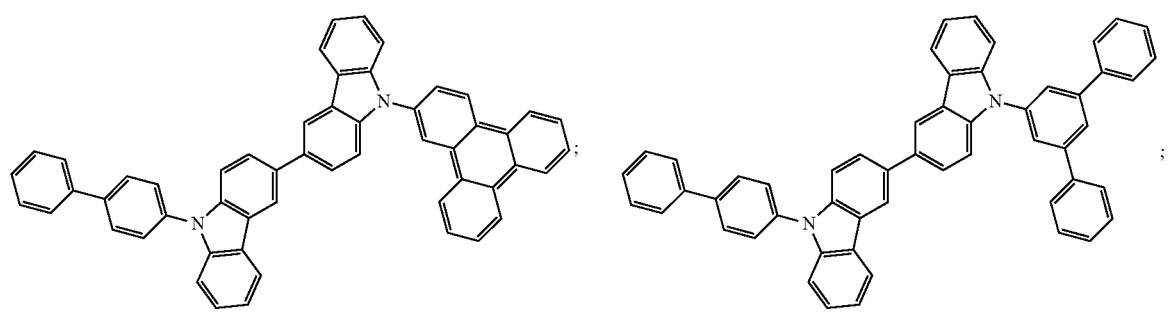
Compound II-9
Compound II-10
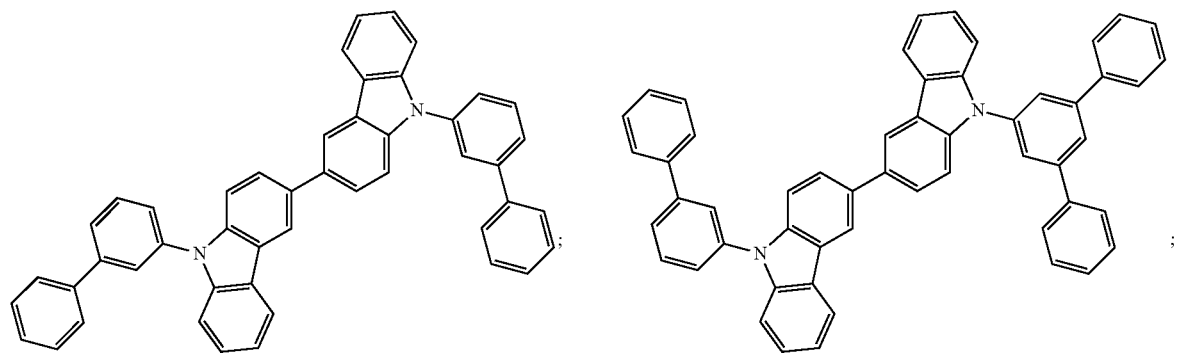

-continued
Compound II-11
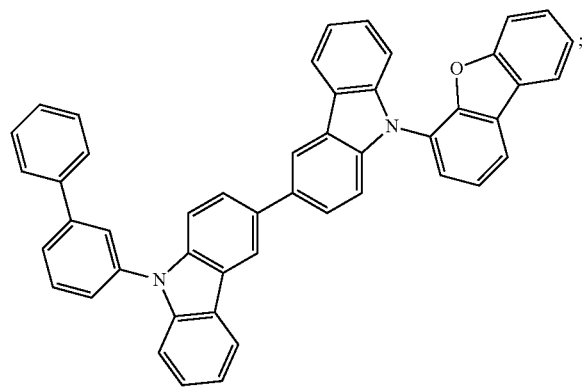
Compound II-12
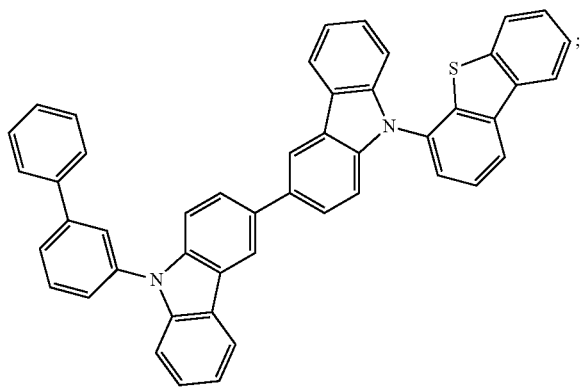
Compound II-13
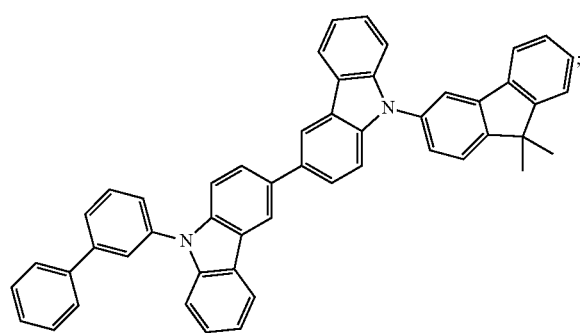
Compound II-14
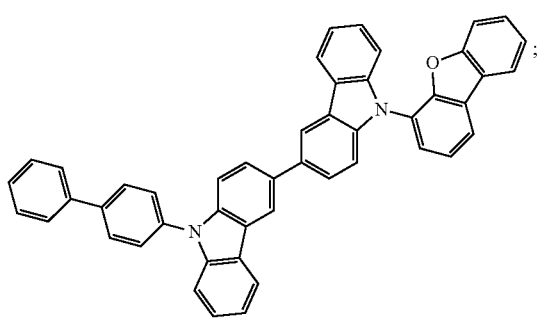
Compound II-15
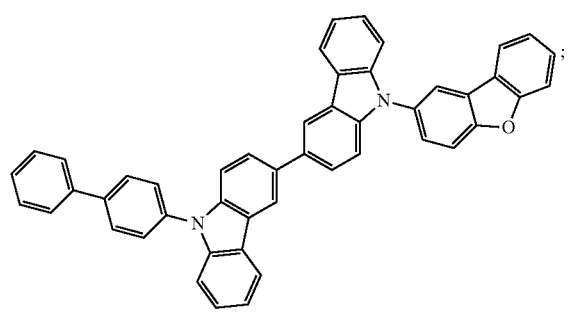
Compound II-16
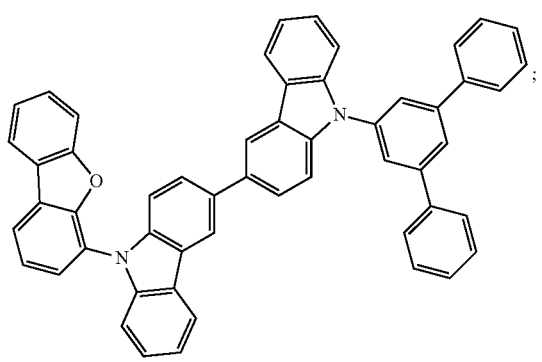
Compound II-17
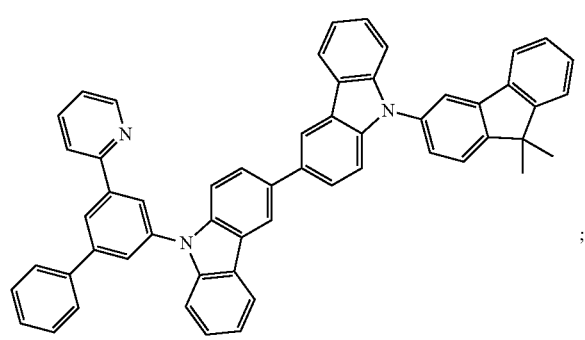
Compound II-18
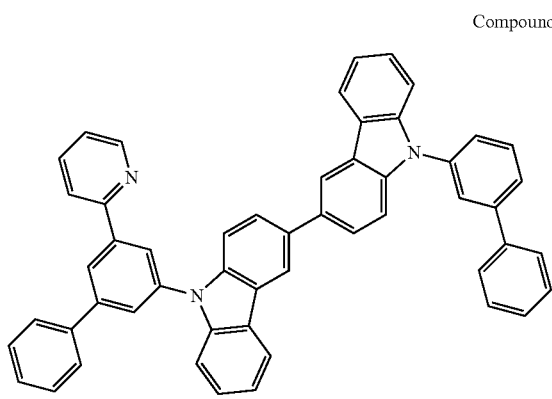

Compound II-19
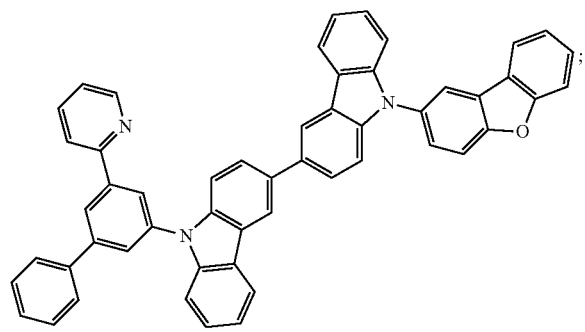
Compound II-20
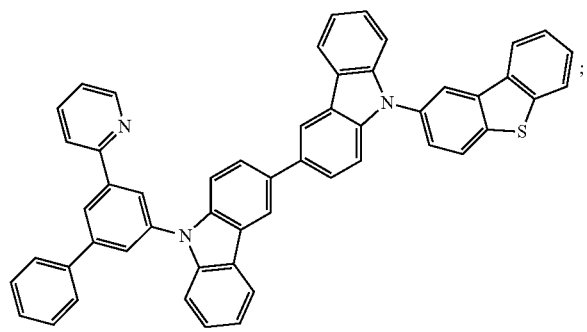
Compound II-21
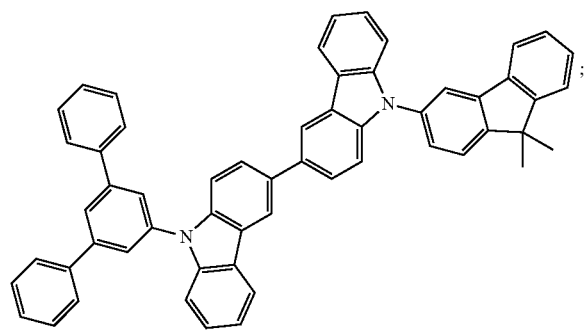
Compound II-22
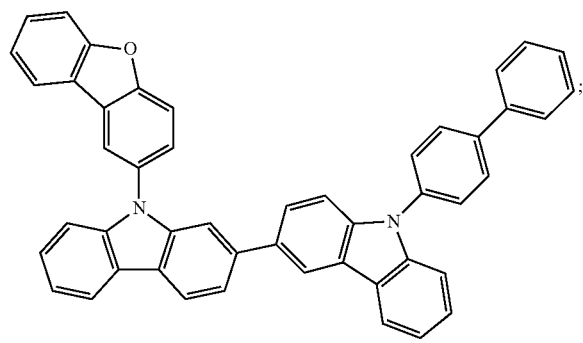
Compound II-23
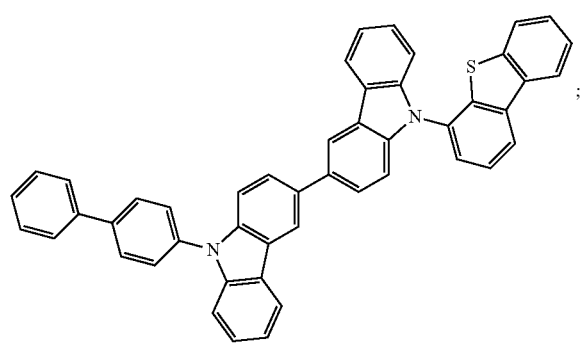
Compound II-24
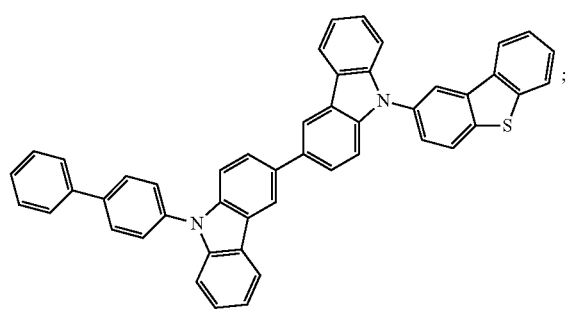
Compound II-25
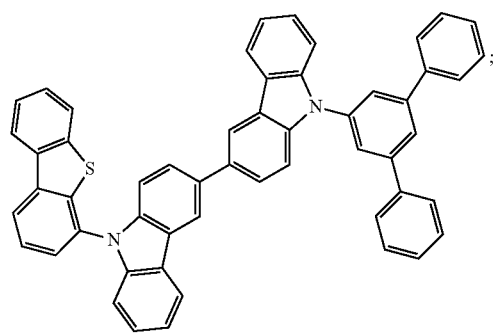

-continued
Compound II-26
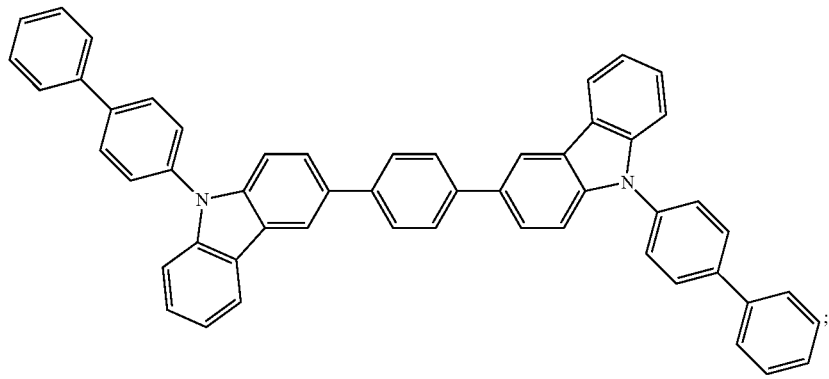
Compound II-27
Compound II-28
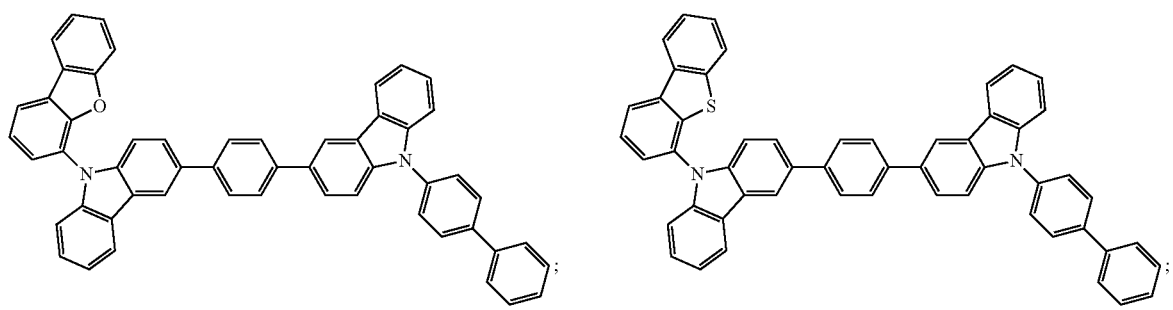
Compound II-29
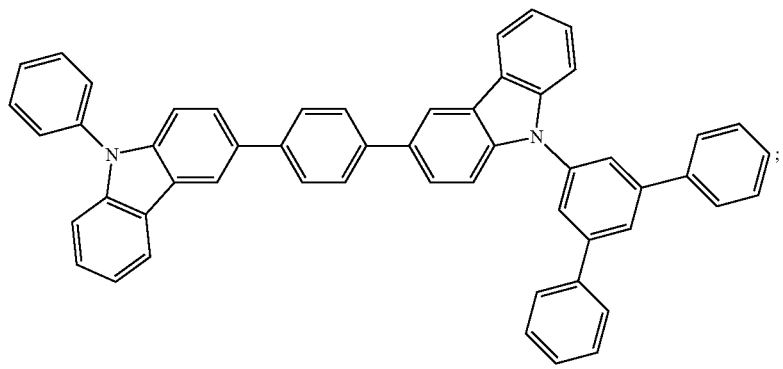
Compound II-30
Compound II-31
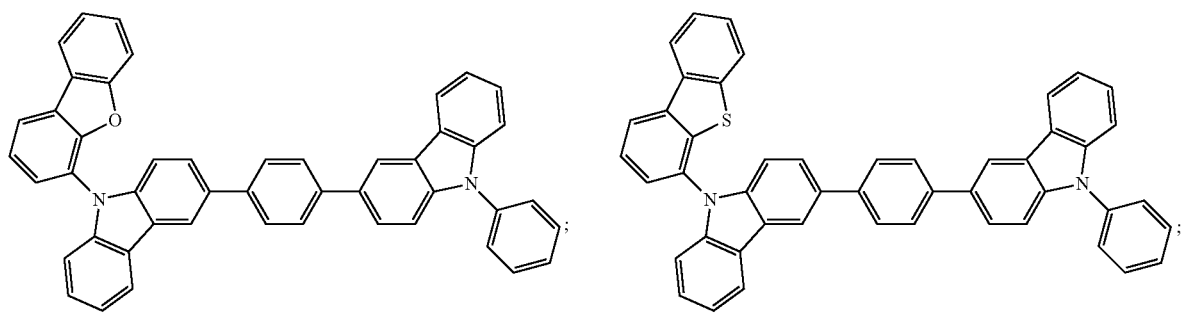

-continued
Compound II-32
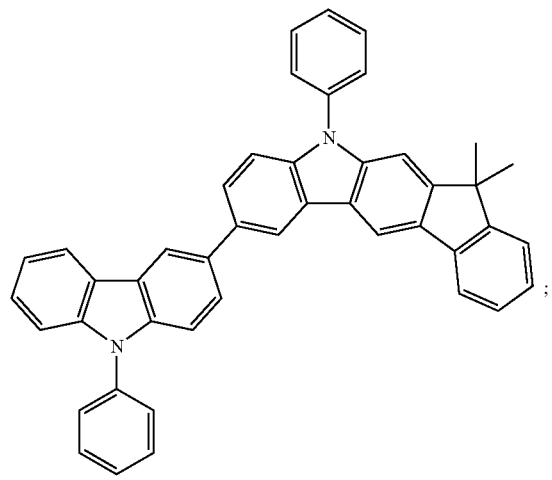
Compound II-33
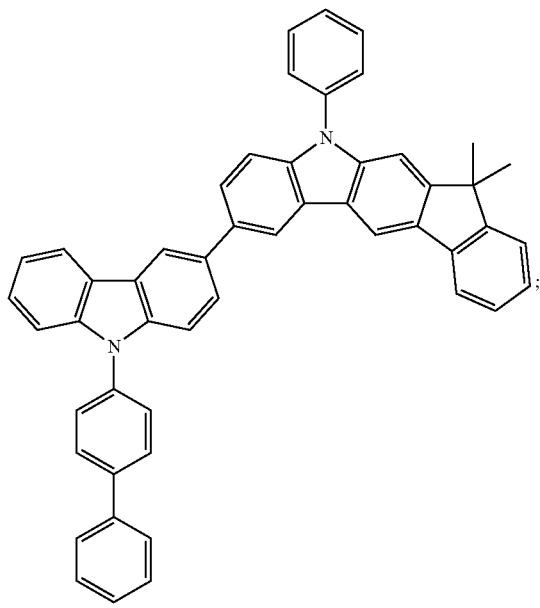
Compound II-34
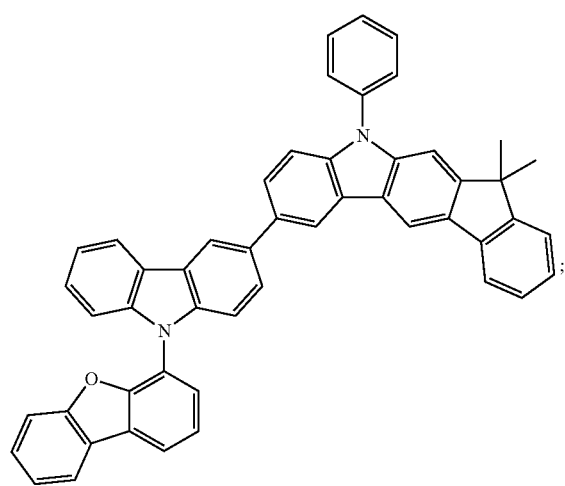
Compound II-35
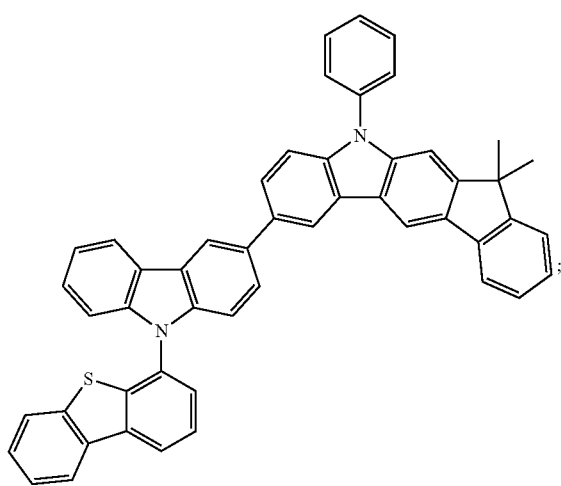

Compound II-36
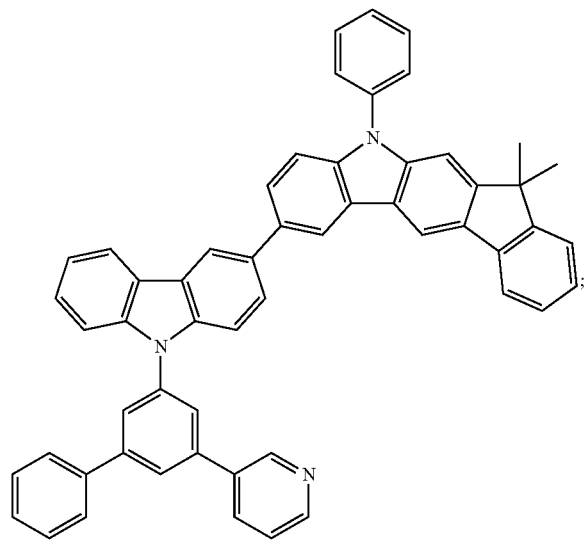
Compound II-37
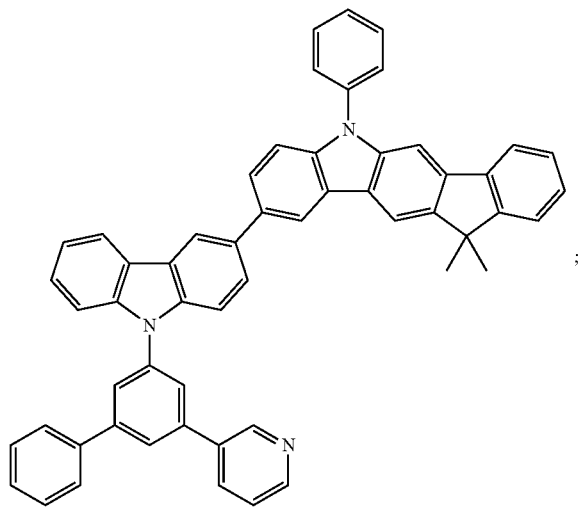
Compound II-38
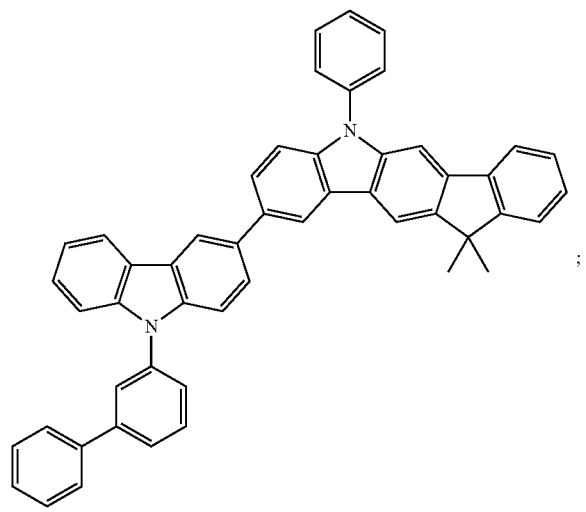
Compound II-39
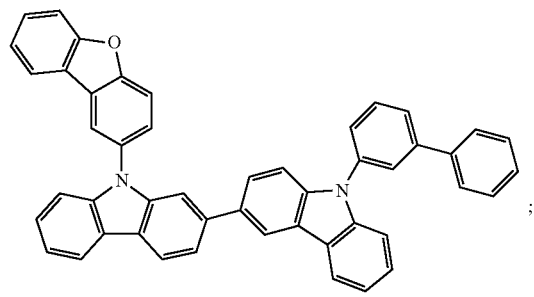

-continued
Compound II-40
Compound II-41
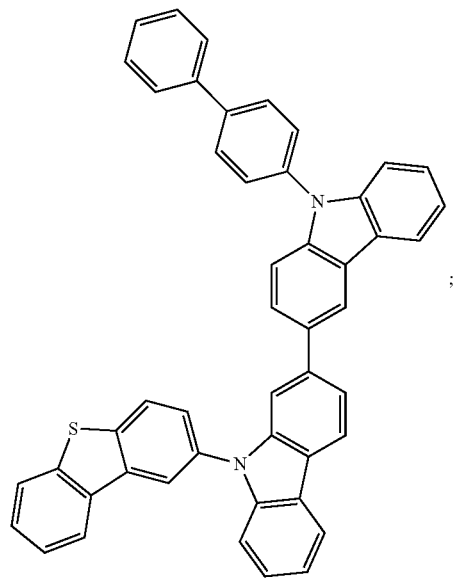
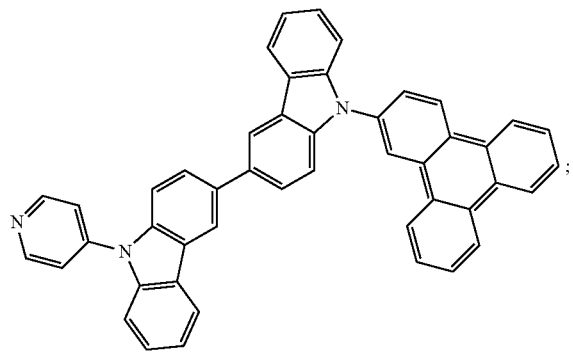
Compound II-42
Compound II-43
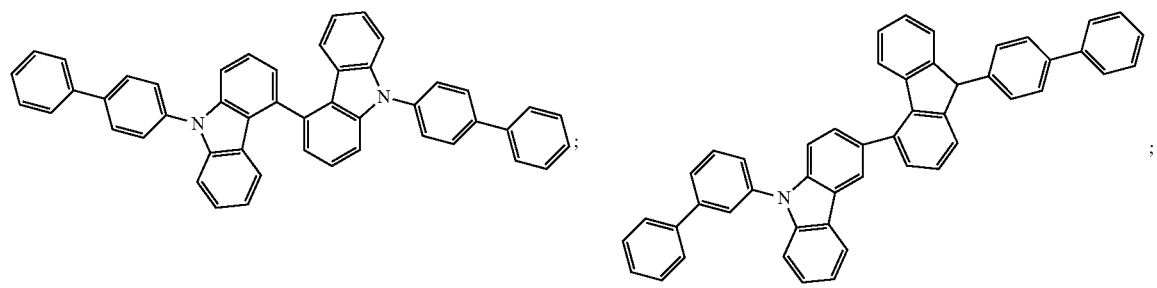
Compound II-44
Compound II-45
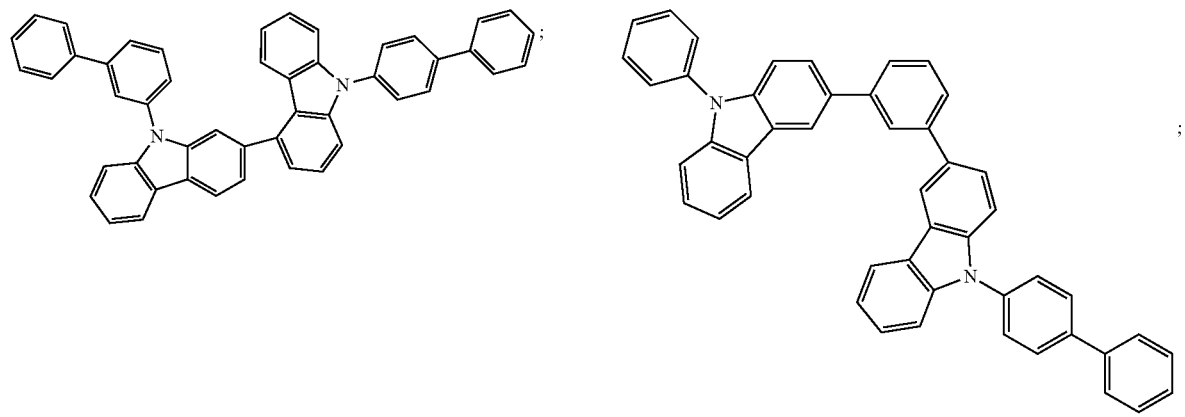

Compound II-46

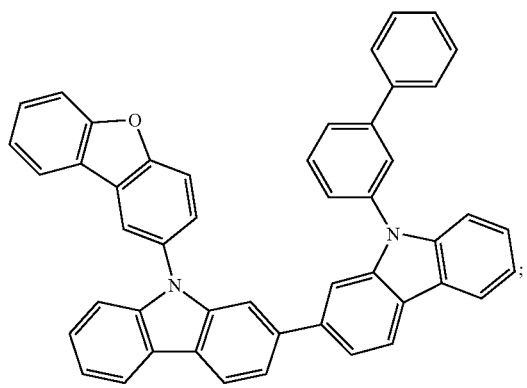

Compound II-47

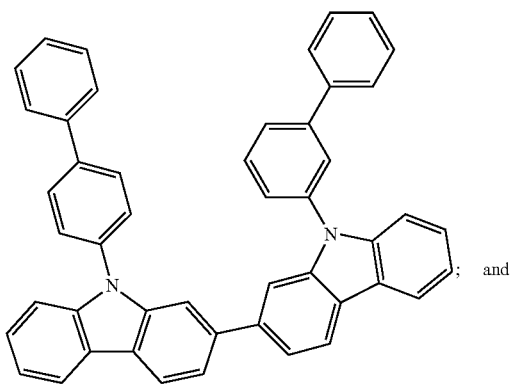
; and

Compound II-48

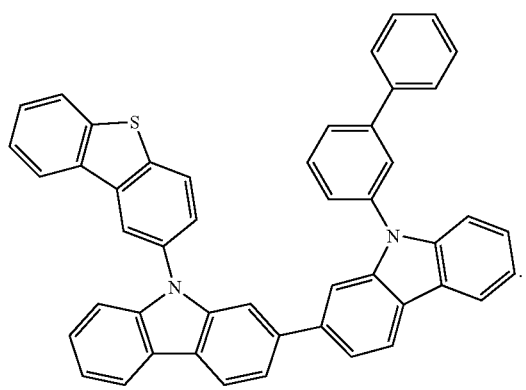

In accordance with the present invention, a weight ratio of the first and second host compounds ranges from 3:7 to 7:3. Preferably, the weight ratio of the first and second host compounds ranges from 4:6 to 6:4. In some cases, the weight ratio of the first and second host compounds ranges from 4.5:5.5 to 5.5:4.5.

In this specification, said "arylene group having 6 to 18 ring carbon atoms" denoted by L', $L^1$, $L^2$, or $L^3$ may be an unsubstituted arylene group having 6 to 18 ring carbon atoms or an arylene group having 6 to 18 ring carbon atoms substituted with at least one substituent except for a hydrogen atom. The at least one substituent on the arylene group may be selected from the group consisting of: a deuterium atom, a halo group, a cyano group, a nitro group, an alkyl group having 1 to 12 carbon atoms, an alkenyl group having 2 to 12 carbon atoms, an alkynyl group having 2 to 12 carbon atoms, an alkoxy group having 1 to 12 carbon atoms.

In this specification, said "aryl group" may be an unsubstituted aryl group or an aryl group substituted with at least one substituent except for a hydrogen atom; said "heteroaryl group" may be an unsubstituted heteroaryl group or a heteroaryl group substituted with at least one substituent except for a hydrogen atom. Similarly, said "aryloxy group" may be an unsubstituted aryloxy group or an aryloxy group substituted with at least one substituent except for a hydrogen atom; said "arylthioxy" may be an unsubstituted arylthioxy group or an arylthioxy group substituted with at least one substituent except for a hydrogen atom.

The at least one substituent on the aryl group may be selected from the group consisting of: a deuterium atom, a halo group, a cyano group, a nitro group, an alkyl group having 1 to 12 carbon atoms, an alkenyl group having 2 to 12 carbon atoms, an alkynyl group having 2 to 12 carbon atoms, and an alkoxy group having 1 to 12 carbon atoms. The substituent on the heteroaryl group, aryloxy group, or arylthioxy group may be similar to any one of the at least one substituent on the aryl group as stated above.

In this specification, said "alkyl group" may be an unsubstituted alkyl group or an alkyl group substituted with at least one substituent except for a hydrogen atom, said "alkenyl group" may be an unsubstituted alkenyl group or an alkenyl group substituted with at least one substituent except for a hydrogen atom, and said "alkynyl group" may be an unsubstituted alkynyl group or an alkynyl group substituted with at least one substituent except for a hydrogen atom. The substituent on the alkyl group, alkenyl group, or alkynyl group may be, for example, but not limited to a deuterium atom.

The present invention also provides an organic electronic device, comprising a first electrode, a second electrode, and an organic layer disposed between the first electrode and the second electrode. The organic layer comprises the composition as described above.

Preferably, the organic electronic device is an organic light emitting device (OLED). More preferably, the organic electronic device is a green organic electronic device or a red organic electronic device. Preferably, the composition of the present invention may be used as a host material of EL, especially as a host material for green or red OLEDs, but it is not limited thereto.

Specifically, the organic light emitting device may comprise:
a hole injection layer formed on the first electrode;
a hole transport layer formed on the hole injection layer;
an emission layer formed on the hole transport layer;
an electron transport layer formed on the emission layer;
an electron injection layer formed between the electron transport layer and the second electrode.

In one embodiment, the organic layer may be the emission layer, i.e., the emission layer comprises a first host material which is the composition comprising the first and second host compounds as stated above.

For example, the emission layer may be a single-layered configuration or a multi-layered configuration. When the emission layer is the multi-layered configuration, e.g., the emission layer comprises a first emission layer and a second emission layer, the first host material of the first emission layer may be made of the single aforesaid composition and the second host material of the second emission layer may be made of another single aforesaid composition or any single conventional compound.

Preferably, the emission layer comprises the composition containing the first host compound such as Compounds I-1 to I-75 and the second host compound such as Compound II-1 to II-48. The OLEDs using the composition as the host material can reduce the driving voltage and improve the current efficiency.

In another embodiment, the emission layer may further comprise a dopant.

For green OLEDs, the dopant of the emission material is, for example, but not limited to: diaminofluorenes; diaminoanthracenes; or organometallic compounds of iridium (II) having phenylpyridine ligands. For red OLEDs, the dopant of the emission material is, for example, but not limited to: organometallic compounds of iridium (II) having quinoline ligands, isoquinoline ligands, fluoranthene ligands or periflanthene ligands. With various host materials of the emission layer as stated above, the OLED can emit lights in green or red.

Preferably, the hole injection layer may be a two-layered structure, i.e., the OLED comprises a first hole injection layer and a second hole injection layer disposed between the first electrode and the hole transport layer.

Said first and second hole injection layers may be made of, for example, but not limited to, polyaniline or polyethylenedioxythiophene.

Preferably, the hole transport layer may be a two-layered structure, i.e., the OLED comprises a first hole transport layer and a second hole transport layer disposed between the two-layered hole injection layer and the emission layer.

Said first and second hole transport layers may be made of, for example, but not limited to: $N^1,N^{1'}$-(biphenyl-4,4'-diyl)bis($N^1$-(naphthalen-1-yl)-$N^4,N^{4'}$-diphenylbenzene-1,4-diamine); or $N^4,N^{4'}$-di(naphthalen-1-yl)-$N^4,N^{4'}$-diphenylbiphenyl-4,4'-diamine (NPB).

Preferably, the OLED comprises a hole blocking layer formed between the electron transport layer and the emission layer, to block holes overflow from the emission layer to the electron transport layer. Said hole blocking layer may be made of 2,9-dimethyl-4,7-diphenyl-1,10-phenanthroline (BCP) or 2,3,5,6-tetramethyl-phenyl-1,4-(bis-phthalimide) (TMPP), but it is not limited thereto.

Preferably, the OLED comprises an electron blocking layer formed between the hole transport layer and the emission layer, to block electrons overflow from the emission layer to the hole transport layer. Said electron blocking layer may be made of 9,9'[1,1'-biphenyl]-4,4'-diylbis-9H-carbazole (CBP) or 4,4',4"-tri(N-carbazolyl)-triphenylamine (TCTA), but it is not limited thereto.

In the presence of such a hole blocking layer and/or an electron blocking layer in an OLED, the OLED has a higher luminous efficiency compared to a conventional OLED.

Preferably, the electron transport layer is made of 3,3'-[5-[3-(3-Pyridinyl)phenyl][1,1':3',1"-terphenyl]-3,3"-diyl]bispyridine (TmPyPb), 3-(Biphenyl-4-yl)-5-(4-tert-butylphenyl)-4-phenyl-4H-1,2,4-triazole (TAZ), tris(2,4,6-trimethyl-3-(pyridin-3-yl)phenyl)borane (3TPYMB), 1,3-bis(3,5-dipyrid-3-yl-phenyl)benzene (BmPyPb), or 9,10-bis(3-(pyridin-3-yl)phenyl)anthracene (DPyPA), but it is not limited thereto.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
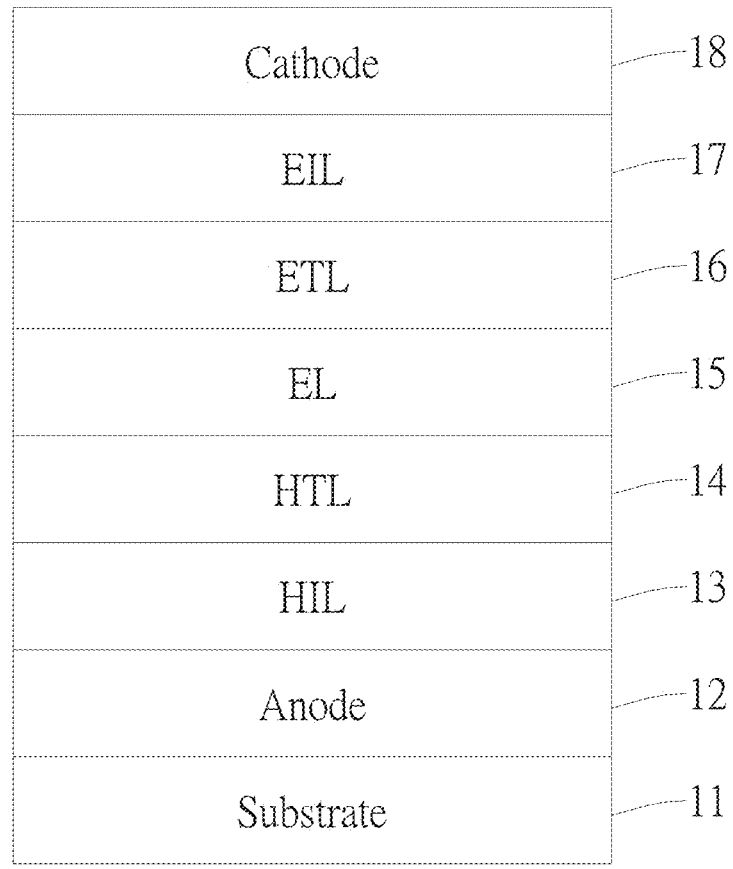
FIG. 1 illustrates a schematic cross-sectional view of an OLED.

Hereinafter, one skilled in the arts can easily realize the advantages and effects of a composition for an organic electronic device and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

First Host Compound of a Composition for an Organic Electronic Device
TABLE 1
chemical structures of the first host compounds
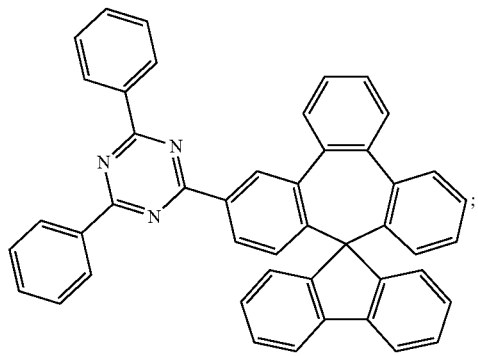 [SMILES: c1ccc(-c2nc(-c3ccccc3)nc(-c3ccc4c(c3)-c3ccccc3-c3ccccc3C43c4ccccc4-c4ccccc43)n2)cc1]
Compound I-1
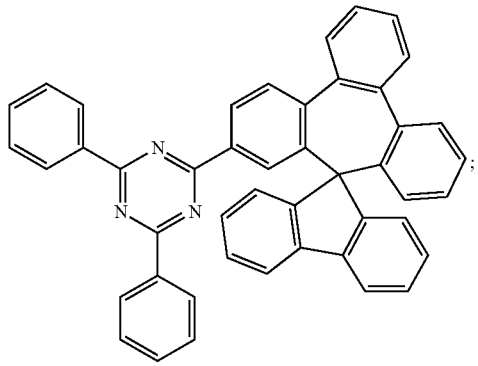 [SMILES: c1ccc(-c2nc(-c3ccccc3)nc(-c3ccc4c(c3)C3(c5ccccc5-c5ccccc5-4)c4ccccc4-c4ccccc43)n2)cc1]
Compound I-2
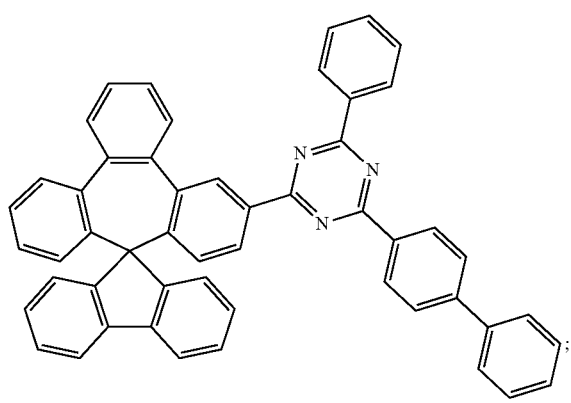 [SMILES: c1ccc(-c2ccc(-c3nc(-c4ccccc4)nc(-c4ccc5c(c4)-c4ccccc4-c4ccccc4C54c5ccccc5-c5ccccc54)n3)cc2)cc1]
Compound I-3

TABLE 1-continued
chemical structures of the first host compounds
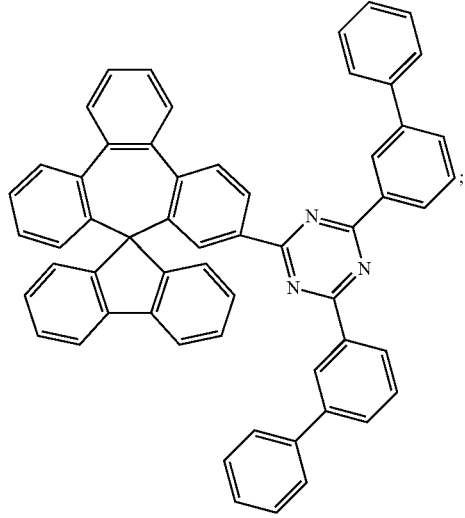 [SMILES: c1ccc(-c2cccc(-c3nc(-c4cccc(-c5ccccc5)c4)nc(-c4ccc5c(c4)C4(c6ccccc6-c6ccccc6-5)c5ccccc5-c5ccccc54)n3)c2)cc1]
Compound I-4
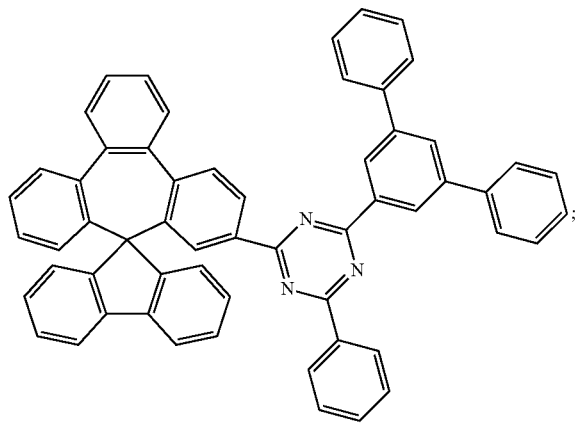 [SMILES: c1ccc(-c2cc(-c3ccccc3)cc(-c3nc(-c4ccccc4)nc(-c4ccc5c(c4)C4(c6ccccc6-c6ccccc6-5)c5ccccc5-c5ccccc54)n3)c2)cc1]
Compound I-5
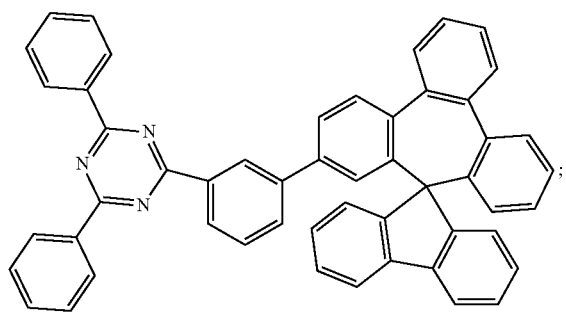 [SMILES: c1ccc(-c2nc(-c3ccccc3)nc(-c3cccc(-c4ccc5c(c4)C4(c6ccccc6-c6ccccc6-5)c5ccccc5-c5ccccc54)c3)n2)cc1]
Compound I-6

TABLE 1-continued
chemical structures of the first host compounds
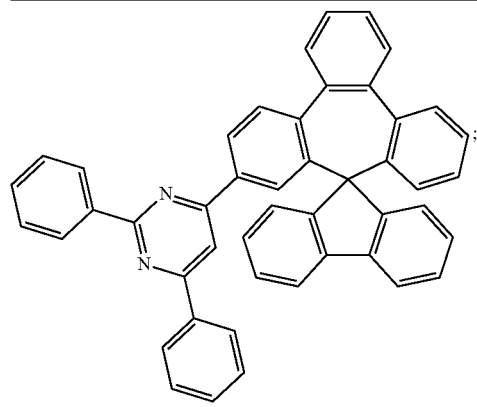
Compound I-7
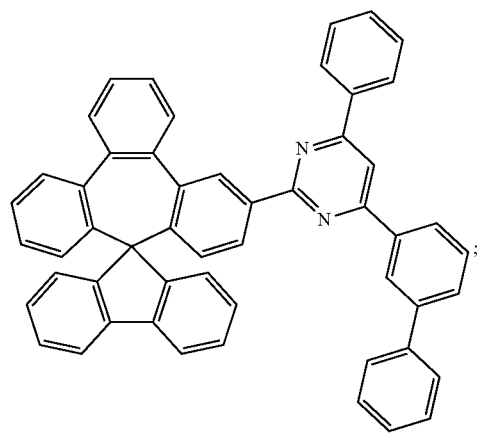 [SMILES: c1ccc(-c2cccc(-c3cc(-c4ccccc4)nc(-c4ccc5c(c4)-c4ccccc4-c4ccccc4C54c5ccccc5-c5ccccc54)n3)c2)cc1]
Compound I-8
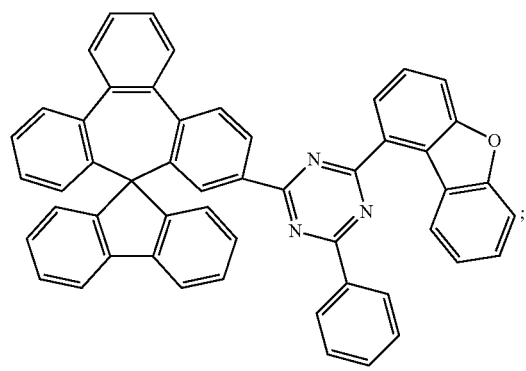 [SMILES: c1ccc(-c2nc(-c3ccc4c(c3)C3(c5ccccc5-c5ccccc5-4)c4ccccc4-c4ccccc43)nc(-c3cccc4oc5ccccc5c34)n2)cc1]
Compound I-9
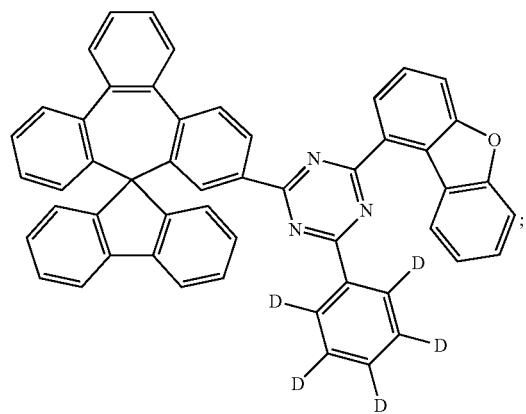 [SMILES: [2H]c1c([2H])c([2H])c(-c2nc(-c3ccc4c(c3)C3(c5ccccc5-c5ccccc5-4)c4ccccc4-c4ccccc43)nc(-c3cccc4oc5ccccc5c34)n2)c([2H])c1[2H]]
Compound I-10

TABLE 1-continued
chemical structures of the first host compounds
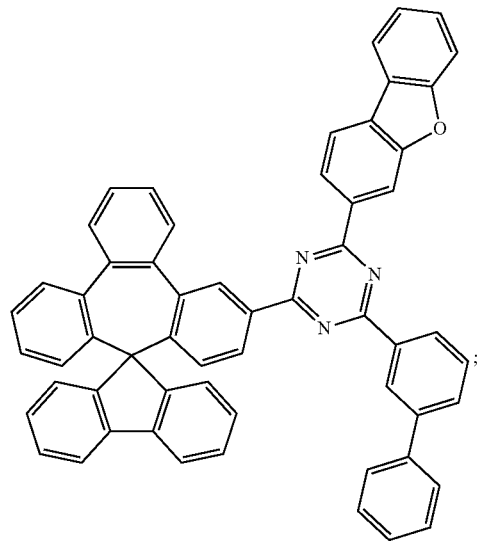 [SMILES: c1ccc(-c2cccc(-c3nc(-c4ccc5c(c4)-c4ccccc4-c4ccccc4C54c5ccccc5-c5ccccc54)nc(-c4ccc5c(c4)oc4ccccc45)n3)c2)cc1]
Compound I-11
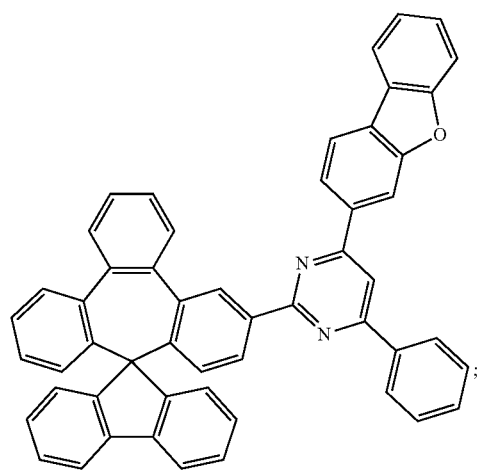 [SMILES: c1ccc(-c2cc(-c3ccc4c(c3)oc3ccccc34)nc(-c3ccc4c(c3)-c3ccccc3-c3ccccc3C43c4ccccc4-c4ccccc43)n2)cc1]
Compound I-12
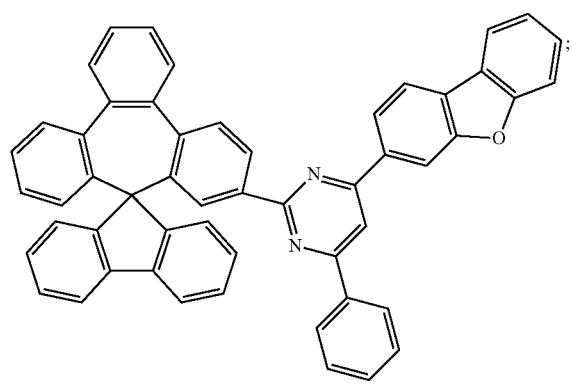 [SMILES: c1ccc(-c2cc(-c3ccc4c(c3)oc3ccccc34)nc(-c3ccc4c(c3)C3(c5ccccc5-c5ccccc5-4)c4ccccc4-c4ccccc43)n2)cc1]
Compound I-13

TABLE 1-continued
chemical structures of the first host compounds
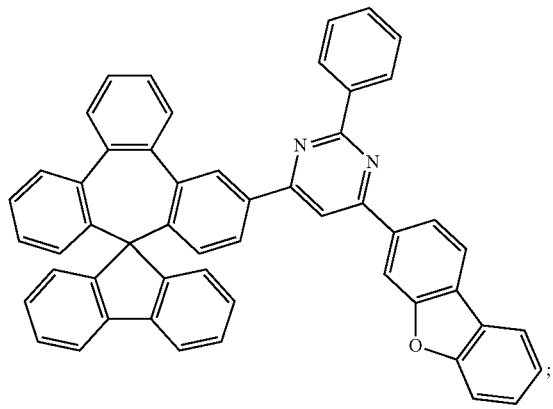 [SMILES: c1ccc(-c2nc(-c3ccc4c(c3)-c3ccccc3-c3ccccc3C43c4ccccc4-c4ccccc43)cc(-c3ccc4c(c3)oc3ccccc34)n2)cc1]
Compound I-14
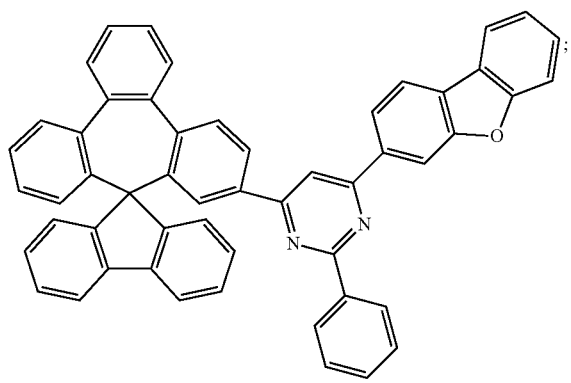 [SMILES: c1ccc(-c2nc(-c3ccc4c(c3)C3(c5ccccc5-c5ccccc5-4)c4ccccc4-c4ccccc43)cc(-c3ccc4c(c3)oc3ccccc34)n2)cc1]
Compound I-15
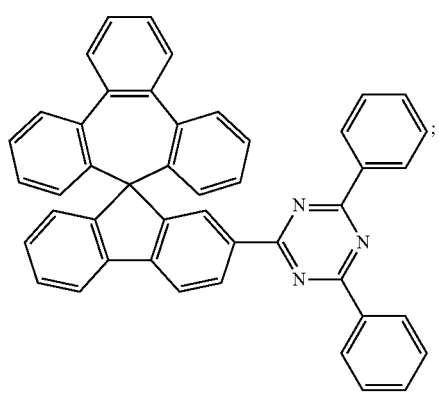 [SMILES: c1ccc(-c2nc(-c3ccccc3)nc(-c3ccc4c(c3)C3(c5ccccc5-c5ccccc5-c5ccccc53)c3ccccc3-4)n2)cc1]
Compound I-16

TABLE 1-continued
chemical structures of the first host compounds
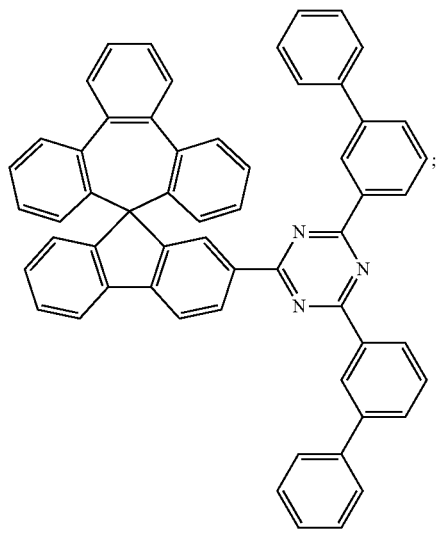 [SMILES: c1ccc(-c2cccc(-c3nc(-c4cccc(-c5ccccc5)c4)nc(-c4ccc5c(c4)C4(c6ccccc6-c6ccccc6-c6ccccc64)c4ccccc4-5)n3)c2)cc1]
Compound I-17
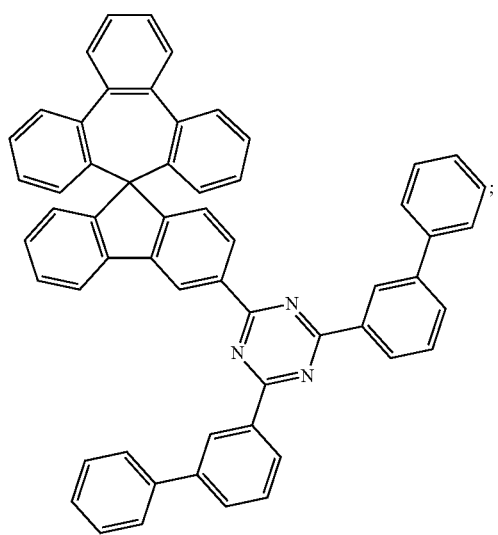 [SMILES: c1ccc(-c2cccc(-c3nc(-c4cccc(-c5ccccc5)c4)nc(-c4ccc5c(c4)-c4ccccc4C54c5ccccc5-c5ccccc5-c5ccccc54)n3)c2)cc1]
Compound I-18
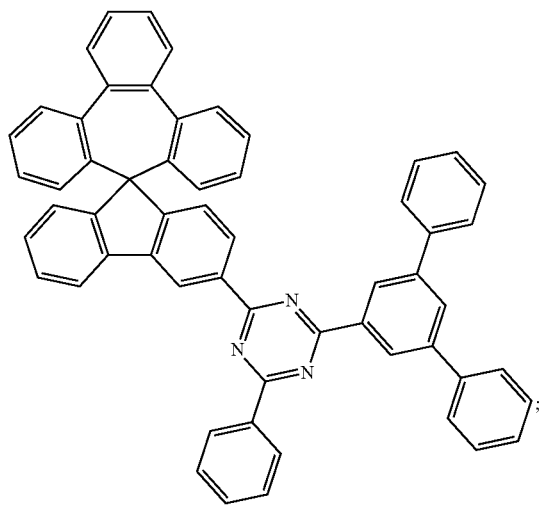 [SMILES: c1ccc(-c2cc(-c3ccccc3)cc(-c3nc(-c4ccccc4)nc(-c4ccc5c(c4)-c4ccccc4C54c5ccccc5-c5ccccc5-c5ccccc54)n3)c2)cc1]
Compound I-19

TABLE 1-continued
chemical structures of the first host compounds
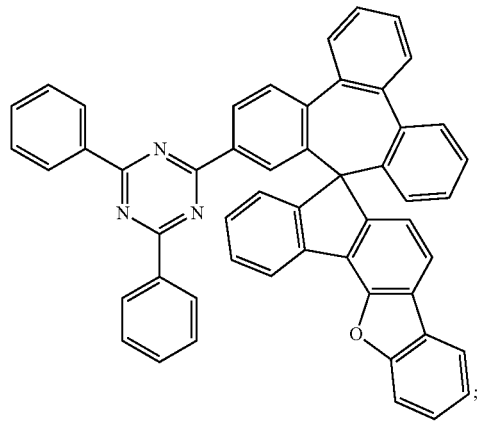 [SMILES: c1ccc(-c2nc(-c3ccccc3)nc(-c3ccc4c(c3)C3(c5ccccc5-c5ccccc5-4)c4ccccc4-c4c3ccc3c4oc4ccccc43)n2)cc1]
Compound I-20
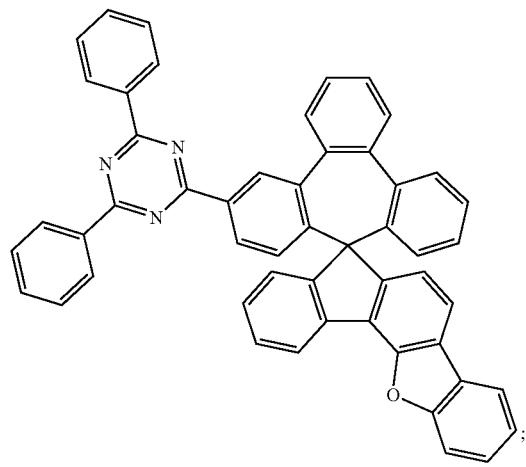 [SMILES: c1ccc(-c2nc(-c3ccccc3)nc(-c3ccc4c(c3)-c3ccccc3-c3ccccc3C43c4ccccc4-c4c3ccc3c4oc4ccccc43)n2)cc1]
Compound I-21
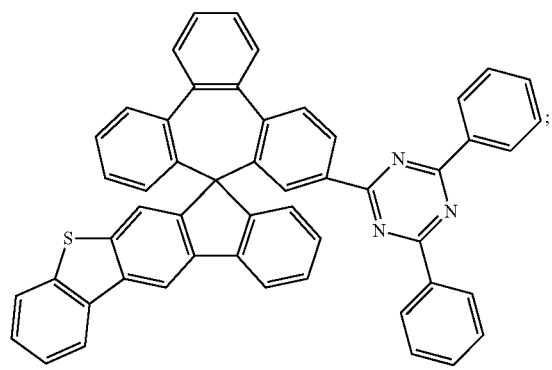 [SMILES: c1ccc(-c2nc(-c3ccccc3)nc(-c3ccc4c(c3)C3(c5ccccc5-c5ccccc5-4)c4ccccc4-c4cc5c(cc43)sc3ccccc35)n2)cc1]
Compound I-22

TABLE 1-continued
chemical structures of the first host compounds
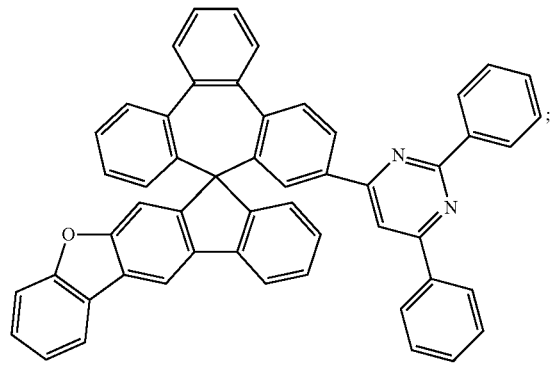 [SMILES: c1ccc(-c2cc(-c3ccc4c(c3)C3(c5ccccc5-c5ccccc5-4)c4ccccc4-c4cc5c(cc43)oc3ccccc35)nc(-c3ccccc3)n2)cc1]
Compound I-23
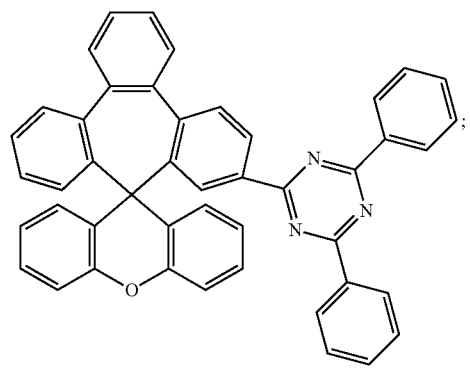 [SMILES: c1ccc(-c2nc(-c3ccccc3)nc(-c3ccc4c(c3)C3(c5ccccc5Oc5ccccc53)c3ccccc3-c3ccccc3-4)n2)cc1]
Compound I-24
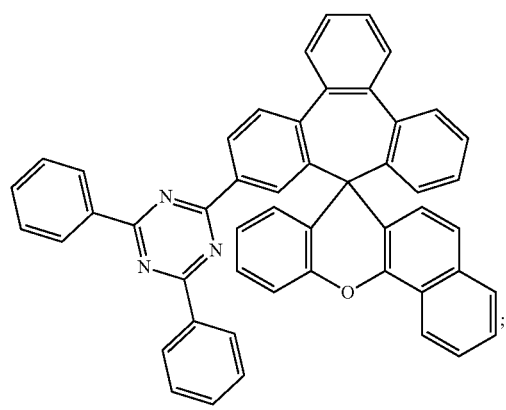 [SMILES: c1ccc(-c2nc(-c3ccccc3)nc(-c3ccc4c(c3)C3(c5ccccc5Oc5c3ccc3ccccc53)c3ccccc3-c3ccccc3-4)n2)cc1]
Compound I-25
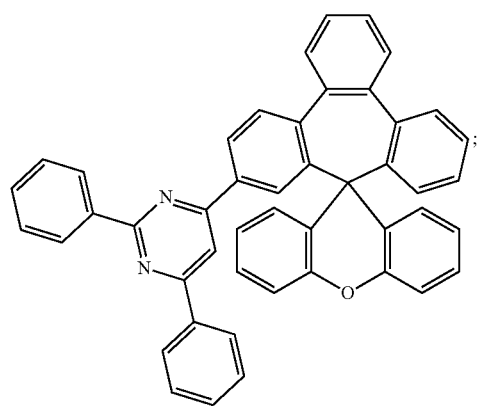 [SMILES: c1ccc(-c2cc(-c3ccc4c(c3)C3(c5ccccc5Oc5ccccc53)c3ccccc3-c3ccccc3-4)nc(-c3ccccc3)n2)cc1]
Compound I-26

TABLE 1-continued chemical structures of the first host compounds

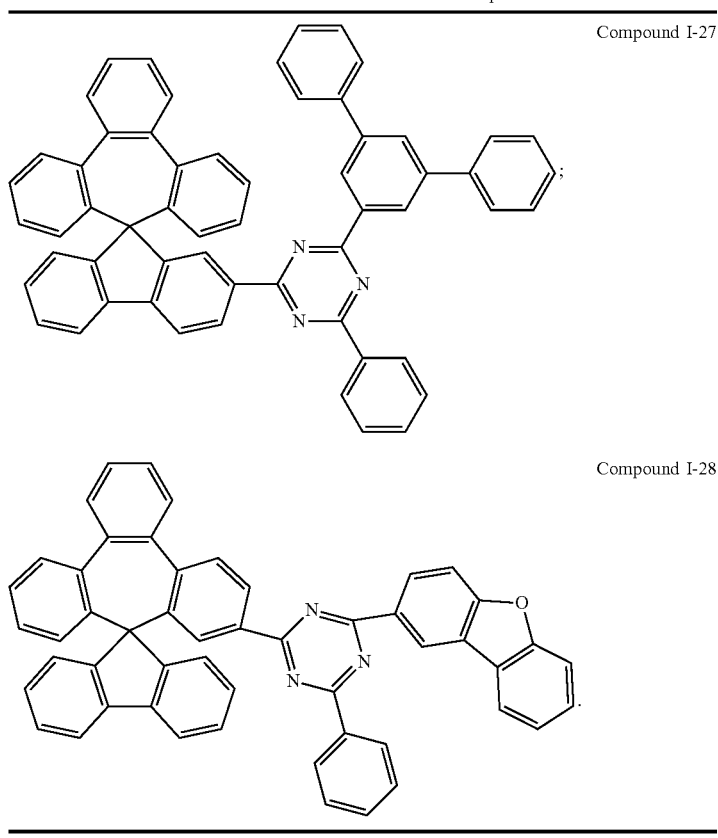

Compound I-27

Compound I-28

Synthesis of Compounds I-1 to I-15 and I-28 for First Host Compound

Compounds I-1 and I-2 used as the first host compound were synthesized by the following steps. The synthesis pathway was summarized in Scheme R1.

Scheme R1:

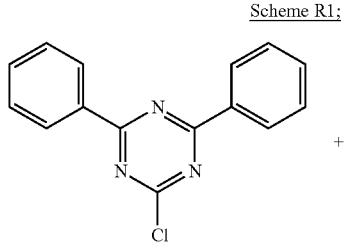

Intermediates C2 or C1 $\xrightarrow{\text{Pd}_2(\text{dba})_3, \text{SPhos}}_{\text{K}_2\text{CO}_3, \text{toluene}}$ Compound I-1 or I-2 wherein Intermediate C1 was

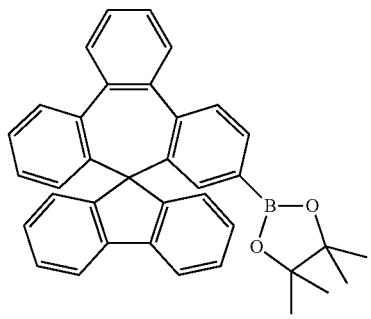 [SMILES: CC1(C)OB(c2ccc3c(c2)C2(c4ccccc4-c4ccccc4-3)c3ccccc3-c3ccccc32)OC1(C)C]

and Intermediate C2 was

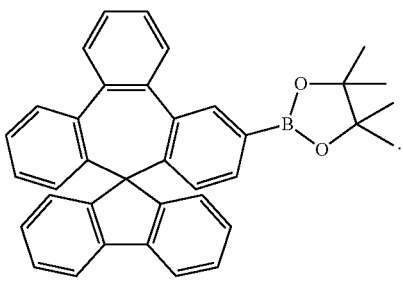 [SMILES: CC1(C)OB(c2ccc3c(c2)-c2ccccc2-c2ccccc2C32c3ccccc3-c3ccccc32)OC1(C)C]

Compounds I-1 and I-2 could be obtained through a reaction mechanism same as the synthetic method of Compounds VII and VI in U.S. Patent Application Publication No. 2017/0213978 A1 by respectively adopting Intermediate C2 and Intermediate C1 stated above.

Besides, Compound I-7 could be obtained through a reaction mechanism same as the synthetic method of Compound III in U.S. Patent Application Publication No. 2017/0213978 A1, and the synthetic method was similar to Scheme R1 using Intermediate C1 stated above but adopting 4-chloro-2, 6-diphenylpyrimidine (CAS No. 29509-91-9) to replace 2-chloro-4,6-diphenyl-1,3,5-triazine (CAS No. 3842-55-5).

For Compounds I-3 to I-6, I-8 to I-15 and I-28, they could be successfully synthesized through a reaction mechanism similar to Scheme R1 by respectively adopting Intermediate C1 or C2 and other reactants including a triazine or pyrimidine moiety to replace 2-chloro-4,6-diphenyl-1,3,5-triazine. The specific reactants including a triazine or pyrimidine moiety and Intermediate C1 or C2 used for synthesizing Compounds I-3 to I-6, I-8 to I-15 and I-28 were listed in Table 2; besides, Compounds I-3 to I-6, I-8 to I-15 and I-28 were identified by FD-MS, and the chemical structure, yield, formula and mass of each of Compounds I-3 to I-6, I-8 to I-15 and I-28 were also listed in Table 2-1. Compounds I-3 to I-6, I-8 to I-15 and I-28 were also identified by H$^1$-NMR and the results thereof were listed in Table 2-2.

Preparation of Reactant for Compound I-10

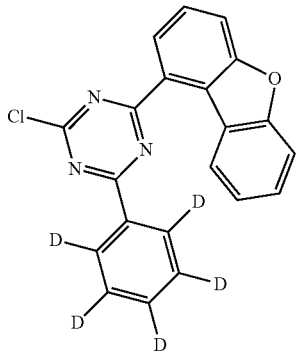 [SMILES: [2H]c1c([2H])c([2H])c(-c2nc(Cl)nc(-c3cccc4oc5ccccc5c34)n2)c([2H])c1[2H]]

used to synthesize Compound I-10 was synthesized by the following steps. The synthesis pathway was summarized in Scheme R1-1.

Scheme R1-1

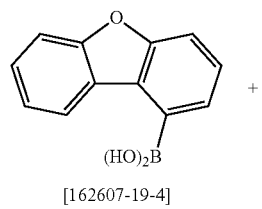

[162607-19-4]

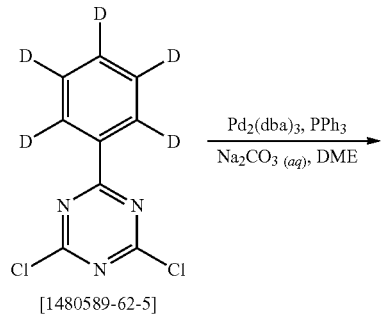

[1480589-62-5]

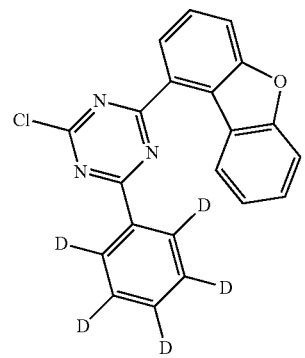 [SMILES: [2H]c1c([2H])c([2H])c(-c2nc(Cl)nc(-c3cccc4oc5ccccc5c34)n2)c([2H])c1[2H]]

A mixture of dibenzo[b,d]furan-1-ylboronic acid (1.0 eq), 2,4-dichloro-6-(D$_5$)phenyl-1,3,5-triazine (1.1 eq), tris(dibenzylideneacetone)dipalladium[Pd$_2$(dba)$_3$] (0.015 eq), triphenylphosphine (PPh$_3$) were stirred in a mixed solution of methoxymethane (DME) (0.5M) and Na$_2$CO$_3$ aqueous solution (2.0 M). The reaction mixture was heated to about 65° C. to 70° C. and stirred for 24 hours under nitrogen atmosphere. After completion of the reaction, water and toluene were added to the reaction mixture. Subsequently, the organic layer was recovered by solvent extraction operation and dried over sodium sulfate. The solvent was then removed from the organic layer under reduced pressure, and the resulting residue was washed with methanol, and dry to obtain a white solid product as

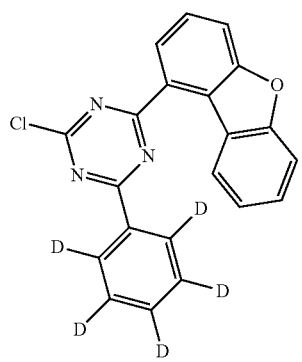

in a yield of 80%. Its FD-MS analysis: C$_{21}$H$_7$D$_5$ClN$_3$O; and observed value of 362.82.

TABLE 2-1
Intermediate C1 or C2 and Reactant adopted to prepare Compounds
I-3 to I-6, I-8 to I-15 and I-28 and their yields, formulae, and FD-MS data
| Intermediate | | First Host Compound | | |
|---|---|---|---|---|
| C1/ Intermediate C2 | Reactant/ CAS No. | Chemical Structure | Yield (%) | Formula/ Mass (M⁺) |
| 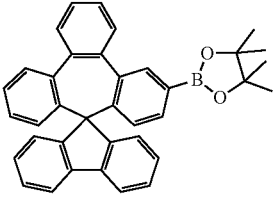 Intermediate C1 | 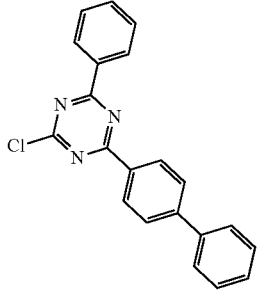 [1472062-94-4] | 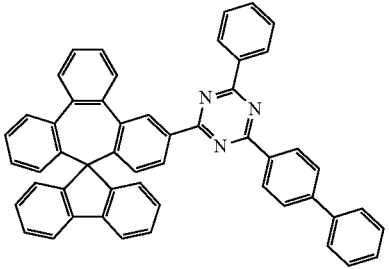 Compound I-3 | 83 | $C_{52}H_{33}N_3$/ 699.84 |
| 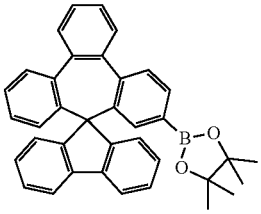 Intermediate C2 | 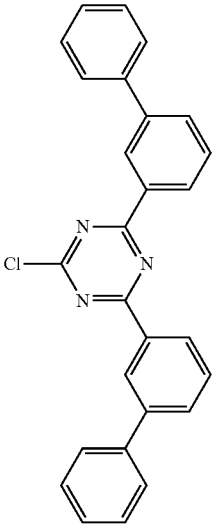 [1205748-61-3] | 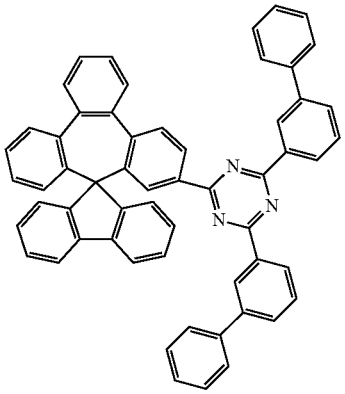 Compound I-4 | 85 | $C_{58}H_{37}N_3$/ 775.93 |
| 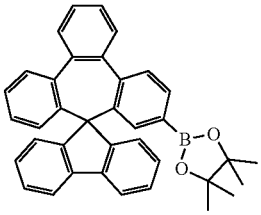 Intermediate C2 | 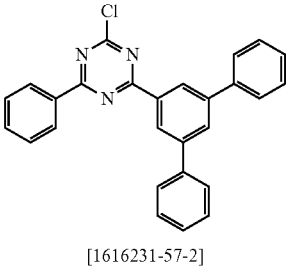 [1616231-57-2] | 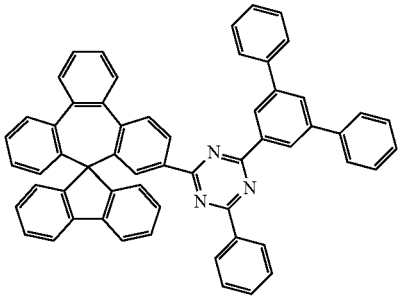 Compound I-5 | 80 | $C_{58}H_{37}N_3$/ 775.93 |

TABLE 2-1-continued

Intermediate C1 or C2 and Reactant adopted to prepare Compounds
I-3 to I-6, I-8 to I-15 and I-28 and their yields, formulae, and FD-MS data

| Intermediate | | First Host Compound | | |
|---|---|---|---|---|
| C1/ Intermediate C2 | Reactant/ CAS No. | Chemical Structure | Yield (%) | Formula/ Mass (M⁺) |
| Intermediate C2 | [307929-32-4] | Compound I-6 | 86 | $C_{52}H_{33}N_3$/ 699.84 |
| Intermediate C1 | [1624289-88-8] | Compound I-8 | 75 | $C_{53}H_{34}N_2$/ 698.85 |
| Intermediate C2 | [1883265-32-4] | Compound I-9 | 81 | $C_{52}H_{31}N_3O$/ 713.82 |
| Intermediate C2 | | Compound I-10 | 82 | $C_{52}H_{26}D_5N_3O$/ 718.85 |

TABLE 2-1-continued

Intermediate C1 or C2 and Reactant adopted to prepare Compounds
I-3 to I-6, I-8 to I-15 and I-28 and their yields, formulae, and FD-MS data

| Intermediate C1/ Intermediate C2 | Reactant/ CAS No. | Chemical Structure | Yield (%) | Formula/ Mass (M+) |
|---|---|---|---|---|
| Intermediate C1 | [2226747-73-3] | Compound I-11 | 81 | C<sub>58</sub>H<sub>35</sub>N<sub>3</sub>O/ 789.92 |
| Intermediate C1 | [2286234-09-9] | Compound I-12 | 75 | C<sub>53</sub>H<sub>32</sub>N<sub>2</sub>O/ 712.83 |
| Intermediate C2 | [2286234-09-9] | Compound I-13 | 76 | C<sub>53</sub>H<sub>32</sub>N<sub>2</sub>O/ 712.83 |

TABLE 2-1-continued

Intermediate C1 or C2 and Reactant adopted to prepare Compounds
I-3 to I-6, I-8 to I-15 and I-28 and their yields, formulae, and FD-MS data

| Intermediate | | First Host Compound | | |
|---|---|---|---|---|
| C1/ Intermediate C2 | Reactant/ CAS No. | Chemical Structure | Yield (%) | Formula/ Mass (M+) |
| 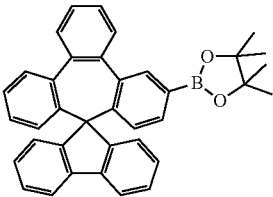<br>Intermediate C1 | 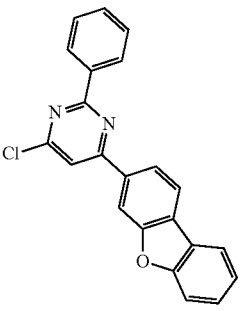<br>[2304744-50-9] | 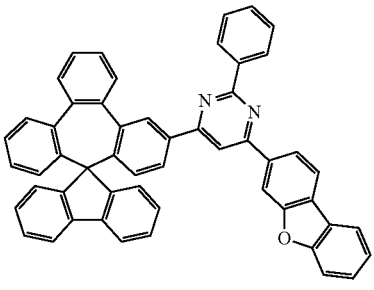<br>Compound I-14 | 70 | $C_{53}H_{32}N_2O$/<br>712.83 |
| 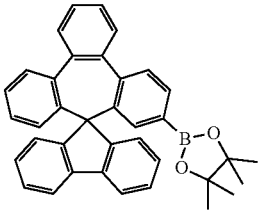<br>Intermediate C2 | 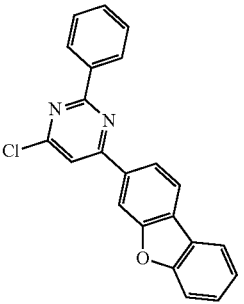<br>[2304744-50-9] | 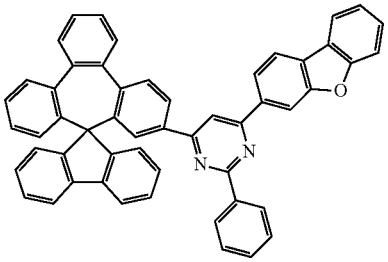<br>Compound I-15 | 79 | $C_{53}H_{32}N_2O$/<br>712.83 |
| 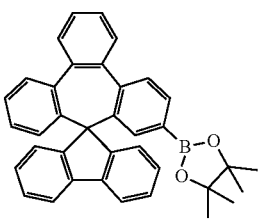<br>Intermediate C2 | 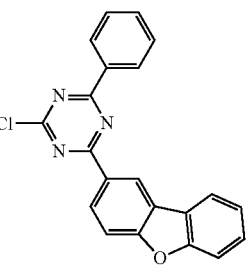<br>[1618107-00-8] | 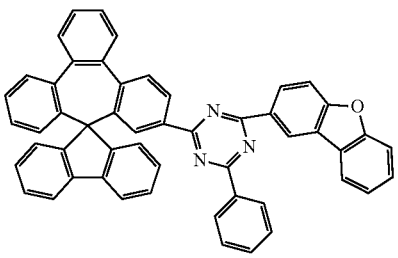<br>Compound I-28 | 85 | $C_{52}H_{31}N_3O$/<br>713.82 |

TABLE 2-2
H[1]-NMR results of Compounds I-3 to I-6, I-8 to I-15 and I-28
| First Host Compound | H[1]-NMR |
|---|---|
| 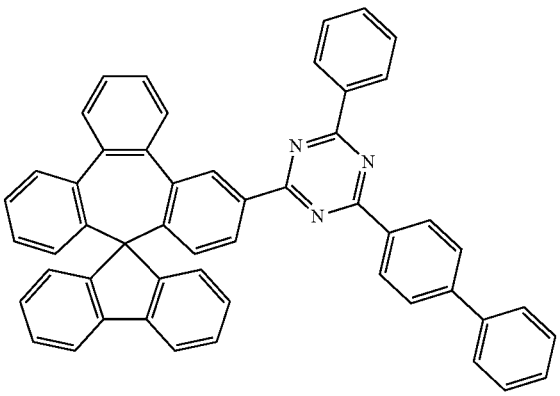<br>Compound I-3 | $^1$H NMR (500 MHz, CDCl$_3$): δ 9.05 (s, 1H) m 8.79-8.73 (dd, 4H) m 8.43 (dd, 1H), 7.91 (d 1H), 7.77-7.46 (m, 18H), 7.47 (t, 1H), 7.46-7.30 (m, 2H), 7.16 (t, 2H), 7.06 (t, 1H), 6.66 (t, 1H), 5.89 (d, 1H) ppm. |
| 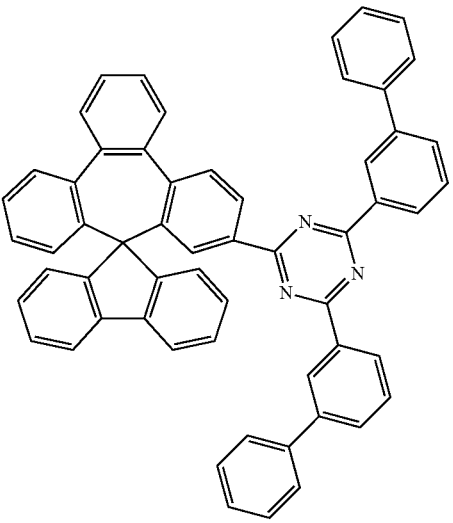<br>Compound I-4 | $^1$H NMR (500 MHz, CDCl$_3$): δ 8.81 (s, 2H), 8.69 (d, J = 2.0 Hz, 1H), 8.67 (d, 1H), 8.64 (d, 2H), 7.90-7.85 (m, 2H), 7.8 g-7.75 (m, 2H), 7.75-7.67 (m, 5H), 7.67-7.55 (m, 8H), 7.55-7.50 (m, 4H), 7.50-7.40 (m, 2H), 7.40-7.30 (m, 1H), 7.30-7.20 (m, 3H), 7.13 (t, 1H), 7.09 (t, 1H), 6.64 (t, 1H), 5.89 (d, 1H) ppm. |
| 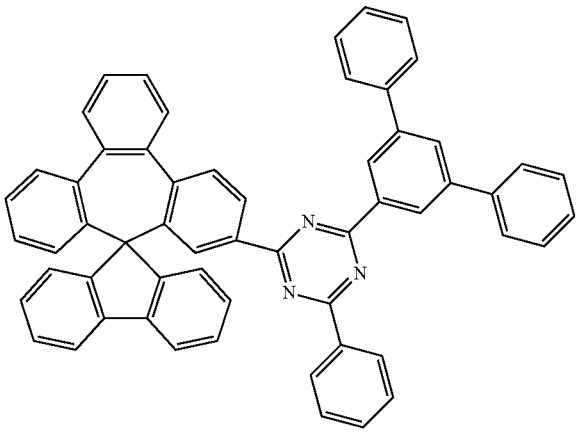<br>Compound I-5 | $^1$H NMR (500 MHz, CDCl$_3$): δ 8.82 (d, 2H), 8.75-8.65 (m, 2H), 8.61 (d, 2H), 8.00 (s, 1H), 8.60 (d, 2H), 7.80-7.70 (m, 4H), 7.70-7.61 (m, 6H), 7.61-7.51 (m, 7H), 7.51-7.40 (m, 3H), 7.30-7.20 (m, 3H), 7.16 (t, 1H), 7.10 (t, 1H), 6.69 (t, 1H), 5.94 (d, J = 10.5 Hz, 1H) ppm. |

TABLE 2-2-continued
H[1]-NMR results of Compounds I-3 to I-6, I-8 to I-15 and I-28
| First Host Compound | H[1]-NMR |
|---|---|
| 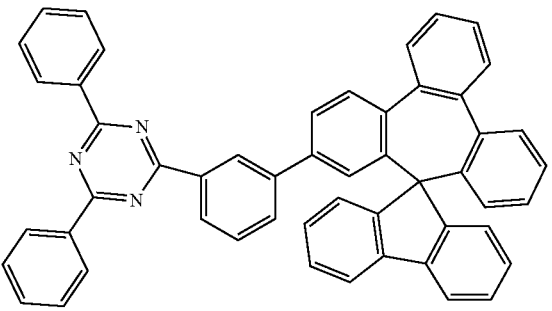<br>Compound I-6 | $^1$H NMR (500 MHz, CDCl$_3$): δ 8.94 (s, 1H), 8.75 (d, 4H), 8.73 (d, 1H), 8.01 (d, 1H), 7.91 (d, 1H), 7.79 (dd, 1H), 7.72 (dd, 1H), 7.71 (m, 1H), 7.63-7.52 (m, 14H), 7.40 (dd, 1H), 7.33 (t, 1H), 7.26 (d, 1H), 7.15-7.07 (m, 3H), 6.64 (t, 1H), 5.87 (d, 1H) ppm. |
| 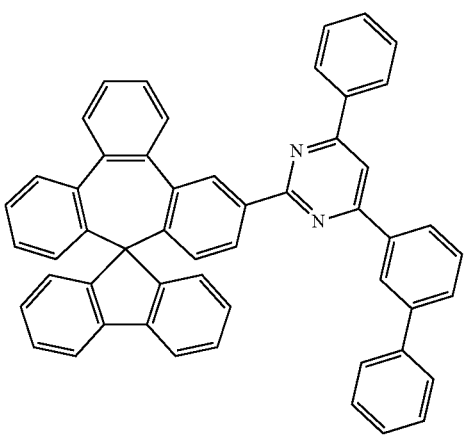<br>Compound I-8 | $^1$H NMR (500 MHz, CDCl$_3$): δ 9.03 (d, 1H), 8.48-8.41 (m, 1H), 8.39 (dd, J = 13, 1H), 8.30-8.24 (m, 2H), 8.21 (d, 1H), 8.02 (s, 1H), 7.91 (d, 1H), 8.03-7.75 (m, 1H), 7.75-7.66 (m, 4H), 7.66-7.58 (m, 6H), 7.58-7.45 (m, 7H), 7.45-7.37 (m, 1H), 7.37-7.26 (m, 2H), 7.19-7.10 (m, 2H), 7.10-7.00 (m, 1H), 6.67 (t, 1H), 5.93 (d, 1H) ppm. |
| 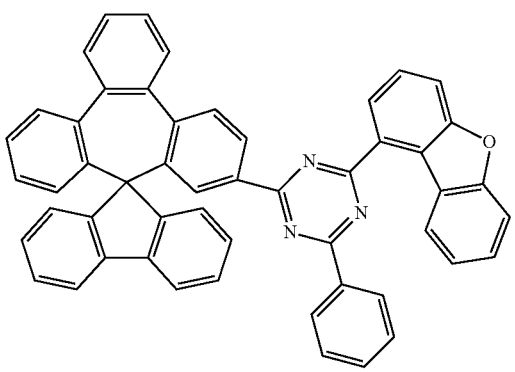<br>Compound I-9 | $^1$H NMR (500 MHz, CDCl$_3$): δ 8.74 (s, 1H), 8.63 (d, 1H), 8.58 (d, 2H), 8.43 (d, 1H), 8.24 (d, 1H), 7.92 (d, 1H), 7.84 (d, 1H), 7.78 (d, 1H), 7.75-7.52 (m, 14H), 7.46 (t, 1H), 7.34 (t, 1H), 7.26 (t, 1H), 7.20-7.05 (m, 3H), 6.65 (t, 1H), 5.90 (d, 1H) ppm. |

TABLE 2-2-continued
H¹-NMR results of Compounds I-3 to I-6, I-8 to I-15 and I-28
| First Host Compound | H¹-NMR |
|---|---|
| 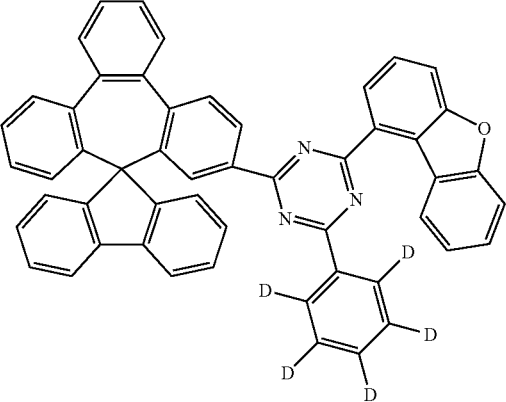<br>Compound I-10 | ¹H NMR (500 MHz, CDCl$_3$): δ 8.75 (d, 1H), 8.38 (dd, 1H), 8.46 (d, 1H), 8.25 (d, 1H), 7.93 (d, 1H), 7.84 (d, 1H), 7.78 (d, 1H), 7.75-7.60 (m, 10H), 7.60-7.53 (m, 1H), 7.52-7.44 (m, 1H), 7.35 (t, 3H), 7.29 (d, J = 10.5 Hz, 1H), 7.20-7.05 (m, 3H), 6.70 (t, 1H), 5.92 (d, 1H) ppm. |
| 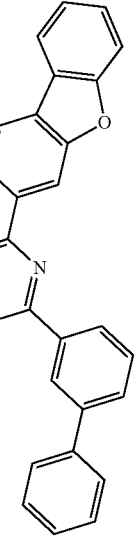<br>Compound I-11 | ¹H NMR (500 MHz, CDCl$_3$): δ 9.04 (s, 1H), 8.93 (s, 1H), 8.88 (s, 1H), 8.71 (d, 1H), 8.67 (d, 1H), 8.48 (d, 1H), 8.05-7.85 (m, 3H), 7.84-7.61 (m, 7H), 7.60-7.49 (m, 9H), 7.49-7.26 (m, 3H), 7.20-7.11 (m, 2H), 7.11-7.00 (m, 1H), 6.68 (t, 1H), 5.92 (d, 1H) ppm. |
| <br>Compound I-12 | ¹H NMR (500 MHz, CDCl$_3$): δ 9.01 (d, 1H), 8.49 (d, 1H), 8.39 (dd, , 1H), 8.30-8.20 (m, 3H), 8.10-8.03 (m, 2H), 7.98 (d, 1H), 7.90 (d, 1H), 7.83-7.73 (m, 1H), 7.72-7.45 (m, 12H), 7.42-7.26 (m, 3H), 7.20-7.10 (m, 2H), 7.09-7.00 (m, 1H), 6.65 (td, 1H), 5.90 (d, 1H) ppm. |

TABLE 2-2-continued
H[1]-NMR results of Compounds I-3 to I-6, I-8 to I-15 and I-28
| First Host Compound | H[1]-NMR |
|---|---|
| 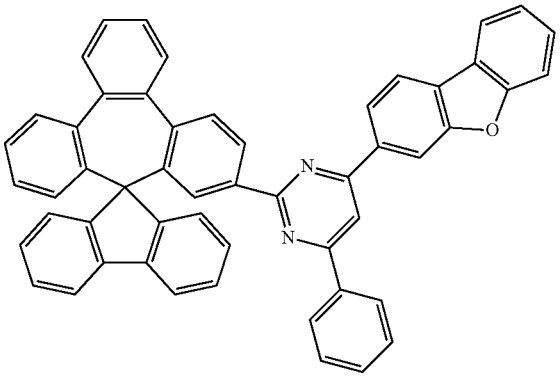 Compound I-13 | $^1$H NMR (500 MHz, CDCl$_3$): δ 8.66 (d, 2H), 8.39 (s, 1H), 8.20-8.12 (m, 2H), 8.09 (d, 1H), 8.05-7.95 (m, 4H), 7.89-7.80 (m, 2H), 7.80-7.69 (m, 3H), 7.69-7.58 (m, 6H), 7.57-7.50 (m, 4H), 7.39 (t, 1H), 7.33 (t, 1H), 7.29 (d, 1H), 7.15-7.04 (m, 2H), 6.64 (t, 1H), 5.91 (d, 1H) ppm. |
| 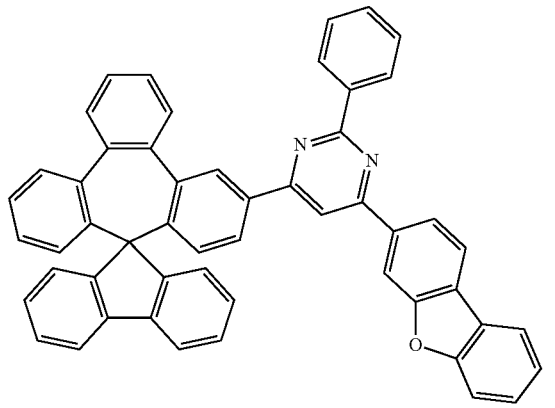 Compound I-14 | $^1$H NMR (500 MHz, CDCl$_3$): δ 8.70(dd, J = 10.0, 3.5 Hz, 2H), 8.58 (d, J = 2.5 Hz, 1H), 8.51 (d, 1H), 8.21 (dd, 1H), 8.05 (s, 1H), 8.03-8.01 (m, 1H), 8.00-7.93 (m, 2H), 7.92-7.88 (m, 1H), 7.76-7.70 (m, 2H), 7.70-7.56 (m, 7H), 7.55-7.45 (m, 5H), 7.4-7.26 (m, 3H), 7.20-7.10 (m, 2H), 7.10-7.02 (m, 1H), 6.66 (t, 1H), 5.89 (d, 1H) ppm. |
| 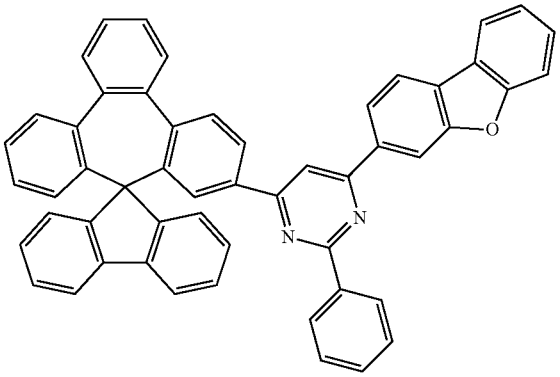 Compound I-15 | $^1$H NMR (500 MHz, CDCl$_3$): δ 8.62-8.52(m, 2H), 8.41 (d, 1H), 8.24 (d, J = 2.0 Hz, 1H), 8.20-8.10 (dd, H), 8.04-7.92 (m, 3H), 7.85-7.69 (m, 5H), 7.69-7.57 (m, 7H), 7.57-7.45 (m, 4H), 7.45-7.31 (m, 2H), 7.28 (dd, 1H), 7.19-7.05 (m, 2H), 6.66 (t, 1H), 5.91 (d, 1H) ppm. |

TABLE 2-2-continued

H¹-NMR results of Compounds I-3 to I-6, I-8 to I-15 and I-28

| First Host Compound | H¹-NMR |
|---|---|
| 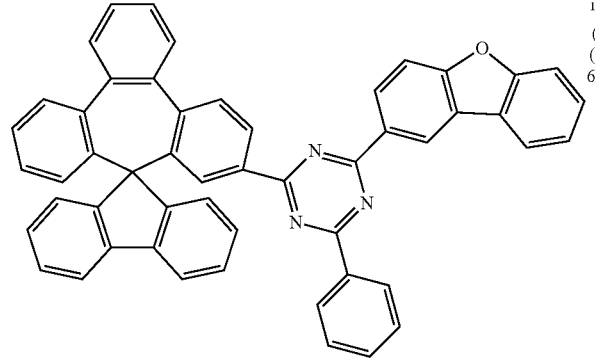<br>Compound I-28 | ¹H NMR (500 MHz, CDCl₃): δ 9.17 (s, 1H), 8.73-8.68 (m, 2H), 8.65 (d, 1H), 8.60 (d, 2H), 8.11 (d, 1H), 8.02 (d, 1H), 7.83 (d, 1H), 7.79-7.69 (m, 4H), 7.69-7.61 (m, 6H), 7.61-7.51 (m, 4H), 7.48 (t, 1H), 7.43-7.31 (m, 2H), 7.26 (t, 1H), 7.20-7.05 (m, 2H), 6.67 (t, 1H), 5.90 (d, 1H) ppm. |

Synthesis of Compounds I-16 to I-19 and I-27 for First Host Compound Compounds I-16 to I-19 and I-27 used as the first host compound were synthesized by the following steps. The synthesis pathway was summarized in Scheme R2.

Scheme R2:

Intermediate C1' or C2' + Reactant Bn $\xrightarrow{\text{Pd(OAc)}_2, \text{P(Cy}_2\text{)(2-biPh)}}_{\text{K}_2\text{CO}_3, \text{toluene/EtOH}}$ Compound I-16 to I-19 or I-27 wherein Intermediate C1' was

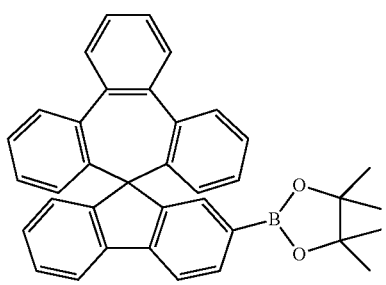 [SMILES: CC1(C)OB(c2ccc3c(c2)C2(c4ccccc4-c4ccccc4-c4ccccc42)c2ccccc2-3)OC1(C)C]

and Intermediate C2' was

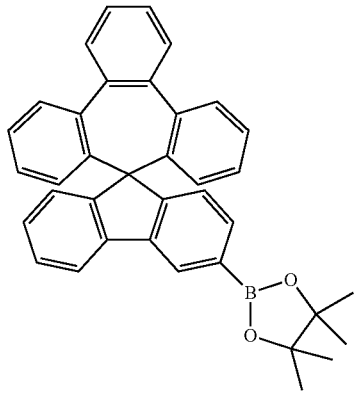

Intermediates C1' and C2' could be obtained through a Suzuki-Miyaura reaction from Intermediates D1 and D2 in U.S. Patent Application Publication No. 2017/0213970 A1.

Intermediate C1' or C2' (1.0 eq), Reactant Bn (1.2 eq), Pd(OAc)₂ (0.01 eq), and 2-(dicyclohexylphosphino)biphenyl[P(Cy)₂(2-biPh)](0.04 eq) were stirred in a mixed solution of toluene/ethanol (0.5M, v/v=10/1) and 3.0 M of K₂CO₃ aqueous solution. The reaction mixture was heated to about 100° C. and stirred for 12 hours under nitrogen atmosphere. After completion of the reaction, water and toluene were added to the reaction mixture. Subsequently, the organic layer was recovered by solvent extraction operation and dried over sodium sulfate. The solvent was then removed under reduced pressure, and the resulting residue was purified by silica gel column chromatography. The obtained residue was recrystallized with toluene to obtain a white solid product as Compounds I-16 to I-19 and I-27.

For Compounds I-16 to I-19 and I-27, they could be successfully synthesized through a reaction mechanism same as Scheme R2 by respectively adopting Intermediate C1' or C2' and other Reactants Bn including a triazine or pyrimidine moiety. Intermediate C1' or C2' and the specific Reactants Bn including a triazine or pyrimidine moiety used for synthesizing Compounds I-16 to I-19 and I-27 were listed in Table 3; besides, Compounds I-16 to I-19 and I-27 were identified by FD-MS, and the chemical structure, yield, formula and mass of each of Compounds I-16 to I-19 and I-27 were also listed in Table 3-1. Compounds I-16 to I-19 and I-27 were also identified by $H^1$-NMR (500 MHz, $CDCl_3$) and the results thereof were listed in Table 3-2.

TABLE 3-1

Intermediate C1' or C2' and Reactant Bn adopted to prepare Compounds I-16 to I-19 and I-27 and their yields, formulae, and FD-MS data

| Intermediate C1'/ Intermediate C2' | Reactant Bn/ CAS No. | First Host Compound | | |
|---|---|---|---|---|
| | | Chemical Structure | Yield (%) | Formula/ Mass (M⁺) |
| 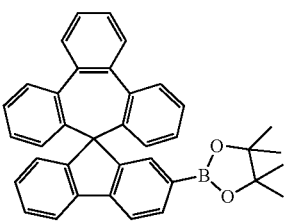 Intermediate C1' | 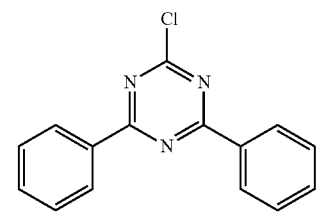 [3842-55-5] | 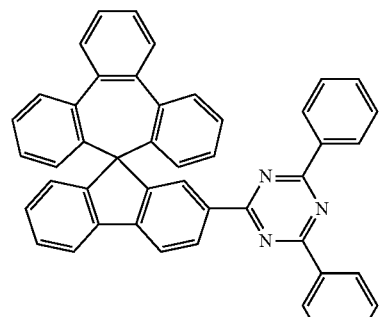 Compound I-16 | 85 | $C_{46}H_{29}N_3$/ 623.74 |
| 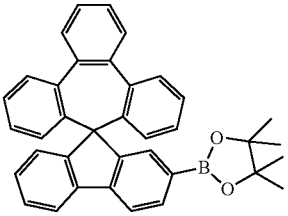 Intermediate C1' | 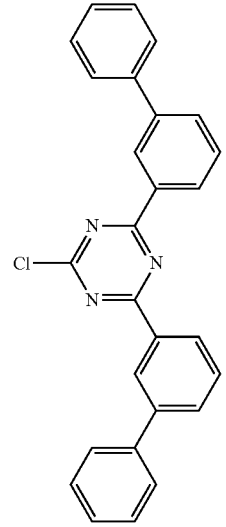 [1205748-61-3] | 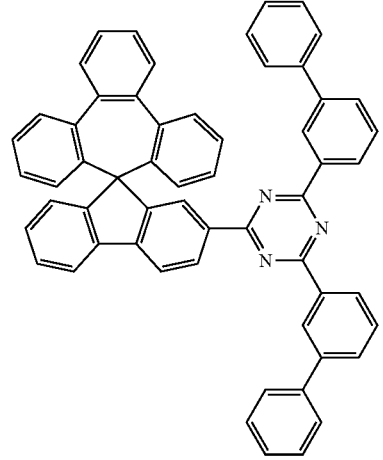 Compound I-17 | 65 | $C_{58}H_{37}N_3$/ 775.93 |

TABLE 3-1-continued

Intermediate C1' or C2' and Reactant Bn adopted to prepare
Compounds I-16 to I-19 and I-27 and their yields, formulae, and FD-MS data

| Intermediate C1'/ Intermediate C2' | Reactant Bn/ CAS No. | First Host Compound | | |
|---|---|---|---|---|
| | | Chemical Structure | Yield (%) | Formula/ Mass (M+) |
| Intermediate C2' | [1205748-61-3] | Compound I-18 | 77 | $C_{58}H_{37}N_3$/ 775.93 |
| Intermediate C2' | [1616231-57-2] | Compound I-19 | 82 | $C_{58}H_{37}N_3$/ 775.93 |
| Intermediate C1' | [1616231-57-2] | Compound I-27 | 76 | $C_{58}H_{37}N_3$/ 775.93 |

TABLE 3-2

H¹-NMR results of Compounds I-16 to I-19 and I-27

| First Host Compound | H¹-NMR |
|---|---|
| 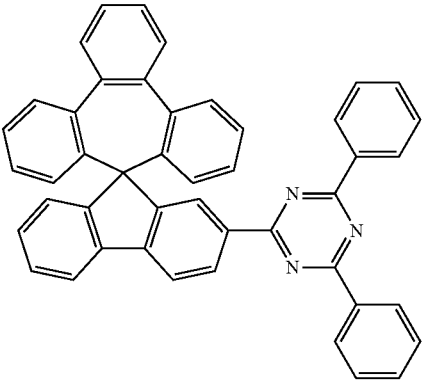<br>Compound I-16 | δ 9.01 ppm (d, 1H), 8.99 ppm (s, 1H), 8.75 ppm (d, 4H), 8.65 ppm (d, 1H), 8.05 ppm (d, 1H), 7.7 ppm (t, 2H), 7.60-7.58 ppm (m, 8H), 7.35-7.31 ppm (m, 4H), 7.29-7.05 ppm (m, 5H), 6.70 ppm (t, 1H), 5.85 ppm (d, 1H). |
| 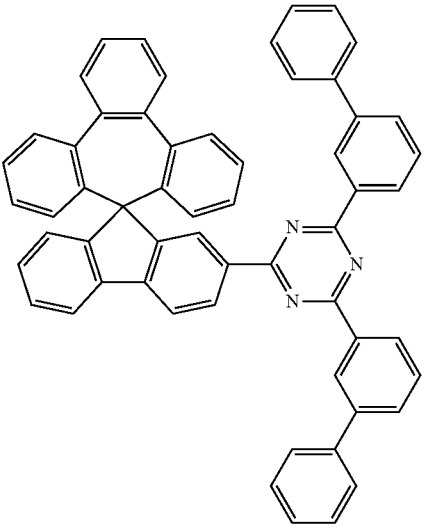<br>Compound I-17 | δ 9.01 ppm (s, 2H), 8.89 ppm (s, 1H), 8.74 ppm (d, 2H), 8.07 ppm (d, 1H), 7.84 ppm (dd, 2H), 7.76-7.68 ppm (m, 6H), 7.66-7.57 ppm (m, 6H),, 7.52-7.46 ppm (m, 5H) 7.44-7.39 ppm (m, 3H), 7.36-7.30 ppm (m, 4H), 7.16 ppm (t, 1H), 7.11-7.06 ppm (m, 2H), 6.70 ppm (t, 1H), 5.89 ppm (d, 1H). |
| 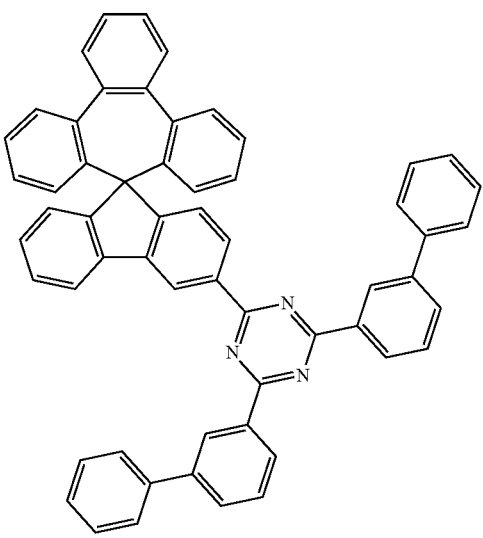<br>Compound I-18 | δ 9.23 ppm (s, 1H), 9.08 ppm (s, 2H), 8.96 ppm (d, 1H), 8.92 ppm (s, 2H), 8.85 ppm (d, 2H), 8.69 ppm (d, 2H), 8.10 ppm (d, 1H), 8.02 ppm (d, 1H), 7.85-7.76 ppm (m, 11H), 7.73-7.67 ppm (m, 10H), 7.64-7.58 ppm (m, 12H), 7.53 ppm (dd, 8H), 7.44 ppm (t, 4H), 7.34 ppm (t, 4H), 7.19-7.12 ppm (m, 6H), 7.05 ppm (t, 4H), 6.69 ppm (t, 1H), 6.05 ppm (d, 1H), 5.85 ppm (d, 1H). |

TABLE 3-2-continued
H¹-NMR results of Compounds I-16 to I-19 and I-27
| First Host Compound | H¹-NMR |
|---|---|
| 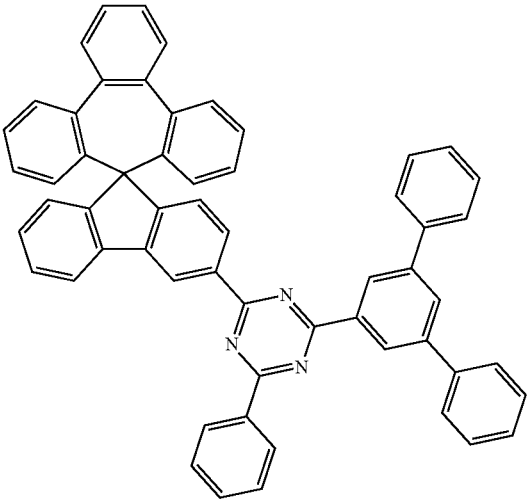<br>Compound I-19 | δ 9.23 ppm (s, 1H), 9.04 ppm (s, 2H), 8.94 ppm (d, IH), 8.92 ppm (s, 1H), 8.88 ppm (s, 2H), 8.86 ppm (d, 2H), 8.73 ppm (d, 2H) 8.10 ppm (d, 1H), 8.19 ppm (s, 1H), 8.02 ppm (d, 1H), 8.00ppm (s, 1H)7.83 ppm (d, 6H), 7.78 ppm (d, 4H), 7.70 ppm (dd, 4H), 7.70-7.51 ppm (m, 25H), 7.46 ppm (t, 4H), 7.34 ppm (t, 4H), 7.20-7.13 ppm (m, 5H), 7.08-7.04 ppm (m, 4H), 6.68 ppm (t, 1H), 6.05 ppm (dd 1H), 5.88 ppm (dd, 1H). |
| 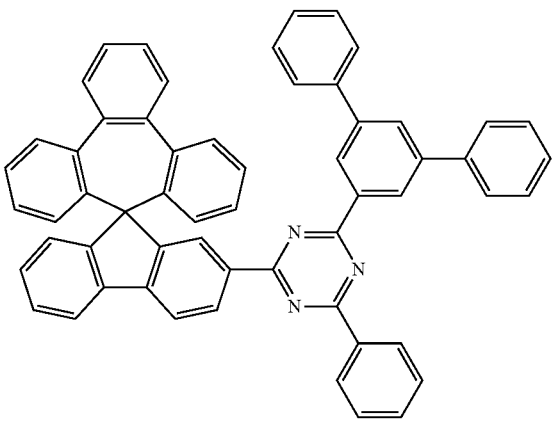<br>Compound I-27 | δ 8.97 ppm (s, 3H), 8.84 ppm (s, 1H), 8.81 ppm (d, 1H), 8.77 ppm (d, 1H), 8.06 ppm (m, 2H), 7.80-7.76 ppm (m, 6H), 7.62-7.49 ppm (m, 12H), 7.47-7.41 ppm (m, 4H), 7.34-7.24 ppm (m, 3H), 7.09-7.05 ppm (m, 2H), 6.68 ppm (t, 1H), 5.87 ppm (d, 1H). |

Synthesis of Compounds 1-20 to 1-23 for First Host Compound

Compounds I-20 to I-23 used as the first host compound were synthesized by the following steps. The synthesis pathway was summarized in Scheme R3.

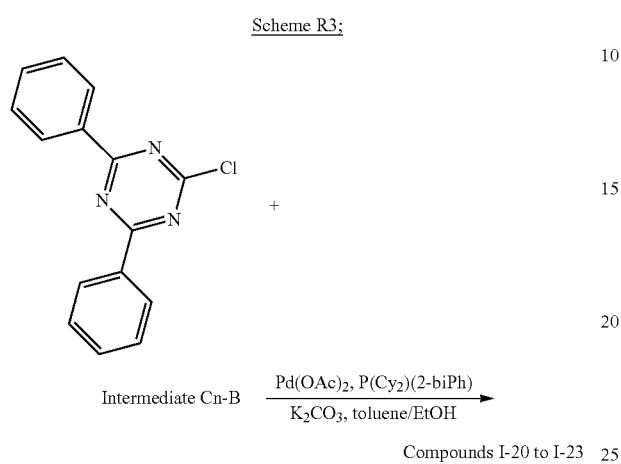

wherein Intermediate Cn-B was (Intermediate C1-B), (Intermediate C2-B),

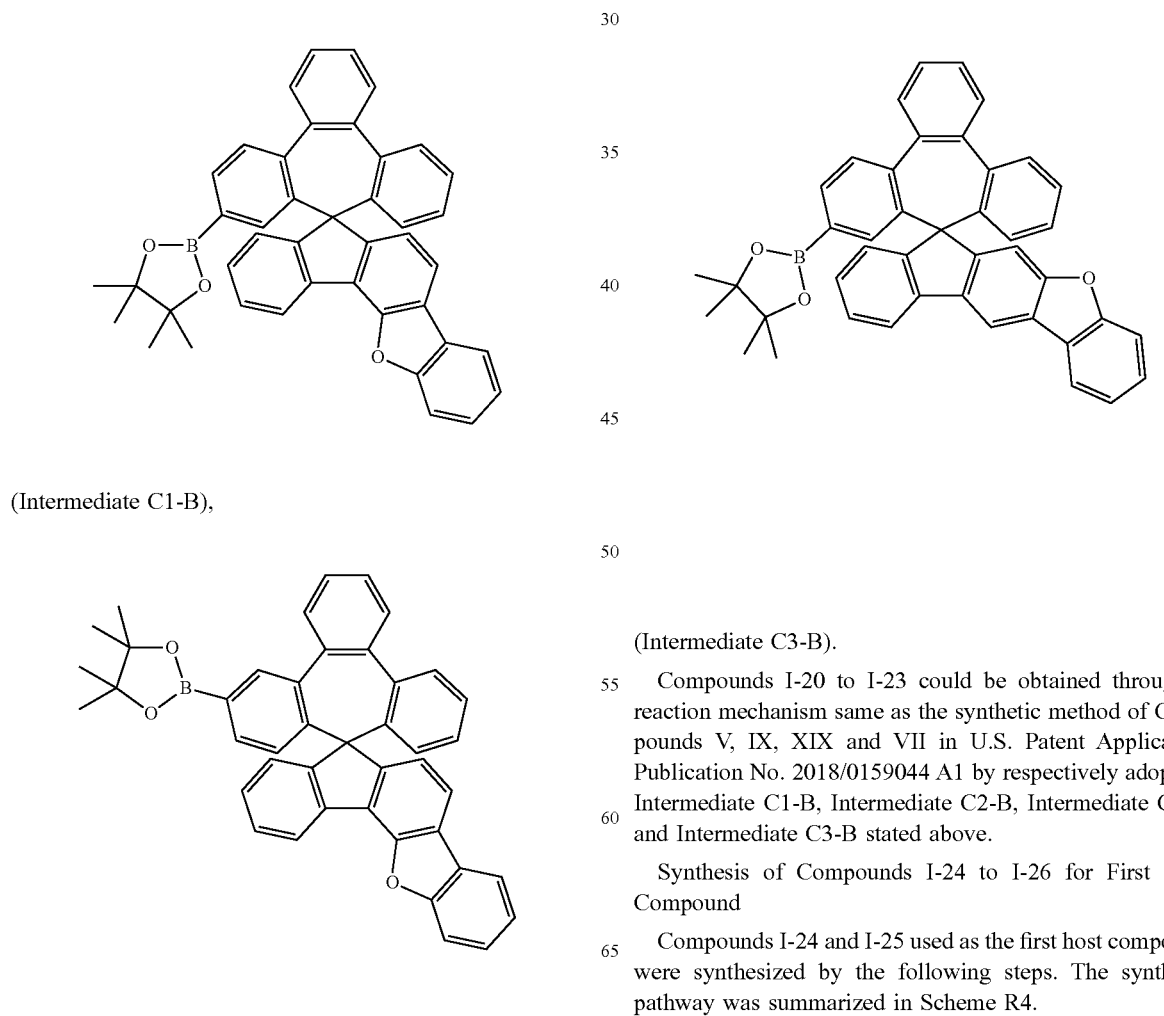

(Intermediate C7-B), or (Intermediate C3-B).

Compounds I-20 to I-23 could be obtained through a reaction mechanism same as the synthetic method of Compounds V, IX, XIX and VII in U.S. Patent Application Publication No. 2018/0159044 A1 by respectively adopting Intermediate C1-B, Intermediate C2-B, Intermediate C7-B and Intermediate C3-B stated above.

Synthesis of Compounds I-24 to I-26 for First Host Compound

Compounds I-24 and I-25 used as the first host compound were synthesized by the following steps. The synthesis pathway was summarized in Scheme R4.

Scheme R4:

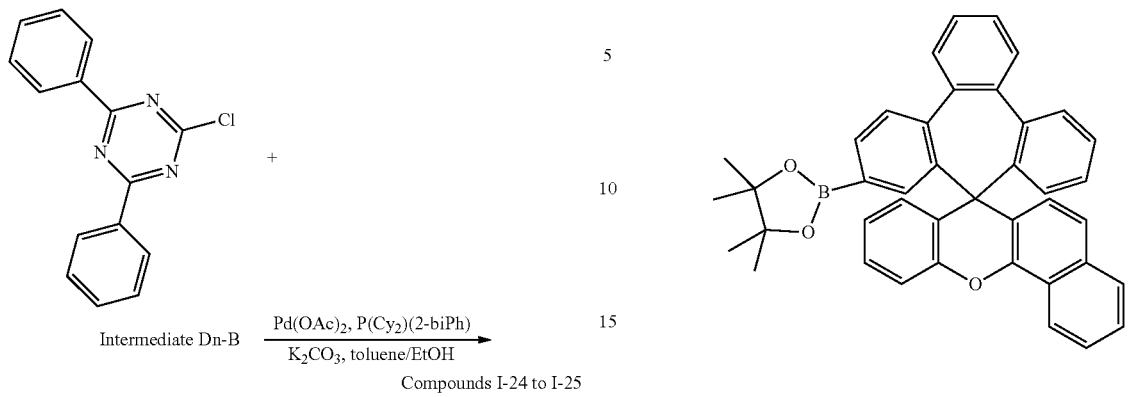

Intermediate Dn-B  →(Pd(OAc)$_2$, P(Cy$_2$)(2-biPh) / K$_2$CO$_3$, toluene/EtOH)  Compounds I-24 to I-25 wherein Intermediate Dn-B was

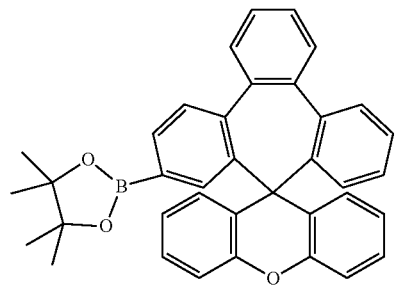 [SMILES: CC1(C)OB(c2ccc3c(c2)C2(c4ccccc4Oc4ccccc42)c2ccccc2-c2ccccc2-3)OC1(C)C]

(Intermediate D1-B) or (Intermediate D4-B).

Compounds I-24 and I-25 could be obtained through a reaction mechanism same as the synthetic method of Compounds VI and VII in U.S. Patent Application Publication No. 2018/0155312 A1 by respectively adopting Intermediate D1-B and Intermediate D4-B stated above.

Besides, Compound I-26 could be obtained through a reaction mechanism same as the synthetic method of Compound III in U.S. Patent Application Publication No. 2018/0155312 A1, and the synthetic method was similar to Scheme R4 using Intermediate D1-B stated above but adopting 4-chloro-2,6-diphenylpyrimidine to replace 2-chloro-4,6-diphenyl-1,3,5-triazine.

Second Host Compound of a Composition for an Organic Electronic Device

TABLE 4 chemical structures and CAS No. of the second host compounds

| Chemical structure | | |
|---|---|---|
| 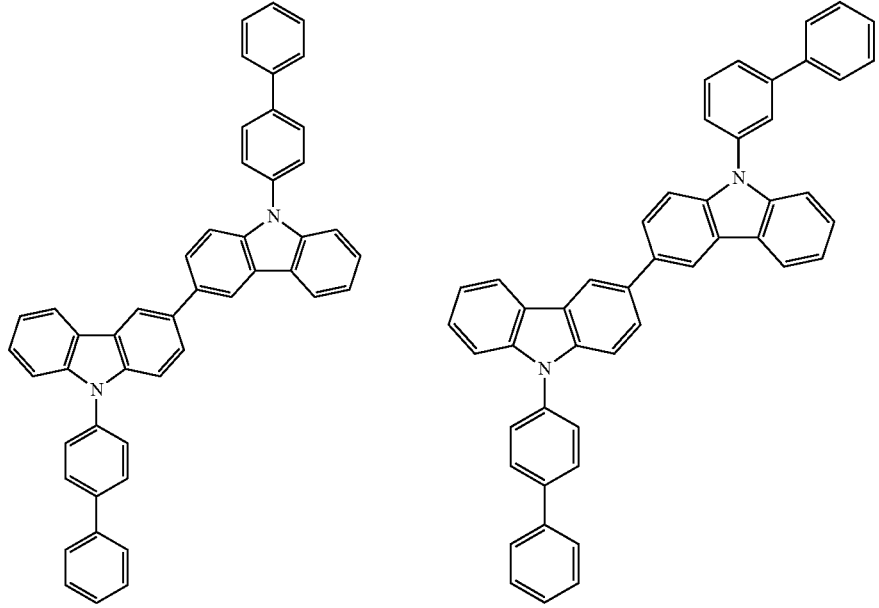 | | |
| Compound II-1 | | Compound II-2 |
| CAS No. [57102-51-9] | | [1643479-47-3] |

TABLE 4-continued chemical structures and CAS No. of the second host compounds

Chemical structure

Compound II-3

Compound II-4

CAS No. [1357150-54-9]  [1541194-36-8]

Preparation of a Composition for an Organic Electronic Device

Compositions 1 to 51 were each obtained by adopting an appropriate amount of aforesaid first host compound listed in Table 1 and second host compound listed in Table 4, and the species of aforesaid first host compound and second host compound used in Compositions 1 to 51 were listed in Table 5. The weight ratio of the first host compound and second host compound in each of Compositions 1 to 47 was 1:1; the weight ratio of the first host compound and second host compound in Compositions 48 to 50 was 6:4; the weight ratio of the first host compound and second host compound in Composition 51 was 4:6.

Compositions 52 and 53 were respectively obtained by adopting a composition of TPBi and Compound II-2 or a composition of TPBi and Compound II-1 at a weight ratio of 1:1 as listed in Table 5.

TABLE 5 materials of first and second host compounds and weight ratio therebetween in Compositions 1 to 53

| Composition No. | First Host Compound | Second Host Compound | Weight ratio of first and second host compounds |
|---|---|---|---|
| 1 | Compound I-1 | Compound II-1 | 1:1 |
| 2 | Compound I-2 | Compound II-1 | 1:1 |
| 3 | Compound I-4 | Compound II-1 | 1:1 |
| 4 | Compound I-5 | Compound II-1 | 1:1 |
| 5 | Compound I-9 | Compound II-1 | 1:1 |
| 6 | Compound I-18 | Compound II-1 | 1:1 |
| 7 | Compound I-19 | Compound II-1 | 1:1 |
| 8 | Compound I-20 | Compound II-1 | 1:1 |
| 9 | Compound I-22 | Compound II-1 | 1:1 |
| 10 | Compound I-24 | Compound II-1 | 1:1 |
| 11 | Compound I-26 | Compound II-1 | 1:1 |
| 12 | Compound I-28 | Compound II-1 | 1:1 |
| 13 | Compound I-1 | Compound II-2 | 1:1 |
| 14 | Compound I-2 | Compound II-2 | 1:1 |
| 15 | Compound I-3 | Compound II-2 | 1:1 |
| 16 | Compound I-4 | Compound II-2 | 1:1 |
| 17 | Compound I-5 | Compound II-2 | 1:1 |
| 18 | Compound I-6 | Compound II-2 | 1:1 |
| 19 | Compound I-7 | Compound II-2 | 1:1 |
| 20 | Compound I-8 | Compound II-2 | 1:1 |
| 21 | Compound I-9 | Compound II-2 | 1:1 |
| 22 | Compound I-10 | Compound II-2 | 1:1 |
| 23 | Compound I-11 | Compound II-2 | 1:1 |
| 24 | Compound I-12 | Compound II-2 | 1:1 |
| 25 | Compound I-13 | Compound II-2 | 1:1 |
| 26 | Compound I-14 | Compound II-2 | 1:1 |
| 27 | Compound I-15 | Compound II-2 | 1:1 |
| 28 | Compound I-16 | Compound II-2 | 1:1 |
| 29 | Compound I-17 | Compound II-2 | 1:1 |
| 30 | Compound I-18 | Compound II-2 | 1:1 |
| 31 | Compound I-19 | Compound II-2 | 1:1 |
| 32 | Compound I-20 | Compound II-2 | 1:1 |
| 33 | Compound I-21 | Compound II-2 | 1:1 |
| 34 | Compound I-22 | Compound II-2 | 1:1 |
| 35 | Compound I-23 | Compound II-2 | 1:1 |
| 36 | Compound I-24 | Compound II-2 | 1:1 |
| 37 | Compound I-25 | Compound II-2 | 1:1 |
| 38 | Compound I-26 | Compound II-2 | 1:1 |
| 39 | Compound I-27 | Compound II-2 | 1:1 |
| 40 | Compound I-2 | Compound II-3 | 1:1 |
| 41 | Compound I-7 | Compound II-3 | 1:1 |
| 42 | Compound I-2 | Compound II-4 | 1:1 |
| 43 | Compound I-5 | Compound II-4 | 1:1 |
| 44 | Compound I-12 | Compound II-4 | 1:1 |
| 45 | Compound I-20 | Compound II-4 | 1:1 |
| 46 | Compound I-22 | Compound II-4 | 1:1 |
| 47 | Compound I-18 | Compound II-4 | 1:1 |
| 48 | Compound I-2 | Compound II-1 | 6:4 |
| 49 | Compound I-26 | Compound II-1 | 6:4 |
| 50 | Compound I-5 | Compound II-4 | 6:4 |
| 51 | Compound I-12 | Compound II-4 | 4:6 |
| 52 | TPBi | Compound II-2 | 1:1 |
| 53 | TPBi | Compound II-1 | 1:1 |

Analysis of Photoluminescence (PL) Spectra

Glass substrates in a thickness of 500 Å cleaned by acetone and isopropyl alcohol were prepared. Compounds I-1 to I-28 listed in Table 1, Compounds II-1 to II-4 listed in Table 4 and Compositions 1 to 53 listed in Table 5 were deposited on each glass substrate under vacuum degree of $10^{-6}$ torr to prepare each PL test film of Compounds I-1 to I-28, Compounds II-1 to II-4 and Compositions 1 to 53.

PL test films of Compositions 2, 8, 9, 13, 14, 16, 17, 19, 28 to 39, 42, 43, 45 to 47, 52 and the first and second host compounds concerned were respectively measured by a fluorescence spectrophotometer (Hitachi Fl-7000) to obtain each set of PL spectra, and then the wavelengths at emission maximum (λ max) thereof in each set of PL spectra were summarized in Table 6.

Figure 2:
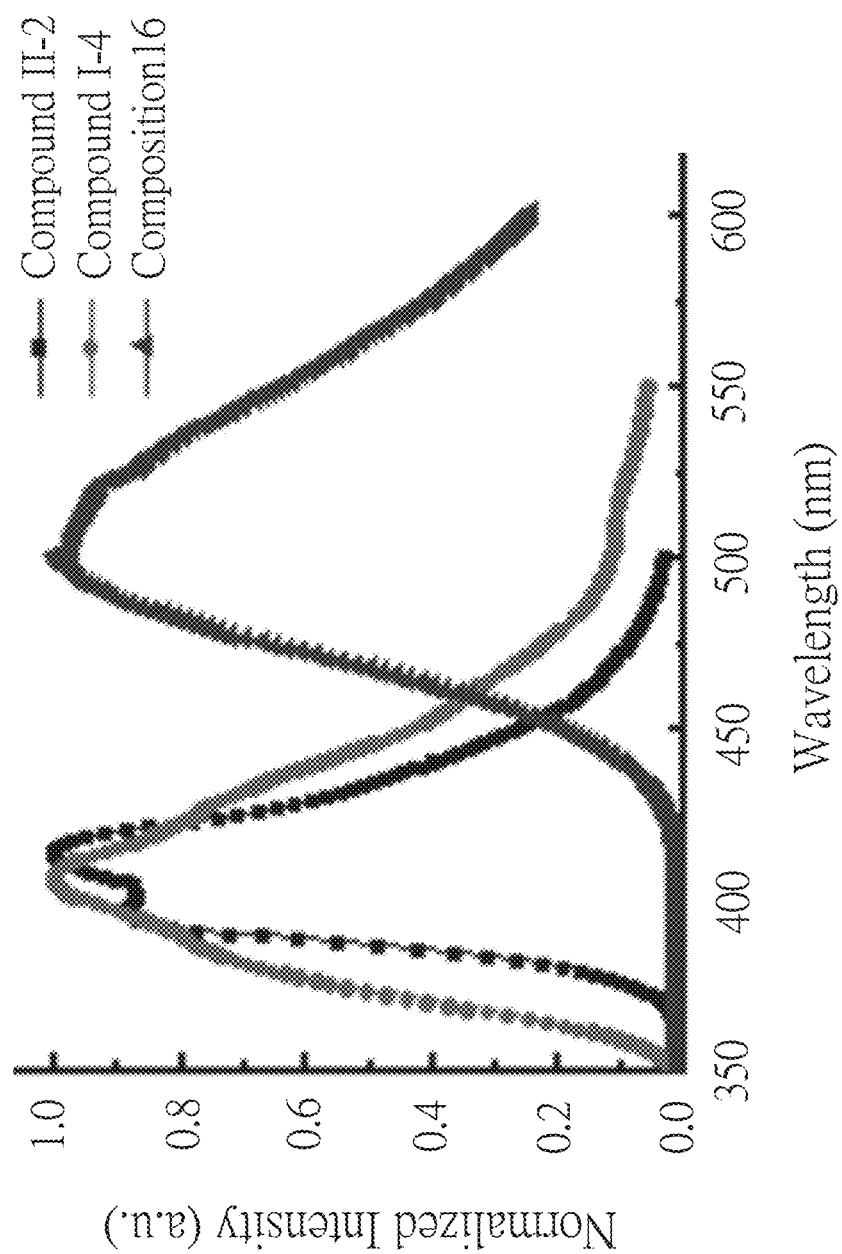
FIG. 2 is a photoluminescence spectra of Compound I-4, Compound II-2 and Composition 16.

The PL spectra of Composition 16 and its components of Compound I-4 and Compound II-2 were measured and recorded as shown in FIG. 2.

TABLE 6

λmax of Compositions 2, 8, 9, 13, 14, 16, 17, 19, 28 to 39, 42, 43, 45 to 47 and 52 and λmax of the first and second host compounds concerned

| Composition No. | First Host Compound | Second Host Compound | λmax of First Host Compound (nm) | λmax of Second Host Compound (nm) | λmax of Composition (nm) |
|---|---|---|---|---|---|
| 2 | I-2 | II-1 | 393 | 413 | 498 |
| 8 | I-20 | II-1 | 445 | 413 | 493 |
| 9 | I-22 | II-1 | 417 | 413 | 500 |
| 13 | I-1 | II-2 | 394 | 414 | 488 |
| 14 | I-2 | II-2 | 393 | 414 | 478 |
| 16 | I-4 | II-2 | 407 | 414 | 500 |
| 17 | I-5 | II-2 | 419 | 414 | 500 |
| 19 | I-7 | II-2 | 387 | 414 | 462 |
| 28 | I-16 | II-2 | 402 | 414 | 478 |
| 29 | I-17 | II-2 | 404 | 414 | 493 |
| 30 | I-18 | II-2 | 398 | 414 | 494 |
| 31 | I-19 | II-2 | 392 | 414 | 499 |
| 32 | I-20 | II-2 | 445 | 414 | 466 |
| 33 | I-21 | II-2 | 401 | 414 | 488 |
| 34 | I-22 | II-2 | 417 | 414 | 505 |
| 35 | I-23 | II-2 | 397 | 414 | 508 |
| 36 | I-24 | II-2 | 395 | 414 | 494 |
| 37 | I-25 | II-2 | 410 | 414 | 483 |
| 38 | I-26 | II-2 | 389 | 414 | 463 |
| 39 | I-27 | II-2 | 403 | 414 | 498 |
| 42 | I-2 | II-4 | 393 | 388 | 469 |
| 43 | I-5 | II-4 | 419 | 388 | 469 |
| 45 | I-20 | II-4 | 445 | 388 | 472 |
| 46 | I-22 | II-4 | 417 | 388 | 477 |
| 47 | I-18 | II-4 | 398 | 388 | 463 |
| 52 | TPBi | Compound II-2 | 382 | 414 | 418 |

As shown in Table 6 and FIG. 2, in each set of PL spectra, the λ max of Compositions 2, 8, 9, 13, 14, 16, 17, 19, 28 to 39, 42, 43, and 45 to 47 were obviously found to red shift to longer wavelength range as compared with the λ max of the first host and second host compounds concerned. However, the degree of red shift for λ max of Composition 52 was obviously smaller than those of Compositions 2, 8, 9, 13, 14, 16, 17, 19, 28 to 39, 42, 43, and 45 to 47. Accordingly, it demonstrated that the first and second host compounds concerned of Compositions 2, 8, 9, 13, 14, 16, 17, 19, 28 to 39, 42, 43 and 45 to 47 respectively formed an exciplex.

Preparation of OLED Devices

A glass substrate coated with an ITO layer (abbreviated as ITO substrate) in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of Examples 1 to 43 and Comparative Examples 1 and 2. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a hole transporting layer (HTL), a green/red emission layer (GEL/REL), an electron transporting layer (ETL), an electron injection layer (EIL), and a cathode (Cthd).

Herein, HI was a material for forming HIL-1 and HIL-2; HI-D was a material for forming HIL-1. HT was material for forming HTL; ET was material for forming ETL. Liq was a material for forming ETL and EIL. Compositions 1 to 53 were respectively a material of GHRH for forming GEL/REL, and GD/RD were respectively a dopant for forming GEL/REL. The main difference of the OLEDs between the Examples and Comparative Example was that the GEL/REL of the OLED in the following comparative example was made of the Compositions 52 and 53 containing TPBi but the GEL/REL of OLED in the following examples was made of Compositions 1 to 51 of the present invention listed in Table 5. The detailed chemical structure of foresaid commercial material was listed in Table 7.

TABLE 7 chemical structures of commercial materials for OLED devices

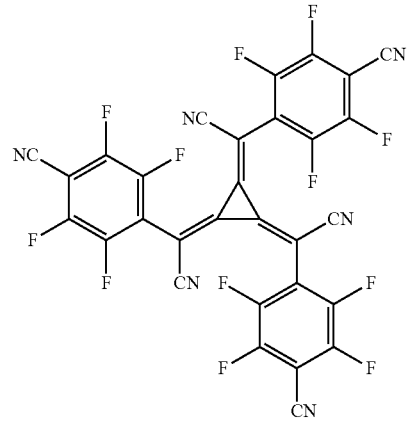

HI-D

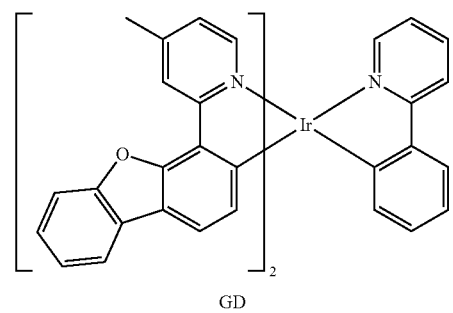

GD

TABLE 7-continued chemical structures of commercial materials for OLED devices

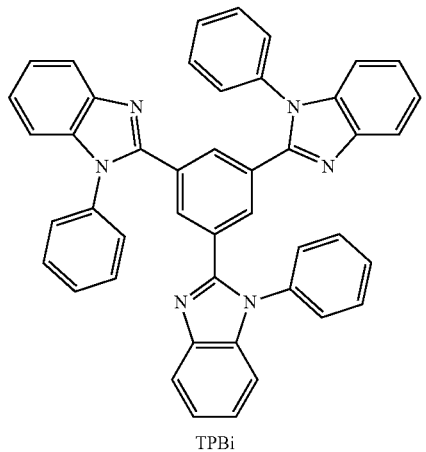
TPBi

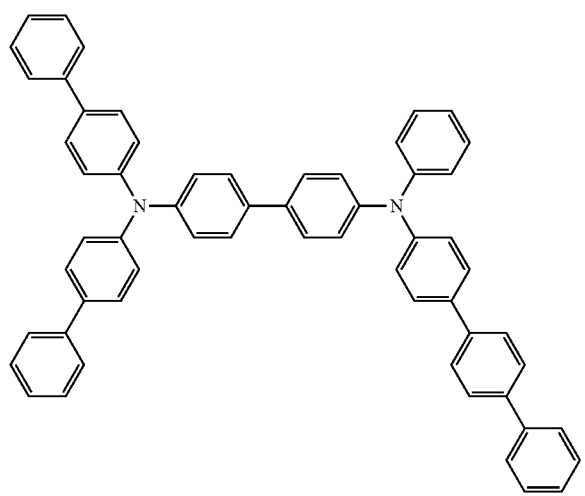
HI

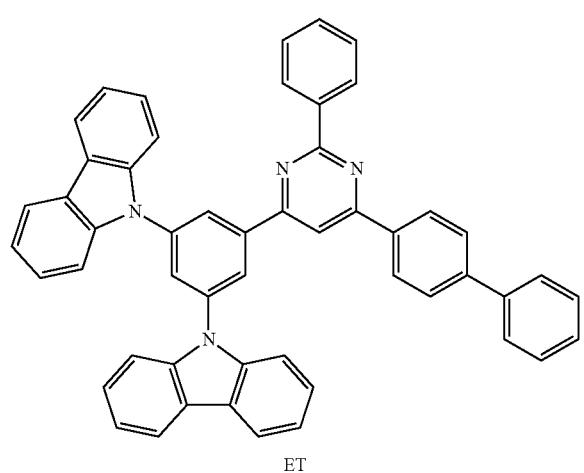 [SMILES: c1ccc(-c2ccc(-c3cc(-c4cc(-n5c6ccccc6c6ccccc65)cc(-n5c6ccccc6c6ccccc65)c4)nc(-c4ccccc4)n3)cc2)cc1]
ET

TABLE 7-continued chemical structures of commercial materials for OLED devices

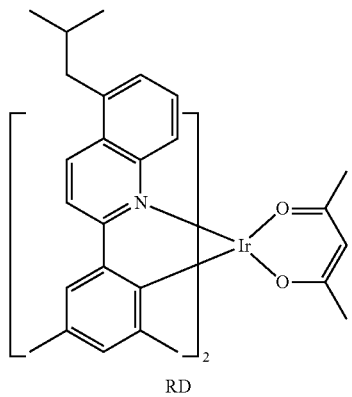
RD

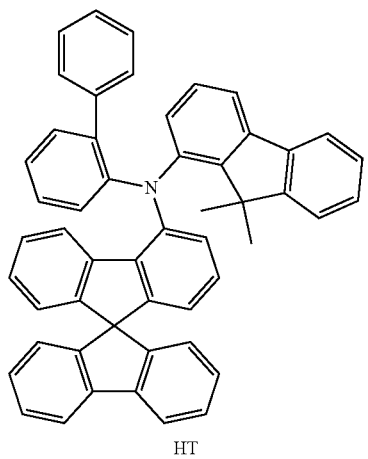
HT

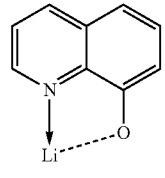
Liq

Preparation of Green OLED Devices

To prepare the green OLED device, multiple organic layers were respectively deposited on the ITO substrate according to the sequence as listed in Table 8, and the materials and the thicknesses of the organic layers in green OLED devices were also listed in Table 8.

TABLE 8 coating sequence, materials and thickness of the organic layers in green OLED device

| Coating Sequence | Layer | Material | Thickness |
|---|---|---|---|
| 1 | HIL-1 | HI doped with 3.0 wt % of HI-D | 100 Å |
| 2 | HIL-2 | HI | 1400 Å |
| 3 | HTL | HT | 100 Å |
| 4 | GEL | Composition for GH doped with 10.0 wt % of GD | 400 Å |

TABLE 8-continued coating sequence, materials and thickness of the organic layers in green OLED device

| Coating Sequence | Layer | Material | Thickness |
|---|---|---|---|
| 5 | ETL | ET doped with 35.0 wt % of Liq | 350 Å |
| 6 | EIL | Liq | 15 Å |
| 7 | Cthd | Al | 1500 Å |

Preparation of Red OLED Devices

To prepare the red OLED device, multiple organic layers were respectively deposited on the ITO substrate according to the sequence as listed in Table 9, and the materials and the thicknesses of the organic layers in red OLED devices were also listed in Table 9.

TABLE 9 coating sequence, materials and thickness of the organic layers in red OLED device

| Coating Sequence | Layer | Material | Thickness |
|---|---|---|---|
| 1 | HIL-1 | HI doped with 3.0 wt % of HI-D | 100 Å |
| 2 | HIL-2 | HI | 2200 Å |
| 3 | HTL | HT | 100 Å |
| 4 | REL | Composition for RH doped with 3.5 wt % of RD | 300 Å |
| 5 | ETL | ET doped with 35.0 wt % of Liq | 350 Å |
| 6 | EIL | Liq | 15 Å |
| 7 | Cthd | Al | 1500 Å |

Performance of OLED Devices

1. Color Coordinates (x,y), Driving Voltage and Current Efficiency

To evaluate the performance of OLED devices, the green or red OLED devices were measured by PR650 as photometer and Keithley 2400 as power supply. Color coordinates (x,y) were determined according to the CIE chromaticity scale (Commission Internationale de L'Eclairage, 1931). The results were shown in Tables 10 and 11. For the green OLED devices, the data were collected with a specific luminance at 9000 nits. For the red OLED devices, the data were collected with a specific luminance at 3000 nits.

Characteristics of manufactured OLED devices of Examples 1 to 43 and Comparative Examples 1 and 2 were measured by the following method.

(1). Measurement of the Current Density Change Depending on Voltage Change

Current values flowing in the devices of the OLEDs were measured, while increasing the voltage from 0V to 6.2V by using the power supply, and the current value of each voltage was measured.

(2). Measurement of the Luminance Change Depending on Voltage Change

Luminance of the manufactured OLEDs was measured by the photometer, while increasing the voltage from 0V to 6.2V by using the power supply.

(3). Measurement of Current Efficiency

Current efficiency (cd/A) was calculated by using the luminance and current density obtained in aforesaid items (1) and (2).

(4). Measurement of Color Coordinates (x,y)

Color coordinates (x,y) were determined according to the CIE chromaticity scale. CIE (x,y) changes depended on voltage from 0V to 6.2V, which were recorded by the photometer.

Compositions 1 to 4, 6, 8, 9, 11, 15, 18, 20 to 29, 31, 33, 35 to 38, 40 to 43, 45 to 51 were respectively used for GH in the GEL of green OLEDs of Examples 1 to 37. Composition 53 was used for GH in the GEL of the green OLED of Comparative Example 1. The composition for GH, and data of CIE, driving voltage and current efficiency of Examples 1 to 37 and Comparative Example 1 were listed in Table 10.

TABLE 10

Compositions for GH, CIEs, driving voltages, and current efficiencies of green OLED devices of Examples 1 to 37 and Comparative Example 1

| Example No. | Composition No. for GH | CIE (x, y) | Driving voltage (V) | Current efficiency (cd/A) |
|---|---|---|---|---|
| Example 1 | 1 | (0.316, 0.632) | 5.24 | 67.3 |
| Example 2 | 2 | (0.319, 0.630) | 4.18 | 68.6 |
| Example 3 | 3 | (0.319, 0.629) | 4.45 | 66.6 |
| Example 4 | 4 | (0.322, 0.629) | 4.72 | 68.8 |
| Example 5 | 6 | (0.314, 0.632) | 5.18 | 61.8 |
| Example 6 | 8 | (0.318, 0.628) | 4.60 | 64.1 |
| Example 7 | 9 | (0.322, 0.628) | 4.22 | 62.3 |
| Example 8 | 11 | (0.328, 0.627) | 4.74 | 73.2 |
| Example 9 | 15 | (0.317, 0.634) | 4.29 | 71.8 |
| Example 10 | 18 | (0.356, 0.598) | 5.41 | 58.6 |
| Example 11 | 20 | (0.314, 0.635) | 4.58 | 63.9 |
| Example 12 | 21 | (0.323, 0.629) | 4.14 | 69.2 |
| Example 13 | 22 | (0.330, 0.625) | 4.22 | 70.2 |
| Example 14 | 23 | (0.317, 0.632) | 4.62 | 66.8 |
| Example 15 | 24 | (0.314, 0.635) | 4.59 | 70.4 |
| Example 16 | 25 | (0.324, 0.630) | 4.63 | 70.7 |
| Example 17 | 26 | (0.313, 0.635) | 4.55 | 70.0 |
| Example 18 | 27 | (0.316, 0.634) | 4.40 | 72.3 |
| Example 19 | 28 | (0.318, 0.629) | 4.45 | 65.2 |
| Example 20 | 29 | (0.320, 0.627) | 4.53 | 61.5 |
| Example 21 | 31 | (0.317, 0.631) | 4.55 | 65.2 |
| Example 22 | 33 | (0.315, 0.631) | 4.34 | 62.3 |
| Example 23 | 35 | (0.321, 0.625) | 5.75 | 58.9 |
| Example 24 | 36 | (0.318, 0.629) | 4.35 | 66.7 |
| Example 25 | 37 | (0.318, 0.628) | 4.14 | 62.7 |
| Example 26 | 38 | (0.312, 0.633) | 4.53 | 65.5 |
| Example 27 | 40 | (0.317, 0.630) | 5.24 | 61.0 |
| Example 28 | 41 | (0.317, 0.629) | 4.70 | 59.9 |
| Example 29 | 42 | (0.320, 0.627) | 4.62 | 63.0 |
| Example 30 | 43 | (0.322, 0.631) | 4.37 | 72.4 |
| Example 31 | 45 | (0.319, 0.627) | 4.46 | 62.9 |
| Example 32 | 46 | (0.322, 0.627) | 4.34 | 63.7 |
| Example 33 | 47 | (0.316, 0.630) | 5.39 | 61.8 |
| Example 34 | 48 | (0.323, 0.629) | 4.23 | 68.2 |
| Example 35 | 49 | (0.317, 0.633) | 4.37 | 76.1 |
| Example 36 | 50 | (0.331, 0.626) | 4.28 | 73.7 |
| Example 37 | 51 | (0.319, 0.633) | 4.91 | 68.1 |
| Comparative Example 1 | 53 | (0.313, 0.634) | 6.30 | 47.2 |

Compositions 5, 7, 10, 12, 19 and 44 were respectively used for RH in the REL of red OLEDs of Examples 38 to 43. Composition 53 was used for RH in the REL of the red OLED of Comparative Example 2. The composition for RH, and data of CIE, driving voltage and current efficiency of Examples 38 to 43 and Comparative Example 2 were listed in Table 11.

TABLE 11

Compositions for RH, CIEs, driving voltages, and current efficiencies of red OLED devices of Examples 38 to 43 and Comparative Example 2

| Example No. | Composition No. for RH | CIE (x, y) | Driving voltage (V) | Current efficiency (cd/A) |
| --- | --- | --- | --- | --- |
| Example 38 | 5 | (0.660, 0.338) | 4.05 | 27.3 |
| Example 39 | 7 | (0.665, 0.333) | 4.31 | 27.0 |
| Example 40 | 10 | (0.660, 0.338) | 4.31 | 28.7 |
| Example 41 | 12 | (0.661, 0.337) | 4.40 | 26.0 |
| Example 42 | 19 | (0.661, 0.336) | 4.74 | 28.7 |
| Example 43 | 44 | (0.661, 0.336) | 4.53 | 28.2 |
| Comparative Example 2 | 53 | (0.658, 0.339) | 5.80 | 17.5 |

2. Measurement of Lifespan (T95)

Lifespan (T95) was measured by OLED life time test system (Chroma model 58131). T95 represents lifespan data evaluating a period taken for luminance to reach 95% with respect to the initial luminance (at 7,000 nits for green OLEDs and at 6000 nits for red OEDs).

The composition for GH and the lifespan of Examples 1 to 7, 12, 13, 18, 29 to 34, 36 and 37 and Comparative Example 1 were listed in Table 12.

TABLE 12

Compositions for GH and lifespan of green OLED devices of Examples 1 to 7, 12, 13, 18, 29 to 34, 36 and 37 and Comparative Example 1

| Example No. | Composition No. | Lifespan (T95) (hrs) |
| --- | --- | --- |
| Example 1 | 1 | 90 |
| Example 2 | 2 | 104 |
| Example 3 | 3 | 47 |
| Example 4 | 4 | 81 |
| Example 5 | 6 | 65 |
| Example 6 | 8 | 61 |
| Example 7 | 9 | 112 |
| Example 12 | 21 | 40 |
| Example 13 | 22 | 20 |
| Example 18 | 27 | 44 |
| Example 29 | 42 | 112 |
| Example 30 | 43 | 30 |
| Example 31 | 45 | 87 |
| Example 32 | 46 | 98 |
| Example 33 | 47 | 56 |
| Example 34 | 48 | 52 |
| Example 36 | 50 | 68 |
| Example 37 | 51 | 20 |
| Comparative Example 1 | 53 | 1 |

The composition for RH and the lifespan of Examples 38, 39, 41 and 43 and Comparative Example 1 were listed in Table 13.

TABLE 13

Compositions for RH and lifespan of red OLED devices of Examples 38, 39, 41 and 43 and Comparative Example 2

| Example No. | Composition No. | Lifespan (T95) (hrs) |
| --- | --- | --- |
| Example 38 | 5 | 32 |
| Example 39 | 7 | 17 |
| Example 41 | 12 | 16 |
| Example 43 | 44 | 14 |
| Comparative Example 2 | 53 | 0.5 |

Based on the results, in comparison with the Composition 53 containing the commercial host material for the green emission layer, adopting Compositions 1 to 4, 6, 8, 9, 11, 15, 18, 20 to 29, 31, 33, 35 to 38, 40 to 43, 45 to 51 of the present invention as the host material for the green emission layer can reduced the driving voltage and improve the current efficiency of the green OLEDs. Similarly, in comparison with the Composition 53 containing the commercial host material for the red emission layer, adopting Compositions 5, 7, 10, 12, 19 and 44 of the present invention as the host material for the red emission layer also can reduce the driving voltage and improve the current efficiency of the red OLEDs.

Even more, adopting Compositions 1 to 4, 6, 8, 9, 21, 22, 27, 42, 43, 45 to 48, 50 and 51 of the present invention as the host material for the green emission layer can prolong the lifespan of the green OLEDs. Similarly, adopting Compositions 5, 7, 12 and 44 of the present invention as the host material for the red emission layer can prolong the lifespan of the red OLEDs.

The reason is that the specific first host compounds had a suitable lowest unoccupied molecular orbital (LUMO) level for the better electron injection to the EL compared to TPBi of Comparative example, leading to the lower driving voltage. In addition, the cooperation of the specific first and second host compounds would respectively form an exciplex as shown in Table 6, and such emission mechanism can effectively use the exciton to lead the high efficiency devices.

It demonstrated that the composition of the present invention is suitable as a host material for any green or red OLEDs, and allows the OLEDs using the same to have low driving voltage and improved current efficiency, and even prolonged lifespan.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A composition for an organic electronic device, comprising:
a first host compound represented by the following Formula (I); and Formula (I)

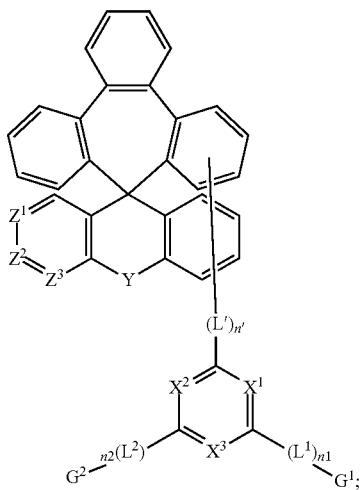

a second host compound represented by any one of the following Formulae (II-I) to (I-III);

Formula (II-I)

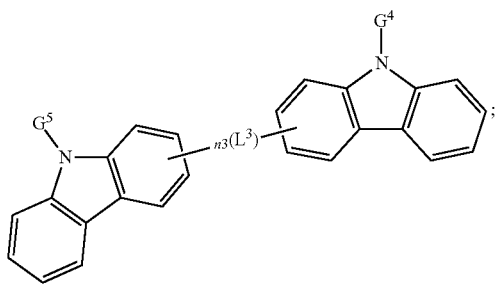

Formula (II-II)

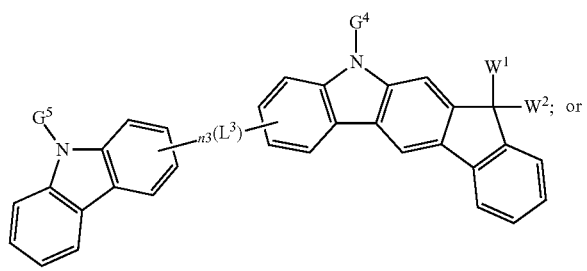

Formula (II-III)

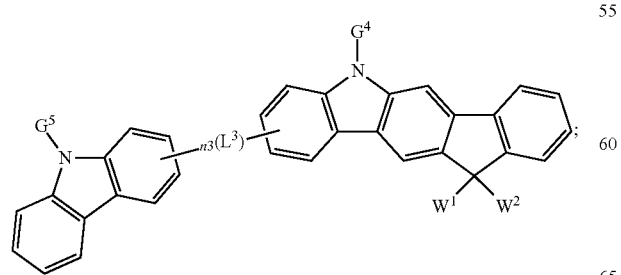

wherein Y in Formula (I) is a single bond, an oxygen atom or a sulfur atom;

$Z^1$ to $Z^3$ in Formula (I) are each independently CH, adjacent two of $Z^1$ to $Z^3$ in Formula (I) are joined together to form an aryl ring and a remaining one of $Z^1$ to $Z^3$ is CH, or adjacent two of $Z^1$ to $Z^3$ in Formula (I) are joined together to form a heteroaryl ring containing at least one furan group or at least one thiophene group and the remaining one of $Z^1$ to $Z^3$ is CH;

two of $X^1$ to $X^3$ in Formula (I) are each independently a nitrogen atom, and the other of $X^1$ to $X^3$ in Formula (I) is CH or a nitrogen atom;

L', $L^1$ and $L^2$ in Formula (I) are each independently an arylene group having 6 to 18 ring carbon atoms;

n', n1 and n2 are each independently an integer from 0 to 2;

$G^1$ and $G^2$ in Formula (I) are each independently an aryl group having 6 to 18 ring carbon atoms, an aryloxy group having 6 to 18 ring carbon atoms, an arylthioxy group having 6 to 18 ring carbon atoms, or a heteroaryl group containing a N, O, or S atom and having 3 to 30 ring carbon atoms;

$L^3$ in Formulae (II-I) to (I-III) is an arylene group having 6 to 18 ring carbon atoms;

n3 is an integer from 0 to 2;

$G^4$ and $G^5$ in Formulae (II-I) to (II-III) are each independently an aryl group having 6 to 18 ring carbon atoms, an aryloxy group having 6 to 18 ring carbon atoms, an arylthioxy group having 6 to 18 ring carbon atoms, or an heteroaryl group containing a N, O, or S atom and having 3 to 30 ring carbon atoms; and wherein $W^1$ and $W^2$ in Formulae (I-I) to (II-III) are each independently a methyl group, an ethyl group, a propyl group, a butyl group or a phenyl group.

2. The composition as claimed in claim 1, wherein the first host compound is represented by the following Formula (I'):

Formula (I')

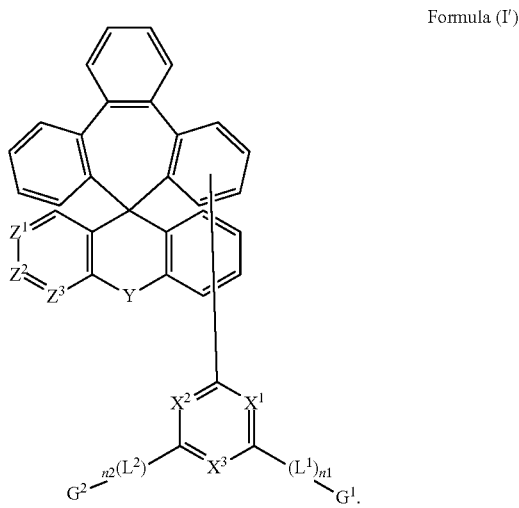

3. The composition as claimed in claim 2, wherein a weight ratio of the first and second host compounds ranges from 3:7 to 7:3.

4. The composition as claimed in claim 2, wherein the first host compound is represented by any one of the following Formulae (I-I) to (I-XVI):
Formula (I-I)
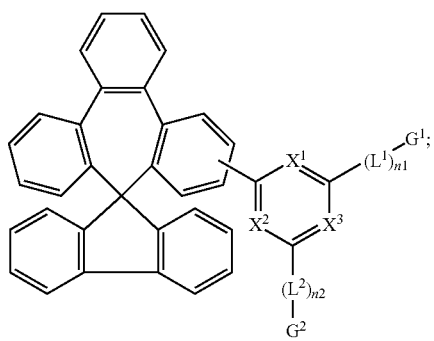
Formula (I-II)
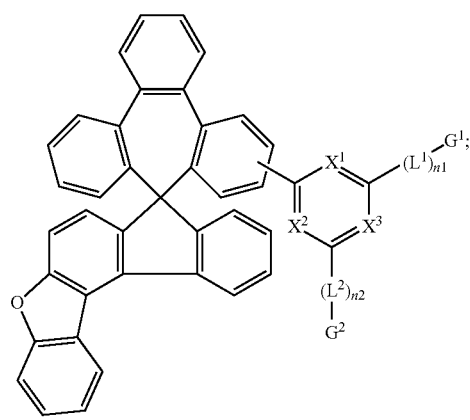
Formula (I-III)
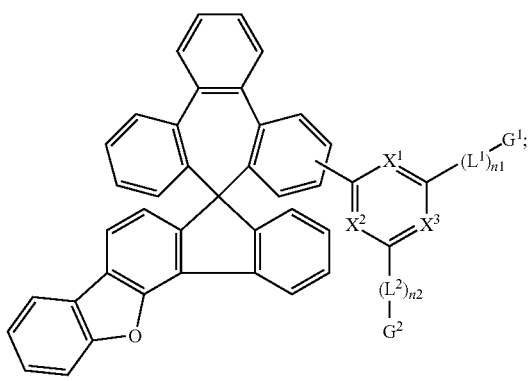
-continued
Formula (I-IV)
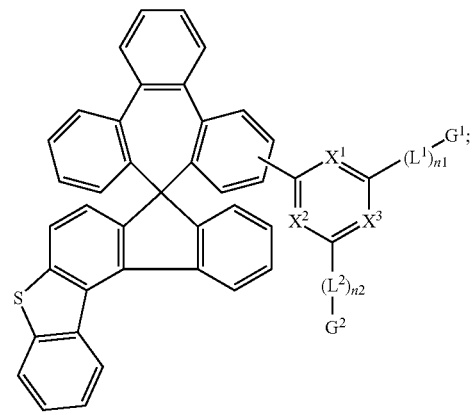
Formuka (I-V)
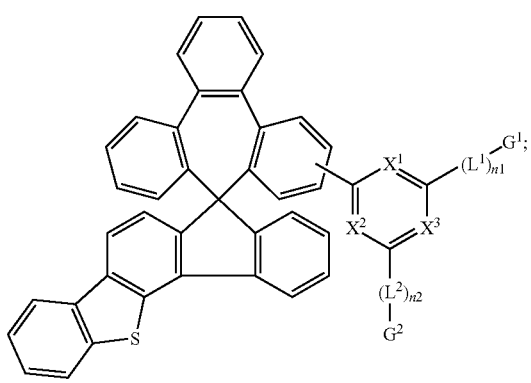
Formula (I-VI)
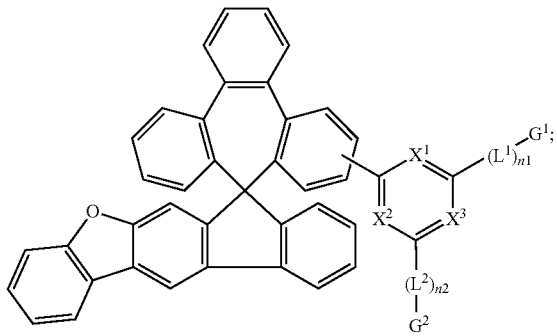
Formula (I-VII)
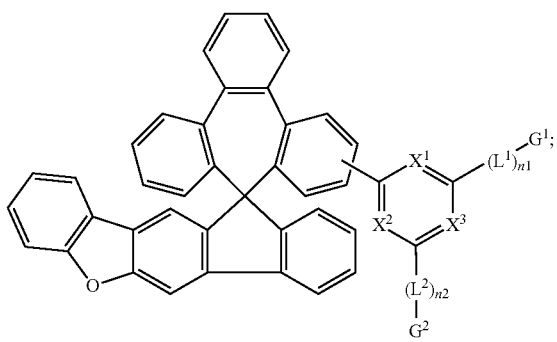

Formula (I-VIII)
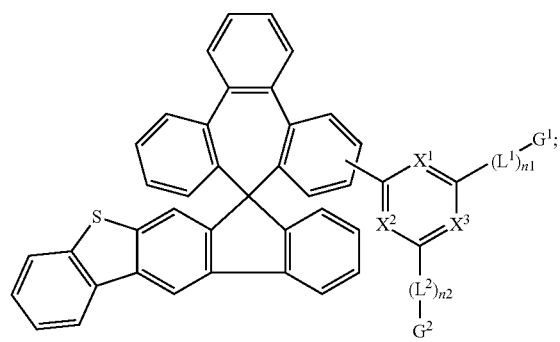
Formula (I-XII)
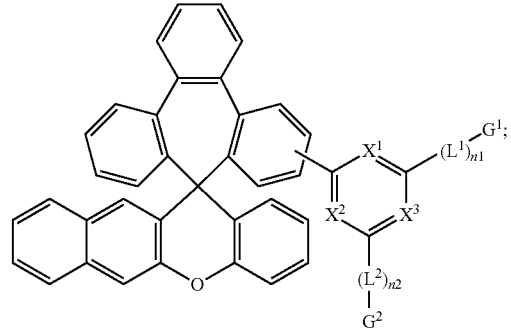
Formula (I-IX)
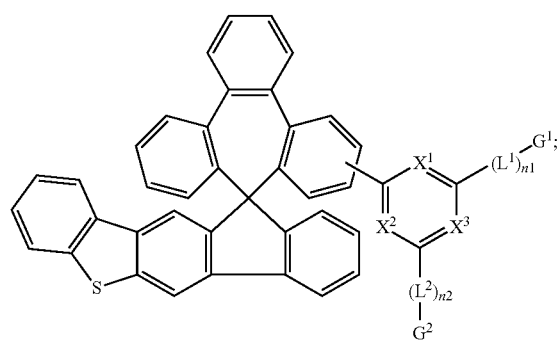
Formula (I-XIII)
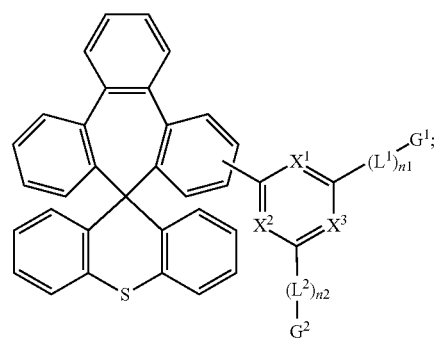
Formula (I-X)
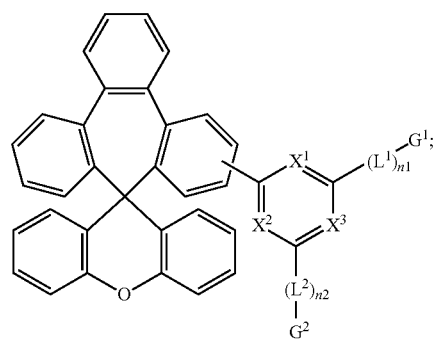
Formula (I-XIV)
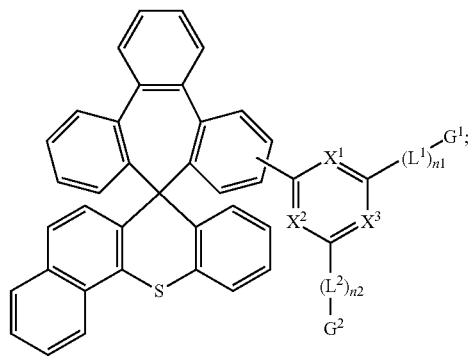
Formula (I-XI)
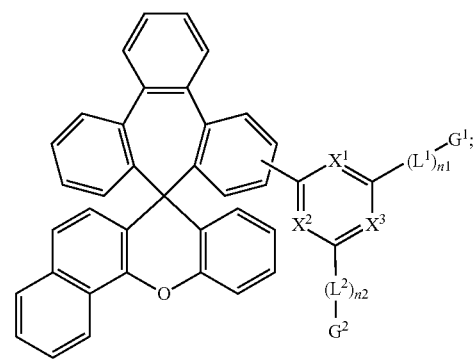
Formula (I-XV)
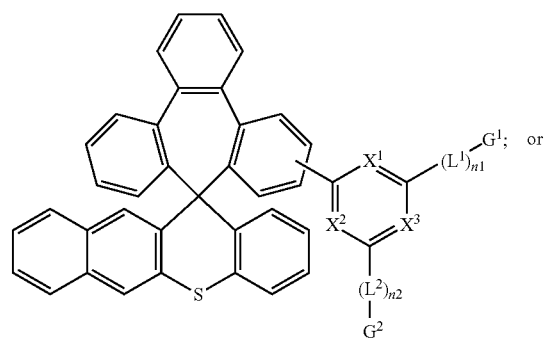

-continued

Formula (I-XVI)

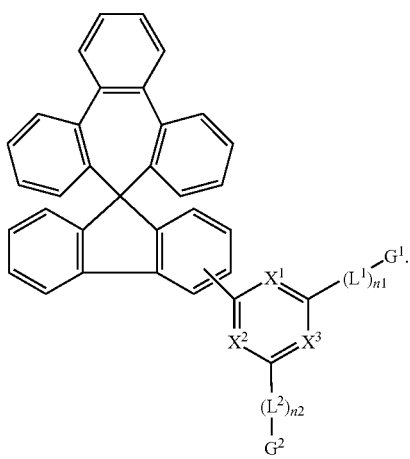

5. The composition as claimed in claim 2, wherein $L^1$ and $L^2$ are each independently a phenylene group.

6. The composition as claimed in claim 2, wherein n1 and n2 are each independently an integer 0 or 1.

7. The composition as claimed in claim 2, wherein $G^1$ and $G^2$ are each independently selected from the group consisting of: a phenyl group, a naphthyl group and a 3,5-diphenylphenyl group.

8. The composition as claimed in claim 2, wherein $G^1$ and $G^2$ are each independently selected from the group consisting of:

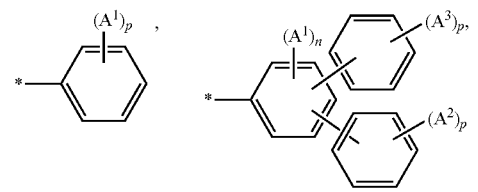

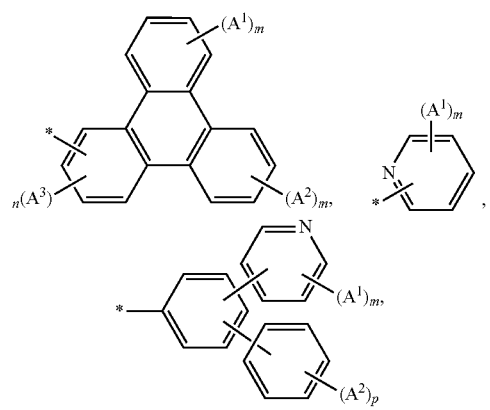

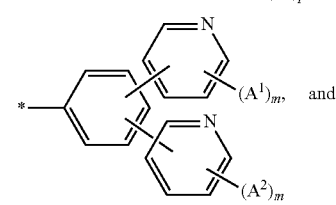

-continued

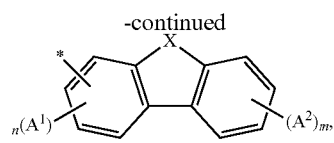

where X is O, S, or

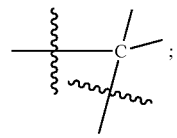

wherein p is an integer from 1 to 5, m is an integer from 1 to 4, and n is an integer from 1 to 3; and $A^1$ to $A^3$ are each independently selected from the group consisting of: a hydrogen atom, a deuterium atom, a halo group, a cyano group, a nitro group, an alkyl group having 1 to 6 carbon atoms, an alkenyl group having 2 to 6 carbon atoms, and an alkynyl group having 2 to 6 carbon atoms.

9. The composition as claimed in claim 2, wherein $L^3$ is a phenylene group.

10. The composition as claimed in claim 2, wherein n3 is an integer 0 or 1.

11. The composition as claimed in claim 2, wherein $G^4$ and $G^5$ are each independently selected from the group consisting of: a phenyl group, a biphenylyl group, and a naphthyl group.

12. The composition as claimed in claim 2, wherein $G^4$ and $G^5$ are each independently selected from the group consisting of:

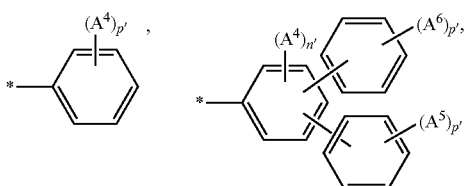

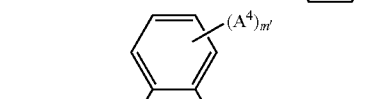

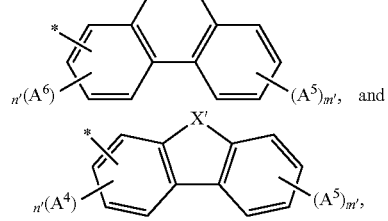

where X' is O, S, or

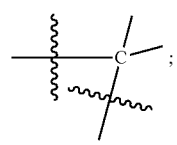

wherein p' is an integer from 1 to 5, m' is an integer from 1 to 4, and n' is an integer from 1 to 3; and A⁴ to A⁶ are each independently selected from the group consisting of: a hydrogen atom, a deuterium atom, a halo group, a cyano group, a nitro group, an alkyl group having 1 to 6 carbon atoms, an alkenyl group having 2 to 6 carbon atoms, and an alkynyl group having 2 to 6 carbon atoms.

13. The composition as claimed in claim 2, wherein a group of

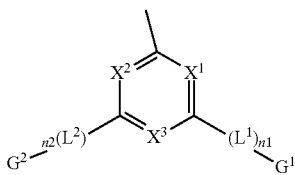

of the first host compound represented by Formula (I') is selected from the group consisting of:

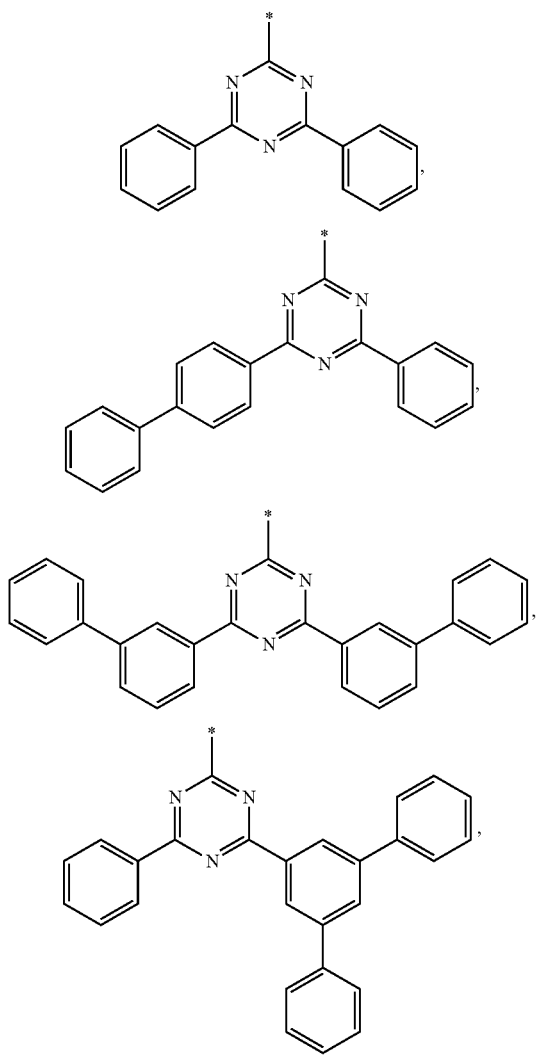

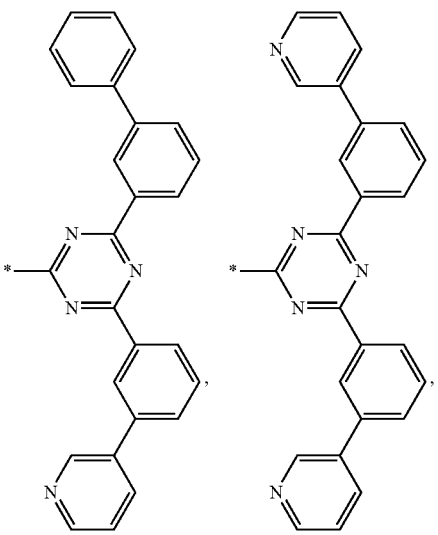

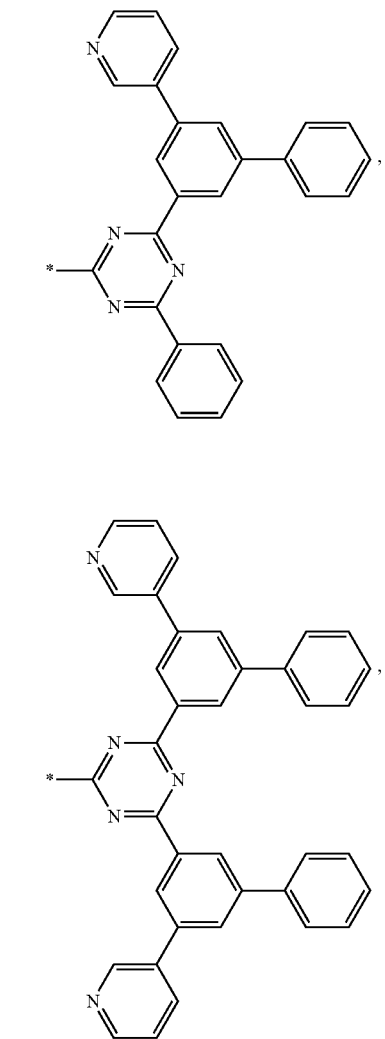

421
-continued
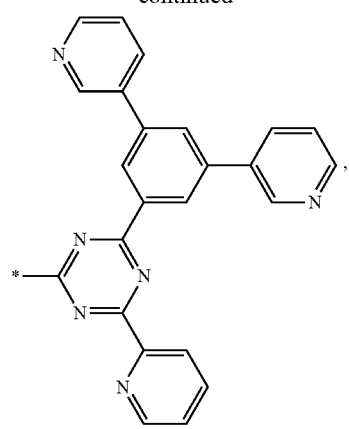
422
-continued
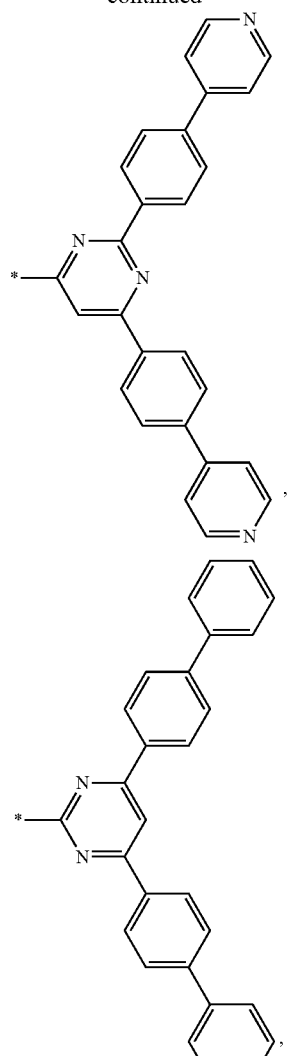
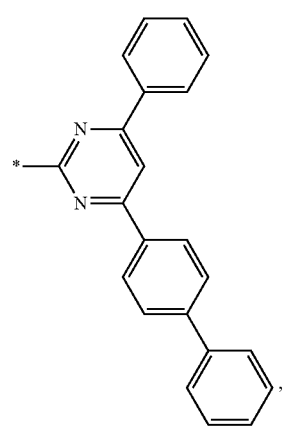

423
-continued
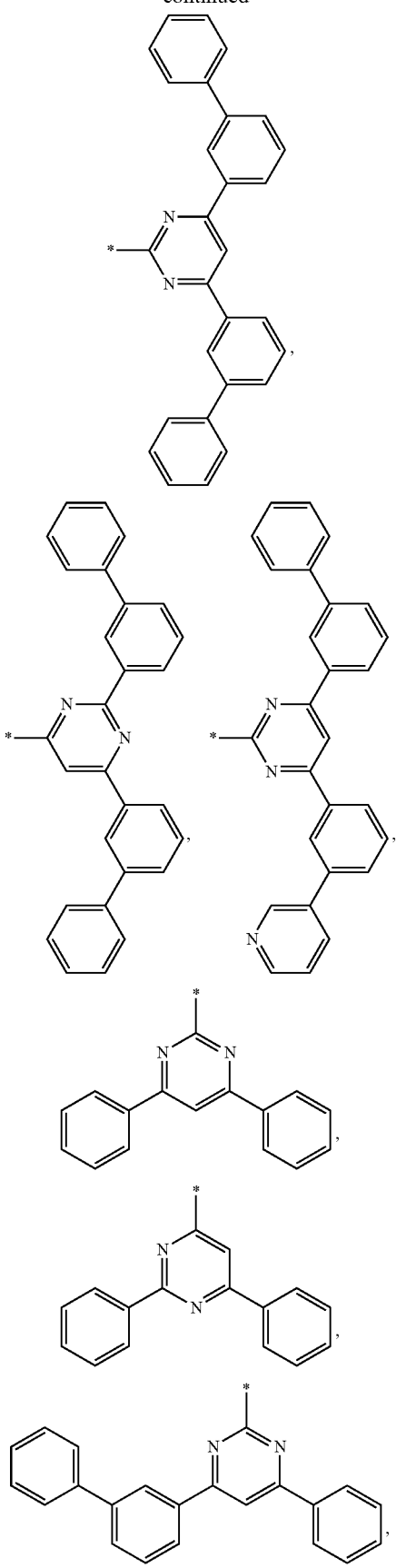
424
-continued
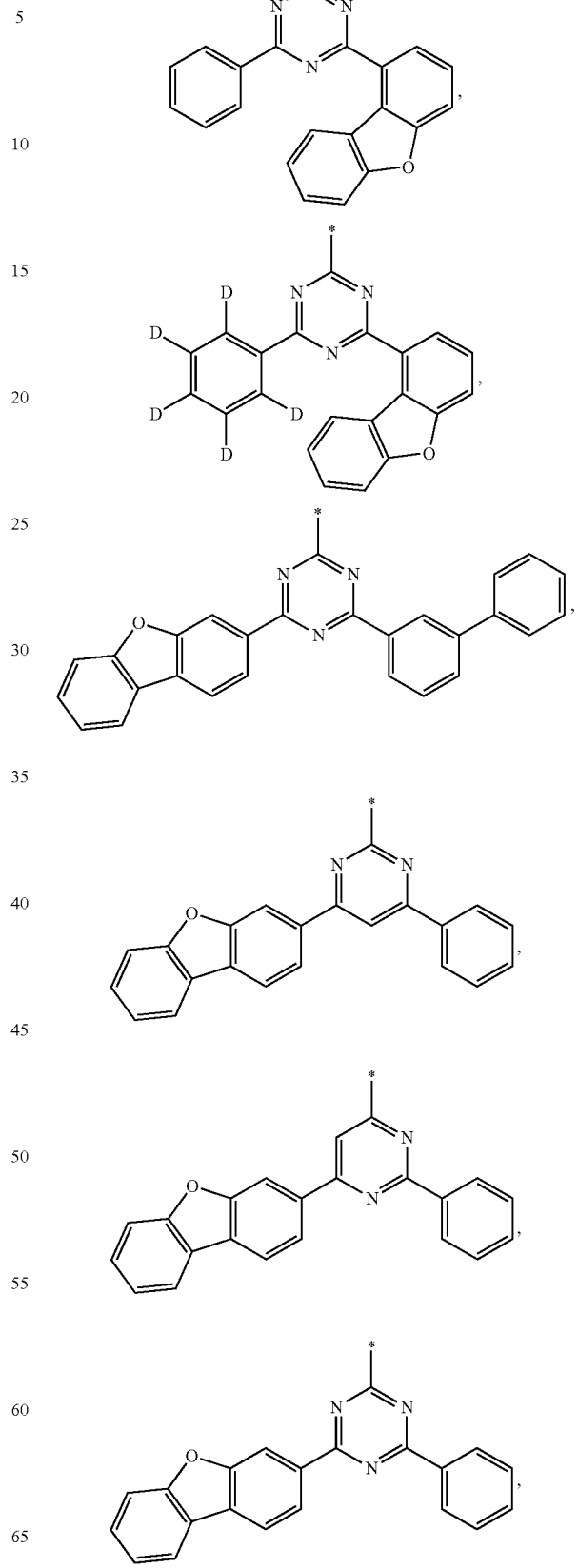

-continued
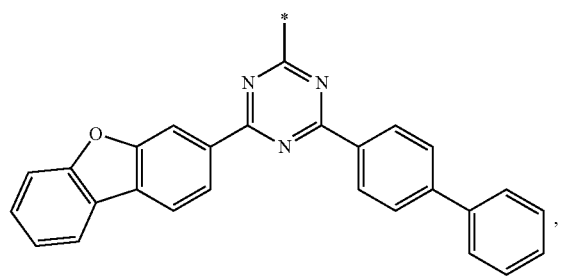
,
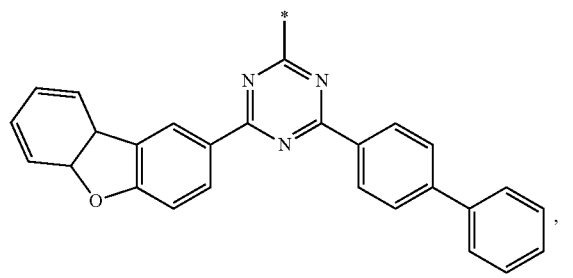
,
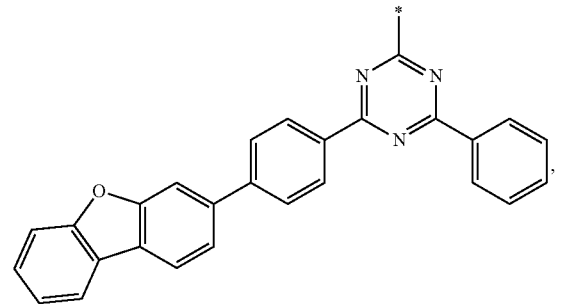
,
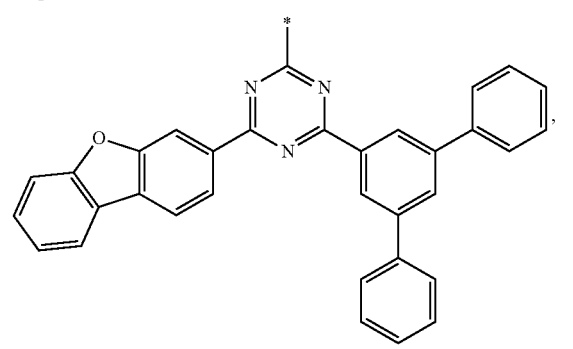
,
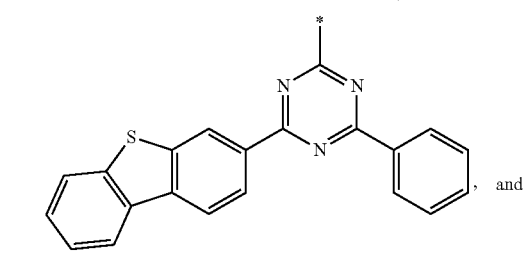
, and
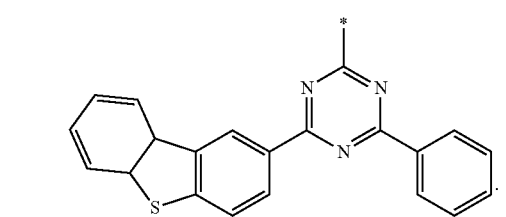
.
14. The composition as claimed in claim 2, wherein $G^4$ and $G^5$ are each independently selected from the group consisting of:
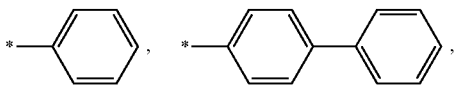
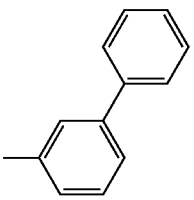
,
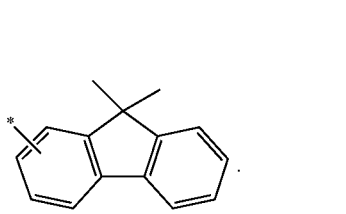
and
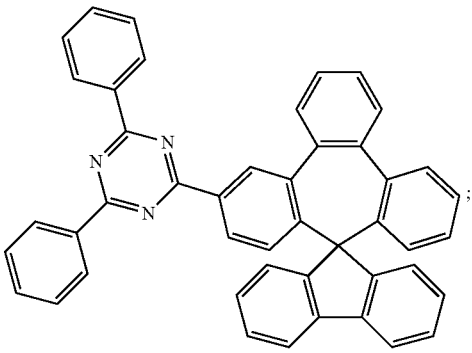
15. The composition as claimed in claim 1, wherein the first host compound is selected from the group consisting of:
Compound I-1
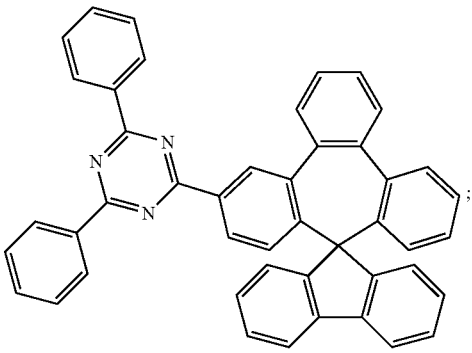
Compound I-2
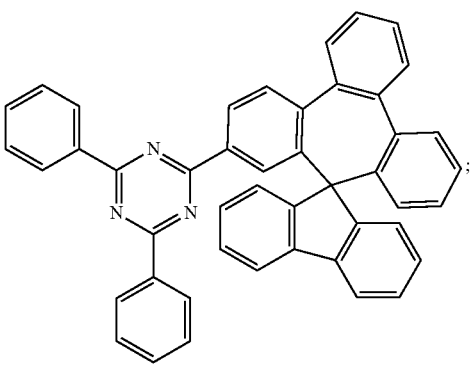

Compound I-3
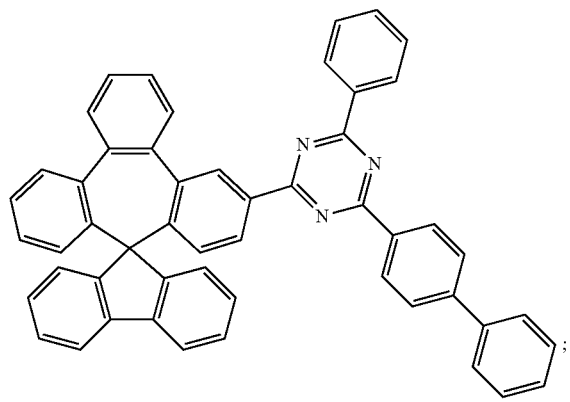
Compound I-4
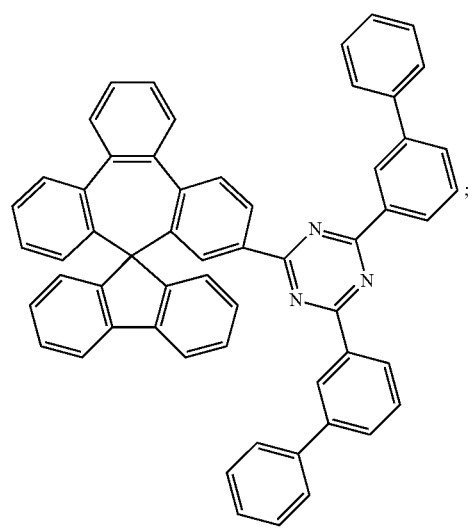
Compound I-5
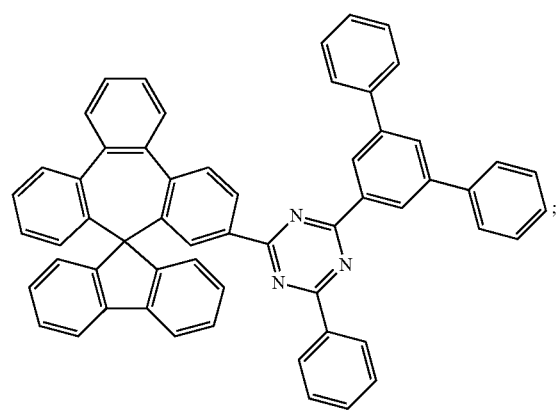
Compound I-6
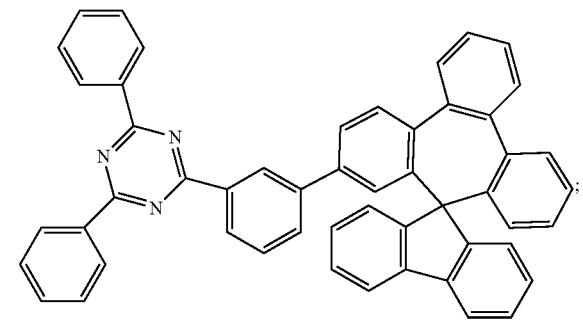
Compound I-7
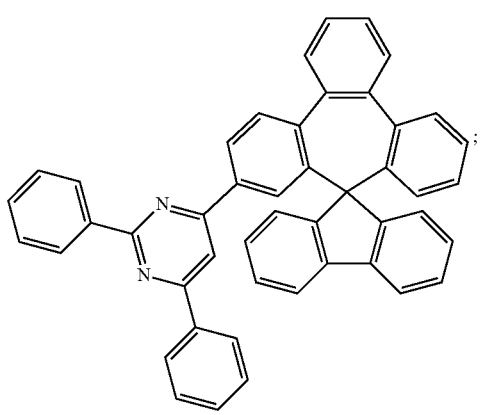
Compound I-8
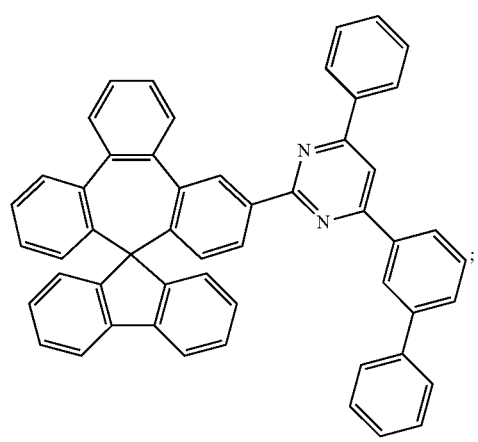
Compound I-9
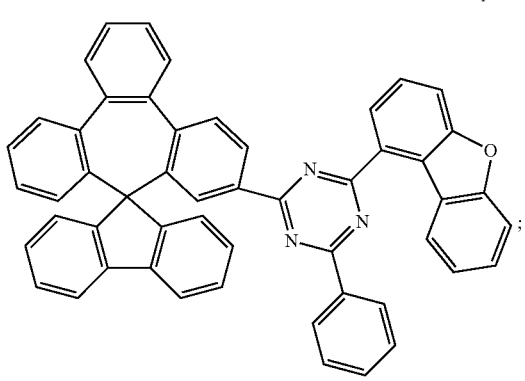

-continued
Compound I-10
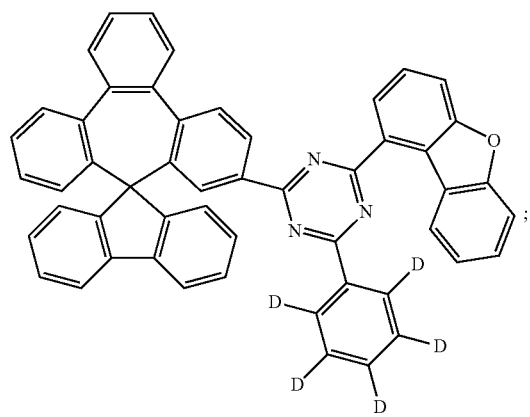
Compound I-11
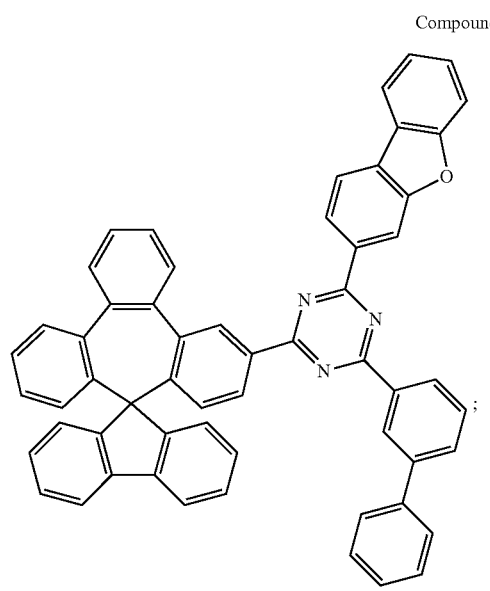
Compound I-12
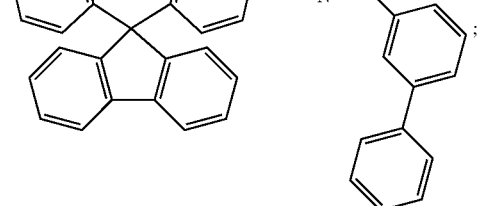
-continued
Compound I-13
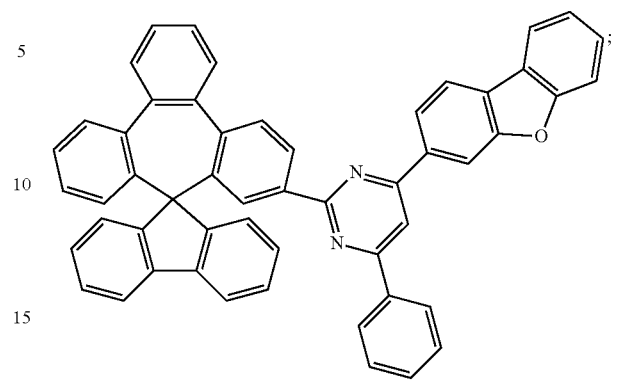
Compound I-14
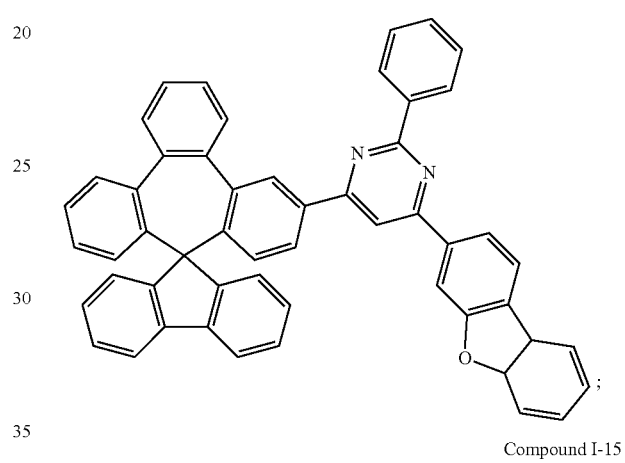
Compound I-15
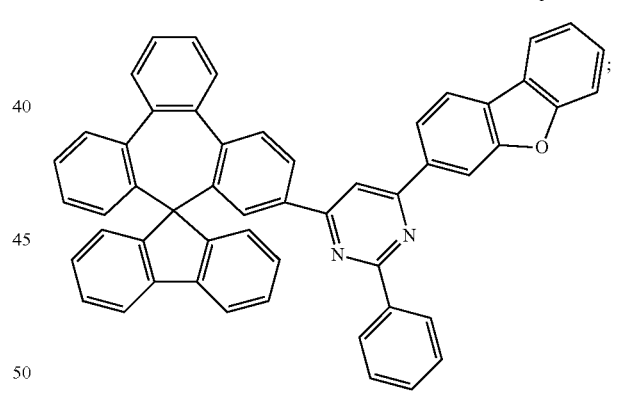
Compound I-16
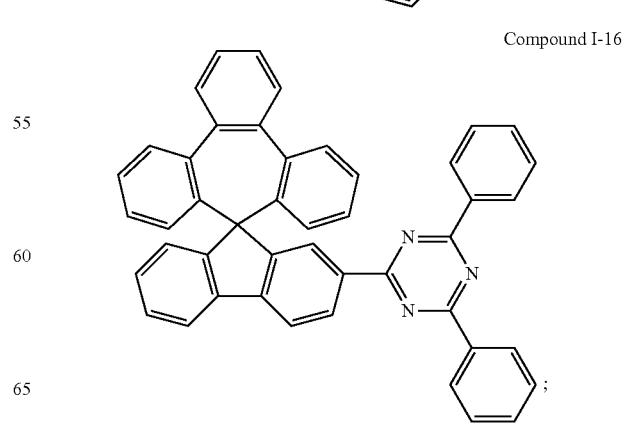

Compound I-17
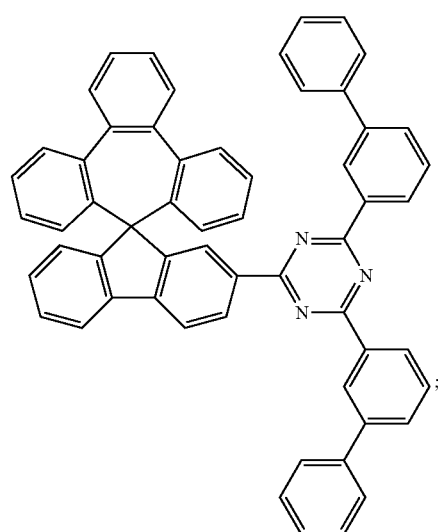
Compound I-18
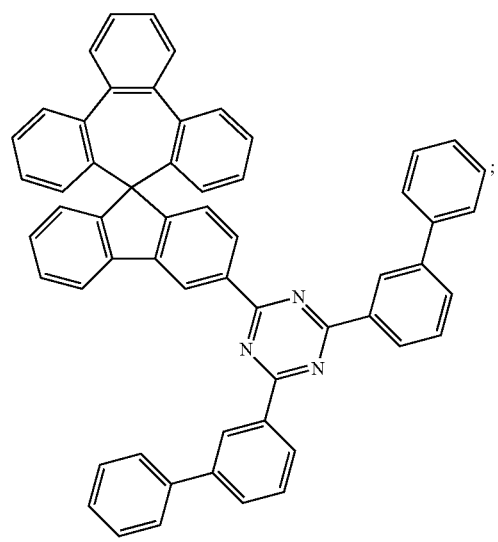
Compound I-19
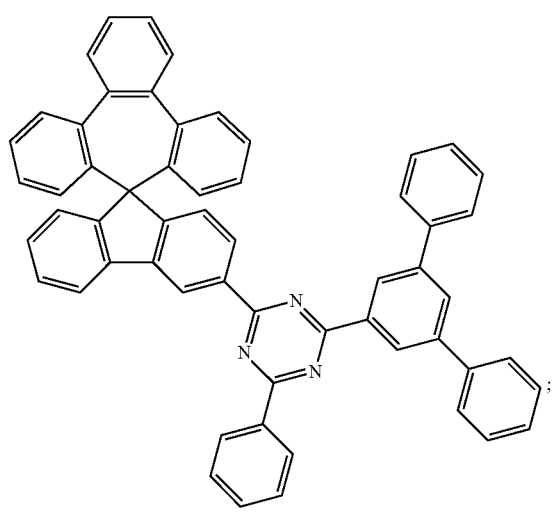
Compound I-20
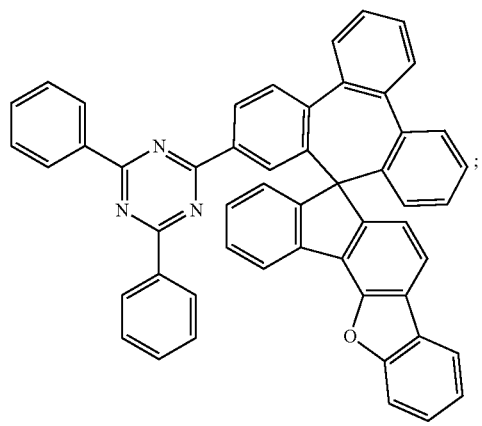
Compound I-21
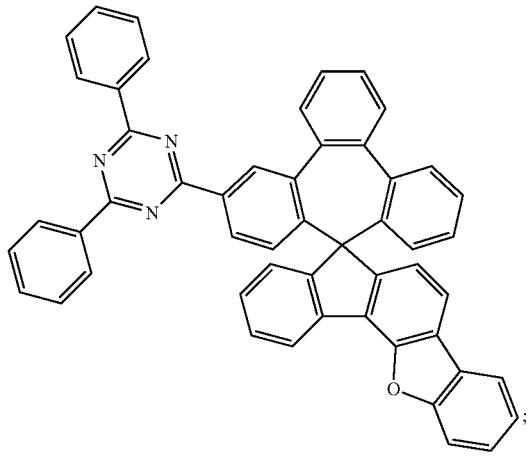
Compound I-22
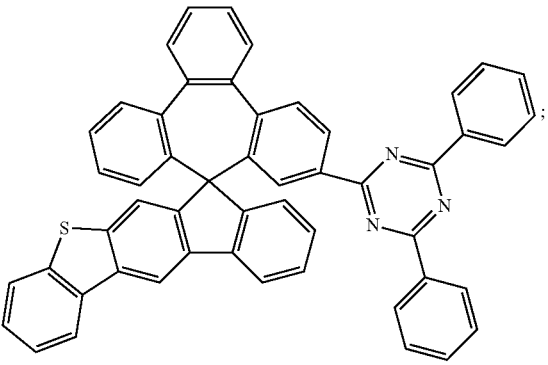

Compound I-23
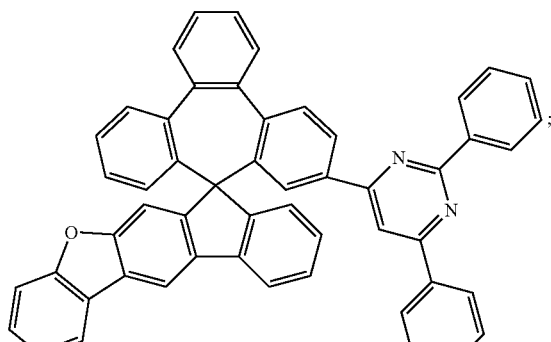
Compound I-24
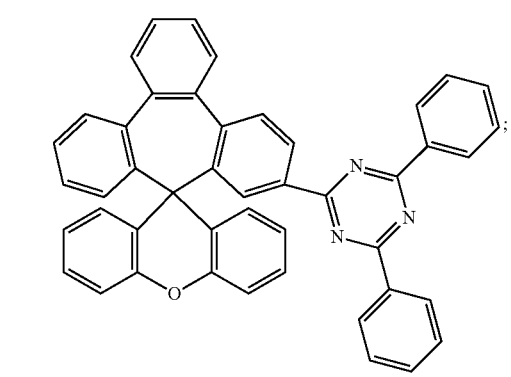
Compound I-25
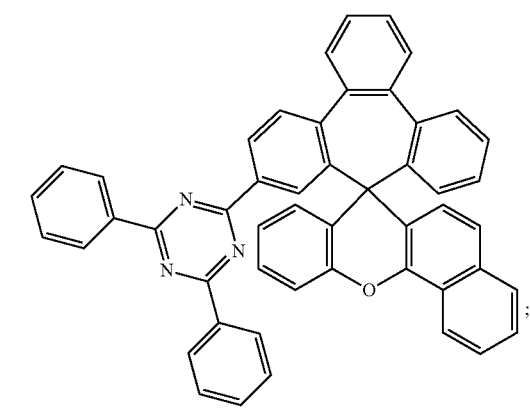
Compound I-26
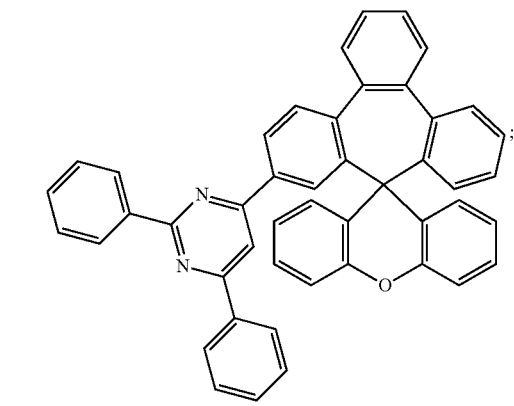
Compound I-27
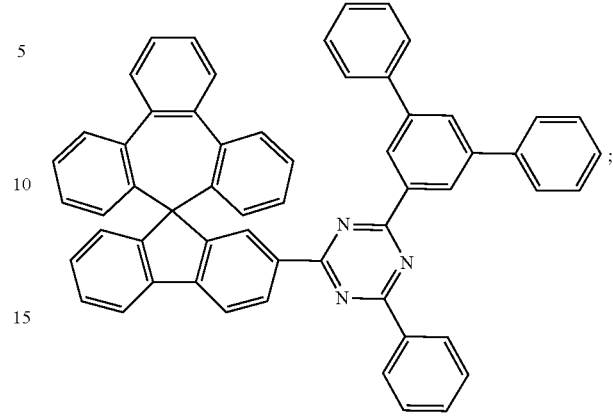
Compound I-28
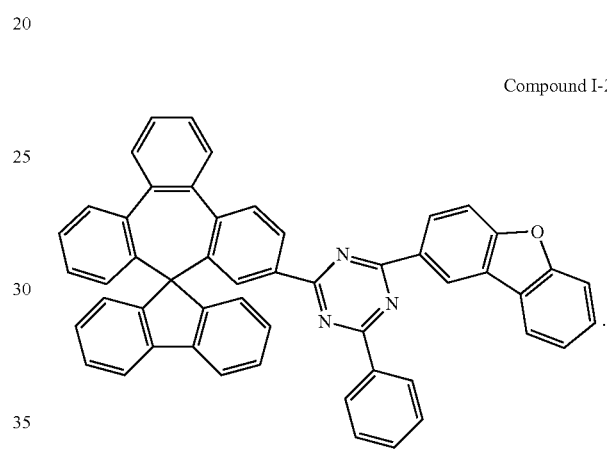
16. The composition as claimed in claim 15, wherein the second host compound is selected from the group consisting of:
Compound II-1
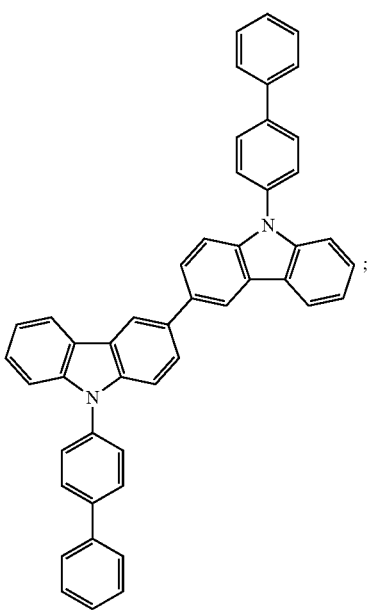

-continued

Compound II-2

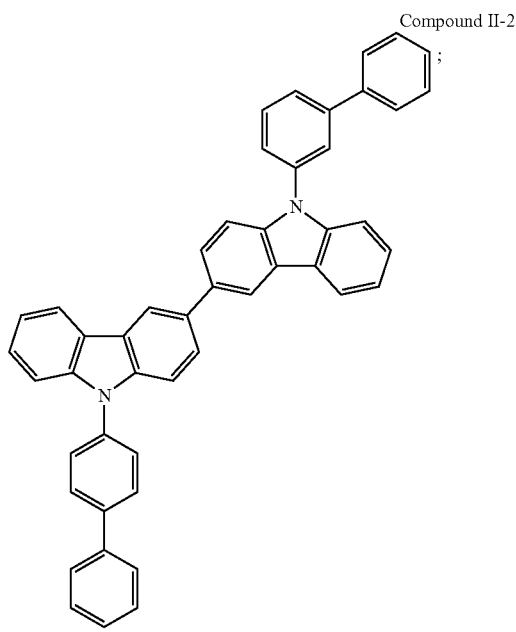

Compound II-3

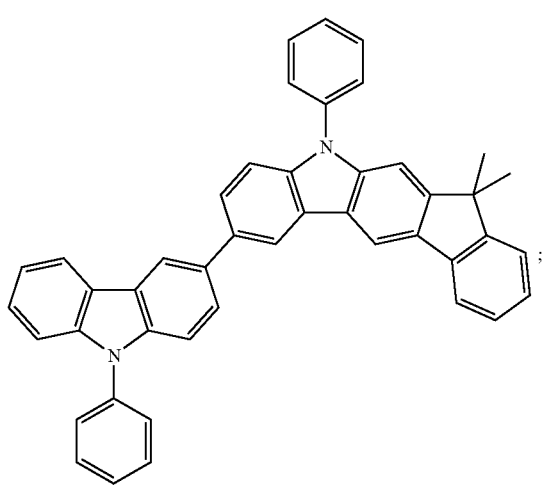

Compound II-4

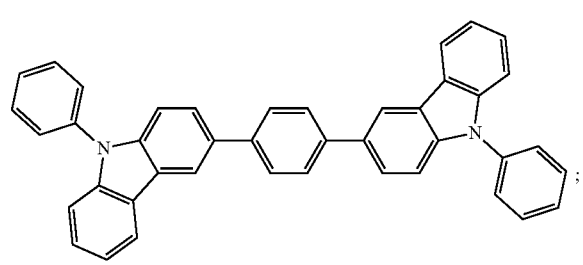

-continued

Compound II-5

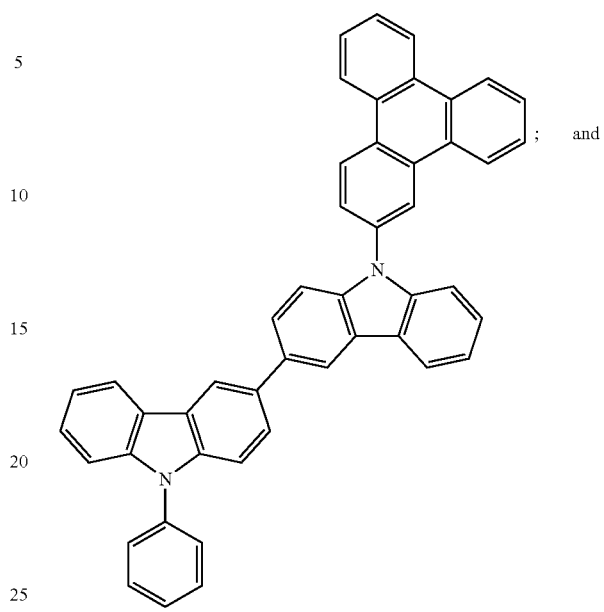

and

Compound II-6

17. An organic electronic device, comprising a first electrode, a second electrode, and an organic layer disposed between the first electrode and the second electrode, wherein the organic layer comprises the composition as claimed in claim 1.

18. The organic electronic device as claimed in claim 17, wherein the organic electronic device is an organic light emitting device.

19. The organic electronic device as claimed in claim 18, wherein the organic light emitting device comprises:
 a hole injection layer formed on the first electrode;
 a hole transport layer formed on the hole injection layer;
 an emission layer formed on the hole transport layer, wherein the emission layer comprises the composition as claimed in claim 1;
 an electron transport layer formed on the emission layer; and an electron injection layer formed between the electron transport layer and the second electrode.

* * * * *